US008367653B2

(12) United States Patent
Bian et al.

(10) Patent No.: US 8,367,653 B2
(45) Date of Patent: *Feb. 5, 2013

(54) AZETIDINYL DIAMIDES AS MONOACYLGLYCEROL LIPASE INHIBITORS

(75) Inventors: Haiyan Bian, Princeton, NJ (US); Kristen Chevalier, Collegeville, PA (US); Jose Clemente, Spring House, PA (US); Pete Connolly, Spring House, PA (US); Chris Flores, Springhouse, PA (US); Shu-Chen Lin, Doylestown, PA (US); Li Liu, Doylestown, PA (US); John Mabus, East Greenville, PA (US); Mark MacIelag, Spring House, PA (US); Mark McDonnell, Lansdale, PA (US); Philip Pitis, No. Wales, PA (US); Yue-Mei Zhang, Springhouse, PA (US); Sui-Po Zhang, Radnor, PA (US); Bin Zhu, Spring House, PA (US)

(73) Assignee: Janssen Pharmaceutica NV, Beerse (BE)

( * ) Notice: Subject to any disclaimer, the term of this patent is extended or adjusted under 35 U.S.C. 154(b) by 204 days.

This patent is subject to a terminal disclaimer.

(21) Appl. No.: 12/765,076

(22) Filed: Apr. 22, 2010

(65) Prior Publication Data

US 2010/0324013 A1  Dec. 23, 2010

Related U.S. Application Data

(60) Provisional application No. 61/171,658, filed on Apr. 22, 2009, provisional application No. 61/171,649, filed on Apr. 22, 2009.

(51) Int. Cl.
*A61K 31/496* (2006.01)
*C07D 401/12* (2006.01)
*C07D 403/14* (2006.01)
*C07D 417/12* (2006.01)
*C07D 417/14* (2006.01)
*C07D 487/04* (2006.01)
*C07D 495/04* (2006.01)

(52) U.S. Cl. .................. 514/210.18; 544/362; 544/363; 544/364; 544/367; 544/369; 544/371; 544/373; 544/284; 544/295

(58) Field of Classification Search .................. None
See application file for complete search history.

(56) References Cited

U.S. PATENT DOCUMENTS

| | | |
|---|---|---|
| 2004/0167224 A1 | 8/2004 | Ozaki et al. |
| 2006/0148844 A1 | 7/2006 | Nakade et al. |
| 2007/0142394 A1 | 6/2007 | Solomon et al. |
| 2007/0293496 A1 | 12/2007 | Ozaki et al. |
| 2010/0041651 A1 | 2/2010 | Even et al. |

FOREIGN PATENT DOCUMENTS

| | | |
|---|---|---|
| WO | WO 98/37077 A1 | 8/1998 |
| WO | WO 99/19297 A1 | 4/1999 |
| WO | WO 00/63168 A1 | 10/2000 |
| WO | WO 01/77101 A1 | 10/2001 |
| WO | WO 2004/056800 A1 | 7/2004 |

OTHER PUBLICATIONS

Benito et al., "Cannabinoid CB2 receptors in human brain inflammation", Brit J Pharmacol, 2008, vol. 153, pp. 277-285.
Ben-Shabat et al.,"An entourage effect: inactive endogenous fatty acid glycerol esters enhance 2-arachidonoyl-glycerol cannabinoid activity", Eur J Pharmacol, 1998, vol. 353, pp. 23-31.
Cravatt et al.,"The Endogenous Cannabinoid System and Its Role in Nociceptive Behavior", J Neurobiol, 2004, vol. 61, pp. 149-160.
Comelli et al., "The inhibition of monoacylglycerol lipase by URB602 showed an anti-inflammatory and anti-nociceptive effect in a murine model of acute inflammation", Brit J Pharmacol, 2007, vol. 152, pp. 787-794.
Cavuoto et al.,"The expression of receptors for endocannabinoids in human and rodent skeletal muscle", Biochem Biophys Res Commun, 2007, vol. 364, pp. 105-110.
Devane et al., "Isolation and Structure of a Brain Constituent That Binds to the Cannabinoid Receptor", Science, 1992, vol. 258, pp. 1946-1949.
Di Marzo et al., "Endocannabinoids: New Targets for Drug Development", Curr Pharm Des, 2000, vol. 6, pp. 1361-1380.
Di Marzo et al., "Endocannabinoids and the Regulation of their levels in Health and Disease", Curr Opin Lipidol, 2007, vol. 18, pp. 129-140.
Dogrul et al., "'Knock-down' of spinal CB1 receptors produces abnormal pain and elevates spinal dynorphin content in mice", Pain, 2002, vol. 100, pp. 203-209.
Guindon et al.,"Cannabinoid CB2 receptors: a therapeutic target for the treatment of inflammatory and neuropathic pain", Brit J Pharmacol, 2008, vol. 153, pp. 319-334.
Hajrasouliha et al., "Endogenous cannabinoids contribute to remote ischemic preconditioning via cannabinoid CB2 receptors in the rat heart", Eur J Pharmacol, 2008, vol. 579, pp. 246-252.
Jhaveri et al., "Endocannabinoid metabolism and uptake: novel targets for neuropathic and inflammatory pain", Brit J Pharmacol, 2007, vol. 152, pp. 624-632.
Kathuria et al., "Modulation of anxiety through blockade of anandamide hydrolysis", Nat Med, 2003, vol. 9, pp. 76-81.
Lichtman et al., "Pharmacological Activity of Fatty Acid Amides Is Regulated, but Not Mediated, by Fatty Acid Amide Hydrolase in Vivo", J Pharmacol Exp Ther, 2002, 302, 73-9.

(Continued)

*Primary Examiner* — Emily Bernhardt

(57) ABSTRACT

Disclosed are compounds, compositions and methods for treating various diseases, syndromes, conditions and disorders, including pain. Such compounds are represented by Formula (I) as follows:

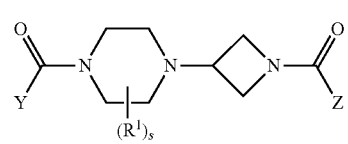

Formula (I)

wherein Y, Z, $R^1$, and s are defined herein.

19 Claims, No Drawings

OTHER PUBLICATIONS

Lichtman et al., "Mice lacking fatty acid amide hydrolase exhibit a cannabinoid receptor-mediated phenotypic hypoalgesia", Pain, 2004, vol. 109, pp. 319-327.
Matsuda et al., "Structure of a Cannabinoid Receptor and Functional Expression of the cloned cDNA", Nature, 1990, vol. 346, pp. 561-564.
McCarberg B. et al., "The Future of Cannabinoids as Analgesic Agents: A Pharmacologic, Pharmacokinetic, and Pharmacodynamic Overview", Amer J Ther, 2007, vol. 14, pp. 475-483.
Mechoulam et al., "Identification of an Endogenous 2-Monoglyceride, Present in Canine Gut, that Binds to Cannabinoid Receptors", Biochem Pharmacol, 1995, vol. 50, pp. 83-90.
Munro et al., "Molecular Characterization of a Peripheral Receptor for Cannabinoids", Nature, 1993, vol. 365, pp. 61-65.
Njie, Ya Fatou et al, "Aqueous humor outflow effects of 2-arachidonylglycerol", Exp. Eye Res., 2008, vol. 87(2), pp. 106-114.
Pacher et al., "Pleiotropic effects of the $CB_2$ cannabinoid receptor activation on human monocyte migration: implications for atherosclerosis and.inflammatory diseases", Amer J Physiol, 2008, vol. 294, pp. H1133-H1134.
Pertwee,"The diverse CB1 and CB2 receptor pharmacology of three plant cannabinoids: $\Delta^9$-tetrahydrocannabinol, cannabidiol and $\Delta^9$-tetrahydrocannabivarin", Brit J Pharmacol, 2008, vol. 153, pp. 199-215.
Piomelli, "The Molecular Logic of Endocannabinoid Signalling", Nat Rev Neurosci, 2003, vol. 4, pp. 873-884.
Sugiura et al., "2-Arachidonoylglycerol: A Possible Endogenous Cannabinoid Receptor Ligand in Brain", Biochem Biophys Res Commun, 1995, vol. 215, pp. 89-97.
Walker et al., "Pain modulation by release of the endogenous cannabinoid anandamide", Proc Natl Acad Sci USA, 1999, vol. 96, pp. 12198-12203.
PCT counterpart to U.S. Appl. No. 12/765,018, International Search Report and Written Opinion, PCT/US2010/032045, dated Jun. 11, 2010, 12 pages.
PCT counterpart to U.S. Appl. No. 12/765,048, International Search Report and Written Opinion, PCT/US2010/032049, dated Jun. 15, 2010, 12 pages.
PCT counterpart to U.S. Appl. No. 12/765,076, International Search Report and Written Opinion, PCT/US2010/032068, dated Jun. 14, 2010, 12 pages.
PCT counterpart to U.S. Appl. No. 12/765,103, International Search Report and Written Opinion, PCT/US2010/032082, dated Jun. 15, 2010, 12 pages.
PCT counterpart to U.S. Appl. No. 12/765,179, International Search Report and Written Opinion, PCT/US2010/032086, dated Jun. 14, 2010, 12 pages.
PCT counterpart to U.S. Appl. No. 12/765,254, International Search Report and Written Opinion, PCT/US2010/032089, dated Jun. 14, 2010, 12 pages.
PCT counterpart to U.S. Appl. No. 12/765,420, International Search Report and Written Opinion, PCT/US2010/032092, dated Jun. 15, 2010, 12 pages.
PCT counterpart to U.S. Appl. No. 12/765,487, International Search Report and Written Opinion, PCT/US2010/032095, dated Jun. 14, 2010, 12 pages.
Bennett et al., "A peripheral mononeuropathy in rat that produces disorders of pain sensation like those seen in man.", Pain, 1988, vol. 33(1), pp. 87-107.
Chaplan et al., "Quantitative assessment of tactile allodynia in the rat paw.", J. Neurosci Methods, 1994, vol. 53(1), pp. 55-63.
Dixon, W. J., "Efficient analysis of experimental observations.", Annu. Rev. Pharmacol. Toxicol., 1980, vol. 20, pp. 441-462.
Matulis et al., "Thermodynamic Stability of Carbonic Anhydrase: Measurements of Binding Affinity and Stoichiometry Using ThermoFluor.", Biochemistry, 2005, vol. 44, pp. 5258-5266.
Pantoliano et al., "High Density Miniaturized Thermal Shift Assays as a General Strategy for Drug Discovery*.", Journal of Biomolecular Screening, 2001, vol. 6(6), pp. 429-440.
Schlosser et al., "In Search in Simplicity and Flexibility: A Rational Access to Twelve Fluoroindolecarboxylic Acids.", Eur. J. Org. Chem. 2006, pp. 2956.

AZETIDINYL DIAMIDES AS MONOACYLGLYCEROL LIPASE INHIBITORS

CROSS-REFERENCE TO RELATED APPLICATIONS

This application claims priority to U.S. provisional patent application Nos. 61/171,658 and 61/171,649, each filed Apr. 22, 2009, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol*, 2008, 153, 199-215). Two cannabinoid G protein-coupled receptors have been cloned, cannabinoid receptor type 1 ($CB_1$ Matsuda et al., *Nature*, 1990, 346, 561-4) and cannabinoid receptor type 2 ($CB_2$ Munro et al., *Nature*, 1993, 365, 61-5). $CB_1$ is expressed centrally in brain areas, such as the hypothalamus and nucleus accumbens as well as peripherally in the liver, gastrointestinal tract, pancreas, adipose tissue, and skeletal muscle (Di Marzo et al., *Curr Opin Lipidol*, 2007, 18, 129-140). $CB_2$ is predominantly expressed in immune cells, such as monocytes (Pacher et al., *Amer J Physiol*, 2008, 294, H1133-H1134), and under certain conditions, also in the brain (Benito et al., *Brit J Pharmacol*, 2008, 153, 277-285) and in skeletal (Cavuoto et al., *Biochem Biophys Res Commun*, 2007, 364, 105-110) and cardiac (Hajrasouliha et al., *Eur J Pharmacol*, 2008, 579, 246-252) muscle. An abundance of pharmacological, anatomical and electrophysiological data, using synthetic agonists, indicate that increased cannabinoid signaling through $CB_1/CB_2$ promotes analgesia in tests of acute nociception and suppresses hyperalgesia in models of chronic neuropathic and inflammatory pain (Cravatt et al., *J Neurobiol*, 2004, 61, 149-60; Guindon et al., *Brit J Pharmacol*, 2008, 153, 319-334).

Efficacy of synthetic cannabinoid receptor agonists is well documented. Moreover, studies using cannabinoid receptor antagonists and knockout mice have also implicated the endocannabinoid system as an important modulator of nociception. Anandamide (AEA) (Devane et al., *Science*, 1992, 258, 1946-9) and 2-arachidinoylglycerol (2-AG) (Mechoulam et al., *Biochem Pharmacol*, 1995, 50, 83-90; Sugiura et al., *Biochem Biophys Res Commun*, 1995, 215, 89-97) are 2 major endocannabinoids. AEA is hydrolyzed by fatty acid amide hydrolase (FAAH) and 2-AG is hydrolyzed by monoacylglycerol lipase (MGL) (Piomelli, *Nat Rev Neurosci*, 2003, 4, 873-884). Genetic ablation of FAAH elevates endogenous AEA and results in a $CB_1$-dependent analgesia in models of acute and inflammatory pain (Lichtman et al., *Pain*, 2004, 109, 319-27), suggesting that the endocannabinoid system functions naturally to inhibit pain (Cravatt et al., *J Neurobiol*, 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med*, 2003, 9, 76-81). Further evidence for an endocannabinoid-mediated antinociceptive tone is demonstrated by the formation of AEA in the periaqueductal grey following noxious stimulation in the periphery (Walker et al., *Proc Natl Acad Sci USA*, 1999, 96, 12198-203) and, conversely, by the induction of hyperalgesia following antisense RNA-mediated inhibition of $CB_1$ in the spinal cord (Dogrul et al., *Pain*, 2002, 100, 203-9).

With respect to 2-AG, intravenous delivery of 2-AG produces analgesia in the tail flick (Mechoulam et al., *Biochem Pharmacol*, 1995, 50, 83-90) and hot plate (Lichtman et al., *J Pharmacol Exp Ther*, 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon termed the "entourage effect" (Ben-Shabat et al., *Eur J Pharmacol*, 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL Inhibitors will have a similar effect. Indeed, URB602, a relatively weak synthetic MGL Inhibitor, showed an antinociceptive effect in a murine model of acute inflammation (Comelli et al., *Brit J Pharmacol*, 2007, 152, 787-794).

Although the use of synthetic cannabinoid agonists have conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL Inhibitors are potentially useful for the treatment of pain, inflammation, and CNS disorders (Di Marzo et al., *Curr Pharm Des*, 2000, 6, 1361-80; Shaveri et al., *Brit J Pharmacol*, 2007, 152, 624-632; McCarberg Bill et al., *Amer J Ther*, 2007, 14, 475-83), as well as glaucoma and disease states arising from elevated intraocular pressure (Njie, Ya Fatou; He, Fang; Qiao, Zhuanhong; Song, Zhao-Hui, *Exp. Eye Res*, 2008, 87(2):106-14).

SUMMARY OF THE INVENTION

The present invention is directed to a compound of Formula (I)

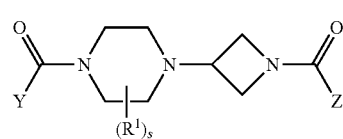

Formula (I)

wherein

Y and Z are independently selected from a) or b) such that one of Y and Z is selected from group a) and the other is selected from group b);

Group a) is
i) substituted $C_{6-10}$ aryl,
ii) $C_{3-8}$ cycloalkyl,
iii) trifluoromethyl, or
iv) heteroaryl selected from the group consisting of thienyl, furanyl, thiazolyl, isothiazolyl, oxazolyl, pyrrolyl, pyridinyl, isoxazolyl, imidazolyl, furazan-3-yl, benzothienyl, thieno[3,2-b]thiophen-2-yl, pyrazolyl, triazolyl, tetrazolyl, and [1,2,3]thiadiazolyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;

Group b) is
i) $C_{6-10}$ aryl;
ii) heteroaryl selected from the group consisting of thiazolyl, pyridinyl, indolyl, indazolyl, pyrrolyl, benzoxazolyl, benzothiazolyl, benzothienyl, imidazo[1,2-a]pyridin-2-yl, quinolinyl, thienyl, 1H-pyrrolo[2,3-b]pyridin-5-yl, 1H-thieno[2,3-c]pyrazol-5-yl, and benzimidazolyl;
iii) 7-(4-chloro-benzylidene)-1-(2,4-dichloro-phenyl)-4,5,6,7-tetrahydro-1H-indazol-3-yl;
iv) 2-oxo-3,3-bis-(3-trifluoromethylphenylmethyl)-2,3-dihydro-1H-indol-5-yl;
v) 5-[2-(4-chloro-phenyl)-1-methyl-vinyl]-1-(2,4-dichloro-phenyl)-4-methyl-1H-pyrazol-3-yl;
vi) 1-(2,4-dichloro-phenyl)-7-(4-fluoro-benzylidene)-1,4,6,7-tetrahydro-thiopyrano[4,3-c]pyrazol-3-yl;
vii) 2,3-dihydro-1H-indolyl;
viii) 7-(4-chloro-benzylidene)-1-(2,4-dichloro-phenyl)-4,5,6,7-tetrahydro-1H-indazol-3-yl;
ix) 4-{1-[1-(2,4-dichloro-phenyl)-7-(4-fluoro-benzylidene)-1,4,6,7-tetrahydro-thiopyrano[4,3-c]pyrazol-3-yl;
x) 1,1,3-tris-(3-trifluoromethylphenylmethyl)indan-2-on-6-yl; or
xi) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$ alkyl, $C_{1-4}$alkoxy, and trifluoromethyl; and are substituted with one additional substituent selected from the group consisting of
   i) $C_{6-10}$aryl($C_{1-4}$)alkyl; wherein $C_{1-4}$alkyl is optionally substituted with one to two fluoro substituents;
   ii) $C_{6-10}$aryl($C_{1-4}$)alkoxy;
   iii) 3-trifluoromethyl-phenylaminocarbonylmethoxy;
   iv) $C_{6-10}$aryl($C_{1-4}$)alkylthio;
   v) phenyl($C_{1-4}$)alkylsulfonyl;
   vi) phenylcarbonyl optionally substituted with chloro or fluoro;
   vii) 2,3-dihydro-1H-indol-5-ylcarbonyl;
   viii) N-methyl-N-phenyl-aminocarbonyl-methyl;
   ix) pyrrolidin-1-ylcarbonylmethyl;
   x) phenyl($C_{2-6}$)alkynyl;
   xi) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
   xii) heteroaryl($C_{1-6}$)alkoxy wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
   xiii) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent;
   xiv) heteroaryl-(Q)-$C_{1-6}$alkyl wherein Q is O or S; wherein heteroaryl is selected from the group consisting of pyridinyl, pyrimidinyl, thiazolyl, benzothienyl, and thienyl, wherein said heteroaryl is optionally substituted with a $C_{1-4}$alkyl, trifluoromethyl, or chloro substituent; and
   xv) phenyl-(Q)-$C_{1-6}$alkyl wherein Q is O, S, $SO_2$, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;

wherein phenyl of the $C_{6-10}$aryl($C_{1-4}$)alkyl, $C_{6-10}$aryl ($C_{1-4}$)alkylthio, phenyl($C_{1-4}$)alkylsulfonyl, and $C_{6-10}$aryl ($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxy; aminosulfonyl; di($C_{1-4}$alkyl)aminosulfonyl; $C_{1-4}$alkylsulfonyl; di($C_{1-4}$alkyl) aminosulfonyl; and $NR^cR^d$; wherein $R^c$ is hydrogen or $C_{1-6}$alkyl and wherein $R^d$ is hydrogen, $C_{1-6}$alkyl, cyano ($C_{1-4}$)alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$alkyl)aminocarbonyl, $C_{6-10}$arylcarbonyl; di($C_{1-4}$ alkyl)aminosulfonyl, and $C_{1-4}$alkylsulfonyl;

s is 0, 1 or 2; provided that when s is 2, $R^1$ is independently selected from the group consisting of phenyl, $C_{1-3}$alkyl, and $C_{6-10}$aryl($C_{1-3}$)alkyl;

$R^1$ is $C_{6-10}$aryl, $C_{1-3}$alkyl, benzyloxymethyl, hydroxy ($C_{1-3}$)alkyl, aminocarbonyl, carboxy, trifluoromethyl, spirofused cyclopropyl, 3-oxo, or aryl($C_{1-3}$)alkyl; or, when s is 2 and $R^1$ is $C_{1-3}$alkyl, the $C_{1-3}$alkyl substituents are taken with the piperizinyl ring to form a 3,8-diaza-bicyclo[3.2.1]octanyl or 2,5-diaza-bicyclo[2.2.2]octanyl ring system;

provided that a compound of formula (I) is other than
a compound wherein Y is thiazol-4-yl, Z is 4-(3-trifluoromethylphenylmethylsulfonyl)phenyl, and s is 0; or
a compound wherein Y is thiazol-2-yl, Z is 4-(phenylmethyl)phenyl, s is 1, and $R^1$ is 3-phenyl;
and enantiomers, diastereomers, solvates, and pharmaceutically acceptable salts thereof.

The present invention is further directed to a compound of Formula (I)

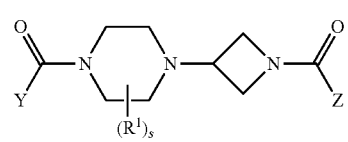

Formula (I)

wherein
Y and Z are independently selected from a) or b) such that one of Y and Z is selected from group a) and the other is selected from group b);
Group a) is
i) substituted $C_{6-10}$ aryl,
ii) trifluoromethyl; or
iii) heteroaryl selected from the group consisting of thiazolyl, isothiazolyl, pyrrolyl, and pyridinyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;

Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl;
vii) 4-{1-[1-(2,4-dichloro-phenyl)-7-(4-fluoro-benzylidene)-1,4,6,7-tetrahydro-thiopyrano[4,3-c]pyrazol-3-yl;
viii) 1,1,3-tris-(3-trifluoromethylphenylmethyl)indan-2-on-6-yl; or
ix) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substituents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenyl($C_{1-4}$)alkylsulfonyl;
v) phenylcarbonyl optionally substituted with chloro or fluoro;
vi) 2,3-dihydro-1H-indol-5-ylcarbonyl;
vii) N-methyl-N-phenyl-aminocarbonyl-methyl;
viii) phenyl($C_{2-6}$)alkynyl;
ix) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
x) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
xi) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
xii) phenyl-(Q)-$C_{1-6}$alkyl wherein Q is O, S, $SO_2$, or NH; and phenyl is optionally independently substituted with one to three substituents selected from the group consisting of bromo, chloro, fluoro, iodo, $C_{1-4}$alkyl, $C_{1-4}$alkoxy, and trifluoromethyl;
wherein phenyl of the $C_{6-10}$aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxyl; di($C_{1-4}$alkyl)aminosulfonyl; and $NR^cR^d$; wherein $R^c$ is hydrogen or $C_{1-6}$alkyl and wherein $R^d$ is hydrogen, $C_{1-6}$alkyl, cyano($C_{1-4}$)alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$alkyl)aminocarbonyl, $C_{6-10}$arylcarbonyl; di($C_{1-4}$alkyl)aminosulfonyl, and $C_{1-4}$alkylsulfonyl;
s is 0 or 1;
$R^1$ is phenyl or $C_{1-3}$alkyl;
provided that a compound of formula (I) is other than
a compound wherein Y is thiazol-4-yl, Z is 4-(3-trifluoromethylphenylmethylsulfonyl)phenyl, and s is 0;
or
a compound wherein Y is thiazol-2-yl, Z is 4-(phenylmethyl)phenyl, s is 1, and $R^1$ is 3-phenyl;
and enantiomers, diastereomers, solvates and pharmaceutically acceptable salts thereof.

The present invention is also directed to a compound of Formula (I)

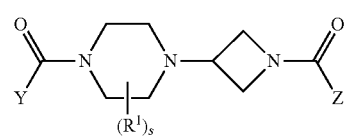

Formula (I)

wherein
Y and Z are independently selected from a) or b) such that one of Y and Z is selected from group a) and the other is selected from group b);
Group a) is
i) substituted $C_{6-10}$ aryl,
ii) trifluoromethyl; or
iii) heteroaryl selected from the group consisting of thiazolyl, pyrrolyl, and pyridinyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl;
vii) 4-{1-[1-(2,4-dichloro-phenyl)-7-(4-fluoro-benzylidene)-1,4,6,7-tetrahydro-thiopyrano[4,3-c]pyrazol-3-yl; or
viii) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substituents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;
vi) N-methyl-N-phenyl-aminocarbonyl-methyl;

vii) phenyl($C_{2-6}$)alkynyl;
viii) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
ix) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
x) phenyl-(Q)-$C_{1-6}$alkyl wherein Q is O, S, or NH; and phenyl is optionally independently substituted with one to three substitutents selected from the group consisting of bromo, chloro, fluoro, iodo, $C_{1-4}$aryl, $C_{1-4}$alkoxy, and trifluoromethyl;
wherein phenyl of the $C_{6-10}$aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio;
s is 0 or 1;
$R^1$ is phenyl or methyl;
provided that a compound of Formula (I) is other than a compound wherein Y is thiazol-2-yl, Z is 4-(phenylmethyl)phenyl, s is 1, and $R^1$ is 3-phenyl; a compound wherein Y is thiazol-2-yl, Z is 2-(pyridin-4-ylmethyl)-3H-benzimidazol-4-yl, and s is 0;
and enantiomers, diastereomers, solvates and pharmaceutically acceptable salts thereof.

The present invention is directed to a compound of Formula (I)

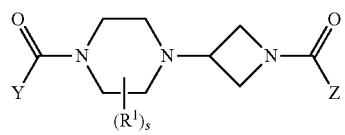

Formula (I)

wherein
Y and Z are independently selected from a) or b) such that one of Y and Z is selected from group a) and the other is selected from group b);
Group a) is
i) substituted phenyl,
ii) trifluoromethyl; or
iii) heteroaryl selected from the group consisting of thiazolyl, pyrrolyl, and pyridinyl;
wherein phenyl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
Group b) is
i) $C_{6-10}$ aryl;
ii) heteroaryl selected from the group consisting of pyridinyl, indolyl, and indazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
wherein $C_{6-10}$aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;
vi) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
vii) heteroaryl($C_{1-2}$)alkylthio, wherein heteroaryl is pyridinyl; wherein said pyridinyl is optionally substituted with a $C_{1-4}$alkyl, trifluoromethyl, or chloro substituent; and
viii) phenyl-(Q)-$C_{1-6}$alkyl wherein Q is O, S, or NH; and phenyl is optionally independently substituted with one to three substitutents selected from the group consisting of bromo, chloro, $C_{1-4}$alkyl, $C_{1-4}$alkoxy, and trifluoromethyl;
wherein phenyl of the $C_{6-10}$aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio;
s is 0 or 1;
$R^1$ is methyl;
and enantiomers, diastereomers, solvates and pharmaceutically acceptable salts thereof.

The present invention is directed to a compound of Formula (I)

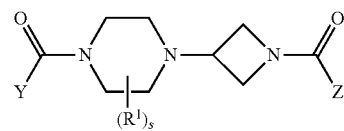

Formula (I)

selected from the group consisting of:
a compound wherein Y is thiazol-2-yl, Z is 4-phenylmethylphenyl, s is 1, and $R^1$ is 2-methyl;
a compound wherein Y is thiazol-2-yl, Z is 4-phenylmethylphenyl, s is 1, and $R^1$ is 3-methyl;
a compound wherein Y is thiazol-2-yl, Z is 3-chloro-4-(pyridin-4-ylmethoxy)phenyl, and s is 0;
a compound wherein Y is thiazol-2-yl, Z is 3-fluoro-4-(3,4-dichlorophenylmethoxy)phenyl, and s is 0;
a compound wherein Y is thiazol-2-yl, Z is 3-chloro-4-(3-chlorophenylmethoxy)phenyl, and s is 0;
a compound wherein Y is thiazol-2-yl, Z is 3-chloro-4-(pyridin-3-ylmethoxy)-phenyl, and s is 0;
a compound wherein Y is thiazol-2-yl, Z is 4-pyridin-4-ylmethoxy-phenyl, and s is 0;
a compound wherein Y is thiazol-2-yl, Z is 3-chloro-4-(3,4-dichlorophenylmethoxy)phenyl, and s is 0;

a compound wherein Y is thiazol-2-yl, Z is 3-fluoro-4-(2,3-dichlorophenylmethoxy)phenyl, and s is 0;
a compound wherein Y is thiazol-2-yl, Z is 3-chloro-4-(pyridin-2-ylmethoxy)phenyl, and s is 0;
a compound wherein Y is thiazol-2-yl, Z is 4-(3-chlorophenylmethylthio)phenyl, and s is 0;
a compound wherein Y is thiazol-2-yl, Z is 4-(2,3-dichlorophenylmethylthio)phenyl, and s is 0;
a compound wherein Y is thiazol-2-yl, Z is 4-(3,4-dichlorophenylmethylthio)phenyl, and s is 0;
a compound wherein Y is thiazol-2-yl, Z is 4-(4-chlorophenylmethylthio)phenyl, and s is 0;
a compound wherein Y is thiazol-2-yl, Z is 4-(pyridin-3-ylmethylthio)phenyl, and s is 0;
a compound wherein Y is thiazol-2-yl, Z is 4-(3-chlorophenoxymethyl)-phenyl, and s is 0;
a compound wherein Y is thiazol-2-yl, Z is 4-(3-chlorophenylthiomethyl)-phenyl, and s is 0;
a compound wherein Y is thiazol-2-yl, Z is 4-(3-chlorophenylaminomethyl)-phenyl, and s is 0;
a compound wherein Y is trifluoromethyl, Z is 4-(3-chlorophenylthiomethyl)-phenyl, and s is 0;
a compound wherein Y is thiazol-4-yl, Z is 4-(3-chlorophenylthiomethyl)-phenyl, and s is 0;
a compound wherein Y is thiazol-2-yl, Z is 4-(3-chlorophenylmethoxy)-phenyl, and s is 0;
a compound wherein Y is trifluoromethyl, Z is 4-(3-chlorophenylmethoxy)-phenyl, and is 0;
a compound wherein Y is thiazol-4-yl, Z is 4-(3-chlorophenoxymethyl)-phenyl, and s is 0;
a compound wherein Y is thiazol-4-yl, Z is 4-(3-chlorophenylmethoxy)-phenyl, and s is 0;
a compound wherein Y is trifluoromethyl, Z is 4-(5-chloro-thien-2-ylmethoxy)-phenyl, and s is 0;
a compound wherein Y is thiazol-2-yl, Z is 4-(5-chloro-thien-2-ylmethoxy)-phenyl, and s is 0;
a compound wherein Y is thiazol-4-yl, Z is 4-(5-chloro-thien-2-ylmethoxy)-phenyl, and s is 0;
a compound wherein Y is trifluoromethyl, Z is 4-(3-chlorophenylaminomethyl)-phenyl, and s is 0;
a compound wherein Y is thiazol-2-yl, Z is 2-(4-chlorophenoxymethyl)-4-methyl-thiazol-5-yl, and s is 0;
a compound wherein Y is thiazol-4-yl, Z is 2-(4-chlorophenoxymethyl)-4-methyl-thiazol-5-yl, and s is 0;
a compound wherein Y is thiazol-2-yl, Z is 4-(quinolin-2-ylmethoxy)-phenyl, and s is 0;
a compound wherein Y is trifluoromethyl, Z is 4-(quinolin-2-ylmethoxy)-phenyl, and s is 0;
a compound wherein Y is thiazol-4-yl, Z is 4-(3-chlorophenylaminomethyl)-phenyl, and s is 0;
a compound wherein Y is thiazol-4-yl, Z is 4-(quinolin-2-ylmethoxy)phenyl, and s is 0;
a compound wherein Y is thiazol-2-yl, Z is 4-(3-trifluoromethylphenylmethylsulfonyl)-phenyl, and s is 0;
a compound wherein Y is thiazol-2-yl, Z is 4-(3-trifluoromethylphenylmethylthio)-phenyl, and s is 0;
a compound wherein Y is trifluoromethyl, Z is 4-(3-trifluoromethylphenylmethylthio)-phenyl, and s is 0;
a compound wherein Y is thiazol-4-yl, Z is 4-(3-trifluoromethylphenylmethylthio)-phenyl, and s is 0;
a compound wherein Y is thiazol-2-yl, Z is 4-(3-trifluoromethylphenylsulfonylmethyl)-phenyl, and s is 0;
a compound wherein Y is thiazol-4-yl, Z is 4-(3-trifluoromethyl-phenylsulfonylmethyl)-phenyl, and s is 0;
a compound wherein Y is thiazol-2-yl, Z is 4-(5-chloro-pyridin-3-ylmethoxy)-phenyl, and s is 0;
a compound wherein Y is trifluoromethyl, Z is 4-(5-chloro-pyridin-3-ylmethoxy)-phenyl, and s is 0;
a compound wherein Y is thiazol-2-yl, Z is 2-(phenylmethyl)-1H-benzimidazol-4-yl, and s is 0;
a compound wherein Y is thiazol-4-yl, Z is 4-(5-chloro-pyridin-3-ylmethoxy)-phenyl, and s is 0;
a compound wherein Y is thiazol-2-yl, Z is 4-(4-trifluoromethyl-phenyl-fluoromethyl)-phenyl, and s is 0;
a compound wherein Y is thiazol-2-yl, Z is 4-(6-bromo-pyridin-2-ylmethoxy)-phenyl, and s is 0;
a compound wherein Y is trifluoromethyl, Z is 4-(6-bromo-pyridin-2-ylmethoxy)-phenyl, and s is 0;
a compound wherein Y is thiazol-2-yl, Z is 4-(4-trifluoromethylphenylmethyl)-phenyl, and s is 0;
a compound wherein Y is thiazol-2-yl, Z is 4-(phenyl-difluoromethyl)-phenyl, and s is 0;
a compound wherein Y is thiazol-4-yl, Z is 4-(6-bromo-pyridin-2-ylmethoxy)-phenyl, and s is 0;
a compound wherein Y is thiazol-2-yl, Z is 1-(2,3-dihydro-1H-indol-5-ylcarbonyl)-1H-indol-5-yl, and s is 0;
a compound wherein Y is thiazol-2-yl, Z is 2-(2-fluoro-phenylmethyl)-3H-benzimidazol-4-yl, and s is 0;
a compound wherein Y is thiazol-2-yl, Z is 2-(3-fluoro-phenylmethyl)-3H-benzimidazol-4-yl, and s is 0;
a compound wherein Y is thiazol-2-yl, Z is 2-(4-chlorophenylmethyl)-3H-benzimidazol-4-yl, and s is 0;
a compound wherein Y is thiazol-2-yl, Z is 2-oxo-3,3-bis-(3-trifluoromethylphenylmethyl)-2,3-dihydro-1H-indol-5-yl, and s is 0;
a compound wherein Y is thiazol-2-yl, Z is 1-(phenylmethyl)-indol-3-yl, and s is 0;
a compound wherein Y is thiazol-2-yl, Z is 1-phenylmethyl-2,3-dihydro-1H-indol-5-yl, and s is 0;
a compound wherein Y is thiazol-2-yl, Z is 4-(3-trifluoromethylphenylmethyl)phenyl, and s is 0;
a compound wherein Y is 4-(4-trifluoromethylphenylmethyl)phenyl, Z is thiazol-4-yl, and s is 0;
a compound wherein Y is 4-(4-trifluoromethylphenylmethyl)phenyl, Z is thiazol-2-yl, and s is 0;
a compound wherein Y is thiazol-4-yl, Z is 4-(3-trifluoromethylphenylmethyl)phenyl, and s is 0;
a compound wherein Y is thiazol-4-yl, Z is 4-(4-trifluoromethyl-phenylmethyl)phenyl, and s is 0;
a compound wherein Y is thiazol-2-yl, Z is 2-(phenylethyl)-1H-benzimidazol-5-yl, and s is 0;
a compound wherein Y is thiazol-2-yl, Z is 2-(phenylmethyl)-3H-benzimidazol-5-yl, and s is 0;
a compound wherein Y is 2-(phenylethyl)-3H-benzimidazol-5-yl, Z is thiazol-4-yl, and s is 0;
a compound wherein Y is thiazol-4-yl, Z is 2-(phenylmethyl)-1H-benzimidazol-5-yl, and s is 0;
a compound wherein Y is thiazol-2-yl, Z is 2-(phenylmethyl)-1H-benzimidazol-5-yl, and s is 0;
a compound wherein Y is thiazol-2-yl, Z is 3-(2-fluorophenylaminomethyl)-phenyl, and s is 0;
a compound wherein Y is thiazol-2-yl, Z is 3-(4-trifluoromethylphenyl-methyl)-4-fluoro-phenyl, and s is 0;
a compound wherein Y is thiazol-2-yl, Z is 3-(4-trifluoromethylphenyl-methyl)-4-fluoro-phenyl, and s is 0;
a compound wherein Y is thiazol-2-yl, Z is 2-methyl-3-(4-trifluoromethylphenyl-methyl)phenyl, and s is 0;
a compound wherein Y is thiazol-4-yl, Z is 2-methyl-3-(4-trifluoromethylphenyl-methyl)phenyl, and s is 0;
a compound wherein Y is thiazol-2-yl, Z is 5-[2-(4-chlorophenyl)-1-methyl-vinyl]-1-(2,4-dichloro-phenyl)-4-methyl-1H-pyrazol-3-yl, and s is 0;

a compound wherein Y is 1H-pyrrol-2-yl, Z is 5-[2-(4-chloro-phenyl)-1-methyl-vinyl]-1-(2,4-dichloro-phenyl)-4-methyl-1H-pyrazol-3-yl, and s is 0;

a compound wherein Y is trifluoromethyl, Z is 5-[2-(4-chloro-phenyl)-1-methyl-vinyl]-1-(2,4-dichloro-phenyl)-4-methyl-1H-pyrazol-3-yl, and s is 0;

a compound wherein Y is 1H-pyrrol-2-yl, Z is 2-methyl-3-(4-trifluoromethylphenyl-methyl)phenyl, and s is 0;

a compound wherein Y is isothiazol-5-yl, Z is 2-methyl-3-(4-trifluoromethylphenyl-methyl)phenyl, and s is 0;

a compound wherein Y is thiazol-4-yl, Z is 2-methyl-3-(4-trifluoromethylphenyl-methyl)-phenyl, and s is 0;

a compound wherein Y is 2-methyl-3-(4-trifluoromethylphenyl-methyl)phenyl, Z is thiazol-5-yl, and s is 0;

a compound wherein Y is thiazol-2-yl, Z is 4-(phenylcarbonyl)phenyl, and s is 0;

a compound wherein Y is thiazol-2-yl, Z is 7-(4-chloro-benzylidene)-1-(2,4-dichloro-phenyl)-4,5,6,7-tetrahydro-1H-indazol-3-yl, and s is 0;

a compound wherein Y is 1H-pyrrol-2-yl, Z is 7-(4-chloro-benzylidene)-1-(2,4-dichloro-phenyl)-4,5,6,7-tetrahydro-1H-indazol-3-yl, and s is 0;

a compound wherein Y is trifluoromethyl, Z is 7-(4-chloro-benzylidene)-1-(2,4-dichloro-phenyl)-4,5,6,7-tetrahydro-1H-indazol-3-yl, and s is 0;

a compound wherein Y is thiazol-2-yl, Z is 1-(2,4-dichloro-phenyl)-7-(4-fluoro-benzylidene)-1,4,6,7-tetrahydro-thiopyrano[4,3-c]pyrazol-3-yl, and s is 0;

a compound wherein Y is trifluoromethyl, Z is 4-{1-[1-(2,4-dichloro-phenyl)-7-(4-fluoro-benzylidene)-1,4,6,7-tetrahydro-thiopyrano[4,3-c]pyrazol-3-yl, and s is 0;

a compound wherein Y is thiazol-4-yl, Z is 7-(4-chloro-benzylidene)-1-(2,4-dichloro-phenyl)-4,5,6,7-tetrahydro-1H-indazol-3-yl, and s is 0;

a compound wherein Y is 1H-pyrrol-2-yl, Z is 4-{1-[1-(2,4-dichloro-phenyl)-7-(4-fluoro-benzylidene)-1,4,6,7-tetrahydro-thiopyrano[4,3-c]pyrazol-3-yl, and s is 0;

a compound wherein Y is thiazol-2-yl, Z is 3-(4-fluorophenylcarbonyl)-indol-6-yl, and s is 0;

a compound wherein Y is thiazol-2-yl, Z is 1-methyl-3-(4-fluorophenylmethyl)-indol-6-yl, and s is 0;

a compound wherein Y is thiazol-4-yl, Z is 1-methyl-3-(4-fluorophenylmethyl)-indol-6-yl, and s is 0;

a compound wherein Y is 1H-pyrrol-2-yl, Z is 1-methyl-3-(4-fluorophenylmethyl)-indol-6-yl, and s is 0;

a compound wherein Y is thiazol-2-yl, Z is 1-(4-fluoro-phenylmethyl)-1H-indazol-5-yl, and s is 0;

a compound wherein Y is thiazol-2-yl, Z is 2-(4-fluorophenylmethyl)-indazol-5-yl, and s is 0;

a compound wherein Y is thiazol-2-yl, Z is 1-(N-methyl-N-phenyl-aminocarbonyl-methyl)-indol-5-yl, and s is 0;

a compound wherein Y is thiazol-4-yl, Z is 1-(N-methyl-N-phenyl-aminocarbonyl-methyl)-indol-5-yl, and s is 0;

a compound wherein Y is thiazol-2-yl, Z is 1-methyl-3-(3-fluorophenylmethyl)-indol-6-yl, and s is 0;

a compound wherein Y is thiazol-2-yl, Z is 1-methyl-3-(phenylmethyl)-indol-6-yl, and s is 0;

a compound wherein Y is thiazol-2-yl, Z is 1-(pyrrolidin-1-ylcarbonylmethyl)-indol-5-yl, and s is 0;

a compound wherein Y is thiazol-2-yl, Z is 1-(4-trifluoromethyl-phenylmethyl)-1H-indazol-5-yl, and s is 0;

a compound wherein Y is thiazol-2-yl, Z is 2-(4-trifluoromethylphenylmethyl)-indazol-5-yl, and s is 0;

a compound wherein Y is thiazol-2-yl, Z is 1-(3-trifluoromethyl-phenylmethyl)-1H-indazol-5-yl, and s is 0;

a compound wherein Y is thiazol-2-yl, Z is 2-(3-trifluoromethylphenylmethyl)-indazol-5-yl, and s is 0;

a compound wherein Y is thiazol-2-yl, Z is (1-phenyl-ethyl)-2H-indazol-5-yl, and s is 0;

a compound wherein Y is thiazol-2-yl, Z is 4-(3-trifluoromethyl-phenylaminocarbonylmethoxy)-phenyl, and s is 0;

a compound wherein Y is thiazol-2-yl, Z is 1-(4-aminosulfonyl-phenylmethyl)-2,5-dimethyl-pyrrol-3-yl, and s is 0;

a compound wherein Y is thiazol-2-yl, Z is 1-(4-fluoro-phenylmethyl)-1H-pyrrolo[2,3-b]pyridin-5-yl, and s is 0;

a compound wherein Y is thiazol-2-yl, Z is 1-(4-aminocarbonyl-phenylmethyl)-indazol-5-yl, and s is 0;

a compound wherein Y is thiazol-2-yl, Z is 1-(4-cyano-phenylmethyl)-indazol-5-yl, and s is 0;

a compound wherein Y is thiazol-2-yl, Z is 1-(pyridin-4-ylmethyl)-indol-5-yl, and s is 0;

a compound wherein Y is thiazol-2-yl, Z is 1-(pyridin-4-ylmethyl)-indol-6-yl, and s is 0;

a compound wherein Y is thiazol-2-yl, Z is 1-(pyridin-3-ylmethyl)-indol-5-yl, and s is 0;

a compound wherein Y is thiazol-2-yl, Z is 1-(4-fluoro-phenylethyl)-indazol-5-yl, and s is 0;

a compound wherein Y is thiazol-2-yl, Z is 2-(4-fluoro-phenylethyl)-indazol-5-yl, and s is 0;

a compound wherein Y is thiazol-2-yl, Z is 1-(4-fluoro-phenylmethyl)-indazol-6-yl, and s is 0;

a compound wherein Y is thiazol-2-yl, Z is 2-(4-fluoro-phenylmethyl)-indazol-6-yl, and s is 0;

a compound wherein Y is thiazol-2-yl, Z is 1-(4-chloro-phenylmethyl)-3-methyl-1H-thieno[2,3-c]pyrazol-5-yl, and s is 0;

a compound wherein Y is thiazol-2-yl, Z is 1,1,3-tris-(3-trifluoromethylphenylmethyl)indan-2-on-6-yl, and s is 0;

a compound wherein Y is thiazol-2-yl, Z is 1,1,3-tris-(phenylmethyl)indan-2-on-6-yl, and s is 0;

or a solvate or a pharmaceutically acceptable salt form thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a MGL-modulated disorder in a subject, including a human or other mammal in which the disease, syndrome, or condition is affected by the modulation of the MGL enzyme, such as pain and the diseases that lead to such pain, inflammation and CNS disorders, using a compound of Formula (I).

The present invention also provides, inter alia, methods for producing the instant compounds and pharmaceutical compositions and medicaments thereof.

DETAILED DESCRIPTION OF THE INVENTION

With reference to substituents, the term "independently" refers to the situation that when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups, such as $(C_{1-6}alkyl)_2$amino, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. When a heteroaryl is bicyclic, at least one heteroatom is present in each ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

Unless otherwise noted, the term "benzo fused heteroaryl" refers to a 5 to 6 membered monocyclic heteroaryl ring fused to a benzene ring. The heteroaryl ring contains carbon atoms and from 1 to 4 heteroatoms independently selected from the group consisting of N, O, and S. Examples of heteroaryl groups with the optionally fused benzene rings include indolyl, isoindolyl, indolinyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the benzo-fused heteroaryl is attached to its pendant group at any heteroatom or carbon atom that results in a stable structure.

The term "halogen" or "halo" refers to fluorine, chlorine, bromine and iodine.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as subcombinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

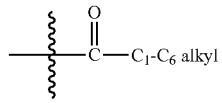

The numbering system shown below is used for describing the position of $R^1$ substituents on the piperazinyl ring of Formula (I):

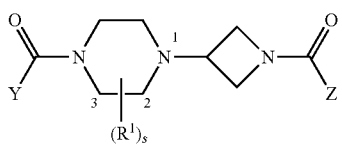

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) as herein defined can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme, such as, for example, pain and the diseases that lead to such pain, inflammation and CNS disorders.

As used herein, unless otherwise noted, the term "affect" or "affected" (when referring to a disease, syndrome, condition or disorder that is affected by inhibition of MGL) shall include a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (I) as herein defined, or an enantiomer, diastereomer, solvate or pharmaceutically acceptable salt thereof. In particular, the compounds of Formula (I) as herein defined are useful for treating, ameliorating and/or preventing pain; diseases, syndromes, conditions, or disorders causing such pain; inflammation and/or CNS disorders. More particularly, the compounds of Formula (I) as herein defined are useful for treating, ameliorating and/or preventing inflammatory pain, inflammatory hypersensitivity conditions and/or neuropathic pain, comprising administering to a subject in need thereof a therapeutically effective amount of a compound of Formula (I), as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease, ulcerative colitis, urinary incontinence, benign prostatic hypertrophy, cough, asthma, rhinitis, nasal hypersensitivity, itch, contact dermintisi and/or dermal allergy and chronic obstructive pulmonary disease.

In an embodiment, the present invention is directed to a method for treating, ameliorating and/or preventing inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (I), as herein defined. In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of formule (I) or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I), as herein defined, or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties, such as social anxiety, post-traumatic stress disorder, phobias, social phobia, special phobias, panic disorder, obsessive-compulsive disorder, acute stress, disorder, separation anxiety disorder, and generalized anxiety disorder, as well as depression, such as major depression, bipolar disorder, seasonal affective disorder, post natal depression, manic depression, and bipolar depression.

The present invention includes a pharmaceutical composition comprising a compound of Formula (I) wherein:

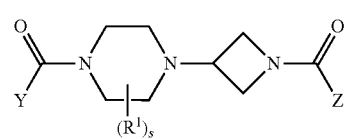

Formula (I)

wherein
a) Group a) is
i) substituted $C_{6-10}$aryl,
ii) trifluoromethyl; or
iii) heteroaryl selected from the group consisting of thiazolyl, isothiazolyl, pyrrolyl, and pyridinyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
b) Group a) is
i) substituted $C_{6-10}$ aryl,
ii) trifluoromethyl; or
iii) heteroaryl selected from the group consisting of thiazolyl, pyrrolyl, and pyridinyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
c) Group a) is
i) substituted phenyl,
ii) trifluoromethyl; or
iii) heteroaryl selected from the group consisting of thiazolyl, pyrrolyl, and pyridinyl;
wherein phenyl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
d) Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
wherein $C_{6-10}$aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenyl($C_{1-4}$)alkylsulfonyl;
v) phenylcarbonyl optionally substituted with chloro or fluoro;

19 vi) 2,3-dihydro-1H-indol-5-ylcarbonyl;
vii) N-methyl-N-phenyl-aminocarbonyl-methyl;
viii) phenyl($C_{2-6}$)alkynyl;
ix) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
x) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
xi) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
xii) phenyl-(Q)-$C_{1-6}$alkyl wherein Q is O, S, $SO_2$, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxyl; di($C_{1-4}$alkyl)aminosulfonyl; and $NR^cR^d$; wherein $R^c$ is hydrogen or $C_{1-4}$alkyl and wherein $R^d$ is hydrogen, $C_{1-6}$alkyl, cyano($C_{1-4}$)alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$alkyl)aminocarbonyl, $C_{6-10}$arylcarbonyl; di($C_{1-4}$alkyl)aminosulfonyl, and $C_{1-4}$alkylsulfonyl;
e) Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;

20 v) 2,3-dihydro-1H-indol-5-ylcarbonyl;
vi) N-methyl-N-phenyl-aminocarbonyl-methyl;
vii) phenyl($C_{2-6}$)alkynyl;
viii) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
ix) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
x) phenyl-(Q)-$C_{1-6}$alkyl wherein Q is O, S, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio;
f) Group b) is
i) $C_{6-10}$ aryl;
ii) heteroaryl selected from the group consisting of pyridinyl, indolyl, and indazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;
vi) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
vii) heteroaryl($C_{1-2}$)alkylthio, wherein heteroaryl is pyridinyl; wherein said pyridinyl is optionally substituted with a $C_{1-4}$alkyl, trifluoromethyl, or chloro substituent; and
viii) phenyl-(Q)-$C_{1-6}$alkyl wherein Q is O, S, or NH; and phenyl is optionally independently substituted with one to three substitutents selected from the group consisting of bromo, chloro, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and C$_{6-10}$aryl(C$_{1-4}$)alkoxy substituents is optionally independently substituted with one to two substituents selected from the group consisting of C$_{1-4}$alkyl; C$_{1-4}$alkoxy; one to three fluoro or chloro substituents; trifluoromethyl; trifluoromethoxy; and trifluoromethylthio;

g) s is 0 or 1;

h) R$^1$ is phenyl or C$_{1-3}$alkyl;

i) R$^1$ is methyl;

and any combination of embodiments a) through i) above, provided that it is understood that combinations in which different embodiments of the same substituent would be combined are excluded;

provided that a compound of formula (I) is other than a compound wherein Y is thiazol-4-yl, Z is 4-(3-trifluoromethylphenylmethylsulfonyl)phenyl, and s is 0;

and enantiomers, diastereomers, solvates, and pharmaceutically acceptable salts thereof.

For use in medicine, salts of compounds of Formula (I) as herein defined refer to non-toxic "pharmaceutically acceptable salts." Other salts may, however, be useful in the preparation of compounds of Formula (I) as herein defined or of their pharmaceutically acceptable salts thereof. Suitable pharmaceutically acceptable salts of compounds of Formula (I) as herein defined include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) as herein defined carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, secondary amine, sodium hydroxide, triethanolamine, tromethamine and zinc hydroxide.

Embodiments of the present invention include prodrugs of compounds of Formula (I) as herein defined. In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) as herein defined wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100$$

Another embodiment of the present invention is a composition, including a pharmaceutical composition, comprising, consisting of, and consisting essentially of the (−)-enantiomer of a compound of Formula (I) as herein defined wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) as herein defined and at least one pharmaceutically acceptable carrier, pharmaceutically acceptable excipient, and/or pharmaceutically acceptable diluent By way of example, in the pharmaceutical compositions of embodiments of the present invention, the compounds of Formula (I) as herein defined may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include exilirs, solutions, syrups, and suspensions; each optionally containing flavoring agents and coloring agents.

Alternatively, compounds of Formula (I) as herein defined can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as herein defined as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) as herein defined or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) as herein defined will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I) as herein defined.

Advantageously, a compound of Formula (I) as herein defined may be administered in a single daily dose, or the total daily dosage may be administered in divided doses of two, three and four times daily.

Optimal dosages of a compound of Formula (I) as herein defined to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) as herein defined may be administered in any of the foregoing compositions and dosage regimens or by means of those compositions and dosage regimens established in the art whenever use of a compound of Formula (I) as herein defined is required for a subject in need thereof.

As MGL Inhibitors, the compounds of Formula (I) as herein defined are useful in methods for treating and preventing a disease, a syndrome, a condition or a disorder in a subject, including an animal, a mammal and a human in which the disease, the syndrome, the condition or the disorder is affected by the modulation of the MGL enzyme. Such methods comprise, consist of and/or consist essentially of administering to a subject, including an animal, a mammal, and a human in need of such treatment or prevention a therapeutically effective amount of a compound, salt or solvate of Formula (I) as herein defined. In particular, the compounds of Formula (I) as herein defined are useful for preventing or treating pain, or diseases, syndromes, conditions, or disorders causing such pain, or for treating inflammation or CNS disorders.

Examples of inflammatory pain include pain due to a disease, condition, syndrome, disorder, or a pain state, including inflammatory bowel disease, visceral pain, migraine, post operative pain, osteoarthritis, rheumatoid arthritis, back pain, lower back pain, joint pain, abdominal pain, chest pain, labor pain, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

Examples of CNS disorders include anxieties, such as social anxiety, post-traumatic stress disorder, phobias, social phobia, special phobias, panic disorder, obsessive-compulsive disorder, acute stress, disorder, separation anxiety disorder, and generalized anxiety disorder, as well as depression, such as major depression, bipolar disorder, seasonal affective disorder, post natal depression, manic depression, and bipolar depression.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

| | |
|---|---|
| AcCl | acetyl chloride |
| AcOH | glacial acetic acid |
| aq. | aqueous |
| Bn or Bzl | benzyl |
| CAN | ceric ammonium nitrate |
| conc. | concentrated |
| DBU | 1,8-diazabicyclo[5.4.0]undec-7-ene |
| DCC | N,N'-dicyclohexyl-carbodiimide |
| DCE | 1,2-dichloroethane |
| DCM | dichloromethane |
| DIAD | diisopropyl azodicarboxylate |
| DIPEA | diisopropyl-ethyl amine |
| DMF | N,N-dimethylformamide |
| DMSO | dimethylsulfoxide |
| DPPA | diphenylphosphoryl azide |
| EDC | N-(3-dimethylaminopropyl)-N'-ethylcarbodiimide hydrochloride |
| ESI | electrospray ionization |
| EtOAc | ethyl acetate |
| EtOH | ethanol |
| h | hour(s) |
| HATU | O-(1H-7-azabenzotriazol-1-yl)-1,1,3,3-tetramethyluronium hexafluorophosphate |
| HBTU | O-(1H-benzotriazol-1-yl)-1,1,3,3-tetramethyluronium hexafluorophosphate |
| HEK | human embryonic kidney |
| HPLC | high performance liquid chromatography |
| mCPBA | meta-chloroperoxybenzoic acid |
| MeCN | acetonitrile |
| MeOH | methanol |
| MeOTf | methyl triflate |
| MHz | megahertz |
| min | minute(s) |
| MS | mass spectrometry |
| NBS | N-bromosuccinimide |
| NMR | nuclear magnetic resonance |
| PyBrOP | bromo-tris-pyrrolidinophosphonium hexafluorophosphate |
| RP | reverse-phase |
| $R_t$ | retention time |
| TEA or $Et_3N$ | triethylamine |
| TFA | trifluoroacetic acid |
| THF | tetrahydrofuran |
| TLC | thin layer chromatography |
| TMS | tetramethylsilane |

Scheme A illustrates a route for the synthesis compounds of Formula (I)-A, wherein $R^1$, s, Y, and Z are as defined herein.

Scheme A

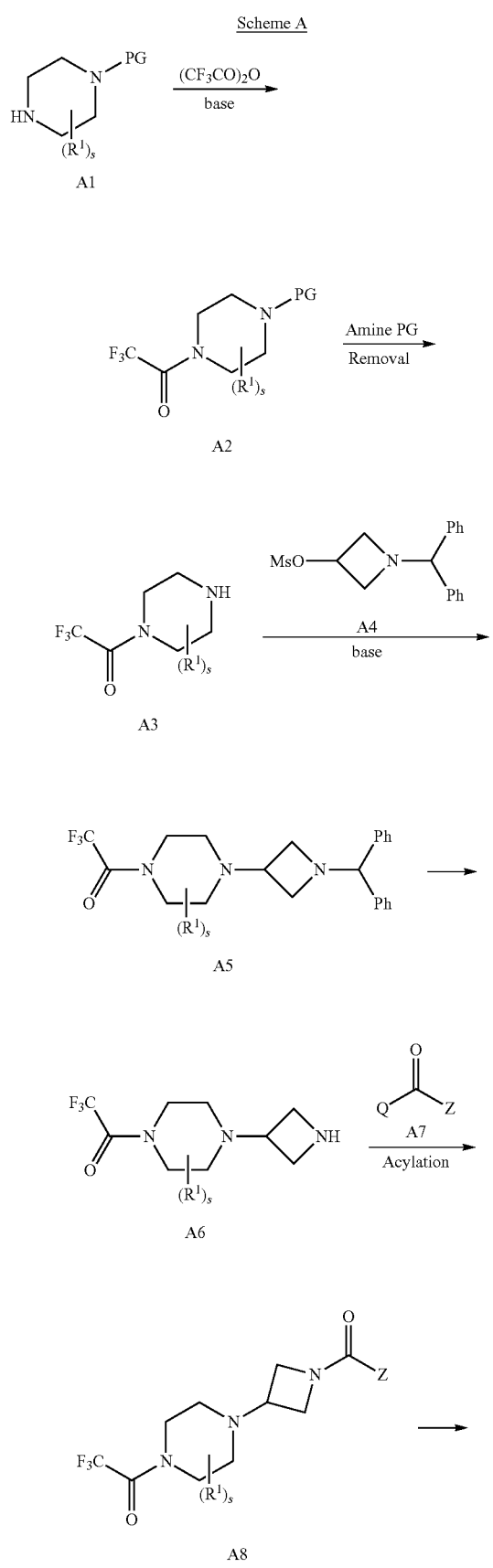

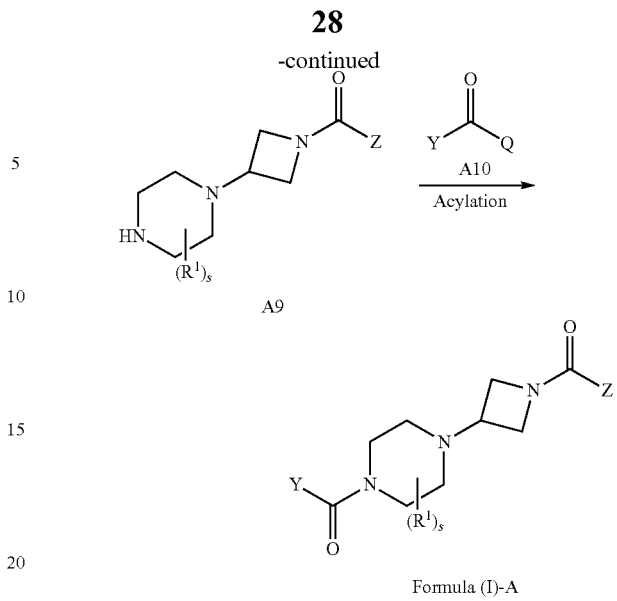

Formula (I)-A

A compound of formula A1, wherein PG is a conventional amino protecting group, such as Boc, Fmoc, Cbz, and the like, is either commercially available or may be prepared by known methods described in the scientific literature. A compound of formula A1 in the presence of a non-nucleophilic base, such as pyridine, may be treated with trifluoroacetic anhydride to afford a compound of formula A2. Removal of the protecting group (PG) by conventional methods affords a compound of formula A3. A compound of formula A3 may be treated with a compound of formula A4 in the presence of a hindered amine base, such as DIPEA, to afford a compound of formula A5. Treatment of a compound of formula A5 with 1-chloroethyl chloroformate followed by methanolysis affords the corresponding amine of formula A6. Similarly, when the $R^1$ substituent of a compound of formula A5 is hydroxy($C_{1-3}$)alkyl, the benzhydryl group may be removed by hydrogenation in the presence of a palladium catalyst to afford the amine of formula A6. A compound of formula A6 may be coupled with a carboxylic acid of formula A7 wherein Q is hydroxy, in the presence of an appropriate coupling agent such as HATU, DCC, EDC, HBTU, PyBrOP, and the like; optionally in the presence of a base such as DIPEA, to afford an amide of formula A8. Similarly, an acid chloride of formula A7 wherein Q is chloro may be used to effect the acylation of a compound of formula A6. In such case a non-nucleophilic base such as pyridine may be added to afford an amide of formula A8. Removal of the trifluoroacetyl group of a compound of formula A8 may be accomplished by the action of potassium carbonate or TEA in the presence of an alcoholic solvent such as methanol to afford a compound of formula A9. A compound of formula A9 may be acylated with a carboxylic acid or acid chloride of formula A10, wherein Q is hydroxy or chloride, respectively. Appropriate coupling conditions when using a compound of formula A10 (wherein Q is OH) include a coupling agent, such as HATU, DCC, EDC, HBTU, PyBrOP, and the like; and a base such as DIPEA to afford a compound of Formula (I)-A. When the acylation is effected by the addition of the corresponding acid chloride, the addition of a non-nucleophilic base such as pyridine affords a compound of Formula (I)-A.

Scheme B illustrates an alternate route for the synthesis compounds of Formula (I)-A, wherein $R^1$, s, Y, and Z are as defined herein.

29

Scheme B

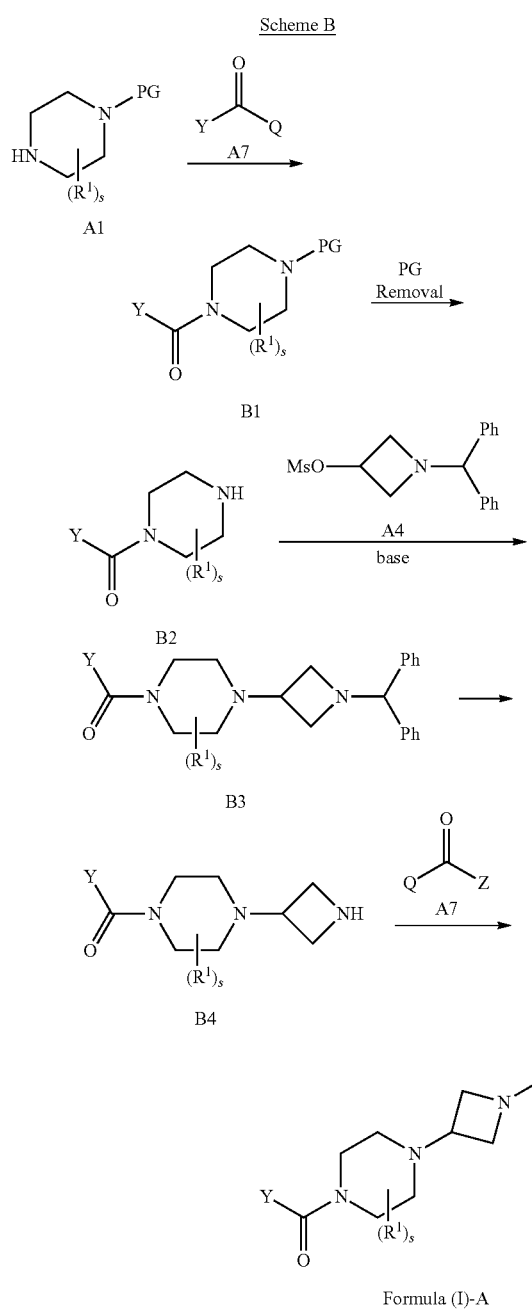

30

B3 is hydroxy($C_{1-3}$)alkyl, the benzhydryl group may be removed by hydrogenation in the presence of a palladium catalyst to afford the amine of formula B4. An acylation reaction with a compound of formula A7 using the methods described in Scheme A affords the corresponding compound of Formula (I)-A.

Scheme C illustrates an alternate route for the synthesis compounds of Formula (I)-A, wherein $R^1$, s, Y, and Z are as defined herein.

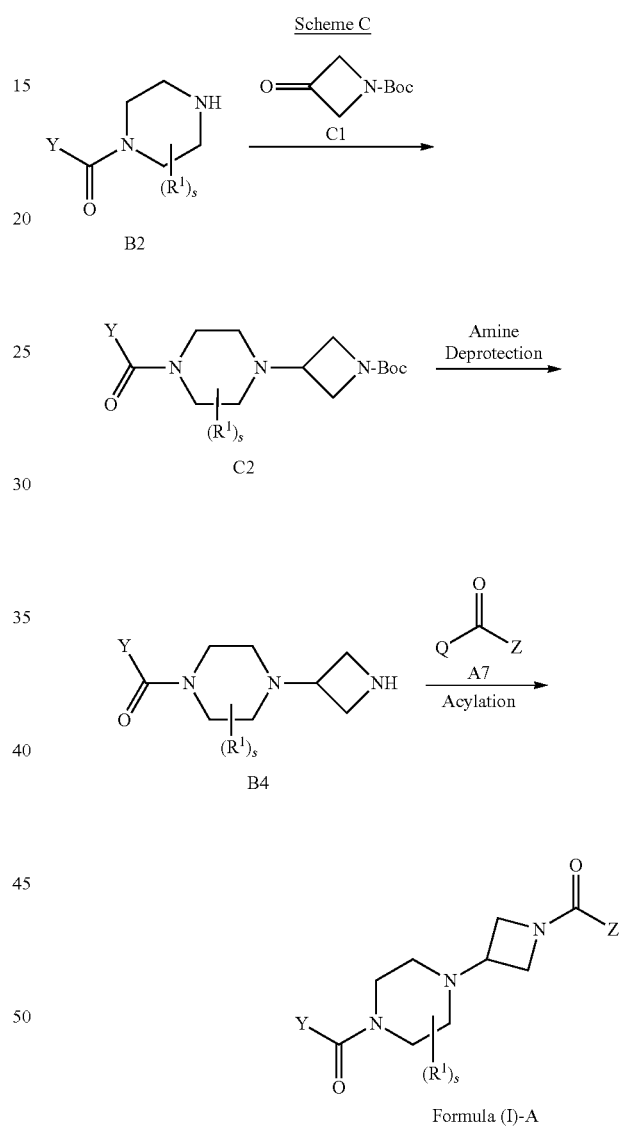

A compound of formula A1, wherein PG is a conventional amino protecting group, such as Boc, Fmoc, Cbz, and the like, is either commercially available or may be prepared by known methods described in the scientific literature. A compound of formula A1 may be acylated with a compound of formula A10 using methods and reagents previously described in Scheme A to afford a compound of formula B1. Upon conventional removal of the protecting group PG, a compound of formula B2 may be treated with a compound of formula A4 in the presence of a hindered amine base such as DIPEA using the methods described in Scheme A to afford a compound of formula B3. Treatment of a compound of formula B3 with 1-chloroethyl chloroformate followed by methanolysis affords the corresponding amine of formula B4. Similarly, when the $R^1$ substituent of a compound of formula A compound of formula B2 may be treated with a ketone of formula C1 in the presence of decaborane or a reducing agent, such as sodium triacetoxyborohydride, to afford a compound of formula C2. Removal of the Boc-amino protecting group, using conventional reagents and methods, affords a compound of formula B4. Coupling with a compound of formula A7 as described herein provides a compound of Formula (I)-A.

Scheme D illustrates a route for the synthesis compounds of Formula (I)-A, wherein $R^1$, s, Y, and Z are as defined herein.

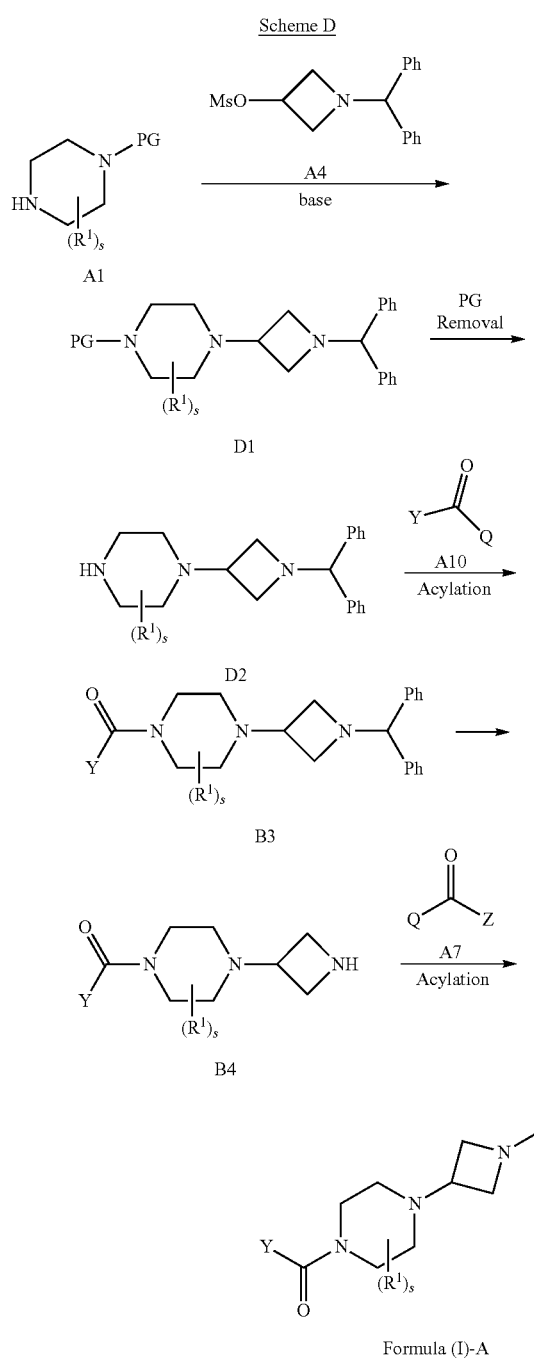

Scheme D

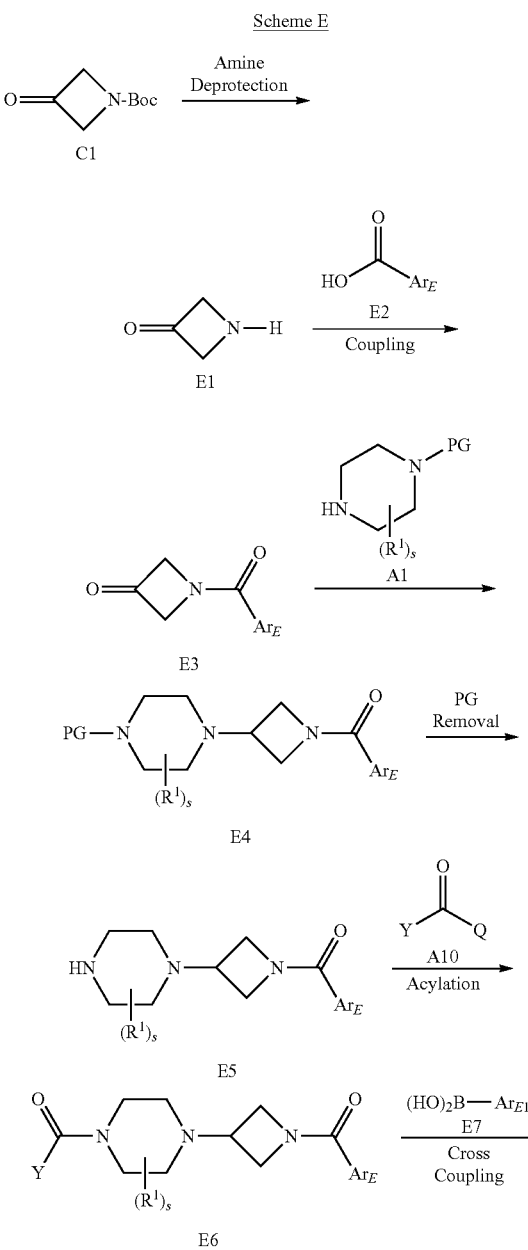

Scheme E non nucleophilic base, such as pyridine, affords a compound of formula B3. Removal of the benzhydryl group as described herein, followed by acylation with a compound of formula A7 affords a compound of Formula (I)-A.

One skilled in the art will recognize that the synthetic sequences of Schemes A, B, C and D may be altered so that the acylation with a compound of formula A7 precedes removal of the benzhydryl group, which is then followed by acylation with a compound of formula A10, thus reversing the order for introduction of groups Y and Z.

Scheme E illustrates a route for the synthesis compounds of Formula (I)-E, wherein $R^1$, s, and Y are as defined herein, and Z is a $C_{6-10}$aryl ring or heteroaryl group, substituted with an optionally substituted $C_{6-10}$aryl or heteroaryl group, as defined herein.

A compound of formula A1, wherein PG is a conventional amino protecting group, such as Boc, Fmoc, Cbz, and the like, is either commercially available or may be prepared by known methods described in the scientific literature. A compound of formula A1 may be treated with a compound of formula A4 to afford a compound of formula D1. Upon conventional removal of protecting group PG, a compound of formula D2 may be coupled with a compound of formula A10 (wherein Q is OH) in the presence of a coupling agent, such as HATU, DCC, EDC, HBTU, PyBrOP, and the like; optionally in the presence of a base such as DIPEA, to afford a compound of formula B3. When the acylation is effected by the addition of the corresponding acid chloride, the addition of a -continued

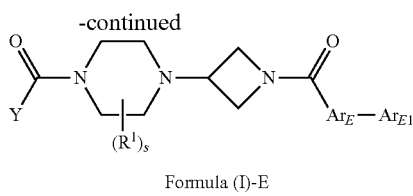

Formula (I)-E

A compound of formula C1 may be deprotected using conventional methods to afford the corresponding free amine of formula E1. Coupling with a carboxylic acid of formula E2, (wherein $Ar_E$ is a $C_{6-10}$aryl or heteroaryl group, and said $Ar_E$ is substituted with one bromo, chloro, or iodo substitutent), in the presence of a coupling agent, such as HATU, DCC, EDC, HBTU, PyBrOP, and the like; optionally in the presence of a base such as DIPEA, affords a compound of formula E3. A ketone of formula E3 may undergo a reductive amination with a compound of formula A1 in the presence of decaborane, sodium triacetoxyborohydride, and the like, to afford a compound of formula E4. Upon conventional removal of the protecting group PG, the free amine of formula E5 may be acylated with a compound of formula A10 as described herein to afford a compound of formula E6. The substituted $Ar_E$ substituent of formula E6 may be treated with an appropriately substituted $Ar_{E1}$-boronic acid or ester (E7), or an appropriately substituted trialkyltin reagent, trialkylsilane, and the like (wherein $Ar_{E1}$ is an optionally substituted $C_{6-10}$aryl or heteroaryl as defined herein), using one of a variety of coupling reactions (e.g., Suzuki, Stille, and Hiyama reactions) that are well known to those versed in the art; in the presence of a suitable catalyst; and in the presence of a base such as cesium carbonate, sodium bicarbonate, potassium fluoride, and the like; to afford a compound of the Formula (I)-E.

Scheme F illustrates a route for the synthesis of compounds of Formula (I)-F, wherein $R^1$, s, and Y are as defined herein, and Z is an optionally substituted $C_{6-10}$aryl($C_{1-6}$)alkyl or $C_{6-10}$aryl($C_{2-6}$)alkenyl group, wherein L is ($C_{1-6}$)alkyl or ($C_{2-6}$)alkenyl, respectively.

Scheme F

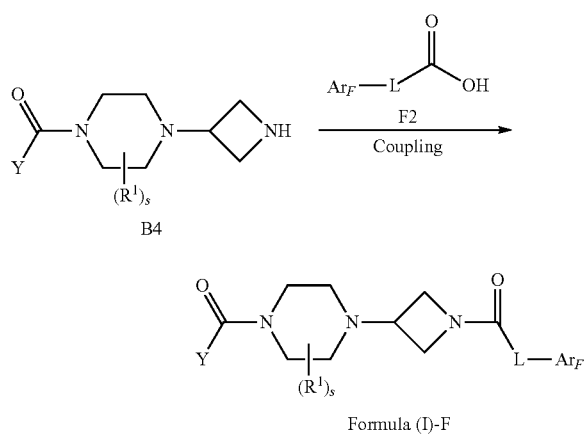

Formula (I)-F

A compound of formula B4 may be coupled with a commercially available compound of formula F2 (wherein $Ar_F$ is an optionally substituted $C_{6-10}$aryl substituent as defined herein) in the presence of a coupling agent, such as HATU, DCC, EDC, HBTU, PyBrOP, and the like; optionally in the presence of a base, such as DIPEA; to afford a compound of Formula (I)-F.

Scheme G illustrates a route for the synthesis of compounds of Formula (I)-G and Formula (I)-G1, wherein $R^1$, s, and Y are as defined herein, and Z is either an optionally substituted $C_{6-10}$aryl ($Ar_G$) substituted with phenyl($C_{2-6}$)alkynyl (Formula (I)-G) or an optionally substituted $C_{6-10}$aryl substituted with phenyl($C_{1-6}$)alkyl.

Scheme G

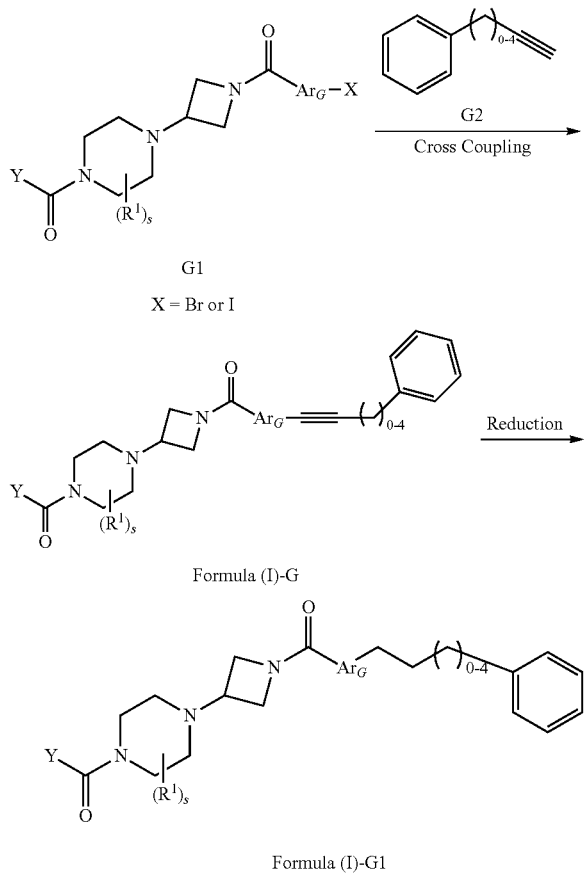

A compound of Formula G1 may be prepared according to the methods described herein, wherein $Ar_G$ is $C_{6-10}$aryl and X is a substituent selected from bromo or iodo. An X-substituted $Ar_G$ ring may be cross-coupled with a compound of formula G2 in the presence of a palladium catalyst, copper iodide, and a base such as triethylamine to afford a compound of Formula (I)-G. The alkynyl functionality of a compound of Formula (I)-G may be reduced to the corresponding alkyl group by transition metal catalyzed hydrogenation, using a transition metal such as palladium on carbon, palladium (II) hydroxide, or platinum, under a hydrogen gas atmosphere, to afford a compound of Formula (I)-G1.

Scheme H illustrates a route for the synthesis of compounds of Formula (I)-H, H1, H2, and H3, wherein $R^1$, s, and Y are as defined herein, and Z is a benzofused heterocyclyl attached via the benzo ring, wherein the heterocyclyl portion contains a nitrogen atom, and wherein the nitrogen atom is optionally substituted. For illustrative purposes only, a 1,2,3,4-tetrahydroisoquinolinyl group has been selected to represent a nitrogen-containing benzofused heterocyclyl of the present invention.

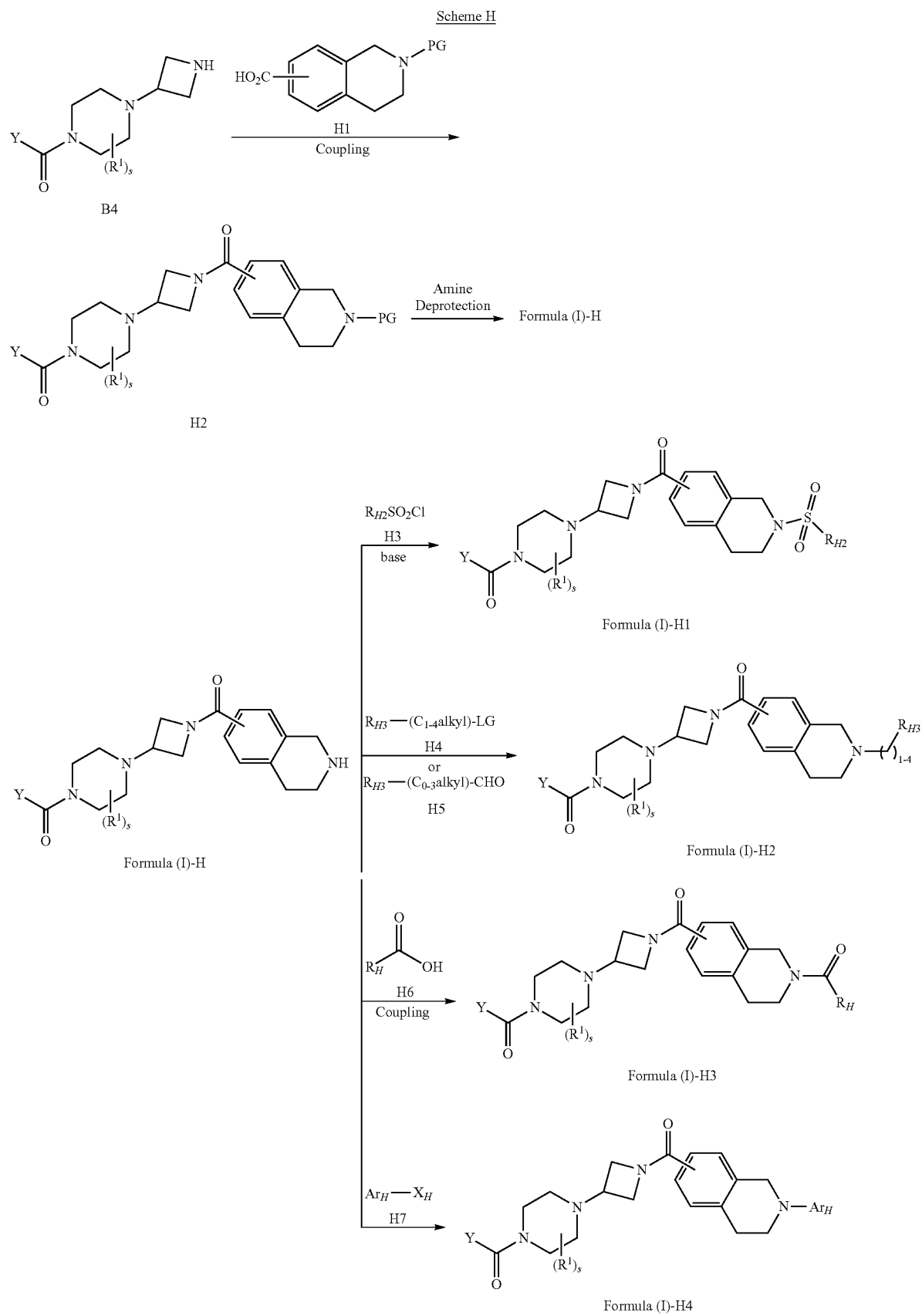

A compound of formula B4 may be coupled with a carboxylic acid-substituted benzofused heterocyclyl of formula Formula H1 (wherein PG is a conventional amino protecting group) to afford a compound of formula H2. Deprotection of the amino functionality of a compound of formula H2 affords the corresponding amine of Formula (I)-H, which may be derivatized using a variety of synthetic methods to form additional compounds of the present invention. For example, a compound of Formula (I)-H may be treated with an appropriately substituted sulfonyl chloride of formula H3 in the presence of an organic base to afford a compound of Formula (I)-H1 (wherein $R_{H2}$ is phenyl or $C_{1-6}$alkyl. Additionally, a compound of the Formula (I)-H2 may be prepared by alkylation of the amino functionality of a compound of Formula (I)-H with an alkylating agent of formula H4 (wherein $R_{H3}$ is phenyl or $C_{1-6}$alkylcarbonyl) in the presence of a base. LG of a compound of formula H4 is a common leaving group, such as a bromide, iodide, tosylate, mesylate, and the like. A compound of Formula (I)-H2 may also be prepared by a reductive amination with a compound of formula H5 in the presence of a reducing agent, such as sodium triacetoxy borohydride. A compound of Formula (I)-H3 may be prepared via a peptide coupling reaction between a compound of Formula (I)-H and an appropriately substituted carboxylic acid of formula H6 (wherein $R_H$ is an optionally substituted cyclohexyl, $C_{1-6}$alkyl, or phenyl as defined herein) in the presence of a suitable coupling agent. Finally, compounds of Formula (I)-H4 of the present invention, wherein $Ar_H$ is pyrimidine or an appropriately substituted phenyl group, may be prepared by the treatment of a compound of Formula (I)-H with a compound of formula H7 (wherein $X_H$ is a group such as chloro, bromo, or iodo and $Ar_H$ is as defined herein) in the presence of a transition metal catalyst, such as palladium acetate, a suitable phosphine ligand, such as BINAP, and a base, such as potassium t-butoxide.

Scheme I illustrates a route for the synthesis of compounds of Formula (I)-I, wherein $R^1$, s, and Y are as defined herein and Z is a $C_{6-10}$aryl substituted with $C_{6-10}$aryl($C_{1-4}$)alkoxy as defined herein. For illustrative purposes only, the Z—$C_{6-10}$aryl ring is depicted as a phenyl group.

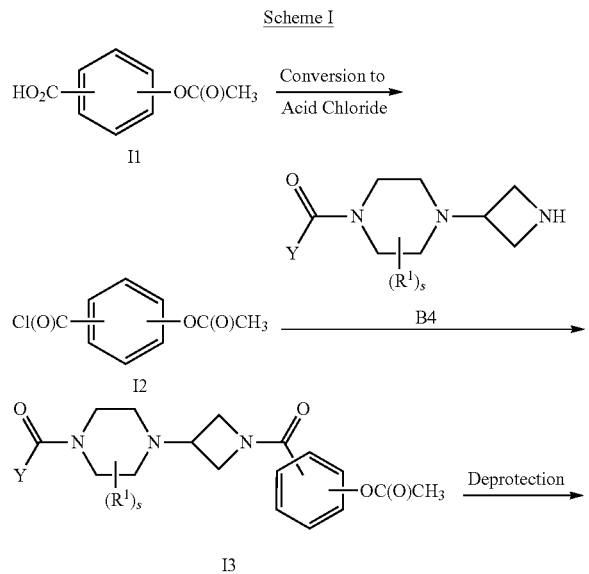

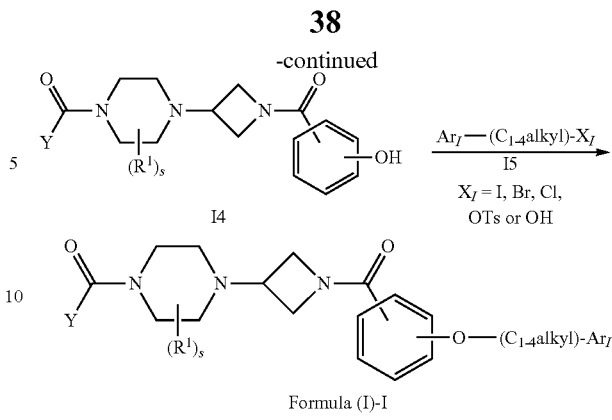

Formula (I)-I

A commercially available compound of formula I1 may be converted to a compound of formula I2 by the action of a chlorinating agent such as oxalyl chloride, thionyl chloride, and the like. A compound of formula B4 may be acylated with a compound of formula I2 to afford a compound of formula I3. Removal of the acetyl functionality of a compound of formula I3 by hydrolysis in the presence of a nucleophilic base like lithium hydroxide, affords the corresponding compound of formula I4. Alkylation with a compound of formula I5 (wherein $Ar_I$ is an optionally substituted $C_{6-10}$aryl group and $X_I$ is I, Br, Cl, or tosylate) affords a compound of Formula (I)-I. Similarly, Mitsunobu chemistry with a compound of formula I6 (wherein $X_I$ is hydroxy) may be used to prepare a compound of Formula (I)-I.

Scheme J illustrates a route for the synthesis of compounds of Formula (I)-J, wherein $R^1$, s, and Y are as defined herein, and Z is a $C_{6-10}$aryl substituted with $C_{6-10}$aryl($C_{1-4}$)alkylthio as defined herein. For illustrative purposes only, the Z $C_{6-10}$aryl ring is depicted as a phenyl group.

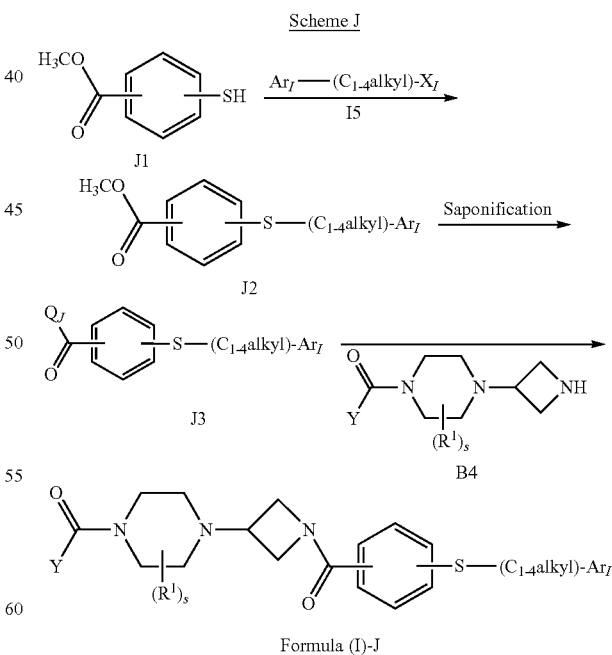

Formula (I)-J

A compound of formula J1 is either commercially available or may be prepared by known methods described in the scientific literature. A compound of formula J1 may be alkylated with a compound of formula I5 (wherein $X_I$ is I, Br, Cl, or tosylate) to afford a compound of formula J2. Saponification of a compound of formula J2 affords a compound of formula J3 (wherein $Q_J$ is hydroxy), which may be coupled with a compound of formula B4; or the carboxylic acid may first be converted to its corresponding acid chloride of formula J3 (wherein $Q_J$ is chloro) followed by the acylation of a compound of formula B4; to afford a compound of Formula (I)-J.

Scheme K illustrates a route for the synthesis of compounds of Formula (I)-K, wherein $R^1$, s, and Y are as defined herein, and Z is an optionally substituted $C_{6-10}$aryl, further substituted with phenyloxy, and wherein phenyloxy is optionally substituted with $C_{1-4}$alkyl, trifluoromethyl, or one to two chloro substituents as defined herein. For illustrative purposes only, the Z $C_{6-10}$aryl ring is depicted as a phenyl group.

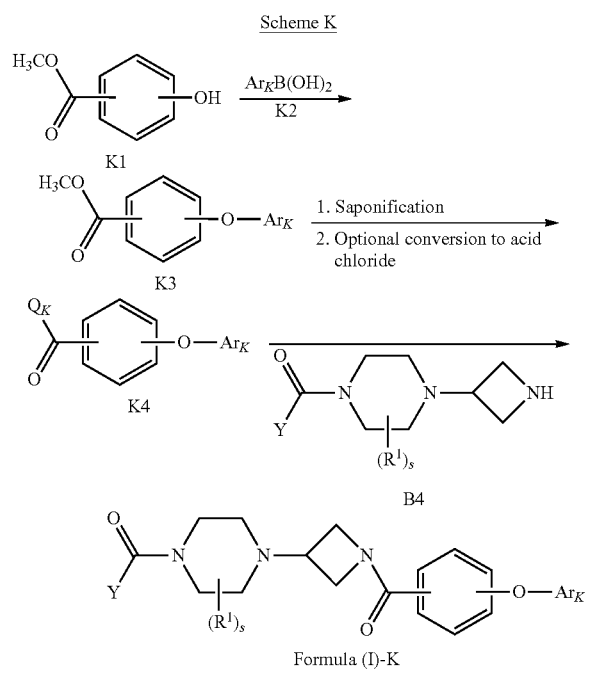

A compound of formula K1 is either commercially available or may be prepared by known methods described in the scientific literature. A compound of formula K1, or an optionally substituted derivative thereof, may be coupled with an aryl boronic acid of formula K2 (wherein $Ar_K$ is phenyl optionally substituted with $C_{1-4}$alkyl, trifluoromethyl, or one to two chloro substituents), in the presence of a copper catalyst, such as copper iodide or copper (II) acetate, appropriate ligands, such as pyridine, 1,10-phenanthroline, ethylene diamine and the like, and an organic base, such as triethylamine, to afford a compound of formula K3. Alternatively, compounds of formula K3 may be prepared by nucleophilic aromatic displacement of an appropriately substituted methyl halobenzoate derivative, wherein the preferred halogen substituent is fluoro, with $Ar_K$-OH, wherein $Ar_K$ is as previously defined, in the presence of a base. Saponification followed by optional treatment with an appropriate chlorinating agent affords a compound of formula K4 wherein $Q_K$ is hydroxy or chloro. Acylation of a compound of formula B4 with a compound of formula K4 affords a compound of Formula (I)-K.

Scheme L illustrates a route for the synthesis of compounds of Formula (I)-L, wherein $R^1$, s, and Y are as defined herein, and Z is an optionally substituted $C_{6-10}$aryl substituted with phenylthio, wherein phenylthio is optionally substituted with $C_{1-4}$alkyl, trifluoromethyl, or one to two chloro substituents as defined herein. For illustrative purposes only, the Z $C_{6-10}$aryl ring is depicted as a phenyl group.

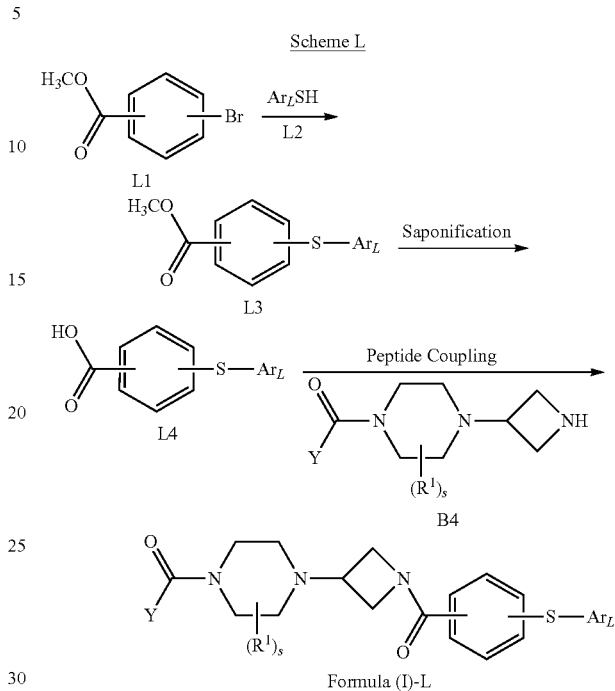

A compound of formula L1 is either commercially available or may be prepared by known methods described in the scientific literature. An aryl bromide of formula L1, or an optionally substituted derivative thereof, may be cross coupled with a compound of formula L2 (wherein $Ar_L$ is phenyl optionally substituted with $C_{1-4}$alkyl, trifluoromethyl, or one to two chloro substituents), in the presence of a palladium catalyst, such as palladium tetrakis(triphenylphosphine), appropriate ligands, such as triphenylphosphine, and a base, such as potassium t-butoxide, to afford a compound of formula L3. Saponification of the methyl ester affords a compound of formula L4. A compound of formula B4 may be coupled with a compound of formula L4 in the presence of an appropriate peptide coupling agent such as DCC, EDC, HBTU, PyBrOP, and the like to afford a compound of Formula (I)-L.

Scheme M illustrates a route for the synthesis of compounds of Formula (I)-M, wherein $R^1$, s, and Y are as defined herein, and Z is a $C_{6-10}$aryl substituted with phenylsulfonyl. For illustrative purposes only, the Z $C_{6-10}$aryl ring is depicted as a phenyl group.

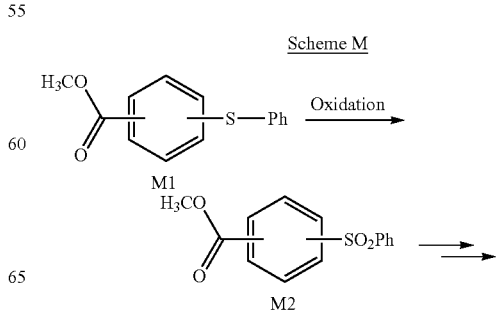

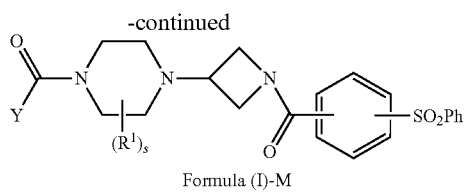

Formula (I)-M

A compound of formula M1 may be prepared according to the methods described in Scheme L. Oxidation of the thioether functionality may be accomplished by the action of an appropriate oxidizing agent, such as mCPBA, hydrogen peroxide, and the like, to afford a compound of formula M2. Upon saponification, and subsequent peptide coupling with a compound of formula B4, a compound of Formula (I)-M may be prepared.

Scheme N illustrates a route for the synthesis of compounds of Formula (I)-N, wherein $R^1$, s, and Y are as defined herein and Z is $C_{6-10}$aryl substituted with a 5 to 8 membered heterocyclyloxy optionally substituted at a nitrogen atom with phenylcarbonyl, $C_{1-4}$alkylcarbonyl, or $C_{1-4}$alkoxycarbonyl. For illustrative purposes only, the Z—$C_{6-10}$aryl ring is depicted as a phenyl group.

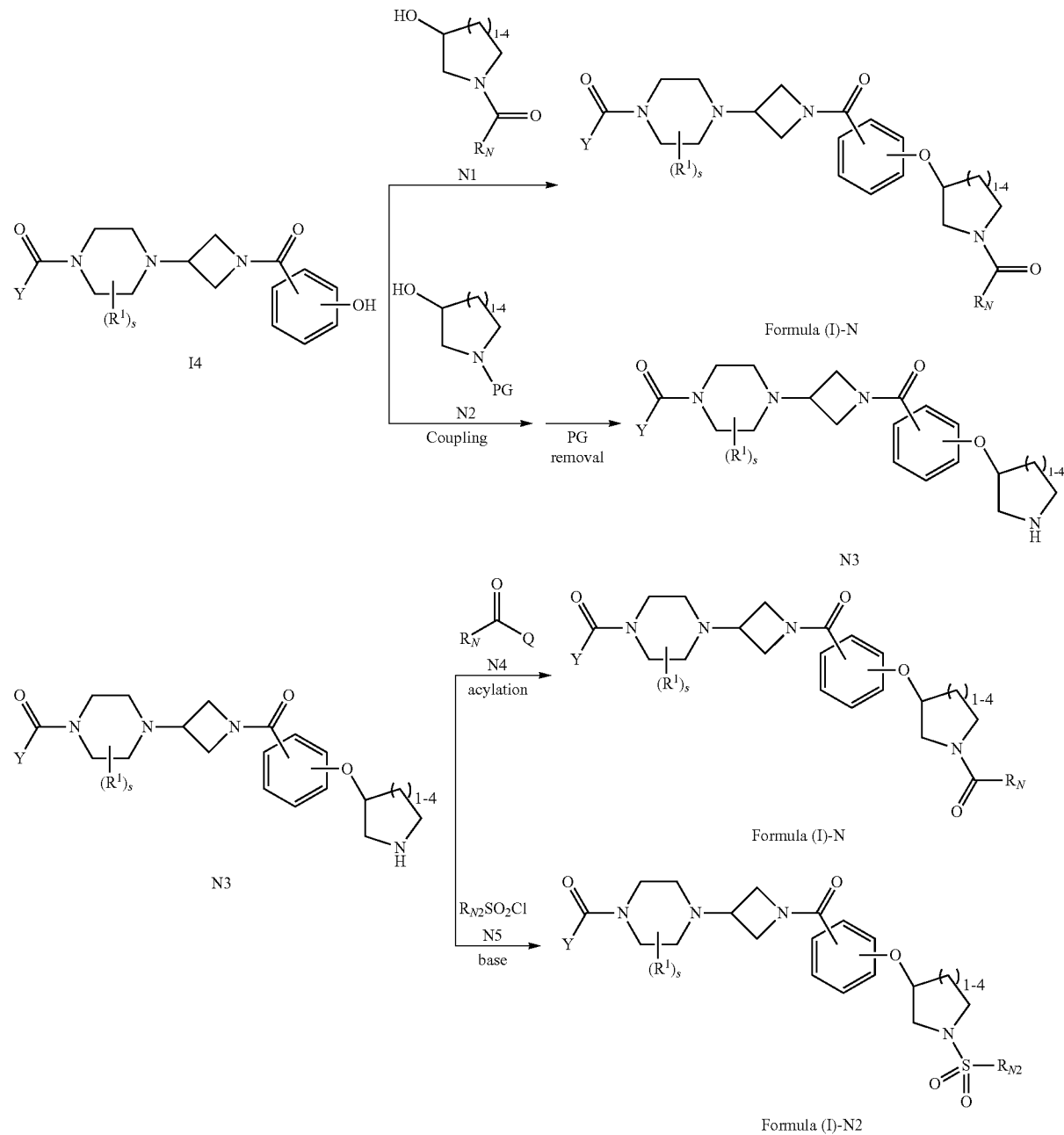

A compound of formula I4 may be coupled with a compound of formula N1 (wherein $R_N$ is phenyl, $C_{1-4}$alkyl, $C_{1-4}$alkoxy, $C_{1-4}$alkylamino, $C_{1-4}$dialkylamino, or N-containing heterocyclyl attached via the nitrogen atom) under Mitsunobu conditions in an aprotic organic solvent, such as THF, to afford a compound of Formula (I)-N. Mitsunobu coupling may also be performed between I4 and a compound of formula N2, where PG is a conventional amino protecting group, such as Boc, Fmoc, Cbz, and the like. Subsequent removal of the protecting group (PG) by conventional methods affords a compound of formula N3, which may be derivatized using a variety of synthetic methods to form additional compounds of the present invention. For example, a compound of formula N3 may be coupled with a carboxylic acid (Q is hydroxy, $R_N$ is phenyl or $C_{1-4}$alkyl), acid chloride (Q is chloride, $R_N$ is phenyl or $C_{1-4}$alkyl), chloroformate (Q is chloride, $R_N$ is $C_{1-4}$alkoxy), or carbamoyl chloride (Q is chloride, $R_N$ is $C_{1-4}$alkylamino, $C_{1-4}$dialkylamino, or N-containing heterocyclyl attached via the nitrogen atom) of formula N4 as described herein to provide a compound of Formula (I)-N. Additionally, a compound of formula N3 may be reacted with a sulfamoyl chloride of formula N5, where $R_{N2}$ is $C_{1-4}$alkylamino, $C_{1-4}$dialkylamino, or N-containing heterocyclyl attached via the nitrogen atom, to afford a compound of Formula (I)-N2.

Scheme O illustrates a route for the synthesis of compounds of Formula (I)-O, wherein $R^1$, s, and Y are as defined herein, and Z is an optionally substituted $C_{6-10}$aryl, further substituted with $R_O$, wherein $R_O$ is (1-$R^2$)-pyrrolidin-3-yloxy, $C_{1-4}$alkyl, or $C_{6-10}$aryl($C_{1-4}$)alkyl. For illustrative purposes only, the Z—$C_{6-10}$aryl ring is depicted as a phenyl group.

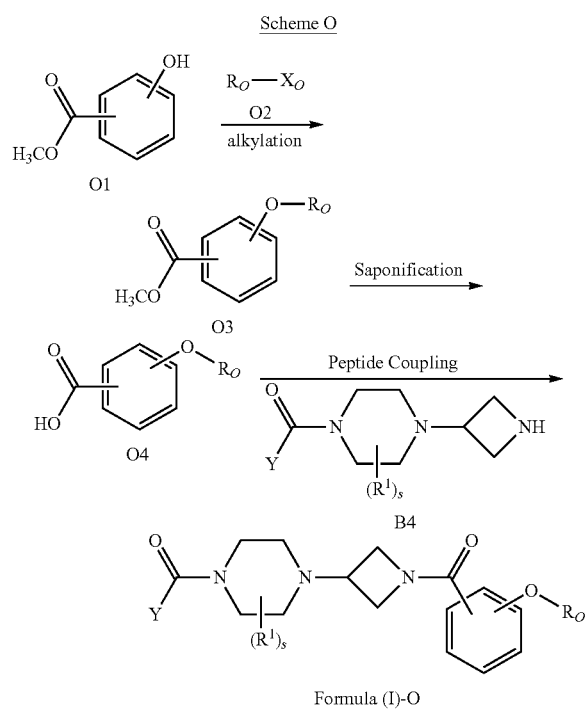

Scheme O

Formula (I)-O

A compound of formula O1 may be coupled with a compound of formula O2 (wherein $X_O$ is hydroxy) under Mitsunobu conditions to afford a compound of formula O3. Alkylation may also be achieved via a nucleophilic displacement reaction with a compound of formula O2 (wherein $X_O$ is I, Br, Cl, or tosylate) in the presence of a base to afford a compound of formula O3. Saponification of the methyl ester of a compound of formula O3 affords the corresponding carboxylic acid of formula O4. A compound of formula O4 may be coupled with a compound of formula B4 as described herein to afford a compound of Formula (I)-O. Furthermore, a compound of formula O3, where $R_O$ is (1-$R^2$)-pyrrolidin-3-yloxy and $R^2$ is a conventional amino protecting group, may be deprotected and additionally derivatized on the pyrrolidine nitrogen as described herein to afford, after conversion to a compound of formula O4 and subsequent coupling with a compound of formula B4, a compound of Formula (I)-O.

Scheme P illustrates a route for the synthesis of compounds of Formula (I)-P, wherein $R^1$, s, and Y are as defined herein, and Z is $C_{6-10}$aryl substituted with phenyl-(Q)-$C_{1-6}$alkyl wherein Q is O, S, or NH; and phenyl of phenyl-(Q)-$C_{1-6}$alkyl is optionally independently substituted with one to two substituents selected from bromo, chloro, fluoro, iodo, $C_{1-4}$alkyl, $C_{1-4}$alkoxy, and trifluoromethyl.

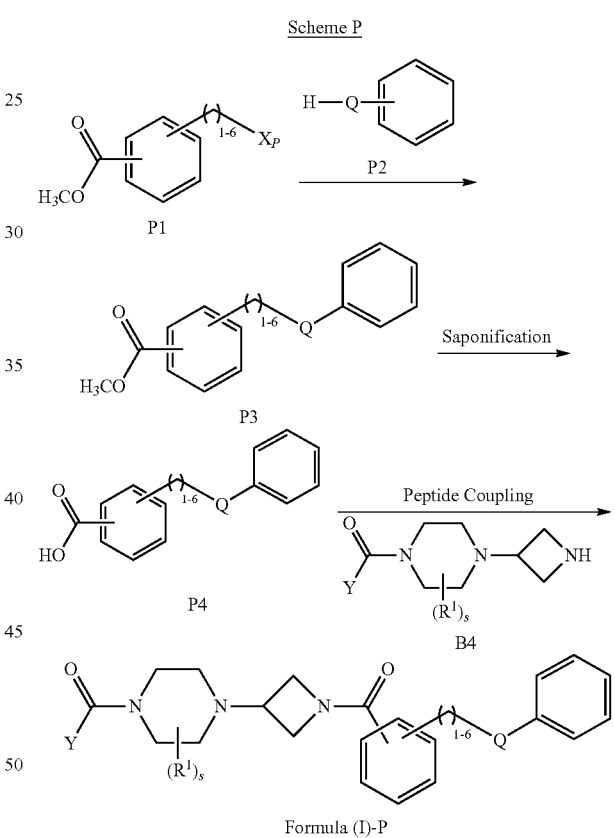

Scheme P

Formula (I)-P

A compound of formula P1 (wherein $X_P$ is hydroxy, chloro, or bromo) is either commercially available or may be prepared by known methods described in the scientific literature. A compound of formula P1 may undergo an alkylation via Mitsunobu reaction or nucleophilic displacement chemistry with a compound of formula P2 to afford a compound of formula P3. Saponification of the methyl ester of a compound of formula P3 affords the corresponding carboxylic acid of formula P4. A compound of formula P4 may be coupled with a compound of formula B4 as described herein to afford a compound of Formula (I)-P.

Scheme Q illustrates the preparation of certain useful intermediates of formula A7 (Q is hydroxy) wherein Z is a heteroaryl substituted with an optionally substituted aryl group (Ar$_Q$). For illustrative purposes only, the heteroaryl ring is represented by an indole.

Scheme Q

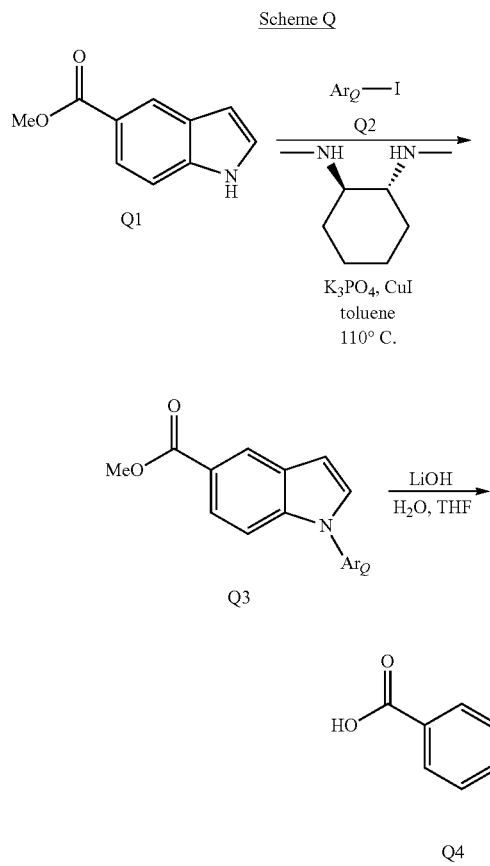

A compound of formula Q1 is either commercially available or may be prepared by known methods described in the scientific literature. The compound Q1 may be treated with an aryl iodide of formula Q2 in the presence of copper iodide, trans-N,N'-dimethylcyclohexane-1,2-diamine, and potassium phosphate to afford a compound of formula Q3. Subsequent saponification affords useful carboxylic acid intermediates of formula Q4.

Scheme R illustrates the preparation of certain useful intermediates of formula A7 (Q is hydroxy) wherein Z is a benzimidazolyl or benzoxazolyl, and Z is substituted with an optionally substituted aryl or heteroaryl group (Ar$_R$) or with Ar$_R$(C$_{1-4}$)alkyl.

Scheme R

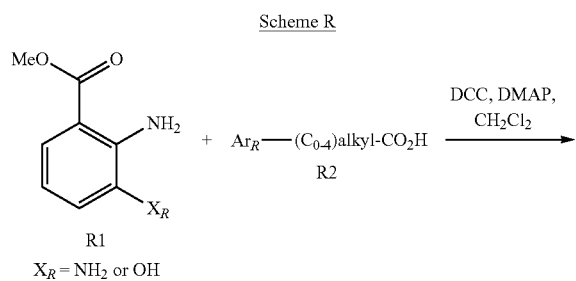

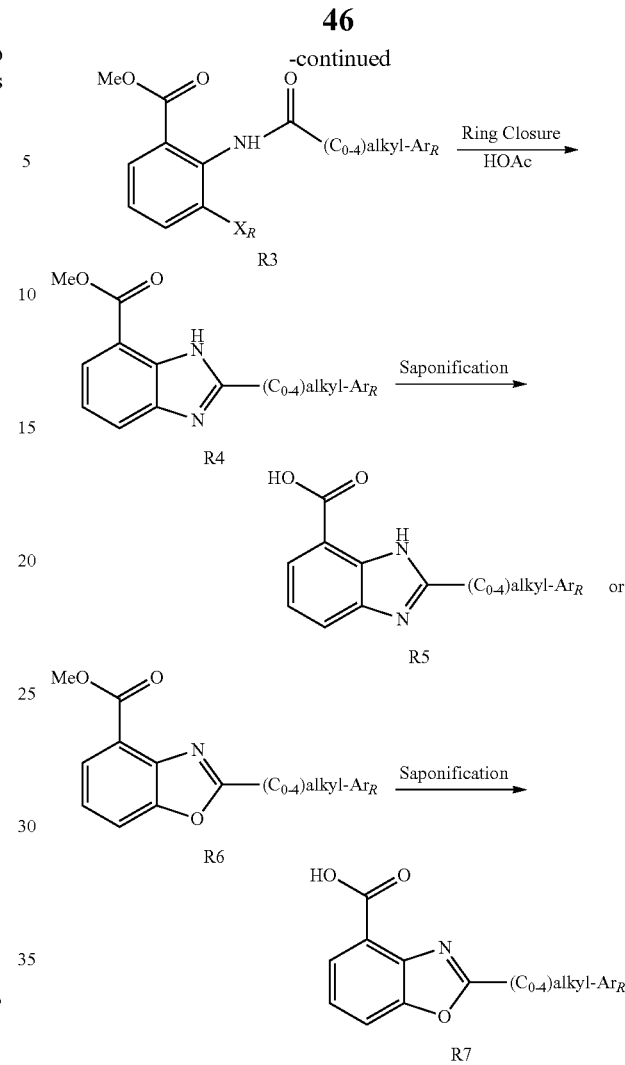

A compound of formula R1 is either commercially available or may be prepared by known methods described in the scientific literature. The compound R1 may be treated with an aryl or heteroaryl substituted carboxylic acid of formula R2 in the presence of a coupling agent such as DCC, and a hindered base such as DMAP, in an aprotic organic solvent to afford a compound of formula R3. Acid catalyzed ring closure of a compound of formula R3 affords the substituted benzimidazole or benzoxazole of formula R4 or R6, respectively. Subsequent saponification affords useful carboxylic acid intermediates of formula R5 or R7.

Scheme S illustrates the preparation of certain useful intermediates of formula A7 (Q is hydroxy) wherein Z is an optionally substituted benzothienyl group, and R$_S$ represents appropriate substituents as defined in Formula (I).

Scheme S

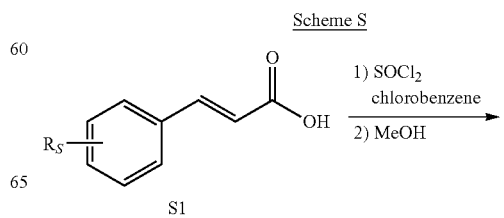

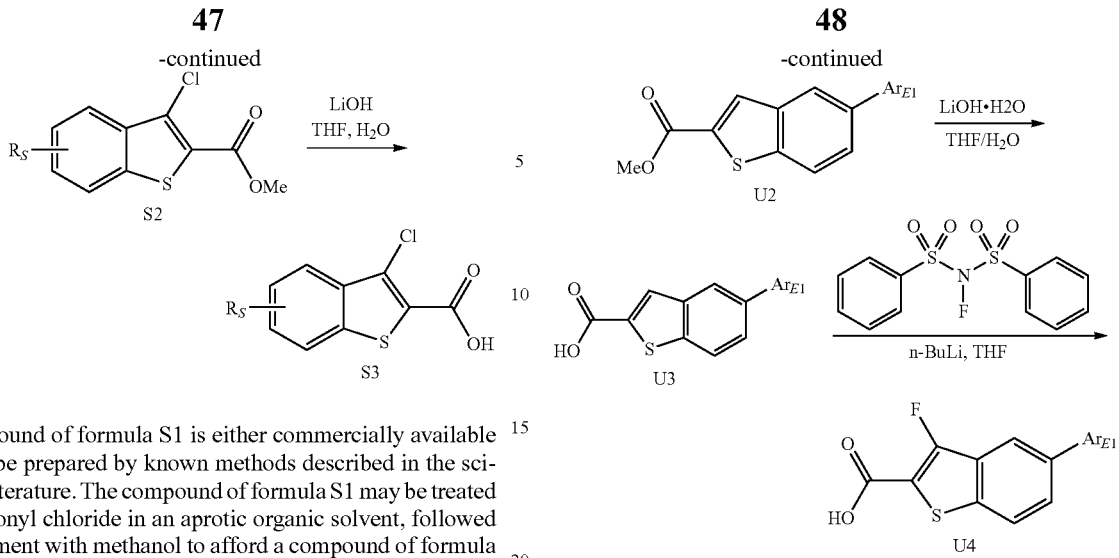

A compound of formula S1 is either commercially available or may be prepared by known methods described in the scientific literature. The compound of formula S1 may be treated with thionyl chloride in an aprotic organic solvent, followed by treatment with methanol to afford a compound of formula S2. Subsequent saponification affords useful carboxylic acid intermediates of formula S3. One skilled in the art will recognize that asymmetrically substituted compounds of formula S1 could lead to mixtures of positional isomers upon cyclization with thionyl chloride. The isomers may then be separated and isolated using conventional chromatography known to those skilled in the art.

Scheme T illustrates the preparation of certain useful intermediates of formula A7 (Q is hydroxy) wherein Z is a $C_{6-10}$aryl ($Ar_T$) substituted by an optionally substituted $C_{6-10}$arylmethyl group.

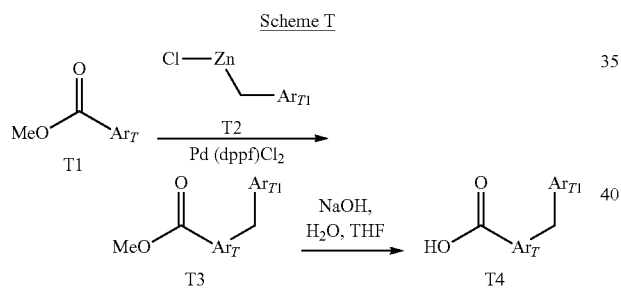

A compound of formula T1 is either commercially available or may be prepared by known methods described in the scientific literature. The compound of formula T1 may be treated with an appropriately substituted organometallic reagent, such as an $Ar_{T1}$-methylzinc chloride of formula T2, in the presence of a palladium catalyst to afford a compound of formula T3. Subsequent saponification affords useful carboxylic acid intermediates of formula T4.

Scheme U illustrates the preparation of certain useful intermediates of formula A7 (Q is hydroxy) wherein Z is a benzothienyl group substituted with a fluoro substituent and an optionally substituted $C_{6-10}$aryl or heteroaryl group ($Ar_{E1}$).

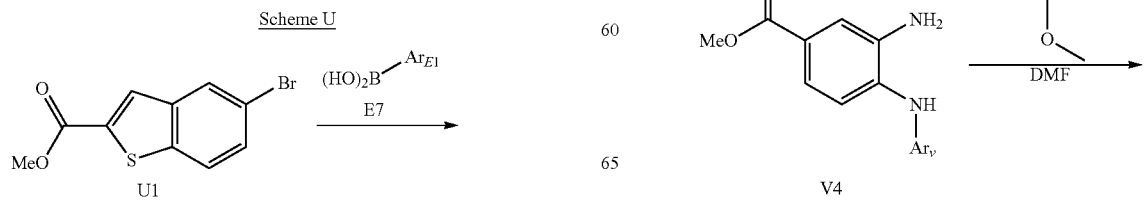

A compound of formula U1 is either commercially available or may be prepared by known methods described in the scientific literature. The compound of formula U1 may be cross-coupled with a boronic acid or ester (E7) in the presence of a palladium catalyst; and in the presence of a suitable base such as potassium carbonate to afford a compound of formula U2. Saponification affords the corresponding carboxylic acid U3, which may be treated with N-fluorobenzenesulfonimide in the presence of an organometallic base such as n-butyllithium, to afford the fluorinated compound of formula U4.

Scheme V illustrates the preparation of certain useful intermediates of formulae V6, V8, and V10 (Q is hydroxy) wherein Z is a benzimidazolyl group substituted with an $Ar_V$ group (wherein $Ar_V$ is an optionally substituted aryl or heteroaryl substituent as defined in Formula (I)) and optionally substituted in the 2-position with methyl or oxo.

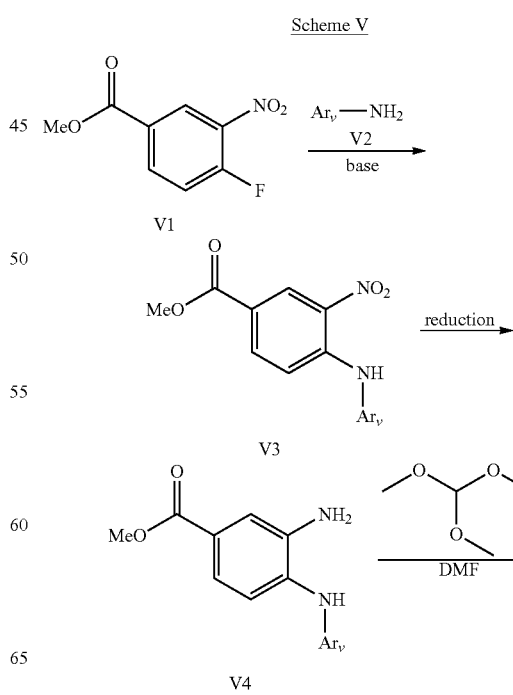

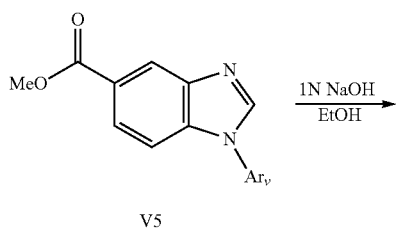

V5

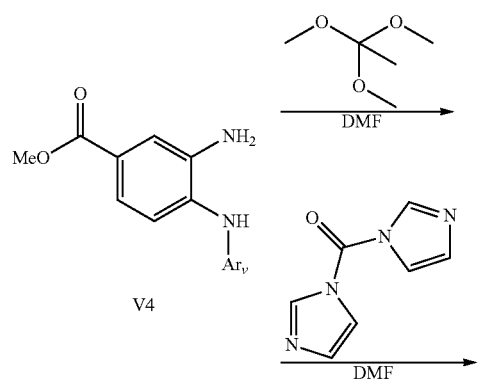

V4

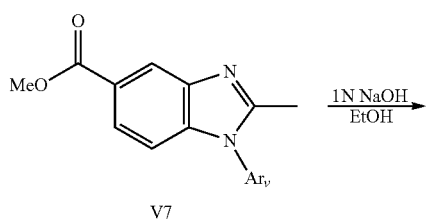

V7

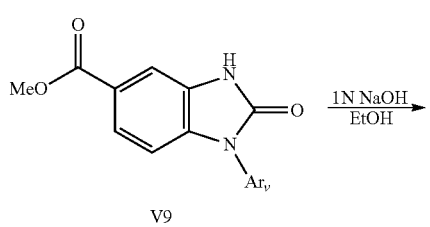

V9

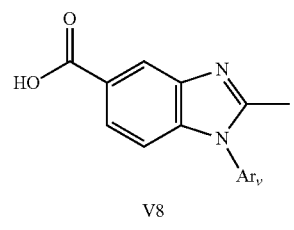

V8

V10

A compound of formula V1 is either commercially available or may be prepared by known methods described in the scientific literature. The compound of formula V1 may be treated with a compound of formula V2 to afford a compound of formula V3. The amino group may be reduced by the action of tin chloride in an alcoholic solvent, or by palladium catalyzed hydrogenation to afford the diamine of formula V4. Treatment with trimethyl orthoformate affords a benzimidazole of formula V5, which may be saponified to afford a compound of formula V6.

A compound of formula V4 may be treated with trimethyl orthoacetate followed by saponification to afford the corresponding 2-methyl substituted benzimidazole, V8. Similarly, a compound of formula V4 may be treated with 1,1'-carbonyldiimidazole in DMF, followed by saponification to afford the corresponding 2-oxo substituted benzimidazole, V10.

Example 1

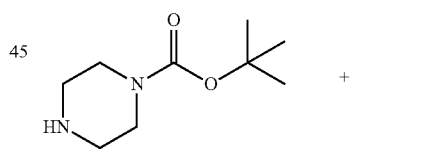

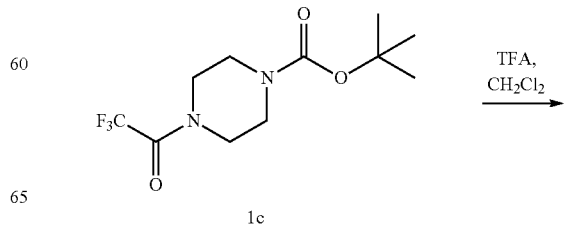

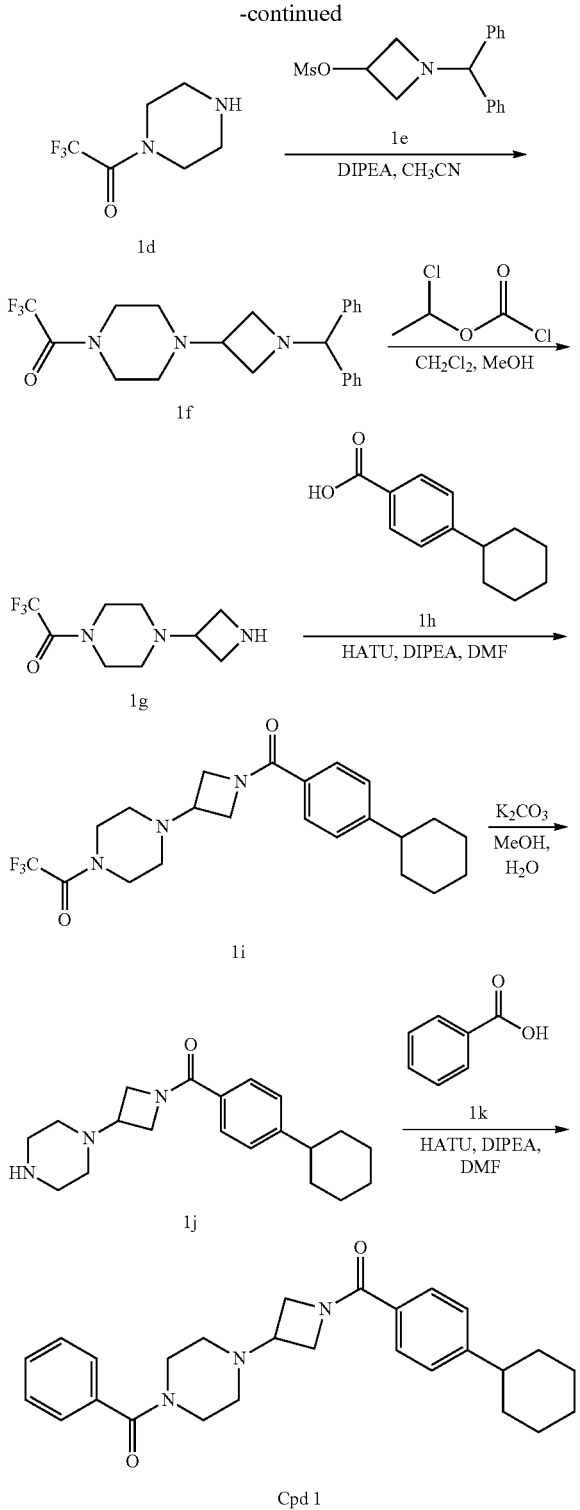

the next reaction without further purification. MS m/z (MH+-Boc) 183.1, (MH+-C$_4$H$_9$) 227.1; $^1$H NMR (300 MHz, CDCl$_3$): δ 3.45-3.7 (m, 8H), 1.5 (s, 9H).

B. 2,2,2-Trifluoro-1-piperazin-1-yl-ethanone, 1d. To a solution of compound 1c (15.15 g, 53.69 mmol) in CH$_2$Cl$_2$ (60 mL) was added trifluoroacetic acid (18 mL) at room temperature. The mixture was stirred at room temperature for 18 h. The solvent was removed by evaporation. Ether (100 mL) was added to the residue. The white solid was collected by filtration, washed with ether, and dried under vacuum. The crude compound 1d was used in the next reaction without further purification. MS m/z (M+H+) 183.1.

C. 1-[4-(1-Benzhydryl-azetidin-3-yl)-piperazin-1-yl]-2,2,2-trifluoro-ethanone, 1f. To a solution of compound 1d (6 g, 32.94 mmol) and compound 1e (12.5 g, 39.38 mmol) in CH$_3$CN (60 mL) was added DIPEA (12 mL, 68.89 mmol) at room temperature. The mixture was refluxed for 2 h. The solvent was removed by evaporation and the residue was partitioned between CH$_2$Cl$_2$ and aq NaHCO$_3$. The organic layer was washed with aq NaHCO$_3$ (2×) and then extracted with 1N HCl (2×). The aqueous layer was cooled and then the pH adjusted with 1N NaOH until basic (pH=10). The mixture was extracted with CH$_2$Cl$_2$ (2×). The organic layer was dried over MgSO$_4$ and concentrated. Compound 1f was purified by reverse phase chromatography. MS m/z (M+H+) 404.2.

D. 1-(4-Azetidin-3-yl-piperazin-1-yl)-2,2,2-trifluoro-ethanone, 1g. To a solution of compound 1f (2.11 g, 5.23 mmol) in CH$_2$Cl$_2$ (60 mL) was added 1-chloroethyl chloroformate (2.0 mL, 18.35 mmol) at 0° C. under N$_2$. The mixture was stirred at 0° C. for 90 min and then MeOH (4 mL) was added. The mixture was refluxed for 1 h. Upon cooling, Et$_2$O (50 mL) was added to the mixture. The resulting solid was collected by filtration and dried. The crude compound 1g was used in the next reaction without further purification. MS m/z (M+H+) 238.1.

E. 1-{4-[1-(4-Cyclohexyl-benzoyl)-azetidin-3-yl]-piperazin-1-yl}-2,2,2-trifluoro-ethanone, 1i. To a solution of compound 1g (2.5 g, 10.54 mmol) and HATU (4 g, 10.52 mmol) in DMF (25 mL) was added DIPEA (5 mL, 28.70 mmol). The mixture was stirred at room temperature for 30 min, and then compound 1h (2 g, 9.79 mmol) was added to the mixture. The reaction was stirred at room temperature for 18 h. Water (40 mL) was added to the reaction. The mixture was extracted with EtOAc (2×20 mL). The organic layer was dried over MgSO$_4$, filtered, and concentrated. The crude compound 1i was purified by reverse phase chromatography. MS m/z (M+H+) 424.2.

F. (4-Cyclohexyl-phenyl)-(3-piperazin-1-yl-azetidin-1-yl)-methanone, 1j. To a solution of compound 1i (0.95 g, 2.24 mmol) in CH$_3$OH (16 mL) and H$_2$O (4 mL) was added K$_2$CO$_3$ (0.8 g, 5.79 mmol). The mixture was stirred at room temperature for 1 h. After filtration, the solvent was removed by evaporation. The crude compound 1j was used in the next reaction without further purification. MS m/z (M+H+) 328.2.

G. 1-{1-[(4-Cyclohexylphenyl)carbonyl]azetidin-3-yl}-4-(phenylcarbonyl)-piperazine, Cpd 1. To a solution of compound 1j (0.08 g, 0.24 mmol) and HATU (0.093 g, 0.24 mmol) in DMF (3 mL) was added DIPEA (0.1 mL). The mixture was stirred at room temperature for 30 min, and then compound 1k (0.03 g, 0.25 mmol) was added to the mixture. The reaction mixture was stirred at room temperature for 18 h. Water (6 mL) was added to the mixture. The mixture was extracted with EtOAc (2×6 mL). The organic layer was dried over MgSO$_4$, filtered, and concentrated. The crude compound 1 was purified by reverse phase chromatography. $^1$H NMR (300 MHz, CD$_3$OD): δ 7.58 (d, 2H), 7.44-7.53 (m, 5H), 7.34

A. 4-(2,2,2-Trifluoro-acetyl)-piperazine-1-carboxylic acid tert-butyl ester, 1c. To a solution of piperazine-1-carboxylic acid tert-butyl ester (1a, 10 g, 53.69 mmol) and pyridine (8.7 mL, 107.57 mmol) in CH$_2$Cl$_2$ (100 mL) was added dropwise compound 1b (10.5 mL, 75.54 mmol) at 0° C. The mixture was stirred at 0° C. for 2 h. 2N HCl (60 mL) was added to the mixture. The organic layer was dried over MgSO$_4$, filtered, and then concentrated. The crude compound 1c was used in (d, 2H), 4.6 (m, 1H), 4.42 (m, 2H), 4.27 (m, 1H), 3.85 (m, 5H), 3.05 (m, 4H), 2.57 (m, 1H), 1.85 (m, 5H), 1.45 (m, 5H). MS m/z (M+H$^+$) 432.3.

Following the procedure described above for Example 1 and substituting the appropriate reagents, starting materials, and purification methods known to those skilled in the art, the following compounds of the present invention were prepared:

| Cpd | Cpd Name and Characterization Data |
|---|---|
| 2 | 1-{1-[(4-Cyclohexylphenyl)carbonyl]azetidin-3-yl}-4-(furan-2-ylcarbonyl)piperazine<br>$^1$H NMR (300 MHz, CD$_3$OD): δ 7.71 (d, 1H), 7.59 (d, 2H), 7.34 (d, 2H), 7.13 (d, 1H), 6.62 (dd, 1H), 4.62 (m, 1H), 4.52 (m, 1H), 4.42 (m, 1H), 4.31 (m, 1H), 4.05 (m, 4H), 3.98 (m, 1H), 3.18 (m, 4H), 2.58 (m, 1H), 1.84 (m, 5H), 1.24-1.52 (m, 5H)<br>MS m/z (M + H$^+$) 422.2 |
| 3 | 1-{1-[(4-Cyclohexylphenyl)carbonyl]azetidin-3-yl}-4-[(1-methyl-1H-imidazol-2-yl)carbonyl]piperazine<br>MS m/z (M + H$^+$) 436.2 |
| 4 | 1-{1-[(4-Cyclohexylphenyl)carbonyl]azetidin-3-yl}-4-(pyridin-2-ylcarbonyl)piperazine<br>MS m/z (M + H$^+$) 433.2 |
| 5 | 1-[1-(Biphenyl-4-ylcarbonyl)azetidin-3-yl]-4-(phenylcarbonyl)piperazine<br>$^1$H NMR (300 MHz, CD$_3$OD): δ 7.65 (m, 4H), 7.56 (d, 2H), 7.25-7.46 (m, 8H), 4.58 (m, 1H), 4.49 (m, 1H), 4.35 (m, 1H), 4.26 (m, 1H), 3.92 (m, 1H), 3.78 (m, 4H), 3.09 (m, 4H)<br>MS m/z (M + H$^+$) 426.1 |
| 6 | 1-[1-(Biphenyl-4-ylcarbonyl)azetidin-3-yl]-4-(furan-2-ylcarbonyl)piperazine<br>$^1$H NMR (300 MHz, CD$_3$OD): δ 7.66 (m, 4H), 7.62 (d, 1H), 7.56 (d, 2H), 7.38 (t, 2H), 7.30 (m, 1H), 7.03 (d, 1H), 6.51 (dd, 1H), 4.56 (m, 1H), 4.44 (m, 1H), 4.33 (m, 1H), 4.22 (m, 1H), 3.95 (m, 4H), 3.81 (m, 1H), 3.01 (m, 4H)<br>MS m/z (M + H$^+$) 416.2 |
| 7 | 1-[1-(Biphenyl-4-ylcarbonyl)azetidin-3-yl]-4-(1,3-thiazol-4-ylcarbonyl)piperazine<br>$^1$H NMR (300 MHz, CD$_3$OD): δ 8.97 (s, 1H), 8.14 (s, 1H), 7.66 (m, 4H), 7.56 (d, 2H), 7.37 (t, 2H), 7.30 (m, 1H), 4.60 (m, 1H), 4.49 (m, 1H), 4.37 (m, 1H), 4.27 (m, 1H), 4.08 (m, 4H), 3.95 (m, 1H), 3.14 (m, 4H)<br>MS m/z (M + H$^+$) 433.2 |
| 8 | 1-[1-(Biphenyl-4-ylcarbonyl)azetidin-3-yl]-4-(1,3-thiazol-5-ylcarbonyl)piperazine<br>$^1$H NMR (300 MHz, CD$_3$OD): δ 9.08 (s, 1H), 8.11 (s, 1H), 7.66 (m, 4H), 7.56 (d, 2H), 7.38 (t, 2H), 7.30 (m, 1H), 4.54 (m, 1H), 4.39 (m, 1H), 4.31 (m, 1H), 4.17 (m, 1H), 3.84 (m, 4H), 3.73 (m, 1H), 2.92 (m, 4H)<br>MS m/z (M + H$^+$) 433.2 |
| 9 | 1-[1-(Biphenyl-4-ylcarbonyl)azetidin-3-yl]-4-(1,3-thiazol-2-ylcarbonyl)piperazine<br>$^1$H NMR (300 MHz, CD$_3$OD): δ 7.88 (d, 1H), 7.78 (d, 1H), 7.66 (m, 4H), 7.57 (d, 2H), 7.38 (t, 2H), 7.30 (m, 1H), 4.62 (m, 3H), 4.48 (m, 1H), 4.37 (m, 1H), 4.26 (m, 1H), 3.91 (m, 3H), 3.13 (m, 4H)<br>MS m/z (M + H$^+$) 433.2 |
| 10 | 1-[1-(Biphenyl-4-ylcarbonyl)azetidin-3-yl]-4-[(2-methyl-1,3-thiazol-4-yl)carbonyl]piperazine<br>MS m/z (M + H$^+$) 447.1 |
| 11 | 1-[1-(Biphenyl-4-ylcarbonyl)azetidin-3-yl]-4-[(1-methyl-1H-pyrrol-2-yl)carbonyl]piperazine<br>MS m/z (M + H$^+$) 429.3 |
| 12 | 1-[1-(Biphenyl-4-ylcarbonyl)azetidin-3-yl]-4-[(5-bromofuran-2-yl)carbonyl]piperazine<br>$^1$H NMR (300 MHz, CD$_3$OD): δ 7.76 (m, 4H), 7.66 (d, 2H), 7.47 (t, 2H), 7.39 (m, 1H), 7.11 (d, 1H), 6.64 (d, 1H), 4.66 (m, 1H), 4.57 (m, 1H), 4.44 (m, 1H), 4.34 (m, 1H), 3.91-4.10 (m, 5H), 3.17 (m, 4H)<br>MS m/z (M + H$^+$) 494.1/496.0 |
| 13 | 1-[1-(Biphenyl-4-ylcarbonyl)azetidin-3-yl]-4-(thiophen-2-ylcarbonyl)piperazine<br>$^1$H NMR (300 MHz, CD$_3$OD): δ 7.75 (m, 4H), 7.61-7.72 (m, 3H), 7.34-7.52 (m, 4H), 7.14 (t, 1H), 4.65 (m, 1H), 4.52 (m, 1H), 4.42 (m, 1H), 4.29 (m, 1H), 3.96 (m, 4H), 3.90 (m, 1H), 3.07 (m, 4H)<br>MS m/z (M + H$^+$) 432.1 (calculated for C$_{25}$H$_{25}$N$_3$O$_2$S, 431.56) |

| Cpd | Cpd Name and Characterization Data |
|---|---|
| 14 | 1-[1-(Biphenyl-4-ylcarbonyl)azetidin-3-yl]-4-[(5-methylthiophen-2-yl)carbonyl]piperazine<br>MS m/z (M + H$^+$) 446.1 |
| 15 | 1-[1-(Biphenyl-4-ylcarbonyl)azetidin-3-yl]-4-[(5-bromothiophen-2-yl)carbonyl]piperazine<br>MS m/z (M + H$^+$) 510.1/512.1 |
| 16 | 1-[1-(Biphenyl-4-ylcarbonyl)azetidin-3-yl]-4-[(5-chlorothiophen-2-yl)carbonyl]piperazine<br>MS m/z (M + H$^+$) 466.1/467.1 |
| 17 | 1-[1-(Biphenyl-4-ylcarbonyl)azetidin-3-yl]-4-[(3-bromothiophen-2-yl)carbonyl]piperazine<br>MS m/z (M + H$^+$) 510.0/512.1 |
| 18 | 1-[1-(Biphenyl-4-ylcarbonyl)azetidin-3-yl]-4-[(4-bromothiophen-2-yl)carbonyl]piperazine<br>MS m/z (M + H$^+$) 510.0/512.1 |
| 19 | 1-[1-(Biphenyl-4-ylcarbonyl)azetidin-3-yl]-4-(thieno[3,2-b]thiophen-2-ylcarbonyl)piperazine<br>MS m/z (M + H$^+$) 488.1 |
| 20 | 1-(1-Benzothiophen-2-ylcarbonyl)-4-[1-(biphenyl-4-ylcarbonyl)azetidin-3-yl]piperazine<br>MS m/z (M + H$^+$) 482.1 |
| 21 | 1-[1-(Biphenyl-4-ylcarbonyl)azetidin-3-yl]-4-[(3-methoxythiophen-2-yl)carbonyl]piperazine<br>MS m/z (M + H$^+$) 462.1 |
| 22 | 1-{1-[(4-Bromo-2-methylphenyl)carbonyl]azetidin-3-yl}-4-(phenylcarbonyl)piperazine<br>MS m/z (M + H$^+$) 442.22/444.19 |
| 23 | 1-{1-[(4-Bromo-3-methoxyphenyl)carbonyl]azetidin-3-yl}-4-(1,3-thiazol-4-ylcarbonyl)piperazine<br>MS m/z (M + H$^+$) 465.0/467.1 |
| 24 | 1-{1-[(4-Bromo-3-methoxyphenyl)carbonyl]azetidin-3-yl}-4-(phenylcarbonyl)piperazine<br>MS m/z (M + H$^+$) 458.1/460.0 |
| 25 | 1-{1-[(4-Bromo-2-chlorophenyl)carbonyl]azetidin-3-yl}-4-(1,3-thiazol-4-ylcarbonyl)piperazine<br>MS m/z (M + H$^+$) 469.04/471.04 |
| 26 | 1-{1-[(4-Bromo-2-chlorophenyl)carbonyl]azetidin-3-yl}-4-(phenylcarbonyl)piperazine<br>MS m/z (M + H$^+$) 462.11/464.11 |
| 581 | 1-(Phenylcarbonyl)-4-[1-({4-[5-(trifluoromethyl)thiophen-2-yl]phenyl}carbonyl)azetidin-3-yl]piperazine<br>MS m/z (M + H$^+$) 500 |
| 1382 | 2-Phenyl-5-({3-[4-(1,3-thiazol-4-ylcarbonyl)piperazin-1-yl]azetidin-1-yl}carbonyl)-1,3-benzoxazole<br>MS m/z (M + H$^+$) 474 |
| 1071 | 1-(1,3-Thiazol-4-ylcarbonyl)-4-[1-({4-[5-(trifluoromethyl)thiophen-2-yl]phenyl}carbonyl)azetidin-3-yl]piperazine<br>MS m/z (M + H$^+$) 507 |
| 1361 | 1-(1,3-Thiazol-2-ylcarbonyl)-4-[1-({4-[5-(trifluoromethyl)thiophen-2-yl]phenyl}carbonyl)azetidin-3-yl]piperazine<br>MS m/z (M + H$^+$) 507 |

Example 1a

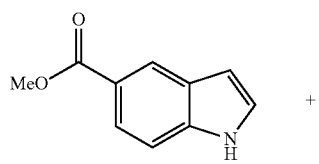

1j

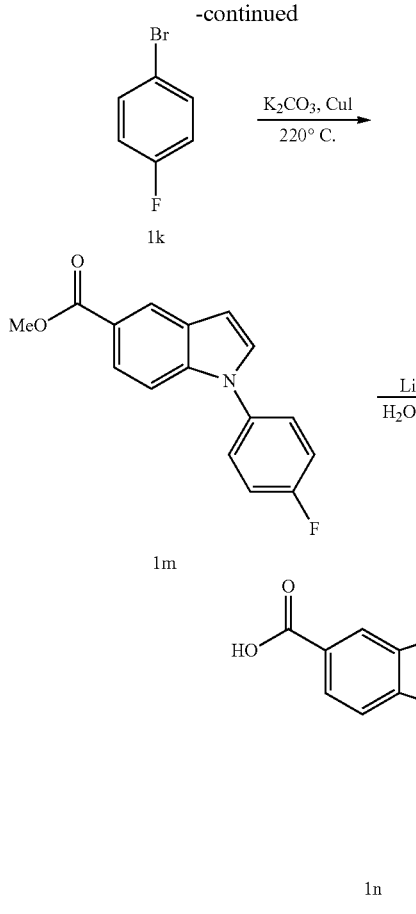

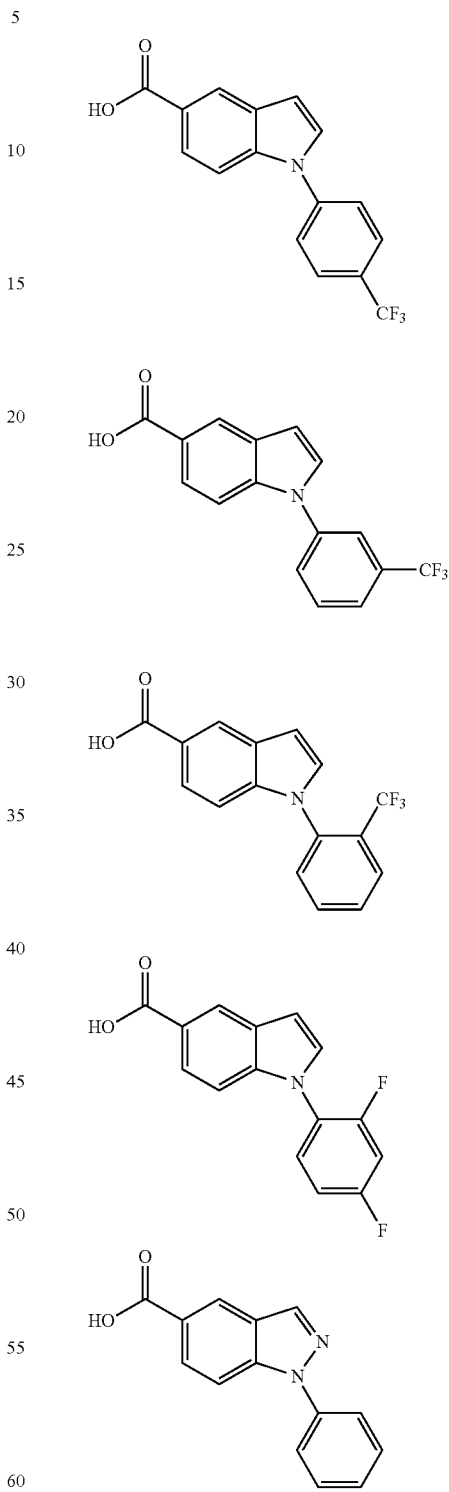

H. Methyl 1-(4-fluorophenyl)-indole-5-carboxylate, 1m. A mixture of methyl indole-5-carboxylate 1j (0.5 g, 2.85 mmol), 1-bromo-4-fluoro-benzene 1k (2 mL, 18.21 mmol), CuI (0.544 g, 2.85 mmol), and $K_2CO_3$ (0.591 g, 4.28 mmol) was heated under microwave at 220° C. for 2.5 hours. The reaction mixture was diluted with $CH_2Cl_2$ and filtered. The solution was concentrated and the residue was purified by flash column chromatography (silica gel, 15% EtOAc/heptane) to give 1m (0.58 g).

I. 1-(4-fluorophenyl)-indole-5-carboxylic acid, 1n. A mixture of methyl 1-(4-fluorophenyl)-indole-5-carboxylate 1m (0.58 g, 2.15 mmol) and LiOH $H_2O$ (0.36 g, 8.6 mmol) in THF (15 mL) and $H_2O$ (10 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 1n (0.5 g).

J. 1-(4-Fluorophenyl)-5-({3-[4-(1,3-thiazol-2-ylcarbonyl)piperazin-1-yl]azetidin-1-yl}carbonyl)-1H-indole, Cpd 487. The title compound, Cpd 487, was prepared according to Example 1 using intermediate 1n from Example 1a and intermediate 1g in Example 1 as starting materials. $^1$H NMR (400 MHz, $CD_3OD$): δ 8.00 (d, J=1.2 Hz, 1H), 7.88 (d, J=3 Hz, 1H), 7.55 (m, 2H), 7.46 (m, 3H), 7.34 (d, J=3 Hz, 1H), 7.27-7.21 (m, 2H), 6.74 (d, J=3 Hz, 1H), 4.52 (bs, 1H), 4.43-4.20 (m, 4H), 4.14 (m, 1H), 3.95-3.80 (m, 2H), 3.25 (m, 1H), 2.60-2.40 (m, 4H). MS m/z (M+H$^+$) 490.

Following the procedure described above for Example 1a, steps H and I, and substituting the appropriate reagents, starting materials, and purification methods known to those skilled in the art, the following intermediate compounds were prepared:

Following the procedure described above for Example 1a, step J, and substituting the appropriate reagents, starting materials, and purification methods known to those skilled in the art, the following compounds of the invention were prepared:

| Cpd | Cpd Name and Data |
|---|---|
| 567 | 1-(4-Fluorophenyl)-5-({3-[4-(phenylcarbonyl)piperazin-1-yl]azetidin-1-yl}carbonyl)-1H-indole<br>$^1$H NMR (400 MHz, CD$_3$OD): d 7.99 (s, 1H), 7.55-7.21 (m, 12H), 6.73 (s, 1H), 4.37 (bs, 1H), 4.25 (m, 2H), 4.10 (bs, 1H), 3.90 (bs, 1H), 3.75 (bs, 1H), 3.48 (bs, 2H), 3.24 (m, 1H), 2.50-2.20 (m, 4H).<br>MS m/z (M + H$^+$) 483 |
| 587 | 1-Phenyl-5-({3-[4-(phenylcarbonyl)piperazin-1-yl]azetidin-1-yl}carbonyl)-1H-indazole<br>MS m/z (M + H$^+$) 466 |
| 579 | 1-(2,4-Difluorophenyl)-5-({3-[4-(phenylcarbonyl)piperazin-1-yl]azetidin-1-yl}carbonyl)-1H-indole<br>MS m/z (M + H$^+$) 501 |
| 1356 | 5-({3-[4-(1,3-Thiazol-2-ylcarbonyl)piperazin-1-yl]azetidin-1-yl}carbonyl)-1-[3-(trifluoromethyl)phenyl]-1H-indole.<br>MS m/z (M + H$^+$) 540 |
| 1408 | 5-({3-[4-(1,3-Thiazol-4-ylcarbonyl)piperazin-1-yl]azetidin-1-yl}carbonyl)-1-[3-(trifluoromethyl)phenyl]-1H-indole<br>MS m/z (M + H$^+$) 540 |
| 1357 | 5-({3-[4-(1,3-Thiazol-2-ylcarbonyl)piperazin-1-yl]azetidin-1-yl}carbonyl)-1-[4-(trifluoromethyl)phenyl]-1H-indole<br>$^1$H NMR (400 MHz, CD$_3$OD): d 8.00 (s, 1H), 7.88 (d, J = 3 Hz, 1H), 7.81 (d, J = 8.6 Hz, 2H), 7.64 (d, J = 8.6 Hz, 2H), 7.59 (s, 2H), 7.54 (d, J = 3 Hz, 1H), 7.41 (d, J = 3.5 Hz, 1H), 6.79 (d, J = 3.5 Hz, 1H), 4.53 (bs, 1H), 4.43 (m, 2H), 4.28 (m, 2H), 4.14 (bs, 1H), 3.86 (m, 2H), 3.26 (m, 1H), 2.50 (m, 4H).<br>MS m/z (M + H$^+$) 540 |
| 1358 | 1-(4-Fluorophenyl)-5-({3-[4-(1,3-thiazol-4-ylcarbonyl)piperazin-1-yl]azetidin-1-yl}carbonyl)-1H-indole<br>MS m/z (M + H$^+$) 490 |
| 1359 | 5-({3-[4-(1,3-Thiazol-4-ylcarbonyl)piperazin-1-yl]azetidin-1-yl}carbonyl)-1-[4-(trifluoromethyl)phenyl]-1H-indole<br>MS m/z (M + H$^+$) 540 |
| 1163 | 1-Phenyl-5-({3-[4-(1,3-thiazol-4-ylcarbonyl)piperazin-1-yl]azetidin-1-yl}carbonyl)-1H-indazole<br>MS m/z (M + H$^+$) 473 |
| 1360 | 1-Phenyl-5-({3-[4-(1,3-thiazol-2-ylcarbonyl)piperazin-1-yl]azetidin-1-yl}carbonyl)-1H-indazole<br>$^1$H NMR (400 MHz, CD$_3$OD): d 8.27 (s, 1H), 8.11 (s, 1H), 7.88 (d, J = 3 Hz, 1H), 7.77 (m, 2H), 7.72 (d, J = 8 Hz, 2H), 7.56 (m, 3H), 7.41 (t, J = 8 Hz, 1H), 4.53 (bs, 1H), 4.44-4.28 (m, 4H), 4.15 (m, 1H), 3.86 (m, 2H), 3.28 (m, 1H), 2.50 (m, 4H). MS m/z 490 (M + H$^+$)<br>MS m/z (M + H$^+$) 473 |
| 1364 | 1-(2,4-Difluorophenyl)-5-({3-[4-(1,3-thiazol-2-ylcarbonyl)piperazin-1-yl]azetidin-1-yl}carbonyl)-1H-indole<br>MS m/z (M + H$^+$) 508 |
| 1139 | 1-(2,4-Difluorophenyl)-5-({3-[4-(1,3-thiazol-4-ylcarbonyl)piperazin-1-yl]azetidin-1-yl}carbonyl)-1H-indole<br>$^1$H NMR (CDCl$_3$, 400 MHz): d = 8.79 (d, J = 2.0 Hz, 1 H), 7.93-8.09 (m, 2 H), 7.39-7.64 (m, 2 H), 7.18-7.34 (m, 2 H), 6.98-7.16 (m, 2 H), 6.76 (d, J = 3.1 Hz, 1 H), 4.20-4.51 (m, 3 H), 4.13 (d, J = 3.9 Hz, 1 H), 3.92 (br. s, 3 H), 3.67-3.84 (m, 1 H), 3.18-3.32 (m, 1 H), 2.49 (br. s., 4 H).<br>MS m/z (M + H$^+$) 508 |
| 1061 | 1-(2,4-Difluorophenyl)-5-({3-[4-(1H-pyrrol-2-ylcarbonyl)piperazin-1-yl]azetidin-1-yl}carbonyl)-1H-indole<br>MS m/z (M + H$^+$) 490 |

Following the procedure described above for Example 1a, steps H and I, and substituting the appropriate reagents, starting materials, and purification methods known to those skilled in the art, the following intermediate compounds were prepared:

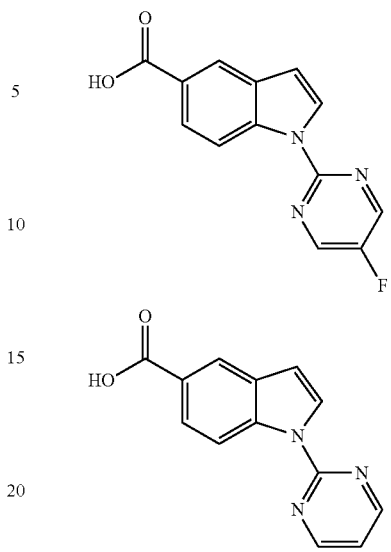

Following the procedure described above for Example 1a, step J, with the exception of using dioxane as a solvent in step A, and substituting the appropriate reagents, starting materials, and purification methods known to those skilled in the art, the following compounds of the present invention were prepared:

| Cpd | Cpd Name and Data |
|---|---|
| 595 | 5-({3-[4-(Phenylcarbonyl)piperazin-1-yl]azetidin-1-yl}carbonyl)-1-pyrimidin-2-yl-1H-indole<br>MS m/z (M + H$^+$) 467 |
| 598 | 1-(5-Fluoropyrimidin-2-yl)-5-({3-[4-(phenylcarbonyl)piperazin-1-yl]azetidin-1-yl}carbonyl)-1H-indole<br>MS m/z (M + H$^+$) 485 |
| 1174 | 1-Pyrimidin-2-yl-5-({3-[4-(1,3-thiazol-2-ylcarbonyl)piperazin-1-yl]azetidin-1-yl}carbonyl)-1H-indole<br>$^1$H NMR (CDCl$_3$, 400 MHz): d = 8.83 (d, J = 8.6 Hz, 1 H), 8.73 (d, J = 4.7 Hz, 2 H), 8.33 (d, J = 3.9 Hz, 1 H), 7.80-8.02 (m, 2 H), 7.64 (dd, J = 8.8, 1.8 Hz, 1 H), 7.54 (d, J = 3.1 Hz, 1 H), 7.10 (t, J = 4.9 Hz, 1 H), 6.75 (d, J = 3.5 Hz, 1 H), 4.03-4.72 (m, 6 H), 3.86 (m, 2 H), 3.08-3.37 (m, 1 H), 2.31-2.68 (m, 3 H).<br>MS m/z (M + H$^+$) 474 |
| 1201 | 1-Pyrimidin-2-yl-5-({3-[4-(1,3-thiazol-4-ylcarbonyl)piperazin-1-yl]azetidin-1-yl}carbonyl)-1H-indole<br>MS m/z (M + H$^+$) 474 |
| 1248 | 1-(5-Fluoropyrimidin-2-yl)-5-({3-[4-(1,3-thiazol-4-ylcarbonyl)piperazin-1-yl]azetidin-1-yl}carbonyl)-1H-indole<br>MS m/z (M + H$^+$) 492 |
| 1147 | 1-(5-Fluoropyrimidin-2-yl)-5-({3-[4-(1,3-thiazol-2-ylcarbonyl)piperazin-1-yl]azetidin-1-yl}carbonyl)-1H-indole<br>MS m/z (M + H$^+$) 492 |

Example 1b

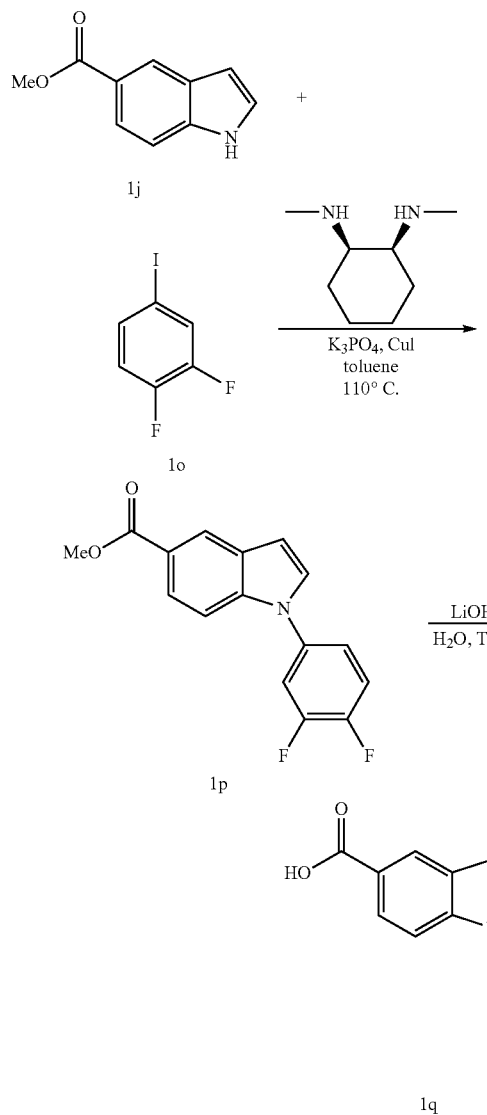

K. Methyl 1-(3,4-difluorophenyl)-indole-5-carboxylate, 1p. A mixture of methyl indole-5-carboxylate 1j (2 g, 11.4 mmol), 1-iodo-3,4-difluoro-benzene 1o (1.5 mL, 12.5 mmol), CuI (0.22 g, 1.14 mmol), trans-N,N'-dimethylcyclohexane-1,2-diamine (0.54 mL, 3.43 mmol), and $K_3PO_4$ (6.06 g, 28.5 mmol) in toluene (12 mL) was heated at 110° C. for 7 hours. The reaction mixture was diluted with $CH_2Cl_2$ and filtered. The solution was concentrated and the residue was purified by flash column chromatography (silica gel, 20% EtOAc/heptane) to give 1p (3.0 g).

L. 1-(3,4-Difluorophenyl)-indole-5-carboxylic acid, 1q. A mixture of methyl 1-(3,4-difluorophenyl)-indole-5-carboxylate 1p (3.0 g, 10.4 mmol) and LiOH (1.0 g, 41.8 mmol) in THF (120 mL) and $H_2O$ (60 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 1q (2.85 g).

M. 1-(3,4-Difluorophenyl)-5-({3-[4-(1,3-thiazol-2-ylcarbonyl)piperazin-1-yl]azetidin-1-yl}carbonyl)-1H-indole, Cpd 1362. The title compound, Cpd 1362, was prepared according to Example 1 using intermediate 1q from Example 1b and intermediate 1g in Example 1 as starting materials. $^1$H NMR (CDCl$_3$, 400 MHz): d=7.99 (d, J=1.6 Hz, 1H), 7.88 (d, J=3.1 Hz, 1H), 7.44-7.64 (m, 3H), 7.18-7.44 (m, 4H), 6.75 (d, 1H), 4.47-4.63 (m, 1H), 4.19-4.47 (m, 4H), 4.07-4.19 (m, 1H), 3.89 (br. s, 2H), 3.18-3.33 (m, 1H), 2.50 (t, J=5.1 Hz, 4H). MS m/z (M+H$^+$) 508.

Following the procedure described above for Example 1b, steps K and L, and substituting the appropriate reagents, starting materials, and purification methods known to those skilled in the art, the following intermediate compounds were prepared:

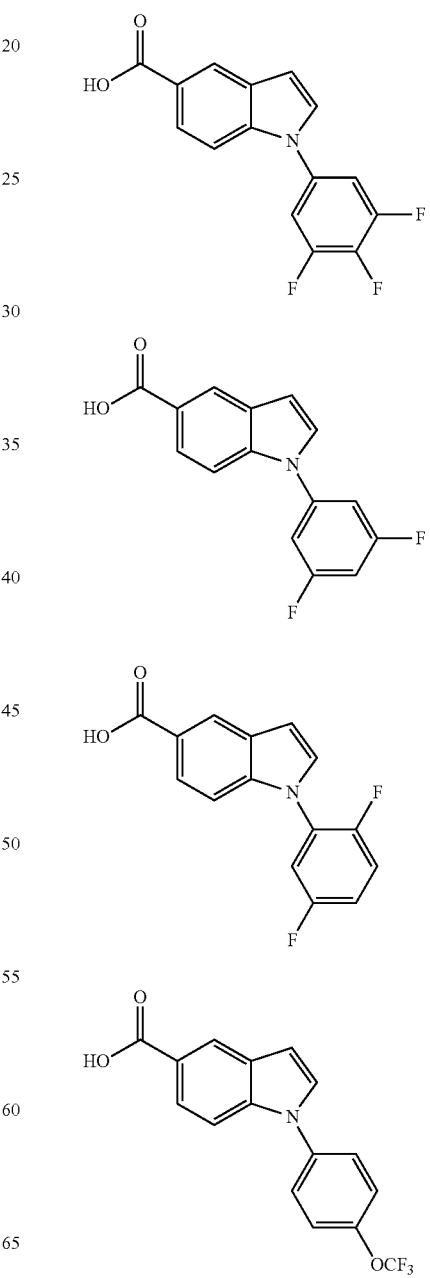

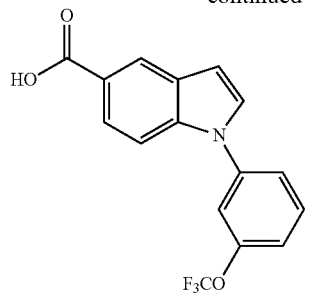
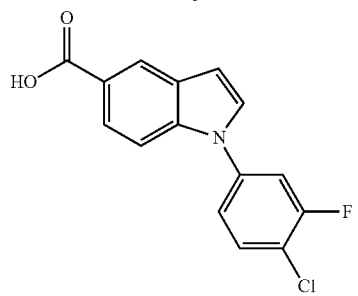
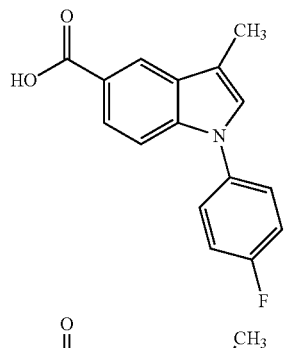
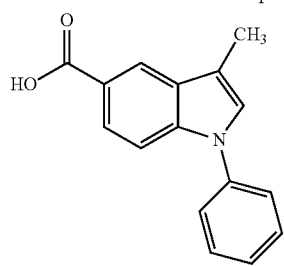
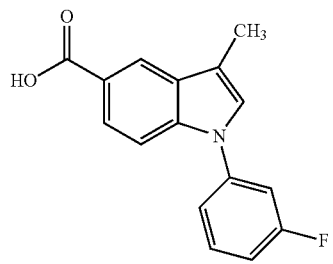
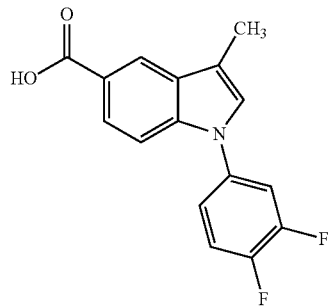

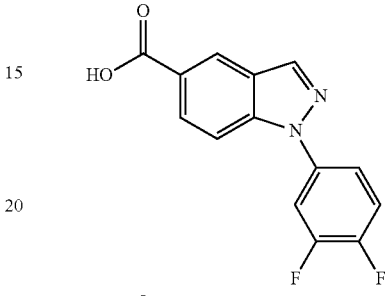
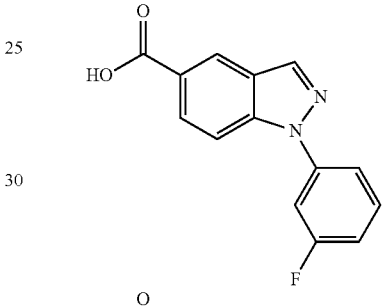
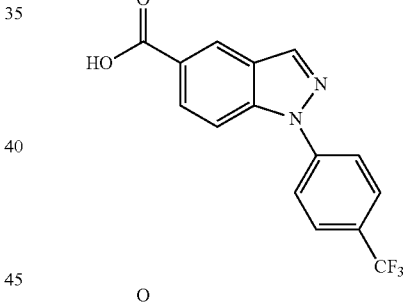
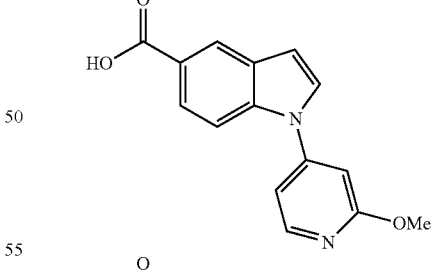
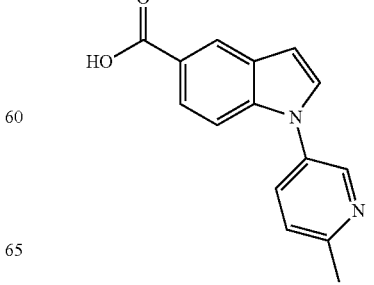

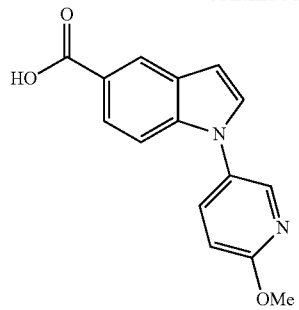
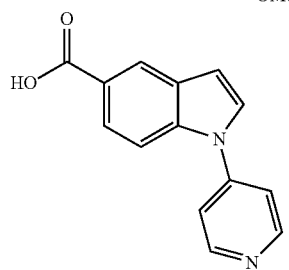
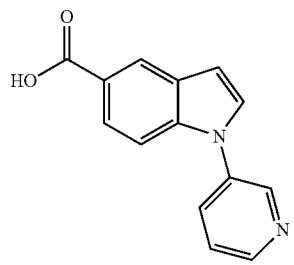
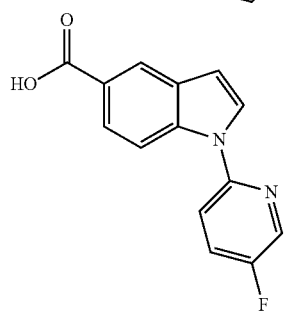
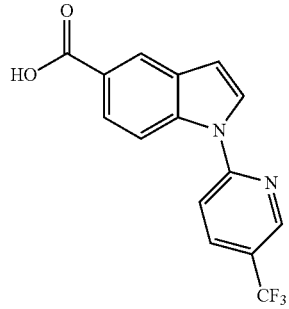
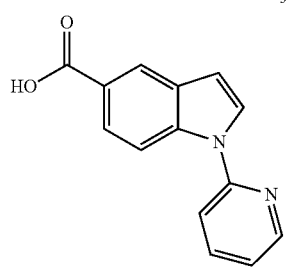
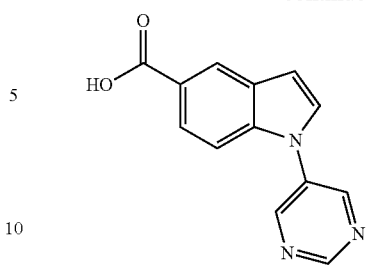
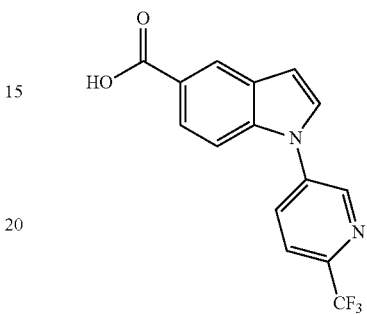
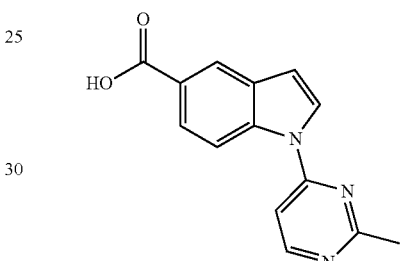
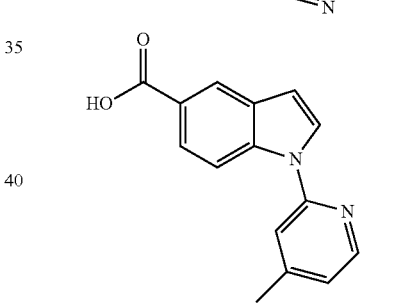
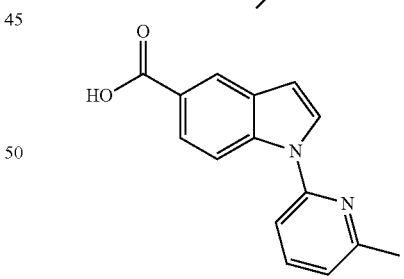
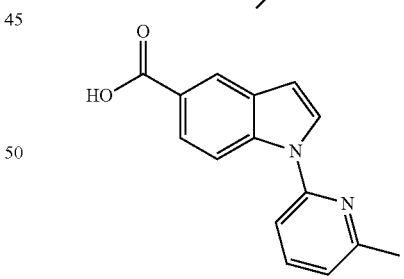

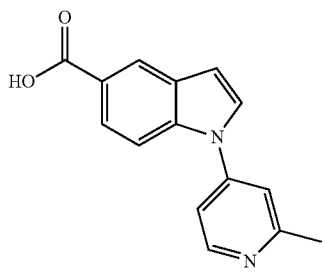
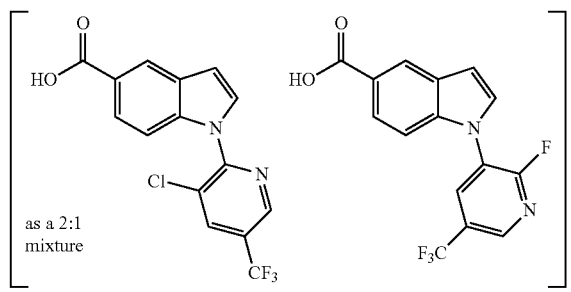

as a 2:1 mixture

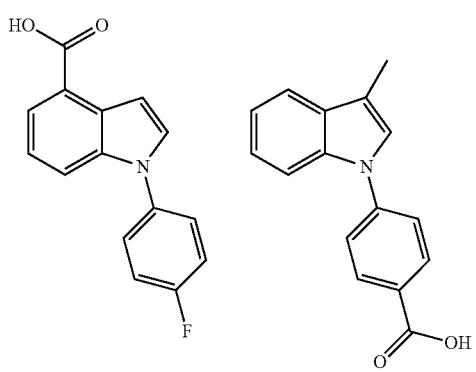

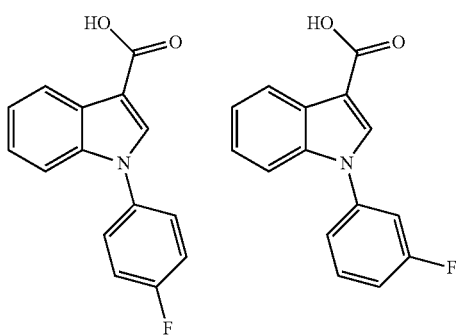

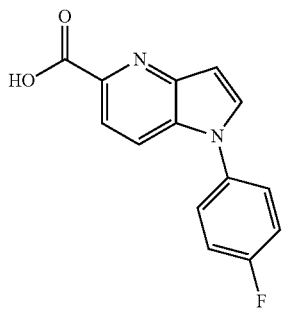

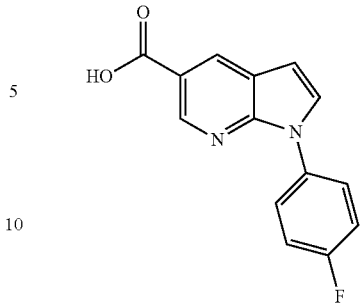

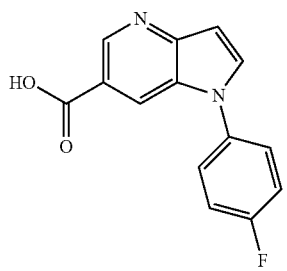

Following the procedure described above for Example 1b, and substituting the appropriate reagents, starting materials, and purification methods known to those skilled in the art, the following compounds of the present invention were prepared:

| Cpd | Cpd Name and Data |
|---|---|
| 1363 | 1-(3,4-Difluorophenyl)-5-({3-[4-(1,3-thiazol-4-ylcarbonyl)piperazin-1-yl]azetidin-1-yl}carbonyl)-1H-indole<br>$^1$H NMR (CDCl$_3$, 400 MHz): d = 8.79 (d, J = 2.0 Hz, 1 H), 8.00 (dd, J = 11.5, 1.8 Hz, 2 H), 7.44-7.65 (m, 2 H), 7.18-7.42 (m, 4 H), 6.75 (d, J = 3.5 Hz, 1 H), 4.20-4.46 (m, 3 H), 4.13 (br. s., 1 H), 3.93 (br. s., 3 H), 3.67-3.85 (m, 1 H), 3.17-3.36 (m, 1 H), 2.49 (br. s., 4 H)<br>MS m/z 508 (M + H$^+$) |
| 1366 | 1-(3,4-Difluorophenyl)-5-({3-[4-(1H-pyrrol-2-ylcarbonyl)piperazin-1-yl]azetidin-1-yl}carbonyl)-1H-indole<br>$^1$H NMR (CDCl$_3$, 400 MHz): d = 9.42-9.61 (m, 1 H), 7.99 (s, 1 H), 7.54-7.64 (m, 1 H), 7.45-7.54 (m, 1 H), 7.15-7.43 (m, 4 H), 6.93 (s, 1 H), 6.75 (d, J = 3.1 Hz, 1 H), 6.52 (br. s., 1 H), 6.18-6.31 (m, 1 H), 4.19-4.42 (m, 3 H), 4.08-4.19 (m, 1 H), 3.90 (br. s., 4 H), 3.24 (s, 1 H), 2.34-2.56 (m, 4 H)<br>MS m/z 490 (M + H$^+$) |
| 603 | 5-({3-[4-(Phenylcarbonyl)piperazin-1-yl]azetidin-1-yl}carbonyl)-1-pyridin-4-yl-1H-indole<br>MS m/z (M + H$^+$) 466.1 |
| 630 | 1-(2-Methylpyridin-4-yl)-5-({3-[4-(phenylcarbonyl)piperazin-1-yl]azetidin-1-yl}carbonyl)-1H-indole<br>MS m/z (M + H$^+$) 480.1 |
| 1192 | 1-Pyridin-3-yl-5-({3-[4-(1,3-thiazol-2-ylcarbonyl)piperazin-1-yl]azetidin-1-yl}carbonyl)-1H-indole<br>MS m/z (M + H$^+$) 473.2 |
| 1247 | 1-Pyridin-3-yl-5-({3-[4-(1H-pyrrol-2-ylcarbonyl)piperazin-1-yl]azetidin-1-yl}carbonyl)-1H-indole<br>MS m/z (M + H$^+$) 456.3 |
| 1127 | 1-Pyridin-4-yl-5-({3-[4-(1,3-thiazol-2-ylcarbonyl)piperazin-1-yl]azetidin-1-yl}carbonyl)-1H-indole<br>MS m/z (M + H$^+$) 473.0 |
| 1072 | 1-(6-Methoxypyridin-3-yl)-5-({3-[4-(1,3-thiazol-2-ylcarbonyl)piperazin-1-yl]azetidin-1-yl}carbonyl)-1H-indole<br>MS m/z (M + H$^+$) 503.2 |

| Cpd | Cpd Name and Data |
|---|---|
| 1176 | 1-(6-Methoxypyridin-3-yl)-5-({3-[4-(1H-pyrrol-2-ylcarbonyl)piperazin-1-yl]azetidin-1-yl}carbonyl)-1H-indole<br>MS m/z (M + H$^+$) 485.4 |
| 1105 | 1-(6-Methylpyridin-3-yl)-5-({3-[4-(1,3-thiazol-2-ylcarbonyl)piperazin-1-yl]azetidin-1-yl}carbonyl)-1H-indole<br>MS m/z (M + H$^+$) 487.3 |
| 1181 | 1-(6-Methylpyridin-3-yl)-5-({3-[4-(1H-pyrrol-2-ylcarbonyl)piperazin-1-yl]azetidin-1-yl}carbonyl)-1H-indole<br>MS m/z (M + H$^+$) 469.3 |
| 1062 | 5-({3-[4-(1H-Pyrrol-2-ylcarbonyl)piperazin-1-yl]azetidin-1-yl}carbonyl)-1-[6-(trifluoromethyl)pyridin-3-yl]-1H-indole<br>MS m/z (M + H$^+$) 523.2 |
| 1312 | 5-({3-[4-(1,3-Thiazol-2-ylcarbonyl)piperazin-1-yl]azetidin-1-yl}carbonyl)-1-[6-(trifluoromethyl)pyridin-3-yl]-1H-indole<br>MS m/z (M + H$^+$) 541.3 |
| 1107 | 1-(2-Methoxypyridin-4-yl)-5-({3-[4-(1,3-thiazol-2-ylcarbonyl)piperazin-1-yl]azetidin-1-yl}carbonyl)-1H-indole<br>MS m/z (M + H$^+$) 503.0 |
| 1263 | 1-Pyrimidin-5-yl-5-({3-[4-(1,3-thiazol-2-ylcarbonyl)piperazin-1-yl]azetidin-1-yl}carbonyl)-1H-indole<br>MS m/z (M + H$^+$) 474.1 |
| 1410 | 1-(2-Methylpyridin-4-yl)-5-({3-[4-(1,3-thiazol-2-ylcarbonyl)piperazin-1-yl]azetidin-1-yl}carbonyl)-1H-indole<br>MS m/z (M + H$^+$) 487.0 |
| 586 | 5-({3-[4-(Phenylcarbonyl)piperazin-1-yl]azetidin-1-yl}carbonyl)-1-[5-(trifluoromethyl)pyridin-2-yl]-1H-indole<br>MS m/z (M + H$^+$) 534.1 |
| 596 | 1-(5-Fluoropyridin-2-yl)-5-({3-[4-(phenylcarbonyl)piperazin-1-yl]azetidin-1-yl}carbonyl)-1H-indole<br>MS m/z (M + H$^+$) 484.0 |
| 1135 | 1-Pyridin-2-yl-5-({3-[4-(1,3-thiazol-2-ylcarbonyl)piperazin-1-yl]azetidin-1-yl}carbonyl)-1H-indole<br>MS m/z (M + H$^+$) 473.2 |
| 1189 | 1-Pyridin-2-yl-5-({3-[4-(1H-pyrrol-2-ylcarbonyl)piperazin-1-yl]azetidin-1-yl}carbonyl)-1H-indole<br>MS m/z (M + H$^+$) 455.2 |
| 1073 | 1-(5-Methylpyridin-2-yl)-5-({3-[4-(1,3-thiazol-2-ylcarbonyl)piperazin-1-yl]azetidin-1-yl}carbonyl)-1H-indole<br>MS m/z (M + H$^+$) 509.0 |
| 1126 | 1-(6-Methylpyridin-2-yl)-5-({3-[4-(1,3-thiazol-2-ylcarbonyl)piperazin-1-yl]azetidin-1-yl}carbonyl)-1H-indole<br>MS m/z (M + H$^+$) 487.3 |
| 1128 | 1-(4-Methylpyridin-2-yl)-5-({3-[4-(1,3-thiazol-2-ylcarbonyl)piperazin-1-yl]azetidin-1-yl}carbonyl)-1H-indole<br>MS m/z (M + H$^+$) 487.2 |
| 1216 | 1-(2-Methylpyrimidin-4-yl)-5-({3-[4-(1,3-thiazol-2-ylcarbonyl)piperazin-1-yl]azetidin-1-yl}carbonyl)-1H-indole<br>MS m/z (M + H$^+$) 488.0 |
| 1314 | 5-({3-[4-(1,3-Thiazol-2-ylcarbonyl)piperazin-1-yl]azetidin-1-yl}carbonyl)-1-[5-(trifluoromethyl)pyridin-2-yl]-1H-indole<br>MS m/z (M + H$^+$) 541.0 |
| 1121 | 1-(5-Fluoropyridin-2-yl)-5-({3-[4-(1,3-thiazol-2-ylcarbonyl)piperazin-1-yl]azetidin-1-yl}carbonyl)-1H-indole<br>MS m/z (M + H$^+$) 491.0 |
| 1197 | 1-(4-Methylpyridin-2-yl)-5-({3-[4-(1,3-thiazol-4-ylcarbonyl)piperazin-1-yl]azetidin-1-yl}carbonyl)-1H-indole<br>MS m/z (M + H$^+$) 487.1 |
| 1337 | 5-({4-[1-(1,3-Thiazol-4-ylcarbonyl)azetidin-3-yl]piperazin-1-yl}carbonyl)-1-[4-(trifluoromethyl)phenyl]-1H-indole<br>$^1$H NMR (400 MHz, CDCl$_3$): δ 9.06 (s, 1H); 8.4 (s, 1H); 7.9-7.68 (m, 8H); 7.4 (ar, 1H); 4.97 (m, 2H); 4.45 (m, 2H); |

| Cpd | Cpd Name and Data |
|---|---|
| | 4.16 (bs, 1H);<br>MS m/z (M + H$^+$) 508.0 |
| 1338 | 5-({4-[1-(1,3-Thiazol-2-ylcarbonyl)azetidin-3-yl]piperazin-1-yl}carbonyl)-1-[4-(trifluoromethyl)phenyl]-1H-indole<br>$^1$H NMR (400 MHz, CDCl$_3$): δ 7.91 (m, 1H); 7.81 (m, 4H); 7.70 (m, 2H); 7.60 (m, 2H); 7.30 (m, 1H); 6.75 (m, 1H); 5.01-4.84 (m, 2H); 4.37 (m, 2H); 4.09 (bm, 1H)<br>MS m/z (M + H$^+$) 540.2 |
| 1339 | 5-({3-[4-(1H-Pyrrol-2-ylcarbonyl)piperazin-1-yl]azetidin-1-yl}carbonyl)-1-[4-(trifluoromethyl)phenyl]-1H-indole<br>MS m/z (M + H$^+$) 522.2 |
| 1097 | 5-({3-[4-(Isothiazol-5-ylcarbonyl)piperazin-1-yl]azetidin-1-yl}carbonyl)-1-[4-(trifluoromethyl)phenyl]-1H-indole<br>$^1$H NMR (400 MHz, CDCl$_3$): δ 8.44 (s, 1H); 7.94 (s, 1H); 7.80 (m, 2H); 7.69 (m, 2H); 7.59 (m, 2H); 7.49 (m, 2H); 6.77 (m, 1H); 4.65-4.15 (bm, 3H); 3.81 (bm, 4H); 3.0 (bm, 4H)<br>MS m/z (M + H$^+$) 540.2 |
| 1230 | 1-(4-Fluorophenyl)-3-methyl-5-({4-[1-(1,3-thiazol-4-ylcarbonyl)azetidin-3-yl]piperazin-1-yl}carbonyl)-1H-indole<br>MS m/z (M + H$^+$) 504.1 |
| 1089 | 1-(4-Fluorophenyl)-3-methyl-5-({4-[1-(1,3-thiazol-2-ylcarbonyl)azetidin-3-yl]piperazin-1-yl}carbonyl)-1H-indole<br>$^1$H NMR (400 MHz, CDCl$_3$): δ 7.92 (d, 1H); 7.78 (d, 1H); 7.69 (m, 1H); 7.42 (m, 3H); 7.21 (m, 6H); 4.94 (m, 1H); 4.40 (dd, 1H); 4.25 (dd, 1H); 4.0 (bm, 1H); 3.85 (bm, 3H); 3.15 (bm, 3H); 2.3 (s, 3H)<br>MS m/z (M + H$^+$) 504.1 |
| 1120 | 5-({4-[1-(1H-Pyrrol-2-ylcarbonyl)azetidin-3-yl]piperazin-1-yl}carbonyl)-1-[4-(trifluoromethyl)phenyl]-1H-indole<br>MS m/z (M + H$^+$) 522.1 |
| 1134 | 1-(3,4-Difluorophenyl)-3-methyl-5-({4-[1-(1,3-thiazol-2-ylcarbonyl)azetidin-3-yl]piperazin-1-yl}carbonyl)-1H-indole<br>$^1$H NMR (400 MHz, CDCl$_3$): δ 8.0 (s, 1H); 7.86 (s, 1H); 7.80 (s, 1H); 7.62-7.42 (m, 3H); 7.36 (m, 3H); 5.05 (m, 1H); 4.5 (m, 1H); 4.35 (m, 1H); 4.08 (bm, 1H); 3.94 (bm, 4H); 3.24 (m, 3H)<br>MS m/z (M + H$^+$) 522.2 |
| 1219 | 1-(3,4-Difluorophenyl)-3-methyl-5-({4-[1-(1H-pyrrol-2-ylcarbonyl)azetidin-3-yl]piperazin-1-yl}carbonyl)-1H-indole<br>MS m/z (M + H$^+$) 465.1 |

Example 1c

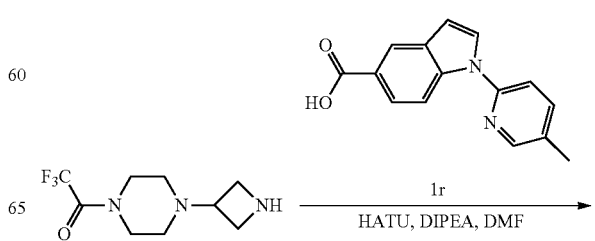

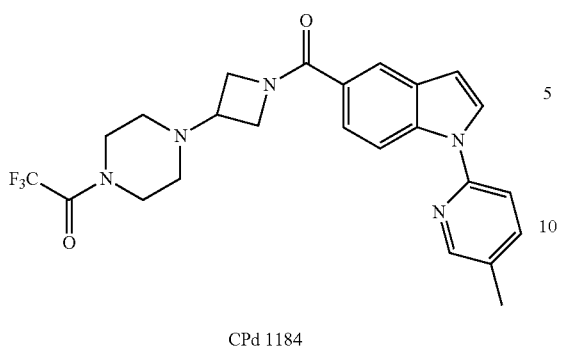

CPd 1184

N. 1-(5-Methylpyridin-2-yl)-5-({3-[4-(trifluoroacetyl)piperazin-1-yl]azetidin-1-yl}carbonyl)-1H-indole; Cpd 1184. The title compound, Cpd 1184, was prepared according to Example 1 using intermediate 1r from Example 1b and intermediate 1g in Example 1 as starting materials. MS m/z (M+H$^+$) 472.1

Following the procedure described above for Example 1c, and substituting the appropriate reagents, starting materials, and purification methods known to those skilled in the art, the following compounds of the present invention were prepared:

| Cpd | Cpd Name and Data | Salt Form |
|---|---|---|
| 1409 | 1-(5-Chloropyridin-2-yl)-5-({3-[4-(trifluoroacetyl)piperazin-1-yl]azetidin-1-yl}carbonyl)-1H-indole<br>MS m/z (M + H$^+$) 492.1 | N-TFA |
| 1199 | 1-(4-Methylpyridin-2-yl)-5-({3-[4-(trifluoroacetyl)piperazin-1-yl]azetidin-1-yl}carbonyl)-1H-indole<br>MS m/z (M + H$^+$) 472.1 | N-TFA |
| 656 | 1-(1-{[3-Chloro-6-(trifluoromethyl)-1-benzothiophen-2-yl]carbonyl}azetidin-3-yl)-4-(trifluoroacetyl)piperazine<br>MS m/z (M + H$^+$) 500.1 | N-TFA |
| 1079 | 1-(4-Fluorophenyl)-5-({3-[4-(trifluoroacetyl)piperazin-1-yl]azetidin-1-yl}carbonyl)-1H-indole<br>MS m/z (M + H$^+$) 475.2 | N-TFA |

Example 1d

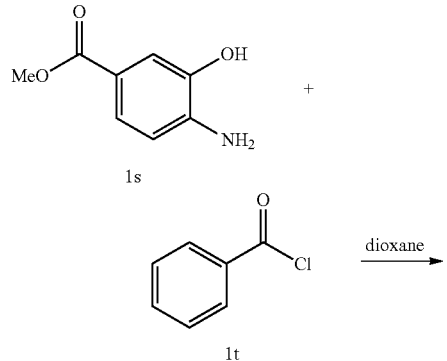

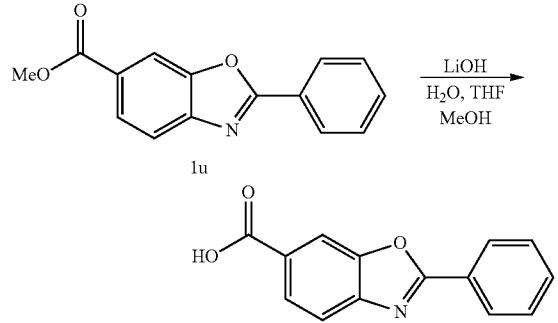

O. Methyl 2-phenyl-benzooxazole-6-carboxylate, 1u. A mixture of methyl 4-amino-3-hydroxy-benzoate is (0.3 g, 1.8 mmol) and benzoyl chloride 1t (0.23 mL, 2.0 mmol) in dioxane (2.5 mL) was heated at 210° C. under microwave for 15 min. The reaction mixture was diluted with CH$_2$Cl$_2$ and washed with aq. NaHCO$_3$. The organic solution was dried over Na$_2$SO$_4$, concentrated and purified by flash column chromatography (silica gel, 20% EtOAc/heptane) to give 1u (0.39 g).

P. 2-Phenyl-benzooxazole-6-carboxylic acid, 1v. A mixture of methyl 2-phenyl-benzooxazole-6-carboxylate 1u (0.37 g, 1.46 mmol) and LiOH (0.10 g, 4.2 mmol) in THF (4 mL), MeOH (4 mL), and H$_2$O (4 mL) was stirred at room temperature for 6 h. Aqueous 1N HCl solution was added to the mixture to adjust pH to 3-4. The resulting mixture was extracted with EtOAc (2×). The organic solution was washed with aq. NaCl, dried over Na$_2$SO$_4$ and concentrated to give 1t (0.34 g).

Following the procedure described above for Example 1d and substituting the appropriate reagents, starting materials, and purification methods known to those skilled in the art, the following intermediate compounds were prepared:

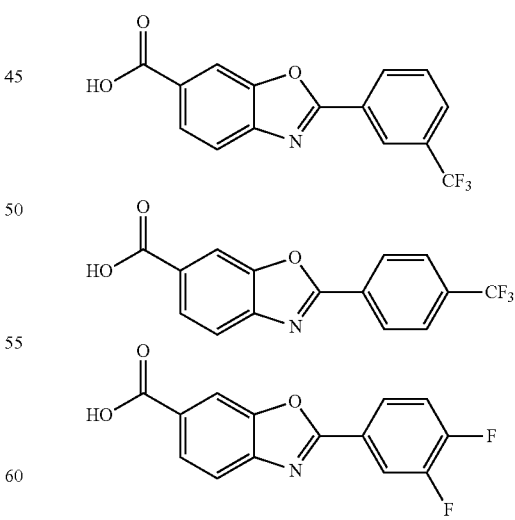

Following the procedure described above for Example 1, and substituting the appropriate reagents, starting materials, and purification methods known to those skilled in the art, the following compounds of the present invention were prepared:

| Cpd | Cpd Name and Data |
|---|---|
| 1141 | 2-Phenyl-6-({3-[4-(1,3-thiazol-4-ylcarbonyl)piperazin-1-yl]azetidin-1-yl}carbonyl)-1,3-benzoxazole<br>MS m/z (M + H+) 474 |
| 1151 | 6-({3-[4-(1,3-Thiazol-4-ylcarbonyl)piperazin-1-yl]azetidin-1-yl}carbonyl)-2-[3-(trifluoromethyl)phenyl]-1,3-benzoxazole<br>MS m/z (M + H+) 542 |
| 1158 | 6-({3-[4-(1,3-Thiazol-2-ylcarbonyl)piperazin-1-yl]azetidin-1-yl}carbonyl)-2-[3-(trifluoromethyl)phenyl]-1,3-benzoxazole<br>MS m/z (M + H+) 542 |

Example 1e

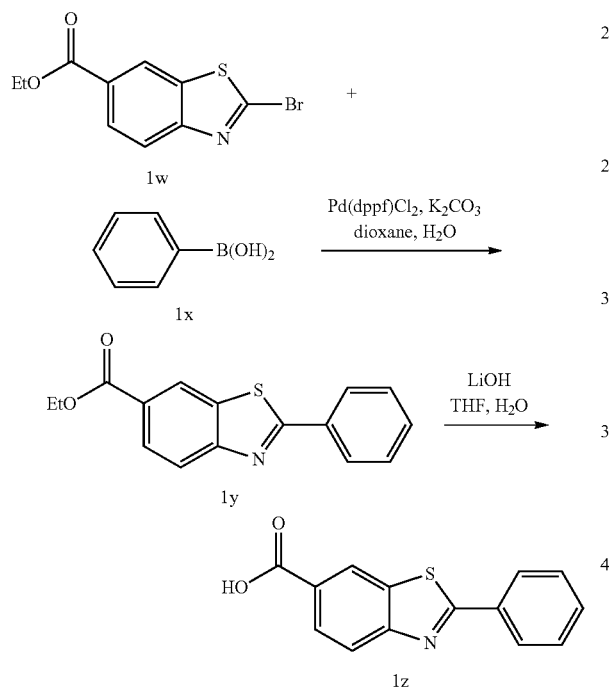

Q. Ethyl 2-phenyl-benzothiazole-6-carboxylate, 1y. A mixture of ethyl 2-bromo-benzothiazole-6-carboxylate 1w (300 mg, 1.05 mmol), phenylboronic acid 1x (192 mg, 1.57 mmol), $K_2CO_3$ (188 mg, 1.36 mmol) and Pd(dppf)$Cl_2.CH_2Cl_2$ (43 mg, 0.05 mmol) in dioxane (2 mL) and $H_2O$ (0.4 ml) was heated at 120° C. for 25 min under microwave. The reaction mixture was diluted with $CH_2Cl_2$, washed with $H_2O$, dried over $Na_2SO_4$, and concentrated. Purification by flash column chromatography (silica gel, 15% EtOAc/heptane) gave 1y (220 mg).

R. 2-Phenyl-benzothiazole-6-carboxylic acid, 1z. Ethyl 2-phenyl-benzothiazole-6-carboxylate 1y (220 mg, 0.78 mmol) was stirred with LiOH (74 mg, 3.1 mmol) in THF (4 mL) and H2O (4 mL) for 16 h. Aqueous 1N HCl solution was added to the mixture to adjust pH to 3-4. The resulting mixture was extracted with EtOAc (2×). The organic solution was washed with aq. NaCl, dried over $Na_2SO_4$ and concentrated to give 1z (200 mg).

Following the procedure described above for Example 1e and substituting the appropriate reagents, starting materials, and purification methods known to those skilled in the art, the following intermediate compound was prepared:

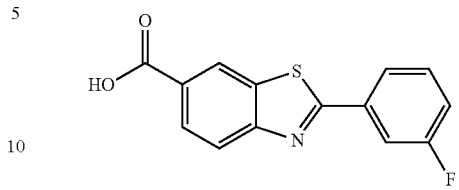

Following the procedure described above for Example 1, and substituting the appropriate reagents, starting materials, and purification methods known to those skilled in the art, the following compounds of the present invention were prepared:

| Cpd | Cpd Name and Data |
|---|---|
| 592 | 2-Phenyl-6-({3-[4-(phenylcarbonyl)piperazin-1-yl]azetidin-1-yl}carbonyl)-1,3-benzothiazole<br>MS m/z (M + H+) 483 |
| 1125 | 2-Phenyl-6-({3-[4-(1,3-thiazol-2-ylcarbonyl)piperazin-1-yl]azetidin-1-yl}carbonyl)-1,3-benzothiazole<br>$^1$H NMR (400 MHz, CD$_3$OD): d 8.25 (s, 1H), 8.12-8.06 (m, 3H), 7.88 (d, J = 3 Hz, 1H), 7.74 (d, J = 8 Hz, 1H), 7.53 (m, 4H), 4.53 (bs, 1H), 4.4-4.26 (m, 4H), 4.15 (m, 1H), 3.86 (m, 2H), 3.27 (m, 1H), 2.50 (m, 4H)<br>MS m/z (M + H+) 490 |
| 1187 | 2-Phenyl-6-({3-[4-(1,3-thiazol-4-ylcarbonyl)piperazin-1-yl]azetidin-1-yl}carbonyl)-1,3-benzothiazole<br>MS m/z 490 (M + H+) |

Example 1f

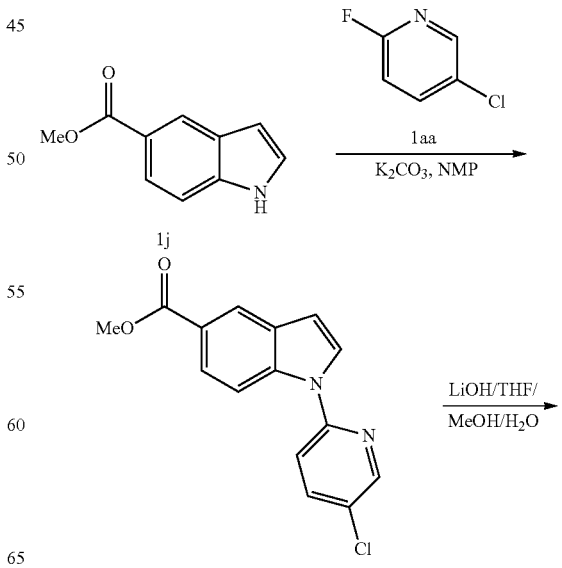

73

-continued

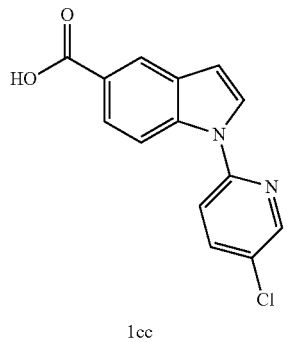

1cc

Q. Methyl 1-(5-chloropyridin-2-yl)-1H-indole-5-carboxylate, 1bb. A mixture of 1j (1.14 mmol, 200 mg), 1aa (1.14 mmol, 150 mg), K$_2$CO$_3$ (2.28 mmol, 315 mg) and NMP (1.5 mL) was heated at 200° C. in a microwave reactor for 2 h. The mixture was poured into water (50 mL) and extracted with EtOAc. The organic layer was washed with brine, dried over Na$_2$SO$_4$ and concentrated under vacuo. Purification was carried by flash column chromatography (silica gel, 15% EtOAc/heptane) to give 290 mg of 1bb (290 mg).

R. (5-Chloropyridin-2-yl)-1H-indole-5-carboxylic acid, 1cc. A mixture of 1bb (0.942 mmol, 270 mg), LiOH (3.77 mmol, 90 mg), THF (3 mL), MeOH (3 mL), and H$_2$O (3 mL) was stirred at room temperature for overnight. The reaction mixture was acidified with 1N aqueous HCl to pH=5. The solid precipitate was filtered, washed with EtOAc, and dried under vacuo to give 202 mg of 1cc.

Following the procedure described above for Example 1, and substituting the appropriate reagents, starting materials, and purification methods known to those skilled in the art, the following compounds of the present invention were prepared:

| Cpd | Cpd Name and Data |
|---|---|
| 1313 | 1-(5-Chloropyridin-2-yl)-5-({3-[4-(1,3-thiazol-2-ylcarbonyl)piperazin-1-yl]azetidin-1-yl}carbonyl)-1H-indole<br>$^1$H NMR (CDCl$_3$) d: 8.52 (d, J = 2.2 Hz, 1H), 8.21 (d, J = 8.6 Hz, 1H), 7.96 (s, 1H), 7.88 (d, J = 3.2 Hz, 1H),<br>7.81 (dd, J = 8.6, 2.4 Hz, 1H), 7.70 (d, J = 3.4 Hz, 1H),<br>7.60 (d, J = 8.8 Hz, 1H), 7.54 (d, J = 2.9 Hz, 1H),<br>7.44 (d, J = 8.6 Hz, 1H), 6.77 (d, J = 3.4 Hz, 1H), 4.51 (br. s., 1H), 4.19-4.47 (m, 4H), 4.12 (q, J = 7.1 Hz, 2H),<br>3.74-3.95 (m, 2H), 3.25 (t, J = 5.6 Hz, 1H), 2.49 (br. s., 4H)<br>MS m/z (M + H$^+$) 508.0 |
| 629 | 1-(5-Chloropyridin-2-yl)-5-({3-[4-(phenylcarbonyl)piperazin-1-yl]azetidin-1-yl}carbonyl)-1H-indole<br>MS m/z (M + H$^+$) 501.0 |
| 1180 | 1-(5-Chloropyridin-2-yl)-5-({3-[4-(1,3-thiazol-4-ylcarbonyl)piperazin-1-yl]azetidin-1-yl}carbonyl)-1H-indole<br>$^1$H NMR (CDCl$_3$) d: 8.79 (s, 1H), 8.49 (s, 1H), 8.21 (d, J = 8.6 Hz, 1H), 7.95 (s, 1H), 8.00 (s, 1H), 7.78 (d, J = 8.6 Hz, 1H), 7.68 (d, J = 2.9 Hz, 1H), 7.59 (d, J = 8.6 Hz, 1H), 7.42 (d, J = 8.6 Hz, 1H), 6.75 (d, J = 2.9 Hz, 1H), 4.31-4.47 (m, 1H), 4.16-4.31 (m, 1H), 4.11 (q, J = 7.0 Hz, 1H), 3.84-4.04 (m, 3H), 3.80 (br. s., 1H),<br>3.18-3.31 (m, 1H), 2.47 (br. s., 3H), 2.40 (br. s., 1H)<br>MS m/z (M + H$^+$) 507.0 |

74

Example 2

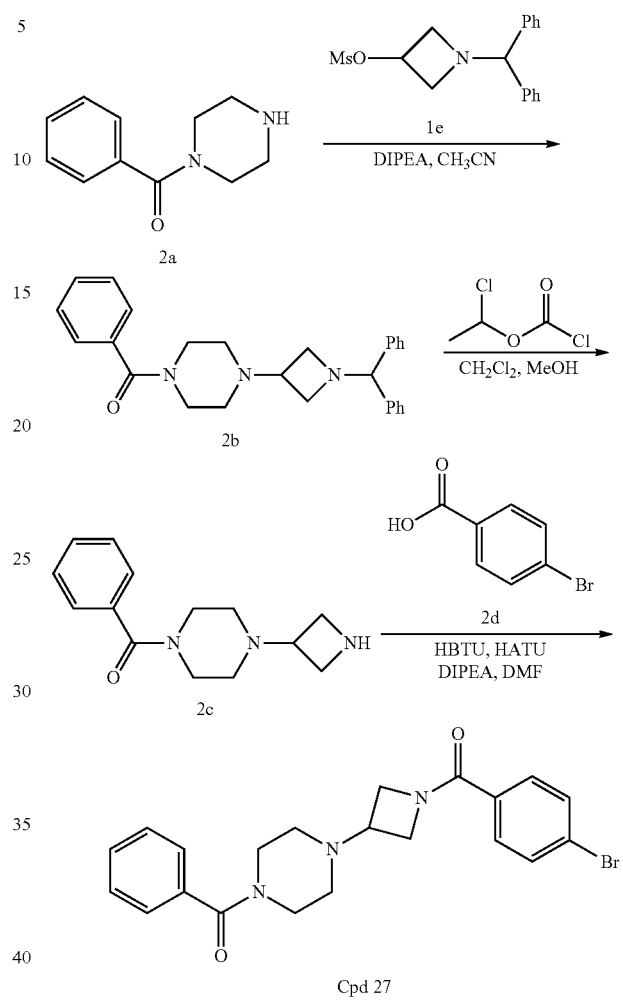

Cpd 27

A. [4-(1-Benzhydryl-azetidin-3-yl)-piperazin-1-yl]-phenyl-methanone, 2b. The title compound 2b was prepared using the method described in Example 1, substituting compound 2a for compound 1d in Procedure C. The crude compound 2b was purified by flash column chromatography. MS m/z (M+H$^+$) 412.2.

B. (4-Azetidin-3-yl-piperazin-1-yl)-phenyl-methanone, 2c. The title compound 2c was prepared using the method described in Example 1, substituting compound 2b for compound 1f in Procedure D. The crude compound 2c was used in the next reaction without further purification. MS m/z (M+H$^+$) 246.1.

C. 1-{1-[(4-Bromophenyl)carbonyl]azetidin-3-yl}-4-(phenylcarbonyl)piperazine, Cpd 27. The title compound 27 was prepared using the method described in Example 1, substituting compound 2c for compound 1g and substituting compound 2d for compound 1h in Procedure E. The crude compound 27 was purified by reverse phase chromatography. MS m/z (M+H$^+$) 428.1/430.0.

Following the procedure described above for Example 2 and substituting the appropriate reagents, starting materials and purification methods known to those skilled in the art, the following compounds of the present invention were prepared:

| Cpd | Cpd Name and Data |
|---|---|
| 28 | 1-(Phenylcarbonyl)-4-(1-{[4-(1H-pyrrol-1-yl)phenyl]carbonyl}azetidin-3-yl)piperazine<br>MS m/z (M + H$^+$) 415.2 |
| 29 | 1-(Phenylcarbonyl)-4-{1-[(4-pyrrolidin-1-ylphenyl)carbonyl]azetidin-3-yl}piperazine<br>MS m/z (M + H$^+$) 419.2 |
| 30 | N,N-Diethyl-4-({3-[4-(phenylcarbonyl)piperazin-1-yl]azetidin-1-yl}carbonyl)aniline<br>LC/MS m/z (M + H$^+$) 421.2 |
| 31 | N,N-Dimethyl-4-({3-[4-(phenylcarbonyl)piperazin-1-yl]azetidin-1-yl}carbonyl)aniline<br>MS m/z (M + H$^+$) 393.2 |
| 32 | 1-{1-[(4-Phenoxyphenyl)carbonyl]azetidin-3-yl}-4-(phenylcarbonyl)piperazine<br>LC/MS m/z (M + H$^+$) 442.2 |
| 33 | 1-{1-[(4'-Fluorobiphenyl-4-yl)carbonyl]azetidin-3-yl}-4-(phenylcarbonyl)piperazine<br>LC/MS m/z (M + H$^+$) 444.1 |
| 34 | 1-{1-[(4'-Methoxybiphenyl-4-yl)carbonyl]azetidin-3-yl}-4-(phenylcarbonyl)piperazine<br>LC/MS m/z (M + H$^+$) 456.1 |
| 35 | 1-(1-{[4-(Benzyloxy)phenyl]carbonyl}azetidin-3-yl)-4-(phenylcarbonyl)piperazine<br>LC/MS (m/z) (M + H$^+$) 456.1 |
| 36 | 1-{1-[(2'-Chlorobiphenyl-4-yl)carbonyl]azetidin-3-yl}-4-(phenylcarbonyl)piperazine<br>LC/MS m/z (M + H$^+$) 460.2 |
| 37 | 1-Cyclohexyl-2-methyl-5-({3-[4-(phenylcarbonyl)piperazin-1-yl]azetidin-1-yl}carbonyl)-1H-benzimidazole<br>LC/MS m/z (M + H$^+$) 486.3 |
| 38 | 1-(1-Methylethyl)-5-({3-[4-(phenylcarbonyl)piperazin-1-yl]azetidin-1-yl}carbonyl)-2-(trifluoromethyl)-1H-benzimidazole<br>LC/MS m/z (M + H$^+$) 500.3 |
| 39 | 1-{1-[(3',4'-Dichlorobiphenyl-4-yl)carbonyl]azetidin-3-yl}-4-(phenylcarbonyl)piperazine<br>$^1$H NMR (300 MHz, CD$_3$OD): δ 7.73 (d, 1H), 7.65 (m, 4H), 7.50 (m, 2H), 7.35-7.46 (m, 5H), 4.55 (m, 2H), 4.35 (m, 2H), 4.01 (m, 1H), 3.80 (m, 4H), 3.17 (m, 4H); LC/MS m/z (M$^+$H$^+$) 494.1 (calculated for C$_{27}$H$_{25}$Cl$_2$N$_3$O$_2$, 494.43) |
| 40 | N-Methyl-N-phenyl-4-({3-[4-(phenylcarbonyl)piperazin-1-yl]azetidin-1-yl}carbonyl)aniline<br>$^1$H NMR (300 MHz, CD$_3$OD): δ 7.45-7.56 (m, 7H), 7.41 (t, 2H), 7.22 (m, 3H), 6.80 (d, 2H), 4.27-4.75 (m, 4H), 4.07 (m, 1H), 3.88 (m, 4H), 3.34 (s, 3H), 3.25 (m, 4H); LC/MS m/z (M + H$^+$) 455.3 (calculated for C$_{28}$H$_{30}$N$_4$O$_2$, 454.58) |
| 41 | 1-[4-({3-[4-(Phenylcarbonyl)piperazin-1-yl]azetidin-1-yl}carbonyl)phenyl]azepane<br>$^1$H NMR (300 MHz, CD$_3$OD): δ 7.45-7.57 (m, 7H), 6.73 (d, 2H), 4.28-4.73 (m, 4H), 4.12 (m, 1H), 3.89 (m, 4H), 3.30 (m, 8H), 1.80 (m, 4H), 1.54 (m, 4H); LC/MS m/z (M + H$^+$) 447.3 (calculated for C$_{27}$H$_{34}$N$_4$O$_2$, 446.6) |
| 42 | 5-({3-[4-(Phenylcarbonyl)piperazin-1-yl]azetidin-1-yl}carbonyl)-1-propyl-1H-indole<br>LC/MS m/z (M + H$^+$) 431.1 |
| 43 | 1-(Biphenyl-4-ylcarbonyl)-2-phenyl-4-[1-(1,3-thiazol-2-ylcarbonyl)azetidin-3-yl]piperazine<br>$^1$H NMR (400 MHz, MeOD): δ 7.86-7.95 (m, 1H), 7.73-7.79 (m, 1H), 7.62-7.68 (m, 2H), 7.53-7.59 (m, 2H), 7.47-7.52 (m, 2H), 7.41-7.47 (m, 2H), 7.33-7.41 (m, 4H), 7.21-7.33 (m, 2H), 5.67 (br. s., 1H), 4.51-4.62 (m, 2H), 4.19-4.38 (m, 1H), 4.01-4.12 (m, 1H), 3.71-3.81 (m, 1H), 3.54-3.67 (m, 1H), 3.32 (m, 1H), 2.98-3.12 (m, 2H), 2.79-2.90 (m, 1H), 2.44-2.56 (m, 1H); MS m/z (M + H$^+$) 509.2 (calculated for C$_{30}$H$_{28}$N$_4$O$_2$S, 508.65) |
| 44 | 1-(Biphenyl-4-ylcarbonyl)-2-phenyl-4-[1-(phenylcarbonyl)azetidin-3-yl]piperazine<br>$^1$H NMR (400 MHz, MeOD): δ 7.67-7.75 (m, 2H), 7.59-7.67 (m, 4H), 7.53-7.58 (m, 2H), 7.40-7.53 (m, 9H), 7.31-7.40 (m, 2 H), 5.73 (br. s., 1 H), 4.34-4.57 (m, 1H), 4.23-4.34 (m, 1H), 4.02-4.18 (m, 1H), 3.69-3.88 (m, 1H), 3.55-3.68 (m, 1H), 3.35-3.46 (m, 2H), 3.07 (m, 1H), 2.81-2.93 (m, 1H), 2.43-2.63 (m, 1H); MS m/z (M$^+$) 502.2 (calculated for C$_{33}$H$_{31}$N$_3$O$_2$, 502.23) |
| 45 | 1-[1-(Biphenyl-4-ylcarbonyl)azetidin-3-yl]-2-methyl-4-(1,3-thiazol-2-ylcarbonyl)piperazine<br>MS m/z (M + H$^+$) 447.29 (calculated for C$_{25}$H$_{26}$N$_4$O$_2$S, 446.58) |
| 46 | 2-Methyl-1-{1-[(4-phenoxyphenyl)carbonyl]azetidin-3-yl}-4-(1,3-thiazol-2-ylcarbonyl)piperazine<br>MS m/z (M + H$^+$) 463.2 (calculated for C$_{25}$H$_{26}$N$_4$O$_3$S, 462.57) |
| 47 | 1-{1-[(4-Benzylphenyl)carbonyl]azetidin-3-yl}-2-methyl-4-(1,3-thiazol-2-ylcarbonyl)piperazine<br>MS m/z (M + H$^+$) 461.0 (calculated for C$_{26}$H$_{28}$N$_4$O$_2$S, 460.60) |
| 48 | 1-[4-({3-[4-(Phenylcarbonyl)piperazin-1-yl]azetidin-1-yl}carbonyl)phenyl]-1H-benzimidazole<br>MS m/z (M + H$^+$) 466.3 (calculated for C$_{28}$H$_{27}$N$_5$O$_2$, 465.56) |
| 49 | 1-{1-[(4-Fluorophenyl)carbonyl]azetidin-3-yl}-4-(phenylcarbonyl)piperazine<br>MS m/z (M + H$^+$) 368.2 (calculated for C$_{21}$H$_{22}$FN$_3$O$_2$, 367.43) |
| 50 | N-Benzyl-5-({3-[4-(phenylcarbonyl)piperazin-1-yl]azetidin-1-yl}carbonyl)-1,3-thiazol-2-amine MS m/z (M + H$^+$) 462.2 (calculated for C$_{25}$H$_{27}$N$_5$O$_2$S, 461.59) |
| 51 | 9-Methyl-3-({3-[4-(phenylcarbonyl)piperazin-1-yl]azetidin-1-yl}carbonyl)-9H-carbazole<br>MS m/z (M + H$^+$) 453.3 (calculated for C$_{28}$H$_{28}$N$_4$O$_2$, 452.56) |
| 52 | N-Benzyl-2-({3-[4-(phenylcarbonyl)piperazin-1-yl]azetidin-1-yl}carbonyl)aniline<br>MS m/z (M + H$^+$) 455.3 (calculated for C$_{28}$H$_{30}$N$_4$O$_2$, 454.58) |
| 53 | 1-(Phenylcarbonyl)-4-{1-[(4-piperidin-1-ylphenyl)carbonyl]azetidin-3-yl}piperazine<br>MS m/z (M + H$^+$) 433.3 (calculated for C$_{26}$H$_{32}$N$_4$O$_2$, 432.57) |
| 54 | N-Butyl-4-({3-[4-(phenylcarbonyl)piperazin-1-yl]azetidin-1-yl}carbonyl)aniline<br>MS m/z (M + H$^+$) 421.2 (calculated for C$_{25}$H$_{32}$N$_4$O$_2$, 420.56) |
| 55 | 6-({3-[4-(Phenylcarbonyl)piperazin-1-yl]azetidin-1-yl}carbonyl)-2,3,4,9-tetrahydro-1H-carbazole<br>MS (m/z) (M + H$^+$) 443.3 (calculated for C$_{27}$H$_{30}$N$_4$O$_2$, 442.57) |
| 56 | 2-[3-({3-[4-(Phenylcarbonyl)piperazin-1-yl]azetidin-1-yl}carbonyl)phenyl]-2,3-dihydro-1H-isoindole<br>MS m/z (M + H$^+$) 467.2 (calculated for C$_{29}$H$_{30}$N$_4$O$_2$, 466.59) |
| 57 | 2-({3-[4-(Phenylcarbonyl)piperazin-1-yl]azetidin-1-yl}carbonyl)-N-[3-(trifluoromethyl)phenyl]aniline<br>MS m/z (M + H$^+$) 509.1 (calculated for C$_{28}$H$_{27}$F$_3$N$_4$O$_2$, 508.55) |
| 58 | N-Phenyl-2-({3-[4-(phenylcarbonyl)piperazin-1-yl]azetidin-1-yl}carbonyl)aniline<br>MS m/z (M + H$^+$) 441.2 (calculated for C$_{27}$H$_{28}$N$_4$O$_2$, 440.55) |
| 59 | N-(3-Fluorophenyl)-2-({3-[4-(phenylcarbonyl)piperazin-1-yl]azetidin-1-yl}carbonyl)aniline<br>MS m/z (M + H$^+$) 459.2 (calculated for C$_{27}$H$_{27}$FN$_4$O$_2$, 458.54) |
| 60 | 2,3-Dimethyl-N-[2-({3-[4-(phenylcarbonyl)piperazin-1-yl]azetidin-1-yl}carbonyl)phenyl]aniline<br>MS m/z (M + H$^+$) 469.2 (calculated for C$_{29}$H$_{32}$N$_4$O$_2$, 468.60) |
| 461 | 1-(1-{[2-(Benzyloxy)phenyl]carbonyl}azetidin-3-yl)-4-(phenylcarbonyl)piperazine<br>MS m/z (M + H$^+$) 456.221 |
| 462 | 1-{1-[(3-Phenoxyphenyl)carbonyl]azetidin-3-yl}-4-(phenylcarbonyl)piperazine<br>MS m/z (M + H$^+$) 442.3 |
| 463 | 1-{1-[(2-Phenoxyphenyl)carbonyl]azetidin-3-yl}-4-(phenylcarbonyl)piperazine<br>MS m/z (M + H$^+$) 442.3 |
| 464 | 1-(Phenylcarbonyl)-4-(1-{[4-(trifluoromethoxy)phenyl]carbonyl}azetidin-3-yl)piperazine<br>MS m/z (M + H$^+$) 434.161 |
| 465 | 1-{1-[(3-Bromo-4-methoxyphenyl)carbonyl]azetidin-3-yl}-4-(phenylcarbonyl)piperazine<br>MS m/z (M + H$^+$) 458.1 |
| 466 | 1-{1-[(3-Chloro-4-methoxyphenyl)carbonyl]azetidin-3-yl}-4-(phenylcarbonyl)piperazine<br>MS m/z (M + H$^+$) 414.151 |
| 467 | 1-{1-[(4-Ethoxyphenyl)carbonyl]azetidin-3-yl}-4-(phenylcarbonyl)piperazine<br>MS m/z (M + H$^+$) 394.205 |
| 468 | 1-{1-[(3-Iodo-4-methoxyphenyl)carbonyl]azetidin-3-yl}-4-(phenylcarbonyl)piperazine<br>MS m/z (M + H$^+$) 506.086 |
| 469 | 1-(1-{[4-(1-Methylethoxy)phenyl]carbonyl}azetidin-3-yl)-4-(phenylcarbonyl)piperazine<br>MS m/z (M + H$^+$) 408.221 |
| 470 | 1-(1-{[4-(Methylsulfanyl)phenyl]carbonyl}azetidin-3-yl)-4-(phenylcarbonyl)piperazine<br>MS m/z (M + H$^+$) 396.167 |
| 471 | 4-({3-[4-(1,3-Thiazol-2-ylcarbonyl)piperazin-1-yl]azetidin-1-yl}carbonyl)phenyl acetate<br>MS m/z (M + H$^+$) 415.136 |
| 472 | 1-(1-{[4-(Methylsulfonyl)phenyl]carbonyl}azetidin-3-yl)-4-(phenylcarbonyl)piperazine<br>MS m/z (M + H$^+$) 428.157 |

-continued

| Cpd | Cpd Name and Data |
|---|---|
| 539 | N-[3-({3-[4-(Phenylcarbonyl)piperazin-1-yl]azetidin-1-yl}carbonyl)phenyl]cyclohexanecarboxamide<br>MS m/z (M + H$^+$) 475.2 |
| 622 | 1-(Phenylcarbonyl)-4-[1-({4-[3-(trifluoromethyl)-1H-pyrazol-1-yl]phenyl}carbonyl)azetidin-3-yl]piperazine<br>MS m/z (M + H$^+$) 484.0 |
| 531 | N-Benzyl-3-({3-[4-(phenylcarbonyl)piperazin-1-yl]azetidin-1-yl}carbonyl)aniline<br>MS m/z (M + H$^+$) 455.1 |
| 565 | 1-Benzyl-5-({3-[4-(phenylcarbonyl)piperazin-1-yl]azetidin-1-yl}carbonyl)pyridin-2(1H)-one<br>MS m/z (M + H$^+$) 457.1 |
| 562 | 1-(3-Chlorobenzyl)-3-({3-[4-(phenylcarbonyl)piperazin-1-yl]azetidin-1-yl}carbonyl)pyridin-2(1H)-one<br>MS m/z (M + H$^+$) 491.1 |
| 627 | 1-(Phenylcarbonyl)-4-(1-{[3-(1H-pyrrol-1-yl)phenyl]carbonyl}azetidin-3-yl)piperazine<br>MS m/z (M + H$^+$) 415.2 |
| 541 | 4-[4-({3-[4-(Phenylcarbonyl)piperazin-1-yl]azetidin-1-yl}carbonyl)phenyl]morpholine<br>MS m/z (M + H$^+$) 435.1 |
| 1485 | 4-[5-({3-[4-(Phenylcarbonyl)piperazin-1-yl]azetidin-1-yl}carbonyl)pyridin-2-yl]morpholine<br>MS m/z (M + H$^+$) 436.0 |

-continued

| Cpd | Cpd Name and Data |
|---|---|
| 559 | 4-{1-[(4-Benzylphenyl)carbonyl]azetidin-3-yl}-2-phenyl-1-(phenylcarbonyl)piperazine<br>MS m/z (M + H$^+$) 516.1 |
| 628 | 4-[1-(Biphenyl-4-ylcarbonyl)azetidin-3-yl]-2-phenyl-1-(phenylcarbonyl)piperazine<br>MS m/z (M + H$^+$) 502.0 |
| 1404 | 4-[1-(Biphenyl-4-ylcarbonyl)azetidin-3-yl]-2-phenyl-1-(1,3-thiazol-2-ylcarbonyl)piperazine<br>MS m/z (M + H$^+$) 509.1 |
| 1464 | 4-{1-[(4-Benzylphenyl)carbonyl]azetidin-3-yl}-2-phenyl-1-(1,3-thiazol-2-ylcarbonyl)piperazine<br>MS m/z (M + H$^+$) 523.1 |
| 1266 | 2-Benzyl-1-(biphenyl-4-ylcarbonyl)-4-[1-(1,3-thiazol-2-ylcarbonyl)azetidin-3-yl]piperazine<br>MS m/z (M + H$^+$) 523.3 |
| 1284 | 2-Benzyl-1-(biphenyl-4-ylcarbonyl)-4-[1-(1,3-thiazol-4-ylcarbonyl)azetidin-3-yl]piperazine<br>MS m/z (M + H$^+$) 523.2 |
| 954 | (2R,6S)-2,6-Dimethyl-1-(1,3-thiazol-2-ylcarbonyl)-4-(1-{[6-(trifluoromethyl)-1-benzothiophen-2-yl]carbonyl}azetidin-3-yl)piperazine<br>MS m/z (M + H$^+$) 509.0 |

Example 3

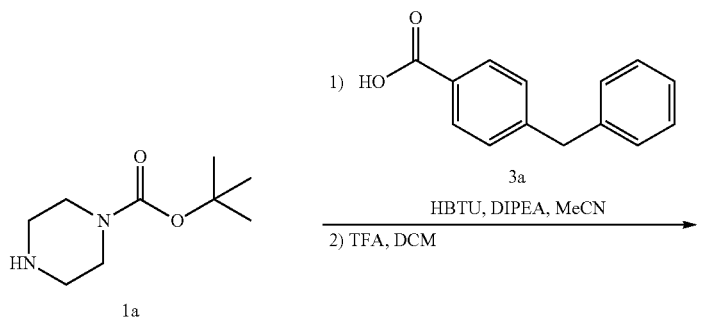

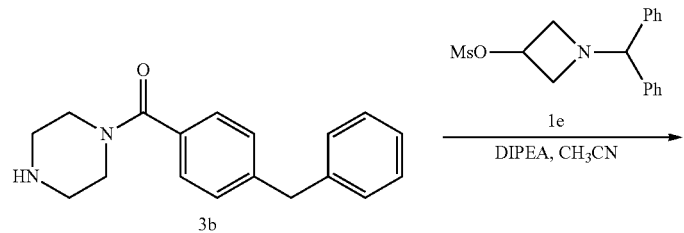

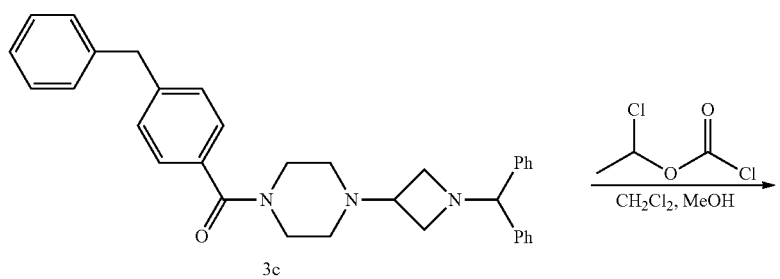

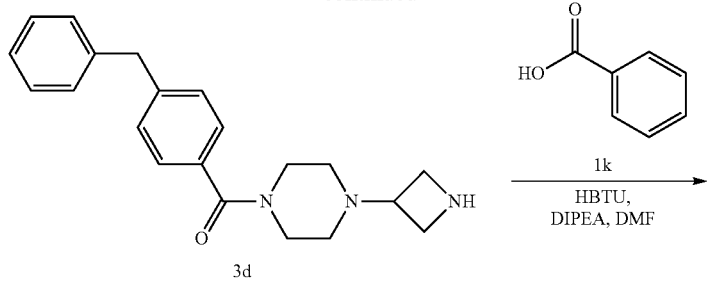

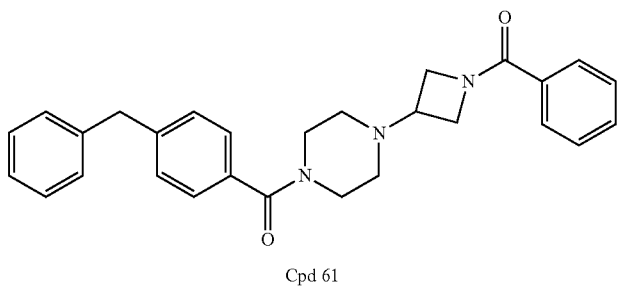

Cpd 61

A. (4-Benzyl-phenyl)-piperazin-1-yl-methanone, 3b. To a solution of compound 1a (1 g, 5.36 mmol), compound 3a (1.14 g, 5.36 mmol), and DIPEA (1.38 g, 10.7 mmol) in acetonitrile (20 mL) was added HBTU (2.64 g, 7.0 mmol). The reaction was stirred for 18 h at which time the solvent was removed under reduced pressure and the crude product purified by reverse phase HPLC. Upon lyophilization, the remaining solid was dissolved in DCM (20 mL) and trifluoroacetic acid was slowly added (15 mL). After stirring at room temperature 2 h, the solvents were removed and the residue partitioned between aqueous 1N NaOH and $CHCl_3$. The organic layer was separated, dried ($MgSO_4$), filtered, and then concentrated to yield compound 3b (1.21 g).

B. [4-(1-Benzhydryl-azetidin-3-yl)-piperazin-1-yl]-4-benzyl-phenyl-methanone, 3c. The title compound 3c was prepared using the method described in Example 1, substituting compound 3b for compound 1d in Procedure C.

C. (4-Azetidin-3-yl-piperazin-1-yl)-4-benzyl-phenyl-methanone, 3d. The title compound 3d was prepared using the method described in Example 1, substituting compound 3c for compound 1f in Procedure D.

D. 1-[(4-Benzylphenyl)carbonyl]-4-[1-(phenylcarbonyl)azetidin-3-yl]piperazine, Cpd 61. Compound 3d was converted into title compound 61 using the method described in Example 2, substituting compound 3d for compound 2c, benzoic acid (compound 1k) for compound 2d, and HBTU for HATU in Procedure D. $^1$H NMR (400 MHz, MeOD): δ 7.64 (d, J=1.7 Hz, 2H), 7.51-7.58 (m, 1H), 7.48 (br. s, 2H), 7.38 (s, 2H), 7.33 (d, J=8.1 Hz, 2H), 7.25 (br. s, 2H), 7.20 (d, J=7.3 Hz, 3H), 4.51-4.64 (m, 1H), 4.33-4.51 (m, 2H), 4.20-4.33 (m, 1H), 4.01 (s, 2H), 3.86-3.96 (m, 2H), 3.69-3.86 (m, 3H), 3.07 (br. s, 4H); MS m/z (M+H$^+$) 440.2 (calculated for $C_{28}H_{29}N_3O_2$, 439.56)

Following the procedure described above for Example 3 and substituting the appropriate reagents, starting materials and purification methods known to those skilled in the art, the following compounds of the present invention were prepared:

| Cpd | Cpd Name and Data |
|---|---|
| 1246 | 1-(Biphenyl-4-ylcarbonyl)-4-[1-(1,3-thiazol-4-ylcarbonyl)azetidin-3-yl]piperazine<br>MS m/z (M + H$^+$) 433.1 |
| 1235 | 1-(Biphenyl-4-ylcarbonyl)-4-[1-(isothiazol-5-ylcarbonyl)azetidin-3-yl]piperazine<br>MS m/z (M + H$^+$) 433.2 |
| 1242 | 1-(Biphenyl-4-ylcarbonyl)-4-{1-[(3-fluorophenyl)carbonyl]azetidin-3-yl}piperazine<br>MS m/z (M + H$^+$) 444.1 |
| 1236 | 1-(Biphenyl-4-ylcarbonyl)-4-[1-(1,3-thiazol-2-ylcarbonyl)azetidin-3-yl]piperazine<br>MS m/z (M + H$^+$) 433.2 |
| 1383 | 1-(Biphenyl-4-ylcarbonyl)-4-[1-(1H-pyrrol-2-ylcarbonyl)azetidin-3-yl]piperazine<br>MS m/z (M + H$^+$) 414.0 |
| 1276 | 1-(Biphenyl-4-ylcarbonyl)-4-[1-(1,2,3-thiadiazol-4-ylcarbonyl)azetidin-3-yl]piperazine<br>MS m/z (M + H$^+$) 434.0 |
| 1292 | 1-(Biphenyl-4-ylcarbonyl)-4-[1-(1H-pyrrol-3-ylcarbonyl)azetidin-3-yl]piperazine<br>MS m/z (M + H$^+$) 413.0 |
| 1400 | 2-({3-[4-(Biphenyl-4-ylcarbonyl)piperazin-1-yl]azetidin-1-yl}carbonyl)pyrimidine<br>MS m/z (M + H$^+$) 428.1 |
| 1283 | 1-(Biphenyl-4-ylcarbonyl)-4-[1-(1,3-oxazol-2-ylcarbonyl)azetidin-3-yl]piperazine<br>MS m/z (M + H$^+$) 417.0 |
| 676 | 1-[1-(1,3-Thiazol-2-ylcarbonyl)azetidin-3-yl]-4-{[5-(trifluoromethyl)-1-benzothiophen-2-yl]carbonyl}piperazine<br>MS m/z (M + H$^+$) 481.1 |
| 722 | 1-[1-(1H-Pyrrol-2-ylcarbonyl)azetidin-3-yl]-4-{[5-(trifluoromethyl)-1-benzothiophen-2-yl]carbonyl}piperazine<br>MS m/z (M + H$^+$) 462.1 |
| 741 | 1-[1-(1H-Pyrrol-3-ylcarbonyl)azetidin-3-yl]-4-{[5-(trifluoromethyl)-1-benzothiophen-2-yl]carbonyl}piperazine<br>MS m/z (M + H$^+$) 461.0 |
| 716 | 1-[1-(1,3-Thiazol-4-ylcarbonyl)azetidin-3-yl]-4-{[5-(trifluoromethyl)-1-benzothiophen-2-yl]carbonyl}piperazine<br>MS m/z (M + H$^+$) 481.0 |

-continued

| Cpd | Cpd Name and Data |
|---|---|
| 703 | 1-[1-(Isothiazol-5-ylcarbonyl)azetidin-3-yl]-4-{[5-(trifluoromethyl)-1-benzothiophen-2-yl]carbonyl}piperazine<br>MS m/z (M + H⁺) 481.0 |
| 921 | 1-[1-(1,2,5-Oxadiazol-3-ylcarbonyl)azetidin-3-yl]-4-{[5-(trifluoromethyl)-1-benzothiophen-2-yl]carbonyl}piperazine<br>MS m/z (M + H⁺) 466.1 |
| 753 | 1-[1-(1,2,3-Thiadiazol-4-ylcarbonyl)azetidin-3-yl]-4-{[5-(trifluoromethyl)-1-benzothiophen-2-yl]carbonyl}piperazine<br>MS m/z (M + H⁺) 482.2 |
| 1067 | 1-[1-(1,3-Thiazol-4-ylcarbonyl)azetidin-3-yl]-4-{[3'-(trifluoromethyl)biphenyl-4-yl]carbonyl}piperazine<br>MS m/z (M + H⁺) 501.0 |
| 1243 | 1-[1-(1H-Pyrrol-3-ylcarbonyl)azetidin-3-yl]-4-{[3'-(trifluoromethyl)biphenyl-4-yl]carbonyl}piperazine<br>MS m/z (M + H⁺) 483.0 |
| 1166 | 1-[1-(1H-Pyrrol-2-ylcarbonyl)azetidin-3-yl]-4-{[3'-(trifluoromethyl)biphenyl-4-yl]carbonyl}piperazine<br>MS m/z (M + H⁺) 483.0 |
| 1402 | 4-(Biphenyl-4-ylcarbonyl)-2-phenyl-1-[1-(1,3-thiazol-4-ylcarbonyl)azetidin-3-yl]piperazine<br>MS m/z (M + H⁺) 509.0 |
| 1401 | 4-(Biphenyl-4-ylcarbonyl)-2-phenyl-1-[1-(1,3-thiazol-2-ylcarbonyl)azetidin-3-yl]piperazine<br>MS m/z (M + H⁺) 509.0 |

Example 4

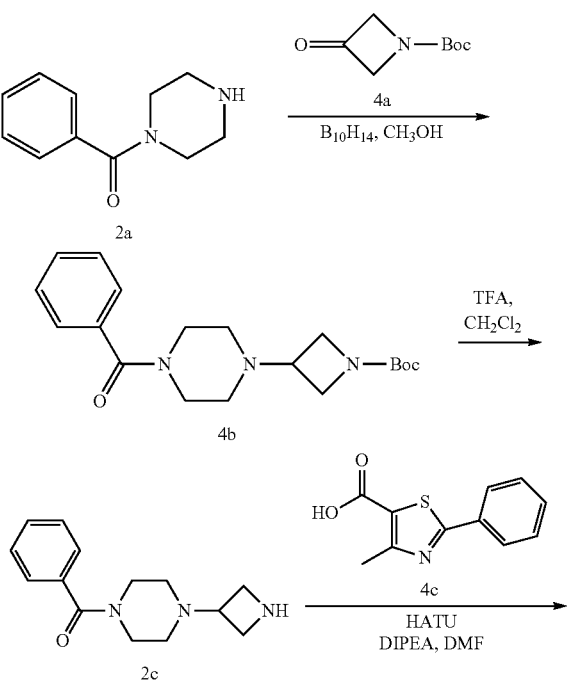

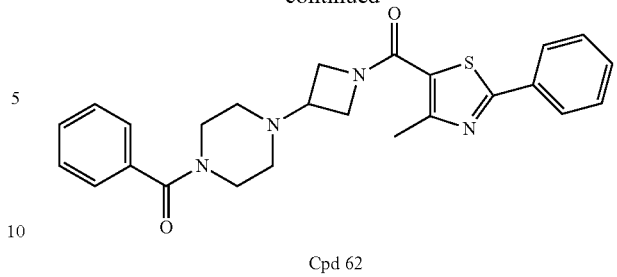

Cpd 62

A. 3-(4-Benzoyl-piperazin-1-yl)-azetidine-1-carboxylic acid tert-butyl ester, 4b. To a solution of 1-Boc-azetidin-3-one (compound 4a) and compound 2a in CH₃OH was added decaborane at room temperature. The reaction mixture was stirred at room temperature for 18 h. The solvent was removed under reduced pressure, and the crude compound 4b was used in the subsequent reaction without further purification. MS m/z (M+H⁺) 346.2.

B. (4-Azetidin-3-yl-piperazin-1-yl)-phenyl-methanone, 2c. The title compound 2c was prepared using the method described in Example 1, substituting compound 4b for compound 1c in Procedure B. The crude compound 2c was used in the next reaction without further purification. MS m/z (M+H⁺) 246.1.

C. 1-{1-[(4-Methyl-2-phenyl-1,3-thiazol-5-yl)carbonyl]azetidin-3-yl}-4-(phenylcarbonyl)piperazine, Cpd 62. The title compound 62 was prepared using the method described in Example 1, substituting compound 2c for compound 1g and substituting compound 4c for compound 1h in Procedure E. The crude compound 62 was purified by reverse phase chromatography. MS m/z (M+H⁺) 447.1.

Following the procedure described above for Example 4 and substituting the appropriate reagents, starting materials and purification methods known to those skilled in the art, the following compounds of the present invention were prepared:

| Cpd | Cpd Name and Data |
|---|---|
| 63 | 1-{1-[(4-Methyl-2-thiophen-2-yl-1,3-thiazol-5-yl)carbonyl]azetidin-3-yl}-4-(phenylcarbonyl)piperazine<br>LC/MS m/z (M + H⁺) 453.1 |
| 64 | 1-(1-{[4-Methyl-2-(4-methylphenyl)-1,3-thiazol-5-yl]carbonyl}azetidin-3-yl)-4-(phenylcarbonyl)piperazine<br>LC/MS m/z (M + H⁺) 461.2 |
| 65 | 1-[1-({4-Methyl-2-[4-(trifluoromethyl)phenyl]-1,3-thiazol-5-yl}carbonyl)azetidin-3-yl]-4-(phenylcarbonyl)piperazine<br>LC/MS m/z (M + H⁺) 515.1 |
| 66 | 1-(Phenylcarbonyl)-4-{1-[(3-thiophen-2-ylphenyl)carbonyl]azetidin-3-yl}piperazine<br>LC/MS m/z (M + H⁺) 432.1 |
| 67 | 1-(Phenylcarbonyl)-4-{1-[(4-thiophen-2-ylphenyl)carbonyl]azetidin-3-yl}piperazine<br>LC/MS m/z (M + H⁺) 432.1 |
| 68 | 1-(Phenylcarbonyl)-4-{1-[(3-pyridin-2-ylphenyl)carbonyl]azetidin-3-yl}piperazine<br>LC/MS m/z (M + H⁺) 427.2 |
| 69 | 1-(Phenylcarbonyl)-4-{1-[(3-pyridin-3-ylphenyl)carbonyl]azetidin-3-yl}piperazine<br>LC/MS m/z (M + H⁺) 427.2 |
| 70 | 1-(Phenylcarbonyl)-4-{1-[(3-pyridin-4-ylphenyl)carbonyl]azetidin-3-yl}piperazine<br>LC/MS m/z (M + H⁺) 427.2 |
| 71 | 1-(Phenylcarbonyl)-4-{1-[(4-pyridin-3-ylphenyl)carbonyl]azetidin-3-yl}piperazine<br>LC/MS m/z (M + H⁺) 427.2 |
| 72 | 1-(Phenylcarbonyl)-4-(1-{[2'-(trifluoromethyl)biphenyl-4-yl]carbonyl}azetidin-3-yl)piperazine |

| Cpd | Cpd Name and Data |
|---|---|
| | $^1$H NMR (300 MHz, CD$_3$OD): δ 7.81 (d, 1H), 7.64-7.77 (m, 3H), 7.59 (t, 1H), 7.42-7.54 (m, 7H), 7.36 (d, 1H), 4.70 (m, 1H), 4.58 (m, 1H), 4.47 (m, 1H), 4.35 (m, 1H), 4.04 (m, 1H), 3.86 (m, 4H), 3.19 (m, 4H); LC/MS m/z (M + H$^+$) 494.2 (calculated for C$_{28}$H$_{26}$F$_3$N$_3$O$_2$, 493.53) |
| 73 | 1-(Phenylcarbonyl)-4-(1-{[2'-(trifluoromethyl)biphenyl-3-yl]carbonyl}azetidin-3-yl)piperazine<br>LC/MS m/z (M + H$^+$) 494.2 |
| 74 | 1-(Phenylcarbonyl)-4-(1-{[4'-(trifluoromethyl)biphenyl-3-yl]carbonyl}azetidin-3-yl)piperazine<br>LC/MS m/z (M + H$^+$) 494.2 |
| 75 | 1-(Phenylcarbonyl)-4-(1-{[4'-(trifluoromethyl)biphenyl-4-yl]carbonyl}azetidin-3-yl)piperazine<br>$^1$H NMR (300 MHz, CD$_3$OD): δ 7.74-7.89 (m, 8H), 7.46-7.54 (m, 5H), 4.68 (m, 1H), 4.61 (m, 1H), 4.47 (m, 1H), 4.38 (m, 1H), 4.07 (m, 1H), 3.88 (m, 4H), 3.23 (m, 4H)); LC/MS m/z (M + H$^+$) 494.2 (calculated for C$_{28}$H$_{26}$F$_3$N$_3$O$_2$, 493.53) |
| 76 | 4'-({3-[4-(Phenylcarbonyl)piperazin-1-yl]azetidin-1-yl}carbonyl)biphenyl-3-carbonitrile<br>LC/MS m/z (M + H$^+$) 451.0 |
| 77 | 1-{1-[(3'-Chlorobiphenyl-4-yl)carbonyl]azetidin-3-yl}-4-(phenylcarbonyl)piperazine<br>$^1$H NMR (300 MHz, DMSO-d$_6$): δ 7.77-7.86 (m, 3H), 7.68-7.76 (m, 3H), 7.43-7.58 (m, 7H), 4.60 (m, 2H), 4.39 (m, 1H), 4.28 (m, 1H), 4.08 (m, 1H), 3.29-3.94 (m, 6H), 3.06 (m, 2H); LC/MS m/z (M + H$^+$) 460.0 (calculated for C$_{27}$H$_{26}$ClN$_3$O$_2$, 459.98) |
| 78 | 1-{1-[(4'-Chlorobiphenyl-4-yl)carbonyl]azetidin-3-yl}-4-(phenylcarbonyl)piperazine<br>LC/MS m/z (M + H$^+$) 460.0 |
| 79 | 1-{1-[(3',5'-Dichlorobiphenyl-4-yl)carbonyl]azetidin-3-yl}-4-(phenylcarbonyl)piperazine<br>$^1$H NMR (300 MHz, DMSO-d$_6$): δ 7.87 (d, 2H), 7.81 (d, 2H), 7.73 (d, 2H), 7.67 (t, 1H), 7.48 (m, 5H), 4.67 (m, 1H), 4.58 (t, 1H), 4.43 (m, 1H), 4.29 (t, 1H), 4.10 (m, 1H), 3.25-3.93 (m, 6H), 3.06 (m, 2H); LC/MS m/z (M + H$^+$) 494.1 (calculated for C$_{27}$H$_{25}$Cl$_2$N$_3$O$_2$, 494.43) |
| 80 | 1-(Phenylcarbonyl)-4-{1-[(5-phenylpyridin-3-yl)carbonyl]azetidin-3-yl}piperazine<br>LC/MS m/z (M + H$^+$) 427.2 |
| 81 | 1-{1-[(2-Fluorobiphenyl-4-yl)carbonyl]azetidin-3-yl}-4-(phenylcarbonyl)piperazine<br>LC/MS m/z (M + H$^+$) 444.1 |
| 82 | 4'-({3-[4-(Phenylcarbonyl)piperazin-1-yl]azetidin-1-yl}carbonyl)biphenyl-4-carbonitrile<br>LC/MS m/z (M + H$^+$) 451.2 |
| 83 | 1-{1-[(4'-Bromobiphenyl-4-yl)carbonyl]azetidin-3-yl}-4-(phenylcarbonyl)piperazine<br>$^1$H NMR (300 MHz, CD$_3$OD): δ 7.25-7.74 (m, 13H), 4.08-4.59 (m, 4H), 3.43-3.97 (m, 5H), 2.92 (m, 4H); LC/MS m/z (M + H$^+$) 504.0/506.1 (calculated for C$_{27}$H$_{26}$BrN$_3$O$_2$, 504.43) |
| 474 | 1-(1-{[2-(4-Chlorophenoxy)pyridin-3-yl]carbonyl}azetidin-3-yl)-4-(phenylcarbonyl)piperazine<br>MS m/z (M + H$^+$) 477.2 |
| 473 | 1-{1-[3-(4-Methylphenyl)propanoyl]azetidin-3-yl}-4-(phenylcarbonyl)piperazine<br>MS m/z (M + H$^+$) 392.3 |
| 84 | 1-{1-[3-(4-Chlorophenyl)propanoyl]azetidin-3-yl}-4-(phenylcarbonyl)piperazine<br>LC/MS m/z (M + H$^+$) 412.21 (calculated for C$_{23}$H$_{26}$ClN$_3$O$_2$, 411.92) |
| 85 | 1-{1-[3-(4-Bromophenyl)propanoyl]azetidin-3-yl}-4-(phenylcarbonyl)piperazine<br>LC/MS m/z (M + H$^+$) 456.15 (calculated for C$_{23}$H$_{26}$BrN$_3$O$_2$, 456.38) |
| 86 | 1-(Phenylcarbonyl)-4-(1-{3-[4-(trifluoromethyl)phenyl]propanoyl}azetidin-3-yl)piperazine<br>LC/MS m/z (M + H$^+$) 446.23 (calculated for C$_{24}$H$_{26}$F$_3$N$_3$O$_2$, 445.48) |
| 87 | 1-{1-[3-(3-Chlorophenyl)propanoyl]azetidin-3-yl}-4-(phenylcarbonyl)piperazine<br>LC/MS m/z (M + H$^+$) 412.18 (calculated for C$_{23}$H$_{26}$ClN$_3$O$_2$, 411.92) |
| 88 | 1-{1-[3-(2-Chlorophenyl)propanoyl]azetidin-3-yl}-4-(phenylcarbonyl)piperazine<br>LC/MS m/z (M + H$^+$) 412.21 (calculated for C$_{23}$H$_{26}$ClN$_3$O$_2$, 411.92) |
| 89 | 1-{1-[3-(2,6-Dichlorophenyl)propanoyl]azetidin-3-yl}-4-(phenylcarbonyl)piperazine<br>LC/MS m/z (M + H$^+$) 446.16 (calculated for C$_{23}$H$_{25}$Cl$_2$N$_3$O$_2$, 446.37) |
| 90 | 1-{1-[3-(1,3-Benzodioxol-5-yl)propanoyl]azetidin-3-yl}-4-(phenylcarbonyl)piperazine<br>LC/MS m/z (M + H$^+$) 422.2 (calculated for C$_{24}$H$_{27}$N$_3$O$_4$, 421.49) |
| 91 | 1-(Phenylcarbonyl)-4-{1-[(2E)-3-{4-[(trifluoromethyl)sulfanyl]phenyl}prop-2-enoyl]azetidin-3-yl}piperazine<br>LC/MS m/z (M + H$^+$) 476.20 (calculated for C$_{24}$H$_{24}$F$_3$N$_3$O$_2$S, 475.54 |
| 92 | 1-(1-{3-[3,5-Bis(trifluoromethyl)phenyl]propanoyl}azetidin-3-yl)-4-(phenylcarbonyl)piperazine<br>LC/MS m/z (M + H$^+$) 514.18 (calculated for C$_{25}$H$_{25}$F$_6$N$_3$O$_2$, 514.18) |
| 93 | 1-[1-(3-Naphthalen-1-ylpropanoyl)azetidin-3-yl]-4-(phenylcarbonyl)piperazine.<br>LC/MS m/z (M + H$^+$) 428.27 (calculated for C$_{27}$H$_{29}$N$_3$O$_2$, 427.54) |
| 94 | 1-{1-[3-(3,4-Dichlorophenyl)propanoyl]azetidin-3-yl}-4-(phenylcarbonyl)piperazine. LC/MS m/z (M + H$^+$) 448.16 (calculated for C$_{23}$H$_{25}$Cl$_2$N$_3$O$_2$, 446.38) |
| 95 | 1-{1-[3-(4-Phenoxyphenyl)propanoyl]azetidin-3-yl}-4-(phenylcarbonyl)piperazine.<br>LC/MS m/z (M + H$^+$) 470.29 (calculated for C$_{29}$H$_{31}$N$_3$O$_3$, 469.59) |
| 96 | 1-{1-[(4-Chlorophenoxy)acetyl]azetidin-3-yl}-4-(phenylcarbonyl)piperazine.<br>LC/MS m/z (M + H$^+$) 414.21 (calculated for C$_{22}$H$_{24}$ClN$_3$O$_3$, 413.91) |
| 97 | 1-(Phenylcarbonyl)-4-{1-[3-(5,5,8,8-tetramethyl-5,6,7,8-tetrahydronaphthalen-2-yl)propanoyl]azetidin-3-yl}piperazine.<br>LC/MS m/z (M + H$^+$) 488.32 (calculated for C$_{31}$H$_{41}$N$_3$O$_2$, 487.69) |
| 98 | 1-{1-[3-(2-Bromophenyl)propanoyl]azetidin-3-yl}-4-(phenylcarbonyl)piperazine.<br>LC/MS m/z (M + H$^+$) 458.18 (calculated for C$_{23}$H$_{26}$BrN$_3$O$_2$, 456.39) |
| 99 | 1-(Phenylcarbonyl)-4-(1-{[4-(trifluoromethoxy)phenoxy]acetyl}azetidin-3-yl)piperazine.<br>LC/MS m/z (M + H$^+$) 464.26 (calculated for C$_{23}$H$_{24}$F$_3$N$_3$O$_4$, 475.54 |
| 100 | N-Cyclopropyl-4-(3-oxo-3-{3-[4-(phenylcarbonyl)piperazin-1-yl]azetidin-1-yl}propyl)benzenesulfonamide.<br>LC/MS m/z (M + H$^+$) 497.23 (calculated for C$_{26}$H$_{32}$N$_4$O$_4$S, 496.21 |
| 101 | N-(Cyclohexylmethyl)-N-methyl-4-(3-oxo-3-{3-[4-(phenylcarbonyl)piperazin-1-yl]azetidin-1-yl}propyl)aniline.<br>LC/MS m/z (M + H$^+$) 503.37 (calculated for C$_{31}$H$_{42}$N$_4$O$_2$, 502.71) |
| 102 | 1-[1-(1-Benzothiophen-2-ylcarbonyl)azetidin-3-yl]-4-(phenylcarbonyl)piperazine.<br>LC/MS m/z (M + H$^+$) 406.2 (calculated for C$_{23}$H$_{23}$N$_3$O$_2$S, 405.52) |
| 103 | 1-{1-[(2E)-3-(2-Chlorophenyl)prop-2-enoyl]azetidin-3-yl}-4-(phenylcarbonyl)piperazine.<br>LC/MS m/z (M + H$^+$) 410.29 (calculated for C$_{23}$H$_{24}$ClN$_3$O$_2$, 409.92) |
| 104 | 1-{1-[(2E)-3-(2-Bromophenyl)prop-2-enoyl]azetidin-3-yl}-4-(phenylcarbonyl)piperazine.<br>LC/MS m/z (M + H$^+$) 456.16 (calculated for C$_{23}$H$_{24}$BrN$_3$O$_2$, 454.37) |
| 105 | 1-{1-[(2E)-3-Naphthalen-2-ylprop-2-enoyl]azetidin-3-yl}-4-(phenylcarbonyl)piperazine.<br>LC/MS m/z (M + H$^+$) 426.32 (calculated for C$_{27}$H$_{27}$N$_3$O$_2$, 425.54) |
| 106 | 1-(Phenylcarbonyl)-4-{1-[(4-phenylcyclohexyl)carbonyl]azetidin-3-yl}piperazine.<br>LC/MS m/z (M + H$^+$) 432.38 (calculated for C$_{27}$H$_{33}$N$_3$O$_2$, 431.58) |
| 107 | 3-Methyl-2-phenyl-8-({3-[4-(phenylcarbonyl)piperazin-1-yl]azetidin-1-yl}carbonyl)-4H-chromen-4-one.<br>LC/MS m/z (M + H$^+$) 508.31 (calculated for C$_{31}$H$_{29}$N$_3$O$_4$, 507.59 |

-continued

| Cpd | Cpd Name and Data |
|---|---|
| 108 | Phenyl[4-({3-[4-(phenylcarbonyl)piperazin-1-yl]azetidin-1-yl}carbonyl)cyclohexyl]methanone.<br>LC/MS m/z (M + H⁺) 460.35 (calculated for $C_{28}H_{33}N_3O_3$, 459.59) |
| 109 | tert-Butyl 4-[4-({3-[4-(phenylcarbonyl)piperazin-1-yl]azetidin-1-yl}carbonyl)phenyl]piperidine-1-carboxylate.<br>¹H NMR (300 MHz, MeOD): δ 7.55 (Ar, 2H), 7.4 (m, 5H). 7.25 (ar, 2H), 4.5 (m, 2H), 4.3 (m, 2H), 4.1 (m, 3H), 3.7 (bm, 4H), 3.0 (bm, 4H), 2.7 (m, 4H), 1.7 (m, 2H), 1.5 (m, 2H), 1.4 (s, 9H).<br>LC/MS m/z (M + H⁺) 533.33 (calculated for $C_{31}H_{40}N_4O_4$, 532.69 |
| 110 | 1-{1-[(2-Phenoxypyridin-3-yl)carbonyl]azetidin-3-yl}-4-(phenylcarbonyl)piperazine. LC/MS m/z (M + H⁺) 443.28 (calculated for $C_{26}H_{26}N_4O_3$, 442.52 |
| 111 | tert-Butyl 3-[2-({3-[4-(phenylcarbonyl)piperazin-1-yl]azetidin-1-yl}carbonyl)phenyl]pyrrolidine-1-carboxylate.<br>LC/MS m/z (M + H⁺) 519.35 (calculated for $C_{30}H_{38}N_4O_4$, 518.66) |
| 496 | tert-Butyl [4-({3-[4-(phenylcarbonyl)piperazin-1-yl]azetidin-1-yl}carbonyl)phenyl]carbamate<br>¹H NMR (400 MHz, CDCl₃): δ 7.57 (d, J = 8.8 Hz, 2H), 7.44 (d, J = 8.8 Hz, 2H), 7.36-7.42 (m, 4H), 7.20 (s, 1H), 4.25-4.34 (m, 1H), 4.17-4.26 (m, 1H), 4.13 (s, 1H), 3.97-4.08 (m, 1H), 3.81-3.95 (m, 1H), 3.68-3.80 (m, 1H), 3.32-3.61 (m, 2H), 3.15-3.27 (m, 1H), 2.16-2.59 (m, 4H), 1.50 (s, 9H)<br>MS (m/z) (M + H⁺) 465.2 |
| 619 | 1-(1-{[2-(4-Chlorophenyl)-4-methyl-1,3-thiazol-5-yl]carbonyl}azetidin-3-yl)-4-(phenylcarbonyl)piperazine<br>MS m/z (M + H⁺) 481.0 |
| 618 | 1-[1-[({4-Methyl-2-[3-(trifluoromethyl)phenyl]-1,3-thiazol-5-yl}carbonyl)azetidin-3-yl]-4-(phenylcarbonyl)piperazine<br>MS m/z (M + H⁺) 515.1 |
| 620 | 1-(1-{[2-(3-Chlorophenyl)-4-methyl-1,3-thiazol-5-yl]carbonyl}azetidin-3-yl)-4-(phenylcarbonyl)piperazine<br>MS m/z (M + H⁺) 481.0 |
| 621 | 1-(1-{[2-(4-Fluorophenyl)-4-methyl-1,3-thiazol-5-yl]carbonyl}azetidin-3-yl)-4-(phenylcarbonyl)piperazine<br>MS m/z (M + H⁺) 465.1 |
| 625 | 1-(Phenylcarbonyl)-4-(1-{[2-phenyl-5-(trifluoromethyl)-1,3-oxazol-4-yl]carbonyl}azetidin-3-yl)piperazine<br>MS m/z (M + H⁺) 485.1 |
| 623 | 1-{1-[(2-Methyl-5-phenylfuran-3-yl)carbonyl]azetidin-3-yl}-4-(phenylcarbonyl)piperazine<br>MS m/z (M + H⁺) 430.2 |
| 624 | 1-(Phenylcarbonyl)-4-(1-{[5-phenyl-2-(trifluoromethyl)furan-3-yl]carbonyl}azetidin-3-yl)piperazine<br>MS m/z (M + H⁺) 484.0 |
| 558 | 1-[1-({2-[(4-Chlorophenoxy)methyl]-4-methyl-1,3-thiazol-5-yl}carbonyl)azetidin-3-yl]-4-(phenylcarbonyl)piperazine<br>MS m/z (M + H⁺) 511.1 |
| 626 | 1-(Phenylcarbonyl)-4-(1-{[1-phenyl-5-(trifluoromethyl)-1H-pyrazol-4-yl]carbonyl}azetidin-3-yl)piperazine<br>MS m/z (M + H⁺) 484.2 |

Example 5

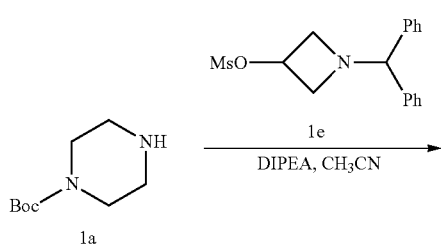

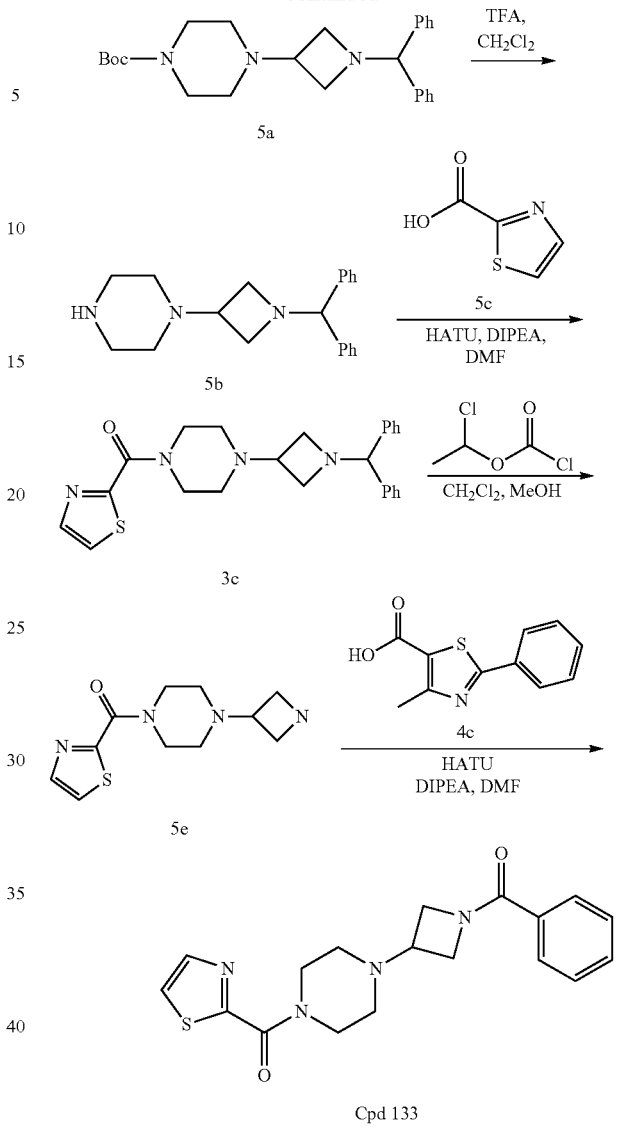

A. 4-(1-Benzhydryl-azetidin-3-yl)-piperazine-1-carboxylic acid tent-butyl ester, 5a. The title compound 5a was prepared using the method described in Example 1, substituting compound 1a for compound 1d in Procedure C. The crude compound 5a was used in the next reaction without further purification. MS m/z (M+H⁺) 408.1.

B. 1-(1-Benzhydryl-azetidin-3-yl)-piperazine, 5b. The title compound 5b was prepared using the method described in Example 1, substituting compound 5a for compound 1c in Procedure B. The crude compound 5b was used in the next reaction without further purification. MS m/z (M+H⁺) 208.1.

C. [4-(1-Benzhydryl-azetidin-3-yl)-piperazin-1-yl]-thiazol-2-yl-methanone, 5d. The title compound 5d was prepared using the method described in Example 1, substituting compound 5b for compound 1g and substituting compound 5c for compound 1h in Procedure E. The crude compound 5d was purified by flash column chromatography. MS m/z (M+H⁺) 419.2.

D. (4-Azetidin-3-yl-piperazin-1-yl)-thiazol-2-yl-methanone, 5e. The title compound 5e was prepared using the method described in Example 1, substituting compound 5d for compound 1f in Procedure D. The crude compound 5e was used in the next reaction without further purification. MS m/z (M+H⁺) 253.2.

E. 1-{1-[(4-Methyl-2-phenyl-1,3-thiazol-5-yl)-carbonyl]azetidin-3-yl}-4-(1,3-thiazol-2-ylcarbonyl)piperazine, Cpd 133. The title compound 133 was prepared using the method described in Example 1, substituting compound 5e for compound 1g and substituting compound 4c for compound 1h in Procedure E. The crude compound 133 was purified by reverse phase chromatography. $^1$H NMR (300 MHz, CD$_3$OD): δ 7.98 (m, 3H), 7.89 (d, 1H), 7.46-7.55 (m, 3H), 4.80 (m, 1H), 4.41-4.69 (m, 4H), 4.09 (m, 3H), 3.35 (m, 5H), 2.68 (s, 3H); LC/MS m/z (M+H⁺) 454.2 (calculated for C$_{22}$H$_{23}$N$_5$O$_2$S$_2$, 453.59).

Following the procedure described above for Example 5 and substituting the appropriate reagents, starting materials and purification methods known to those skilled in the art, the following compounds of the present invention were prepared:

| Cpd | Cpd Name and Data |
|---|---|
| 134 | 1-{1-[(4-Methyl-2-thiophen-2-yl-1,3-thiazol-5-yl)carbonyl]azetidin-3-yl}-4-(1,3-thiazol-2-ylcarbonyl)piperazine<br>$^1$H NMR (300 MHz, CD$_3$OD): δ 7.98 (s, 1H), 7.88 (s, 1H), 7.67 (m, 2H), 7.16 (m, 1H), 4.79 (m, 1H), 4.35-4.69 (m, 4H), 4.07 (m, 3H), 3.33 (m, 5H), 2.62 (s, 3H); LC/MS m/z (M + H⁺) 460.0 (calculated for C$_{20}$H$_{21}$N$_5$O$_2$S$_3$, 459.61) |
| 135 | 1-(1-{[4-Methyl-2-(4-methylphenyl)-1,3-thiazol-5-yl]carbonyl}azetidin-3-yl)-4-(1,3-thiazol-2-ylcarbonyl)piperazine<br>$^1$H NMR (300 MHz, CD$_3$OD): δ 7.98 (d, 1H), 7.82-7.91 (m, 3H), 7.32 (d, 2H), 4.80 (m, 1H), 4.40-4.66 (m, 4H), 4.08 (m, 3H), 3.34 (m, 5H), 2.66 (s, 3H), 2.46 (s, 3H); LC/MS m/z (M + H⁺) 468.1 (calculated for C$_{23}$H$_{25}$N$_5$O$_2$S$_2$, 467.62) |
| 136 | 1-[1-({4-Methyl-2-[4-(trifluoromethyl)phenyl]-1,3-thiazol-5-yl}carbonyl)azetidin-3-yl]-4-(1,3-thiazol-2-ylcarbonyl)piperazine<br>$^1$H NMR (300 MHz, CD$_3$OD): δ 8.19 (d, 2H), 7.97 (d, 1H), 7.86 (d, 1H), 7.82 (d, 2H), 4.25-4.76 (m, 5H), 3.95 (m, 2H), 3.76 (m, 1H), 3.33 (m, 2H), 2.99 (m, 3H), 2.69 (s, 3H); LC/MS m/z (M + H⁺) 522.2 (calculated for C$_{23}$H$_{22}$F$_3$N$_5$O$_2$S$_2$, 521.59) |
| 137 | 1-(1,3-Thiazol-2-ylcarbonyl)-4-{1-[(3-thiophen-2-ylphenyl)carbonyl]azetidin-3-yl}piperazine<br>$^1$H NMR (300 MHz, CD$_3$OD): δ 7.97 (d, 1H), 7.91 (t, 1H), 7.88 (d, 1H), 7.83 (dt, 1H), 7.54 (m, 2H), 7.47 (dd, 2H), 7.13 (dd, 1H), 4.30-4.79 (m, 5H), 4.02 (m, 3H), 3.24 (m, 5H); LC/MS m/z (M + H⁺) 439.0 (calculated for C$_{22}$H$_{22}$N$_4$O$_2$S$_2$, 438.57) |
| 138 | 1-(1,3-Thiazol-2-ylcarbonyl)-4-{1-[(4-thiophen-2-ylphenyl)carbonyl]azetidin-3-yl}piperazine<br>$^1$H NMR (300 MHz, CD$_3$OD): δ 7.97 (d, 1H), 7.89 (d, 1H), 7.75 (m, 4H), 7.51 (m, 2H), 7.14 (m, 1H), 4.28-4.82 (m, 5H), 4.02 (m, 3H), 3.25 (m, 5H); LC/MS m/z (M + H⁺) 439.1 (calculated for C$_{22}$H$_{22}$N$_4$O$_2$S$_2$, 438.57) |
| 139 | 1-{1-[(3-Pyridin-2-ylphenyl)carbonyl]azetidin-3-yl}-4-(1,3-thiazol-2-ylcarbonyl)piperazine<br>LC/MS m/z (M + H⁺) 434.0 |
| 140 | 1-{1-[(3-Pyridin-3-ylphenyl)carbonyl]azetidin-3-yl}-4-(1,3-thiazol-2-ylcarbonyl)piperazine<br>LC/MS m/z (M + H⁺) 434.0 |
| 141 | 1-{1-[(3-Pyridin-4-ylphenyl)carbonyl]azetidin-3-yl}-4-(1,3-thiazol-2-ylcarbonyl)piperazine<br>LC/MS m/z (M + H⁺) 434.0 |
| 142 | 1-{1-[(4-Pyridin-3-ylphenyl)carbonyl]azetidin-3-yl}-4-(1,3-thiazol-2-ylcarbonyl)piperazine<br>LC/MS m/z (M + H⁺) 434.0 |
| 143 | 5-[3-({3-[4-(1,3-Thiazol-2-ylcarbonyl)piperazin-1-yl]azetidin-1-yl}carbonyl)phenyl]pyrimidine<br>LC/MS m/z (M + H⁺) 435.0 |
| 144 | 5-[4-({3-[4-(1,3-Thiazol-2-ylcarbonyl)piperazin-1-yl]azetidin-1-yl}carbonyl)phenyl]pyrimidine<br>LC/MS m/z (M + H⁺) 435.0 |
| 145 | 2-[3-({3-[4-(1,3-Thiazol-2-ylcarbonyl)piperazin-1-yl]azetidin-1-yl}carbonyl)phenyl]pyrimidine<br>LC/MS m/z (M + H⁺) 435.0 |
| 146 | 2-[4-({3-[4-(1,3-Thiazol-2-ylcarbonyl)piperazin-1-yl]azetidin-1-yl}carbonyl)phenyl]pyrimidine<br>LC/MS m/z (M + H⁺) 435.0 |
| 147 | 1-(1,3-Thiazol-2-ylcarbonyl)-4-(1-{[2'-(trifluoromethyl)biphenyl-4-yl]carbonyl}azetidin-3-yl)piperazine<br>$^1$H NMR (300 MHz, CD$_3$OD): δ 7.97 (d, 1H), 7.88 (d, 1H), 7.81 (d, 1H), 7.74 (d, 2H), 7.68 (t, 1H), 7.59 (t, 1H), 7.45 (d, 2H), 7.37 (d, 1H), 4.33-4.82 (m, 5H), 4.04 (m, 3H), 3.27 (m, 5H); LC/MS m/z (M + H⁺) 501.0 (calculated for C$_{25}$H$_{23}$F$_3$N$_4$O$_2$S, 500.55) |

-continued

| Cpd | Cpd Name and Data |
|---|---|
| 148 | 1-(1,3-Thiazol-2-ylcarbonyl)-4-(1-{[2'-(trifluoromethyl)biphenyl-3-yl]carbonyl}azetidin-3-yl)piperazine<br>$^1$H NMR (300 MHz, CD$_3$OD): δ 7.97 (d, 1H), 7.88 (d, 1H), 7.81 (d, 1H), 7.73 (dt, 1H), 7.67 (d, 1H), 7.49-7.64 (m, 4H), 7.39 (d, 1H), 4.30-4.81 (m, 5H), 4.03 (m, 3H), 3.25 (m, 5H); LC/MS m/z (M + H$^+$) 501.0 (calculated for C$_{25}$H$_{23}$F$_3$N$_4$O$_2$S, 500.55) |
| 149 | 1-(1,3-Thiazol-2-ylcarbonyl)-4-(1-{[4'-(trifluoromethyl)biphenyl-3-yl]carbonyl}azetidin-3-yl)piperazine<br>LC/MS m/z (M + H$^+$) 501.0 |
| 150 | 1-(1,3-Thiazol-2-ylcarbonyl)-4-(1-{[4'-(trifluoromethyl)biphenyl-4-yl]carbonyl}azetidin-3-yl)piperazine<br>$^1$H NMR (300 MHz, CD$_3$OD): δ 7.97 (d, 1H), 7.76-7.89 (m, 9H), 4.62-4.77 (m, 5H), 3.97 (m, 3H), 3.13 (m, 5H); LC/MS m/z (M + H$^+$) 501.0 (calculated for C$_{25}$H$_{23}$F$_3$N$_4$O$_2$S, 500.55) |
| 151 | 1-(1-{[3-(6-Bromopyridin-2-yl)phenyl]carbonyl}azetidin-3-yl)-4-(1,3-thiazol-2-ylcarbonyl)piperazine<br>$^1$H NMR (300 MHz, CD$_3$OD): δ 8.34 (t, 1H), 8.21 (dt, 1H), 7.97 (d, 1H), 7.94 (dd, 1H), 7.87 (d, 1H), 7.72-7.82 (m, 2H), 7.54-7.67 (m, 2H), 4.26-4.68 (m, 6H), 3.84-4.06 (m, 3H), 3.13 (m, 4H); LC/MS m/z (M + H$^+$) 512.0/513.9 (calculated for C$_{23}$H$_{22}$BrN$_5$O$_2$S, 512.43) |
| 152 | 1-(1-{[3-(5-Nitropyridin-2-yl)phenyl]carbonyl}azetidin-3-yl)-4-(1,3-thiazol-2-ylcarbonyl)piperazine<br>LC/MS m/z (M + H$^+$) 479.0 |
| 153 | 1-(1-{[4-(5-Nitropyridin-2-yl)phenyl]carbonyl}azetidin-3-yl)-4-(1,3-thiazol-2-ylcarbonyl)piperazine<br>LC/MS m/z (M + H$^+$) 479.0 |
| 154 | 1-(1-{[5-(4-Fluorophenyl)pyridin-2-yl]carbonyl}azetidin-3-yl)-4-(1,3-thiazol-2-ylcarbonyl)piperazine<br>LC/MS m/z (M + H$^+$) 452.0 |
| 155 | 1-(1-{[2-(4-Fluorophenyl)-1,3-thiazol-4-yl]carbonyl}azetidin-3-yl)-4-(1,3-thiazol-2-ylcarbonyl)piperazine<br>LC/MS m/z (M + H$^+$) 458.0 |
| 156 | 1-(1-{[2-(3-Fluorophenyl)-1,3-thiazol-4-yl]carbonyl}azetidin-3-yl)-4-(1,3-thiazol-2-ylcarbonyl)piperazine<br>LC/MS m/z (M + H$^+$) 458.0 |
| 157 | 1-(1-{[2-(2,4-Dichlorophenyl)-1,3-thiazol-4-yl]carbonyl}azetidin-3-yl)-4-(1,3-thiazol-2-ylcarbonyl)piperazine<br>LC/MS m/z (M + H$^+$) 507.9 |
| 158 | 1-(1-{[2-(3,5-Dichlorophenyl)-1,3-thiazol-4-yl]carbonyl}azetidin-3-yl)-4-(1,3-thiazol-2-ylcarbonyl)piperazine<br>$^1$H NMR (300 MHz, CD$_3$OD): δ 8.31 (s, 1H), 7.89 (m, 3H), 7.79 (d, 1H), 7.52 (t, 1H), 5.01 (m, 1H), 4.84 (m, 2H), 4.65 (m, 1H), 4.38 (dd, 1H), 4.26 (dd, 1H), 3.93 (m, 3H), 3.17 (m, 4H); LC/MS m/z (M + H$^+$) 507.9 (calculated for C$_{21}$H$_{19}$Cl$_2$N$_5$O$_2$S$_2$, 508.45) |
| 159 | 1-(1-{[2-(4-Methoxyphenyl)-1,3-thiazol-4-yl]carbonyl}azetidin-3-yl)-4-(1,3-thiazol-2-ylcarbonyl)piperazine<br>LC/MS m/z (M + H$^+$) 470.0 |
| 160 | 1-{1-[(2-Phenyl-1,3-thiazol-4-yl)carbonyl]azetidin-3-yl}-4-(1,3-thiazol-2-ylcarbonyl)piperazine<br>LC/MS m/z (M + H$^+$) 440.0 |
| 161 | 4'-({3-[4-(1,3-Thiazol-2-ylcarbonyl)piperazin-1-yl]azetidin-1-yl}carbonyl)biphenyl-3-carbonitrile<br>$^1$H NMR (300 MHz, DMSO-d$_6$): δ 8.10 (d, 1H), 8.06 (d, 1H), 7.78-7.86 (m, 3H), 7.68-7.77 (m, 3H), 7.46-7.58 (m, 2H), 4.62 (m, 2H), 4.40 (m, 1H), 4.30 (m, 1H), 4.08 (m, 1H), 4.27-3.87 (m, 6H), 3.12 (m, 2H); LC/MS m/z (M + H$^+$) 458.1 (calculated for C$_{25}$H$_{23}$N$_5$O$_2$S, 457.56) |
| 162 | 1-{1-[(3'-Chlorobiphenyl-4-yl)carbonyl]azetidin-3-yl}-4-(1,3-thiazol-2-ylcarbonyl)piperazine<br>$^1$H NMR (300 MHz, DMSO-d$_6$): δ 8.10 (d, 1H), 8.06 (d, 1H), 7.78-7.86 (m, 3H), 7.68-7.77 (m, 3H), 7.46-7.58 (m, 2H), 4.61 (m, 2H), 4.37 (m, 1H), 4.29 (m, 1H), 4.05 (m, 1H), 4.30-3.84 (m, 6H), 3.08 (m, 2H); LC/MS m/z (M + H$^+$) 467.1 (calculated for C$_{24}$H$_{23}$ClN$_4$O$_2$S, 466.99) |
| 163 | 1-{1-[(4'-Chlorobiphenyl-4-yl)carbonyl]azetidin-3-yl}-4-(1,3-thiazol-2-ylcarbonyl)piperazine<br>$^1$H NMR (300 MHz, CD$_3$OD): δ 7.98 (d, 1H), 7.88 (d, 1H), 7.76 (m, 4H), 7.66 (m, 2H), 7.48 (m, 2H), 4.71 (m, 3H), 4.58 (m, 1H), 4.47 (m, 1H), 4.36 (m, 1H), 4.02 (m, 3H), 3.23 (m, 4H); LC/MS m/z (M + H$^+$) 467.1 (calculated for C$_{24}$H$_{23}$ClN$_4$O$_2$S, 466.99) |

-continued

| Cpd | Cpd Name and Data |
|---|---|
| 164 | 1-{1-[(3',5'-Dichlorobiphenyl-4-yl)carbonyl]azetidin-3-yl}-4-(1,3-thiazol-2-ylcarbonyl)piperazine<br>$^1$H NMR (300 MHz, CD$_3$OD): δ 7.88 (d, 1H), 7.78 (d, 1H), 7.68 (m, 4H), 7.55 (d, 2H), 7.39 (t, 1H), 4.57 (m, 3H), 4.45 (m, 1H), 4.35 (m, 1H), 4.23 (m, 1H), 3.91 (m, 2H), 3.81 (m, 1H), 3.03 (m, 4H); LC/MS m/z (M + H$^+$) 501.0 (calculated for C$_{24}$H$_{22}$Cl$_2$N$_4$O$_2$S, 501.44) |
| 165 | 1-{1-[(5-Phenylpyridin-3-yl)carbonyl]azetidin-3-yl}-4-(1,3-thiazol-2-ylcarbonyl)piperazine<br>LC/MS m/z (M + H$^+$) 434.1 |
| 166 | 1-{1-[(2-Fluorobiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.37-7.67 (m, 8H), 4.66 (m, 3H), 4.53 (m, 1H), 4.42 (m, 1H), 4.30 (m, 1H), 3.98 (m, 2H), 3.85 (m, 1H), 3.07 (m, 4H); LC/MS m/z (M + H$^+$) 451.0 (calculated for C$_{24}$H$_{23}$FN$_4$O$_2$S, 450.54) |
| 167 | 4'-({3-[4-(1,3-Thiazol-2-ylcarbonyl)piperazin-1-yl]azetidin-1-yl}carbonyl)biphenyl-4-carbonitrile<br>$^1$H NMR (300 MHz, CD$_3$OD): δ 7.98 (d, 1H), 7.77-7.92 (m, 9 H), 4.63-4.79 (m, 3H), 4.57 (m, 1H), 4.46 (m, 1H), 4.35 (m, 1H), 3.90-4.13 (m, 3 H), 3.19 (m, 4 H); LC/MS m/z (M + H$^+$) 458.1 (calculated for C$_{25}$H$_{23}$N$_5$O$_2$S, 457.56) |
| 168 | 1-{1-[(4'-Bromobiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.76 (m, 4H), 7.62 (dd, 4H), 4.67 (m, 3H), 4.51 (m, 1H), 4.44 (m, 1H), 4.30 (m, 1H), 3.98 (m, 2H), 3.88 (m, 1H), 3.10 (m, 4H); LC/MS m/z (M + H$^+$) 511.0/513.0 (calculated for C$_{24}$H$_{23}$BrN$_4$O$_2$S, 511.44) |
| 169 | 1-{1-[(5-Phenylpyridin-3-yl)carbonyl]azetidin-3-yl}-4-(1,3-thiazol-4-ylcarbonyl)piperazine<br>LC/MS m/z (M + H$^+$) 434.1 |
| 170 | 1-{1-[(2-Fluorobiphenyl-4-yl)carbonyl]azetidin-3-yl}-4-(1,3-thiazol-4-ylcarbonyl)piperazine<br>$^1$H NMR (300 MHz, CD$_3$OD): δ 9.06 (s, 1H), 8.22 (s, 1H), 7.37-7.67 (m, 8H), 4.70 (m, 1H), 4.57 (m, 1H), 4.45 (m, 1H), 4.34 (m, 1H), 4.11 (m, 4H), 3.99 (m, 1H), 3.17 (m, 4H); LC/MS m/z (M + H$^+$) 451.0 (calculated for C$_{24}$H$_{23}$FN$_4$O$_2$S, 450.54) |
| 171 | 4'-({3-[4-(1,3-Thiazol-4-ylcarbonyl)piperazin-1-yl]azetidin-1-yl}carbonyl)biphenyl-4-carbonitrile<br>LC/MS m/z (M + H$^+$) 458.1 |
| 172 | 1-{1-[(4'-Bromobiphenyl-4-yl)carbonyl]azetidin-3-yl}-4-(1,3-thiazol-4-ylcarbonyl)piperazine<br>$^1$H NMR (300 MHz, CD$_3$OD): δ 9.06 (s, 1H), 8.22 (s, 1H), 7.76 (m, 4H), 7.61 (dd, 4H), 4.68 (m, 1H), 4.57 (m, 1H), 4.46 (m, 1H), 4.36 (m, 1H), 4.15 (m, 4H), 4.04 (m, 1H), 3.22 (m, 4H); LC/MS m/z (M + H$^+$) 511.0/513.0 (calculated for C$_{24}$H$_{23}$BrN$_4$O$_2$S, 511.44) |
| 475 | 1-{1-[(4-Phenylcyclohexyl)carbonyl]azetidin-3-yl}-4-(1,3-thiazol-2-ylcarbonyl)piperazine<br>MS m/z (M + H$^+$) 439.2 |
| 476 | 3-Methyl-2-phenyl-8-({3-[4-(1,3-thiazol-2-ylcarbonyl)piperazin-1-yl]azetidin-1-yl}carbonyl)-4H-chromen-4-one<br>MS m/z (M + H$^+$) 515.2 |
| 477 | 1-[1-(3-Phenylprop-2-ynoyl)azetidin-3-yl]-4-(1,3-thiazol-2-ylcarbonyl)piperazine<br>MS m/z (M + H$^+$) 381.1 |
| 478 | Phenyl-[4-({3-[4-(1,3-thiazol-4-ylcarbonyl)piperazin-1-yl]azetidin-1-yl}carbonyl)cyclohexyl]methanone<br>MS m/z (M + H$^+$) 467.2 |
| 479 | 1-[1-({2-[(4-Methylphenyl)sulfanyl]pyridin-3-yl}carbonyl)azetidin-3-yl]-4-(1,3-thiazol-4-ylcarbonyl)piperazine<br>MS m/z (M + H$^+$) 480.1 |
| 298 | 1-(1-{[5-(4-Methylphenyl)-1H-pyrrol-2-yl]carbonyl}azetidin-3-yl)-4-(1,3-thiazol-4-ylcarbonyl)piperazine<br>LC/MS m/z (M + H$^+$) 436.2 |
| 112 | 2-Methyl-4-{1-[(4-phenoxyphenyl)carbonyl]azetidin-3-yl}-1-(1,3-thiazol-2-ylcarbonyl)piperazine<br>MS m/z (M + H$^+$) 463.2 (calculated for C$_{25}$H$_{26}$N$_4$O$_3$S, 462.57) |
| 113 | 2-Methyl-4-{1-[(3-phenoxyphenyl)carbonyl]azetidin-3-yl}-1-(1,3-thiazol-2-ylcarbonyl)piperazine<br>MS m/z (M + H$^+$) 463.2 (calculated for C$_{25}$H$_{26}$N$_4$O$_3$S, 462.57) |
| 114 | 1-[1-(Biphenyl-4-ylcarbonyl)azetidin-3-yl]-2-phenyl-4-(1,3-thiazol-2-ylcarbonyl)piperazine<br>MS m/z (M + H$^+$) 509.0 (calculated for C$_{30}$H$_{28}$N$_4$O$_2$S, 508.65) |
| 115 | 4-{1-[(4-Benzylphenyl)carbonyl]azetidin-3-yl}-2-methyl-1-(1,3-thiazol-2-ylcarbonyl)piperazine<br>MS m/z (M + H$^+$) 461.0 (calculated for C$_{26}$H$_{28}$N$_4$O$_2$S, 460.60) |

-continued

| Cpd | Cpd Name and Data |
|---|---|
| 116 | 4-[1-(Biphenyl-3-ylcarbonyl)azetidin-3-yl]-2-methyl-1-(1,3-thiazol-2-ylcarbonyl)piperazine<br>MS m/z (M + H$^+$) 446.9 (calculated for C$_{25}$H$_{26}$N$_4$O$_2$S, 446.58) |
| 117 | 4-[1-(Biphenyl-4-ylcarbonyl)azetidin-3-yl]-2-methyl-1-(1,3-thiazol-2-ylcarbonyl)piperazine<br>MS m/z (M + H$^+$) 447.3 (calculated for C$_{25}$H$_{26}$N$_4$O$_2$S, 446.58) |
| 489 | 1-(1-{[2-(4-Chlorophenyl)-4-methyl-1,3-thiazol-5-yl]carbonyl}azetidin-3-yl)-4-(1,3-thiazol-2-ylcarbonyl)piperazine<br>$^1$H NMR (300 MHz, CD$_3$OD): δ 7.81-8.02 (m, 4H), 7.52 (d, 2H), 4.30-4.64 (m, 6H) 3.84-4.09 (m, 3H), 3.10-3.29 (m, 4H), 2.67 (s, 3H); LC/MS m/z (M + H$^+$) 488.1 (calculated for C$_{22}$H$_{22}$ClN$_5$O$_2$S$_2$, 488.03) |
| 490 | 1-(1-{[2-(3-Chlorophenyl)-4-methyl-1,3-thiazol-5-yl]carbonyl}azetidin-3-yl)-4-(1,3-thiazol-2-ylcarbonyl)piperazine<br>$^1$H NMR (300 MHz, CD$_3$OD): δ 7.95-8.05 (m, 2H), 7.84-7.94 (m, 2H), 7.45-7.60 (m, 2H), 4.32-4.84 (m, 6H) 3.92-4.09 (m, 3H), 3.15-3.27 (m, 4H), 2.68 (s, 3H); LC/MS m/z (M + H$^+$) 488.1 (calculated for C$_{22}$H$_{22}$ClN$_5$O$_2$S$_2$, 488.03) |
| 485 | 1-[1-({4-Methyl-2-[3-(trifluoromethyl)phenyl]-1,3-thiazol-5-yl}carbonyl)azetidin-3-yl]-4-(1,3-thiazol-4-ylcarbonyl)piperazine<br>$^1$H NMR (300 MHz, CD$_3$OD): δ 9.06 (s, 1H), 8.16-8.36 (m, 3H), 7.79-7.89 (m, 1H), 7.66-7.78 (m, 1H), 4.23-4.76 (m, 4H) 3.84-4.22 (m, 5H), 3.04-3.22 (m, 4H), 2.70 (s, 3H); LC/MS m/z (M + H$^+$) 522.2 (calculated for C$_{23}$H$_{22}$F$_2$N$_5$O$_2$S$_2$, 521.59) |
| 744 | 2,3-Dimethyl-N-[2-({3-[4-(1,3-thiazol-2-ylcarbonyl)piperazin-1-yl]azetidin-1-yl}carbonyl)phenyl]aniline<br>MS m/z (M + H$^+$) 476.1 |
| 1297 | 1-{1-[(1,5-Diphenyl-1H-pyrazol-4-yl)carbonyl]azetidin-3-yl}-4-(1,3-thiazol-2-ylcarbonyl)piperazine<br>MS m/z (M + H$^+$) 499.1 |
| 768 | 2-({3-[4-(1,3-Thiazol-2-ylcarbonyl)piperazin-1-yl]azetidin-1-yl}carbonyl)-N-[3-(trifluoromethyl)phenyl]aniline<br>MS m/z (M + H$^+$) 516.2 |
| 781 | N-Phenyl-2-({3-[4-(1,3-thiazol-2-ylcarbonyl)piperazin-1-yl]azetidin-1-yl}carbonyl)aniline<br>MS m/z (M + H$^+$) 448.0 |
| 1460 | N-(3-Bromophenyl)-2-({3-[4-(1,3-thiazol-2-ylcarbonyl)piperazin-1-yl]azetidin-1-yl}carbonyl)benzamide<br>MS m/z (M + H$^+$) 552.0/554.0 |
| 1214 | 1-(1-{[5-Methyl-2-(4-methylphenyl)-2H-1,2,3-triazol-4-yl]carbonyl}azetidin-3-yl)-4-(1,3-thiazol-2-ylcarbonyl)piperazine<br>MS m/z (M + H$^+$) 452.1 |
| 754 | N-(3-Fluorophenyl)-2-({3-[4-(1,3-thiazol-2-ylcarbonyl)piperazin-1-yl]azetidin-1-yl}carbonyl)aniline<br>MS m/z (M + H$^+$) 466.0 |
| 1103 | 1-(1-{[5-(4-Chlorophenyl)-1-(2,4-dichlorophenyl)-4-methyl-1H-pyrazol-3-yl]carbonyl}azetidin-3-yl)-4-(1,3-thiazol-2-ylcarbonyl)piperazine<br>MS m/z (M + H$^+$) 615.0 |
| 886 | 1-[1-(Phenoxathiin-2-ylcarbonyl)azetidin-3-yl]-4-(1,3-thiazol-2-ylcarbonyl)piperazine<br>MS m/z (M + H$^+$) 479.1 |
| 1301 | 1-(1-{[1-(4-Fluorophenyl)-3,5-dimethyl-1H-pyrazol-4-yl]carbonyl}azetidin-3-yl)-4-(1,3-thiazol-2-ylcarbonyl)piperazine<br>MS m/z (M + H$^+$) 469.1 |
| 1164 | 1-{1-[(1,5-Diphenyl-1H-pyrazol-3-yl)carbonyl]azetidin-3-yl}-4-(1,3-thiazol-2-ylcarbonyl)piperazine<br>MS m/z (M + H$^+$) 499.1 |
| 1218 | 1-(1-{[2-(4-Chlorophenyl)-5-methyl-2H-1,2,3-triazol-4-yl]carbonyl}azetidin-3-yl)-4-(1,3-thiazol-2-ylcarbonyl)piperazine<br>MS m/z (M + H$^+$) 472.1 |
| 843 | 4-[4-({3-[4-(1,3-Thiazol-2-ylcarbonyl)piperazin-1-yl]azetidin-1-yl}carbonyl)phenyl]thiomorpholine 1,1-dioxide<br>MS m/z (M + H$^+$) 490.0 |
| 815 | 4-[4-({3-[4-(1,3-Thiazol-2-ylcarbonyl)piperazin-1-yl]azetidin-1-yl}carbonyl)phenyl]morpholine<br>MS m/z (M + H$^+$) 442.0 |
| 1249 | 1-(1,3-Thiazol-2-ylcarbonyl)-4-[1-({4-[3-(trifluoromethyl)-1H-pyrazol-1-yl]phenyl}carbonyl)azetidin-3-yl]piperazine<br>MS m/z (M + H$^+$) 491.1 |

-continued

| Cpd | Cpd Name and Data |
|---|---|
| 1300 | 1-{1-[(2-Phenyl-2H-1,2,3-triazol-4-yl)carbonyl]azetidin-3-yl}-4-(1,3-thiazol-2-ylcarbonyl)piperazine<br>MS m/z (M + H$^+$) 424.0 |
| 646 | 4-[4-({3-[4-(1,3-Thiazol-2-ylcarbonyl)piperazin-1-yl]azetidin-1-yl}carbonyl)piperidin-1-yl]benzonitrile<br>MS m/z (M + H$^+$) 465.1 |
| 763 | 6-({3-[4-(1,3-Thiazol-2-ylcarbonyl)piperazin-1-yl]azetidin-1-yl}carbonyl)-2,3,4,9-tetrahydro-1H-carbazole<br>MS m/z (M + H$^+$) 450.1 |
| 750 | 9-Methyl-3-({3-[4-(1,3-thiazol-2-ylcarbonyl)piperazin-1-yl]azetidin-1-yl}carbonyl)-9H-carbazole<br>MS m/z (M + H$^+$) 460.2 |
| 795 | N-Benzyl-5-({3-[4-(1,3-thiazol-2-ylcarbonyl)piperazin-1-yl]azetidin-1-yl}carbonyl)-1,3-thiazol-2-amine<br>MS m/z (M + H$^+$) 469.0 |
| 1225 | 1-(1-{[1-(3,4-Dichlorophenyl)-3,5-dimethyl-1H-pyrazol-4-yl]carbonyl}azetidin-3-yl)-4-(1,3-thiazol-2-ylcarbonyl)piperazine<br>MS m/z (M + H$^+$) 519.0 |
| 636 | 1-(1-Hexadecanoylazetidin-3-yl)-4-(1,3-thiazol-2-ylcarbonyl)piperazine<br>MS m/z (M + H$^+$) 491.4 |
| 687 | 1-Propyl-5-({3-[4-(1,3-thiazol-2-ylcarbonyl)piperazin-1-yl]azetidin-1-yl}carbonyl)-1H-indole<br>MS m/z (M + H$^+$) 438.3 |
| 776 | 1-{1-[(3,5-Di-tert-butylphenyl)carbonyl]azetidin-3-yl}-4-(1,3-thiazol-2-ylcarbonyl)piperazine<br>MS m/z (M + H$^+$) 469.4 |
| 637 | 1-(1-{[4-(4-Chlorophenyl)cyclohexyl]carbonyl}azetidin-3-yl)-4-(1,3-thiazol-2-ylcarbonyl)piperazine<br>MS m/z (M + H$^+$) 473.2 |
| 672 | 1-{1-[(4-tert-Butylphenyl)carbonyl]azetidin-3-yl}-4-(1,3-thiazol-2-ylcarbonyl)piperazine<br>MS m/z (M + H$^+$) 413.3 |
| 669 | 1-{1-[(4-Pyrrolidin-1-ylphenyl)carbonyl]azetidin-3-yl}-4-(1,3-thiazol-2-ylcarbonyl)piperazine<br>MS m/z (M + H$^+$) 426.3 |
| 887 | 1-(1-{[4-(1,1-Dimethylpropyl)phenyl]carbonyl}azetidin-3-yl)-4-(1,3-thiazol-2-ylcarbonyl)piperazine<br>MS m/z (M + H$^+$) 427.2 |
| 1434 | 1-[1-(4-Phenylbutanoyl)azetidin-3-yl]-4-(1,3-thiazol-2-ylcarbonyl)piperazine<br>MS m/z (M + H$^+$) 399.3 |
| 888 | 1-[4-({3-[4-(1,3-Thiazol-2-ylcarbonyl)piperazin-1-yl]azetidin-1-yl}carbonyl)phenyl]azepane<br>MS m/z (M + H$^+$) 454.4 |
| 889 | 1-{1-[(4-Cyclohexylphenyl)carbonyl]azetidin-3-yl}-4-(1,3-thiazol-2-ylcarbonyl)piperazine<br>MS m/z (M + H$^+$) 439.2 |
| 890 | 1-{1-[(1-Chloronaphtho[2,1-b]thiophen-2-yl)carbonyl]azetidin-3-yl}-4-(1,3-thiazol-2-ylcarbonyl)piperazine<br>MS m/z (M + H$^+$) 497.1 |
| 891 | 1-(1-{[4-(2-Methylpropyl)phenyl]carbonyl}azetidin-3-yl)-4-(1,3-thiazol-2-ylcarbonyl)piperazine<br>MS m/z (M + H$^+$) 413.3 |
| 892 | 1-{1-[(4-Heptylphenyl)carbonyl]azetidin-3-yl}-4-(1,3-thiazol-2-ylcarbonyl)piperazine<br>MS m/z (M + H$^+$) 455.3 |
| 893 | 1-{1-[(4-Pentylphenyl)carbonyl]azetidin-3-yl}-4-(1,3-thiazol-2-ylcarbonyl)piperazine<br>MS m/z (M + H$^+$) 427.2 |
| 655 | 1-{1-[(4-Propylphenyl)carbonyl]azetidin-3-yl}-4-(1,3-thiazol-2-ylcarbonyl)piperazine<br>MS m/z (M + H$^+$) 399.1 |
| 894 | 1-{1-[(4-Butylphenyl)carbonyl]azetidin-3-yl}-4-(1,3-thiazol-2-ylcarbonyl)piperazine<br>MS m/z (M + H$^+$) 413.3 |
| 849 | 1-{1-[(5-tert-Butyl-2-methoxyphenyl)carbonyl]azetidin-3-yl}-4-(1,3-thiazol-2-ylcarbonyl)piperazine<br>MS m/z (M + H$^+$) 443.2 |
| 639 | 1-{1-[(5Z,8Z,11Z,14Z)-Icosa-5,8,11,14-tetraenoyl]azetidin-3-yl}-4-(1,3-thiazol-2-ylcarbonyl)piperazine<br>MS m/z (M + H$^+$) 539.4 |
| 641 | 1-{1-[(9Z)-Octadec-9-enoyl]azetidin-3-yl}-4-(1,3-thiazol-2-ylcarbonyl)piperazine<br>MS m/z (M + H$^+$) 517.3 |

-continued

| Cpd | Cpd Name and Data |
|---|---|
| 638 | 1-{1-[(9Z,12Z)-Octadeca-9,12-dienoyl]azetidin-3-yl}-4-(1,3-thiazol-2-ylcarbonyl)piperazine<br>MS m/z (M + H$^+$) 515.4 |
| 1017 | Phenyl[4-({3-[4-(1,3-thiazol-2-ylcarbonyl)piperazin-1-yl]azetidin-1-yl}carbonyl)phenyl]methanone<br>MS m/z (M + H$^+$) 461.1 |
| 1082 | 1-[1-({4-[4-(4-Fluorophenyl)-1,3-thiazol-2-yl]phenyl}carbonyl)azetidin-3-yl]-4-(1,3-thiazol-2-ylcarbonyl)piperazine<br>MS m/z (M + H$^+$) 534.2 |
| 1245 | 1-[1-({4-[5-(4-Methylphenyl)-1H-1,2,3-triazol-1-yl]phenyl}carbonyl)azetidin-3-yl]-4-(1,3-thiazol-2-ylcarbonyl)piperazine<br>MS m/z (M + H$^+$) 500.1 |
| 1326 | 1-(1-{[4-(4-Phenyl-1,3-thiazol-2-yl)phenyl]carbonyl}azetidin-3-yl)-4-(1,3-thiazol-2-ylcarbonyl)piperazine<br>MS m/z (M + H$^+$) 516.2 |
| 1327 | 3-(4-Chlorophenyl)-2-[4-({3-[4-(1,3-thiazol-2-ylcarbonyl)piperazin-1-yl]azetidin-1-yl}carbonyl)phenyl]-4,5,6,7-tetrahydro-2H-indazole<br>MS m/z (M + H$^+$) 587.3 |
| 1179 | 1-(1-{[4-(4,5-Diphenyl-1H-imidazol-2-yl)phenyl]carbonyl}azetidin-3-yl)-4-(1,3-thiazol-2-ylcarbonyl)piperazine<br>MS m/z (M + H$^+$) 575.2 |
| 693 | 1-(1-{[3-Chloro-4-(trifluoromethoxy)phenyl]carbonyl}azetidin-3-yl)-4-(1,3-thiazol-2-ylcarbonyl)piperazine<br>MS m/z (M + H$^+$) 475.0 |
| 667 | 4-(3-Chlorophenyl)-8-({3-[4-(1,3-thiazol-2-ylcarbonyl)piperazin-1-yl]azetidin-1-yl}carbonyl)-3a,4,5,9b-tetrahydro-3H-cyclopenta[c]quinoline<br>MS m/z (M + H$^+$) 560.2 |
| 1328 | 1-[1-({4-[4-(2-Chlorophenyl)-1,3-thiazol-2-yl]phenyl}carbonyl)azetidin-3-yl]-4-(1,3-thiazol-2-ylcarbonyl)piperazine<br>MS m/z (M + H$^+$) 550.0 |
| 1329 | 1-[1-({4-[4-(2,4-Dichlorophenyl)-1,3-thiazol-2-yl]phenyl}carbonyl)azetidin-3-yl]-4-(1,3-thiazol-2-ylcarbonyl)piperazine<br>MS m/z (M + H$^+$) 584.1 |
| 640 | 1-(1-Icosanoylazetidin-3-yl)-4-(1,3-thiazol-2-ylcarbonyl)piperazine<br>MS m/z (M + H$^+$) 547.3 |
| 1156 | 1-[1-({4-[5-(4-Methylphenyl)-1,3,4-oxadiazol-2-yl]phenyl}carbonyl)azetidin-3-yl]-4-(1,3-thiazol-2-ylcarbonyl)piperazine<br>MS m/z (M + H$^+$) 515.2 |
| 1330 | 2-[4-({3-[4-(1,3-Thiazol-2-ylcarbonyl)piperazin-1-yl]azetidin-1-yl}carbonyl)phenyl]-3-[3-(trifluoromethyl)phenyl]-2,4,5,6-tetrahydrocyclopenta[c]pyrazole<br>MS m/z (M + H$^+$) 607.3 |
| 826 | 7-Chloro-2-methyl-3-({3-[4-(1,3-thiazol-2-ylcarbonyl)piperazin-1-yl]azetidin-1-yl}carbonyl)quinoline<br>MS m/z (M + H$^+$) 456.1 |
| 797 | 6-Chloro-3-({3-[4-(1,3-thiazol-2-ylcarbonyl)piperazin-1-yl]azetidin-1-yl}carbonyl)quinoline<br>MS m/z (M + H$^+$) 442.2 |
| 787 | 7-Chloro-3-({3-[4-(1,3-thiazol-2-ylcarbonyl)piperazin-1-yl]azetidin-1-yl}carbonyl)quinoline<br>MS m/z (M + H$^+$) 442.2 |
| 835 | 6-Chloro-2-methyl-3-({3-[4-(1,3-thiazol-2-ylcarbonyl)piperazin-1-yl]azetidin-1-yl}carbonyl)quinoline<br>MS m/z (M + H$^+$) 456.1 |
| 743 | 6,7-Dichloro-3-({3-[4-(1,3-thiazol-2-ylcarbonyl)piperazin-1-yl]azetidin-1-yl}carbonyl)quinoline<br>MS m/z (M + H$^+$) 476.1 |
| 1331 | 1-[1-({4-[4-(3,4-Dichlorophenyl)-1,3-thiazol-2-yl]phenyl}carbonyl)azetidin-3-yl]-4-(1,3-thiazol-2-ylcarbonyl)piperazine<br>MS m/z (M + H$^+$) 584.1 |
| 727 | 1-{1-[(4-Bromo-3-methylphenyl)carbonyl]azetidin-3-yl}-4-(1,3-thiazol-2-ylcarbonyl)piperazine<br>MS m/z (M + H$^+$) 447.1/449.1 |
| 786 | 1-{1-[(4-Bromo-2-methylphenyl)carbonyl]azetidin-3-yl}-4-(1,3-thiazol-2-ylcarbonyl)piperazine<br>MS m/z (M + H$^+$) 447.1/449.1 |
| 766 | 1-{1-[(2,2-Dimethyl-2,3-dihydro-1-benzofuran-5-yl)carbonyl]azetidin-3-yl}-4-(1,3-thiazol-2- |

-continued

| Cpd | Cpd Name and Data |
|---|---|
| | ylcarbonyl)piperazine<br>MS m/z (M + H⁺) 427.2 |
| 658 | N,N-Dipropyl-4-({3-[4-(1,3-thiazol-2-ylcarbonyl)piperazin-1-yl]azetidin-1-yl}carbonyl)benzenesulfonamide<br>MS m/z (M + H⁺) 520.2 |
| 816 | N-Ethyl-2-[4-({3-[4-(1,3-thiazol-2-ylcarbonyl)piperazin-1-yl]azetidin-1-yl}carbonyl)phenoxy]acetamide<br>MS m/z (M + H⁺) 458.3 |
| 874 | Phenyl[5-({3-[4-(1,3-thiazol-2-ylcarbonyl)piperazin-1-yl]azetidin-1-yl}carbonyl)-1H-pyrrol-3-yl]methanone<br>MS m/z (M + H⁺) 450.1 |
| 1332 | 1-(1,3-Thiazol-2-ylcarbonyl)-4-{1-[(4-{3-(trifluoromethyl)phenyl]-1,3-thiazol-2-yl}phenyl)carbonyl]azetidin-3-yl}piperazine<br>MS m/z (M + H⁺) 584.1 |
| 1333 | 2-Phenyl-6-({3-[4-(1,3-thiazol-2-ylcarbonyl)piperazin-1-yl]azetidin-1-yl}carbonyl)-1H-indole<br>MS m/z (M + H⁺) 472.2 |
| 1083 | 1-(1-{[5-(4-Chlorophenyl)-1-(3,4-dichlorophenyl)-1H-pyrazol-3-yl]carbonyl}azetidin-3-yl)-4-(1,3-thiazol-2-ylcarbonyl)piperazine<br>MS m/z (M + H⁺) 601.0 |
| 788 | 1-(1-{[2,5-Dimethyl-1-(2,2,2-trifluoroethyl)-1H-pyrrol-3-yl]carbonyl}azetidin-3-yl)-4-(1,3-thiazol-2-ylcarbonyl)piperazine<br>MS m/z (M + H⁺) 456.1 |
| 702 | 2-Chloro-5-fluoro-N-[4-({3-[4-(1,3-thiazol-2-ylcarbonyl)piperazin-1-yl]azetidin-1-yl}carbonyl)phenyl]benzamide<br>MS m/z (M + H⁺) 529.0 |
| 770 | 1-[1-[(3,4-Dihydro-2H-1,5-benzodioxepin-7-ylcarbonyl)azetidin-3-yl]-4-(1,3-thiazol-2-ylcarbonyl)piperazine<br>MS m/z (M + H⁺) 429.1 |
| 783 | 2-Methyl-5-({3-[4-(1,3-thiazol-2-ylcarbonyl)piperazin-1-yl]azetidin-1-yl}carbonyl)-1,3-benzothiazole<br>MS m/z (M + H⁺) 428.1 |
| 694 | 1-(1,3-Thiazol-2-ylcarbonyl)-4-[1-({4-[(2,2,2-trifluoroethoxy)methyl]phenyl}carbonyl)azetidin-3-yl]piperazine<br>MS m/z (M + H⁺) 469.2 |
| 836 | N-{2-[4-({3-[4-(1,3-Thiazol-2-ylcarbonyl)piperazin-1-yl]azetidin-1-yl}carbonyl)phenoxy]ethyl}acetamide<br>MS m/z (M + H⁺) 458.3 |
| 730 | 1-(1,3-Thiazol-2-ylcarbonyl)-4-(1-{[4-(2,2,2-trifluoroethoxy)phenyl]carbonyl}azetidin-3-yl)piperazine<br>MS m/z (M + H⁺) 455.1 |
| 1334 | 1-[1-({4-[4-(4-Chlorophenyl)-1H-pyrazol-1-yl]phenyl}carbonyl)azetidin-3-yl]-4-(1,3-thiazol-2-ylcarbonyl)piperazine<br>MS m/z (M + H⁺) 533.1 |
| 1203 | 1-(4-Fluorophenyl)-3-methyl-5-({3-[4-(1,3-thiazol-2-ylcarbonyl)piperazin-1-yl]azetidin-1-yl}carbonyl)-1H-pyrazolo[3,4-b]pyridine<br>MS m/z (M + H⁺) 506.2 |
| 1146 | 3-Methyl-5-({3-[4-(1,3-thiazol-2-ylcarbonyl)piperazin-1-yl]azetidin-1-yl}carbonyl)-1-[3-(trifluoromethyl)phenyl]-1H-thieno[2,3-c]pyrazole<br>MS m/z (M + H⁺) 561.0 |
| 1272 | 1-{1-[(4-Methyl-2-pyridin-4-yl-1,3-thiazol-5-yl)carbonyl]azetidin-3-yl}-4-(1,3-thiazol-2-ylcarbonyl)piperazine<br>MS m/z (M + H⁺) 455.1 |
| 1119 | 2,3-Diphenyl-6-({3-[4-(1,3-thiazol-2-ylcarbonyl)piperazin-1-yl]azetidin-1-yl}carbonyl)-1H-indole<br>MS m/z (M + H⁺) 548.2 |
| 824 | 3-Methyl-2-({3-[4-(1,3-thiazol-2-ylcarbonyl)piperazin-1-yl]azetidin-1-yl}carbonyl)-7,8-dihydropyrrolo[1,2-a]thieno[2,3-d]pyrimidin-4(6H)-one<br>MS m/z (M + H⁺) 485.1 |
| 710 | 3-({3-[4-(1,3-Thiazol-2-ylcarbonyl)piperazin-1-yl]azetidin-1-yl}carbonyl)-9H-xanthen-9-one<br>MS m/z (M + H⁺) 475.1 |
| 823 | 5,7-Dichloro-2-methyl-3-({3-[4-(1,3-thiazol-2-ylcarbonyl)piperazin-1-yl]azetidin-1-yl}carbonyl)quinoline<br>MS m/z (M + H⁺) 490.0 |
| 782 | 1-(1-{[4-(2-Methoxyethoxy)phenyl]carbonyl}azetidin-3-yl)-4-(1,3-thiazol-2-ylcarbonyl)piperazine<br>MS m/z (M + H⁺) 431.3 |

-continued

| Cpd | Cpd Name and Data |
|---|---|
| 698 | 2-({3-[4-(1,3-Thiazol-2-ylcarbonyl)piperazin-1-yl]azetidin-1-yl}carbonyl)-9H-fluoren-9-one<br>MS m/z (M + H$^+$) 459.1 |
| 1123 | 1-[1-({4-[4-(3,5-Difluorophenyl)-1H-pyrazol-1-yl]phenyl}carbonyl)azetidin-3-yl]-4-(1,3-thiazol-2-ylcarbonyl)piperazine<br>MS m/z (M + H$^+$) 535.2 |
| 791 | 5-Chloro-2,8-dimethyl-3-({3-[4-(1,3-thiazol-2-ylcarbonyl)piperazin-1-yl]azetidin-1-yl}carbonyl)quinoline<br>MS m/z (M + H$^+$) 470.1 |
| 845 | 7-Methoxy-2-methyl-3-({3-[4-(1,3-thiazol-2-ylcarbonyl)piperazin-1-yl]azetidin-1-yl}carbonyl)quinoline<br>MS m/z (M + H$^+$) 452.2 |
| 1412 | 1-[1-({4-[5-(4-Fluorophenyl)-1H-pyrazol-1-yl]phenyl}carbonyl)azetidin-3-yl]-4-(1,3-thiazol-2-ylcarbonyl)piperazine<br>MS m/z (M + H$^+$) 518.1 |
| 946 | N-Methyl-N-phenyl-4-({3-[4-(1,3-thiazol-2-ylcarbonyl)piperazin-1-yl]azetidin-1-yl}carbonyl)benzenesulfonamide<br>MS m/z (M + H$^+$) 526.0 |
| 1041 | 2-[4-({3-[4-(1,3-Thiazol-2-ylcarbonyl)piperazin-1-yl]azetidin-1-yl}carbonyl)phenoxy]-N-[3-(trifluoromethyl)phenyl]acetamide<br>MS m/z (M + H$^+$) 574.0 |
| 1042 | 4-{[2,5-Dimethyl-3-({3-[4-(1,3-thiazol-2-ylcarbonyl)piperazin-1-yl]azetidin-1-yl}carbonyl)-1H-pyrrol-1-yl]methyl}benzenesulfonamide<br>MS m/z (M + H$^+$) 544.0 |
| 947 | 1-(1-{[4-(Piperidin-1-ylsulfonyl)phenyl]carbonyl}azetidin-3-yl)-4-(1,3-thiazol-2-ylcarbonyl)piperazine<br>MS m/z (M + H$^+$) 504.1 |
| 1053 | 1-(4-Chlorobenzyl)-3-methyl-5-({3-[4-(1,3-thiazol-2-ylcarbonyl)piperazin-1-yl]azetidin-1-yl}carbonyl)-1H-thieno[2,3-c]pyrazole<br>MS m/z (M + H$^+$) 542.2 |
| 952 | 1-{1-[(9,9-Dimethyl-9H-fluoren-2-yl)carbonyl]azetidin-3-yl}-4-(1,3-thiazol-2-ylcarbonyl)piperazine<br>MS m/z (M + H$^+$) 473.0 |
| 1407 | 1-[1-({4-Methyl-2-[3-(trifluoromethyl)phenyl]-1,3-thiazol-5-yl}carbonyl)azetidin-3-yl]-4-(1,3-thiazol-2-ylcarbonyl)piperazine<br>$^1$H NMR (300 MHz, CD$_3$OD): d 8.28 (s, 1H), 8.23 (d, 1H), 7.98 (d, 1H), 7.88 (d, 1H), 7.82 (d, 1H), 7.72 (t, 1H), 4.35-4.81 (m, 6H), 3.92-4.13 (m, 3H), 3.19-3.27 (m, 4H), 2.71 (s, 3H)<br>MS m/z (M + H$^+$) 522.2 |
| 1384 | 1-(1-{[2-(4-Chlorophenyl)-4-methyl-1,3-thiazol-5-yl]carbonyl}azetidin-3-yl)-4-(1,3-thiazol-4-ylcarbonyl)piperazine<br>MS m/z (M + H$^+$) 488.1 |
| 1381 | 1-(1-{[2-(3-Chlorophenyl)-4-methyl-1,3-thiazol-5-yl]carbonyl}azetidin-3-yl)-4-(1,3-thiazol-4-ylcarbonyl)piperazine<br>MS m/z (M + H$^+$) 488.1 |
| 1150 | 1-(1-{[2-(4-Fluorophenyl)-4-methyl-1,3-thiazol-5-yl]carbonyl}azetidin-3-yl)-4-(1,3-thiazol-2-ylcarbonyl)piperazine<br>MS m/z (M + H$^+$) 472.0 |
| 1386 | 1-(1-{[2-(4-Fluorophenyl)-4-methyl-1,3-thiazol-5-yl]carbonyl}azetidin-3-yl)-4-(1,3-thiazol-4-ylcarbonyl)piperazine<br>MS m/z (M + H$^+$) 472.0 |
| 1385 | 1-(1-{[2-Phenyl-5-(trifluoromethyl)-1,3-oxazol-4-yl]carbonyl}azetidin-3-yl)-4-(1,3-thiazol-2-ylcarbonyl)piperazine<br>MS m/z (M + H$^+$) 492.1 |
| 1378 | 1-{1-[(2-Methyl-5-phenylfuran-3-yl)carbonyl]azetidin-3-yl}-4-(1,3-thiazol-2-ylcarbonyl)piperazine<br>MS m/z (M + H$^+$) 437.1 |
| 1379 | 1-(1-{[5-Phenyl-2-(trifluoromethyl)furan-3-yl]carbonyl}azetidin-3-yl)-4-(1,3-thiazol-2-ylcarbonyl)piperazine<br>MS m/z (M + H$^+$) 491.1 |
| 965 | 1-[1-({2-[(4-Chlorophenoxy)methyl]-4-methyl-1,3-thiazol-5-yl}carbonyl)azetidin-3-yl]-4-(1,3-thiazol-2-ylcarbonyl)piperazine<br>MS m/z (M + H$^+$) 518.1 |
| 1392 | 1-(1-{[1-Phenyl-5-(trifluoromethyl)-1H-pyrazol-4-yl]carbonyl}azetidin-3-yl)-4-(1,3-thiazol-2- |

| Cpd | Cpd Name and Data |
|---|---|
| | ylcarbonyl)piperazine<br>MS m/z (M + H⁺) 491.1 |
| 1403 | 1-(1-{[2-Phenyl-5-(trifluoromethyl)-1,3-oxazol-4-yl]carbonyl}azetidin-3-yl)-4-(1,3-thiazol-4-ylcarbonyl)piperazine<br>MS m/z (M + H⁺) 492.1 |
| 1396 | 1-{1-[(2-Methyl-5-phenylfuran-3-yl)carbonyl]azetidin-3-yl}-4-(1,3-thiazol-4-ylcarbonyl)piperazine<br>MS m/z (M + H⁺) 437.1 |
| 1397 | 1-(1-{[5-Phenyl-2-(trifluoromethyl)furan-3-yl]carbonyl}azetidin-3-yl)-4-(1,3-thiazol-4-ylcarbonyl)piperazine<br>MS m/z (M + H⁺) 491.1 |
| 966 | 1-[1-({2-[(4-Chlorophenoxy)methyl]-4-methyl-1,3-thiazol-5-yl}carbonyl)azetidin-3-yl]-4-(1,3-thiazol-4-ylcarbonyl)piperazine<br>MS m/z (M + H⁺) 518.1 |
| 1477 | 1-(1-{[1-Phenyl-5-(trifluoromethyl)-1H-pyrazol-4-yl]carbonyl}azetidin-3-yl)-4-(1,3-thiazol-4-ylcarbonyl)piperazine<br>MS m/z (M + H⁺) 491.1 |
| 1395 | 1-(1-{[2-(3,5-Dichlorophenyl)-1,3-thiazol-4-yl]carbonyl}azetidin-3-yl)-4-(1,3-thiazol-4-ylcarbonyl)piperazine<br>MS m/z (M + H⁺) 507.9/508.8 |
| 923 | 1-(1-{[3-Bromo-5-(trifluoromethyl)phenyl]carbonyl}azetidin-3-yl)-4-(1,3-thiazol-4-ylcarbonyl)piperazine<br>MS m/z (M + H⁺) 503/505 |
| 910 | 1-(1-{[3-Bromo-5-(trifluoromethyl)phenyl]carbonyl}azetidin-3-yl)-4-(1,3-thiazol-2-ylcarbonyl)piperazine<br>MS m/z (M + H⁺) 503/505 |
| 915 | 1-{1-[(5-Bromo-2-fluorophenyl)carbonyl]azetidin-3-yl}-4-(1,3-thiazol-2-ylcarbonyl)piperazine<br>MS m/z (M + H⁺) 453/455 |
| 912 | 1-{1-[(3-Bromo-5-fluorophenyl)carbonyl]azetidin-3-yl}-4-(1,3-thiazol-2-ylcarbonyl)piperazine<br>MS m/z (M + H⁺) 453/455 |
| 925 | 1-{1-[(5-Bromo-2-fluorophenyl)carbonyl]azetidin-3-yl}-4-(1,3-thiazol-4-ylcarbonyl)piperazine<br>MS m/z (M + H⁺) 453/455 |
| 926 | 1-{1-[(3-Bromo-5-fluorophenyl)carbonyl]azetidin-3-yl}-4-(1,3-thiazol-4-ylcarbonyl)piperazine<br>MS m/z (M + H⁺) 453/455 |
| 1202 | 1-(1-{[2-(2-Fluorophenyl)-4-methyl-1,3-thiazol-5-yl]carbonyl}azetidin-3-yl)-4-(1,3-thiazol-2-ylcarbonyl)piperazine<br>MS m/z (M + H⁺) 472.2 |
| 1287 | 1-(1-{[2-(2-Fluorophenyl)-4-methyl-1,3-thiazol-5-yl]carbonyl}azetidin-3-yl)-4-(1,3-thiazol-4-ylcarbonyl)piperazine<br>MS m/z (M + H⁺) 472.2 |
| 831 | 1-(1-Methylethyl)-5-({3-[4-(1,3-thiazol-4-ylcarbonyl)piperazin-1-yl]azetidin-1-yl}carbonyl)-2-(trifluoromethyl)-1H-benzimidazole<br>MS m/z (M + H⁺) 507.1 |
| 740 | 1-(1-Methylethyl)-5-({3-[4-(1,3-thiazol-2-ylcarbonyl)piperazin-1-yl]azetidin-1-yl}carbonyl)-2-(trifluoromethyl)-1H-benzimidazole<br>MS m/z (M + H⁺) 507.1 |
| 1432 | 2-(2-Oxo-2-{3-[4-(1,3-thiazol-2-ylcarbonyl)piperazin-1-yl]azetidin-1-yl}ethyl)-1,2-benzisothiazol-3(2H)-one 1,1-dioxide<br>MS m/z (M + H⁺) 476.1 |
| 517 | 2-Phenyl-4-[1-(phenylcarbonyl)azetidin-3-yl]-1-{[5-(trifluoromethyl)-1-benzothiophen-2-yl]carbonyl}piperazine<br>MS m/z (M + H⁺) 550.03 |
| 1489 | 3-Methyl-2-phenyl-8-({2-phenyl-4-[1-(phenylcarbonyl)azetidin-3-yl]piperazin-1-yl}carbonyl)-4H-chromen-4-one<br>MS m/z (M + H⁺) 584.34 |
| 1490 | 1-{1-[(5-Fluoro-3-methyl-1-benzofuran-2-yl)carbonyl]azetidin-3-yl}-4-(phenylcarbonyl)piperazine<br>MS m/z (M + H⁺) 422.06 |
| 526 | 7-Methoxy-3-methyl-2-({3-[4-(phenylcarbonyl)piperazin-1-yl]azetidin-1-yl}carbonyl)-1H-indole<br>MS m/z (M + H⁺) 433.2 |
| 610 | 1-[4-({4-[1-(Phenylcarbonyl)azetidin-3-yl]piperazin-1-yl}carbonyl)phenyl]-1H-benzimidazole<br>MS m/z (M + H⁺) 466.2 |

-continued

| Cpd | Cpd Name and Data |
|---|---|
| 523 | 1-Cyclohexyl-2-methyl-5-({4-[1-(phenylcarbonyl)azetidin-3-yl]piperazin-1-yl}carbonyl)-1H-benzimidazole<br>MS m/z (M + H$^+$) 486.3 |
| 1491 | 1-{1-[(5-Chloro-1-benzofuran-2-yl)carbonyl]azetidin-3-yl}-4-(phenylcarbonyl)piperazine<br>MS m/z (M + H$^+$) 424 |
| 611 | 2-Phenyl-5-({4-[1-(phenylcarbonyl)azetidin-3-yl]piperazin-1-yl}carbonyl)-1H-benzimidazole<br>MS m/z (M + H$^+$) 466.2 |
| 524 | 1-[(5-Chloro-1-benzofuran-2-yl)carbonyl]-4-[1-(phenylcarbonyl)azetidin-3-yl]piperazine<br>MS m/z (M + H$^+$) 432.9 |
| 502 | 1-(Phenylcarbonyl)-4-(1-{[4-(trifluoromethyl)cyclohexyl]carbonyl}azetidin-3-yl)piperazine<br>MS m/z (M + H$^+$) 424 |
| 503 | 1-(1-{[4-(4-Chlorophenyl)cyclohexyl]carbonyl}azetidin-3-yl)-4-(phenylcarbonyl)piperazine<br>MS m/z (M + H$^+$) 466 |
| 648 | 1-(1,3-Thiazol-4-ylcarbonyl)-4-{1-[(2E)-3-{4-[(trifluoromethyl)sulfanyl]phenyl}prop-2-enoyl]azetidin-3-yl}piperazine<br>MS m/z (M + H$^+$) 483.3 |
| 644 | 1-(1,3-Thiazol-4-ylcarbonyl)-4-(1-{[4-(trifluoromethyl)cyclohexyl]carbonyl}azetidin-3-yl)piperazine<br>MS m/z (M + H$^+$) 431.29 |
| 643 | 1-(1-{[4-(4-Chlorophenyl)cyclohexyl]carbonyl}azetidin-3-yl)-4-(1,3-thiazol-4-ylcarbonyl)piperazine<br>MS m/z (M + H$^+$) 473.27 |
| 1481 | 4-[1-(Biphenyl-4-ylcarbonyl)azetidin-3-yl]-2-phenyl-1-(1,3-thiazol-4-ylcarbonyl)piperazine<br>MS m/z (M + H$^+$) 509.28 |
| 804 | 2-Phenyl-4-[1-(1,3-thiazol-2-ylcarbonyl)azetidin-3-yl]-1-{[5-(trifluoromethyl)-1-benzothiophen-2-yl]carbonyl}piperazine<br>MS m/z (M + H$^+$) 557.14 |
| 905 | 2-Phenyl-4-[1-(1,3-thiazol-4-ylcarbonyl)azetidin-3-yl]-1-{[5-(trifluoromethyl)-1-benzothiophen-2-yl]carbonyl}piperazine<br>$^1$H NMR (CDCl$_3$): δ 9.02 (d, 1H); 8.31 (s, 1H); 8.22 (s, 1H); 8.12 (m, 1H); 7.77 (s, 1H); 7.69 (m, 1H); 7.50 (m, 5H); 7.35 (m, 1H); 5.91 (bm, 1H); 4.83 (m, 1H); 4.64 (m, 1H); 4.48-4.46 (m, 2H); 4.14 (m, 1H); 3.86 (m, 1H); 3.87 (m, 1H); 3.51 (m, 1H); 3.12 (t, 1H); 2.97 (m, 1H).<br>MS m/z (M + H$^+$) 557.18 |
| 1436 | 3-Methyl-2-phenyl-8-({2-phenyl-4-[1-(1,3-thiazol-4-ylcarbonyl)azetidin-3-yl]piperazin-1-yl}carbonyl)-4H-chromen-4-one<br>MS m/z (M + H$^+$) 591.26 |
| 854 | 3-Methyl-2-phenyl-8-({2-phenyl-4-[1-(1,3-thiazol-2-ylcarbonyl)azetidin-3-yl]piperazin-1-yl}carbonyl)-4H-chromen-4-one<br>MS m/z (M + H$^+$) 591.24 |
| 1307 | 1-(1-{[5-(4-Chlorophenyl)-1H-pyrrol-2-yl]carbonyl}azetidin-3-yl)-4-(1,3-thiazol-2-ylcarbonyl)piperazine<br>MS m/z (M + H$^+$) 256 |
| 1122 | 1-{1-[(5-Phenylthiophen-2-yl)carbonyl]azetidin-3-yl}-4-(1,3-thiazol-2-ylcarbonyl)piperazine<br>$^1$H NMR (CDCl$_3$): δ 7.99 (d, 1H), 7.88 (d, 1H); 7.71 9m, 2H); 7.52-7.32 (m, 4H); 4.75 (b, 4H); 4.0 (bm, 3H); 3.22 (bm, 4H)<br>MS m/z (M + H$^+$) 439.16 |
| 1473 | 1-(1-{[5-(4-Chlorophenyl)-1,3-oxazol-4-yl]carbonyl}azetidin-3-yl)-4-(1,3-thiazol-2-ylcarbonyl)piperazine<br>MS m/z (M + H$^+$) 458.13 |
| 838 | 1-Methyl-3-({3-[4-(1,3-thiazol-2-ylcarbonyl)piperazin-1-yl]azetidin-1-yl}carbonyl)-1H-indole<br>MS m/z (M + H$^+$) 410.12 |
| 796 | 1,2-Dimethyl-3-({3-[4-(1,3-thiazol-2-ylcarbonyl)piperazin-1-yl]azetidin-1-yl}carbonyl)-1H-indole<br>MS m/z (M + H$^+$) 424.21 |
| 1475 | 1-{1-[(3-Phenyl-1H-pyrazol-4-yl)carbonyl]azetidin-3-yl}-4-(1,3-thiazol-2-ylcarbonyl)piperazine<br>MS m/z (M + H$^+$) 323.13 |
| 993 | 1-Benzyl-3-({3-[4-(1,3-thiazol-2-ylcarbonyl)piperazin-1-yl]azetidin-1-yl}carbonyl)-1H-indole<br>MS m/z (M + H$^+$) 486 |
| 850 | 1-{1-[(6-Methoxy-3-methyl-1-benzofuran-2-yl)carbonyl]azetidin-3-yl}-4-(1,3-thiazol-4-ylcarbonyl)piperazine<br>MS m/z (M + H$^+$) 441.1 |
| 721 | 1-{1-[(6-Methoxy-3-methyl-1-benzofuran-2-yl)carbonyl]azetidin-3-yl}-4-(1,3-thiazol-2- |

| Cpd | Cpd Name and Data |
|---|---|
| | ylcarbonyl)piperazine<br>MS m/z (M + H$^+$) 441.1 |
| 862 | 1-{1-[(5-Fluoro-3-methyl-1-benzofuran-2-yl)carbonyl]azetidin-3-yl}-4-(1,3-thiazol-4-ylcarbonyl)piperazine<br>MS m/z (M + H$^+$) 429.1 |
| 751 | 1-{1-[(5-Fluoro-3-methyl-1-benzofuran-2-yl)carbonyl]azetidin-3-yl}-4-(1,3-thiazol-2-ylcarbonyl)piperazine<br>MS m/z (M + H$^+$) 429.1 |
| 840 | 7-Methoxy-3-methyl-2-({3-[4-(1,3-thiazol-4-ylcarbonyl)piperazin-1-yl]azetidin-1-yl}carbonyl)-1H-indole<br>MS m/z (M + H$^+$) 440.1 |
| 760 | 7-Methoxy-3-methyl-2-({3-[4-(1,3-thiazol-2-ylcarbonyl)piperazin-1-yl]azetidin-1-yl}carbonyl)-1H-indole<br>MS m/z (M + H$^+$) 440.1 |
| 1442 | 6-Fluoro-2-({3-[4-(1,3-thiazol-4-ylcarbonyl)piperazin-1-yl]azetidin-1-yl}carbonyl)-1H-benzimidazole<br>MS m/z (M + H$^+$) 415 |
| 846 | 7-Methoxy-3-methyl-2-({4-[1-(1,3-thiazol-2-ylcarbonyl)azetidin-3-yl]piperazin-1-yl}carbonyl)-1H-indole<br>MS m/z (M + H$^+$) 439.7/440.3 |
| 871 | 1-{1-[(7-Fluoro-3-methyl-1-benzofuran-2-yl)carbonyl]azetidin-3-yl}-4-(1,3-thiazol-4-ylcarbonyl)piperazine<br>MS m/z (M + H$^+$) 428.8 |
| 857 | 7-Methoxy-3-methyl-2-({4-[1-(1,3-thiazol-4-ylcarbonyl)azetidin-3-yl]piperazin-1-yl}carbonyl)-1H-indole<br>MS m/z (M + H$^+$) 440.1 |
| 755 | 5-Chloro-3-methyl-2-({3-[4-(1,3-thiazol-4-ylcarbonyl)piperazin-1-yl]azetidin-1-yl}carbonyl)-1H-indole<br>MS m/z (M + H$^+$) 444.1 |
| 1443 | 5-Fluoro-2-({3-[4-(1,3-thiazol-2-ylcarbonyl)piperazin-1-yl]azetidin-1-yl}carbonyl)-1H-benzimidazole<br>MS m/z (M + H$^+$) 415.2 |
| 794 | 1-{1-[(7-Fluoro-3-methyl-1-benzofuran-2-yl)carbonyl]azetidin-3-yl}-4-(1,3-thiazol-2-ylcarbonyl)piperazine<br>MS m/z (M + H$^+$) 428.8 |
| 688 | 5-Chloro-3-methyl-2-({3-[4-(1,3-thiazol-2-ylcarbonyl)piperazin-1-yl]azetidin-1-yl}carbonyl)-1H-indole<br>$^1$H NMR (CDCl$_3$): δ 7.88 (d, 1H); 7.78 (d, 1H); 7.5 (m, 1H); 7.27 (m, 1H); 7.12 (m, 1H); 4.16 (bm, 1H); 4.32 (bm, 2H); 3.16 (m, 3H); 2.36 (s, 3H)<br>MS m/z (M + H$^+$) 443.1 |
| 1293 | 1-[4-({3-[4-(1,3-Thiazol-4-ylcarbonyl)piperazin-1-yl]azetidin-1-yl}carbonyl)phenyl]-1H-benzimidazole<br>MS m/z (M + H$^+$) 472.83 |
| 1223 | 1-[4-({3-[4-(1,3-Thiazol-2-ylcarbonyl)piperazin-1-yl]azetidin-1-yl}carbonyl)phenyl]-1H-benzimidazole<br>MS m/z (M + H$^+$) 473.1 |
| 1305 | 1-[4-({4-[1-(1,3-Thiazol-4-ylcarbonyl)azetidin-3-yl]piperazin-1-yl}carbonyl)phenyl]-1H-benzimidazole<br>MS m/z (M + H$^+$) 473.1 |
| 1298 | 1-[4-({4-[1-(1,3-Thiazol-2-ylcarbonyl)azetidin-3-yl]piperazin-1-yl}carbonyl)phenyl]-1H-benzimidazole<br>MS m/z (M + H$^+$) 473.1 |
| 732 | 1-Cyclohexyl-2-methyl-5-({3-[4-(1,3-thiazol-2-ylcarbonyl)piperazin-1-yl]azetidin-1-yl}carbonyl)-1H-benzimidazole<br>MS m/z (M + H$^+$) 493.2 |
| 793 | 1-Cyclohexyl-2-methyl-5-({4-[1-(1,3-thiazol-2-ylcarbonyl)azetidin-3-yl]piperazin-1-yl}carbonyl)-1H-benzimidazole<br>MS m/z (M + H$^+$) 493.2 |
| 814 | 1-{[3-Methyl-6-(trifluoromethyl)-1-benzothiophen-2-yl]carbonyl}-4-(1-{[4-(trifluoromethyl)-1,3-thiazol-2-yl]carbonyl}azetidin-3-yl)piperazine<br>MS m/z (M + H$^+$) 563.1 |
| 800 | 2-Cyclohexyl-5-({3-[4-(1,3-thiazol-4-ylcarbonyl)piperazin-1-yl]azetidin-1-yl}carbonyl)-1H-benzimidazole<br>MS m/z (M + H$^+$) 479.1 |
| 735 | 2-Cyclohexyl-5-({3-[4-(1,3-thiazol-2-ylcarbonyl)piperazin-1-yl]azetidin-1-yl}carbonyl)-1H-benzimidazole<br>MS m/z (M + H$^+$) 479.1 |
| 827 | 2-Cyclohexyl-5-({4-[1-(1,3-thiazol-2-ylcarbonyl)azetidin-3-yl]piperazin-1-yl}carbonyl)-1H-benzimidazole<br>MS m/z (M + H$^+$) 479.1 |
| 853 | 2-Cyclohexyl-5-({4-[1-(1,3-thiazol-4-ylcarbonyl)azetidin-3-yl]piperazin-1-yl}carbonyl)-1H-benzimidazole<br>MS m/z (M + H$^+$) 479.1 |

-continued

| Cpd | Cpd Name and Data |
|---|---|
| 1299 | 2-Phenyl-5-({3-[4-(1,3-thiazol-4-ylcarbonyl)piperazin-1-yl]azetidin-1-yl}carbonyl)-1H-benzimidazole<br>MS m/z (M + H$^+$) 473.1 |
| 1194 | 2-Phenyl-5-({3-[4-(1,3-thiazol-2-ylcarbonyl)piperazin-1-yl]azetidin-1-yl}carbonyl)-1H-benzimidazole<br>MS m/z (M + H$^+$) 473.1 |
| 1271 | 2-Phenyl-5-({4-[1-(1,3-thiazol-2-ylcarbonyl)azetidin-3-yl]piperazin-1-yl}carbonyl)-1H-benzimidazole<br>MS m/z (M + H$^+$) 473.1 |
| 1444 | 1-{1-[(5-Chloro-1-benzofuran-2-yl)carbonyl]azetidin-3-yl}-4-(1,3-thiazol-4-ylcarbonyl)piperazine<br>MS m/z (M + H$^+$) 431 |
| 818 | 1-{1-[(5-Chloro-1-benzofuran-2-yl)carbonyl]azetidin-3-yl}-4-(1,3-thiazol-2-ylcarbonyl)piperazine<br>MS m/z (M + H$^+$) 431 |
| 785 | 1-[(5-Chloro-1-benzofuran-2-yl)carbonyl]-4-[1-(1,3-thiazol-2-ylcarbonyl)azetidin-3-yl]piperazine<br>MS m/z (M + H$^+$) 430.86 |
| 809 | 1-[(5-Chloro-1-benzofuran-2-yl)carbonyl]-4-[1-(1,3-thiazol-4-ylcarbonyl)azetidin-3-yl]piperazine<br>MS m/z (M + H$^+$) 430.93 |
| 1000 | 2-(2-Phenylethyl)-5-({3-[4-(1,3-thiazol-2-ylcarbonyl)piperazin-1-yl]azetidin-1-yl}carbonyl)-1H-benzimidazole<br>MS m/z (M + H$^+$) 501.1 |
| 1001 | 2-Benzyl-6-({4-[1-(1,3-thiazol-2-ylcarbonyl)azetidin-3-yl]piperazin-1-yl}carbonyl)-1H-benzimidazole<br>MS m/z (M + H$^+$) 486.9 |
| 855 | 5-Chloro-2-({3-[4-(1,3-thiazol-4-ylcarbonyl)piperazin-1-yl]azetidin-1-yl}carbonyl)-1,3-benzothiazole<br>MS m/z (M + H$^+$) 447.6 |
| 1002 | 2-(2-Phenylethyl)-6-({4-[1-(1,3-thiazol-4-ylcarbonyl)azetidin-3-yl]piperazin-1-yl}carbonyl)-1H-benzimidazole<br>MS m/z (M + H$^+$) 501.1 |
| 728 | 5-Chloro-2-({3-[4-(1,3-thiazol-2-ylcarbonyl)piperazin-1-yl]azetidin-1-yl}carbonyl)-1,3-benzothiazole<br>MS m/z (M + H$^+$) 448 |
| 764 | 5-Chloro-2-({4-[1-(1,3-thiazol-2-ylcarbonyl)azetidin-3-yl]piperazin-1-yl}carbonyl)-1,3-benzothiazole<br>MS m/z (M + H$^+$) 448 |
| 1003 | 2-Benzyl-5-({3-[4-(1,3-thiazol-4-ylcarbonyl)piperazin-1-yl]azetidin-1-yl}carbonyl)-1H-benzimidazole<br>MS m/z (M + H$^+$) 487 |
| 1004 | 2-Benzyl-5-({3-[4-(1,3-thiazol-2-ylcarbonyl)piperazin-1-yl]azetidin-1-yl}carbonyl)-1H-benzimidazole<br>MS m/z (M + H$^+$) 487 |
| 821 | 5-Chloro-2-({4-[1-(1,3-thiazol-4-ylcarbonyl)azetidin-3-yl]piperazin-1-yl}carbonyl)-1,3-benzothiazole<br>MS m/z (M + H$^+$) 448.1 |
| 779 | 4-Chloro-6-({3-[4-(1,3-thiazol-2-ylcarbonyl)piperazin-1-yl]azetidin-1-yl}carbonyl)-2-(trifluoromethyl)quinoline<br>MS m/z (M + H$^+$) 5.1 |
| 848 | 4-Chloro-6-({3-[4-(1,3-thiazol-4-ylcarbonyl)piperazin-1-yl]azetidin-1-yl}carbonyl)-2-(trifluoromethyl)quinoline<br>MS m/z (M + H$^+$) 509.72 |
| 859 | 4-Chloro-6-({4-[1-(1,3-thiazol-4-ylcarbonyl)azetidin-3-yl]piperazin-1-yl}carbonyl)-2-(trifluoromethyl)quinoline<br>MS m/z (M + H$^+$) 510 |
| 842 | 4-Chloro-6-({4-[1-(1,3-thiazol-2-ylcarbonyl)azetidin-3-yl]piperazin-1-yl}carbonyl)-2-(trifluoromethyl)quinoline<br>MS m/z (M + H$^+$) 510 |
| 756 | 2-({3-[4-(1,3-Thiazol-2-ylcarbonyl)piperazin-1-yl]azetidin-1-yl}carbonyl)-6-(trifluoromethyl)-1H-indole<br>MS m/z (M + H$^+$) 463.81 |
| 828 | 2-({3-[4-(1,3-Thiazol-4-ylcarbonyl)piperazin-1-yl]azetidin-1-yl}carbonyl)-6-(trifluoromethyl)-1H-indole<br>MS m/z (M + H$^+$) 463.81 |
| 1445 | 2-({3-[4-(Isothiazol-5-ylcarbonyl)piperazin-1-yl]azetidin-1-yl}carbonyl)-6-(trifluoromethyl)-1H-indole<br>MS m/z (M + H$^+$) 463.81 |
| 747 | 2-({4-[1-(1,3-Thiazol-2-ylcarbonyl)azetidin-3-yl]piperazin-1-yl}carbonyl)-5-(trifluoromethyl)-1H-indole<br>MS m/z (M + H$^+$) 464.1 |
| 772 | 2-({4-[1-(1,3-Thiazol-4-ylcarbonyl)azetidin-3-yl]piperazin-1-yl}carbonyl)-5-(trifluoromethyl)-1H-indole<br>MS m/z (M + H$^+$) 464.1 |
| 726 | 1-{[3-Methyl-6-(trifluoromethyl)-1-benzothiophen-2-yl]carbonyl}-4-[1-(1,3-thiazol-5-ylcarbonyl)azetidin-3- |

| Cpd | Cpd Name and Data |
|---|---|
| | yl]piperazine<br>MS m/z (M + H$^+$) 494.97 |
| 731 | 1-{[3-Methyl-6-(trifluoromethyl)-1-benzothiophen-2-yl]carbonyl}-4-[1-(1H-pyrrol-2-ylcarbonyl)azetidin-3-yl]piperazine<br>MS m/z (M + H$^+$) 477.02 |
| 748 | 1-{[3-Methyl-6-(trifluoromethyl)-1-benzothiophen-2-yl]carbonyl}-4-[1-(1H-pyrrol-3-ylcarbonyl)azetidin-3-yl]piperazine<br>MS m/z (M + H$^+$) 477.02 |
| 844 | 2-({3-[4-(1,3-Thiazol-2-ylcarbonyl)piperazin-1-yl]azetidin-1-yl}carbonyl)-6-(trifluoromethyl)furo[2,3-b]pyridine<br>MS m/z (M + H$^+$) 466.1 |
| 808 | 2-({3-[4-(1,3-Thiazol-4-ylcarbonyl)piperazin-1-yl]azetidin-1-yl}carbonyl)-6-(trifluoromethyl)furo[2,3-b]pyridine<br>MS m/z (M + H$^+$) 465.98 |
| 1446 | 2-({3-[4-(1H-Pyrrol-2-ylcarbonyl)piperazin-1-yl]azetidin-1-yl}carbonyl)-6-(trifluoromethyl)furo[2,3-b]pyridine<br>MS m/z (M + H$^+$) 448.2 |
| 860 | 2-({4-[1-(1,3-Thiazol-2-ylcarbonyl)azetidin-3-yl]piperazin-1-yl}carbonyl)-6-(trifluoromethyl)furo[2,3-b]pyridine<br>MS m/z (M + H$^+$) 466 |
| 678 | 1-[1-(Phenoxathiin-2-ylcarbonyl)azetidin-3-yl]-4-(1H-pyrrol-2-ylcarbonyl)piperazine<br>$^1$H NMR (CDCl$_3$): δ 7.38 (m, 2H); 7.19-6.84 (m, 5H); 6.88 (m, 1H); 6.56 (m, 1H); 6.13 (m, 1H); 4.67-4.21 (m, 3H); 4.12-3.90 (bd, 4H); 3.25 (bm, 3H)<br>MS m/z (M + H$^+$) 461.2 |
| 799 | 2-({3-[4-(1,3-Thiazol-2-ylcarbonyl)piperazin-1-yl]azetidin-1-yl}carbonyl)-6-(trifluoromethyl)-1H-pyrrolo[2,3-b]pyridine<br>MS m/z (M + H$^+$) 465.2 |
| 865 | 2-({3-[4-(1,3-Thiazol-4-ylcarbonyl)piperazin-1-yl]azetidin-1-yl}carbonyl)-6-(trifluoromethyl)-1H-pyrrolo[2,3-b]pyridine<br>MS m/z (M + H$^+$) 465.1 |
| 1447 | 2-({3-[4-(1H-Pyrrol-2-ylcarbonyl)piperazin-1-yl]azetidin-1-yl}carbonyl)-6-(trifluoromethyl)-1H-pyrrolo[2,3-b]pyridine<br>MS m/z (M + H$^+$) 447.1 |
| 1448 | 5-Bromo-2-({3-[4-(1,3-thiazol-4-ylcarbonyl)piperazin-1-yl]azetidin-1-yl}carbonyl)furo[2,3-b]pyridine<br>MS m/z (M + H$^+$) 477.1 |
| 864 | 5-Bromo-2-({3-[4-(1,3-thiazol-2-ylcarbonyl)piperazin-1-yl]azetidin-1-yl}carbonyl)furo[2,3-b]pyridine<br>MS m/z (M + H$^+$) 477.1 |
| 1449 | 5-Bromo-2-({4-[1-(1,3-thiazol-4-ylcarbonyl)azetidin-3-yl]piperazin-1-yl}carbonyl)furo[2,3-b]pyridine<br>MS m/z (M + H$^+$) 477.1 |
| 696 | 5-Chloro-1,3-dimethyl-2-({3-[4-(1,3-thiazol-2-ylcarbonyl)piperazin-1-yl]azetidin-1-yl}carbonyl)-1H-indole<br>MS m/z (M + H$^+$) 458.2 |
| 758 | 5-Chloro-1,3-dimethyl-2-({3-[4-(1,3-thiazol-4-ylcarbonyl)piperazin-1-yl]azetidin-1-yl}carbonyl)-1H-indole<br>MS m/z (M + H$^+$) 458.1 |
| 762 | 5-Chloro-1,3-dimethyl-2-({4-[1-(1,3-thiazol-2-ylcarbonyl)azetidin-3-yl]piperazin-1-yl}carbonyl)-1H-indole<br>MS m/z (M + H$^+$) 485.1 |
| 839 | 5-Chloro-1,3-dimethyl-2-({4-[1-(1H-pyrrol-2-ylcarbonyl)azetidin-3-yl]piperazin-1-yl}carbonyl)-1H-indole<br>MS m/z (M + H$^+$) 440.2 |
| 774 | 3-Bromo-2-({3-[4-(1,3-thiazol-4-ylcarbonyl)piperazin-1-yl]azetidin-1-yl}carbonyl)-6-(trifluoromethyl)-1H-pyrrolo[2,3-b]pyridine<br>MS m/z (M + H$^+$) 543.1 |
| 733 | 5-Chloro-1,3-dimethyl-2-({3-[4-(1H-pyrrol-2-ylcarbonyl)piperazin-1-yl]azetidin-1-yl}carbonyl)-1H-indole<br>MS m/z (M + H$^+$) 440.2 |
| 675 | 3-Bromo-2-({3-[4-(1,3-thiazol-2-ylcarbonyl)piperazin-1-yl]azetidin-1-yl}carbonyl)-6-(trifluoromethyl)-1H-pyrrolo[2,3-b]pyridine<br>MS m/z (M + H$^+$) 543.1 |
| 739 | 3-Bromo-2-({3-[4-(1H-pyrrol-2-ylcarbonyl)piperazin-1-yl]azetidin-1-yl}carbonyl)-6-(trifluoromethyl)-1H-pyrrolo[2,3-b]pyridine<br>MS m/z (M + H$^+$) 525.2 |
| 746 | 3-Bromo-2-({4-[1-(1,3-thiazol-2-ylcarbonyl)azetidin-3-yl]piperazin-1-yl}carbonyl)-6-(trifluoromethyl)-1H-pyrrolo[2,3-b]pyridine<br>MS m/z (M + H$^+$) 543 |

-continued

| Cpd | Cpd Name and Data |
|---|---|
| 863 | 2-({3-[4-(1,3-Thiazol-2-ylcarbonyl)piperazin-1-yl]azetidin-1-yl}carbonyl)-5-(trifluoromethyl)-1H-pyrrolo[3,2-b]pyridine<br>MS m/z (M + H$^+$) 465.1 |
| 830 | 2-({4-[1-(1,3-Thiazol-4-ylcarbonyl)azetidin-3-yl]piperazin-1-yl}carbonyl)-5-(trifluoromethyl)-1H-pyrrolo[3,2-b]pyridine<br>MS m/z (M + H$^+$) 465.1 |
| 1450 | 2-({3-[4-(1,3-Thiazol-4-ylcarbonyl)piperazin-1-yl]azetidin-1-yl}carbonyl)-5-(trifluoromethyl)-1H-pyrrolo[3,2-b]pyridine<br>MS m/z (M + H$^+$) 465.1 |
| 719 | 5-Fluoro-3-methyl-2-({3-[4-(1,3-thiazol-2-ylcarbonyl)piperazin-1-yl]azetidin-1-yl}carbonyl)-1H-indole<br>MS m/z (M + H$^+$) 428.3 |
| 852 | 6-Bromo-7-methyl-2-({3-[4-(1,3-thiazol-2-ylcarbonyl)piperazin-1-yl]azetidin-1-yl}carbonyl)imidazo[1,2-a]pyridine<br>MS m/z (M + H$^+$) 495.1 |
| 1451 | 6-Bromo-7-methyl-2-({3-[4-(1H-pyrrol-2-ylcarbonyl)piperazin-1-yl]azetidin-1-yl}carbonyl)imidazo[1,2-a]pyridine<br>MS m/z (M + H$^+$) 472.8 |
| 1452 | 8-Bromo-6-chloro-2-({3-[4-(1,3-thiazol-2-ylcarbonyl)piperazin-1-yl]azetidin-1-yl}carbonyl)imidazo[1,2-a]pyridine<br>MS m/z (M + H$^+$) 472.8 |
| 1453 | 2-({3-[4-(1,3-Thiazol-2-ylcarbonyl)piperazin-1-yl]azetidin-1-yl}carbonyl)-6-(trifluoromethyl)imidazo[1,2-a]pyridine<br>MS m/z (M + H$^+$) 465.1 |
| 682 | 5-Bromo-3-methyl-2-({3-[4-(1,3-thiazol-2-ylcarbonyl)piperazin-1-yl]azetidin-1-yl}carbonyl)-1H-indole<br>MS m/z (M + H$^+$) 488.1 |
| 868 | 6-Bromo-3-methyl-2-({3-[4-(1,3-thiazol-2-ylcarbonyl)piperazin-1-yl]azetidin-1-yl}carbonyl)imidazo[1,2-a]pyridine<br>MS m/z (M + H$^+$) 490.1 |
| 873 | 6-Bromo-2-({3-[4-(1,3-thiazol-2-ylcarbonyl)piperazin-1-yl]azetidin-1-yl}carbonyl)imidazo[1,2-a]pyridine<br>MS m/z (M + H$^+$) 475 |
| 825 | 6-Bromo-3-methyl-2-({3-[4-(1H-pyrrol-2-ylcarbonyl)piperazin-1-yl]azetidin-1-yl}carbonyl)imidazo[1,2-a]pyridine<br>MS m/z (M + H$^+$) 471.1 |
| 792 | 6-Bromo-2-({3-[4-(1,3-thiazol-2-ylcarbonyl)piperazin-1-yl]azetidin-1-yl}carbonyl)-1H-indole<br>MS m/z (M + H$^+$) 476.1 |
| 953 | (2R,6S)-2,6-Dimethyl-4-(1,3-thiazol-2-ylcarbonyl)-1-(1-{[6-(trifluoromethyl)-1-benzothiophen-2-yl]carbonyl}azetidin-3-yl)piperazine<br>MS m/z (M + H$^+$) 509.0 |

Example 6

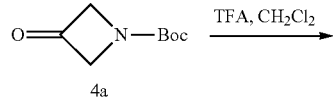

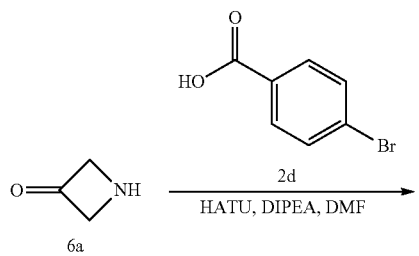

-continued

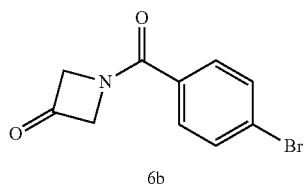

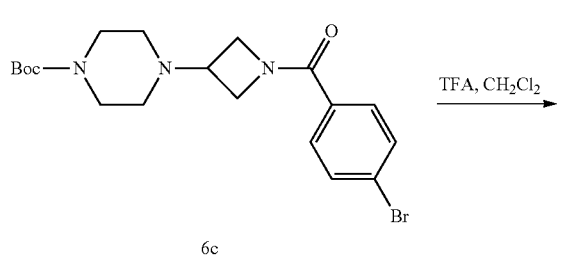

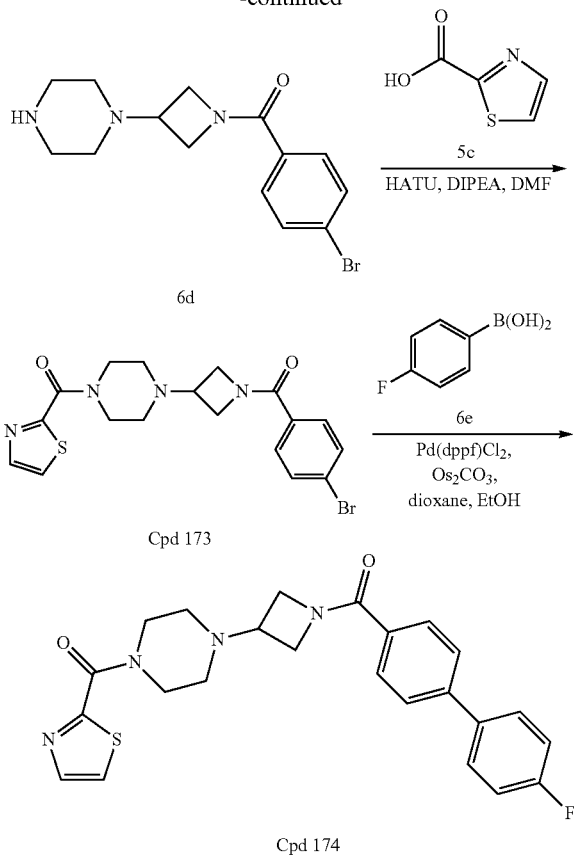

A. Azetidin-3-one, 6a. The title compound 6a was prepared using the method described in Example 1, substituting compound 4a for compound 1c in Procedure B. The crude compound 6a was used in the next reaction without further purification. MS m/z (M+H$^+$+CF$_3$CO$_2$H) 186.1.

B. 1-(4-Bromo-benzoyl)-azetidin-3-one, 6b. The title compound 6b was prepared using the method described in Example 1, substituting compound 6a for compound 1g and substituting compound 2d for compound 1h in Procedure E. The crude compound 6b was used in the next reaction without further purification. MS m/z (M+H$^+$) 419.2.

C. 4-[1-(4-Bromo-benzoyl)-azetidin-3-yl]-piperazine-1-carboxylic acid tert-butyl ester, 6c. The title compound 6c was prepared using the method described in Example 4, substituting compound 6b for compound 4a and substituting compound 1a for compound 2a in Procedure A. The crude product 6c was purified by flash column chromatography. MS m/z (M+H$^+$) 424.0/426.1.

D. (4-Bromo-phenyl)-(3-piperazin-1-yl-azetidin-1-yl)-methanone, 6d. The title compound 6d was prepared using the method described in Example 1, substituting compound 6c for compound 1c in Procedure B. The crude product 6d was used in the next reaction without further purification. MS m/z (M+H$^+$) 324.09/326.08.

E. 1-{1-[(4-Bromophenyl)carbonyl]azetidin-3-yl}-4-(1,3-thiazol-2-ylcarbonyl)piperazine, Cpd 173 The title compound Cpd 173 was prepared using the method described in Example 1, substituting compound 6d for compound 1g and substituting compound 5c for compound 1h in Procedure E. The crude product Cpd 173 was used in the next reaction without further purification. MS m/z (M+H$^+$) 435.0/437.0.

F. 1-{1-[(4'-Fluorobiphenyl-4-yl)carbonyl]azetidin-3-yl}-4-(1,3-thiazol-2-ylcarbonyl)piperazine, Cpd 174. To a suspension of compound 173 (0.05 g, 0.115 mmol), compound 6e (0.0193 g, 0.14 mmol), and Cs$_2$CO$_3$ (0.094 g, 0.288 mmol) in dioxane (3 mL) and EtOH (1 mL) was added Pd(dppf)Cl$_2$ (0.0084 g, 0.0115 mmol). The reaction mixture was stirred at 80° C. for 3 h. After cooling, the solid was removed by filtration and washed with CH$_3$OH. The filtrate was concentrated. The crude compound 174 was purified by reverse phase chromatography. $^1$H NMR (300 MHz, CD$_3$OD): δ 7.97 (d, 1H), 7.87 (d, 1H), 7.65-7.79 (m, 6H), 7.21 (t, 2H), 4.67 (m, 3H), 4.52 (m, 1H), 4.43 (m, 1H), 4.31 (m, 1H), 3.98 (m, 2H), 3.89 (m, 1H), 3.11 (m, 4H); MS m/z (M+H$^+$) 451.2 (calculated for C$_{24}$H$_{23}$FN$_4$O$_2$S, 450.54).

Following the procedure described above for Example 6 and substituting the appropriate reagents, starting materials and purification methods known to those skilled in the art, the following compounds of the present invention were prepared:

| Cpd | Cpd Name and Data |
|---|---|
| 175 | 1-{1-[(3',4'-Dichlorobiphenyl-4-yl)carbonyl]azetidin-3-yl}-4-(1,3-thiazol-2-ylcarbonyl)piperazine<br>$^1$H NMR (300 MHz, CD$_3$OD): δ 7.98 (d, 1H), 7.88 (d, 1H), 7.85 (d, 1H), 7.77 (m, 4H), 7.62 (m, 2H), 4.54-4.81 (m, 4H) 4.46 (m, 1H), 4.38 (m, 1H), 4.04 (m, 3H), 3.25 (m, 4H); LC/MS m/z (M + H$^+$) 501.0/503.1 (calculated for C$_{24}$H$_{22}$Cl$_2$N$_4$O$_2$, 501.44) |
| 176 | 1-{1-[(3'-Methylbiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.74 (m, 4H), 7.45 (m, 2H), 7.35 (t, 1H), 7.22 (d, 1H), 4.68 (m, 3H), 4.53 (m, 1H), 4.44 (m, 1H), 4.32 (m, 1H), 3.87-4.05 (m, 3H), 3.15 (m, 4H); LC/MS m/z (M + H$^+$) 447.1 (calculated for C$_{25}$H$_{26}$N$_4$O$_2$S, 446.58) |
| 177 | 1-{1-[(5'-Fluoro-2'-methylbiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.76 (d, 2H), 7.46 (d, 2H), 7.30 (dd, 1H), 7.02 (td, 1H), 6.94 (dd, 1H), 4.68 (m, 3H), 4.55 (m, 1H), 4.44 (m, 1H), 4.33 (m, 1H), 4.01 (m, 2H), 3.92 (m, 1H), 3.14 (m, 4H); LC/MS m/z (M + H$^+$) 465.1 (calculated for C$_{25}$H$_{25}$FN$_4$O$_2$S, 464.57) |
| 178 | 1-{1-[(3'-Chloro-4'-fluorobiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.80 (dd, 1H), 7.76 (m, 4H), 7.64 (m, 1H), 7.36 (t, 1H), 4.68 (m, 3H), 4.52 (m, 1H), 4.45 (m, 1H), 4.32 (m, 1H), 3.89-4.06 (m, 3H), 3.16 (m, 4H); LC/MS m/z (M + H$^+$) 485.1 (calculated for C$_{24}$H$_{22}$ClFN$_4$O$_2$S, 484.98) |
| 179 | 1-{1-[(2',4'-Difluorobiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.77 (d, 2H), 7.65 (d, 2H), 7.55 (m, 1H), 7.10 (m, 2H), 4.65 (m, 3H), 4.50 (m, 1H), 4.42 (m, 1H), 4.30 (m, 1H), 3.97 (m, 2H), 3.86 (m, 1H), 3.07 (m, 4H); LC/MS m/z (M + H$^+$) 469.0 (calculated for C$_{24}$H$_{22}$F$_2$N$_4$O$_2$S, 468.53) |
| 180 | 1-{1-[(3'-Methoxybiphenyl-4-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.87 (d, 1H), 7.75 (m, 4H), 7.39 (t, 1H), 7.22 (d, 1H), 7.18 (t, 1H), 6.97 (dd, 1H), 4.67 (m, 3H), 4.51 (m, 1H), 4.43 (m, 1H), 4.32 (m, 1H), 3.96 (m, 3H), 3.86 (s, 3H), 3.15 (m, 4H); LC/MS m/z (M + H$^+$) 463.2 (calculated for C$_{25}$H$_{26}$N$_4$O$_3$S, 462.57) |
| 181 | 1-(1-{[4-(1,3-Benzodioxol-5-yl)phenyl]carbonyl}azetidin-3-yl)-4-(1,3-thiazol-2-ylcarbonyl)piperazine<br>$^1$H NMR (300 MHz, CD$_3$OD): δ 7.98 (d, 1H), 7.87 (d, 1H), 7.70 (m, 4H), 7.16 (m, 2H), 6.92 (d, 1H), 6.01 (s, 2H), 4.69 (m, 3H), 4.54 (m, 1H), 4.44 (m, 1H), 4.33 (m, 1H), 3.97 (m, 3H), 3.17 (m, 4H); LC/MS m/z (M + H$^+$) 477.1 (calculated for C$_{25}$H$_{24}$N$_4$O$_4$S, 476.56) |
| 182 | 1-{1-[(4-Naphthalen-2-ylphenyl)carbonyl]azetidin-3-yl}-4-(1,3-thiazol-2-ylcarbonyl)piperazine<br>$^1$H NMR (300 MHz, CD$_3$OD): δ 7.79-8.01 (m, 11H), 7.50-7.56 (m, 2H), 4.60 (m, 1H), 4.49 (m, 1H), 4.37 (m, 1H), 4.27 (m, 1H), 4.08 (m, 4H), |

| Cpd | Cpd Name and Data |
|---|---|
| | 3.95 (m, 1H), 3.14 (m, 4H); LC/MS m/z (M + H⁺) 483.1 (calculated for $C_{28}H_{26}N_4O_2S$, 482.61) |
| 183 | 1-{1-[(3'-Nitrobiphenyl-4-yl)carbonyl]azetidin-3-yl}-4-(1,3-thiazol-2-ylcarbonyl)piperazine
¹H NMR (300 MHz, CD₃OD): δ 8.53 (t, 1H), 8.29 (m, 1H), 8.10 (m, 1H), 7.97 (d, 1H), 7.82-7.90 (m, 5H), 7.75 (t, 1H), 4.69 (m, 3H), 4.55 (m, 1H), 4.46 (m, 1H), 4.34 (m, 1H), 3.88-4.07 (m, 3H), 3.15 (m, 4H); LC/MS m/z (M + H⁺) 478.2 (calculated for $C_{24}H_{23}N_5O_4S$, 477.55) |
| 184 | 5-[4-({3-[4-(1,3-Thiazol-2-ylcarbonyl)piperazin-1-yl]azetidin-1-yl}carbonyl)phenyl]quinoline
¹H NMR (300 MHz, CD₃OD): δ 9.14 (d, 1H), 8.80 (d, 1H), 8.24 (d, 1H), 8.13 (dd, 1H), 7.97 (d, 1H), 7.89 (m, 5H), 7.68 (m, 2H), 4.70 (m, 3H), 4.60 (m, 1H), 4.47 (m, 1H), 4.36 (m, 1H), 4.00 (m, 2H), 3.91 (m, 1H), 3.12 (m, 4H); LC/MS m/z (M + H⁺) 484.2 (calculated for $C_{27}H_{25}N_5O_2S$, 483.6) |
| 185 | 1-{1-[(2',4'-Dimethoxybiphenyl-4-yl)carbonyl]azetidin-3-yl}-4-(phenylcarbonyl)piperazine
LC/MS m/z (M + H⁺) 486.1 |
| 186 | 1-(Phenylcarbonyl)-4-(1-{[3'-(trifluoromethyl)biphenyl-4-yl]carbonyl}azetidin-3-yl)piperazine
¹H NMR (300 MHz, CD₃OD): δ 7.94 (m, 2H), 7.80 (m, 4H), 7.70 (m, 2H), 7.45-7.53 (m, 5H), 4.66 (m, 1H), 4.52 (m, 1H), 4.44 (m, 1H), 4.31 (m, 1H), 3.95 (m, 1H), 3.84 (m, 4H), 3.10 (m, 4H); LC/MS m/z (M + H⁺) 494.1 (calculated for $C_{28}H_{26}F_3N_3O_2$, 493.53) |
| 187 | 1-{1-[(2'-Fluorobiphenyl-4-yl)carbonyl]azetidin-3-yl}-4-(phenylcarbonyl)piperazine
LC/MS m/z (M + H⁺) 444.1 |
| 188 | 1-(1-{[3'-(1-Methylethoxy)biphenyl-4-yl]carbonyl}azetidin-3-yl)-4-(phenylcarbonyl)piperazine
¹H NMR (300 MHz, CD₃OD): δ 7.73 (m, 4H), 7.48 (m, 5H), 7.36 (t, 1H), 7.19 (d, 1H), 7.14 (t, 1H), 6.94 (dd, 1H), 4.19-4.82 (m, 5H), 3.83 (m, 5H), 2.98 (m, 4H), 1.34 (d, 6H); LC/MS m/z (M + H⁺) 484.2 (calculated for $C_{30}H_{33}N_3O_3$, 483.62) |
| 189 | 1-(Phenylcarbonyl)-4-(1-{[4'-(trifluoromethoxy)biphenyl-4-yl]carbonyl}azetidin-3-yl)piperazine
LC/MS m/z (M + H⁺) 510.1 |
| 190 | 1-(1-{[4-(2-Fluoropyridin-4-yl)phenyl]carbonyl}azetidin-3-yl)-4-(phenylcarbonyl)piperazine
LC/MS m/z (M + H⁺) 445.2 |
| 191 | 1-{1-[(3'-Fluoro-4'-methoxybiphenyl-4-yl)carbonyl]azetidin-3-yl}-4-(phenylcarbonyl)piperazine
LC/MS m/z (M + H⁺) 474.1 |
| 192 | Methyl 4'-({3-[4-(phenylcarbonyl)piperazin-1-yl]azetidin-1-yl}carbonyl)biphenyl-4-carboxylate
LC/MS m/z (M + H⁺) 484.2 |
| 193 | 1-(Phenylcarbonyl)-4-{1-[(3',4',5'-trifluorobiphenyl-4-yl)carbonyl]azetidin-3-yl}piperazine
LC/MS m/z (M + H⁺) 480.1 |
| 194 | N,N-Diethyl-4'-({3-[4-(phenylcarbonyl)piperazin-1-yl]azetidin-1-yl}carbonyl)biphenyl-3-carboxamide
LC/MS m/z (M + H⁺) 525.3 |
| 195 | 1-{1-[(3'-Fluorobiphenyl-4-yl)carbonyl]azetidin-3-yl}-4-(phenylcarbonyl)piperazine
¹H NMR (300 MHz, CD₃OD): δ 7.76 (m, 4H), 7.38-7.54 (m, 8H), 7.13 (m, 1H), 4.66 (m, 1H), 4.53 (m, 1H), 4.43 (m, 1H), 4.31 (m, 1H), 3.95 (m, 1H), 3.83 (m, 4H), 3.11 (m, 4H); LC/MS m/z (M + H⁺) 444.1 (calculated for $C_{27}H_{26}FN_3O_2$, 443.53) |
| 196 | 1-(Phenylcarbonyl)-4-(1-{[2'-(trifluoromethoxy)biphenyl-4-yl]carbonyl}azetidin-3-yl)piperazine
¹H NMR (300 MHz, CD₃OD): δ 7.77 (d, 2H), 7.60 (d, 2H), 7.39-7.55 (m, 9H), 4.68 (m, 1H), 4.57 (m, 1H), 4.45 (m, 1H), 4.33 (m, 1H), 3.97 (m, 1H), 3.83 (m, 4H), 3.13 (m, 4H); LC/MS m/z (M + H⁺) 510.1 (calculated for $C_{28}H_{26}F_3N_3O_3$, 509.53) |
| 197 | 1-{1-[(4'-Methylbiphenyl-4-yl)carbonyl]azetidin-3-yl}-4-(phenylcarbonyl)piperazine
LC/MS m/z (M + H⁺) 440.2 |
| 198 | 1-(1-{[2'-(Methylethoxy)biphenyl-4-yl]carbonyl}azetidin-3-yl)-4-(phenylcarbonyl)piperazine
LC/MS m/z (M + H⁺) 484.2 |
| 199 | Methyl 4'-({3-[4-(phenylcarbonyl)piperazin-1-yl]azetidin-1-yl}carbonyl)biphenyl-2-carboxylate
LC/MS m/z (M + H⁺) 484.2 |
| 200 | 1-{1-[(4'-Fluoro-2'-methoxybiphenyl-4-yl)carbonyl]azetidin-3-yl}-4-(phenylcarbonyl)piperazine
LC/MS m/z (M + H⁺) 474.3 |
| 201 | 1-{1-[(2',3'-Dimethoxybiphenyl-4-yl)carbonyl]azetidin-3-yl}-4-(phenylcarbonyl)piperazine
LC/MS m/z (M + H⁺) 486.3 |
| 202 | 1-{1-[(2',5'-Difluorobiphenyl-4-yl)carbonyl]azetidin-3-yl}-4-(phenylcarbonyl)piperazine
LC/MS m/z (M + H⁺) 462.1 |
| 203 | 1-{1-[(2'-Fluoro-6'-methoxybiphenyl-4-yl)carbonyl]azetidin-3-yl}-4-(phenylcarbonyl)piperazine
LC/MS m/z (M + H⁺) 474.3 |
| 204 | 1-{1-[(2',3'-Difluorobiphenyl-4-yl)carbonyl]azetidin-3-yl}-4-(phenylcarbonyl)piperazine
LC/MS m/z (M + H⁺) 462.1 |
| 205 | N,N-Dimethyl-N'-[4'-({3-[4-(phenylcarbonyl)piperazin-1-yl]azetidin-1-yl}carbonyl)biphenyl-3-yl]sulfamide
¹H NMR (300 MHz, CD₃OD): δ 7.73 (dd, 4H), 7.33-7.54 (m, 8H), 7.23 (dt, 1H), 4.18-4.72 (m, 4H), 3.83 (m, 5H), 3.01 (m, 4H), 2.80 (s, 6H); LC/MS m/z (M + H⁺) 548.3 (calculated for $C_{29}H_{33}N_5O_4S$, 547.68) |
| 206 | 4'-({3-[4-(1,3-Thiazol-2-ylcarbonyl)piperazin-1-yl]azetidin-1-yl}carbonyl)biphenyl-3-carboxylic acid
LC/MS m/z (M + H⁺) 477.1 |
| 207 | [4'-({3-[4-(1,3-Thiazol-2-ylcarbonyl)piperazin-1-yl]azetidin-1-yl}carbonyl)biphenyl-3-yl]acetonitrile
¹H NMR (300 MHz, CD₃OD): δ 7.97 (d, 1H), 7.87 (d, 1H), 7.78 (m, 4H), 7.65 (m, 2H), 7.51 (t, 1H), 7.42 (d, 1H), 4.25-4.76 (m, 6H), 4.00 (s, 2H), 3.86-4.03 (m, 3H), 3.13 (m, 4H); LC/MS m/z (M + H⁺) 472.2 (calculated for $C_{26}H_{25}N_5O_2S$, 471.59) |
| 208 | 1-(1-{[3'-(Methylsulfonyl)biphenyl-4-yl]carbonyl}azetidin-3-yl)-4-(1,3-thiazol-2-ylcarbonyl)piperazine
¹H NMR (300 MHz, CD₃OD): δ 8.22 (m, 1H), 7.95-8.07 (m, 3H), 7.71-7.90 (m, 6H), 4.31-4.81 (m, 6H), 4.03 (m, 3H), 3.21-3.36 (m, 3H), 3.19 (s, 3H); LC/MS m/z (M + H⁺) 511.2 (calculated for $C_{25}H_{26}N_4O_4S_2$, 510.64) |
| 209 | 1-[4'-({3-[4-(1,3-Thiazol-2-ylcarbonyl)piperazin-1-yl]azetidin-1-yl}carbonyl)biphenyl-4-yl]ethanone
¹H NMR (300 MHz, CD₃OD): δ 8.11 (d, 2H), 7.97 (d, 1H), 7.76-7.91 (m, 7H), 4.70 (m, 3H), 4.55 (m, 1H), 4.45 (m, 1H), 4.34 (m, 1H), 3.98 (m, 3H), 3.16 (m, 4H), 2.65 (s, 3H); LC/MS m/z (M + H⁺) 475.2 (calculated for $C_{26}H_{26}N_4O_3S$, 474.59) |
| 210 | 4'-({3-[4-(1,3-Thiazol-2-ylcarbonyl)piperazin-1-yl]azetidin-1-yl}carbonyl)biphenyl-3-carbaldehyde
¹H NMR (300 MHz, CD₃OD): δ 7.97 (d, 1H), 7.87 (d, 1H), 7.76 (m, 4H), 7.72 (m, 1H), 7.65 (m, 1H), 7.49 (m, 2H), 4.69 (m, 3H), 4.53 (m, 1H), 4.44 (m, 1H), 4.32 (m, 1H), 3.96 (m, 3H), 3.15 (m, 4H); LC/MS m/z (M + H⁺) 461.2 (calculated for $C_{25}H_{24}N_4O_3S$, 460.56) |
| 211 | 4'-({3-[4-(1,3-Thiazol-2-ylcarbonyl)piperazin-1-yl]azetidin-1-yl}carbonyl)biphenyl-4-ol
¹H NMR (300 MHz, CD₃OD): δ 7.97 (d, 1H), 7.86 (d, 1H), 7.69 (m, 4H), 7.52 (d, 2H), 6.88 (d, 2H), 4.66 (m, 3H), 4.51 (m, 1H), 4.42 (m, 1H), 4.29 (m, 1H), 3.98 (m, 3H), 3.86 (m, 1H), 3.09 (m, 4H); LC/MS m/z (M + H⁺) 449.2 (calculated for $C_{24}H_{24}N_4O_3S$, 448.55) |
| 212 | 1-(1-{[4'-Chloro-3'-(trifluoromethyl)biphenyl-4-yl]carbonyl}azetidin-3-yl)-4-(1,3-thiazol-2-ylcarbonyl)piperazine
¹H NMR (300 MHz, CD₃OD): δ 8.03 (d, 1H), 7.97 (d, 1H), 7.92 (dd, 1H), 7.86 (d, 1H), 7.80 (m, 4H), 7.73 (d, 1H), 4.62 (m, 3H), 4.45 (m, 2H), 4.28 (m, 1H), 3.96 (m, 2H), 3.82 (m, 1H), 3.03 (m, 4H); LC/MS m/z (M + H⁺) 535.0 (calculated for $C_{25}H_{22}ClF_3N_4O_2S$, 534.99) |
| 213 | N,N-Dimethyl-4'-({3-[4-(1,3-thiazol-2-ylcarbonyl)piperazin-1-yl]azetidin-1-yl}carbonyl)biphenyl-4-sulfonamide
¹H NMR (300 MHz, CD₃OD): δ 7.97 (d, 1H), 7.78-7.95 (m, 9H), 4.70 (m, 3H), 4.55 (m, 1H), 4.45 (m, 1H), 4.34 (m, 1H), 3.97 (m, 3H), 3.17 (m, 4H), 2.72 (s, 6H); LC/MS m/z (M + H⁺) 540.2 (calculated for $C_{26}H_{29}N_5O_4S_2$, 539.68) |
| 214 | 1-{1-[(4',5'-Difluoro-2'-methoxybiphenyl-4-yl)carbonyl]azetidin-3-yl}-4-(1,3-thiazol-2-ylcarbonyl)piperazine
¹H NMR (300 MHz, CD₃OD): δ 7.97 (d, 1H), 7.88 (d, 1H), 7.71 (d, 2H), 7.69 (d, 2H), 7.26 (dd, 1H), 7.08 (dd, 1H), |

| Cpd | Cpd Name and Data |
|---|---|
| | 4.70 (m, 3H), 4.56 (m, 1H), 4.46 (m, 1H), 4.35 (m, 1H), 3.99 (m, 3H), 3.20 (m, 4H); LC/MS m/z (M + H$^+$) 499.2 (calculated for C$_{25}$H$_{24}$F$_2$N$_4$O$_3$S, 498.56) |
| 215 | 1-{1-[(4'-Nitrobiphenyl-4-yl)carbonyl]azetidin-3-yl}-4-(1,3-thiazol-2-ylcarbonyl)piperazine<br>$^1$H NMR (300 MHz, CD$_3$OD): δ 8.36 (d, 2H), 7.78-7.99 (m, 8H), 4.67 (m, 3H), 4.52 (m, 1H), 4.44 (m, 1H), 4.31 (m, 1H), 3.98 (m, 2H), 3.99 (m, 1H), 3.12 (m, 4H); LC/MS m/z (M + H$^+$) 478.2 (calculated for C$_{24}$H$_{23}$N$_5$O$_4$S, 477.55) |
| 216 | 4-Methoxy-4'-({3-[4-(1,3-thiazol-2-ylcarbonyl)piperazin-1-yl]azetidin-1-yl}carbonyl)biphenyl-3-carbaldehyde<br>$^1$H NMR (300 MHz, CD$_3$CN): δ 10.38 (s, 1H), 7.96 (d, 1H), 7.84-7.91 (m, 2H), 7.59-7.69 (m, 5H), 7.19 (d, 1H), 4.33-4.64 (m, 4H), 4.23 (m, 2H), 3.91 (s, 3H), 3.89 (m, 1H), 3.74 (m, 2H), 3.02 (m, 4H); LC/MS m/z (M + H$^+$) 491.2 (calculated for C$_{26}$H$_{26}$N$_4$O$_4$S, 490.59) |
| 217 | 4'-({3-[4-(1,3-Thiazol-2-ylcarbonyl)piperazin-1-yl]azetidin-1-yl}carbonyl)biphenyl-3-carboxamide<br>LC/MS m/z (M + H$^+$) 476.1 |
| 218 | 4'-({3-[4-(1,3-Thiazol-2-ylcarbonyl)piperazin-1-yl]azetidin-1-yl}carbonyl)biphenyl-3-ol<br>$^1$H NMR (300 MHz, CD$_3$OD): δ 7.97 (d, 1H), 7.87 (d, 1H), 7.72 (m, 4H), 7.28 (t, 1H), 7.11 (d, 1H), 7.06 (t, 1H), 6.82 (dd, 1H), 4.64 (m, 3H), 4.49 (m, 1H), 4.40 (m, 1H), 4.28 (m, 1H), 3.96 (m, 2H), 3.81 (m, 1H), 3.03 (m, 4H); LC/MS m/z (M + H$^+$) 449.2 (calculated for C$_{24}$H$_{24}$N$_4$O$_3$S, 448.55) |
| 219 | N-[4'-({3-[4-(1,3-Thiazol-2-ylcarbonyl)piperazin-1-yl]azetidin-1-yl}carbonyl)biphenyl-3-yl]methanesulfonamide<br>$^1$H NMR (300 MHz, CD$_3$OD): δ 7.98 (d, 1H), 7.88 (d, 1H), 7.76 (m, 4H), 7.55 (m, 1H), 7.45 (m, 2H), 7.28 (m, 1H), 4.73 (m, 3H), 4.60 (m, 1H), 4.47 (m, 1H), 4.38 (m, 1H), 4.03 (m, 3H), 3.26 (m, 4H), 3.00 (s, 1H); LC/MS m/z (M + H$^+$) 526.2 (calculated for C$_{25}$H$_{27}$N$_5$O$_4$S$_2$, 525.65) |
| 220 | tert-Butyl [4'-({3-[4-(1,3-thiazol-2-ylcarbonyl)piperazin-1-yl]azetidin-1-yl}carbonyl)biphenyl-3-yl]carbamate<br>$^1$H NMR (300 MHz, CD$_3$OD): δ 7.97 (d, 1H), 7.87 (d, 1H), 7.80 (m, 1H), 7.75 (m, 4H), 7.37 (m, 2H), 7.30 (m, 1H), 4.69 (m, 3H), 4.52 (m, 1H), 4.44 (m, 1H), 4.31 (m, 1H), 3.85-4.07 (m, 3H), 3.13 (m, 4H), 1.53 (s, 9H); LC/MS m/z (M + H$^+$) 548.3 (calculated for C$_{29}$H$_{33}$N$_5$O$_4$S, 547.68) |
| 221 | 1-(1-{[3'-(2-Methylpropoxy)biphenyl-4-yl]carbonyl}azetidin-3-yl)-4-(1,3-thiazol-2-ylcarbonyl)piperazine<br>$^1$H NMR (300 MHz, CD$_3$OD): δ 7.97 (d, 1H), 7.87 (d, 1H), 7.75 (m, 4H), 7.37 (t, 1H), 7.21 (d, 1H), 7.17 (t, 1H), 6.96 (dd, 1H), 4.67 (m, 3H), 4.52 (m, 1H), 4.43 (m, 1H), 4.30 (m, 1H), 3.76-4.04 (m, 5H), 3.10 (m, 4H), 2.08 (m, 1H), 1.06 (d, 6H); LC/MS m/z (M + H$^+$) 505.2 (calculated for C$_{28}$H$_{32}$N$_4$O$_3$S, 504.66) |
| 222 | N-(2-Cyanoethyl)-4'-({3-[4-(1,3-thiazol-2-ylcarbonyl)piperazin-1-yl]azetidin-1-yl}carbonyl)biphenyl-3-carboxamide<br>LC/MS m/z (M + H$^+$) 529.2 |
| 223 | 3-[4'-({3-[4-(1,3-Thiazol-2-ylcarbonyl)piperazin-1-yl]azetidin-1-yl}carbonyl)biphenyl-3-yl]prop-2-enenitrile<br>$^1$H NMR (300 MHz, CD$_3$OD): δ 7.97 (d, 1H), 8.14 (s, 1H), 7.89 (m, 1H), 7.86 (d, 1H), 7.79 (m, 4H), 7.76 (m, 1H), 7.50-7.69 (m, 2H), 6.36 (d, 1H), 4.62 (m, 3H), 4.48 (m, 1H), 4.40 (m, 1H), 4.27 (m, 1H), 4.95 (m, 2H), 3.77 (m, 1H), 3.00 (m, 4H); LC/MS m/z (M + H$^+$) 484.2 (calculated for C$_{27}$H$_{25}$N$_5$O$_2$S, 483.6) |
| 224 | Methyl 3-[4'-({3-[4-(1,3-thiazol-2-ylcarbonyl)piperazin-1-yl]azetidin-1-yl}carbonyl)biphenyl-4-yl]prop-2-enoate<br>$^1$H NMR (300 MHz, CD$_3$OD): δ 7.97 (d, 1H), 7.87 (d, 1H), 7.79 (m, 4H), 7.74 (m, 5H), 6.60 (d, 1H), 4.66 (m, 3H), 4.53 (m, 1H), 4.43 (m, 1H), 4.31 (m, 1H), 3.98 (m, 2H), 3.88 (m, 1H), 3.80 (s, 3H), 3.11 (m, 4H); LC/MS m/z (M + H$^+$) 517.2 (calculated for C$_{28}$H$_{28}$N$_4$O$_4$S, 516.62) |
| 225 | 1-{1-[(4'-Fluorobiphenyl-4-yl)carbonyl]azetidin-3-yl}-4-(1,3-thiazol-4-ylcarbonyl)piperazine<br>$^1$H NMR (300 MHz, CD$_3$OD): δ 9.06 (s, 1H), 8.22 (s, 1H), 7.74 (m, 4H), 7.69 (dd, 2H), 7.21 (t, 2H), 4.67 (m, 1H), 4.56 (m, 1H), 4.45 (m, 1H), 4.34 (m, 1H), 3.94-4.22 (m, 5H), 3.18 (m, 4H); LC/MS m/z (M + H$^+$) 451.2 (calculated for C$_{24}$H$_{23}$FN$_4$O$_2$S, 450.54) |
| 226 | 1-{1-[(2',4'-Difluorobiphenyl-4-yl)carbonyl]azetidin-3-yl}-4-(1,3-thiazol-4-ylcarbonyl)piperazine<br>$^1$H NMR (300 MHz, CD$_3$OD): δ 9.06 (s, 1H), 8.22 (s, 1H), 7.77 (d, 2H), 7.65 (d, 2H), 7.55 (m, 1H), 7.12 (m, 1H), 7.08 (d, 1H), 4.69 (m, 1H), 4.57 (m, 1H), 4.45 (m, 1H), 4.36 (m, 1H), 3.94-4.22 (m, 5H), 3.20 (m, 4H); LC/MS m/z (M + H$^+$) 469.1 (calculated for C$_{24}$H$_{22}$F$_2$N$_4$O$_2$S, 468.53) |
| 227 | 1-{1-[(3'-Chloro-4'-fluorobiphenyl-4-yl)carbonyl]azetidin-3-yl}-4-(1,3-thiazol-4-ylcarbonyl)piperazine<br>$^1$H NMR (300 MHz, CD$_3$OD): δ 9.06 (s, 1H), 8.22 (s, 1H), 7.79 (dd, 1H), 7.76 (m, 4H), 7.63 (m, 1H), 7.35 (t, 1H), 4.67 (m, 1H), 4.56 (m, 1H), 4.46 (m, 1H), 4.35 (m, 1H), 3.95-4.23 (m, 5H), 3.21 (m, 4H); LC/MS m/z (M + H$^+$) 485.1 (calculated for C$_{24}$H$_{22}$ClFN$_4$O$_2$S, 484.98) |
| 228 | 1-{1-[(3',4'-Dichlorobiphenyl-4-yl)carbonyl]azetidin-3-yl}-4-(1,3-thiazol-4-ylcarbonyl)piperazine<br>$^1$H NMR (300 MHz, CD$_3$OD): δ 8.96 (s, 1H), 8.12 (s, 1H), 7.75 (d, 1H), 7.67 (m, 4H), 7.52 (m, 2H), 4.57 (m, 1H), 4.50 (m, 1H), 4.37 (m, 1H), 4.27 (m, 1H), 3.88-4.15 (m, 5H), 3.13 (m, 4H); LC/MS m/z (M + H$^+$) 501.1 (calculated for C$_{24}$H$_{22}$Cl$_2$N$_4$O$_2$S, 501.44) |
| 229 | 1-(1,3-Thiazol-4-ylcarbonyl)-4-(1-{[3'-(trifluoromethyl)biphenyl-4-yl]carbonyl}azetidin-3-yl)piperazine<br>$^1$H NMR (300 MHz, CD$_3$OD): δ 9.06 (s, 1H), 8.23 (s, 1H), 7.94 (m, 2H), 7.80 (m, 4H), 7.70 (m, 2H), 4.67 (m, 2H), 4.45 (m, 2H), 4.01-4.29 (m, 5H), 3.30 (m, 4H); LC/MS m/z (M + H$^+$) 501.1 (calculated for C$_{25}$H$_{23}$F$_3$N$_4$O$_2$S, 500.55) |
| 230 | 4'-({3-[4-(1,3-Thiazol-2-ylcarbonyl)piperazin-1-yl]azetidin-1-yl}carbonyl)biphenyl-3-amine<br>$^1$H NMR (300 MHz, CD$_3$OD): δ 7.97 (d, 1H), 7.87 (d, 1H), 7.79 (m, 4H), 7.75 (d, 1H), 7.63 (m, 2H), 7.38 (d, 1H), 4.52-4.80 (m, 4H), 4.45 (m, 1H), 4.38 (m, 1H), 3.89-4.10 (m, 3H), 3.17 (m, 4H); LC/MS m/z (M + H$^+$) 448.0 (calculated for C$_{24}$H$_{25}$N$_5$O$_2$S, 447.56) |
| 231 | 1-(1-{[3'-(Methylsulfonyl)biphenyl-4-yl]carbonyl}azetidin-3-yl)-4-(phenylcarbonyl)piperazine<br>LC/MS m/z (M + H$^+$) 504.0 |
| 232 | 1-(1-{[4'-Chloro-3'-(trifluoromethyl)biphenyl-4-yl]carbonyl}azetidin-3-yl)-4-(phenylcarbonyl)piperazine<br>$^1$H NMR (300 MHz, DMSO-d$_6$): δ 8.21 (s, 1H), 8.10 (d, 1H), 7.97 (d, 1H), 7.89 (d, 2H), 7.79 (m, 3H), 7.48 (m, 4H), 4.62 (m, 2H), 4.40 (m, 1H), 4.30 (m, 1H), 4.10 (m, 1H), 3.86 (m, 4H), 3.55 (m, 2H), 3.06 (m, 2H); LC/MS m/z (M + H$^+$) 528.0 (calculated for C$_{28}$H$_{25}$ClF$_3$N$_3$O$_2$, 527.98) |
| 233 | N-[4'-({3-[4-(Phenylcarbonyl)piperazin-1-yl]azetidin-1-yl}carbonyl)biphenyl-3-yl]acetamide<br>LC/MS m/z (M + H$^+$) 483.3 |
| 234 | N-[4'-({3-[4-(1,3-Thiazol-2-ylcarbonyl)piperazin-1-yl]azetidin-1-yl}carbonyl)biphenyl-3-yl]acetamide<br>$^1$H NMR (300 MHz, DMSO-d$_6$): δ 8.10 (d, 1H), 8.06 (d, 1H), 8.00 (m, 1H), 7.75 (d, 2H), 7.70 (d, 2H), 7.57 (dt, 1H), 7.34-7.46 (m, 2H), 4.61 (m, 2H), 4.37 (m, 1H), 4.29 (m, 1H), 4.05 (m, 1H), 3.35-3.82 (m, 6H), 3.09 (m, 2H), 2.07 (s, 3H); LC/MS m/z (M + H$^+$) 490.2 (calculated for C$_{26}$H$_{27}$N$_5$O$_3$S, 489.6) |
| 235 | N-[4'-({3-[4-(1,3-Thiazol-4-ylcarbonyl)piperazin-1-yl]azetidin-1-yl}carbonyl)biphenyl-3-yl]acetamide<br>LC/MS m/z (MH+) 490.2 |
| 236 | 1-(1-{[3'-(Methylsulfonyl)biphenyl-4-yl]carbonyl}azetidin-3-yl)-4-(1,3-thiazol-4-ylcarbonyl)piperazine<br>LC/MS m/z (M + H$^+$) 511.2 |
| 237 | 1-(1,3-Thiazol-2-ylcarbonyl)-4-(1-{[3'-(trifluoromethyl)biphenyl-4-yl]carbonyl}azetidin-3-yl)piperazine<br>$^1$H NMR (300 MHz, DMSO-d$_6$): δ 8.01-8.14 (m, 4H), 7.88 (d, 2H), 7.67-7.83 (m, 4H), 4.60 (m, 2H), 4.39 (m, 1H), 4.28 (m, 1H), 4.06 (m, 2H), 3.22-3.85 (m, 5H), 3.10 (m, 2H); LC/MS m/z (M + H$^+$) 501.1 (calculated for C$_{25}$H$_{23}$F$_3$N$_4$O$_2$S, 500.55) |
| 238 | 1-(1-{[3-Methyl-3'-(trifluoromethyl)biphenyl-4-yl]carbonyl}azetidin-3-yl)-4-(phenylcarbonyl)piperazine<br>$^1$H NMR (300 MHz, CD$_3$OD): δ 7.85-7.94 (m, 2H), 7.40-7.73 (m, 10H), 4.42 (m, 1H), 4.26 (m, 2H), 4.16 (m, 1H), 3.61-3.96 (m, 5H), 2.99 (m, 4H), 2.47 (s, 3H); LC/MS m/z (M + H$^+$) 508.2 (calculated for C$_{29}$H$_{28}$F$_3$N$_3$O$_2$, 507.56) |
| 239 | 1-(1-{[3-Methyl-3'-(trifluoromethyl)biphenyl-4-yl]carbonyl}azetidin-3-yl)-4-(1,3-thiazol-2-ylcarbonyl)piperazine |

| Cpd | Cpd Name and Data |
|---|---|
| | ¹H NMR (300 MHz, CD₃OD): δ 7.85-8.01 (m, 4H), 7.54-7.72 (m, 4H), 7.45 (d, 1H), 4.69 (m, 2H), 4.44 (m, 1H), 4.29 (m, 2H), 4.20 (m, 1H), 3.99 (m, 2H), 3.90 (m, 1H), 3.10 (m, 4H), 2.49 (s, 3H); LC/MS m/z (M + H⁺) 515.1 (calculated for $C_{26}H_{25}F_3N_4O_2S$, 514.57) |
| 240 | 1-(1-{[3-Methyl-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.04 (s, 1H), 8.21 (s, 1H), 7.89 (m, 2H), 7.51-7.72 (m, 4H), 7.45 (d, 1H), 3.87-4.54 (m, 9H) 3.14 (m, 4H), 2.48 (s, 3H); LC/MS m/z (M + H⁺) 515.1 (calculated for $C_{26}H_{25}F_3N_4O_2S$, 514.57) |
| 241 | 1-(1-{[2-Methyl-3'-(trifluoromethyl)biphenyl-4-yl]carbonyl}azetidin-3-yl)-4-(1,3-thiazol-2-ylcarbonyl)piperazine<br>¹H NMR (300 MHz, CD₃OD): δ 7.98 (d, 1H), 7.88 (d, 1H), 7.54-7.77 (m, 6H), 7.36 (d, 1H), 4.64-4.80 (m, 3H), 4.59 (m, H), 4.48 (m, 1H), 4.38 (m, 1H), 3.92-4.12 (m, 3H), 3.27 (m, 4H), 2.30 (s, 3H); LC/MS m/z (M + H⁺) 515.1 (calculated for $C_{26}H_{25}F_3N_4O_2S$, 514.57) |
| 242 | 1-(1-{[2-Methyl-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.07 (s, 1H), 8.22 (s, 1H), 7.49-7.78 (m, 6H), 7.34 (d, 1H), 4.66 (m, 1H), 4.39-4.58 (m, 2H), 4.33 (m, 1H), 3.87-4.20 (m, 5H), 3.14 (m, 4H), 2.31 (s, 3H); LC/MS m/z (M + H⁺) 515.1 (calculated for $C_{26}H_{25}F_3N_4O_2S$, 514.57) |
| 243 | 1-(1-{[2-Methyl-3'-(trifluoromethyl)biphenyl-4-yl]carbonyl}azetidin-3-yl)-4-(phenylcarbonyl)piperazine<br>¹H NMR (300 MHz, CD₃OD): δ 7.44-7.75 (m, 11H), 7.34 (d, 1H), 4.64 (m, 1H), 4.34-4.55 (m, 2H), 4.29 (m, 1H), 3.66-3.97 (m, 5H), 3.03 (m, 4H), 2.30 (s, 3H); LC/MS m/z (M + H⁺) 508.2 (calculated for $C_{29}H_{28}F_3N_3O_2$, 507.56) |
| 244 | 1-(1-{[3-Fluoro-3'-(trifluoromethyl)biphenyl-4-yl]carbonyl}azetidin-3-yl)-4-(1,3-thiazol-2-ylcarbonyl)piperazine<br>¹H NMR (300 MHz, CD₃OD): δ 7.91-8.05 (m, 3H), 7.87 (d, 1H), 7.56-7.80 (m, 5H), 4.60-4.77 (m, 2H), 4.38-4.51 (m, 2H), 4.24-4.38 (m, 2H), 3.84-4.09 (m, 3H), 3.10 (m, 4H); LC/MS m/z (M + H⁺) 519.2 (calculated for $C_{25}H_{22}F_4N_4O_2S$, 518.54) |
| 245 | 1-(1-{[3-Fluoro-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.06 (s, 1H), 8.20 (s, 1H), 7.95 (m, 2H), 7.55-7.80 (m, 5H), 4.38-4.51 (m, 2H), 4.25-4.38 (m, 2H), 3.86-4.19 (m, 5H), 3.08 (m, 4H); LC/MS m/z (M + H⁺) 519.2 (calculated for $C_{25}H_{22}F_4N_4O_2S$, 518.54) |
| 246 | 1-(1-{[3-Fluoro-3'-(trifluoromethyl)biphenyl-4-yl]carbonyl}azetidin-3-yl)-4-(phenylcarbonyl)piperazine<br>¹H NMR (300 MHz, CD₃OD): δ 7.90-8.01 (m, 2H), 7.56-7.80 (m, 5H), 7.42-7.56 (m, 5H), 4.35-4.50 (m, 2H), 4.20-4.35 (m, 2H), 3.66-3.98 (m, 5H), 3.00 (m, 4H); LC/MS m/z (M + H⁺) 512.1 (calculated for $C_{28}H_{25}F_4N_3O_2$, 511.52) |
| 247 | 1-(1-{[2-Methoxy-3'-(trifluoromethyl)biphenyl-4-yl]carbonyl}azetidin-3-yl)-4-(1,3-thiazol-2-ylcarbonyl)piperazine<br>¹H NMR (300 MHz, CD₃OD): δ 7.79 (d, 1H), 7.88 (d, 1H), 7.71-7.82 (m, 2H), 7.56-7.69 (m, 2H), 7.45 (d, 1H), 7.39 (d, 1H), 7.34 (dd, 1H), 4.61-4.78 (m, 3H), 4.57 (m, 1H), 4.46 (m, 1H), 4.34 (m, 1H), 3.87-4.06 (m, 3H), 3.89 (s, 3H), 3.17 (m, 4 H); LC/MS m/z (M + H⁺) 531.2 (calculated for $C_{26}H_{25}F_3N_4O_3S$, 530.57) |
| 248 | 1-(1-{[2-Methoxy-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.06 (s, 1H), 8.22 (s, 1H), 7.71-7.81 (m, 2H), 7.55-7.69 (m, 2H), 7.45 (d, 1H), 7.38 (s, 1H), 7.33 (dd, 3H), 4.70 (m, 1H), 4.58 (m, 1H), 4.47 (m, 1H), 4.36 (m, 1H), 3.94-4.25 (m, 5H), 3.89 (s, 3H), 3.21 (m, 4H); LC/MS m/z (M + H⁺) 531.2 (calculated for $C_{26}H_{25}F_3N_4O_3S$, 530.57) |
| 249 | 1-(1-{[2-Methoxy-3'-(trifluoromethyl)biphenyl-4-yl]carbonyl}azetidin-3-yl)-4-(phenylcarbonyl)piperazine<br>¹H NMR (300 MHz, CD₃OD): δ 7.72-7.84 (m, 2H), 7.56-7.71 (m, 2H), 7.27-7.56 (m, 8H), 4.66 (m, 1H), 4.37-4.59 (m, 2H), 4.32 (m, 1H), 3.66-4.03 (m, 8H), 3.08 (m, 4H); LC/MS m/z (M + H⁺) 524.3 (calculated for $C_{29}H_{28}F_3N_3O_3$, 523.56) |
| 250 | 1-(1-{[3-Chloro-3'-(trifluoromethyl)biphenyl-4-yl]carbonyl}azetidin-3-yl)-4-(1,3-thiazol-2-ylcarbonyl)piperazine<br>¹H NMR (300 MHz, CD₃OD): δ 7.90-8.03 (m, 3H), 7.82-7.90 (m, 2H), 7.62-7.79 (m, 3H), 7.57 (d, 1H), 4.62-4.78 (m, 2H), 4.41-4.54 (m, 1H), 4.20-4.40 (m, 3H), 3.90-4.10 (m, 3H), 3.02-3.24 (m, 4H); LC/MS m/z (M + H⁺) 535.0 (calculated for $C_{25}H_{22}ClF_3N_4O_2S$, 534.99) |
| 251 | 1-(1-{[3-Chloro-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.05 (s, 1H), 8.20 (s, 1H), 7.90-8.02 (m, 2H), 7.85 (s, 1H), 7.63-7.81 (m, 3H), 7.56 (d, 1H), 4.40-4.54 (m, 1H), 4.17-4.38 (m, 3H), 3.85-4.17 (m, 5H), 2.98-3.15 (m, 4H); LC/MS m/z (M + H⁺) 535.0 (calculated for $C_{25}H_{22}ClF_3N_4O_2S$, 534.99) |
| 252 | 1-(1-{[3-Chloro-3'-(trifluoromethyl)biphenyl-4-yl]carbonyl}azetidin-3-yl)-4-(phenylcarbonyl)piperazine<br>¹H NMR (300 MHz, CD₃OD): δ 7.87-7.97 (m, 2H), 7.84 (d, 1H), 7.64-7.79 (m, 3H), 7.55 (d, 1H), 7.41-7.52 (m, 5H), 4.41 (dd, 1H), 4.21-4.34 (m, 2H), 4.17 (dd, 1H), 3.65-3.99 (m, 5H), 2.94 (m, 4H); LC/MS m/z (M + H⁺) 528.2 (calculated for $C_{28}H_{25}ClF_3N_3O_2$, 527.98) |
| 253 | 1-{1-[(3'-Chloro-4'-fluoro-3-methylbiphenyl-4-yl)carbonyl]azetidin-3-yl}-4-(1,3-thiazol-4-ylcarbonyl)piperazine<br>¹H NMR (300 MHz, CD₃OD): δ 9.05 (s, 1H), 8.19 (d, 1H), 7.75 (dd, 1H), 7.55-7.66 (m, 2H), 7.51 (dd, 1 H), 7.27-7.45 (m, 2H), 4.42 (dd, 1H), 4.21-4.34 (m, 2H), 3.95-4.21 (m, 5H), 3.88 (m, 1H), 2.94-3.15 (m, 4H), 2.46 (s, 3H); LC/MS m/z (M + H⁺) 499.0 (calculated for $C_{25}H_{24}ClFN_4O_2S$, 499.01) |
| 254 | 1-(1-{[4'-Chloro-3-methyl-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.05 (s, 1H), 8.19 (d, 1H), 7.98 (d, 1H), 7.88 (dd, 1H), 7.71 (d, 1H), 7.63 (m, 1H), 7.57 (dd, 1 H), 7.45 (d, 1H), 4.44 (dd, 1H), 4.23-4.35 (m, 2H), 3.85-4.23 (m, 6H), 2.96-3.19 (m, 4H), 2.48 (s, 3H); LC/MS m/z (M + H⁺) 549.2 (calculated for $C_{26}H_{24}ClF_3N_4O_2S$, 549.02) |
| 255 | 1-{1-[(3'-Chloro-4'-fluoro-3-methylbiphenyl-4-yl)carbonyl]azetidin-3-yl}-4-(phenylcarbonyl)piperazine<br>¹H NMR (300 MHz, CD₃OD): δ 7.75 (dd, 1H), 7.28-7.65 (m, 10H), 4.38 (dd, 1H), 4.16-4.29 (m, 2H), 4.10 (m, 1H), 3.60-3.95 (m, 5H), 2.91 (m, 4H), 2.45 (s, 3 H); LC/MS m/z (M + H⁺) 492.1 (calculated for $C_{28}H_{27}ClFN_3O_2$, 492.00) |
| 256 | 1-(1-{[4'-Chloro-3-methyl-3'-(trifluoromethyl)biphenyl-4-yl]carbonyl}azetidin-3-yl)-4-(phenylcarbonyl)piperazine<br>¹H NMR (300 MHz, CD₃OD): δ 7.97 (m, 1H), 7.87 (dd, 1H), 7.71 (d, 1H), 7.62 (m, 1H), 7.56 (m, 1H), 7.38-7.52 (m, 6H), 4.39 (dd, 1H), 4.16-4.28 (m, 2H), 4.11 (m, 1H), 3.63-3.93 (m, 5H), 2.91 (m, 4H), 2.47 (s, 3H); LC/MS m/z (M + H⁺) 542.1 (calculated for $C_{29}H_{27}ClF_3N_3O_2$, 542.01) |
| 257 | 1-{1-[(3'-Chloro-4'-fluoro-2-methylbiphenyl-4-yl)carbonyl]azetidin-3-yl}-4-(1,3-thiazol-4-ylcarbonyl)piperazine<br>¹H NMR (300 MHz, CD₃OD): δ 9.06 (s, 1H), 8.20 (s, 1H), 7.49-7.67 (m, 2H), 7.44 (dd, 1H), 7.20-7.37 (m, 3H), 4.63 (m, 1H), 4.37-4.56 (m, 2H), 4.31 (m, 1H), 3.84-4.19 (m, 5H), 3.12 (m, 4H), 2.30 (s, 3H); LC/MS m/z (M + H⁺) 499.0 (calculated for $C_{25}H_{24}ClFN_4O_2S$, 499.01) |
| 258 | 1-(1-{[4'-Chloro-2-methyl-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.06 (s, 1H), 8.20 (s, 1H), 7.66-7.76 (m, 2H), 7.51-7.65 (m, 3H), 7.36 (d, 1H), 4.63 (m, 1H), 4.37-4.56 (m, 2H), 4.29 (m, 1H), 3.84-4.21 (m, 5H), |

123

-continued

| Cpd | Cpd Name and Data |
|---|---|
| | 3.09 (m, 4H), 2.30 (s, 3H); LC/MS m/z (M + H⁺) 549.2 (calculated for $C_{26}H_{24}ClF_3N_4O_2S$, 549.02) |
| 259 | 1-{1-[(3'-Chloro-4'-fluoro-2-methylbiphenyl-4-yl)carbonyl]azetidin-3-yl}-4-(phenylcarbonyl)piperazine<br>¹H NMR (300 MHz, CD₃OD): δ 7.59 (m, 1H), 7.40-7.57 (m, 7H), 7.23-7.39 (m, 3H), 4.65 (m, 1H), 4.37-4.58 (m, 2H), 4.32 (m, 1H), 3.67-4.05 (m, 5H), 3.11 (m, 4H), 2.30 (s, 3H); LC/MS m/z (M + H⁺) 492.1 (calculated for $C_{28}H_{27}ClFN_3O_2$, 492.00) |
| 260 | 1-(1-{[4'-Chloro-2-methyl-3'-(trifluoromethyl)biphenyl-4-yl]carbonyl}azetidin-3-yl)-4-(phenylcarbonyl)piperazine<br>¹H NMR (300 MHz, CD₃OD): δ 7.70-7.80 (m, 3H), 7.42-7.68 (m, 7H), 7.35 (d, 1H), 4.63 (m, 1H), 4.34-4.55 (m, 2H), 4.28 (m, 1H), 3.67-3.98 (m, 5H), 3.02 (m, 4H), 2.30 (s, 3H); LC/MS m/z (M + H⁺) 542.1 (calculated for $C_{29}H_{27}ClF_3N_3O_2$, 542.01) |
| 261 | 1-{1-[(3'-Chloro-4'-fluoro-2-methoxybiphenyl-4-yl)carbonyl]azetidin-3-yl}-4-(1,3-thiazol-4-ylcarbonyl)piperazine<br>¹H NMR (300 MHz, CD₃OD): δ 9.06 (s, 1H), 8.20 (s, 1H), 7.61 (d, 1H), 7.20-7.50 (m, 5H), 4.67 (m, 1H), 4.55 (m, 1H), 4.43 (m, 1H), 4.31 (m, 1H), 3.90-4.25 (m, 5H), 3.90 (s, 3H), 3.11 (m, 4H); LC/MS m/z (M + H⁺) 515.1 (calculated for $C_{25}H_{24}ClFN_4O_3S$, 515.01) |
| 262 | 1-(1-{[4'-Chloro-2-methoxy-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.06 (s, 1H), 8.17 (s, 1H), 7.88 (s, 1H), 7.74 (dd, 1H), 7.66 (d, 1H), 7.45 (d, 1H), 7.38 (m, 1H), 7.33 (dd, 1H), 4.65 (m, 1H), 4.33-4.56 (m, 2H), 4.26 (m, 1H), 3.89-4.12 (m, 5H), 3.89 (s, 3H), 2.97 (m, 4H); LC/MS m/z (M + H⁺) 565.0 (calculated for $C_{26}H_{24}ClF_3N_4O_3S$, 565.02) |
| 263 | 1-{1-[(3'-Chloro-4'-fluoro-2-methoxybiphenyl-4-yl)carbonyl]azetidin-3-yl}-4-(phenylcarbonyl)piperazine<br>¹H NMR (300 MHz, CD₃OD): δ 7.61 (dd, 1H), 7.38-7.57 (m, 7H), 7.35 (d, 1H), 7.23-7.33 (m, 2H), 4.65 (m, 1H) 4.36-4.57 (m, 2H), 4.30 (m, 1H), 3.88 (s, 3H), 3.67-3.97 (m, 5H), 3.05 (m, 4H); LC/MS m/z (M + H⁺) 508.0 (calculated for $C_{28}H_{27}ClFN_3O_3$, 508.00) |
| 264 | 1-(1-{[4'-Chloro-2-methoxy-3'-(trifluoromethyl)biphenyl-4-yl]carbonyl}azetidin-3-yl)-4-(phenylcarbonyl)piperazine<br>¹H NMR (300 MHz, CD₃OD): δ 7.88 (d, 1H), 7.74 (dd, 1H), 7.66 (d, 1 H), 7.42-7.57 (m, 6H), 7.38 (m, 1H), 7.32 (dd, 1H), 4.58-4.69 (m, 1H), 4.36-4.58 (m, 2H), 4.20-4.33 (m, 1H), 3.89 (s, 3H), 3.60-4.04 (m, 5H), 3.03 (m, 4 H); LC/MS m/z (M + H⁺) 558.2 (calculated for $C_{29}H_{27}ClF_3N_3O_3$, 558.01) |
| 265 | 1-{1-[(3,3'-Dichloro-4'-fluorobiphenyl-4-yl)carbonyl]azetidin-3-yl}-4-(1,3-thiazol-4-ylcarbonyl)piperazine<br>¹H NMR (300 MHz, CD₃OD): δ 9.05 (s, 1H), 8.18 (s, 1H), 7.77-7.83 (m, 2H), 7.68 (dd, 1H), 7.58-7.67 (m, 1H), 7.53 (d, 1H), 7.36 (t, 1H), 4.42 (dd, 1H), 4.22-4.35 (m, 2H), 4.18 (dd, 1H), 3.80-4.13 (m, 5H), 2.90-3.11 (m, 4H); LC/MS m/z (M + H⁺) 519.0 (calculated for $C_{24}H_{21}Cl_2FN_4O_2S$, 519.43) |
| 266 | 1-(1-{[3,4'-Dichloro-3'-(trifluoromethyl)biphenyl-4-yl]carbonyl}azetidin-3-yl)-4-(1,3-thiazol-4-ylcarbonyl)piperazine<br>¹H NMR (300 MHz, CD₃OD): δ 9.05 (s, 1H), 8.18 (s, 1H), 8.01 (m, 1H), 7.81-7.98 (m, 2H), 7.74 (d, 2H), 7.56 (d, 1H), 4.36-4.49 (dd, 1H), 4.22-4.35 (m, 2H), 4.19 (dd, 1H), 3.80-4.13 (m, 5H), 2.90-3.11 (m, 4H); LC/MS m/z (M + H⁺) 569.0 (calculated for $C_{25}H_{21}Cl_2F_3N_4O_2S$, 569.44) |
| 267 | 1-{1-[(3,3'-Dichloro-4'-fluorobiphenyl-4-yl)carbonyl]azetidin-3-yl}-4-(phenylcarbonyl)piperazine<br>¹H NMR (300 MHz, CD₃OD): δ 7.77-7.84 (m, 2H), 7.58-7.71 (m, 2H), 7.42-7.57 (m, 6H), 7.36 (t, 1H), 4.42 (dd, 1H) 4.13-4.34 (m, 3H), 3.62-4.01 (m, 5H), 2.98 (m, 4H); LC/MS m/z (M + H⁺) 512.1 (calculated for $C_{27}H_{24}Cl_2FN_3O_2$, 512.42) |
| 268 | 1-(1-{[3,4'-Dichloro-3'-(trifluoromethyl)biphenyl-4-yl]carbonyl}azetidin-3-yl)-4-(phenylcarbonyl)piperazine<br>¹H NMR (300 MHz, CD₃OD): δ 8.01 (d, 1H), 7.90 (dd, 1H), 7.85 (d, 1H), 7.74 (d, 2H), 7.56 (d, 1H), 7.41-7.53 (m, 5H), 4.43 (dd, 1H), 4.14-4.35 (m, 3H), |

124

-continued

| Cpd | Cpd Name and Data |
|---|---|
| | 3.63-4.04 (m, 5H), 2.99 (m, 4H);<br>LC/MS m/z (M + H⁺) 562.0 (calculated for $C_{28}H_{24}Cl_2F_3N_3O_2$, 562.42) |
| 488 | 1-{1-[(3-Methylbiphenyl-4-yl)carbonyl]azetidin-3-yl}-4-(1,3-thiazol-4-ylcarbonyl)piperazine<br>¹H NMR (300 MHz, CD₃OD): δ 9.06 (s, 1H), 8.22 (s, 1H), 7.30-7.71 (m, 8H), 3.92-4.57 (m, 9H) 3.11-3.29 (m, 4H), 2.46 (s, 3H); LC/MS m/z (M + H⁺) 447.1 (calculated for $C_{25}H_{26}N_4O_2S$, 446.58) |
| 1070 | 1-(1-{[2-Fluoro-3'-(trifluoromethyl)biphenyl-4-yl]carbonyl}azetidin-3-yl)-4-(1,3-thiazol-4-ylcarbonyl)piperazine<br>MS m/z (M + H⁺) 518.9 |
| 1102 | 1-(1-{[2-Chloro-3'-(trifluoromethyl)biphenyl-4-yl]carbonyl}azetidin-3-yl)-4-(1,3-thiazol-4-ylcarbonyl)piperazine<br>MS m/z (M + H⁺) 434.9 |

Example 7

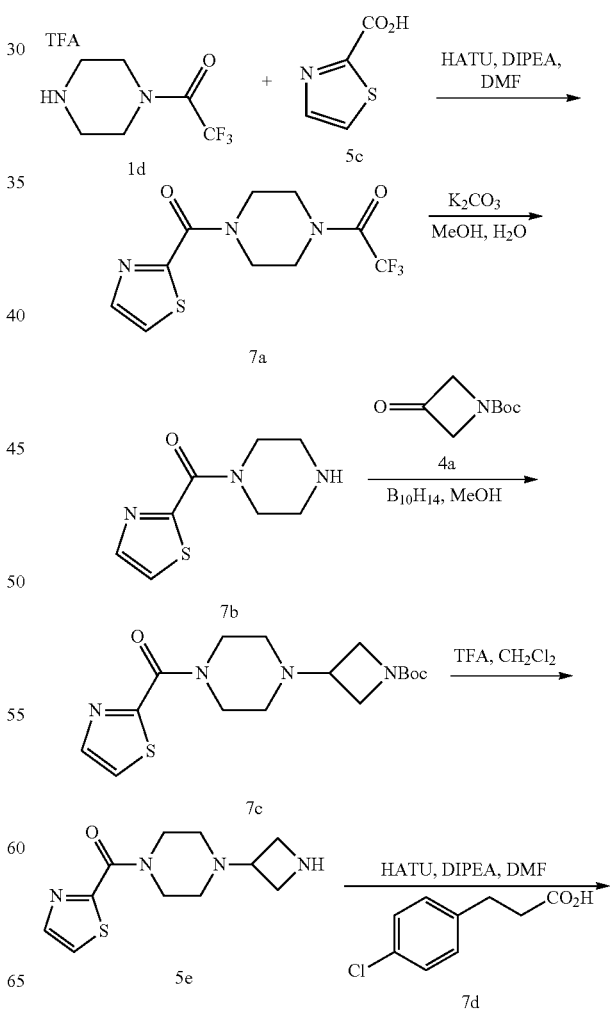

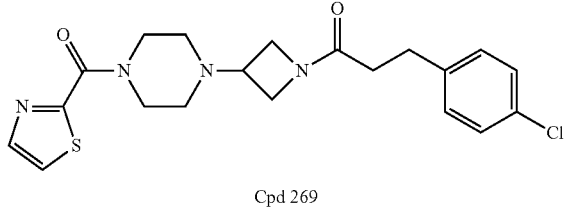

Cpd 269

A. 2,2,2-Trifluoro-1-[4-(thiazole-2-carbonyl)-piperazin-1-yl]-ethanone, 7a. To a solution of compound 1d (5 g, 0.027 mol) in DMF (50 mL) and DIPEA (19.5 mL, 0.11 mol) was added compound 5c (3.3 g, 0.0255 mol) and HATU (12.6 g, 0.033 mol). The reaction was stirred for 4 h then poured into water and extracted with EtOAc. The organic portions were washed with water and brine, and dried over $MgSO_4$. The solvent was evaporated in vacuo. The residue was passed through a silica gel column (30-10%: EtOAc-heptane) to give compound 7a (3.8 g). MS m/z (M+H$^+$) 294.1.

B. piperazin-1-yl-thiazol-2-yl-methanone, 7b. A solution of compound 7a (3.8 g, 0.013 mol) and $K_2CO_3$ (3.5 g, 0.026 mol) in MeOH (40 mL) and water (10 mL), was stirred for 4 h. The solid was collected by filtration and the solvent evaporated in vacuo to give compound 7b (6.12 g). MS m/z (M+H$^+$) 198.1.

C. 3-[4-(Thiazole-2-carbonyl)-piperazin-1-yl]-azetidine-1-carboxylic acid tert-butyl ester, 7c. A solution of compound 7b (6.1 g, 0.031 mol) and (5.1 g, 0.03 mol) compound 4a in MeOH (30 mL) was stirred for 15 min. Decaborane (1 g, 0.008 mol) was added and the reaction was stirred for 18 h. The solvent was evaporated in vacuo. The residue was used without further purification for the next step. MS m/z (M+H$^+$) 353.1.

D. (4-Azetidin-3-yl-piperazin-1-yl)-thiazol-2-yl-methanone, 5e. To a solution of compound 7c in $CH_2Cl_2$ (100 mL) was added TFA (30 mL). The reaction was stirred for 3.5 h and the solvent was evaporated in vacuo. The residue was purified by reverse phase preparative HPLC to give compound 5e (5.15 g). MS m/z (M+H$^+$) 253.1.

E. 1-{1-[3-(4-Chlorophenyl)propanoyl]azetidin-3-yl}-4-(1,3-thiazol-2-ylcarbonyl)piperazine, Cpd 269. To a solution of compound 5e (150 mg, 0.52 mmol) in DMF (5 mL) and DIPEA (0.40 mL, 2.2 mmol) was added compound 7d (125 mg, 0.067 mmol), and HATU (0.25 g, 0.067 mmol). The reaction was stirred for 4 h, then poured into water and extracted with EtOAc. The combined extracts were concentrated in vacuo. The resultant residue was purified by reverse phase HPLC to give compound 269 (20.2 mg). LC/MS m/z (M+H$^+$) 419.15 (calculated for $C_{20}H_{23}ClN_4O_2S$, 418.95).

Following the procedure described above for Example 7 and substituting the appropriate reagents, starting materials and purification methods known to those skilled in the art, the following compounds of the present invention were prepared.

| Cpd | Cpd Name and Data |
|---|---|
| 270 | 1-{1-[3-(4-Bromophenyl)propanoyl]azetidin-3-yl}-4-(1,3-thiazol-2-ylcarbonyl)piperazine<br>LC/MS m/z (M + 2H$^+$) 465.05 (calculated for $C_{20}H_{23}BrN_4O_2S$, 463.40) |
| 271 | 1-(1,3-Thiazol-2-ylcarbonyl)-4-(1-{3-[4-(trifluoromethyl)phenyl]propanoyl}azetidin-3-yl)piperazine.<br>LC/MS m/z (M + H$^+$) 453.15 (calculated for $C_{21}H_{23}F_3N_4O_2S$, 452.50) |
| 272 | 1-{1-[3-(3-Chlorophenyl)propanoyl]azetidin-3-yl}-4-(1,3-thiazol-2-ylcarbonyl)piperazine.<br>LC/MS m/z (M + H$^+$) 419.17 (calculated for $C_{20}H_{23}ClN_4O_2S$, 418.95) |
| 273 | 1-{1-[3-(2-Chlorophenyl)propanoyl]azetidin-3-yl}-4-(1,3-thiazol-2-ylcarbonyl)piperazine.<br>$^1$H NMR (300 MHz, MeOD): δ 8.0 (d, 1H), 7.9 (d, 2H), 4.7 (bm, 2H), 4.4 (m, 2H), 4.3-4.1 (m, 2H), 4.0 (bm, 2H), 3.25 (m, 5H), 3.0 (m, 2H), 2.5 (m, 2H)<br>LC/MS m/z (M + H$^+$) 419.16 (calculated for $C_{20}H_{23}ClN_4O_2S$, 418.95) |
| 274 | 1-{1-[3-(2,6-Dichlorophenyl)propanoyl]azetidin-3-yl}-4-(1,3-thiazol-2-ylcarbonyl)piperazine.<br>$^1$H NMR (300 MHz, MeOD): δ 8 (d, 1H), 7.9 (d, 1H), 7.4 (ar, 2H), 7.2 (m, 1H), 4.75 (m, 2H), 4.5-4.1 (m, 5H), 4.0 (m, 3H), 3.2 (m, 5H), 2.4 (m, 3H)<br>LC/MS m/z (M + 2H$^+$) 455.10 (calculated for $C_{20}H_{22}Cl_2N_4O_2S$, 453.39) |
| 275 | 1-{1-[3-(3,4-Difluorophenyl)propanoyl]azetidin-3-yl}-4-(1,3-thiazol-2-ylcarbonyl)piperazine.<br>LC/MS m/z (M + H$^+$) 421.19 (calculated for $C_{20}H_{22}F_2N_4O_2S$, 420.48) |
| 276 | 1-{1-[3-(4-Methylphenyl)propanoyl]azetidin-3-yl}-4-(1,3-thiazol-2-ylcarbonyl)piperazine<br>LC/MS m/z (M + H$^+$) 399.23 (calculated for $C_{21}H_{26}N_4O_2S$, 398.53) |
| 277 | 1-{1-[3-(4-Methoxyphenyl)propanoyl]azetidin-3-yl}-4-(1,3-thiazol-2-ylcarbonyl)piperazine3<br>LC/MS m/z (M + H$^+$) 415.23 (calculated for $C_{21}H_{26}N_4O_3S$, 414.53) |
| 278 | 1-(1-{3-[3,5-Bis(trifluoromethyl)phenyl]propanoyl}azetidin-3-yl)-4-(1,3-thiazol-2-ylcarbonyl)piperazine.<br>LC/MS m/z (M + H$^+$) 521.14 (calculated for $C_{22}H_{22}F_6N_4O_2S$, 520.50) |
| 279 | 1-[1-(3-Naphthalen-1-ylpropanoyl)azetidin-3-yl]-4-(1,3-thiazol-2-ylcarbonyl)piperazine.<br>LC/MS m/z (M + H$^+$) 435.22 (calculated for $C_{24}H_{26}N_4O_2S$, 434.56) |
| 280 | 1-{1-[3-(4-Phenoxyphenyl)propanoyl]azetidin-3-yl}-4-(1,3-thiazol-2-ylcarbonyl)piperazine.<br>LC/MS m/z (M + H$^+$) 477.20 (calculated for $C_{26}H_{28}N_4O_3S$, 476.60) |
| 281 | 1-{1-[3-(3,4-Dichlorophenyl)propanoyl]azetidin-3-yl}-4-(1,3-thiazol-2-ylcarbonyl)piperazine.<br>$^1$H NMR (300 MHz, MeOD) d 8.0 (ar, 1H), 7.9 (ar, 1H), 7.4 (m, 2H), 7.2 (m, 1H), 4.4 (dd, 1H), 4.3-4.2 (m, 2H), 4.1 (m, 1H), 3.9 (m, 1H), 3.3 (m, 3H), 3.2 (m, 4H), 3.0 (bs, 1H), 2.9 (m, 2H), 2.5 (m, 2H)<br>LC/MS m/z (M + 2H$^+$) 455.10 (calculated for $C_{20}H_{22}Cl_2N_4O_2S$, 453.39) |
| 282 | 1-{1-[3-(5,5,8,8-Tetramethyl-5,6,7,8-tetrahydronaphthalen-2-yl)propanoyl]azetidin-3-yl}-4-(1,3-thiazol-2-ylcarbonyl)piperazine.<br>$^1$H NMR (300 MHz, MeOD): δ 7.9 (ar, 1H), 7.7 (ar, 1H), 7.13 (ar, 1H), 7.0 (ar, 1H), 6.9 (ar, 1H), 4.2-4.1 (m, 2H), 4.1-4.0 (m, 1H), 3.9, (bs, 1H), 3.8 (m, 1H), 3.2 (m, 2H), 3.11 (m, 4H), 2.7 (t, 2H), 2.3 (t, 2H), 1.5 (s, 4H), 1.1 (dd, 12H).<br>LC/MS m/z (M + H$^+$) 495.24 (calculated for $C_{28}H_{38}N_4O_2S$, 494.70) |
| 283 | 1-(1,3-Thiazol-2-ylcarbonyl)-4-{1-[(2E)-3-{4-[(trifluoromethyl)sulfanyl]phenyl}prop-2-enoyl]azetidin-3-yl}piperazine<br>LC/MS m/z (M + H$^+$) 483.18 (calculated for $C_{21}H_{21}F_3N_4O_2S_2$, 482.55) |
| 284 | 1-{1-[(3-Chlorophenoxy)acetyl]azetidin-3-yl}-4-(1,3-thiazol-2-ylcarbonyl)piperazine.<br>LC/MS m/z (M + H$^+$) 421.12 (calculated for $C_{19}H_{21}ClN_4O_3S$, 420.92) |
| 285 | 1-{1-[(2-Chlorophenoxy)acetyl]azetidin-3-yl}-4-(1,3-thiazol-2-ylcarbonyl)piperazine.<br>LC/MS m/z (M + H$^+$) 421.12 (calculated for $C_{19}H_{21}ClN_4O_3S$, 420.92) |
| 286 | 1-{1-[3-(2-Bromophenyl)propanoyl]azetidin-3-yl}-4-(1,3-thiazol-2-ylcarbonyl)piperazine.<br>LC/MS m/z (M + 2H$^+$) 465.07 (calculated for $C_{20}H_{23}BrN_4O_2S$, 463.40) |

| Cpd | Cpd Name and Data |
|---|---|
| 287 | 1-(1-{3-[4-(3,4-Dimethyl-1H-pyrazol-1-yl)phenyl]propanoyl}azetidin-3-yl)-4-(1,3-thiazol-2-ylcarbonyl)piperazine.<br>LC/MS m/z (M + H⁺) 479.29 (calculated for $C_{25}H_{30}N_6O_2S$, 478.62) |
| 288 | 1-{1-[(2,4-Dichlorophenoxy)acetyl]azetidin-3-yl}-4-(1,3-thiazol-2-ylcarbonyl)piperazine.<br>LC/MS m/z (M + 2H⁺) 457.13 (calculated for $C_{19}H_{20}Cl_2N_4O_3S$, 455.37) |
| 289 | 1-(1,3-Thiazol-2-ylcarbonyl)-4-(1-{[4-(trifluoromethoxy)phenoxy]acetyl}azetidin-3-yl)piperazine.<br>LC/MS m/z (M + H⁺) 471.16 (calculated for $C_{20}H_{21}F_3N_4O_4S$, 470.47) |
| 290 | N-Cyclopropyl-4-(3-oxo-3-{3-[4-(1,3-thiazol-2-ylcarbonyl)piperazin-1-yl]azetidin-1-yl}propyl)benzenesulfonamide.<br>¹H NMR (300 MHz, MeOD) d 8.0 (d, 1H); 7.9 (d, 1H); 7.4 (m, 4H); 4.7 (bs, 2H), 4.4-4.1 (m, 3H), 4.1-3.9 (m, 3H), 3.8 (m, 1H), 3.1 (m, 3H), 3.0 (t, 2H), 2.5 (t, 2H), 2.1 m, 1H), 0.5 (m, 4H)<br>LC/MS m/z (M + H⁺) 504.20 (calculated for $C_{23}H_{29}N_5O_4S_2$, 503.65) |
| 291 | N-(Cyclohexylmethyl)-N-methyl-4-(3-oxo-3-{3-[4-(1,3-thiazol-2-ylcarbonyl)piperazin-1-yl]azetidin-1-yl}propyl)aniline.<br>¹H NMR (300 MHz, MeOD): δ 8.0 (d, 1H), 7.9 (d, 1H), 7.5 (m, 4H), 4.4 (bm, 2H), 4.25-4.0 (m, 4H), 3.8 (m, 1H), 3.4 (d, 2H), 3.2 (s, m, 3H), 3.1 (bs, 3H), 3.0 (t, 2H), 2.5 (t, 2H), 1.7 (m, 5H), 1.1 (m, 5H)<br>LC/MS m/z (M + H⁺) 510.32 (calculated for $C_{28}H_{39}N_5O_2S$, 509.72) |
| 292 | 1-(1,3-Thiazol-2-ylcarbonyl)-4-[1-({[4-(trifluoromethyl)phenyl]sulfanyl}acetyl)azetidin-3-yl]piperazine<br>LC/MS m/z (M + H⁺) 471.18 (calculated for $C_{20}H_{21}F_3N_4O_2S_2$, 470.54) |
| 293 | 1-[1-(1-Benzothiophen-2-ylcarbonyl)azetidin-3-yl]-4-(1,3-thiazol-2-ylcarbonyl)piperazine<br>LC/MS m/z (M + H⁺) 413.20 (calculated for $C_{20}H_{20}N_4O_2S_2$, 412.54) |
| 294 | 1-{1-[3-(4-Ethoxyphenyl)propanoyl]azetidin-3-yl}-4-(1,3-thiazol-2-ylcarbonyl)piperazine.<br>LC/MS m/z (M + H⁺) 429.27 (calculated for $C_{22}H_{28}N_4O_3S$, 428.56) |
| 295 | 1-{1-[(2E)-3-(2-Chlorophenyl)prop-2-enoyl]azetidin-3-yl}-4-(1,3-thiazol-2-ylcarbonyl)piperazine.<br>LC/MS m/z (M + H⁺) 417.0 (calculated for $C_{20}H_{21}ClN_4O_2S$, 416.93) |
| 296 | 1-{1-[(2E)-3-(2-Bromophenyl)prop-2-enoyl]azetidin-3-yl}-4-(1,3-thiazol-2-ylcarbonyl)piperazine.<br>LC/MS m/z (M + H⁺) 462.9 (calculated for $C_{20}H_{21}BrN_4O_2S$, 461.38) |
| 297 | 3-Naphthalen-2-yl-1-{3-[4-(thiazole-2-carbonyl)-piperazin-1-yl]-azetidin-1-yl}-propenone<br>LC/MS m/z (M + H⁺) 433.29 (calculated for $C_{24}H_{24}N_4O_2S$, 432.55) |

Example 8

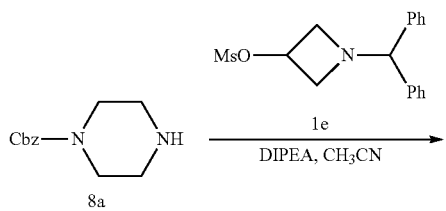

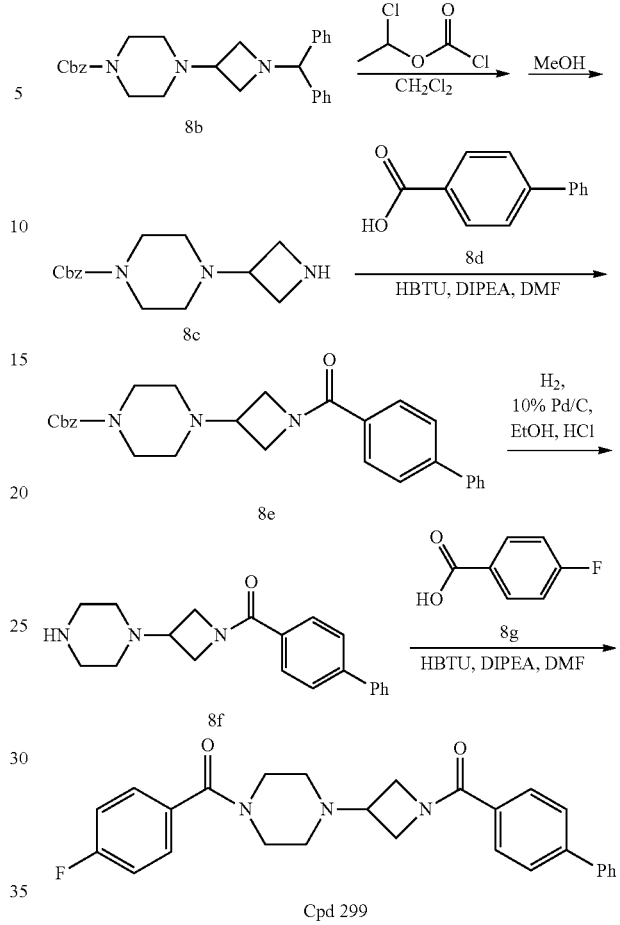

A. 4-(1-Benzhydryl-azetidin-3-yl)-piperazine-1-carboxylic acid benzyl ester, 8b. To a solution of compound 8a (1.4 g, 6.3 mmol) and compound 1e (2 g, 6.3 mmol) in CH₃CN (30 mL) was added DIPEA (1.5 mL, 8.1 mmol) at room temperature. The mixture was refluxed for 18 h. The solvent was removed under reduced pressure and the residue was partitioned between CHCl₃ and water. The organic layer was dried over K₂CO₃, filtered, and concentrated to give crude compound 8b (2.65 g). MS m/z (M+H⁺) 442.

B. 4-Azetidin-3-yl-piperazine-1-carboxylic acid benzyl ester, 8c. To a solution of compound 8b (3.4 g, 7.7 mmol) in CH₂Cl₂ was added 1-chloroethyl chloroformate (2.5 mL, 23.1 mmol) at 0° C. under a N₂ atmosphere. The ice bath was removed and the reaction stirred for 2 h. The organic phase was concentrated under reduced pressure, and MeOH was added to the resultant residue. The reaction was refluxed for 2 h at which time the solvent was removed under reduced pressure. The residue was partitioned between chloroform and aqueous HCl (1N). The aqueous layer was separated, made basic with aqueous NaOH (3N), and extracted with chloroform. The organic layer was then dried (K₂CO₃), filtered and concentrated to afford compound 8c (2.65 g). MS m/z (M+H⁺) 276.

C. 4-[1-(Biphenyl-4-carbonyl)-azetidin-3-yl]-piperazine-1-carboxylic acid benzyl ester, 8e. To a solution of compound 8c (2.6 g, 9.4 mmol), compound 8d (1.87 g, 9.4 mmol), and DIPEA (2.43 g, 18.9 mmol) in acetonitrile was added HBTU (4.6 g, 12.3 mmol). The reaction was stirred for 18 h at which time the solvent was removed under reduced pressure and the crude product purified by reverse phase HPLC. Lyophilization provided compound 8e (1.74 g). MS m/z (M+H⁺) 456.2.

D. Biphenyl-4-yl-(3-piperazin-1-yl-azetidin-1-yl)-methanone, 8f. A mixture of compound 8e (1.7 g, 2.9 mmol), and 10% Palladium on carbon (300 mg) was hydrogenated (50 psi hydrogen gas) using a Parr apparatus for 18 h. The catalyst was removed by filtration, and the solvent concentrated under reduced pressure to afford crude compound 8f (1.5 g). MS m/z (M+H⁺) 322.

E. 1-[1-(Biphenyl-4-ylcarbonyl)azetidin-3-yl]-4-[(4-fluorophenyl)-carbonyl]piperazine, Cpd 299. To a solution of compound 8f (100 mg, 0.3 mmol), compound 8g (44 mg, 0.31 mmol), and DIPEA (80 mg, 0.6 mmol) in dimethylformamide was added HBTU (141 mg, 0.37 mmol). After stirring for 18 h, the reaction was purified by preparative reverse phase HPLC to yield compound 299. $^1$H NMR (400 MHz, MeOD): δ 7.93-8.03 (m, 1H), 7.61-7.71 (m, 4H), 7.54-7.61 (m, 2H), 7.43-7.50 (m, 2H), 7.35-7.43 (m, 2H), 7.27-7.35 (m, 1H), 7.07-7.20 (m, 2H), 4.55-4.67 (m, 1H), 4.43-4.53 (m, 1H), 4.32-4.43 (m, 1H), 4.19-4.32 (m, 1H), 3.89-4.00 (m, 1H), 3.66-3.89 (m, 4H), 3.08 (br. s, 4H); MS m/z (M+H⁺) 444.2 (calculated for $C_{27}H_{26}FN_3O_2$, 443.53).

Following the procedure described above for Example 8 and substituting the appropriate reagents, starting materials and purification methods known to those skilled in the art, the following compounds of the present invention were prepared:

| | |
|---|---|
| 300 | 1-[1-(Biphenyl-4-ylcarbonyl)azetidin-3-yl]-4-[(2-fluorophenyl)carbonyl]piperazine<br>MS m/z (M + H⁺) 444.2 (calculated for $C_{27}H_{26}FN_3O_2$, 443.53) |
| 301 | 1-[1-(Biphenyl-4-ylcarbonyl)azetidin-3-yl]-4-(thiophen-3-ylcarbonyl)piperazine<br>MS m/z (M + H⁺) 432.1 (calculated for $C_{25}H_{25}N_3O_2S$, 431.56) |
| 302 | 1-[1-(Biphenyl-4-ylcarbonyl)azetidin-3-yl]-4-(1H-pyrrol-2-ylcarbonyl)piperazine<br>MS m/z (M + 2H⁺) 416.2 (calculated for $C_{25}H_{26}N_4O_2$, 414.51) |
| 303 | 1-[1-(Biphenyl-4-ylcarbonyl)azetidin-3-yl]-4-(cyclopropylcarbonyl)piperazine<br>MS m/z (M + H⁺) 390.23 (calculated for $C_{24}H_{27}N_3O_2$, 389.5) |
| 304 | 1-[1-(Biphenyl-4-ylcarbonyl)azetidin-3-yl]-4-[(3-fluorophenyl)carbonyl]piperazine<br>MS m/z (M + H⁺) 444.2 (calculated for $C_{27}H_{26}FN_3O_2$, 443.53) |
| 305 | 1-[1-(Biphenyl-4-ylcarbonyl)azetidin-3-yl]-4-(1,3-oxazol-2-ylcarbonyl)piperazine<br>MS m/z (M + H⁺) 417.2 (calculated for $C_{24}H_{24}N_4O_3$, 416.48) |
| 306 | 1-[1-(Biphenyl-4-ylcarbonyl)azetidin-3-yl]-4-(1,2,3-thiadiazol-4-ylcarbonyl)piperazine<br>MS m/z (M + H⁺) 434.1 (calculated for $C_{23}H_{23}N_5O_2S$, 433.54) |
| 307 | 1-[1-(Biphenyl-4-ylcarbonyl)azetidin-3-yl]-4-(isoxazol-5-ylcarbonyl)piperazine<br>MS m/z (M + H⁺) 417.2 (calculated for $C_{24}H_{24}N_4O_3$, 416.48) |
| 308 | 1-[1-(Biphenyl-4-ylcarbonyl)azetidin-3-yl]-4-(1,2,5-oxadiazol-3-ylcarbonyl)piperazine<br>MS m/z (M + H⁺) 418.2 (calculated for $C_{23}H_{23}N_5O_3$, 417.47) |
| 309 | 5-({4-[1-(Biphenyl-4-ylcarbonyl)azetidin-3-yl]piperazin-1-yl}carbonyl)thiophene-3-carbonitrile<br>MS m/z (M + H⁺) 457.2 (calculated for $C_{26}H_{24}N_4O_2S$, 456.57) |
| 310 | 1-[1-(Biphenyl-4-ylcarbonyl)azetidin-3-yl]-4-(isothiazol-5-ylcarbonyl)piperazine<br>$^1$H NMR (400 MHz, MeOD): δ 8.44 (s, 1H), 7.65 (s, 4H), 7.53-7.58 (m, 2H), 7.47 (d, J = 1.71 Hz, 1H), 7.34-7.40 (m, 2H), 7.26-7.32 (m, 1H), 4.49-4.60 (m, 1H), 4.37-4.49 (m, 1H), 4.27-4.37 (m, 1H), 4.15-4.27 (m, 1H), 3.72-3.88 (m, 5H), 2.92-3.02 (m, 4H);<br>MS m/z (M + H⁺) 433.2 (calculated for $C_{24}H_{24}N_4O_2S$, 432.55) |
| 311 | 1-[1-(Biphenyl-4-ylcarbonyl)azetidin-3-yl]-4-(1H-pyrrol-3-ylcarbonyl)piperazine<br>$^1$H NMR (400 MHz, MeOD): δ 7.66 (s, 4H), 7.56-7.59 (m, 1H), 7.54-7.56 (m, 1H), 7.35-7.41 (m, 2H), 7.26-7.33 (m, 1H), 7.08-7.15 (m, 1H), 6.64-6.75 (m, 1H), 6.24-6.31 (m, 1H), 4.54-4.64 (m, 1H), 4.43-4.51 (m, 1H), 4.32-4.41 (m, 1H), 4.20-4.28 (m, 1H), 3.85-3.97 (m, 5H), 3.06 (br. s., 4H);<br>MS m/z (M + H⁺) 415.2 (calculated for $C_{25}H_{26}N_4O_2$, 414.51) |
| 312 | 1-[1-(Biphenyl-4-ylcarbonyl)azetidin-3-yl]-4-[(5-chlorofuran-2-yl)carbonyl]piperazine<br>$^1$H NMR (400 MHz, MeOD): δ 7.66 (s, 4H), 7.54-7.59 (m, 2H), 7.38 (d, J = 7.58 Hz, 2H), 7.26-7.33 (m, 1H), 7.05 (d, J = 3.67 Hz, 1H), 6.42 (d, J = 3.42 Hz, 1H), 4.50-4.63 (m, 1H), 4.40-4.48 (m, 1H), 4.28-4.39 (m, 1H), 4.17-4.28 (m, 1H), 3.87-3.97 (m, 4H), 3.78-3.87 (m, 1H), 2.97-3.07 (m, 4H);<br>MS m/z (M + H⁺) 450.1 (calculated for $C_{25}H_{24}ClN_3O_3$, 449.94) |
| 480 | N-[4-({4-[1-(Biphenyl-4-ylcarbonyl)azetidin-3-yl]piperazin-1-yl}carbonyl)-1,3-thiazol-2-yl]acetamide<br>MS m/z (M + H⁺) 490.2 |
| 1478 | 2-({4-[1-(Biphenyl-4-ylcarbonyl)azetidin-3-yl]piperazin-1-yl}carbonyl)pyrimidine<br>MS m/z (M + H⁺) 428.0 |
| 1398 | 1-[1-(Biphenyl-4-ylcarbonyl)azetidin-3-yl]-4-(cyclopentylcarbonyl)piperazine<br>MS m/z (M + H⁺) 418.2 |
| 1465 | 1-[1-(Biphenyl-4-ylcarbonyl)azetidin-3-yl]-4-[(5-methylisoxazol-3-yl)carbonyl]piperazine<br>MS m/z (M + H⁺) 431.3 |
| 1258 | 1-[1-(1,3-Oxazol-4-ylcarbonyl)azetidin-3-yl]-4-{[3'-(trifluoromethyl)biphenyl-4-yl]carbonyl}piperazine<br>MS m/z (M + H⁺) 485.0 |
| 1262 | 1-[1-(Biphenyl-4-ylcarbonyl)azetidin-3-yl]-4-(isoxazol-3-ylcarbonyl)piperazine<br>MS m/z (M + H⁺) 417.1 |
| 1222 | 1-[1-(Biphenyl-4-ylcarbonyl)azetidin-3-yl]-4-(1,3-oxazol-4-ylcarbonyl)piperazine<br>MS m/z (M + H⁺) 417.0 |
| 1269 | 1-[1-(Biphenyl-4-ylcarbonyl)azetidin-3-yl]-4-(1H-1,2,3-triazol-4-ylcarbonyl)piperazine<br>MS m/z (M + H⁺) 417.0 |
| 1256 | 1-[1-(Biphenyl-4-ylcarbonyl)azetidin-3-yl]-4-[(2,2-difluorocyclopropyl)carbonyl]piperazine<br>MS m/z (M + H⁺) 426.0 |
| 1310 | 1-[1-(Biphenyl-4-ylcarbonyl)azetidin-3-yl]-4-(1H-pyrazol-4-ylcarbonyl)piperazine<br>MS m/z (M + H⁺) 416.2 |
| 1140 | 1-[1-(Biphenyl-4-ylcarbonyl)azetidin-3-yl]-4-(furan-3-ylcarbonyl)piperazine<br>MS m/z (M + H⁺) 416.2 |
| 1232 | 1-[1-(Biphenyl-4-ylcarbonyl)azetidin-3-yl]-4-(cyclobutylcarbonyl)piperazine<br>MS m/z (M + H⁺) 404.2 |
| 1308 | 3-({4-[1-(Biphenyl-4-ylcarbonyl)azetidin-3-yl]piperazin-1-yl}carbonyl)-1H-indole<br>MS m/z (M + H⁺) 465.3 |
| 1324 | 1-(1H-Pyrrol-3-ylcarbonyl)-4-(1-{[3'-(trifluoromethyl)biphenyl-4-yl]carbonyl}azetidin-3-yl)piperazine<br>MS m/z (M + H⁺) 481.0 |
| 1325 | 1-(1H-Pyrrol-2-ylcarbonyl)-4-(1-{[3'-(trifluoromethyl)biphenyl-4-yl]carbonyl}azetidin-3-yl)piperazine<br>MS m/z (M + H⁺) 483.1 |
| 186-A | 1-[($D_5$)Phenylcarbonyl]-4-(1-{[3'-(trifluoromethyl)biphenyl-4-yl]carbonyl}azetidin-3-yl)piperazine<br>MS m/z (M + H⁺) 499.4 |
| 1169 | 1-(1,3-Oxazol-5-ylcarbonyl)-4-(1-{[3'-(trifluoromethyl)biphenyl-4-yl]carbonyl}azetidin-3-yl)piperazine<br>MS m/z (M + H⁺) 485.0 |
| 1335 | 1-[(5-Bromofuran-2-yl)carbonyl]-4-(1-{[3'-(trifluoromethyl)biphenyl-4-yl]carbonyl}azetidin-3-yl)piperazine<br>MS m/z (M + H⁺) 560.0/562.0 |
| 1087 | 1-[(4-Bromothiophen-2-yl)carbonyl]-4-(1-{[3'-(trifluoromethyl)biphenyl-4-yl]carbonyl}azetidin-3-yl)piperazine<br>MS m/z (M + H⁺) 576.0/578.0 |
| 1078 | 1-[(5-Chlorofuran-2-yl)carbonyl]-4-(1-{[3'-(trifluoromethyl)biphenyl-4-yl]carbonyl}azetidin-3-yl)piperazine<br>MS m/z (M + H⁺) 518.2 |
| 1118 | 1-(Isoxazol-5-ylcarbonyl)-4-(1-{[3'-(trifluoromethyl)biphenyl-4-yl]carbonyl}azetidin-3-yl)piperazine<br>MS m/z (M + H⁺) 485.1 |

-continued

| 1336 | 1-[(5-Fluorothiophen-2-yl)carbonyl]-4-(1-{[3'-(trifluoromethyl)biphenyl-4-yl]carbonyl}azetidin-3-yl)piperazine<br>MS m/z (M + H+) 519.2 |
|---|---|
| 1145 | 1-(Isoxazol-3-ylcarbonyl)-4-(1-{[3'-(trifluoromethyl)biphenyl-4-yl]carbonyl}azetidin-3-yl)piperazine<br>MS m/z (M + H+) 485.2 |
| 1143 | 1-[(5-Chlorothiophen-2-yl)carbonyl]-4-(1-{[3'-(trifluoromethyl)biphenyl-4-yl]carbonyl}azetidin-3-yl)piperazine<br>MS m/z (M + H+) 535.2 |
| 1085 | 1-(1,3-Oxazol-2-ylcarbonyl)-4-(1-{[3'-(trifluoromethyl)biphenyl-4-yl]carbonyl}azetidin-3-yl)piperazine<br>MS m/z (M + H+) 485.1 |
| 1112 | 1-[(2,2-Difluorocyclopropyl)carbonyl]-4-(1-{[3'-(trifluoromethyl)biphenyl-4-yl]carbonyl}azetidin-3-yl)piperazine<br>MS m/z (M + H+) 494.2 |
| 1094 | 1-(1,3-Oxazol-4-ylcarbonyl)-4-(1-{[3'-(trifluoromethyl)biphenyl-4-yl]carbonyl}azetidin-3-yl)piperazine MS m/z (M + H+) 485.2 |
| 1057 | 1-(Cyclopropylcarbonyl)-4-(1-{[3'-(trifluoromethyl)biphenyl-4-yl]carbonyl}azetidin-3-yl)piperazine<br>MS m/z (M + H+) 458.3 |
| 1217 | 1-[(2-Methyl-1,3-thiazol-4-yl)carbonyl]-4-(1-{[3'-(trifluoromethyl)biphenyl-4-yl]carbonyl}azetidin-3-yl)piperazine<br>MS m/z (M + H+) 516.3 |
| 1423 | 5-[(3-{4-[(5-Chlorothiophen-2-yl)carbonyl]piperazin-1-yl}azetidin-1-yl)carbonyl]-1-(4-fluorophenyl)-1H-indole<br>MS m/z (M + H+) 523.2 |
| 1424 | 1-(4-Fluorophenyl)-5-[(3-{4-[(3-fluorophenyl)carbonyl]piperazin-1-yl}azetidin-1-yl)carbonyl]-1H-indole<br>MS m/z (M + H+) 501.2 |
| 1425 | 5-[(3-{4-[(5-Chlorofuran-2-yl)carbonyl]piperazin-1-yl}azetidin-1-yl)carbonyl]-1-(4-fluorophenyl)-1H-indole<br>MS m/z (M + H+) 507.1 |
| 1426 | 1-(4-Fluorophenyl)-5-({3-[4-(1,3-oxazol-2-ylcarbonyl)piperazin-1-yl]azetidin-1-yl}carbonyl)-1H-indole<br>MS m/z (M + H+) 474.1 |
| 567-A | 1-(4-Fluorophenyl)-5-[(3-{4-[(~2~H_5_)phenylcarbonyl]piperazin-1-yl}azetidin-1-yl)carbonyl]-1H-indole<br>MS m/z (M + H+) 488.1 |
| 1427 | 1-(4-Fluorophenyl)-5-[(3-{4-[(5-fluorothiophen-2-yl)carbonyl]piperazin-1-yl}azetidin-1-yl)carbonyl]-1H-indole<br>MS m/z (M + H+) 507.1 |
| 1428 | 1-(4-Fluorophenyl)-5-({3-[4-(1,3-oxazol-4-ylcarbonyl)piperazin-1-yl]azetidin-1-yl}carbonyl)-1H-indole<br>MS m/z (M + H+) 474.1 |
| 1429 | 1-(4-Fluorophenyl)-5-({3-[4-(1,3-oxazol-5-ylcarbonyl)piperazin-1-yl]azetidin-1-yl}carbonyl)-1H-indole<br>MS m/z (M + H+) 474.1 |

Example 9

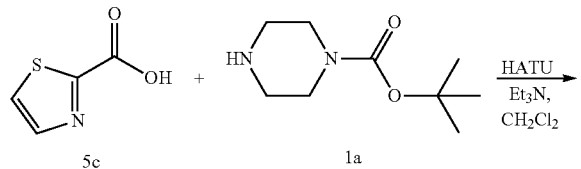

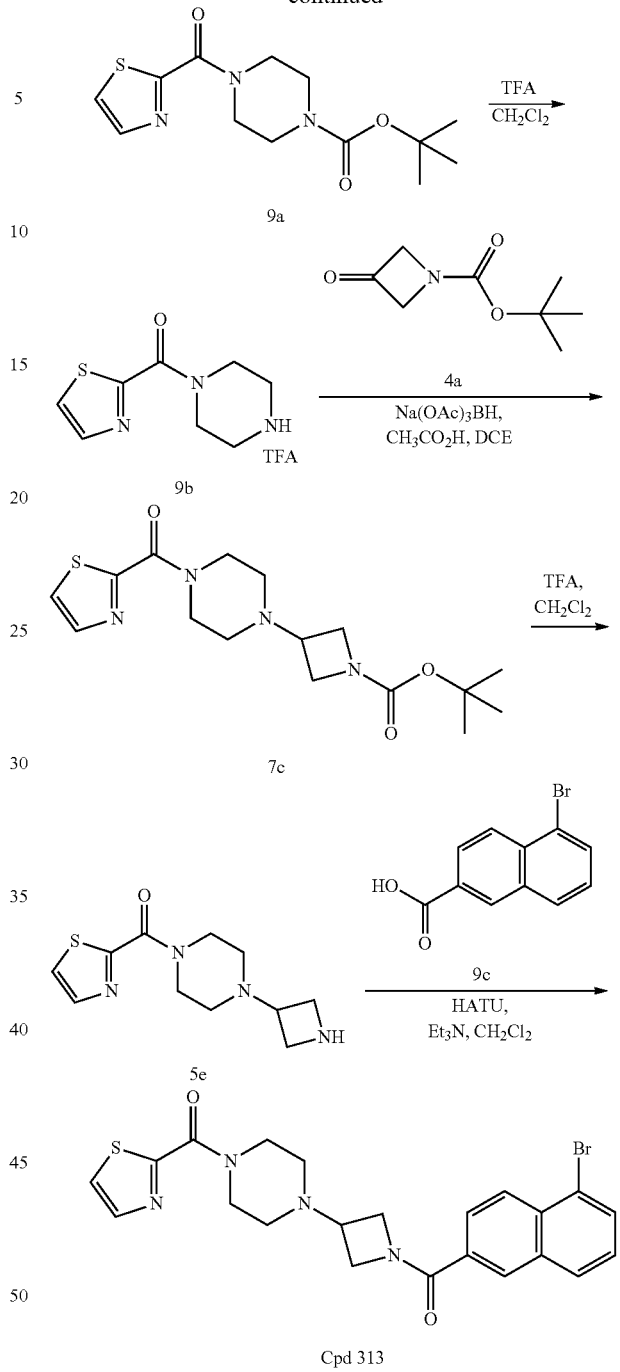

A. 4-(Thiazole-2-carbonyl)-piperazine-1-carboxylic acid tert-butyl ester, 9a. To a solution of compound 5c (2.0 g, 15.50 mmol), compound 1a (3.2 g, 17.20 mmol), and Et₃N (8.6 mL, 61.2 mmol) in CH₂Cl₂ (100 mL) was added HATU (6.5 g, 17.1 mmol). The reaction mixture was stirred at room temperature for 18 h. The mixture was then diluted with CH₂Cl₂ and washed with aq. NaHCO₃. The organic phase was dried over Na₂SO₄, filtered, and concentrated. Purification by flash column chromatography (silica gel, 30% EtOAc/heptane) gave compound 9a (4.0 g).

B. piperazin-1-yl-thiazol-2-yl-methanone trifluoroacetic acid salt, 9b. To a solution of compound 9a (3.5 g, 11.78 mmol) in CH₂Cl₂ (40 mL) was added TFA (10 mL). The reaction mixture was stirred at room temperature for 2 h. It was then concentrated to give compound 9b, which was used in the next reaction without further purification.

C. 3-[4-(Thiazole-2-carbonyl)-piperazin-1-yl]-azetidine-1-carboxylic acid tert-butyl ester, 7c. To a solution of compound 9b (11.78 mmol) and compound 4a (2.2 g, 12.87 mmol) in 1,2-DCE (35 mL) and acetic acid (2 mL) was added Na(OAc)$_3$BH (2.75 g, 12.97 mmol). The reaction was stirred at room temperature for 5 h. To the reaction mixture was added aq. NaHCO$_3$, and the resultant mixture was extracted with CH$_2$Cl$_2$. The organic layer was dried over Na$_2$SO$_4$ and concentrated. Purification by flash column chromatography (silica gel, 80% EtOAc/heptane) gave compound 7c (3.78 g).

D. (4-Azetidin-3-yl-piperazin-1-yl)-thiazol-2-yl-methanone, 5e. To a solution of compound 7c (1.2 g, 3.41 mmol) in CH$_2$Cl$_2$ (12 mL) was added TFA (3 mL). The reaction mixture was stirred at room temperature for 4.5 h, concentrated, and to the resulting residue was added aq. NaHCO$_3$. The mixture was extracted with 2% MeOH/CH$_2$Cl$_2$ (3×). The organic solution was dried over Na$_2$SO$_4$ and concentrated to give compound 5e, which was used in the next reaction without further purification.

D. 1-{1-[(5-Bromonaphthalen-2-yl)carbonyl]azetidin-3-yl}-4-(1,3-thiazol-2-ylcarbonyl)piperazine, Cpd 313. To a solution of compound 5e (63 mg, 0.25 mmol), compound 9c (95 mg, 0.38 mmol), and Et$_3$N (0.14 mL, 1.01 mmol) in CH$_2$Cl$_2$ (3 mL) was added HATU (143 mg, 0.38 mmol). The reaction mixture was stirred at room temperature for 18 h, then diluted with diethyl ether and washed with aq. NaHCO$_3$ and aq. NaCl. The organic layer was dried over Na$_2$SO$_4$ and concentrated. Purification by flash column chromatography (silica gel, 3% MeOH/CH$_2$Cl$_2$) gave compound 313. $^1$H NMR (400 MHz, CD$_3$OD): δ 8.28 (d, J=9 Hz, 1H), 8.14 (d, J=1.6 Hz, 1H), 7.88-7.85 (m, 3H), 7.81 (d, J=8.4 Hz, 1H), 7.54 (d, J=3 Hz, 1H), 7.39 (t, J=7.8 Hz, 1H), 4.53 (bs, 1H), 4.45 (bs, 1H), 4.34 (m, 2H), 4.26 (m, 1H), 4.16 (m, 1H), 3.95-3.80 (m, 2H), 3.28 (m, 1H), 2.60-2.40 (m, 4H). MS m/z (M+H$^+$) 485/487.

Following the procedure described above for Example 9 and substituting the appropriate reagents, starting materials and purification methods known to those skilled in the art, the following compounds of the present invention were prepared:

314 6-({3-[4-(1,3-Thiazol-2-ylcarbonyl)piperazin-1-yl]azetidin-1-yl}carbonyl)-2-[4-(trifluoromethyl)phenyl]-1,3-benzoxazole
$^1$H NMR (400 MHz, CD$_3$OD): δ 8.40 (d, J = 7.8 Hz, 1H), 7.95 (s, 1H), 7.88 (d, J = 3 Hz, 1H), 7.83-7.80 (m, 2H), 7.69 (d, J = 8 Hz, 1H), 7.55 (d, J = 3 Hz, 1H), 4.53 (m, 1H), 4.45-4.25 (m, 4H), 4.16 (m, 1H), 3.95-3.80 (m, 2H), 3.27 (m, 1H), 2.60-2.40 (m, 4H).
MS m/z (M + H$^+$) 542

315 6-Bromo-2-({3-[4-(1,3-thiazol-2-ylcarbonyl)piperazin-1-yl]azetidin-1-yl}carbonyl)-1H-benzimidazole
MS m/z (M + H$^+$) 475/477

316 1-(1,3-Thiazol-2-ylcarbonyl)-4-(1-{[5-(trifluoromethyl)-1-benzothiophen-2-yl]carbonyl}azetidin-3-yl)piperazine
$^1$H NMR (400 MHz, CD$_3$OD): δ 8.13 (s, 1H), 7.98 (d, J = 8.6 Hz, 1H), 7.89 (d, J = 3 Hz, 1H), 7.75 (s, 1H), 7.65 (d, J = 8.6 Hz, 1H), 7.56 (d, J = 3 Hz, 1H), 4.62-4.40 (m, 4H), 4.31 (m, 1H), 4.16 (m, 1H), 3.35 (m, 1H), 2.60-2.40 (m, 4H).
MS m/z (M + H$^+$) 481

317 2-Phenyl-5-({3-[4-(1,3-thiazol-2-ylcarbonyl)piperazin-1-yl]azetidin-1-yl}carbonyl)-1,3-benzoxazole
$^1$H NMR (400 MHz, CD$_3$OD): δ 8.26 (m, 2H), 8.00 (s, 1H), 7.88 (d, J = 3 Hz, 1H), 7.76 (d, J = 8.6 Hz, 1H), 7.63 (d, J = 8.6 Hz, 1H), 7.60-7.52 (m, 4H), 4.60-4.40 (m, 2H), 4.38 (m, 1H), 4.28 (m, 2H), 4.15 (m, 1H), 3.86 (m, 2H), 3.27 (m, 1H), 2.50 (m, 4H).
MS m/z (M + H$^+$) 474

318 2-Phenyl-6-({3-[4-(1,3-thiazol-2-ylcarbonyl)piperazin-1-yl]azetidin-1-yl}carbonyl)-1,3-benzoxazole
$^1$H NMR (400 MHz, CD$_3$OD): δ 8.28 (m, 2H), 7.92 (s, 1H), 7.88 (d, J = 3.2 Hz, 1H), 7.79 (d, J = 8 Hz, 1H), 7.66 (d, J = 8 Hz, 1H), 4.60-4.20 (m, 5H), 4.15 (m, 1H), 3.86 (m, 2H), 3.28 (m, 1H), 2.50 (m, 4H).
MS m/z (M + H$^+$) 474

319 tert-Butyl 6-({3-[4-(phenylcarbonyl)piperazin-1-yl]azetidin-1-yl}carbonyl)-3,4-dihydroisoquinoline-2(1H)-carboxylate,
$^1$H NMR (CDCl$_3$): δ 7.44-7.39 (m, 7H), 7.13 (d, J = 0.02, 1H), 4.59 (s, 2H), 4.27 (m, 2H), 4.15 (m, 1H), 4.06 (m, 1H), 3.90 (m, 1H), 3.74 (m, 1H), 3.65 (m, 2H), 3.46 (m, 2H), 3.22 (m, 1H), 2.85 (m, 2H), 2.27-2.23 (m, 4H), 1.49 (s, 9H)
MS m/z 405.0 (M-Boc), 449.0 (M-Bu-t), 527 (M + Na), 1009.2 (2M + H)

320 1-{1-[(4,5-Dibromothiophen-2-yl)carbonyl]azetidin-3-yl}-4-(phenylcarbonyl)piperazine
MS m/z (M + H$^+$) 511.8, 513.8, 514.8

321 1-{1-[(5-Benzylthiophen-2-yl)carbonyl]azetidin-3-yl}-4-(phenylcarbonyl)piperazine,
$^1$H NMR (CDCl$_3$): δ 7.42-7.38 (m, 5H), 7.33-7.29 (m, 3H), 7.26 (m, 3H), 6.78 (d, J = 0.01, 1H), 4.41 (m, 1H), 4.24 (m, 2H), 4.13 (s, 2H), 4.03 (m, 1H), 3.92-3.74 (m, 2H), 3.47 (m, 2H), 3.24 (m, 1H), 2.42-2.29 (m, 4H)
MS m/z (M + H$^+$) 446.6

322 1-{1-[(5-Bromothiophen-2-yl)carbonyl]azetidin-3-yl}-4-(phenylcarbonyl)piperazine
MS m/z (M + H$^+$) 432.4, 434.4

832 1-Cyclohexyl-2-methyl-5-({3-[4-(1,3-thiazol-4-ylcarbonyl)piperazin-1-yl]azetidin-1-yl}carbonyl)-1H-benzimidazole
MS m/z (M + H$^+$) 493.0

1198 1-(1-{[5-(4-Chlorophenyl)-1-(2,4-dichlorophenyl)-4-methyl-1H-pyrazol-3-yl]carbonyl}azetidin-3-yl)-4-(1,3-thiazol-4-ylcarbonyl)piperazine
MS m/z (M + H$^+$) 615.0

647 4-[4-({3-[4-(1,3-Thiazol-4-ylcarbonyl)piperazin-1-yl]azetidin-1-yl}carbonyl)piperidin-1-yl]benzonitrile
MS m/z (M + H$^+$) 465.1

1302 1-(1,3-Thiazol-4-ylcarbonyl)-4-[1-({4-[3-(trifluoromethyl)-1H-pyrazol-1-yl]phenyl}carbonyl)azetidin-3-yl]piperazine
MS m/z (M + H$^+$) 491.1

1261 1-{1-[(1,5-Diphenyl-1H-pyrazol-3-yl)carbonyl]azetidin-3-yl}-4-(1,3-thiazol-4-ylcarbonyl)piperazine
MS m/z (M + H$^+$) 499.2

654 1-[1-(Phenoxathiin-2-ylcarbonyl)azetidin-3-yl]-4-(1,3-thiazol-4-ylcarbonyl)piperazine
MS m/z (M + H$^+$) 479.1

767 9-Methyl-3-({3-[4-(1,3-thiazol-4-ylcarbonyl)piperazin-1-yl]azetidin-1-yl}carbonyl)-9H-carbazole
MS m/z (M + H$^+$) 460.0

822 1-(1-{[4-(Phenylsulfonyl)phenyl]carbonyl}azetidin-3-yl)-4-(1,3-thiazol-4-ylcarbonyl)piperazine
MS m/z (M + H$^+$) 497.1

817 6-({3-[4-(1,3-Thiazol-4-ylcarbonyl)piperazin-1-yl]azetidin-1-yl}carbonyl)-2,3,4,9-tetrahydro-1H-carbazole
MS m/z (M + H$^+$) 450.1

775 N-Benzyl-2-({3-[4-(1,3-thiazol-2-ylcarbonyl)piperazin-1-yl]azetidin-1-yl}carbonyl)aniline
MS m/z (M + H$^+$) 462.3

713 N-Benzyl-3-({3-[4-(1,3-thiazol-2-ylcarbonyl)piperazin-1-yl]azetidin-1-yl}carbonyl)aniline
MS m/z (M + H$^+$) 462.3

1413 3-Methyl-1-[4-({3-[4-(1,3-thiazol-2-ylcarbonyl)piperazin-1-yl]azetidin-1-yl}carbonyl)phenyl]-1H-indole
MS m/z (M + H$^+$) 486.1

918 5-({3-[4-(1,3-Thiazol-2-ylcarbonyl)piperazin-1-yl]azetidin-1-yl}carbonyl)-1,3-dihydro-2H-indol-2-one
MS m/z (M + H$^+$) 412.1

829 5-({3-[4-(1,3-Thiazol-2-ylcarbonyl)piperazin-1-yl]azetidin-1-yl}carbonyl)-2,3-dihydro-1H-indole
$^1$H NMR (400 MHz, CD$_3$OD): δ 7.99 (d, 1H), 7.89 (d, 1H), 7.57 (s, 1H), 7.52 (d, J = 8.1 Hz, 1H), 7.03 (d, J = 8.1 Hz, 1H), 4.28-4.90 (m, 6H), 4.01-4.22 (m, 3H), 3.73 (t, J = 8.2 Hz,

| | |
|---|---|
| | 2H), 3.37 (br. s., 4H), 3.19 (t, J = 8.2 Hz, 2H)<br>MS m/z (M + H⁺) 398.1 |
| 1320 | 1-(4-Fluorophenyl)-4-({3-[4-(1,3-thiazol-2-ylcarbonyl)piperazin-1-yl]azetidin-1-yl}carbonyl)-1H-indole<br>¹H NMR (400 MHz, CDCl₃): δ 7.88 (d, J = 3.2 Hz, 1H), 7.50-7.57 (m, 2H), 7.42-7.48 (m, 2H), 7.38 (d, J = 3.2 Hz, 1H), 7.33 (d, J = 7.3 Hz, 1H), 7.18-7.26 (m, 3H), 6.99 (d, J = 3.2 Hz, 1H), 4.05-4.63 (m, 6H), 3.75-3.99 (m, 2H), 3.22-3.32 (m, 1H), 2.37-2.62 (m, 4H)<br>MS m/z (M + H⁺) 490.1 |
| 806 | 1-{1-[(4-Bromothiophen-2-yl)carbonyl]azetidin-3-yl}-4-(1,3-thiazol-2-ylcarbonyl)piperazine<br>MS m/z (M⁺) 440.0, (M + 2⁺) 442.0 |
| 718 | 6-({3-[4-(1,3-Thiazol-2-ylcarbonyl)piperazin-1-yl]azetidin-1-yl}carbonyl)-2-(trifluoromethyl)-1,3-benzothiazole<br>MS m/z 482 (M + H⁺) |
| 1088 | 1-(4-Fluorophenyl)-3-methyl-5-({3-[4-(1,3-thiazol-2-ylcarbonyl)piperazin-1-yl]azetidin-1-yl}carbonyl)-1H-indole<br>¹H NMR (CDCl₃, 400 MHz): δ 7.98 (s, 1 H), 7.88 (d, J = 3.1 Hz, 1 H), 7.47-7.58 (m, 2 H), 7.38-7.47 (m, 3 H), 7.16-7.26 (m, 2 H), 7.12 (s, 1 H), 4.47-4.64 (m, 1 H), 4.38 (br. s., 4 H), 4.07-4.19 (m, 1 H), 3.74-3.97 (m, 2 H), 3.17-3.33 (m, 1 H), 2.50 (t, J = 4.9 Hz, 4 H), 2.39 (s, 3 H).<br>MS m/z 504 (M + H⁺) |
| 1131 | 2-(3-Fluorophenyl)-6-({3-[4-(1,3-thiazol-2-ylcarbonyl)piperazin-1-yl]azetidin-1-yl}carbonyl)-1,3-benzothiazole<br>MS m/z 508 (M + H⁺) |
| 1054 | 3-Methyl-1-phenyl-5-({3-[4-(1,3-thiazol-2-ylcarbonyl)piperazin-1-yl]azetidin-1-yl}carbonyl)-1H-indole<br>MS m/z 486 (M + H⁺) |
| 1152 | 3-Methyl-1-phenyl-5-({3-[4-(1,3-thiazol-4-ylcarbonyl)piperazin-1-yl]azetidin-1-yl}carbonyl)-1H-indole<br>MS m/z 486 (M + H⁺) |
| 1367 | 5-({3-[4-(1,3-Thiazol-2-ylcarbonyl)piperazin-1-yl]azetidin-1-yl}carbonyl)-1-(3,4,5-trifluorophenyl)-1H-indole<br>MS m/z 526 (M + H⁺) |
| 1106 | 1-(3,4-Difluorophenyl)-5-({3-[4-(1,3-thiazol-2-ylcarbonyl)piperazin-1-yl]azetidin-1-yl}carbonyl)-1H-indazole<br>¹H NMR (CDCl₃, 400 MHz): δ 8.27 (s, 1 H), 8.12 (s, 1 H), 7.88 (br. s., 1 H), 7.67-7.85 (m, 2 H), 7.42-7.67 (m, 3 H), 7.36 (q, J = 8.7 Hz, 1 H), 4.49-4.62 (m, 1 H), 4.20-4.48 (m, 4 H), 4.05-4.20 (m, 1 H), 3.84 (br. s., 2 H), 3.20-3.38 (m, 1 H), 2.51 (m, 4 H).<br>MS m/z 509 (M + H⁺) |
| 1129 | 1-(3,4-Difluorophenyl)-5-({3-[4-(1,3-thiazol-4-ylcarbonyl)piperazin-1-yl]azetidin-1-yl}carbonyl)-1H-indazole<br>MS m/z 509 (M + H⁺) |
| 1055 | 5-({3-[4-(1,3-Thiazol-4-ylcarbonyl)piperazin-1-yl]azetidin-1-yl}carbonyl)-1-(3,4,5-trifluorophenyl)-1H-indole<br>MS m/z 526 (M + H⁺) |
| 1077 | 2-(3,4-Difluorophenyl)-6-({3-[4-(1,3-thiazol-2-ylcarbonyl)piperazin-1-yl]azetidin-1-yl}carbonyl)-1,3-benzoxazole<br>MS m/z 510 (M + H⁺) |
| 1178 | 2-(3,4-Difluorophenyl)-6-({3-[4-(1,3-thiazol-4-ylcarbonyl)piperazin-1-yl]azetidin-1-yl}carbonyl)-1,3-benzoxazole<br>MS m/z 510 (M + H⁺) |
| 1368 | 1-(3-Fluorophenyl)-3-methyl-5-({3-[4-(1,3-thiazol-2-ylcarbonyl)piperazin-1-yl]azetidin-1-yl}carbonyl)-1H-indole<br>MS m/z 504 (M + H⁺) |
| 1369 | 5-({3-[4-(1,3-Thiazol-2-ylcarbonyl)piperazin-1-yl]azetidin-1-yl}carbonyl)-1-[4-(trifluoromethoxy)phenyl]-1H-indole<br>MS m/z 556 (M + H⁺) |
| 1370 | 5-({3-[4-(1,3-Thiazol-4-ylcarbonyl)piperazin-1-yl]azetidin-1-yl}carbonyl)-1-[4-(trifluoromethoxy)phenyl]-1H-indole<br>MS m/z 556 (M + H⁺) |
| 1371 | 1-(3,5-Difluorophenyl)-5-({3-[4-(1,3-thiazol-2-ylcarbonyl)piperazin-1-yl]azetidin-1-yl}carbonyl)-1H-indole<br>MS m/z 508 (M + H⁺) |
| 1068 | 3-Methyl-5-({3-[4-(1,3-thiazol-2-ylcarbonyl)piperazin-1-yl]azetidin-1-yl}carbonyl)-1-[3-(trifluoromethoxy)phenyl]-1H-indole<br>MS m/z 570 (M + H⁺) |
| 1110 | 1-(3-Fluorophenyl)-5-({3-[4-(1,3-thiazol-2-ylcarbonyl)piperazin-1-yl]azetidin-1-yl}carbonyl)-1H-indazole<br>MS m/z 491 (M + H⁺) |
| 1372 | 1-(4-Chloro-3-fluorophenyl)-5-({3-[4-(1,3-thiazol-2-ylcarbonyl)piperazin-1-yl]azetidin-1-yl}carbonyl)-1H-indole<br>MS m/z 523 (M + H⁺) |
| 1373 | 1-(2,5-Difluorophenyl)-5-({3-[4-(1,3-thiazol-2-ylcarbonyl)piperazin-1-yl]azetidin-1-yl}carbonyl)-1H-indole<br>MS m/z 508 (M + H⁺) |
| 1090 | 1-(4-Fluorophenyl)-5-({3-[4-(1,3-thiazol-2-ylcarbonyl)piperazin-1-yl]azetidin-1-yl}carbonyl)-1H-indazole<br>MS m/z 491 (M + H⁺) |
| 1492 | 1-{1-[(5-Bromo-1-benzofuran-2-yl)carbonyl]azetidin-3-yl}-4-(phenylcarbonyl)piperazine<br>MS m/z (M + H⁺) 455, 457 |
| 812 | 1-{1-[(5-Bromo-1-benzofuran-2-yl)carbonyl]azetidin-3-yl}-4-(1,3-thiazol-2-ylcarbonyl)piperazine<br>MS m/z (M + H⁺) 468, 470 |
| 681 | 7-Bromo-1-methyl-5-({3-[4-(1,3-thiazol-2-ylcarbonyl)piperazin-1-yl]azetidin-1-yl}carbonyl)-1H-indole<br>MS m/z (M + H⁺) 488, 490 |
| 723 | 1-{1-[(5-Bromo-4-methylthiophen-2-yl)carbonyl]azetidin-3-yl}-4-(1,3-thiazol-2-ylcarbonyl)piperazine<br>MS m/z (M + H⁺) 455, 457 |
| 745 | 1-{1-[(4-Bromo-5-methylthiophen-2-yl)carbonyl]azetidin-3-yl}-4-(1,3-thiazol-2-ylcarbonyl)piperazine<br>MS m/z (M + H⁺) 475, 477 |
| 1224 | 1-(4-Fluorophenyl)-3-({3-[4-(1,3-thiazol-2-ylcarbonyl)piperazin-1-yl]azetidin-1-yl}carbonyl)-1H-indole<br>MS m/z (M + H⁺) 490 |
| 1226 | 1-(3-Fluorophenyl)-3-({3-[4-(1,3-thiazol-2-ylcarbonyl)piperazin-1-yl]azetidin-1-yl}carbonyl)-1H-indole<br>MS m/z (M + H⁺) 490 |
| 1279 | 1-(3-Fluorophenyl)-3-({3-[4-(1,3-thiazol-4-ylcarbonyl)piperazin-1-yl]azetidin-1-yl}carbonyl)-1H-indole<br>MS m/z (M + H⁺) 490 |
| 1295 | 1-(4-Fluorophenyl)-3-({3-[4-(1,3-thiazol-4-ylcarbonyl)piperazin-1-yl]azetidin-1-yl}carbonyl)-1H-indole<br>MS m/z (M + H⁺) 490 |
| 1275 | 2-Phenyl-6-({4-[1-(1,3-thiazol-4-ylcarbonyl)azetidin-3-yl]piperazin-1-yl}carbonyl)-1,3-benzoxazole<br>MS m/z (M + H⁺) 474.1 |
| 606 | 7-(Biphenyl-4-ylcarbonyl)-4-[1-(phenylcarbonyl)azetidin-3-yl]-4,7-diazaspiro[2.5]octane<br>MS m/z (M + H⁺) 452.4 |
| 1286 | 7-(Biphenyl-4-ylcarbonyl)-4-[1-(1,3-thiazol-4-ylcarbonyl)azetidin-3-yl]-4,7-diazaspiro[2.5]octane<br>MS m/z (M + H⁺) 459.3 |
| 1499 | 4-[1-(Biphenyl-4-ylcarbonyl)azetidin-3-yl]-7-(phenylcarbonyl)-4,7-diazaspiro[2.5]octane<br>MS m/z (M + H⁺) 272 |
| 820 | 5-({3-[4-(1,3-Thiazol-2-ylcarbonyl)piperazin-1-yl]azetidin-1-yl}carbonyl)-1H-indazole<br>¹H NMR (400 MHz, CDCl₃): δ 3.34-3.48 (m, 1 H), 3.89 (br. s., 3 H), 4.08-4.66 (m, 8 H), 7.55 (d, J = 8.8 Hz, 1 H), 7.62 (d, J = 3.2 Hz, 1 H), 7.66 (dd, J = 8.8, 1.5 Hz, 1 H), 7.89 (d, J = 3.2 Hz, 1 H), 8.04 (s, 1 H), 8.09 (s, 2 H)<br>MS m/z (M + H⁺) 397.2 |
| 1277 | 1-(4-Fluorophenyl)-6-({3-[4-(1,3-thiazol-2-ylcarbonyl)piperazin-1-yl]azetidin-1-yl}carbonyl)-1H-pyrrolo[3,2-b]pyridine |

-continued

¹H NMR (400 MHz, CDCl₃): δ 2.92-3.16 (m, 4 H), 3.76 (t, J = 5.3 Hz, 1 H), 4.06 (br. s., 2 H), 4.39 (br. s., 1 H), 4.49-4.93 (m, 5 H), 7.23 (d, J = 3.2 Hz, 1 H), 7.30-7.38 (m, 2 H), 7.44-7.54 (m, 2 H), 7.60 (d, J = 3.2 Hz, 1 H), 7.89 (d, J = 3.2 Hz, 1 H), 7.97 (d, J = 3.2 Hz, 1 H), 8.63 (s, 1 H), 9.12 (s, 1 H)
MS m/z (M + H⁺) 491.2

1056 1-(4-Fluorophenyl)-5-({3-[4-(1,3-thiazol-2-ylcarbonyl)piperazin-1-yl]azetidin-1-yl}carbonyl)-1H-pyrrolo[2,3-b]pyridine
¹H NMR (400 MHz, CDCl₃): δ 3.75 (s, 1 H), 4.11 (br. s., 2 H), 4.32-5.02 (m, 10 H), 6.75 (d, J = 3.6 Hz, 1 H), 7.23 (d, J = 8.9 Hz, 2 H), 7.53 (d, J = 3.7 Hz, 1 H), 7.61 (d, J = 3.2 Hz, 1 H), 7.65 (m, J = 9.0, 4.7 Hz, 2 H), 7.89 (d, J = 3.2 Hz, 1 H), 8.33 (d, J = 2.0 Hz, 1 H), 8.60 (d, J = 1.7 Hz, 1 H)
MS m/z (M + H⁺) 491.2

1153 1-(4-Fluorophenyl)-5-({3-[4-(1,3-thiazol-2-ylcarbonyl)piperazin-1-yl]azetidin-1-yl}carbonyl)-1H-pyrrolo[3,2-b]pyridine
¹H NMR (400 MHz, CDCl₃): δ 3.83-4.34 (m, 9 H), 4.41-4.70 (m, 2 H), 5.14 (d, J = 5.8 Hz, 2 H), 6.90 (br. s., 1 H), 7.28 (d, J = 8.2 Hz, 2 H), 7.38-7.51 (m, 2 H), 7.62 (d, J = 3.2 Hz, 1 H), 7.65 (d, J = 2.9 Hz, 1 H), 7.85 (d, J = 8.6 Hz, 1 H), 7.90 (d, J = 3.2 Hz, 1 H), 7.99 (d, J = 8.6 Hz, 1 H)
MS m/z (M + H⁺) 491.2

1306 1-[1-(Biphenyl-4-ylcarbonyl)azetidin-3-yl]-4-(1,3-thiazol-2-ylcarbonyl)-2-(trifluoromethyl)piperazine
¹H NMR (400 MHz, CD₃OD): δ 2.14 (dd, J = 22.7, 10.5 Hz, 1 H), 2.43 (dd, J = 41.6, 11.7 Hz, 1 H), 2.87-3.18 (m, 1 H), 3.18-3.44 (m, 1.5 H), 3.58-3.81 (m, 0.5 H), 3.95-4.17 (m, 1 H), 4.18-4.40 (m, 2 H), 4.49 (m, 1.5 H), 5.43 (d, J = 26.4 Hz, 1 H), 6.95 (br. s., 0.5 H), 7.33-7.43 (m, 1 H), 7.43-7.51 (m, 2 H), 7.66 (d, J = 7.6 Hz, 2 H), 7.70-7.80 (m, 4 H), 7.88 (br. s., 1 H), 7.93-8.03 (m, 1 H)
MS m/z (M + H⁺) 501.1

856 5-({3-[4-(1H-Pyrrol-2-ylcarbonyl)piperazin-1-yl]azetidin-1-yl}carbonyl)-1H-indole
MS m/z (M + H⁺) 378

1116 2:1 mixture of 2 components:
Major: 1-[3-Chloro-5-(trifluoromethyl)pyridin-2-yl]-5-({3-[4-(1,3-thiazol-2-ylcarbonyl)piperazin-1-yl]azetidin-1-yl}carbonyl)-1H-indole
MS m/z (M + H⁺) 575.1
Minor: 1-[2-Fluoro-5-(trifluoromethyl)pyridin-3-yl]-5-({3-[4-(1,3-thiazol-2-ylcarbonyl)piperazin-1-yl]azetidin-1-yl}carbonyl)-1H-indole
MS m/z (M + H⁺) 559.0

1233 2-Phenyl-6-({4-[1-(1,3-thiazol-2-ylcarbonyl)azetidin-3-yl]piperazin-1-yl}carbonyl)-1,3-benzoxazole
MS m/z (M + H⁺)) 474.1

Example 9b

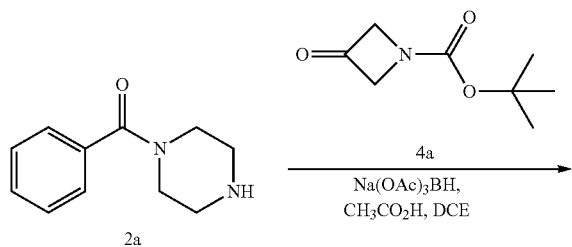

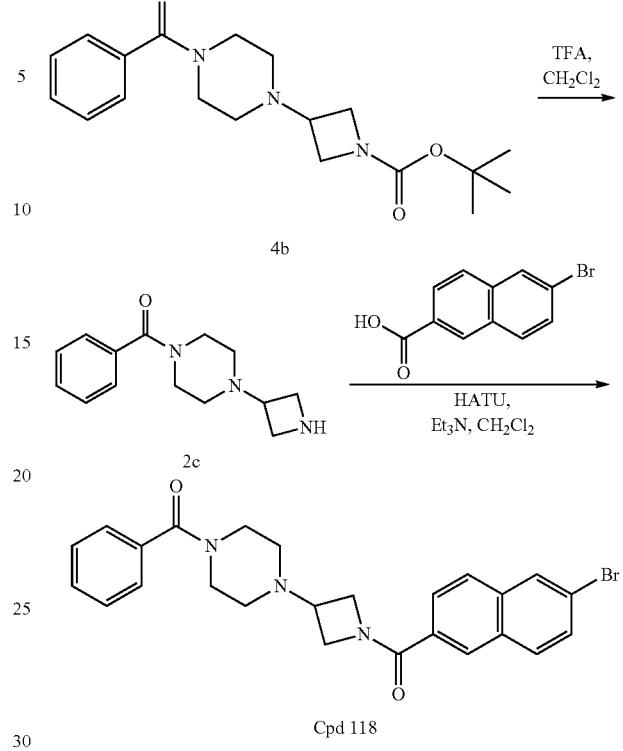

1-{1-[(6-Bromonaphthalen-2-yl)carbonyl]azetidin-3-yl}-4-(phenylcarbonyl)piperazine, Cpd 118: The title compound was prepared in an analogous manner to the preparation of Cpd 313 of Example 9, except commercially available N-benzoylpiperazine was used as starting material, instead of intermediate 9b. MS 478/480 (M+H⁺).

Following the procedure described above for Example 9b and substituting the appropriate reagents, starting materials and purification methods known to those skilled in the art, the following compounds of the present invention were prepared:

| Cpd | Cpd Name and Data |
|---|---|
| 119 | 7-Bromo-3-({3-[4-(phenylcarbonyl)piperazin-1-yl]azetidin-1-yl}carbonyl)quinoline<br>MS m/z (M + H⁺) 479/481 |
| 120 | 1-{1-[(5-Chloro-3-methyl-1-benzothiophen-2-yl)carbonyl]azetidin-3-yl}-4-(phenylcarbonyl)piperazine<br>¹H NMR (400 MHz, CD₃OD): δ 7.74 (d, J = 2 Hz, 1H), 7.71 (d, J = 8.6 Hz, 1H), 7.43-7.36 (m, 6H), 4.28 (m, 2H), 4.20-4.00 (m, 2H), 4.00-3.70 (m, 2H), 3.48 (m, 2H), 3.24 (m, 1H), 2.58 (s, 3H), 2.50-2.20 (m, 4H).<br>MS m/z (M + H⁺) 454 |
| 121 | 2-Phenyl-6-({3-[4-(phenylcarbonyl)piperazin-1-yl]azetidin-1-yl}carbonyl)-1,3-benzoxazole<br>MS m/z (M + H⁺) 467 |
| 122 | 2-Methyl-6-({3-[4-(phenylcarbonyl)piperazin-1-yl]azetidin-1-yl}carbonyl)-1,3-benzothiazole<br>MS m/z (M + H⁺) 421 |
| 123 | 2-(4-Methoxyphenyl)-6-({3-[4-(phenylcarbonyl)piperazin-1-yl]azetidin-1-yl}carbonyl)-1,3-benzoxazole<br>MS m/z (M + H⁺) 497 |
| 124 | 1-(Phenylcarbonyl)-4-(1-{[5-(trifluoromethyl)-1-benzothiophen-2-yl]carbonyl}azetidin-3-yl)piperazine<br>MS m/z (M + H⁺) 474 |
| 125 | 1-{1-[(6-Bromo-1-benzothiophen-2-yl)carbonyl]azetidin-3-yl}-4-(phenylcarbonyl)piperazine<br>MS m/z (M + H⁺) 484/486 |

| Cpd | Cpd Name and Data |
|---|---|
| 126 | 5-({3-[4-(Phenylcarbonyl)piperazin-1-yl]azetidin-1-yl}carbonyl)-1-[4-(trifluoromethyl)phenyl]-1H-indole<br>$^1$H NMR (400 MHz, CD$_3$OD): δ 8.00 (s, 1H), 7.81 (d, J = 8.2 Hz, 2H), 7.63 (d, J = 8.6 Hz, 2H), 7.58 (s, 2H), 7.40 (m, 6H), 6.78 (d, J = 3.5 Hz, 1H), 4.37 (m, 1H), 4.30-4.20 (m, 2H), 4.11 (m, 1H), 3.60-3.40 (m, 2H), 3.24 (m, 1H), 2.50-2.20 (m, 4H).<br>MS m/z (M + H$^+$) 533 |
| 127 | 2-(4-Chlorophenyl)-6-({3-[4-(phenylcarbonyl)piperazin-1-yl]azetidin-1-yl}carbonyl)-1H-benzimidazole<br>MS m/z (M + H$^+$) 500 |
| 128 | 1-Phenyl-5-({3-[4-(phenylcarbonyl)piperazin-1-yl]azetidin-1-yl}carbonyl)-1H-indole<br>$^1$H NMR (400 MHz, CD$_3$OD): δ 7.98 (s, 1H), 7.56-7.37 (m, 13H), 6.73 (d, J = 3.2 Hz, 1H), 4.37 (m, 1H), 4.29-4.20 (m, 2H), 4.10 (bs, 1H), 3.90 (bs, 1H), 3.74 (bs, 1H), 3.38 (m, 2H), 3.23 (m, 1H), 2.50-2.20 (m, 4H).<br>MS m/z (M + H$^+$) 465 |
| 129 | 1-[3-(Trifluoromethyl)phenyl]-5-({3-[4-(phenylcarbonyl)piperazin-1-yl]azetidin-1-yl}carbonyl)-1H-indole<br>$^1$H NMR (400 MHz, CD$_3$OD): δ 8.00 (s, 1H), 7.76 (s, 1H), 7.72-7.64 (m, 3H), 7.58-7.50 (m, 2H), 7.41 (m, 6 H), 6.78 (d, J = 3 Hz, 1H), 4.37 (m, 1H), 4.30-4.20 (m, 2H), 4.11 (m, 1H), 3.91 (bs, 1H), 3.75 (bs, 1H), 3.48 (m, 2H), 3.25 (m, 1H), 2.55-2.20 (m, 4H).<br>MS m/z (M + H$^+$) 533 |
| 130 | 5-({3-[4-(Phenylcarbonyl)piperazin-1-yl]azetidin-1-yl}carbonyl)-1-(phenylsulfonyl)-1H-indole<br>MS m/z (M + H$^+$) 529 |
| 131 | 6-({3-[4-(Phenylcarbonyl)piperazin-1-yl]azetidin-1-yl}carbonyl)-2-[3-(trifluoromethyl)phenyl]-1,3-benzoxazole<br>$^1$H NMR (400 MHz, CD$_3$OD): δ 8.54 (s, 1H), 8.45 (d, J = 8.2 Hz, 1H), 7.94 (d, J = 1.2 Hz, 1H), 7.82 (m, 2H), 7.69 (m, 2H), 7.41 (m, 5H), 4.38 (m, 1H), 4.32-4.22 (m, 2H), 4.12 (m, 1H), 3.90 (bs, 1H), 3.76 (bs, 1H), 3.50 (bs, 2H), 3.27 (m, 1H), 2.50-2.20 (m, 4H).<br>MS m/z (M + H$^+$) 535 |
| 132 | 2-Phenyl-5-({3-[4-(phenylcarbonyl)piperazin-1-yl]azetidin-1-yl}carbonyl)-1,3-benzoxazole<br>MS m/z (M + H$^+$) 467 |
| 617 | 1-(4-Fluorophenyl)-5-({3-[4-(phenylcarbonyl)piperazin-1-yl]azetidin-1-yl}carbonyl)-1H-indazole<br>MS m/z 484 (M + H$^+$) |
| 571 | 1-(3,4-Difluorophenyl)-5-({3-[4-(phenylcarbonyl)piperazin-1-yl]azetidin-1-yl}carbonyl)-1H-indole<br>$^1$H NMR (CDCl$_3$, 400 MHz): δ 7.99 (s, 1 H), 7.53-7.63 (m, 1 H), 7.45-7.53 (m, 1 H), 7.16-7.45 (m, 9 H), 6.74 (d, J = 3.1 Hz, 1 H), 4.37 (br. s., 1 H), 4.16-4.32 (m, 2 H), 4.11 (br. s., 1 H), 3.83-4.00 (m, 1 H), 3.65-3.83 (m, 1 H), 3.48 (br. s., 2 H), 3.17-3.31 (m, 1 H), 2.44 (br. s., 4 H)<br>MS m/z 501 (M + H$^+$) |
| 584 | 1-(4-Fluorophenyl)-3-methyl-5-({3-[4-(phenylcarbonyl)piperazin-1-yl]azetidin-1-yl}carbonyl)-1H-indole<br>MS m/z 497 (M + H$^+$) |
| 599 | 2-(3-Fluorophenyl)-6-({3-[4-(phenylcarbonyl)piperazin-1-yl]azetidin-1-yl}carbonyl)-1,3-benzothiazole<br>MS m/z 501 (M + H$^+$) |
| 583 | 1-(3-Fluorophenyl)-3-methyl-5-({3-[4-(phenylcarbonyl)piperazin-1-yl]azetidin-1-yl}carbonyl)-1H-indole<br>MS m/z 497 (M + H$^+$) |
| 577 | 3-Methyl-1-phenyl-5-({3-[4-(phenylcarbonyl)piperazin-1-yl]azetidin-1-yl}carbonyl)-1H-indole<br>MS m/z 479 (M + H$^+$) |
| 569 | 5-({3-[4-(Phenylcarbonyl)piperazin-1-yl]azetidin-1-yl}carbonyl)-1-(3,4,5-trifluorophenyl)-1H-indole<br>MS m/z 519 (M + H$^+$) |
| 573 | 5-({3-[4-(Phenylcarbonyl)piperazin-1-yl]azetidin-1-yl}carbonyl)-1-[4-(trifluoromethoxy)phenyl]-1H-indole<br>MS m/z 549 (M + H$^+$) |
| 580 | 1-(3,5-Difluorophenyl)-5-({3-[4-(phenylcarbonyl)piperazin-1-yl]azetidin-1-yl}carbonyl)-1H-indole<br>MS m/z 501 (M + H$^+$) |
| 568 | 1-(4-Chloro-3-fluorophenyl)-5-({3-[4-(phenylcarbonyl)piperazin-1-yl]azetidin-1-yl}carbonyl)-1H-indole<br>MS m/z 517 (M + H$^+$) |
| 578 | 1-(2,5-Difluorophenyl)-5-({3-[4-(phenylcarbonyl)piperazin-1-yl]azetidin-1-yl}carbonyl)-1H-indole<br>MS m/z 501 (M + H$^+$) |
| 590 | 1-(3,4-Difluorophenyl)-5-({3-[4-(phenylcarbonyl)piperazin-1-yl]azetidin-1-yl}carbonyl)-1H-indazole<br>MS m/z 502 (M + H$^+$) |

Example 9c

Following the procedure described above for Example 1b, with the exception of using 1,10-phenanthroline instead of trans-N,N'-dimethylcyclohexane-1,2-diamine as a ligand in step K, and substituting the appropriate reagents, starting materials, and purification methods known to those skilled in the art, the following intermediate compound:

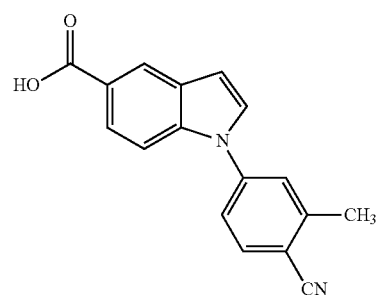 [SMILES: Cc1cc(-n2ccc3cc(C(=O)O)ccc32)ccc1C#N]

Following the procedure described above for Example 9, step D, and substituting the appropriate reagents, starting materials, and purification methods known to those skilled in the art, the following compounds of the present invention were prepared:

| Cpd | Cpd Name and Data |
|---|---|
| 1375 | 2-Methyl-4-[5-({3-[4-(1,3-thiazol-2-ylcarbonyl)piperazin-1-yl]azetidin-1-yl}carbonyl)-1H-indol-1-yl]benzonitrile<br>MS m/z (M + H$^+$) 511 |
| 1421 | 2-Methyl-4-[5-({3-[4-(1,3-thiazol-4-ylcarbonyl)piperazin-1-yl]azetidin-1-yl}carbonyl)-1H-indol-1-yl]benzonitrile<br>MS m/z (M + H$^+$) 511 |
| 566 | 2-Methyl-4-[5-({3-[4-(phenylcarbonyl)piperazin-1-yl]azetidin-1-yl}carbonyl)-1H-indol-1-yl]benzonitrile<br>MS m/z (M + H$^+$) 504 |

Example 9d

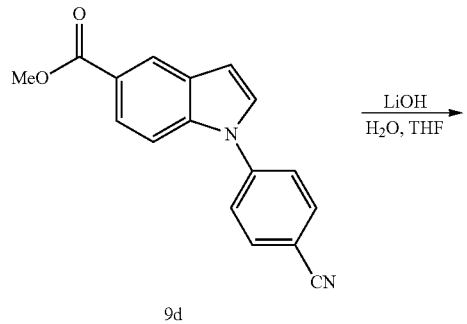

E. Methyl 1-(4-cyanophenyl)-indole-5-carboxylate, 9d was prepared according to Example 1a step H.

F. 1-(4-cyanophenyl)-indole-5-carboxylic acid, 9e and 1-(4-carbamoyl-phenyl)-indole-5-carboxylic acid, 9f. A mixture of methyl 1-(4-cyanophenyl)-indole-5-carboxylate, 9d (156 mg, 0.57 mmol) and LiOH (54 mg, 2.26 mmol) in THF (4 mL) and H₂O (2 mL) was stirred at room temperature for 4 days. Aqueous 10% HCl solution was added to the reaction mixture to adjust pH=3~4. The resulting mixture was extracted with EtOAc (2×). The organic solution was washed with aq. NaCl, dried over Na₂SO₄ and concentrated. Purification by flash column chromatography (silica gel, 4-8% MeOH/CH₂Cl₂) gave 9e (75 mg), followed by 9f (27 mg).

Following the procedure described above for Example 9d and substituting the appropriate reagents, starting materials, and purification methods known to those skilled in the art, the following intermediate compounds were prepared:

Following the procedure described above for Example 9, and substituting the appropriate reagents, starting materials, and purification methods known to those skilled in the art, the following compounds of the present invention were prepared:

| Cpd | Cpd Name and Data |
|---|---|
| 1159 | 4-[5-({3-[4-(1,3-Thiazol-2-ylcarbonyl)piperazin-1-yl]azetidin-1-yl}carbonyl)-1H-indol-1-yl]benzonitrile MS m/z (M + H⁺) 497 |
| 1171 | 4-[5-({3-[4-(1,3-Thiazol-2-ylcarbonyl)piperazin-1-yl]azetidin-1-yl}carbonyl)-1H-indol-1-yl]benzamide MS m/z (M + H⁺) 515 |
| 1133 | 4-[5-({3-[4-(1,3-Thiazol-4-ylcarbonyl)piperazin-1-yl]azetidin-1-yl}carbonyl)-1H-indol-1-yl]benzonitrile MS m/z (M + H⁺) 497 |
| 1109 | 2-[5-({3-[4-(1,3-Thiazol-2-ylcarbonyl)piperazin-1-yl]azetidin-1-yl}carbonyl)-1H-indol-1-yl]benzonitrile MS m/z (M + H⁺) 497 |
| 1182 | 2-[5-({3-[4-(1,3-Thiazol-4-ylcarbonyl)piperazin-1-yl]azetidin-1-yl}carbonyl)-1H-indol-1-yl]benzonitrile MS m/z (M + H⁺) 497 |
| 1113 | 3-[5-({3-[4-(1,3-Thiazol-2-ylcarbonyl)piperazin-1-yl]azetidin-1-yl}carbonyl)-1H-indol-1-yl]benzonitrile MS m/z (M + H⁺) 497 |
| 1177 | 3-[5-({3-[4-(1,3-Thiazol-2-ylcarbonyl)piperazin-1-yl]azetidin-1-yl}carbonyl)-1H-indol-1-yl]benzamide MS m/z (M + H⁺) 515 |

Following the procedure described above for Example 9b, and substituting the appropriate reagents, starting materials, and purification methods known to those skilled in the art, the following compounds of the present invention were prepared:

| Cpd | Cpd Name and Data |
|-----|-------------------|
| 582 | 4-[5-({3-[4-(Phenylcarbonyl)piperazin-1-yl]azetidin-1-yl}carbonyl)-1H-indol-1-yl]benzonitrile<br>MS m/z (M + H$^+$) 490 |
| 588 | 2-[5-({3-[4-(Phenylcarbonyl)piperazin-1-yl]azetidin-1-yl}carbonyl)-1H-indol-1-yl]benzonitrile<br>MS m/z (M + H$^+$) 490 |
| 594 | 3-[5-({3-[4-(Phenylcarbonyl)piperazin-1-yl]azetidin-1-yl}carbonyl)-1H-indol-1-yl]benzamide<br>MS m/z (M + H$^+$) 508 |

Example 9e

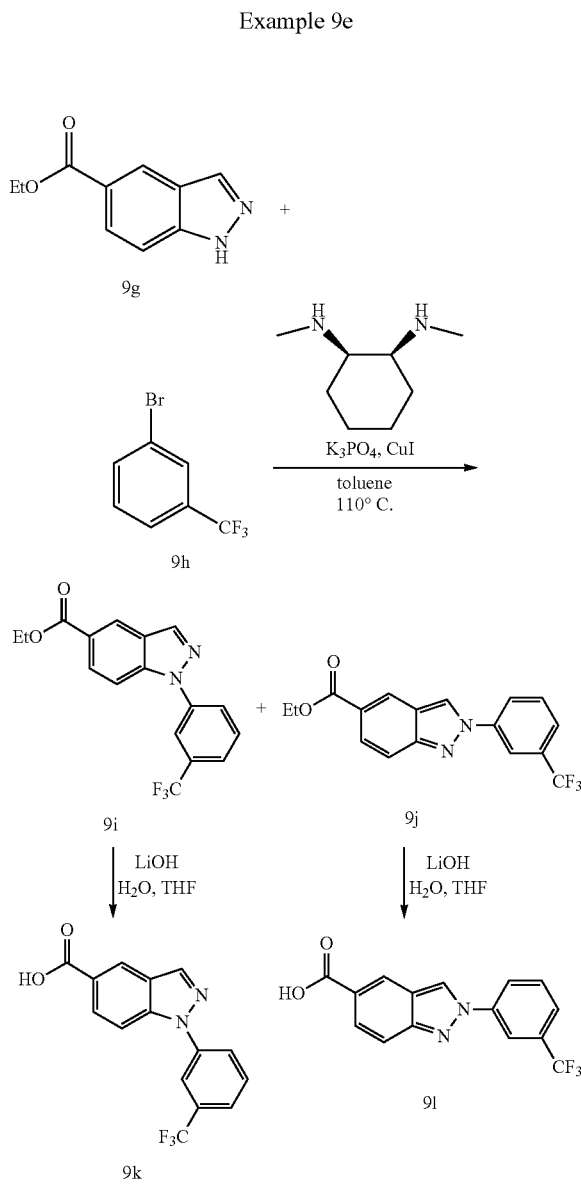

G. Ethyl 1-(3-trifluoromethyl-phenyl)-1H-indazole-5-carboxylate, 9i and Ethyl 1-(3-trifluoromethyl-phenyl)-1H-indazole-5-carboxylate, 9j. A mixture of ethyl 1H-Indazole-5-carboxylate 9g (150 mg, 0.79 mmol), 1-bromo-3-trifluoromethylbenzene 9h (0.13 mL, 0.95 mmol), CuI (22.5 mg, 0.12 mmol), trans-N,N'-dimethylcyclohexane-1,2-diamine (0.056 mL, 0.36 mmol), and K$_3$PO$_4$ (0.37 g, 1.74 mmol) in toluene (1.5 mL) was heated at 110° C. for 16 hours. The reaction mixture was diluted with CH$_2$Cl$_2$ and filtered. The solution was concentrated and the residue was purified by flash column chromatography (silica gel, 10% EtOAc/heptane) to give 9i (190 mg), followed by 9j (37 mg).

H. 1-(3-Trifluoromethyl-phenyl)-1H-indazole-5-carboxylic acid, 9k and 1-(3-Trifluoromethyl-phenyl)-1H-indazole-5-carboxylic acid, 9l. 9k and 9l were prepared according to Example 1b Step L from 9i and 9j respectively.

Following the procedure described above for Example 9e, and substituting the appropriate reagents, starting materials, and purification methods known to those skilled in the art, the following intermediate compounds were prepared:

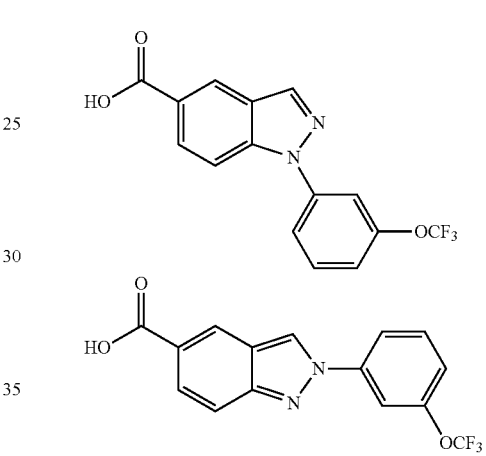

Following the procedure described above for Example 9, and substituting the appropriate reagents, starting materials, and purification methods known to those skilled in the art, the following compounds of the present invention were prepared:

| Cpd | Cpd Name and Data |
|-----|-------------------|
| 1080 | 5-({3-[4-(1,3-Thiazol-2-ylcarbonyl)piperazin-1-yl]azetidin-1-yl}carbonyl)-1-[4-(trifluoromethyl)phenyl]-1H-indazole<br>MS m/z (M + H$^+$) 541 |
| 1374 | 5-({3-[4-(1,3-Thiazol-2-ylcarbonyl)piperazin-1-yl]azetidin-1-yl}carbonyl)-1-[3-(trifluoromethoxy)phenyl]-1H-indazole<br>MS m/z (M + H$^+$) 557 |
| 1376 | 5-({3-[4-(1,3-Thiazol-2-ylcarbonyl)piperazin-1-yl]azetidin-1-yl}carbonyl)-2-[3-(trifluoromethoxy)phenyl]-2H-indazole<br>MS m/z (M + H$^+$) 557 |
| 1419 | 5-({3-[4-(1,3-Thiazol-2-ylcarbonyl)piperazin-1-yl]azetidin-1-yl}carbonyl)-1-[3-(trifluoromethyl)phenyl]-1H-indazole<br>MS m/z (M + H$^+$) 541 |
| 1420 | 5-({3-[4-(1,3-Thiazol-2-ylcarbonyl)piperazin-1-yl]azetidin-1-yl}carbonyl)-2-[3-(trifluoromethyl)phenyl]-2H-indazole<br>MS m/z (M + H$^+$) 541 |
| 1422 | 5-({3-[4-(1,3-Thiazol-4-ylcarbonyl)piperazin-1-yl]azetidin-1-yl}carbonyl)-2-[3-(trifluoromethoxy)phenyl]-2H-indazole<br>MS m/z (M + H$^+$) 557 |

Following the procedure described above for Example 9b, and substituting the appropriate reagents, starting materials, and purification methods known to those skilled in the art, the following compounds of the present invention were prepared:

| Cpd | Cpd Name and Data |
|---|---|
| 575 | 5-({3-[4-(Phenylcarbonyl)piperazin-1-yl]azetidin-1-yl}carbonyl)-1-[4-(trifluoromethyl)phenyl]-1H-indazole<br>MS m/z (M + H$^+$) 534 |
| 576 | 5-({3-[4-(Phenylcarbonyl)piperazin-1-yl]azetidin-1-yl}carbonyl)-1-[3-(trifluoromethoxy)phenyl]-1H-indazole<br>MS m/z (M + H$^+$) 550 |

Example 9f

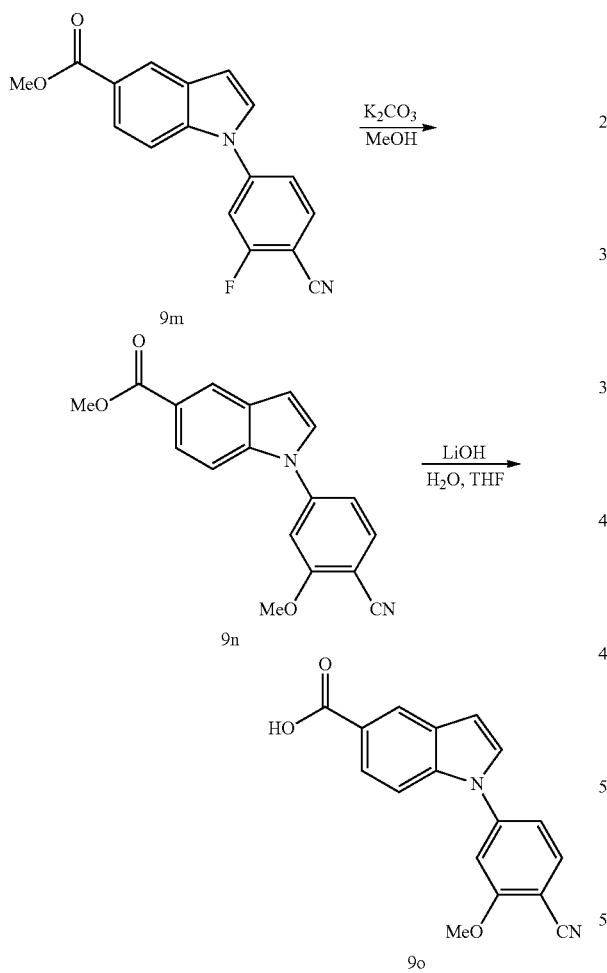

K. 1-(4-cyano-3-methoxyphenyl)-indole-5-carboxylic acid, 93 and 1-(4-carbamoyl-phenyl)-indole-5-carboxylic acid, 9o. A mixture of 100 mg (0.33 mmol) of compound 9m and LiOH (31 mg, 1.3 mmol) in THF (4 mL) and H$_2$O (2 mL) was stirred at room temperature for 3 days. Aqueous 10% HCl solution was added to the reaction mixture to adjust pH=3~4. The resulting mixture was extracted with EtOAc (2×). The organic solution was washed with aq. NaCl, dried over Na$_2$SO$_4$ and concentrated to give 90 mg (94%) of compound 9o as a white solid.

Following the procedure described above for Example 9, and substituting the appropriate reagents, starting materials, and purification methods known to those skilled in the art, the following compounds of the present invention were prepared:

| Cpd | Cpd Name and Data |
|---|---|
| 1115 | 2-Methoxy-4-[5-({3-[4-(1,3-thiazol-2-ylcarbonyl)piperazin-1-yl]azetidin-1-yl}carbonyl)-1H-indol-1-yl]benzonitrile<br>MS m/z (M + H$^+$) 527 |
| 633 | 2-Methoxy-4-[5-({3-[4-(phenylcarbonyl)piperazin-1-yl]azetidin-1-yl}carbonyl)-1H-indol-1-yl]benzonitrile<br>MS m/z (M + H$^+$) 520 |

Example 9g

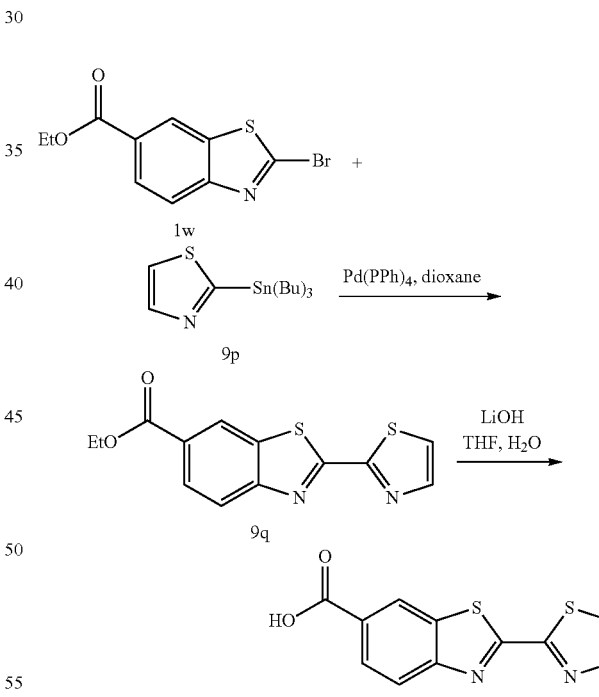

I. Methyl 1-(4-cyano-3-fluorophenyl)-indole-5-carboxylate, 9m was prepared according to Example 9e step H.

J. Methyl 1-(4-cyano-3-methoxyphenyl)-indole-5-carboxylate, 9n. A solution of 95 mg (0.32 mmol) of compound 9m was combined with 120 mg (0.87 mmol) of K$_2$CO$_3$ in 8 mL of MeOH and heated at 75° C. for 5 h. The mixture was cooled, diluted with water, and extracted with CH$_2$Cl$_2$. The organic solution was concentrated to give 100 mg (100%) of 9n as a white solid.

L. Ethyl 2-(thiazol-2-yl)benzo[d]thiazole-6-carboxylate, 9q. A mixture of ethyl 2-bromo-benzothiazole-6-carboxylate 1w (150 mg, 0.53 mmol), 2-tributylstannylthiazole 9p (0.25 mL, 0.79 mmol), and Pd(PPh$_3$)$_4$ (30 mg, 0.03 mmol) in dioxane (2 mL) was heated at 130° C. for 30 min under microwave. The reaction mixture was diluted with CH$_2$Cl$_2$, washed with aq. NaHCO$_3$, dried over Na$_2$SO$_4$, and concentrated. Purification by flash column chromatography (silica gel, 10% EtOAc/heptane) gave 9q (130 mg).

M. 2-(Thiazol-2-yl)benzo[d]thiazole-6-carboxylic acid, 9r. Ethyl 2-phenyl-benzothiazole-6-carboxylate 9q (130 mg, 0.45 mmol) was stirred with LiOH (43 mg, 1.8 mmol) in THF (4 mL) and H$_2$O (2 mL) for 6 h. Aqueous 1N HCl solution was added to the mixture to adjust pH to 3-4. The resulting mixture was extracted with EtOAc (2×). The organic solution was washed with aq. NaCl, dried over Na$_2$SO$_4$ and concentrated to give 9r (110 mg).

Following the procedure described above for Example 9g and substituting the appropriate reagents, starting materials, and purification methods known to those skilled in the art, the following intermediate compounds were prepared:

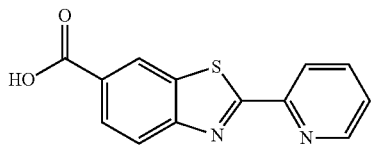 [SMILES: O=C(O)c1ccc2nc(-c3ccccn3)sc2c1]

Following the procedure described above for Example 9, and substituting the appropriate reagents, starting materials, and purification methods known to those skilled in the art, the following compounds of the present invention were prepared:

| Cpd | Cpd Name and Data |
|---|---|
| 1210 | 2-(1,3-Thiazol-2-yl)-6-({3-[4-(1,3-thiazol-2-ylcarbonyl)piperazin-1-yl]azetidin-1-yl}carbonyl)-1,3-benzothiazole<br>MS m/z (M + H$^+$) 497 |
| 1165 | 2-Pyridin-2-yl-6-({3-[4-(1,3-thiazol-2-ylcarbonyl)piperazin-1-yl]azetidin-1-yl}carbonyl)-1,3-benzothiazole<br>MS m/z (M + H$^+$) 491 |

Example 9h

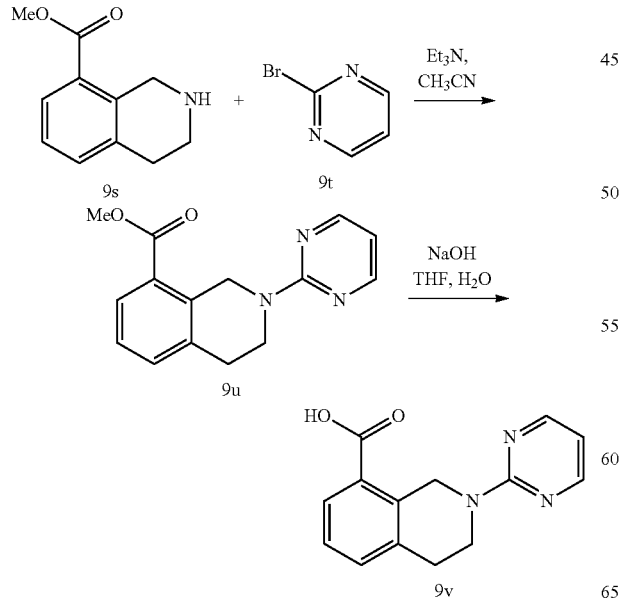

N. Methyl 2-(pyrimidin-2-yl)-1,2,3,4-tetrahydroisoquinoline-8-carboxylate, 9u. A mixture of methyl 1,2,3,4-tetrahydroisoquinoline-8-carboxylate 9s (100 mg, 0.44 mmol), 2-bromopyrimidine 9t (77 nm, 0.48 mmol), and Et$_3$N (0.13 mL, 0.92 mmol) in acetonitrile (5 mL) was stirred at room temperature overnight. The reaction mixture was worked up to give crude 9v (187 mg).

M. 2-(Pyrimidin-2-yl)-1,2,3,4-tetrahydroisoquinoline-8-carboxylic acid, 9v. Compound 9u (187 mg, 0.44 mmol) was refluxed with 3N aqueous NaOH (0.25 mL mg, 0.75 mmol) in THF (6 mL) overnight. Concentrated HCl solution was added to the mixture to adjust pH to 3-4. The resulting mixture was concentrated to give 9v (350 mg) as the tris-HCl salt.

Following the procedure described above for Example 9, and substituting the appropriate reagents, starting materials, and purification methods known to those skilled in the art, the following compound of the present invention was prepared:

| Cpd | Cpd Name and Data |
|---|---|
| | 2-Pyrimidin-2-yl-8-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 490.1 |

Example 9i

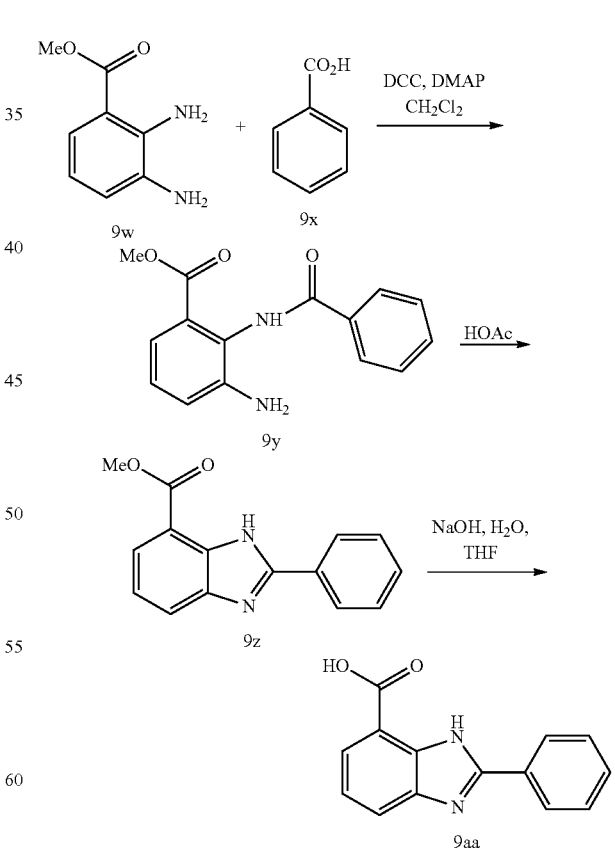

N. Methyl 3-Amino-2-benzoylamino-benzoate, 9y: To a solution of 500 mg (3.0 mmol) of methyl 2,3-diaminobenzoate 9w and 730 mg (6.0 mmol) of benzoic acid 9x in 8 mL of CH$_2$Cl$_2$ was added 620 mg (3.0 mmol) of dicyclohexyl-carbodiimide (DCC) and 4 mg (0.033 mmol) of DMAP. The reaction was stirred overnight and the solid was filtered off. The solid was purified by flash column chromatography (silica gel, 10-30% gradient of EtOAc in heptanes) to give 220 mg (27%) of methyl 3-Amino-2-benzoylamino-benzoate, 9y. MS m/z (M+H$^+$) 271.2

O. Methyl 2-phenyl-1H-benzo[d]imidazole-7-carboxylate, 9z. A solution of 810 mg (3.0 mmol) of methyl 3-amino-2-benzoylamino-benzoate 9y in 15 ml acetic acid was heated to 125° C. for 1.5 h. The reaction was cooled and poured into ice/water. The aqueous layer was made basic with NaHCO$_3$ and extracted with CH$_2$Cl$_2$. The organic solution was dried over Na$_2$SO$_4$ and evaporated to give 540 mg (71%) of methyl 2-phenyl-1H-benzo[d]imidazole-7-carboxylate, 9z. MS m/z (M+H$^+$) 253.2

P. Phenyl-1H-benzo[d]imidazole-7-carboxylic acid, 9aa. A mixture of 540 mg (2.1 mmol) of methyl 2-phenyl-1H-benzo[d]imidazole-7-carboxylate 9z and 3 mL (9 mmol) of 3N aqueous NaOH was refluxed in 8 mL of THF overnight. After cooling, the mixture was poured into ice water and acidified with conc. HCl. The resulting solid was filtered and dried to give 440 mg (86%) of phenyl-1H-benzo[d]imidazole-7-carboxylic acid, 9aa. MS m/z (M+H$^+$) 238.9.

Following the procedure described above for Example 9i, and substituting the appropriate reagents, starting materials, and purification methods known to those skilled in the art, the following intermediate compounds were prepared:

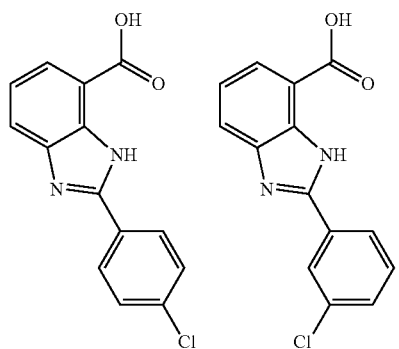

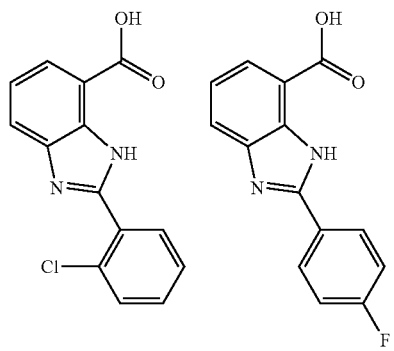

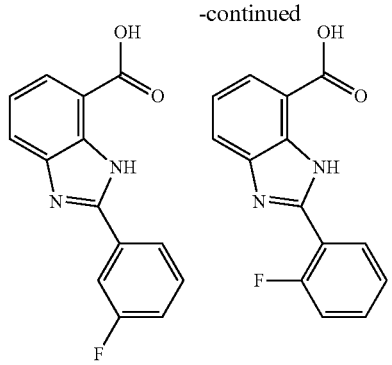

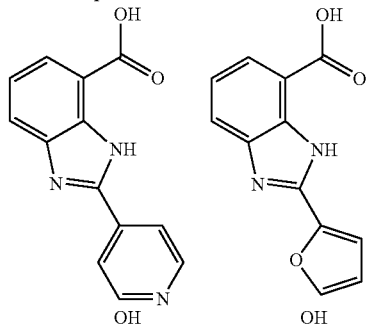

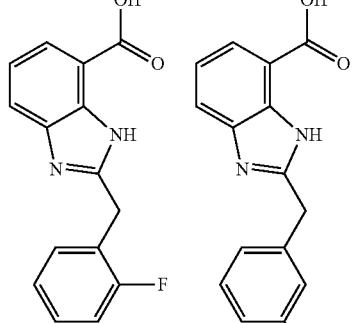

Following the procedure described above for Example 9, and substituting the appropriate reagents, starting materials, and purification methods known to those skilled in the art, the following compounds of the present invention were prepared:

| Cpd | Cpd Name and Data |
|---|---|
| 608 | 2-(2-Chlorophenyl)-4-({3-[4-(phenylcarbonyl)piperazin-1-yl]azetidin-1-yl}carbonyl)-1H-benzimidazole<br>MS m/z (M + H$^+$) 500.3 |

-continued

| Cpd | Cpd Name and Data |
|---|---|
| 609 | 2-(3-Fluorophenyl)-4-({3-[4-(phenylcarbonyl)piperazin-1-yl]azetidin-1-yl}carbonyl)-1H-benzimidazole<br>MS m/z (M + H$^+$) 484.3 |
| 602 | 2-(4-Fluorophenyl)-4-({3-[4-(phenylcarbonyl)piperazin-1-yl]azetidin-1-yl}carbonyl)-1H-benzimidazole<br>MS m/z (M + H$^+$) 484.3 |
| 607 | 2-(4-Chlorophenyl)-4-({3-[4-(phenylcarbonyl)piperazin-1-yl]azetidin-1-yl}carbonyl)-1H-benzimidazole<br>MS m/z (M + H$^+$) 500.3 |
| 601 | 2-Phenyl-4-({3-[4-(phenylcarbonyl)piperazin-1-yl]azetidin-1-yl}carbonyl)-1H-benzimidazole<br>MS m/z (M + H$^+$) 466.3 |
| 1389 | 2-(3-Chlorophenyl)-7-({3-[4-(1,3-thiazol-4-ylcarbonyl)piperazin-1-yl]azetidin-1-yl}carbonyl)-1H-benzimidazole<br>MS m/z (M + H$^+$) 507.2 |
| 1399 | 2-Furan-2-yl-7-({3-[4-(1,3-thiazol-4-ylcarbonyl)piperazin-1-yl]azetidin-1-yl}carbonyl)-1H-benzimidazole<br>MS m/z (M + H$^+$) 463.2 |
| 1390 | 2-Phenyl-7-({3-[4-(1,3-thiazol-4-ylcarbonyl)piperazin-1-yl]azetidin-1-yl}carbonyl)-1H-benzimidazole<br>MS m/z (M + H$^+$) 473.2 |
| 1387 | 2-Pyridin-4-yl-7-({3-[4-(1,3-thiazol-2-ylcarbonyl)piperazin-1-yl]azetidin-1-yl}carbonyl)-1H-benzimidazole<br>MS m/z (M + H$^+$) 474.3 |
| 1252 | 2-Furan-2-yl-7-({3-[4-(1,3-thiazol-2-ylcarbonyl)piperazin-1-yl]azetidin-1-yl}carbonyl)-1H-benzimidazole<br>MS m/z (M + H$^+$) 463.3 |
| 1255 | 2-Phenyl-7-({3-[4-(1,3-thiazol-2-ylcarbonyl)piperazin-1-yl]azetidin-1-yl}carbonyl)-1H-benzimidazole<br>MS m/z (M + H$^+$) 463.3 |
| 1388 | 2-(2-Fluorophenyl)-4-({3-[4-(1,3-thiazol-4-ylcarbonyl)piperazin-1-yl]azetidin-1-yl}carbonyl)-1H-benzimidazole<br>MS m/z (M + H$^+$) 491.2 |
| 1391 | 2-(3-Fluorophenyl)-4-({3-[4-(1,3-thiazol-4-ylcarbonyl)piperazin-1-yl]azetidin-1-yl}carbonyl)-1H-benzimidazole<br>MS m/z (M + H$^+$) 491.2 |
| 1393 | 2-(4-Fluorophenyl)-4-({3-[4-(1,3-thiazol-4-ylcarbonyl)piperazin-1-yl]azetidin-1-yl}carbonyl)-1H-benzimidazole<br>MS m/z (M + H$^+$) 491.2 |
| 1394 | 2-(2-Chlorophenyl)-4-({3-[4-(1,3-thiazol-4-ylcarbonyl)piperazin-1-yl]azetidin-1-yl}carbonyl)-1H-benzimidazole<br>MS m/z (M + H$^+$) 507.2 |
| 1290 | 2-(4-Chlorophenyl)-4-({3-[4-(1,3-thiazol-4-ylcarbonyl)piperazin-1-yl]azetidin-1-yl}carbonyl)-1H-benzimidazole<br>MS m/z (M + H$^+$) 507.2 |
| 980 | 2-Benzyl-4-({3-[4-(1,3-thiazol-2-ylcarbonyl)piperazin-1-yl]azetidin-1-yl}carbonyl)-1H-benzimidazole<br>MS m/z (M + H$^+$) 487 |
| 989 | 2-(2-Fluorobenzyl)-7-({3-[4-(1,3-thiazol-2-ylcarbonyl)piperazin-1-yl]azetidin-1-yl}carbonyl)-1H-benzimidazole<br>MS m/z (M + H$^+$) 505.2 |
| 990 | 2-(3-Fluorobenzyl)-7-({3-[4-(1,3-thiazol-2-ylcarbonyl)piperazin-1-yl]azetidin-1-yl}carbonyl)-1H-benzimidazole<br>MS m/z (M + H$^+$) 505.2 |
| 991 | 2-(4-Chlorobenzyl)-7-({3-[4-(1,3-thiazol-2-ylcarbonyl)piperazin-1-yl]azetidin-1-yl}carbonyl)-1H-benzimidazole<br>MS m/z (M + H$^+$) 521.2 |
| 1461 | 2-(Pyridin-4-ylmethyl)-7-({3-[4-(1,3-thiazol-2-ylcarbonyl)piperazin-1-yl]azetidin-1-yl}carbonyl)-1H-benzimidazole<br>MS m/z (M + H$^+$) 488.2 |

Example 9j

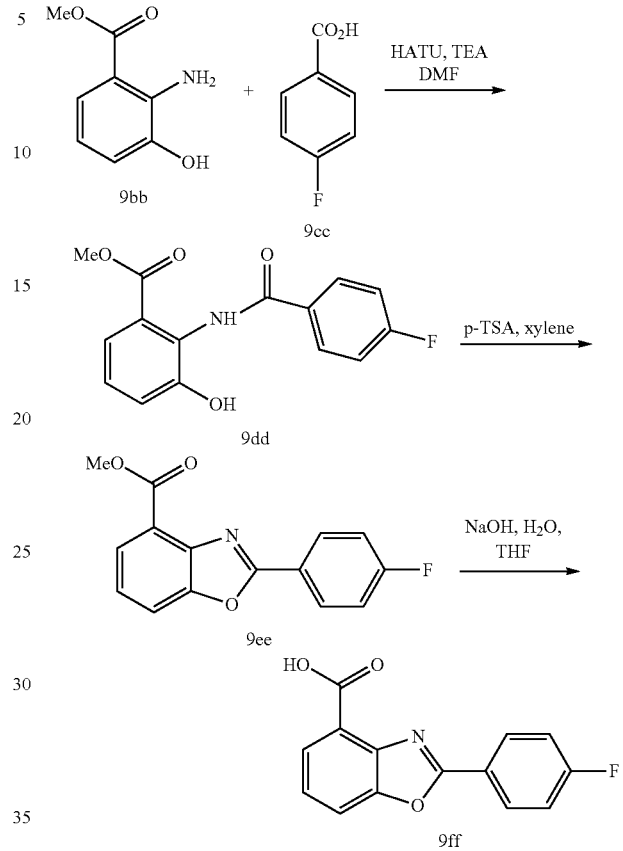

Q. Methyl 2-(4-fluoro-benzoylamino)-3-hydroxy-benzoate, 9dd. A solution of 1.0 g (4.9 mmol) of methyl 2-amino-3-hydroxybenzoate 9bb, 1.03 g (7.4 mmol) of 4-fluorobenzoic acid 9 cc, 10 mL DMF and 2.9 mL (20.6 mmol) of TEA were placed into a flask and stirred for 10 min. HATU (7.4 mmol, 2.8 g) was added and the reaction was stirred overnight. The reaction mixture was poured into water and extracted with EtOAc. The organics were washed with water and brine and the solvent was evaporated to give 1.2 g of crude product, methyl 2-(4-fluoro-benzoylamino)-3-hydroxy-benzoate, 9dd, which was used without purification. MS m/z (M+H$^+$) 290.1.

R. Methyl 2-(4-fluorophenyl)benzo[d]oxazole-4-carboxylate, 9ee. Methyl 2-(4-fluoro-benzoylamino)-3-hydroxybenzoate 9dd (7.4 mmol, 1.2 g crude) and 1.3 g (7.5 mmol) of p-toluenesulfonic acid was refluxed in 10 mL of xylene overnight. After cooling saturated NaHCO$_3$ was added and the resulting mixture was extracted with EtOAc. The organic solvent was evaporated to give 1.1 g (55%) of methyl 2-(4-fluorophenyl)benzo[d]oxazole-4-carboxylate, 9ee. MS m/z (M+H$^+$) 272.0.

S. 2-(4-Fluorophenyl)-benzo[d]oxazole-4-carboxylic acid, 9ff. A mixture of 1.1 g (4.0 mmol) methyl 2-(4-fluorophenyl)benzo[d]oxazole-4-carboxylate 9ee and 3.7 mL of 3N aqueous NaOH in 10 mL of THF was refluxed overnight. After cooling the reaction mixture was poured into water and acidified with conc. HCl. The resulting solid was filtered and dried to give 830 mg (79%) of 2-(4-fluorophenyl)-benzo[d]oxazole-4-carboxylic acid, 9ff. MS m/z (M+H$^+$) 258.1.

Following the procedure described above for Example 9j, and substituting the appropriate reagents, starting materials, and purification methods known to those skilled in the art, the following intermediate compounds were prepared:

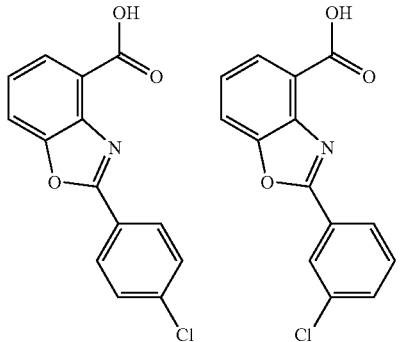

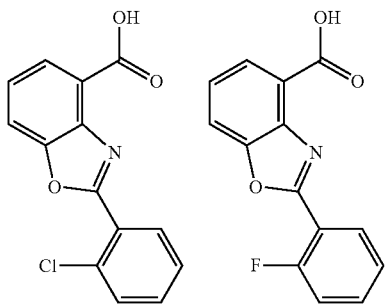

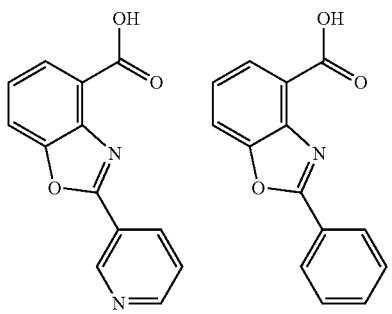

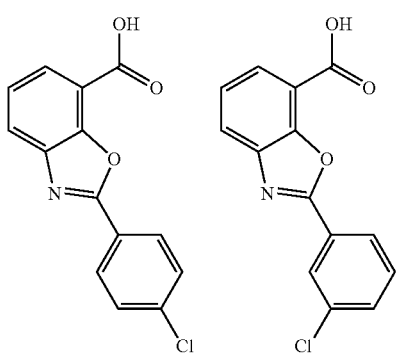

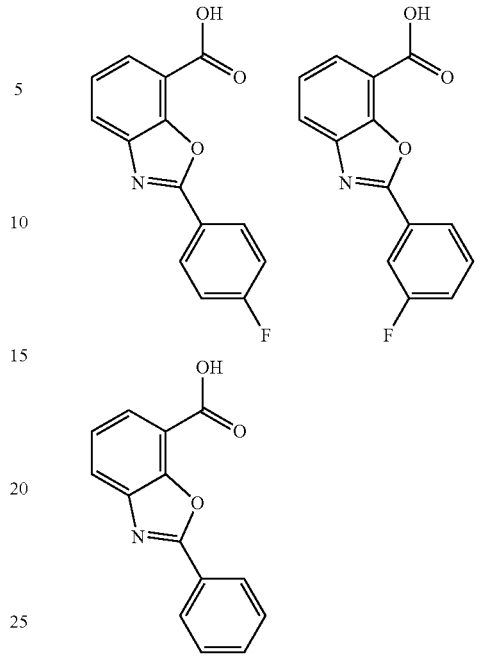

Following the procedure described above for Example 9, and substituting the appropriate reagents, starting materials, and purification methods known to those skilled in the art, the following compounds of the present invention were prepared:

| Cpd | Cpd Name and Data |
|---|---|
| 1154 | 2-Phenyl-7-({3-[4-(1,3-thiazol-2-ylcarbonyl)piperazin-1-yl]azetidin-1-yl}carbonyl)-1,3-benzoxazole<br>$^1$H NMR (400 MHz, CDCl$_3$): δ 8.32 (m, 2H); 7.95 (m, 2H); 7.85 (m, 1H); 7.71-7.49 (m, 5H); 4.85-4.44 (bm, 3H); 4.15-3.91 (bm, 3H); 3.23 (bm, 3H)<br>MS m/z (M + H$^+$) 474.2 |
| 1254 | 2-(3-Fluorophenyl)-7-({3-[4-(1,3-thiazol-4-ylcarbonyl)piperazin-1-yl]azetidin-1-yl}carbonyl)-1,3-benzoxazole<br>MS m/z (M + H$^+$) 492.1 |
| 1282 | 2-(4-Fluorophenyl)-7-({3-[4-(1,3-thiazol-4-ylcarbonyl)piperazin-1-yl]azetidin-1-yl}carbonyl)-1,3-benzoxazole<br>MS m/z (M + H$^+$) 492.1 |
| 1238 | 2-(3-Chlorophenyl)-7-({3-[4-(1,3-thiazol-4-ylcarbonyl)piperazin-1-yl]azetidin-1-yl}carbonyl)-1,3-benzoxazole<br>MS m/z (M + H$^+$) 507.9 |
| 1380 | 2-(4-Chlorophenyl)-7-({3-[4-(1,3-thiazol-4-ylcarbonyl)piperazin-1-yl]azetidin-1-yl}carbonyl)-1,3-benzoxazole<br>$^1$H NMR (400 MHz, CDCl$_3$): δ 9.05 (bs, 1H); 8.3 (d, 2H); 8.2 (m, 1H); 7.95 (d, 1H); 7.66 (t, 3H); 7.44 (t, 1H); 4.69-4.52 (m, 1H); 4.44 (m, 2H); 4.10 (bm, 2H); 3.20 (m, 4H).<br>MS m/z (M + H$^+$) 507.9 |
| 1190 | 2-Phenyl-4-({3-[4-(1,3-thiazol-2-ylcarbonyl)piperazin-1-yl]azetidin-1-yl}carbonyl)-1,3-benzoxazole<br>MS m/z (M + H$^+$) 474 |
| 1193 | 2-(2-Fluorophenyl)-4-({3-[4-(1,3-thiazol-2-ylcarbonyl)piperazin-1-yl]azetidin-1-yl}carbonyl)-1,3-benzoxazole<br>MS m/z (M + H$^+$) 492.2 |
| 1257 | 2-(4-Fluorophenyl)-4-({3-[4-(1,3-thiazol-2-ylcarbonyl)piperazin-1-yl]azetidin-1-yl}carbonyl)-1,3-benzoxazole<br>MS m/z (M + H$^+$) 492.2 |

-continued

| Cpd | Cpd Name and Data |
|---|---|
| 1173 | 2-(2-Chlorophenyl)-4-({3-[4-(1,3-thiazol-2-ylcarbonyl)piperazin-1-yl]azetidin-1-yl}carbonyl)-1,3-benzoxazole<br>MS m/z (M + H$^+$) 508.2 |
| 1191 | 2-(3-Chlorophenyl)-4-({3-[4-(1,3-thiazol-2-ylcarbonyl)piperazin-1-yl]azetidin-1-yl}carbonyl)-1,3-benzoxazole<br>MS m/z (M + H$^+$) 508.2 |
| 1220 | 2-(4-Chlorophenyl)-4-({3-[4-(1,3-thiazol-2-ylcarbonyl)piperazin-1-yl]azetidin-1-yl}carbonyl)-1,3-benzoxazole<br>MS m/z (M + H$^+$) 508.9 |
| 1237 | 2-Phenyl-7-({3-[4-(1,3-thiazol-4-ylcarbonyl)piperazin-1-yl]azetidin-1-yl}carbonyl)-1,3-benzoxazole<br>MS m/z (M + H$^+$) 474.2 |
| 1251 | 2-Pyridin-3-yl-4-({3-[4-(1,3-thiazol-2-ylcarbonyl)piperazin-1-yl]azetidin-1-yl}carbonyl)-1,3-benzoxazole<br>MS m/z (M + H$^+$) 475.1 |

Example 10

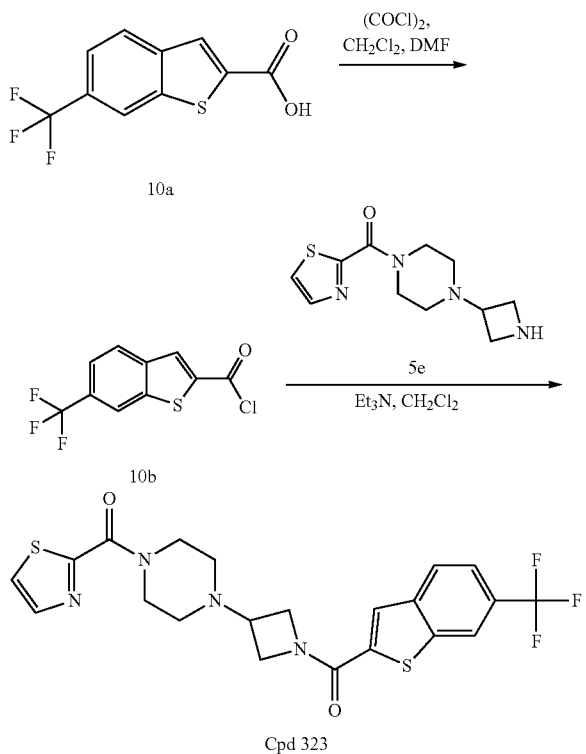

A. 6-Trifluoromethyl-benzo[b]thiophene-2-carbonyl chloride, 10b. To compound 10a (0.13 g, 0.53 mmol) in CH$_2$Cl$_2$ (5 mL) at room temperature was added (COCl)$_2$ (0.051 mL, 0.58 mmol), followed by 2 drops of DMF. The reaction mixture was stirred at room temperature for 18 h. The reaction mixture was then concentrated to give compound 10b, which was used in the next reaction without further purification.

B. 1-(1,3-Thiazol-2-ylcarbonyl)-4-(1-{[6-(trifluoromethyl)-1-benzothiophen-2-yl]carbonyl}azetidin-3-yl)piperazine. To a solution of compound 5e (60 mg, 0.24 mmol) and Et$_3$N (0.08 mL, 0.58 mmol) in CH$_2$Cl$_2$ (3 mL) at 0° C. was added a solution of compound 10b (0.53 mmol) in CH$_2$Cl$_2$ (1 mL). The reaction was slowly warmed up to room temperature over 4.5 h, diluted with CH$_2$Cl$_2$, and washed with aq. NaHCO$_3$. The organic layer was dried over Na$_2$SO$_4$ and concentrated. Purification by flash column chromatography (silica gel, 3% MeOH/CH$_2$Cl$_2$) afforded compound 323. $^1$H NMR (400 MHz, CD$_3$OD): δ 8.15 (s, 1H), 7.94 (d, J=8.6 Hz, 1H), 7.89 (d, J=3 Hz, 1H), 7.74 (s, 1H), 7.62 (d, J=8.6 Hz, 1H), 7.56 (d, J=3 Hz, 1H), 4.60 (m, 2H), 4.45 (m, 2H), 4.30 (m, 1H), 4.16 (m, 1H), 3.95-3.89 (m, 2H), 3.35 (m, 1H), 2.55 (bs, 4H). MS m/z (M+H$^+$) 481.

Following the procedure described above for Example 10 and substituting the appropriate reagents, starting materials and purification methods known to those skilled in the art, the following compounds of the present invention were prepared:

| Cpd | Cpd Name and Data |
|---|---|
| 324 | 1-(1-{[-Chloro-6-(trifluoromethyl)-1-benzothiophen-2-yl]carbonyl}azetidin-3-yl)-4-(1,3-thiazol-2-ylcarbonyl)piperazine<br>$^1$H NMR (400 MHz, CD$_3$OD): δ 8.13 (s, 1H), 8.01 (d, J = 8 Hz, 1H), 7.88 (d, J = 3 Hz, 1H), 7.73 (d, J = 8 Hz, 1H), 7.55 (d, J = 3 Hz, 1H), 4.53 (bs, 1H), 4.46 (bs, 1H), 4.31 (m, 2H), 4.22 (m, 1H), 4.16 (m, 1H), 3.33 (m, 1H), 2.60-2.40 (m, 4H).<br>MS m/z (M + H$^+$) 515 |
| 325 | 1-(Phenylcarbonyl)-4-(1-{[6-(trifluoromethyl)-1-benzothiophen-2-yl]carbonyl}azetidin-3-yl)piperazine<br>$^1$H NMR (400 MHz, CD$_3$OD): δ 8.15 (s, 1H), 7.94 (d, J = 8.6 Hz, 1H), 7.73 (s, 1H), 7.62 (d, J = 8.6 Hz, 1H), 7.42 (m, 5H), 4.58 (m, 1H), 4.42 (m, 1H), 4.28 (m, 1H), 4.12 (m, 1H), 3.93 (bs, 1H), 3.77 (bs, 1H), 3.51 (bs, 2H), 3.34 (m, 1H), 2.60-2.30 (m, 4H).<br>MS m/z (M + H$^+$) 474 |
| 686 | 3-Methyl-2-({3-[4-(1,3-thiazol-2-ylcarbonyl)piperazin-1-yl]azetidin-1-yl}carbonyl)-6-(trifluoromethyl)thieno[2,3-b]pyridine<br>MS m/z (M + H$^+$) 496 |
| 749 | 3-Methyl-2-({3-[4-(1,3-thiazol-4-ylcarbonyl)piperazin-1-yl]azetidin-1-yl}carbonyl)-6-(trifluoromethyl)thieno[2,3-b]pyridine<br>MS m/z (M + H$^+$) 496 |
| 801 | 1-(1-{[3-Chloro-6-(trifluoromethyl)-1-benzothiophen-2-yl]carbonyl}azetidin-3-yl)-4-(1,3-thiazol-4-ylcarbonyl)-2-(trifluoromethyl)piperazine<br>MS m/z (M + H$^+$) 583.0 |
| 833 | 4-(1-{[3-Chloro-6-(trifluoromethyl)-1-benzothiophen-2-yl]carbonyl}azetidin-3-yl)-1-(1,3-thiazol-4-ylcarbonyl)-2-(trifluoromethyl)piperazine<br>MS m/z (M + H$^+$) 583.0 |
| 778 | 1-(1-{[3-Chloro-6-(trifluoromethyl)-1-benzothiophen-2-yl]carbonyl}azetidin-3-yl)-4-(1,3-thiazol-2-ylcarbonyl)-2-(trifluoromethyl)piperazine<br>$^1$H NMR (400 MHz, CD$_3$OD): δ 2.13 (d, J = 13.2 Hz, 1 H), 2.41 (d, J = 47.2 Hz, 1 H), 2.8-3.3 (m, 2.5 H), 3.69 (d, J = 13.7 Hz, 0.5 H), 3.98-4.42 (m, 4 H), 4.51 (t, J = 13.4 Hz, 0.5 H), 5.27-5.54 (m, 1 H), 6.93 (br. s., 0.5 H), 7.83 (d, J = 8.6 Hz, 1 H), 7.88 (br. s., 1 H), 7.97 (t, J = 6.8 Hz, 1 H), 8.11 (d, J = 8.8 Hz, 1 H), 8.42 (s, 1 H)<br>MS m/z (M + H$^+$) 583.0 |

Example 10a

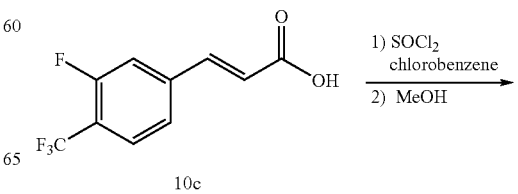

-continued

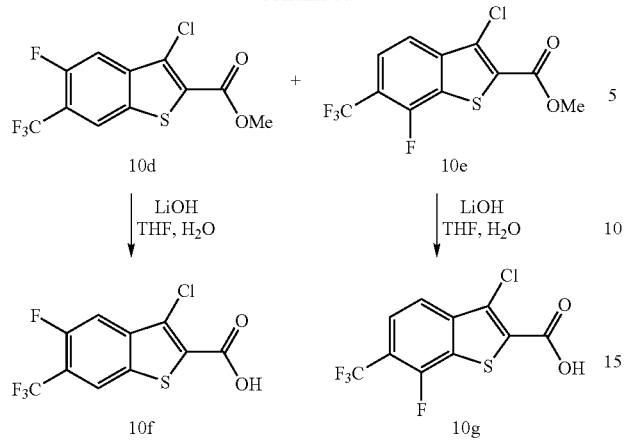

C. Methyl 3-chloro-5-fluoro-6-trifluoromethyl-benzo[b]thiophene-2-carboxylate, 10d and methyl 3-chloro-6-trifluoromethyl-7-fluoro-benzo[b]thiophene-2-carboxylate, 10e. A mixture of 3-fluoro-4-(trifluoromethyl)-cinnamic acid 10c (1.5 g, 6.4 mmol), $SOCl_2$ (2.33 mL, 32 mmol), DMF (0.05 mL, 0.64 mmol), and pyridine (0.05 mL, 0.64 mmol) in chlorobenzene (5 mL) was heated to reflux for 24 h. The reaction mixture was cooled to room temperature and concentrated. The resulting residue was dissolved in MeOH (50 mL) and stirred at room temperature for 16 h. The solution was concentrated, diluted with $CH_2Cl_2$ and washed with $H_2O$. The organic solution was dried over $Na_2SO_4$ and concentrated. Recrystallization with heptanes, followed by flash column chromatography (silica gel, 2% EtOAc/heptane) gave 10d (580 mg) and 10e (380 mg).

D. 3-Chloro-5-fluoro-6-trifluoromethyl-benzo[b]thiophene-2-carboxylic acid, 10f. Methyl 3-chloro-5-fluoro-6-trifluoromethyl-benzo[b]thiophene-2-carboxylate 10d (180 mg, 0.58 mmol) was stirred with LiOH (55 mg, 2.3 mmol) in THF (5 mL) and $H_2O$ (2.5 mL) for 4 h. Aqueous 1N HCl solution was added to the mixture to adjust pH to 3~4. The resulting mixture was extracted with EtOAc (2×). The organic solution was washed with aq. NaCl, dried over $Na_2SO_4$ and concentrated to give 10f (150 mg).

E. 3-Chloro-6-trifluoromethyl-7-fluoro-benzo[b]thiophene-2-carboxylic acid, 10g. Compound 10g was prepared from 10e following the procedure described in above step D.

Following the procedure described above for Example 10, and substituting the appropriate reagents, starting materials, and purification methods known to those skilled in the art, the following compounds of the present invention were prepared:

| Cpd | Cpd Name and Data |
|---|---|
| 666 | 1-(1-{[3-Chloro-5-fluoro-6-(trifluoromethyl)-1-benzothiophen-2-yl]carbonyl}azetidin-3-yl)-4-(1,3-thiazol-4-ylcarbonyl)piperazine<br>MS m/z (M + H⁺) 533 |
| 900 | 1-(1-{[3-Chloro-5-fluoro-6-(trifluoromethyl)-1-benzothiophen-2-yl]carbonyl}azetidin-3-yl)-4-(1,3-thiazol-2-ylcarbonyl)piperazine<br>MS m/z (M + H⁺) 533 |
| 670 | 1-(1-{[3-Chloro-7-fluoro-6-(trifluoromethyl)-1-benzothiophen-2-yl]carbonyl}azetidin-3-yl)-4-(1,3-thiazol-4-ylcarbonyl)piperazine<br>MS m/z (M + H⁺) 533 |
| 650 | 1-(1-{[3-Chloro-7-fluoro-6-(trifluoromethyl)-1-benzothiophen-2-yl]carbonyl}azetidin-3-yl)-4-(1,3-thiazol-2-ylcarbonyl)piperazine<br>MS m/z (M + H⁺) 533 |

Example 10b

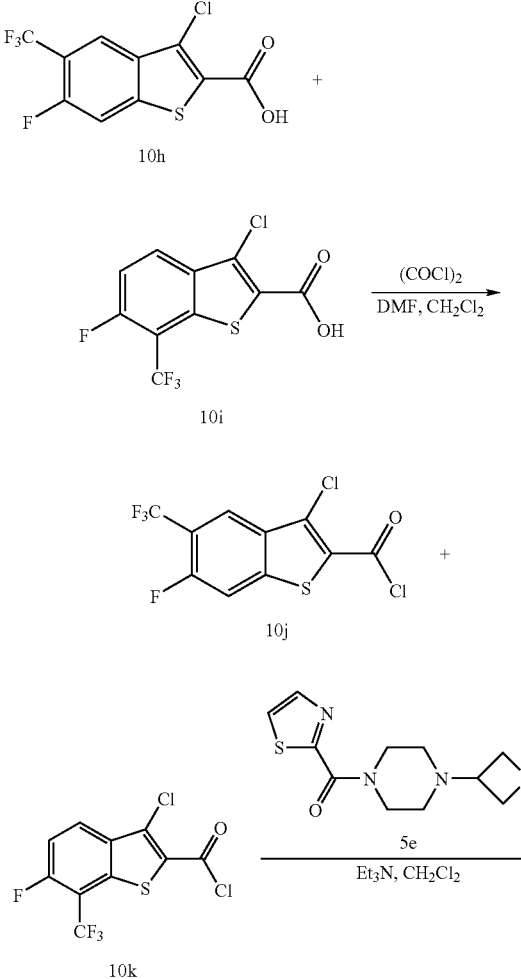

Cpd 901

Example 11

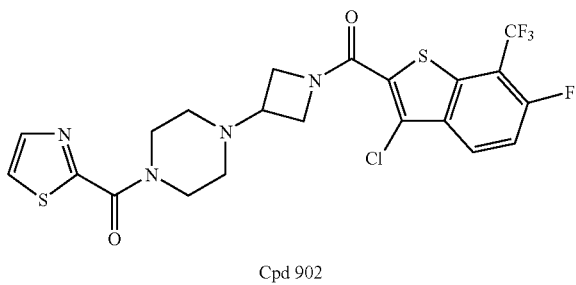

Cpd 902

F. 3-Chloro-5-trifluoromethyl-6-fluoro-benzo[b]thiophene-2-carboxylic acid, 10h and 3-chloro-6-fluoro-7-trifluoromethyl-benzo[b]thiophene-2-carboxylic acid, 10i. Compounds 10h and 10i were prepared according to Example 10a, using 4-fluoro-3-(trifluoromethyl)-cinnamic acid in place of 10c, and were obtained as a ~2:1 mixture.

G. 3-Chloro-5-trifluoromethyl-6-fluoro-benzo[b]thiophene-2-carbonyl chloride, 10j and 3-chloro-6-fluoro-7-trifluoromethyl-benzo[b]thiophene-2-carbonyl chloride, 10k. Compounds 10j and 10k were prepared according to Example 10a from 10h and 10i, and were obtained as a ~2:1 mixture.

H. 1-(1-{[3-Chloro-6-fluoro-5-(trifluoromethyl)-1-benzothiophen-2-yl]carbonyl}azetidin-3-yl)-4-(1,3-thiazol-2-ylcarbonyl)piperazine, Cpd 901, and 1-(1-{[3-chloro-6-fluoro-7-(trifluoromethyl)-1-benzothiophen-2-yl]carbonyl}azetidin-3-yl)-4-(1,3-thiazol-2-ylcarbonyl)piperazine, Cpd 902. Cpd 901 and Cpd 902 were prepared according to Example 10 from 5e bis HCl salt (0.31 mmol, 150 mg), the mixture of 10j and 10k (0.24 mmol, 76 mg), and Et$_3$N (1.44 mol, 0.2 mL) in 7 mL of CH$_2$Cl$_2$. Workup and purification by flash column chromatography (silica gel, 2% MeOH/CH$_2$Cl$_2$) gave 50 mg (39%) of Cpd 901 followed by 18 mg (14%) of Cpd 902. Cpd 901: MS m/z (M+H$^+$) 533. Cpd 902: MS m/z (M+H$^+$) 533.

Following the procedure described above for Example 10b, and substituting the appropriate reagents, starting materials, and purification methods known to those skilled in the art, the following compounds of the present invention were prepared:

| Cpd | Cpd Name and Data |
|---|---|
| 659 | 1-(1-{[3-Chloro-6-fluoro-5-(trifluoromethyl)-1-benzothiophen-2-yl]carbonyl}azetidin-3-yl)-4-(1,3-thiazol-4-ylcarbonyl)piperazine<br>MS m/z (M + H$^+$) 533 |
| 697 | 1-(1-{[3-Chloro-6-fluoro-7-(trifluoromethyl)-1-benzothiophen-2-yl]carbonyl}azetidin-3-yl)-4-(1,3-thiazol-4-ylcarbonyl)piperazine<br>MS m/z (M + H$^+$) 533 |

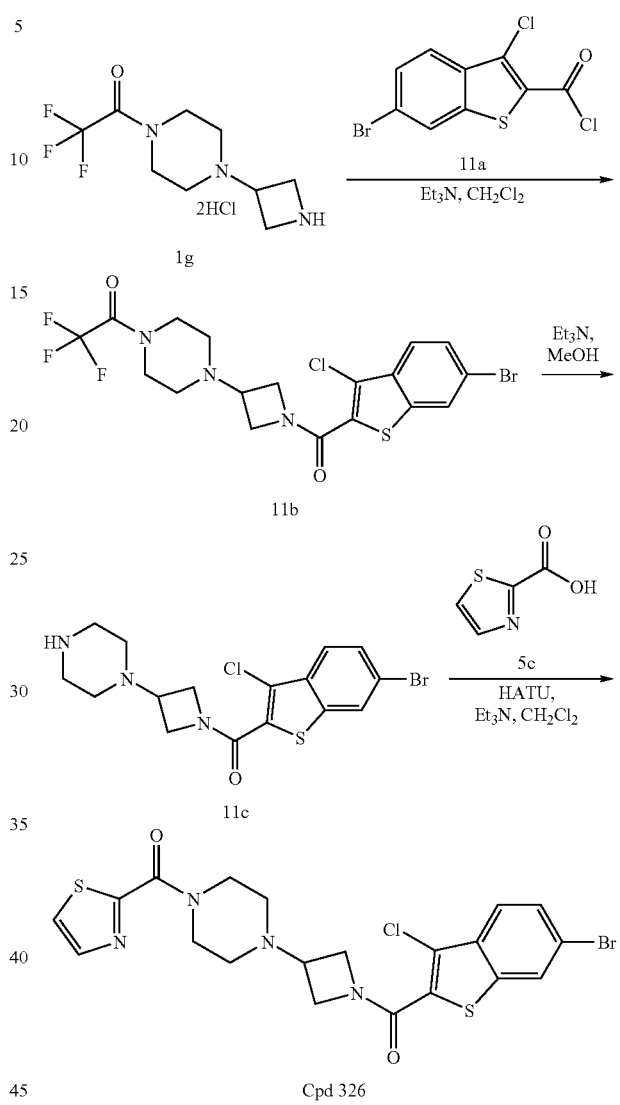

Cpd 326

A. 1-{4-[1-(6-Bromo-3-chloro-benzo[b]thiophene-2-carbonyl)-azetidin-3-yl]-piperazin-1-yl}-2,2,2-trifluoro-ethanone, 11b. To a solution of compound 1g (0.19 g, 0.61 mmol) and Et$_3$N (0.51 mL, 3.67 mmol) in CH$_2$Cl$_2$ (4 mL) at 0° C. was added a solution of compound 11a (prepared in an analogous manner to that of compound 10b of Example 10) (0.69 mmol) in CH$_2$Cl$_2$ (2 mL). The reaction mixture was slowly warmed up to room temperature over 18 h. The reaction mixture was diluted with CH$_2$Cl$_2$ and washed with aq. NaHCO$_3$. The organic layer was dried over Na$_2$SO$_4$ and concentrated. Purification by flash column chromatography (silica gel, 3% MeOH/CH$_2$Cl$_2$) gave compound 11b (0.3 g).

B. (6-Bromo-3-chloro-benzo[b]thiophen-2-yl)-(3-piperazin-1-yl-azetidin-1-yl)-methanone, 11c. A solution of compound 11b (0.3 g, 0.59 mmol) in Et$_3$N (1 mL) and MeOH (9 mL) was stirred at room temperature for 3 days. It was then concentrated to give compound 11c, which was used in the next reaction without further purification.

C. 1-{1-[(6-Bromo-3-chloro-1-benzothiophen-2-yl)carbonyl]azetidin-3-yl}-4-(1,3-thiazol-2-ylcarbonyl)piperazine, Cpd 326. To a mixture of compound 11c (0.2 mmol), compound 5c (31 mg, 0.24 mmol), and Et$_3$N (0.08 mL, 0.58 mmol) in CH$_2$Cl$_2$ (3 mL) at room temperature was added HATU (91 mg, 0.24 mmol). The reaction mixture was stirred at room temperature for 18 h. It was diluted with diethyl ether, washed with aq. NaHCO$_3$ and aq. NaCl, dried over Na$_2$SO$_4$, filtered, and concentrated. Purification by flash column chromatography (silica gel, 3% MeOH/CH$_2$Cl$_2$) gave compound 326 (57 mg). $^1$H NMR (400 MHz, CD$_3$OD): δ 7.98 (s, 1H), 7.88 (d, J=3 Hz, 1H), 7.75 (d, J=8.6 Hz, 1H), 7.61 (d, J=8.6 Hz, 1H), 7.55 (d, J=3 Hz, 1H), 4.53 (bs, 1H), 4.44 (bs, 1H), 4.30 (bs, 2H), 4.21 (bs, 1H), 4.13 (bs, 1H), 3.89 (bs, 1H), 3.84 (bs, 1H), 3.31 (m, 1H), 2.60-2.40 (m, 4H). MS m/z (M+H$^+$) 525/527/529.

Following the procedure described above for Example 11 and substituting the appropriate reagents, starting materials and purification methods known to those skilled in the art, the following compounds of the present invention were prepared:

| Cpd | Cpd Name and Data |
|---|---|
| 327 | 1-(1,3-Thiazol-2-ylcarbonyl)-4-(1-{[4-(trifluoromethyl)-1-benzothiophen-2-yl]carbonyl}azetidin-3-yl)piperazine<br>$^1$H NMR (400 MHz, CD$_3$OD): δ 8.05 (d, J = 8.2 Hz, 1H), 7.89 (d, J = 3 Hz, 1H), 7.85 (s, 1H), 7.72 (d, J = 7.4 Hz, 1H), 7.55 (d, J = 3 Hz, 1H), 7.51 (t, J = 7.8 Hz, 1H), 4.60 (m, 2H), 4.45 (m, 2H), 4.31 (m, 1H), 4.17 (m, 1H), 3.95-3.80 (m, 2H), 3.35 (m, 1H), 2.56 (bs, 4H).<br>MS m/z (M + H$^+$) 481 |
| 328 | 1-(1,3-Thiazol-2-ylcarbonyl)-4-(1-{[7-(trifluoromethyl)-1-benzothiophen-2-yl]carbonyl}azetidin-3-yl)piperazine<br>MS m/z (M + H$^+$) 481 |
| 329 | 1-(Phenylcarbonyl)-4-(1-{[7-(trifluoromethyl)-1-benzothiophen-2-yl]carbonyl}azetidin-3-yl)piperazine<br>$^1$H NMR (400 MHz, CD$_3$OD): δ 8.02 (d, J = 8.2 Hz, 1H), 7.80 (s, 1H), 7.73 (d, J = 7.4 Hz, 1H), 7.51 (t, J = 8.2 Hz, 1H), 7.42 (m, 5H), 4.60 (m, 1H), 4.43 (m, 1H), 4.28 (m, 1H), 4.12 (m, 1H), 3.94 (bs, 1H), 3.76 (bs, 1H), 3.51 (bs, 2H), 3.33 (m, 1H), 2.60-2.30 (m, 4H).<br>MS m/z (M + H$^+$) 474 |
| 330 | 1-(Phenylcarbonyl)-4-(1-{[4-(trifluoromethyl)-1-benzothiophen-2-yl]carbonyl}azetidin-3-yl)piperazine<br>$^1$H NMR (400 MHz, CD$_3$OD): δ 8.05 (d, J = 8 Hz, 1H), 7.84 (s, 1S), 7.71 (d, J = 8 Hz, 1H), 7.50 (t, J = 8 Hz, 1H), 7.42 (m, 5H), 4.59 (m, 1H), 4.42 (m, 1H), 4.29 (m, 1H), 4.13 (m, 1H), 3.92 (bs, 1H), 3.79 (bs, 1H), 3.51 (bs, 1H), 3.34 (m, 1H), 2.60-2.30 (m, 4H).<br>MS m/z (M + H$^+$) 474 |
| 331 | 1-{1-[(6-Bromo-3-chloro-1-benzothiophen-2-yl)carbonyl]azetidin-3-yl}-4-(phenylcarbonyl)piperazine<br>MS m/z (M + H$^+$) 518/520/522 |
| 332 | 1-(1,3-Thiazol-4-ylcarbonyl)-4-(1-{[7-(trifluoromethyl)-1-benzothiophen-2-yl]carbonyl}azetidin-3-yl)piperazine<br>$^1$H NMR (400 MHz, CD$_3$OD): δ 8.80 (s, 1H), 8.04 (s, 1H), 8.02 (d, J = 8 Hz, 1H), 7.81 (s, 1H), 7.73 (d, J = 7.6 Hz, 1H), 7.51 (t, J = 7.6 Hz, 1H), 4.60 (m, 1H), 4.45 (m, 1H), 4.30 (m, 1H), 4.15 (m, 1H), 4.02 (bs, 1H), 3.95 (m, 2H), 3.82 (bs, 1H), 3.35 (m, 1H), 2.60-2.40 (m, 4H).<br>MS m/z (M + H$^+$) 481 |
| 333 | 1-{1-[(6-Bromo-3-chloro-1-benzothiophen-2-yl)carbonyl]azetidin-3-yl}-4-(1,3-thiazol-4-ylcarbonyl)piperazine<br>$^1$H NMR (400 MHz, CD$_3$OD): δ 8.80 (s, 1H), 8.02 (s, 1H), 7.97 (s, 1H), 7.74 (m, 1H), 7.60 (m, 1H), 4.30 (m, 2H), 4.21 (bs, 1H), 4.12 (bs, 1H), 4.00 (bs, 1H), 3.92 (m, 2H), 3.81 (bs, 1H), 3.31 (m, 1H), 2.50-2.30 (m, 4H).<br>MS m/z (M + H$^+$) 525/527/529 |
| 334 | 1-(1,3-Thiazol-4-ylcarbonyl)-4-(1-{[4-(trifluoromethyl)-1-benzothiophen-2-yl]carbonyl}azetidin-3-yl)piperazine<br>$^1$H NMR (400 MHz, CD$_3$OD): δ 8.80 (s, 1H), 8.05 (d, J = 8 Hz, 1H), 8.04 (s, 1H), 7.85 (s, 1H), 7.72 (d, J = 8 Hz, 1H), 7.51 (t, J = 7.6 Hz, 1H), 4.60 (m, 1H), 4.44 (m, 1H), 4.30 (m, 1H), 4.16 (m, 1H), 4.10-3.80 (m, 4H), 3.36 (m, 1H), 2.60-2.40 (m, 4H).<br>MS m/z (M + H$^+$) 481 |
| 335 | 1-(1-{[3-Chloro-6-(trifluoromethyl)-1-benzothiophen-2-yl]carbonyl}azetidin-3-yl)-4-(1,3-thiazol-4-ylcarbonyl)piperazine<br>$^1$H NMR (400 MHz, CD$_3$OD): δ 8.80 (d, J = 2 Hz, 1H), 8.13 (t, J = 0.8 Hz, 1H), 8.03 (d, J = 2 Hz, 1H), 8.01 (d, J = 8.6 Hz, 1H), 7.73 (dd, J = 1.2 Hz, 8.6 Hz, 1H), 4.31 (m, 2H), 4.21 (m, 1H), 4.15 (m, 1H), 4.01 (m, 1H), 3.93 (m, 2H), 3.81 (m, 1H), 3.33 (m, 1J), 2.55-2.40 (m, 4H).<br>MS m/z (M + H$^+$) 515 |
| 336 | 1-(1-{[3-Chloro-6-(trifluoromethyl)-1-benzothiophen-2-yl]carbonyl}azetidin-3-yl)-4-(phenylcarbonyl)piperazine<br>MS m/z (M + H$^+$) 508 |
| 337 | 1-(1,3-Thiazol-4-ylcarbonyl)-4-(1-{[6-(trifluoromethyl)-1-benzothiophen-2-yl]carbonyl}azetidin-3-yl)piperazine<br>MS m/z (M + H$^+$) 481 |
| 504 | 1-(1-{[3-Methyl-5-(trifluoromethyl)-1-benzothiophen-2-yl]carbonyl}azetidin-3-yl)-4-(phenylcarbonyl)piperazine<br>MS m/z (M + H$^+$) 488 |
| 543 | 1-{1-[(3-Chloro-6-fluoro-1-benzothiophen-2-yl)carbonyl]azetidin-3-yl}-4-(phenylcarbonyl)piperazine<br>MS m/z (M + H$^+$) 458 |
| 516 | 1-{1-[(6-Fluoro-3-methyl-1-benzothiophen-2-yl)carbonyl]azetidin-3-yl}-4-(phenylcarbonyl)piperazine<br>MS m/z (M + H$^+$) 438 |
| 908 | 1-(1,3-Thiazol-4-ylcarbonyl)-4-(1-{[5-(trifluoromethyl)-1-benzothiophen-2-yl]carbonyl}azetidin-3-yl)piperazine<br>MS m/z (M + H$^+$) 481 |
| 897 | 1-(1-{[3-Methyl-5-(trifluoromethyl)-1-benzothiophen-2-yl]carbonyl}azetidin-3-yl)-4-(1,3-thiazol-2-ylcarbonyl)piperazine<br>MS m/z (M + H$^+$) 495 |
| 898 | 1-(1-{[3-Methyl-5-(trifluoromethyl)-1-benzothiophen-2-yl]carbonyl}azetidin-3-yl)-4-(1,3-thiazol-4-ylcarbonyl)piperazine<br>MS m/z (M + H$^+$) 495 |
| 929 | 1-{1-[(3-Chloro-6-fluoro-1-benzothiophen-2-yl)carbonyl]azetidin-3-yl}-4-(1,3-thiazol-4-ylcarbonyl)piperazine<br>MS m/z (M + H$^+$) 465 |
| 930 | 1-{1-[(3-Chloro-6-fluoro-1-benzothiophen-2-yl)carbonyl]azetidin-3-yl}-4-(1,3-thiazol-2-ylcarbonyl)piperazine<br>MS m/z (M + H$^+$) 465 |
| 810 | 1-{1-[(3-Chloro-6-fluoro-1-benzothiophen-2-yl)carbonyl]azetidin-3-yl}-4-(pyridin-2-ylcarbonyl)piperazine<br>MS m/z (M + H$^+$) 459 |
| 742 | 1-{1-[(6-Fluoro-3-methyl-1-benzothiophen-2-yl)carbonyl]azetidin-3-yl}-4-(1,3-thiazol-4-ylcarbonyl)piperazine<br>MS m/z (M + H$^+$) 445 |
| 684 | 1-{1-[(6-Fluoro-3-methyl-1-benzothiophen-2-yl)carbonyl]azetidin-3-yl}-4-(1,3-thiazol-2-ylcarbonyl)piperazine<br>MS m/z (M + H$^+$) 445 |

Example 12

Cpd 313

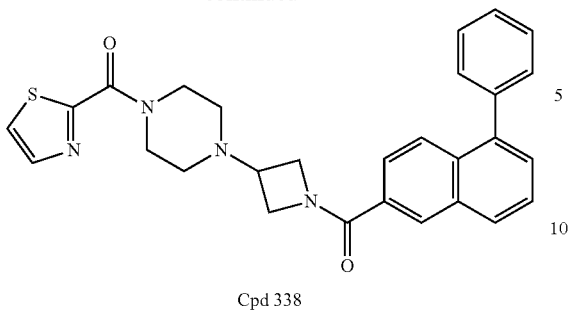

Cpd 338

1-{1-[(5-Phenylnaphthalen-2-yl)carbonyl]azetidin-3-yl}-4-(1,3-thiazol-2-ylcarbonyl)piperazine, Cpd 338. A mixture of compound 313 (48 mg, 0.1 mmol), compound 12a (24 mg, 0.2 mmol), K₂CO₃ (27 mg, 0.2 mmol) and Pd(dppf)C₂·CH₂Cl₂ (4 mg, 0.005 mmol) in EtOH (1 mL) and H₂O (0.2 mL) was heated in a microwave reactor at 130° C. for 30 min. The reaction mixture was cooled to room temperature, diluted with CH₂Cl₂, and washed with H₂O. The organic layer was dried over Na₂SO₄ and concentrated. Purification by flash column chromatography (silica gel, 3% MeOH/CH₂Cl₂) gave compound 338 (28 mg). ¹H NMR (400 MHz, CD₃OD): δ 8.20 (d, J=1.6 Hz, 1H), 7.93 (t, J=9.6 Hz, 2H), 7.88 (d, J=3 Hz, 1H), 7.66-7.43 (m, 9H), 4.52 (bs, 1H), 4.50-4.20 (m, 4H), 4.16 (m, 1H), 3.88 (bs, 1H), 3.83 (bs, 1H), 3.28 (m, 1H), 2.60-2.40 (m, 4H). MS m/z (M+H⁺) 483.

Following the procedure described above for Example 12 and substituting the appropriate reagents, starting materials and purification methods known to those skilled in the art, the following compounds of the present invention were prepared:

| Cpd | Cpd Name and Data |
|---|---|
| 339 | 1-(Phenylcarbonyl)-4-{1-[(6-phenylnaphthalen-2-yl)carbonyl]azetidin-3-yl}piperazine<br>MS m/z (M + H⁺) 476 |
| 340 | 7-Phenyl-3-({3-[4-(phenylcarbonyl)piperazin-1-yl]azetidin-1-yl}carbonyl)quinoline<br>MS m/z (M + H⁺) 477 |
| 341 | 1-(Phenylcarbonyl)-4-[1-({6-[4-(trifluoromethyl)phenyl]-1-benzothiophen-2-yl}carbonyl)azetidin-3-yl]piperazine<br>MS m/z (M + H⁺) 550 |
| 342 | 1-{1-[(6-Phenyl-1-benzothiophen-2-yl)carbonyl]azetidin-3-yl}-4-(phenylcarbonyl)piperazine<br>¹H NMR (400 MHz, CD₃OD): δ 8.05 (s, 1H), 7.88 (d, J = 8.6 Hz, 1H), 7.70 (s, 1H), 7.66-7.62 (m, 3H), 7.49-7.36 (m, 8H), 4.58 (m, 1H), 4.42 (m, 1H), 4.28 (m, 1H), 4.11 (m, 1H), 3.92 (bs, 1H), 3.76 (bs, 1H), 3.49 (bs, 2H), 3.31 (m, 1H), 2.60-2.25 (m, 4H).<br>MS m/z (M + H⁺) 482 |

Example 13

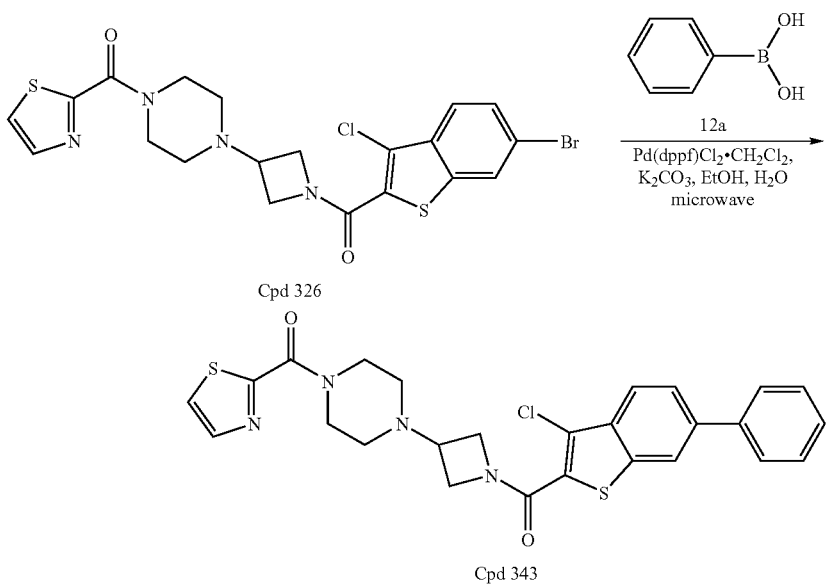

1-{1-[(3-Chloro-6-phenyl-1-benzothiophen-2-yl)carbonyl]azetidin-3-yl}-4-(1,3-thiazol-2-ylcarbonyl)piperazine, Cpd 343. The title compound was prepared in an analogous manner to that of compound 338 of Example 12, using 1 equivalent of compound 12a, and substituting compound 326 for compound 313. The reaction was heated in a microwave reactor at 120° C. for 20 min. ¹H NMR (400 MHz, CD₃OD): δ 8.01 (d, J=1.2 Hz, 1H), 7.95 (d, J=8.6 Hz, 1H), 7.88 (d, J=3 Hz, 1H), 7.74 (d, J=8.6 Hz, 1H), 7.66 (d, J=8.2 Hz, 2H), 7.55 (d, J=3 Hz, 1H), 7.49 (m, 2H), 7.41 (m, 1H), 4.54 (bs, 1H), 4.46 (bs, 1H), 4.33 (m, 2H), 4.25 (m, 1H), 4.14 (m, 1H), 3.89 (bs, 1H), 3.84 (bs, 1H), 3.32 (m, 1H), 2.50 (m, 4H). MS m/z (M+H⁺) 523.

Following the procedure described above for Example 13 and substituting the appropriate reagents, starting materials and purification methods known to those skilled in the art, the following compounds of the present invention were prepared:

| Cpd | Cpd Name and Data |
|---|---|
| 344 | 1-{1-[(3-Chloro-6-phenyl-1-benzothiophen-2-yl)carbonyl]azetidin-3-yl}-4-(phenylcarbonyl)piperazine<br>MS m/z (M + H⁺) 516 (M + H⁺). |

-continued

| Cpd | Cpd Name and Data |
|---|---|
| 345 | 1-{1-[(3-Chloro-6-phenyl-1-benzothiophen-2-yl)carbonyl]azetidin-3-yl}-4-(1,3-thiazol-4-ylcarbonyl)piperazine<br>MS m/z (M + H$^+$) 523 |
| 591 | 1-(Phenylcarbonyl)-4-(1-{[3-phenyl-6-(trifluoromethyl)-1-benzothiophen-2-yl]carbonyl}azetidin-3-yl)piperazine<br>MS m/z (M + H$^+$) 550 |
| 515 | 1-(1-{[3-Cyclopropyl-6-(trifluoromethyl)-1-benzothiophen-2-yl]carbonyl}azetidin-3-yl)-4-(phenylcarbonyl)piperazine<br>MS m/z (M + H$^+$) 514 |
| 511 | 1-(1-{[3-(2-Methylprop-1-en-1-yl)-6-(trifluoromethyl)-1-benzothiophen-2-yl]carbonyl}azetidin-3-yl)-4-(phenylcarbonyl)piperazine<br>MS m/z (M + H$^+$) 528 |

Example 14

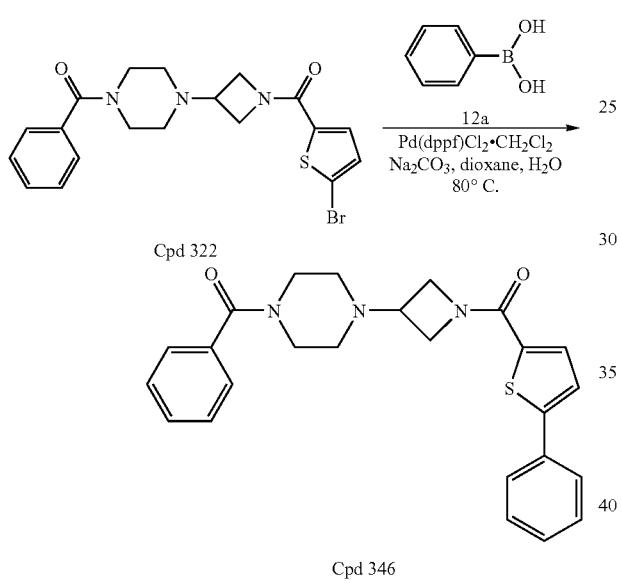

Cpd 346

1-(Phenylcarbonyl)-4-{1-[(5-phenylthiophen-2-yl)carbonyl]azetidin-3-yl}piperazine, Cpd 346. A mixture of compound 322 (40 mg), compound 12a (16 mg), Pd(dppf)Cl$_2$·CH$_2$Cl$_2$ (8 mg), and Na$_2$CO$_3$ (19 mg), in a dioxane (0.8 mL)/water (0.2 mL) mixture, was placed in a capped vial and heated at 80° C. for 4 h. The reaction mixture was then diluted with EtOAc and water. The organic layer was concentrated under reduced pressure and purified by flash column chromatography (silica gel, 5% MeOH/EtOAc) to give compound 346 (17 mg). MS m/z (M+H$^+$) 432.6.

Following the procedure described above for Example 14 and substituting the appropriate reagents, starting materials and purification methods known to those skilled in the art, the following compounds of the present invention were prepared:

| Cpd | Cpd Name and Data |
|---|---|
| 347 | 1-(Phenylcarbonyl)-4-[1-({5-[4-(trifluoromethyl)phenyl]thiophen-2-yl}carbonyl)azetidin-3-yl]piperazine<br>MS m/z (M + H$^+$) 500.0 |
| 924 | 1-Acetyl-6-phenyl-2-({3-[4-(1,3-thiazol-2-ylcarbonyl)piperazin-1-yl]azetidin-1-yl}carbonyl)-1,2,3,4-tetrahydroquinoline<br>MS m/z (M + H$^+$) 530.0 |
| 917 | 1-Acetyl-2-({3-[4-(1,3-thiazol-2-ylcarbonyl)piperazin-1-yl]azetidin-1-yl}carbonyl)-6-[3-(trifluoromethyl)phenyl]-1,2,3,4-tetrahydroquinoline<br>MS m/z (M + H$^+$) 598.0 |
| 919 | 1-Acetyl-2-({3-[4-(1,3-thiazol-2-ylcarbonyl)piperazin-1-yl]azetidin-1-yl}carbonyl)-6-[4-(trifluoromethyl)phenyl]-1,2,3,4-tetrahydroquinoline<br>MS m/z (M + H$^+$) 598.0 |
| 920 | 1-Acetyl-6-(5-chlorothiophen-2-yl)-2-({3-[4-(1,3-thiazol-2-ylcarbonyl)piperazin-1-yl]azetidin-1-yl}carbonyl)-1,2,3,4-tetrahydroquinoline<br>MS m/z (M + H$^+$) 570.1 |
| 1157 | 1-(1-{[4-(4-Fluorophenyl)thiophen-2-yl]carbonyl}azetidin-3-yl)-4-(1,3-thiazol-2-ylcarbonyl)piperazine<br>MS m/z (M + H$^+$) 457.0 |
| 1160 | 1-(1-{[4-(3-Fluorophenyl)thiophen-2-yl]carbonyl}azetidin-3-yl)-4-(1,3-thiazol-2-ylcarbonyl)piperazine<br>MS m/z (M + H$^+$) 457.0 |
| 1321 | 1-(1,3-Thiazol-2-ylcarbonyl)-4-[1-({4-[3-(trifluoromethyl)phenyl]thiophen-2-yl}carbonyl)azetidin-3-yl]piperazine<br>MS m/z (M + H$^+$) 507.0 |
| 605 | 1-{1-[(5-Phenyl-1-benzofuran-2-yl)carbonyl]azetidin-3-yl}-4-(phenylcarbonyl)piperazine<br>MS m/z (M + H$^+$) 466 |
| 600 | 7-(3-Fluorophenyl)-5-({3-[4-(phenylcarbonyl)piperazin-1-yl]azetidin-1-yl}carbonyl)-1H-indole<br>MS m/z (M + H$^+$) 483 |
| 1342 | 1-{1-[(5-Phenyl-1-benzofuran-2-yl)carbonyl]azetidin-3-yl}-4-(1,3-thiazol-2-ylcarbonyl)piperazine<br>MS m/z (M + H$^+$) 473 |
| 1343 | 1-(1,3-Thiazol-2-ylcarbonyl)-4-[1-({5-[3-(trifluoromethyl)phenyl]-1-benzofuran-2-yl}carbonyl)azetidin-3-yl]piperazine<br>MS m/z (M + H$^+$) 541 |
| 1059 | 1-(1-{[4-(3-Fluorophenyl)-5-methylthiophen-2-yl]carbonyl}azetidin-3-yl)-4-(1,3-thiazol-2-ylcarbonyl)piperazine<br>MS m/z (M + H$^+$) 471 |
| 1351 | 1-[1-({5-Methyl-4-[3-(trifluoromethyl)phenyl]thiophen-2-yl}carbonyl)azetidin-3-yl]-4-(1,3-thiazol-2-ylcarbonyl)piperazine<br>MS m/z (M + H$^+$) 521 |
| 1066 | 7-(3-Fluorophenyl)-1-methyl-5-({3-[4-(1,3-thiazol-2-ylcarbonyl)piperazin-1-yl]azetidin-1-yl}carbonyl)-1H-indole<br>MS m/z (M + H$^+$) 504 |
| 1101 | 7-(4-Fluorophenyl)-1-methyl-5-({3-[4-(1,3-thiazol-2-ylcarbonyl)piperazin-1-yl]azetidin-1-yl}carbonyl)-1H-indole<br>MS m/z (M + H$^+$) 504 |
| 1060 | 1-Methyl-5-({3-[4-(1,3-thiazol-2-ylcarbonyl)piperazin-1-yl]azetidin-1-yl}carbonyl)-7-[3-(trifluoromethyl)phenyl]-1H-indole<br>MS m/z (M + H$^+$) 554 |
| 1352 | 1-[1-({4-Methyl-5-[4-(trifluoromethyl)phenyl]thiophen-2-yl}carbonyl)azetidin-3-yl]-4-(1,3-thiazol-2-ylcarbonyl)piperazine<br>MS m/z (M + H$^+$) 521 |
| 1353 | 1-(1-{[5-(4-Fluorophenyl)-4-methylthiophen-2-yl]carbonyl}azetidin-3-yl)-4-(1,3-thiazol-2-ylcarbonyl)piperazine |
| 1065 | 1-(1-{[5-(3-Fluorophenyl)-4-methylthiophen-2-yl]carbonyl}azetidin-3-yl)-4-(1,3-thiazol-2-ylcarbonyl)piperazine<br>MS m/z (M + H$^+$) 471 |
| 1354 | 1-[1-({4-Methyl-5-[3-(trifluoromethyl)phenyl]thiophen-2-yl}carbonyl)azetidin-3-yl]-4-(1,3-thiazol-2-ylcarbonyl)piperazine<br>MS m/z (M + H$^+$) 521 |
| 1183 | 7-(3-Fluorophenyl)-5-({3-[4-(1,3-thiazol-2-ylcarbonyl)piperazin-1-yl]azetidin-1-yl}carbonyl)-1H-indole<br>MS m/z (M + H$^+$) 490 |

| Cpd | Cpd Name and Data |
|---|---|
| 1096 | 1-(1-{[4-(4-Fluorophenyl)-5-methylthiophen-2-yl]carbonyl}azetidin-3-yl)-4-(1,3-thiazol-2-ylcarbonyl)piperazine<br>MS m/z (M + H$^+$) 471 |

Example 14a

Following the procedure described above for Example 14, substituting Cpd 682 of Example 5 for Cpd 322 and substituting the appropriate reagents, starting materials, and purification methods known to those skilled in the art, the following compounds of the present invention were prepared:

| Cpd | Cpd Name and Data |
|---|---|
| 1075 | 5-(4-Fluorophenyl)-3-methyl-2-({3-[4-(1,3-thiazol-2-ylcarbonyl)piperazin-1-yl]azetidin-1-yl}carbonyl)-1H-indole<br>$^1$H NMR (400 MHz, CDCl$_3$): δ 7.93 (ar, 1H); 7.82 (ar, 1H); 7.76 (ar, 1H); 7.64 (m, 2H); 7.46 (m, 2H); 7.15 (m, 2H); 4.47-4.0 (bm, 6H); 3.82 (b, 2H); 2.5 (s, 3H)<br>MS m/z (M + H$^+$) 504.1 |
| 1149 | 5-(2-Fluoropyridin-3-yl)-3-methyl-2-({3-[4-(1,3-thiazol-2-ylcarbonyl)piperazin-1-yl]azetidin-1-yl}carbonyl)-1H-indole<br>$^1$H NMR (400 MHz, CDCl$_3$): δ 8.09-7.97 9m, 2H); 7.88 (ar, 1H); 7.82-7.72 (m, 2H); 7.42 (ar, 2H); 7.31 (m, 1H); 7.62 (bm, 1H); 4.48 (bm, 1H); 4.35 (bm, 2H); 3.96 (bm, 2H); 3.14 (m, 4H); 2.44 (s, 3H)<br>MS m/z (M + H$^+$) 505.2 |
| 1175 | 5-(5-Methoxypyridin-3-yl)-3-methyl-2-({3-[4-(1,3-thiazol-2-ylcarbonyl)piperazin-1-yl]azetidin-1-yl}carbonyl)-1H-indole<br>MS m/z (M + H$^+$) 517.2 |
| 1205 | 3-Methyl-5-(1-methyl-1H-pyrazol-5-yl)-2-({3-[4-(1,3-thiazol-2-ylcarbonyl)piperazin-1-yl]azetidin-1-yl}carbonyl)-1H-indole<br>MS m/z (M + H$^+$) 490.2 |

Example 14b

Following the procedure described above for Example 14, substituting Cpd 792 of Example 5 for Cpd 322 and substituting the appropriate reagents, starting materials, and purification methods known to those skilled in the art, the following compounds of the present invention were prepared:

| Cpd | Cpd Name and Data |
|---|---|
| 1204 | 6-(4-Fluorophenyl)-2-({3-[4-(1,3-thiazol-2-ylcarbonyl)piperazin-1-yl]azetidin-1-yl}carbonyl)-1H-indole<br>MS m/z (M + H$^+$) 491.1 |
| 1241 | 6-(1-Methyl-1H-pyrazol-5-yl)-2-({3-[4-(1,3-thiazol-2-ylcarbonyl)piperazin-1-yl]azetidin-1-yl}carbonyl)-1H-indole<br>MS m/z (M + H$^+$) 477.3 |
| 1244 | 6-(2-Fluoropyridin-3-yl)-2-({3-[4-(1,3-thiazol-2-ylcarbonyl)piperazin-1-yl]azetidin-1-yl}carbonyl)-1H-indole<br>MS m/z (M + H$^+$) 491.2 |
| 1211 | 6-(3,5-Dimethylisoxazol-4-yl)-2-({3-[4-(1,3-thiazol-2-ylcarbonyl)piperazin-1-yl]azetidin-1-yl}carbonyl)-1H-indole<br>MS m/z (M + H$^+$) 491.1 |
| 1196 | 6-(5-Methoxypyridin-3-yl)-2-({3-[4-(1,3-thiazol-2-ylcarbonyl)piperazin-1-yl]azetidin-1-yl}carbonyl)-1H-indole<br>MS m/z (M + H$^+$) 503.1 |

Example 14c

Following the procedure described above for Example 14, substituting Cpd 864 of Example 5 for Cpd 322 and substituting the appropriate reagents, starting materials, and purification methods known to those skilled in the art, the following compounds of the present invention were prepared:

| Cpd | Cpd Name and Data |
|---|---|
| 1213 | 5-(4-Fluorophenyl)-2-({3-[4-(1,3-thiazol-2-ylcarbonyl)piperazin-1-yl]azetidin-1-yl}carbonyl)furo[2,3-b]pyridine<br>MS m/z (M + H$^+$) 492.1 |
| 1209 | 5-Phenyl-2-({3-[4-(1,3-thiazol-2-ylcarbonyl)piperazin-1-yl]azetidin-1-yl}carbonyl)furo[2,3-b]pyridine<br>MS m/z (M + H$^+$) 474.1 |

Example 14d

Following the procedure described above for Example 14, substituting Cpd 315 of Example 5 for Cpd 322 and substituting the appropriate reagents, starting materials, and purification methods known to those skilled in the art, the following compounds of the present invention were prepared:

| Cpd | Cpd Name and Data |
|---|---|
| 1443 | 5-Fluoro-2-({3-[4-(1,3-thiazol-2-ylcarbonyl)piperazin-1-yl]azetidin-1-yl}carbonyl)-1H-benzimidazole<br>MS m/z (M + H$^+$) 415.2 |
| 1476 | 5-(2-Fluoropyridin-3-yl)-2-({3-[4-(1,3-thiazol-2-ylcarbonyl)piperazin-1-yl]azetidin-1-yl}carbonyl)-1H-benzimidazole<br>MS m/z (M + H$^+$) 492.1 |
| 1303 | 2-({3-[4-(1,3-Thiazol-2-ylcarbonyl)piperazin-1-yl]azetidin-1-yl}carbonyl)-5-[4-(trifluoromethoxy)phenyl]-1H-benzimidazole<br>MS m/z (M + H$^+$) 494.97 |
| 1294 | 5-(4-Fluorophenyl)-2-({3-[4-(1,3-thiazol-2-ylcarbonyl)piperazin-1-yl]azetidin-1-yl}carbonyl)-1H-benzimidazole;<br>MS m/z (M + H$^+$) 491.1 |

Example 15

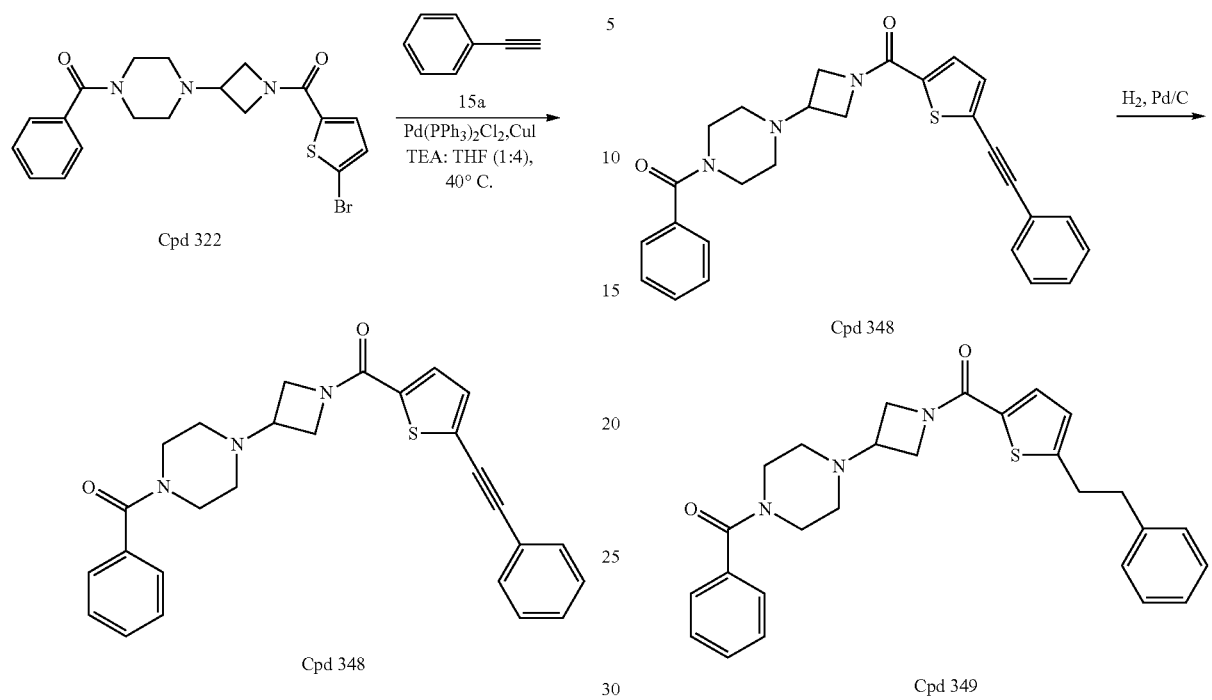

1-(Phenylcarbonyl)-4-(1-{[5-(phenylethynyl)thiophen-2-yl]carbonyl}azetidin-3-yl)piperazine, Cpd 348. To a solution of compound 322 (100 mg), compound 15a (0.46 mmol, 0.05 mL), CuI (4.4 mg), and Pd(PPh$_3$)$_2$Cl$_2$ (16 mg) in THF (1 mL) was added TEA (0.25 mL) and the mixture was heated at 40° C. for 1 h. The reaction was diluted with EtOAc and water. The organics were concentrated and purified by flash column chromatography (silica gel, 5% MeOH/EtOAc) to yield compound 348 (75 mg). MS m/z (M+H$^+$) 456.6.

Example 16

1-(Phenylcarbonyl)-4-(1-{[5-(2-phenylethyl)thiophen-2-yl]carbonyl}azetidin-3-yl)piperazine, Cpd 349. To a solution of compound 348 (30 mg) in EtOH (20 mL) was added 10% Pd/C (10 mg) and the mixture was subjected to hydrogenation (45 psi H$_2$) for 1.5 h. The reaction mixture was filtered and the filtrate was concentrated under reduced pressure to give compound 349 (30 mg). MS m/z (M+H$^+$) 460.6.

Example 17

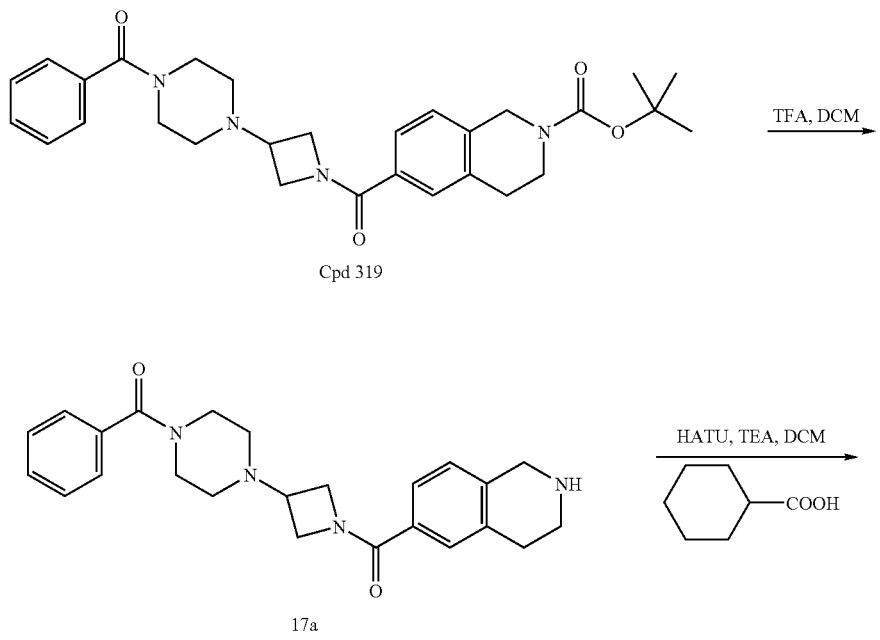

-continued

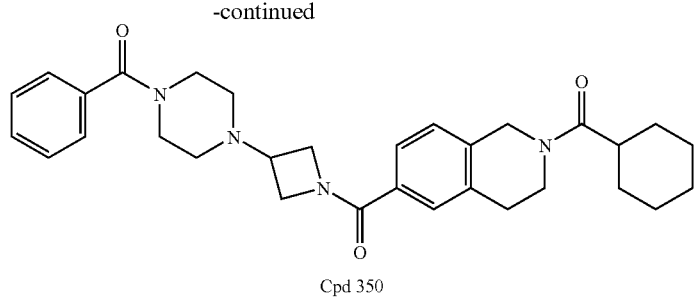

Cpd 350

A. 6-({3-[4-(Phenylcarbonyl)piperazin-1-yl]azetidin-1-yl}carbonyl)-1,2,3,4-tetrahydroisoquinoline, 17a. To a solution of compound 319 (500 mg) in $CH_2Cl_2$ (6 mL) was added TFA (4 mL) at room temperature. The mixture was stirred for 1.5 h and was then concentrated under reduced pressure. The residue was diluted with $CH_2Cl_2$ and made basic with aqueous 2N NaOH solution. The organic layer was washed with water and brine, dried over anhydrous $K_2CO_3$, filtered, and concentrated to give compound 17a, which was used without further purification.

B. 2-(Cyclohexylcarbonyl)-6-({3-[4-(phenylcarbonyl)piperazin-1-yl]azetidin-1-yl}carbonyl)-1,2,3,4-tetrahydroisoquinoline, Cpd 350. A mixture of compound 17a (31 mg, 0.03 mL), HATU (100 mg), and TEA (0.11 mL) in DCM (1 mL) was stirred at room temperature for 5 h. The reaction was diluted with DCM and water. The organics were concentrated and purified by flash column chromatography (silica gel, 8% MeOH/EtOAc) to give compound 350 (65 mg). $^1$H NMR (CDCl$_3$): δ 7.47-7.39 (m, 7H), 7.17 (d, J=0.02, 1H), 4.74 (s, 1.2H), 4.48 (s, 0.8H), 4.25 (m, 2H), 4.10 (m, 2H), 3.92-3.71 (m, 4H), 3.43 (m, 2H), 3.19 (m, 1H), 2.93 (m, 1.2H), 2.86 (m, 0.8H), 2.55 (m, 1H), 2.42-2.24 (m, 4H), 1.83-1.57 (m, 8H), 1.26 (m, 2H). MS m/z (M+H$^+$) 515.7.

Following the procedure described above for Example 17 and substituting the appropriate reagents, starting materials and purification methods known to those skilled in the art, the following compounds of the present invention were prepared:

| Cpd | Cpd Name and Data |
|---|---|
| 351 | 2-(3,3-Dimethylbutanoyl)-6-({3-[4-(phenylcarbonyl)piperazin-1-yl]azetidin-1-yl}carbonyl)-1,2,3,4-tetrahydroisoquinoline<br>MS m/z (M + H$^+$) 503.7 |
| 352 | 2-(3,3-Dimethylbutanoyl)-6-({3-[4-(phenylcarbonyl)piperazin-1-yl]azetidin-1-yl}carbonyl)-1,2,3,4-tetrahydroisoquinoline<br>MS m/z (M + H$^+$) 509.6 |
| 353 | 2-[(4,4-Difluorocyclohexyl)carbonyl]-6-({3-[4-(phenylcarbonyl)piperazin-1-yl]azetidin-1-yl}carbonyl)-1,2,3,4-tetrahydroisoquinoline<br>MS m/z (M + H$^+$) 463.6 |
| 354 | 6-({3-[4-(Phenylcarbonyl)piperazin-1-yl]azetidin-1-yl}carbonyl)-2-{[4-(trifluoromethyl)cyclohexyl]carbonyl}-1,2,3,4-tetrahydroisoquinoline<br>MS m/z (M + H$^+$) 583.7 |
| 546 | 1-(1-{[4-(1-Acetylpiperidin-4-yl)phenyl]carbonyl}azetidin-3-yl)-4-(phenylcarbonyl)piperazine<br>MS m/z (M + H$^+$) 475.2 |
| 1486 | 1-[1-({2-[(3S)-1-Acetylpyrrolidin-3-yl]phenyl}carbonyl)azetidin-3-yl]-4-(phenylcarbonyl)piperazine<br>MS m/z (M + H$^+$) 461.2 |
| 1437 | 2-(Phenylcarbonyl)-8-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 516.2 |

Example 17a

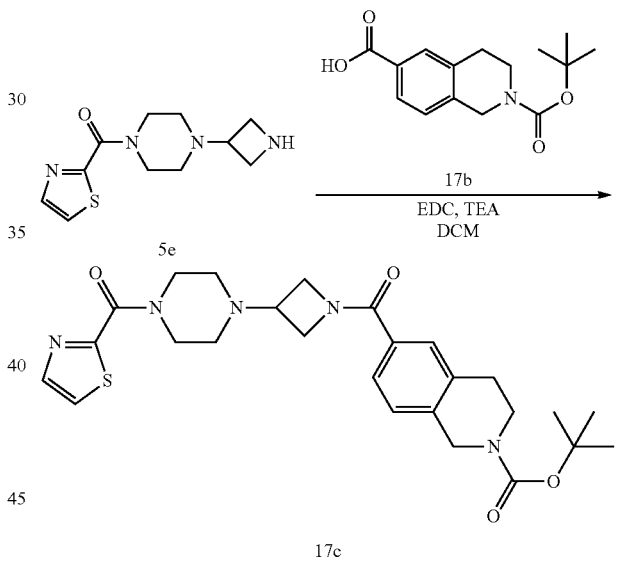

D. 6-{3-[4-(Thiazole-2-carbonyl)-piperazin-1-yl]-azetidine-1-carbonyl}-3,4-dihydro-1H-isoquinoline-2-carboxylic acid tert-butyl ester, 17c. To a solution of compound 5e (651 mg, 2 mmol), 3,4-dihydro-1H-isoquinoline-2,6-dicarboxylic acid 2-tert-butyl ester 17b (555 mg, 2 mmol), and EDC (466 mg, 3 mmol) in $CH_2Cl_2$ (20 mL) was added Et$_3$N (0.84 mL, 6 mmol). The reaction mixture was stirred at room temperature overnight. The mixture was extracted with $CH_2Cl_2$, and $H_2O$ after acidifying the water layer to pH~6 with 1N aqueous HCl. The organic solution was dried over $Na_2SO_4$ and concentrated. Purification of the residue by flash column chromatography (silica gel, 2% MeOH/EtOAc) gave 17c (826 mg). MS m/z (M+H$^+$) 512.1.

Following the procedure described above for Example 17a, and substituting the appropriate reagents, starting materials, and purification methods known to those skilled in the art, the following intermediate compounds were prepared:

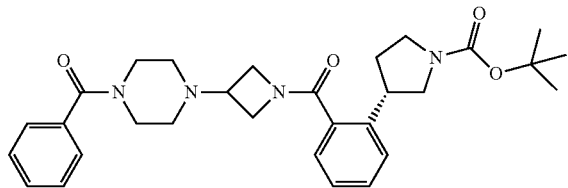 [SMILES: CC(C)(C)OC(=O)N1CC[C@@H](c2ccccc2C(=O)N2CC(N3CCN(C(=O)c4ccccc4)CC3)C2)C1]

Following the procedure described above for Example 17a, and substituting the appropriate reagents, starting materials, and purification methods known to those skilled in the art, the following compounds of the present invention were prepared:

| Cpd | Cpd Name and Data |
|-----|-------------------|
| 538 | tert-Butyl 4-[3-({3-[4-(phenylcarbonyl)piperazin-1-yl]azetidin-1-yl}carbonyl)phenyl]piperidine-1-carboxylate MS m/z (M + H$^+$) 533.4 |
| 903 | tert-Butyl 4-[4-({3-[4-(1,3-thiazol-4-ylcarbonyl)piperazin-1-yl]azetidin-1-yl}carbonyl)phenyl]piperidine-1-carboxylate MS m/z (M + H$^+$) 540.1 |
| 861 | tert-Butyl 8-({3-[4-(1,3-thiazol-4-ylcarbonyl)piperazin-1-yl]azetidin-1-yl}carbonyl)-3,4-dihydroisoquinoline-2(1H)-carboxylate MS m/z (M + H$^+$) 512.2 |

Example 17b

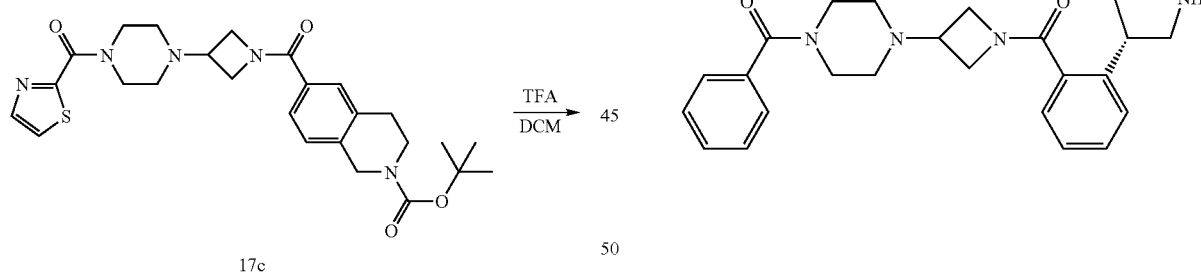

17c

Cpd 916

E. 6-({3-[4-(1,3-Thiazol-2-ylcarbonyl)piperazin-1-yl]azetidin-1-yl}carbonyl)-1,2,3,4-tetrahydroisoquinoline, Cpd 916. To a solution of compound 17c (826 mg, 1.61 mmol) in CH$_2$Cl$_2$ (5 mL) was added trifluoroacetic acid (1 mL) at room temperature. The mixture was stirred at room temperature for 18 h. The mixture was extracted with CH$_2$Cl$_2$, and H$_2$O after basifying the water layer to pH~8 with 1N aqueous NaOH. The organic solution was dried over Na$_2$SO$_4$ and concentrated. Purification of the residue by flash column chromatography (silica gel, 2% MeOH/EtOAc) gave Cpd 916 (675 mg). $^1$H NMR (400 MHz, CDCl$_3$): δ 7.88 (d, J=3.3 Hz, 1H), 7.55 (d, J=3.3 Hz, 1H), 7.41 (s, 1H), 7.37 (d, J=8.03 Hz, 1H), 7.05 (d, J=8.3 Hz, 1H), 4.54 (br. s, 1H), 4.44 (br. s, 1H), 4.01-4.35 (m, 6H), 3.75-3.95 (m, 2H), 3.12-3.31 (m, 2H), 2.85 (t, J=5.8 Hz, 1H), 2.49 (br. s, 4H). MS m/z (M+H$^+$) 412.0.

Following the procedure described above for Example 17b, and substituting the appropriate reagents, starting materials, and purification methods known to those skilled in the art, the following intermediate compounds were prepared:

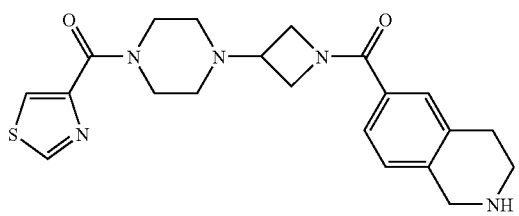

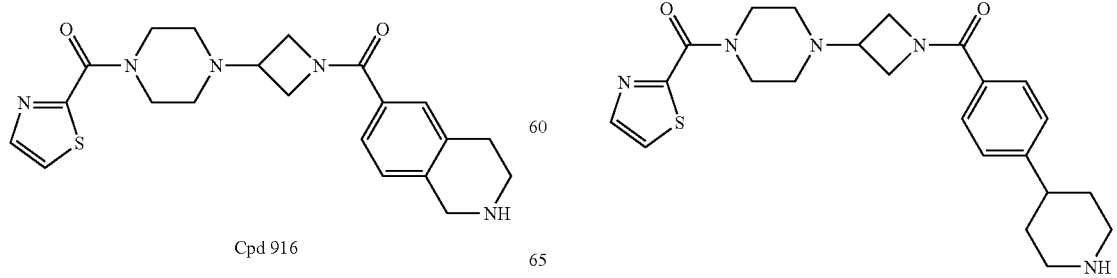

-continued

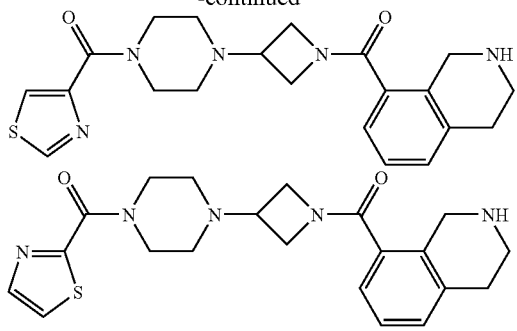

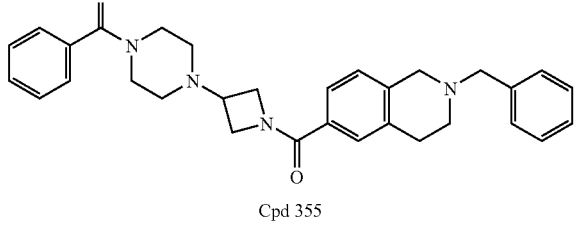

Cpd 355

Example 18

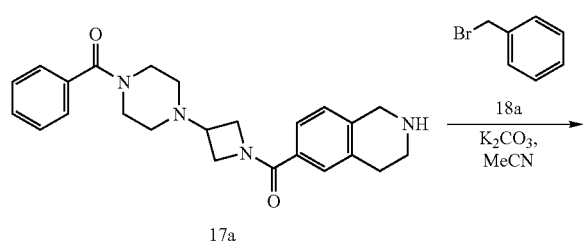

2-Benzyl-6-({3-[4-(phenylcarbonyl)piperazin-1-yl]azetidin-1-yl}carbonyl)-1,2,3,4-tetrahydroisoquinoline, Cpd 355. To a suspension of compound 17a (100 mg) and $K_2CO_3$ (69 mg) in MeCN was added compound 18a (0.0353 mL) and the mixture was stirred at room temperature for 30 min. The reaction was concentrated and the residue was diluted with EtOAc and water. The organics were concentrated and purified by flash column chromatography (silica gel, 8% MeOH/EtOAc) to afford compound 355 (85 mg). MS m/z (M+H$^+$) 495.6.

Example 19

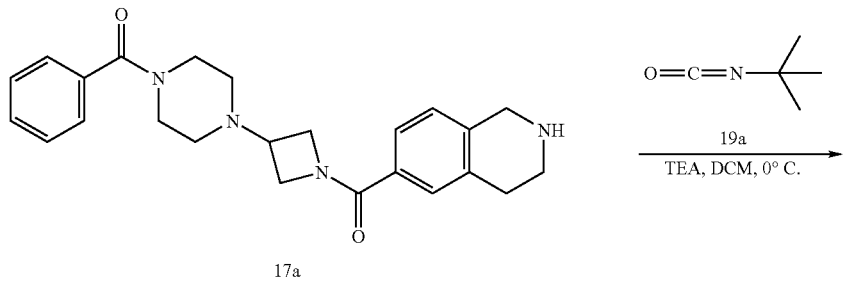

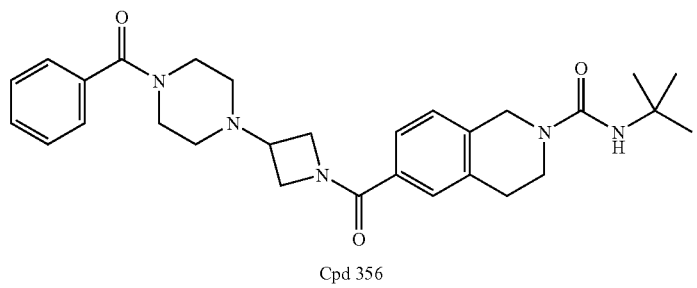

Cpd 356

N-tert-Butyl-6-({3-[4-(phenylcarbonyl)piperazin-1-yl]azetidin-1-yl}carbonyl)-3,4-dihydroisoquinoline-2(1H)-carboxamide, Cpd 356. To a solution of compound 17a (75 mg) in DCM (1 mL) was dropwise added compound 19a (0.026 mL) at 0° C. After 30 min, the reaction mixture was quenched with DCM and water at 0° C. The organics were concentrated and purified by flash column chromatography (silica gel, 5% MeOH/EtOAc) to give compound 356 (60 mg). MS m/z (M+H⁺) 504.7.

Example 20

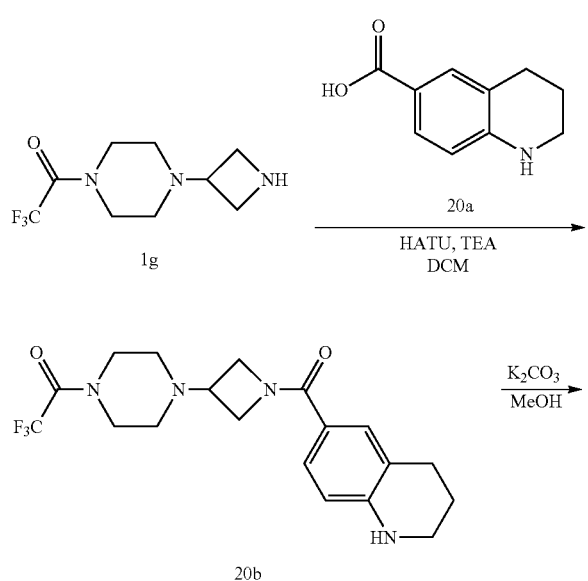

was diluted with CH₂Cl₂ and washed with aq. NaHCO₃. The organic phase was dried over Na₂SO₄, filtered, and concentrated under reduced pressure. Purification by flash column chromatography (silica gel, 2% MeOH/EtOAc+0.5% Et₃N) gave compound 20b (279 mg). LC/MS m/z (M+H⁺) 397.0.

B. 6-([3-piperazin-1-yl]-azetidin-1-yl)carbonyl-1,2,3,4-tetrahydroquinoline, 20c. To a solution of compound 20b (529 mg, 1.33 mmol) in MeOH (10 mL) was added K₂CO₃ (368 mg, 2.66 mmol). The reaction mixture was stirred at room temperature for 30 min. The resultant mixture was filtered, concentrated under reduced pressure, and the resultant residue was partitioned between CH₂Cl₂ and H₂O. The organic phase was dried over Na₂SO₄, filtered, and concentrated under reduced pressure to give compound 20c (370 mg). LC/MS m/z (M+H⁺) 301.0.

C. 6-(3-[4-(1,3-Thiazol-2-ylcarbonyl)piperazin-1-yl]-azetidin-1-yl)carbonyl-1,2,3,4-tetrahydroquinoline, Cpd 357. To a solution of compound 20c (370 mg, 1.23 mmol), compound 5c (160 mg, 1.24 mmol), and Et₃N (0.51 mL, 3.69 mmol) in CH₂Cl₂ (10 mL) was added HATU (703 mg, 1.85 mmol). The reaction mixture was stirred at room temperature for 18 h. The resultant mixture was diluted with CH₂Cl₂ and washed with aq. NaHCO₃. The organic phase was dried over Na₂SO₄, filtered, and concentrated under reduced pressure. Purification of the residue by flash column chromatography (silica gel, 2% MeOH/EtOAc+0.5% Et₃N) gave compound 357 (483 mg). ¹H NMR (400 MHz, CDCl₃): δ 7.88 (d, J=3.0 Hz, 1H), 7.53-7.58 (m, 1H), 7.33 (s, 1H), 7.24-7.30 (m, 1H), 6.39 (d, J=8.1 Hz, 1H), 3.97-4.66 (m, 6H), 3.86 (d, J=18.4 Hz, 2H), 3.35 (t, J=5.4 Hz, 2H), 3.16-3.26 (m, 1H), 2.77 (t, J=6.2 Hz, 2H), 2.39-2.59 (m, 4H), 1.94 (dt, J=11.8, 6.1 Hz, 2H); LC/MS m/z (M+H⁺) 412.0.

Example 21

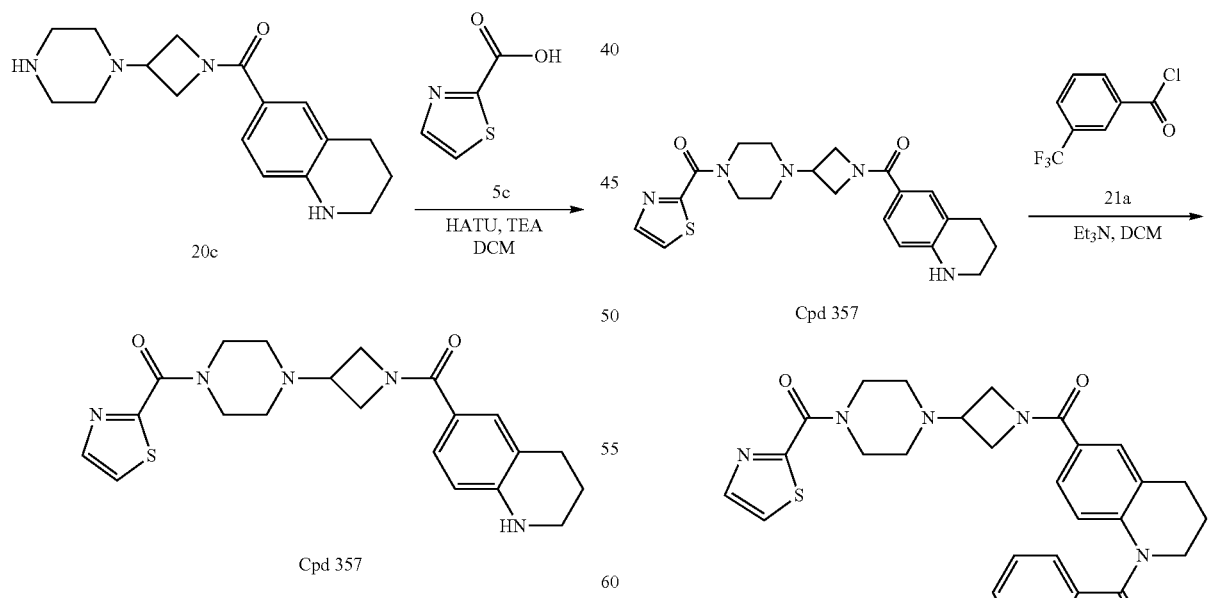

A. 6-({3-[4-(Trifluoroacetyl)piperazin-1-yl]azetidin-1-yl}carbonyl)-1,2,3,4-tetrahydroquinoline, 20b. To a solution of compound 1g (308 mg, 1 mmol), compound 20a (177 mg, 1 mmol), and Et₃N (0.42 mL, 3 mmol) in CH₂Cl₂ (10 mL) was added HATU (570 mg, 1.5 mmol). The reaction mixture was stirred at room temperature for 18 h. The resultant mixture 6-(3-[4-(1,3-Thiazol-2-ylcarbonyl)piperazin-1-yl]-azetidin-1-yl)-carbonyl 1-[3-(trifluoromethyl)phenyl]carbonyl-1,2,3,4-tetrahydroquinoline, Cpd 358. To a solution of compound 357 (30 mg, 0.073 mmol) in $CH_2Cl_2$ (1 mL), at 0° C., was added compound 1f (0.013 mL, 0.088 mmol), then $Et_3N$ (0.03 mL, 0.22 mmol). The reaction mixture was stirred at 0° C. for 2 h. The resultant mixture was partitioned between $CH_2Cl_2$ and $H_2O$. The organic phase was dried over $Na_2SO_4$, filtered, and concentrated under reduced pressure. Purification of the residue by flash column chromatography (silica gel, 2% MeOH/EtOAc+0.5% $Et_3N$) gave compound 358 (42 mg). $^1$H NMR (400 MHz, CDCl$_3$): δ 7.88 (d, J=3.3 Hz, 1H), 7.65 (d, J=7.8 Hz, 1H), 7.61 (s, 1H), 7.52-7.59 (m, 3H), 7.41-7.49 (m, 1H), 7.12 (dd, J=8.3, 1.8 Hz, 1H), 6.73 (d, J=7.8 Hz, 1H), 4.35-4.59 (m, 2H), 4.18-4.26 (m, 2H), 4.01-4.16 (m, 2H), 3.75-3.95 (m, 4H), 3.17-3.26 (m, 1H), 2.90 (t, J=6.6 Hz, 2H), 2.37-2.57 (m, 4H), 2.02-2.12 (m, 2H); LC/MS m/z (M+H$^+$) 584.0.

Following the procedure described above for Example 21 and substituting the appropriate reagents, starting materials and purification methods known to those skilled in the art, the following compounds of the present invention were prepared:

| Cpd | Cpd Name and Data |
|---|---|
| 359 | 1-(Cyclopropylcarbonyl)-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 7.88 (d, J = 3.3 Hz, 1H), 7.55 (d, J = 3.3 Hz, 1H), 7.50 (s, 1H), 7.43-7.47 (m, 2H), 4.05-4.62 (m, 6H), 3.75-3.97 (m, 4H), 3.21-3.31 (m, 1H), 2.78 (t, J = 6.6 Hz, 2H), 2.38-2.59 (m, 4H), 1.90-2.03 (m, 3H), 1.13-1.21 (m, 2H), 0.80-0.86 (m, 2H); LC/MS m/z (M + H$^+$) 480.0. |
| 360 | 1-(Cyclohexylcarbonyl)-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 7.89 (d, J = 3.0 Hz, 1H), 7.55 (d, J = 3.3 Hz, 1H), 7.50 (s, 1H), 7.44 (dd, J = 8.2, 1.6 Hz, 1H), 7.28-7.33 (m, 1H), 4.04-4.62 (m, 6H), 3.73-3.96 (m, 4H), 3.21-3.30 (m, 1H), 2.72-2.82 (m, 3H), 2.40-2.59 (m, 4H), 1.98 (quin, J = 6.6 Hz, 2H), 1.71-1.83 (m, 4H), 1.49-1.70 (m, 2H), 1.10-1.36 (m, 4H); LC/MS m/z (M + H$^+$) 522.2. |
| 361 | 1-(Methylsulfonyl)-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 7.89 (d, J = 3.0 Hz, 1H), 7.74 (d, J = 8.6 Hz, 1H), 7.55 (d, J = 3.3 Hz, 1H), 7.51 (d, J = 1.8 Hz, 1H), 7.40 (dd, J = 8.6, 2.3 Hz, 1H), 4.03-4.61 (m, 6H), 3.78-3.96 (m, 4H), 3.21-3.29 (m, 1H), 2.95 (s, 3H), 2.89 (t, J = 6.6 Hz, 2H), 2.40-2.59 (m, 4H), 1.97-2.08 (m, 2H); LC/MS m/z (M + H$^+$) 490.0. |
| 362 | 1-(Methylsulfonyl)-6-({3-[4-(1,3-thiazol-4-ylcarbonyl)piperazin-1-yl]azetidin-1-yl}carbonyl)-1,2,3,4-tetrahydroquinoline<br>$^1$H NMR (400 MHz, CDCl$_3$): δ 8.79 (d, J = 2.0 Hz, 1H), 8.02 (d, J = 2.3 Hz, 1H), 7.73 (d, J = 8.6 Hz, 1H), 7.49 (s, 1H), 7.39 (dd, J = 8.7, 2.1 Hz, 1H), 3.72-4.37 (m, 10H), 3.19-3.30 (m, 1H), 2.94 (s, 3H), 2.87 (t, J = 6.6 Hz, 2H), 2.33-2.56 (m, 4H), 1.96-2.04 (m, 2H); LC/MS m/z (M + H$^+$) 490.0. |
| 363 | 1-(Methylsulfonyl)-6-({3-[4-(phenylcarbonyl)piperazin-1-yl]azetidin-1-yl}carbonyl)-1,2,3,4-tetrahydroquinoline<br>$^1$H NMR (400 MHz, CDCl$_3$): δ 7.73 (d, J = 8.6 Hz, 1H), 7.49 (s, 1H), 7.35-7.44 (m, 6H), 4.00-4.36 (m, 4H), 3.64-3.97 (m, 4H), 3.48 (br. s., 2H), 3.18-3.27 (m, 1H), 2.91-2.97 (m, 3H), 2.87 (t, J = 6.6 Hz, 2H), 2.19-2.56 (m, 4H), 1.97-2.04 (m, 2H); LC/MS m/z (M + H$^+$) 483.0. |
| 364 | 1-(Cyclobutylcarbonyl)-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 7.88 (d, J = 3.0 Hz, 1H), 7.55 (d, J = 3.3 Hz, 1H), 7.48 (s, 1H), 7.39-7.44 (m, 1H), 7.24-7.28 (m, 1H), 4.01-4.63 (m, 6H), 3.78-3.97 (m, 2H), 3.67-3.76 (m, 2H), 3.48 (quin, J = 8.4 Hz, 1H), 3.20-3.30 (m, 1H), 2.76 (t, J = 6.3 Hz, 2H), 2.34-2.60 (m, 6H), 2.08 (m, 2H), 1.83-2.02 (m, 4H); LC/MS m/z (M + H$^+$) 494.0. |

-continued

| Cpd | Cpd Name and Data |
|---|---|
| 365 | 6-({3-[4-(1,3-Thiazol-2-ylcarbonyl)piperazin-1-yl]azetidin-1-yl}carbonyl)-1-(4-trifluoromethylbenzoyl)-1,2,3,4-tetrahydroquinoline<br>$^1$H NMR (400 MHz, CDCl$_3$): δ 7.88 (d, J = 3.3 Hz, 1H), 7.52-7.61 (m, 4H), 7.49 (d, J = 8.1 Hz, 2H), 7.12-7.18 (m, 1H), 6.75-6.85 (m, 1H), 4.00-4.60 (m, 6H), 3.76-3.95 (m, 4H), 3.18-3.27 (m, 1H), 2.90 (t, J = 6.6 Hz, 2H), 2.37-2.57 (m, 4H), 2.02-2.12 (m, 2H); LC/MS m/z (M + H$^+$) 584.0. |
| 729 | 2-[(4,4-Difluorocyclohexyl)carbonyl]-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 558.0 |
| 679 | 6-({3-[4-(1,3-Thiazol-2-ylcarbonyl)piperazin-1-yl]azetidin-1-yl}carbonyl)-2-{[3-(trifluoromethyl)phenyl]carbonyl}-1,2,3,4-tetrahydroisoquinoline<br>$^1$H NMR (400 MHz, CDCl$_3$): δ 7.89 (d, J = 3.3 Hz, 1H), 7.70-7.79 (m, 2H), 7.63-7.68 (m, 1H), 7.57-7.62 (m, 1H), 7.55 (d, J = 3.3 Hz, 1H), 7.50 (s, 1H), 7.45 (br. s., 1H), 7.26 (s, 1H), 4.94 (br. s., 1H), 4.48-4.66 (m, 2H), 4.44 (br. s., 1H), 3.97-4.36 (m, 5H), 3.75-3.96 (m, 2H), 3.65 (br. s., 1H), 3.19-3.33 (m, 1H), 2.85-3.12 (m, 2H), 2.37-2.62 (m, 4H)<br>MS m/z (M + H$^+$) 584.0 |
| 907 | 6-({3-[4-(1,3-Thiazol-2-ylcarbonyl)piperazin-1-yl]azetidin-1-yl}carbonyl)-2-{[4-(trifluoromethyl)phenyl]carbonyl}-1,2,3,4-tetrahydroisoquinoline<br>$^1$H NMR (400 MHz, CDCl$_3$): δ 7.88 (d, J = 3.3 Hz, 1H), 7.72 (d, J = 7.6 Hz, 2H), 7.58 (d, J = 7.6 Hz, 2H), 7.55 (d, J = 3.3 Hz, 1H), 7.38-7.52 (m, 2H), 7.21-7.27 (m, 1H), 4.94 (br. s., 1H), 4.48-4.65 (m, 2H), 4.43 (br. s., 1H), 3.95-4.36 (m, 5H), 3.73-3.95 (m, 2H), 3.62 (br. s., 1H), 3.19-3.32 (m, 1H), 2.85-3.10 (m, 2H), 2.38-2.59 (m, 4H)<br>MS m/z (M + H$^+$) 584.0 |
| 685 | 6-({3-[4-(1,3-Thiazol-2-ylcarbonyl)piperazin-1-yl]azetidin-1-yl}carbonyl)-2-{[4-(trifluoromethyl)cyclohexyl]carbonyl}-1,2,3,4-tetrahydroisoquinoline<br>MS m/z (M + H$^+$) 590.0 |
| 736 | 2-(Phenylcarbonyl)-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 516.0 |
| 665 | 6-({3-[4-(1,3-Thiazol-2-ylcarbonyl)piperazin-1-yl]azetidin-1-yl}carbonyl)-2-(thiophen-2-ylcarbonyl)-1,2,3,4-tetrahydroisoquinoline<br>MS m/z (M + H$^+$) 522.0 |
| 690 | 2-(1H-Pyrrol-2-ylcarbonyl)-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 505 |

Example 22

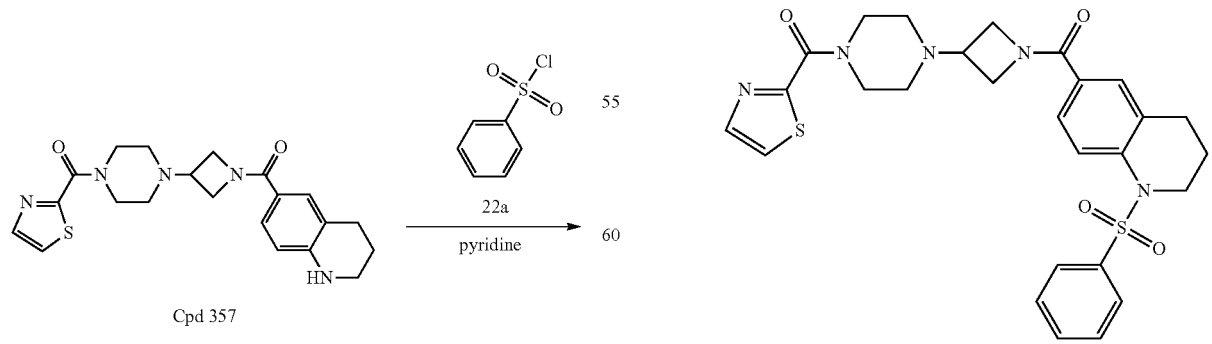

-(Phenylsulfonyl)-6-({3-[4-(1,3-thiazol-2-ylcarbonyl)piper-azin-1-yl]azetidin-1-yl}carbonyl)-1,2,3,4-tetrahydroquino-line, Cpd 366. To a solution of compound 357 (60 mg, 0.015 mmol) in pyridine (1 mL) was added compound 22a (0.023 mL, 0.017 mmol). The reaction mixture was stirred at room temperature for 2 h. The resultant mixture was concentrated under reduced pressure and purified by flash column chromatography (silica gel, 2% MeOH/EtOAc+0.5% Et$_3$N) to give compound 366 (66 mg). $^1$H NMR (400 MHz, CDCl$_3$): δ 7.89 (d, J=3.3 Hz, 1H), 7.84 (d, J=8.3 Hz, 1H), 7.61-7.67 (m, 2H), 7.52-7.59 (m, 2H), 7.36-7.47 (m, 4H), 4.03-4.61 (m, 6H), 3.78-3.93 (m, 4H), 3.20-3.30 (m, 1H), 2.41-2.58 (m, 6H), 1.63-1.71 (m, 2H); LC/MS m/z (M+H$^+$) 552.0.

Following the procedure described above for Example 22 and substituting the appropriate reagents, starting materials and purification methods known to those skilled in the art, the following compounds of the present invention were prepared:

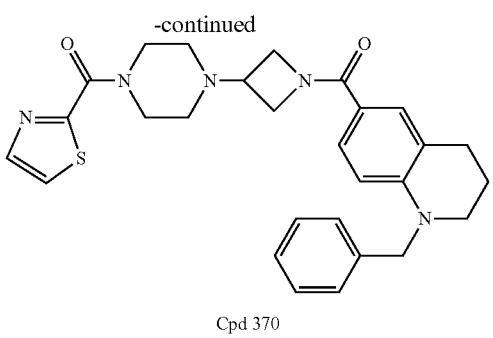

Cpd 370

1-Benzyl-6-({3-[4-(1,3-thiazol-2-ylcarbonyl)piperazin-1-yl]azetidin-1-yl}carbonyl)-1,2,3,4-tetrahydroquinoline, Cpd 370. To a solution of compound 357 (30 mg, 0.0073 mmol) in

| Cpd | Cpd Name and Data |
|-----|-------------------|
| 367 | 6-({3-[4-(1,3-Thiazol-2-ylcarbonyl)piperazin-1-yl]azetidin-1-yl}carbonyl)-1-{[3-(trifluoromethyl)phenyl]sulfonyl}-1,2,3,4-tetrahydroquinoline<br>$^1$H NMR (400 MHz, CDCl$_3$): δ 7.87-7.91 (m, 2H),<br>7.78-7.86 (m, 3H), 7.57-7.63 (m, 1H), 7.54-7.57 (m, 1H), 7.39-7.45 (m, 2H), 4.07-4.61 (m, 6H), 3.77-3.95 (m, 4H), 3.20-3.30 (m, 1H),<br>2.41-2.59 (m, 6H), 1.70 (quin, J = 6.3 Hz, 2H); LC/MS m/z (M + H$^+$) 620.0. |
| 368 | 1-[(3-Fluorophenyl)sulfonyl]-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 7.88 (d, J = 3.0 Hz, 1H),<br>7.81 (d, J = 8.3 Hz, 1H), 7.55 (d, J = 3.0 Hz, 1H), 7.38-7.47 (m, 4H),<br>7.32-7.37 (m, 1H), 7.22-7.29 (m, 1H), 4.02-4.61 (m, 6H),<br>3.77-3.96 (m, 4H), 3.20-3.30 (m, 1H), 2.40-2.60 (m, 6H),<br>1.65-1.77 (m, 2H); LC/MS m/z (M + H$^+$) 570.0. |
| 369 | 6-({3-[4-(1,3-thiazol-2-ylcarbonyl)piperazin-1-yl]azetidin-1-yl}carbonyl)-1-[(4-trifluoromethylphenyl)sulfonyl]-1,2,3,4-tetrahydroquinoline<br>$^1$H NMR (400 MHz, CDCl$_3$): δ 7.88 (d, J = 3.3 Hz, 1H),<br>7.80-7.85 (m, 1H), 7.73-7.79 (m, 2H), 7.68-7.73 (m, 2H), 7.55 (d, J = 3.3 Hz, 1H), 7.39-7.44 (m, 2H), 4.02-4.61 (m, 6H),<br>3.77-3.95 (m, 4H), 3.21-3.29 (m, 1H), 2.39-2.59 (m, 6H), 1.65-1.73 (m, 2H); LC/MS m/z (M + H$^+$) 620.0 |
| 927 | 2-(Phenylsulfonyl)-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 552.0 |
| 928 | 6-({3-[4-(1,3-Thiazol-2-ylcarbonyl)piperazin-1-yl]azetidin-1-yl}carbonyl)-2-{[4-(trifluoromethyl)phenyl]sulfonyl}-1,2,3,4-tetrahydroisoquinoline<br>MS m/z (M + H$^+$) 619.8 |
| 906 | 2-(Cyclohexylsulfonyl)-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 558.0 |

Example 23

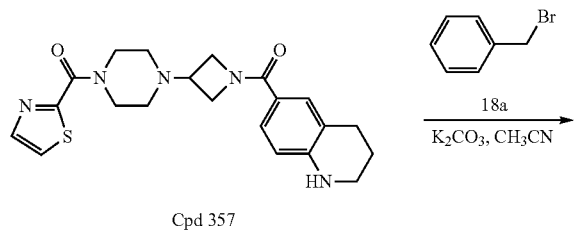

Cpd 357

CH$_3$CN (1 mL) was added compound 18a (0.01 mL, 0.0088 mmol), followed by the addition of K$_2$CO$_3$ (20 mg, 0.015 mmol). The reaction mixture was stirred at room temperature for 18 h. The resultant mixture was partitioned between CH$_2$Cl$_2$ and H$_2$O. The organic solution was dried over Na$_2$SO$_4$, filtered, and concentrated under reduced pressure. Purification of the residue by flash column chromatography (silica gel, 1% MeOH/EtOAc+0.5% Et$_3$N) gave compound 370 (14 mg). $^1$H NMR (400 MHz, CDCl$_3$): δ 7.88 (d, J=3.3 Hz, 1H), 7.54 (d, J=3.0 Hz, 1H), 7.38 (d, J=2.0 Hz, 1H), 7.30-7.36 (m, 2H), 7.19-7.30 (m, 4H), 6.44 (d, J=8.6 Hz, 1H), 4.54 (s, 2H), 3.97-4.52 (m, 6H), 3.77-3.96 (m, 2H), 3.40-3.47 (m, 2H), 3.15-3.24 (m, 1H), 2.83 (t, J=6.2 Hz, 2H), 2.38-2.59 (m, 4H), 1.98-2.05 (m, 2H); LC/MS m/z (M+H$^+$) 502.2.

Following the procedure described above for Example 23 and substituting the appropriate reagents, starting materials and purification methods known to those skilled in the art, the following compounds of the present invention were prepared:

| Cpd | Cpd Name and Data |
|---|---|
| 371 | 6-({3-[4-(1,3-Thiazol-2-ylcarbonyl)piperazin-1-yl]azetidin-1-yl}carbonyl)-1-(4-trifluoromethylbenzyl)-1,2,3,4-tetrahydroquinoline<br>$^1$H NMR (400 MHz, CDCl$_3$): δ 7.88 (d, J = 3.0 Hz, 1H), 7.59 (d, J = 8.3 Hz, 2H), 7.54 (d, J = 3.0 Hz, 1H), 7.39 (s, 1H), 7.34 (d, J = 8.1 Hz, 2H), 7.23-7.29 (m, 1H), 6.35 (d, J = 8.6 Hz, 1H), 4.58 (s, 2H), 3.97-4.54 (m, 6H), 3.74-3.97 (m, 2H), 3.39-3.49 (m, 2H), 3.15-3.26 (m, 1H), 2.85 (t, J = 6.1 Hz, 2H), 2.38-2.59 (m, 4H), 1.99-2.10 (m, 2H); LC/MS m/z (M + H$^+$) 570.0. |
| 879 | 6-({3-[4-(1,3-Thiazol-2-ylcarbonyl)piperazin-1-yl]azetidin-1-yl}carbonyl)-2-[3-(trifluoromethyl)benzyl]-1,2,3,4-tetrahydroisoquinoline<br>MS m/z (M + H$^+$) 570.0. |
| 880 | 6-({3-[4-(1,3-Thiazol-2-ylcarbonyl)piperazin-1-yl]azetidin-1-yl}carbonyl)-2-[4-(trifluoromethyl)benzyl]-1,2,3,4-tetrahydroisoquinoline<br>MS m/z (M + H$^+$) 570.0. |

| Cpd | Cpd Name and Data |
|---|---|
| 1458 | 2-Benzyl-8-({3-[4-(1,3-thiazol-4-ylcarbonyl)piperazin-1-yl]azetidin-1-yl}carbonyl)-1,2,3,4-tetrahydroisoquinoline<br>MS m/z (M + H$^+$) 502.3 |

Example 23a

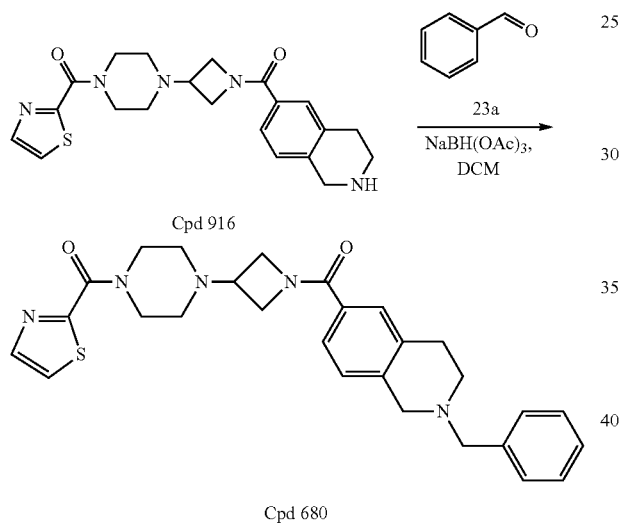

Cpd 916

Cpd 680

2-Benzyl-6-({3-[4-(1,3-thiazol-2-ylcarbonyl)piperazin-1-yl]azetidin-1-yl}carbonyl)-1,2,3,4-tetrahydroisoquinoline, Cpd 680. A solution of Cpd 916 (50 mg, 0.121 mmol) and benzaldehyde 23a (0.014 mL, 0.134 mmol) in CH$_2$Cl$_2$ (2 mL) was stirred at room temperature for 30 min. Sodium triacetoxyborohydride (38.6 mg, 0.182 mmol) was added and the mixture was stirred overnight. The resulting mixture was combined with CH$_2$Cl$_2$ and H$_2$O, and pH of the water layer was adjusted to pH~8 with 1N aqueous NaOH. The organic solution was dried over Na$_2$SO$_4$ and concentrated. Purification the residue by flash column chromatography (silica gel, 2% MeOH/EtOAc) gave Cpd 680 (38.6 mg). $^1$H NMR (400 MHz, CDCl$_3$): δ 7.89 (d, J=3.2 Hz, 1H), 7.55 (d, J=3.2 Hz, 1H), 7.32-7.44 (m, 6H), 7.3 (d, J=8.1 Hz, 1H), 7.02 (d, J=8.1 Hz, 1H), 4.33-4.63 (m, 2H), 3.99-4.34 (m, 4H), 3.75-3.98 (m, 2H), 3.70 (s, 2H), 3.65 (s, 2H), 3.16-3.30 (m, 1H), 2.93 (t, J=5.7 Hz, 2H), 2.76 (t, J=5.7 Hz, 2H), 2.37-2.60 (m, 4H). MS m/z (M+H$^+$) 502.0.

Following the procedure described above for Example 23a, and substituting the appropriate reagents, starting materials, and purification methods known to those skilled in the art, the following compounds of the present invention were prepared:

Example 24

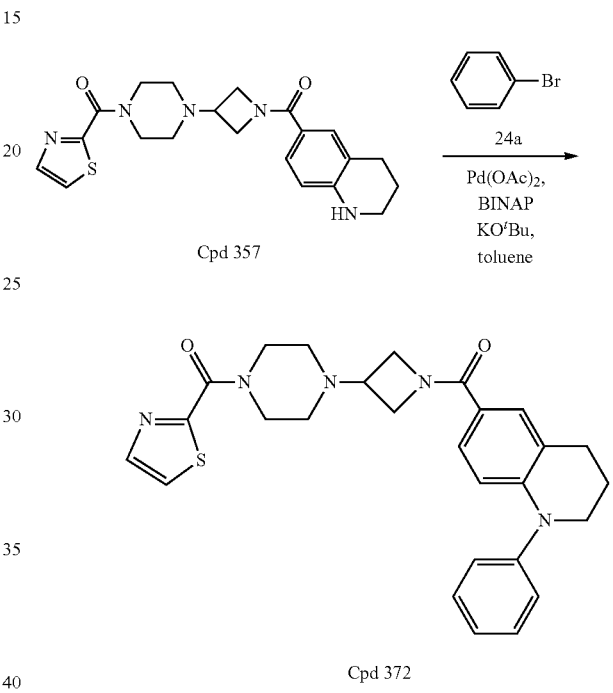

Cpd 357

Cpd 372

1-Phenyl-6-({3-[4-(1,3-thiazol-2-ylcarbonyl)piperazin-1-yl]azetidin-1-yl}carbonyl)-1,2,3,4-tetrahydroquinoline, Cpd 372. To a dry Schlenk tube was added a mixture of compound 11 (30 mg; 0.0073 mmol), palladium (II) acetate (1 mg; 0.00037 mmol), BINAP (3 mg; 0.00044 mmol), and KO$^t$Bu (12 mg; 0.01 mmol). The tube, equipped with a teflon-lined septum, was evacuated, and filled with argon. Bromobenzene (14 mg; 0.0088 mmol), and toluene (0.8 mL) were added to the reaction mixture via syringe. The reaction mixture was heated at 110° C. for 21 h. The resultant mixture was diluted with CH$_2$Cl$_2$, and washed sequentially with saturated NH$_4$Cl$_{(aq)}$ and H$_2$O. The organic phase was dried over Na$_2$SO$_4$, filtered, and concentrated. Purification of the residue by preparative TLC (silica gel, 2% MeOH/EtOAc+0.5% Et$_3$N) gave compound 372 (1.3 mg). $^1$H NMR (400 MHz, CDCl$_3$): δ 7.88 (d, J=3.3 Hz, 1H), 7.55 (d, J=3.0 Hz, 1H), 7.36-7.45 (m, 3H), 7.14-7.26 (m, 4H), 6.55 (d, J=8.6 Hz, 1H), 3.98-4.64 (m, 6H), 3.74-3.96 (m, 2H), 3.61-3.72 (m, 2H), 3.16-3.27 (m, 1H), 2.88 (t, J=6.3 Hz, 2H), 2.37-2.61 (m, 4H), 2.05-2.13 (m, 2H); LC/MS m/z (M+H$^+$) 488.0.

Following the procedure described above for Example 24 and substituting the appropriate reagents, starting materials and purification methods known to those skilled in the art, the following compounds of the present invention were prepared:

| | |
|---|---|
| 373 | 6-({3-[4-(1,3-Thiazol-2-ylcarbonyl)piperazin-1-yl]azetidin-1-yl}carbonyl)-1-[4-(trifluoromethyl)phenyl]-1,2,3,4-tetrahydroquinoline<br>$^1$H NMR (400 MHz, CDCl$_3$): δ 7.89 (d, J = 3.3 Hz, 1H), 7.60 (d, J = 8.3 Hz, 2H), 7.55 (d, J = 3.0 Hz, 1H), 7.46 (s, 1H), 7.33 (d, J = 8.3 Hz, 2H), 7.24 (dd, J = 8.7, 2.1 Hz, 1H), 6.84 (d, J = 8.6 Hz, 1H), 4.01-4.62 (m, 6H), 3.75-3.98 (m, 2H), 3.64-3.73 (m, 2H), 3.18-3.30 (m, 1H), 2.87 (t, J = 6.3 Hz, 2H), 2.36-2.62 (m, 4H), 2.02-2.12 (m, 2H); LC/MS m/z (M + H$^+$) 556.0. |
| 374 | 6-({3-[4-(1,3-Thiazol-2-ylcarbonyl)piperazin-1-yl]azetidin-1-yl}carbonyl)-1-[3-(trifluoromethyl)phenyl]-1,2,3,4-tetrahydroquinoline<br>$^1$H NMR (400 MHz, CDCl$_3$): δ 7.88 (d, J = 3.0 Hz, 1H), 7.55 (d, J = 3.0 Hz, 1H), 7.37-7.52 (m, 5H), 7.22 (dd, J = 8.6, 2.0 Hz, 1H), 6.66 (d, J = 8.6 Hz, 1H), 4.03-4.59 (m, 6H), 3.74-3.96 (m, 2H), 3.61-3.72 (m, 2H), 3.18-3.27 (m, 1H), 2.89 (t, J = 6.3 Hz, 2H), 2.37-2.60 (m, 4H), 2.03-2.14 (m, 2H); LC/MS m/z (M + H$^+$) 556.0. |
| 375 | 1-Pyrimidin-2-yl-6-({3-[4-(1,3-thiazol-2-ylcarbonyl)piperazin-1-yl]azetidin-1-yl}carbonyl)-1,2,3,4-tetrahydroquinoline<br>$^1$H NMR (400 MHz, CDCl$_3$): δ 8.46 (d, J = 4.8 Hz, 2H), 7.89 (d, J = 3.0 Hz, 1H), 7.83 (d, J = 8.6 Hz, 1H), 7.55 (d, J = 3.3 Hz, 1H), 7.50 (s, 1H), 7.41 (dd, J = 8.6, 2.0 Hz, 1H), 6.75 (t, J = 4.8 Hz, 1H), 4.06-4.61 (m, 6H), 3.99-4.06 (m, 2H), 3.77-3.96 (m, 2H), 3.18-3.29 (m, 1H), 2.83 (t, J = 6.4 Hz, 2H), 2.39-2.59 (m, 4H), 1.99-2.07 (m, 2H); LC/MS m/z (M + H$^+$) 490.0. |
| 883 | 2-Phenyl-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 488.1 |
| 668 | 2-Pyrimidin-2-yl-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 490.0 |
| 661 | 2-Pyridin-2-yl-6-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 489.0 |
| 805 | 2-Phenyl-8-({3-[4-(1,3-thiazol-2-ylcarbonyl)piperazin-1-yl]azetidin-1-yl}carbonyl)-1,2,3,4-tetrahydroisoquinoline<br>MS m/z (M + H$^+$) 490.1 |

Example 25

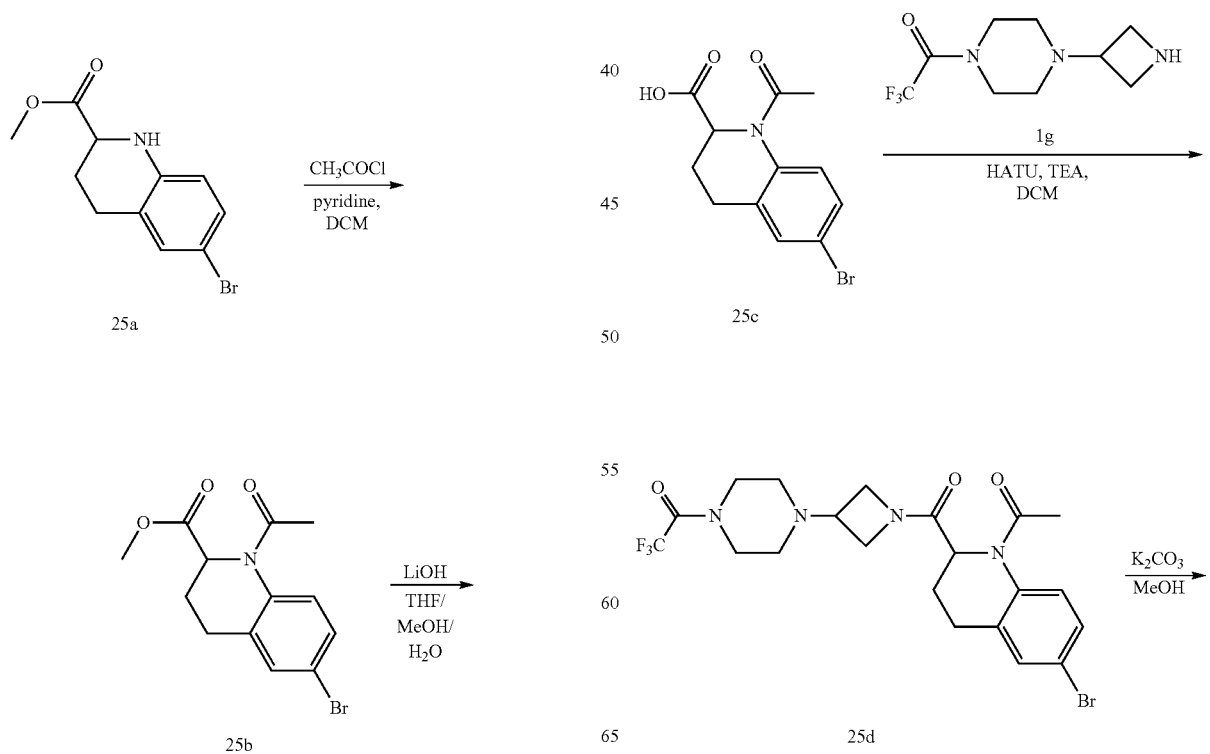

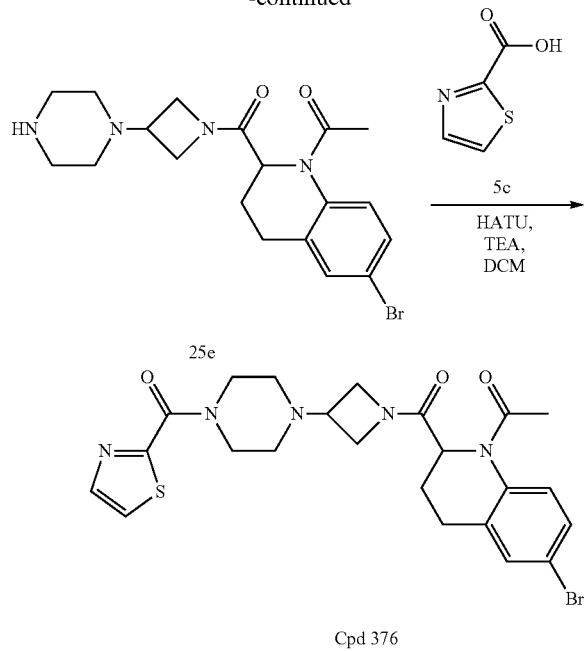

mixture was filtered, the filtrate concentrated under reduced pressure, and the resultant residue partitioned between $CH_2Cl_2$ and $H_2O$. The organic phase was dried over $Na_2SO_4$, filtered, and concentrated under reduced pressure to give compound 25e (158 mg). LC/MS m/z (M+H⁺) 421.0, (M+2H⁺) 423.0.

E. 1-Acetyl-6-bromo-2-({3-[4-(1,3-thiazol-2-ylcarbonyl)piperazin-1-yl]azetidin-1-yl}carbonyl)-1,2,3,4-tetrahydroquinoline, Cpd 376. The title compound was prepared in an analogous manner to that of compound 357 substituting compound 25e for compound 20c. LC/MS m/z (M+H⁺) 532.0, (M+2H⁺) 534.0.

Following the procedure described above for Example 25 and substituting the appropriate reagents, starting materials and purification methods known to those skilled in the art, the following compounds of the present invention were prepared:

| Cpd | Cpd Name and Data |
|-----|-------------------|
| 377 | 1-Acetyl-6-bromo-2-({3-[4-(1,3-thiazol-4-ylcarbonyl)piperazin-1-yl]azetidin-1-yl}carbonyl)-1,2,3,4-tetrahydroquinoline<br>LC/MS m/z (M + H⁺) 532.0, (M + 2H⁺) 534.0. |
| 378 | 1-Acetyl-6-bromo-2-({3-[4-(phenylcarbonyl)piperazin-1-yl]azetidin-1-yl}carbonyl)-1,2,3,4-tetrahydroquinoline<br>LC/MS m/z (M + H⁺) 525.0, (M + 2H⁺) 527.0. |

Example 26

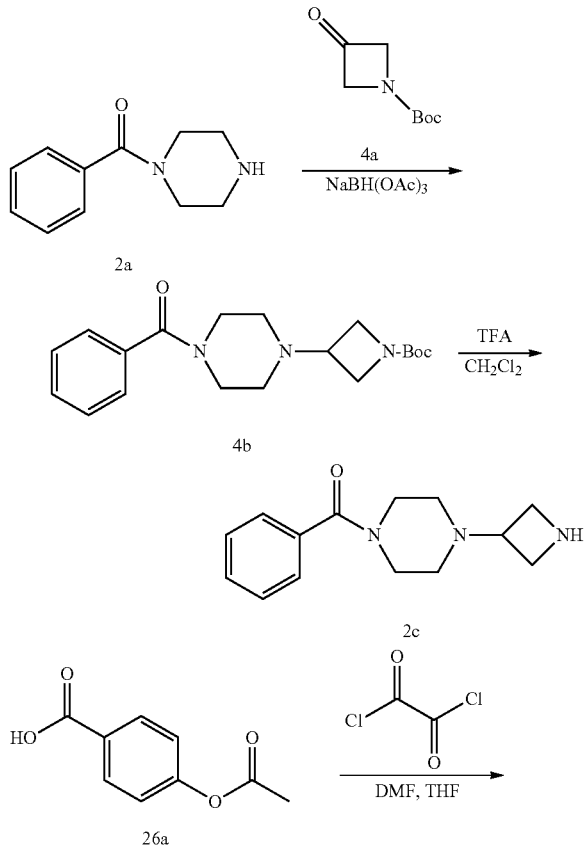

A. 1-Acetyl-6-bromo-1,2,3,4-tetrahydro-quinoline-2-carboxylic acid methyl ester, 25b. To a solution of compound 25a (100 mg, 0.37 mmol) in $CH_2Cl_2$ (5 mL) was added acetyl chloride (0.1 mL), and pyridine (0.1 mL). The reaction mixture was stirred at room temperature for 2 h. The resultant mixture was partitioned between $CH_2Cl_2$ and $H_2O$. The organic phase was dried over $Na_2SO_4$, filtered, and concentrated to give the crude compound 25b (116 mg), which was used in the next step without further purification. LC/MS m/z 312.0 (M+H⁺), 314.0 (M+2H⁺).

B. 1-Acetyl-6-bromo-1,2,3,4-tetrahydro-quinoline-2-carboxylic acid, 25c. To a solution of compound 25b (116 mg, 0.37 mmol) in THF/MeOH/$H_2O$ (2/2/2 mL) was added LiOH (62 mg, 1.48 mmol). The reaction mixture was stirred at room temperature for 3 h. The resultant mixture was concentrated under reduced pressure, partitioned between $CH_2Cl_2$ and $H_2O$, and the aqueous phase was brought to pH 5 by the addition of 2N HCl (aq). The organic phase was dried over $Na_2SO_4$, filtered, and concentrated under reduced pressure to give the crude compound 25c, which was used in the next step without further purification. LC/MS m/z 298.0 (M+H⁺), 300.0 (M+2H⁺).

C. 1-Acetyl-6-bromo-2-({3-[4-(trifluoroacetyl)piperazin-1-yl]azetidin-1-yl}carbonyl)-1,2,3,4-tetrahydroquinoline, 25d. To a solution of compound 1g (228 mg, 0.74 mmol), compound 25c (22 mg, 0.74 mmol), and $Et_3N$ (0.3 mL, 2.22 mmol) in $CH_2Cl_2$ (7 mL) was added HATU (338 mg, 0.89 mmol). The reaction mixture was stirred at room temperature for 18 h. The resultant mixture was diluted with $CH_2Cl_2$ and washed with aqueous $NaHCO_3$. The organic phase was dried over $Na_2SO_4$, filtered, and concentrated under reduced pressure. Purification of the residue by flash column chromatography (silica gel, 2% MeOH/EtOAc+0.5% $Et_3N$) gave compound 25d (265 mg). LC/MS m/z (M+H⁺), 517.0 (M+2H⁺), 519.0.

D. 1-Acetyl-6-bromo-2-({3-[piperazin-1-yl]azetidin-1-yl}carbonyl)-1,2,3,4-tetrahydroquinoline, 25e. To a solution of compound 25d (261 mg, 0.505 mmol) in MeOH (3 mL) was added $K_2CO_3$ (140 mg, 1.01 mmol). The reaction mixture was stirred at room temperature for 30 min. The resultant

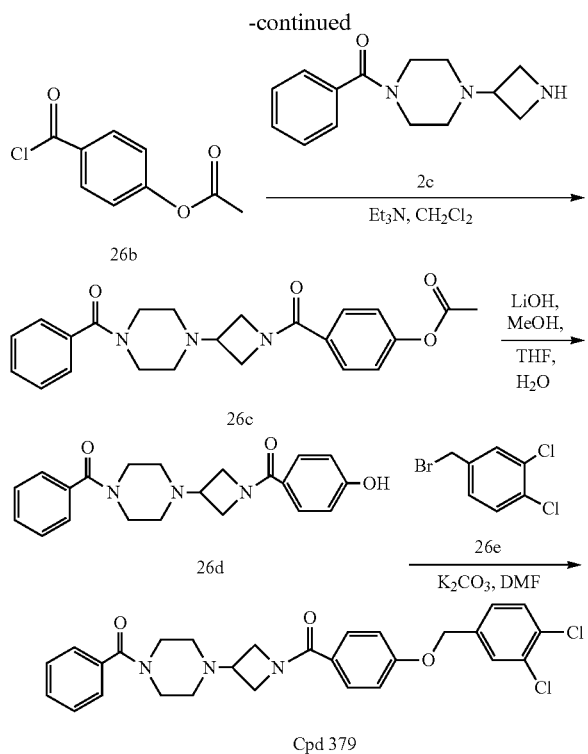

A. tert-Butyl 3-(4-Benzoyl-piperazin-1-yl)-azetidine-1-carboxylate, 4b. To a solution of compound 2a (5g) and compound 4a (6.75 g) in 1,2 dichloroethane (50 mL) was added AcOH (1.0 mL) and 4 Å molecular sieves. The resultant mixture was stirred for 2 h, at which time NaBH(OAc)$_3$ (11 g) was added in three portions. The mixture was stirred for 18 h, poured into 2N KOH (aq., 50 mL), and then extracted with EtOAc (3×). The combined organic extracts were dried over Na$_2$SO$_4$, filtered, and concentrated under reduced pressure reduced pressure. The residue was purified by flash column chromatography (5% MeOH/CH$_2$Cl$_2$) to give compound 4b (11.6 g).

B. 3-(4-Benzoyl-piperazin-1-yl)-azetidine, HCl salt 2c. To a solution of compound 4b (5.1 g) in CH$_2$Cl$_2$ (20 mL) was added TFA (10 mL). The resultant mixture was stirred at room temperature for 4 h. The solvents were removed under reduced pressure. The resultant residue was dissolved in CH$_2$Cl$_2$ (5 mL), to which was added 4M HCl in dioxane (3.67 mL). The resulting solid was collected by filtration, washed with ether, and dried under reduced pressure to give compound 2c as its hydrochloride salt (4.0 g).

C. 4-Acetoxy benzoyl chloride, 26b. To a solution of compound 26a (200 mg, 1.11 mmol) in THF (5 mL) was added oxalyl dichloride (97 µL, 1.11 mmol) dropwise at 0° C., followed by the addition of 2 drops of DMF. The resultant mixture was stirred at 0° C. for 3 h, and then warmed to room temperature for 18 h. The solvents were removed under reduced pressure and the crude residue, compound 26b, was dried under reduced pressure for 2 h, and used in the next step without further purification.

D. 4-({3-[4-(Phenylcarbonyl)piperazin-1-yl]azetidin-1-yl}carbonyl)phenyl acetate (26c). To a mixture of the HCl salt of compound 2c (373 mg, 1.33 mmol), Et$_3$N (0.5 mL) and CH$_2$Cl$_2$ (5 mL) was added a solution of compound 26b in CH$_2$Cl$_2$ (1 mL). The resultant mixture was stirred at room temperature for 4 h. The solvent was removed under reduced pressure, the residue dissolved in CH$_2$Cl$_2$ (1 mL), and then purified by flash column chromatography (silica gel, 5% MeOH/CH$_2$Cl$_2$) to give compound 26c (442 mg).

E. 4-({3-[4-(Phenylcarbonyl)piperazin-1-yl]azetidin-1-yl}carbonyl)phenol, 26d. A mixture of compound 26c (420 mg, 1.03 mmol) and LiOH (100 mg, 4.0 mmol) in a solvent mixture of THF/MeOH/H2O (2/2/2 mL) was stirred at room temperature for 4 h, at which time it was brought to pH 5 by the addition of 2N HCl (aq). The mixture was extracted with EtOAc (3×). The combined extracts were dried over Na$_2$SO$_4$, filtered, and concentrated under reduced pressure. The resultant residue (crude compound 26d) was dried under reduced pressure for 18 h, and used in the following step without further purification.

F. 1-[1-({4-[(3,4-dichlorobenzyl)oxy]phenyl}carbonyl)azetidin-3-yl]-4-(phenylcarbonyl)piperazine, Cpd 379. A mixture of compound 26d (70 mg, 0.191 mmol), K$_2$CO$_3$ (53 mg, 0.382 mmol), compound 26e (68 mg, 0.287 mmol) and DMF (3 mL) was stirred at room temperature for 18 h. Water was added to the reaction mixture and the mixture was extracted with EtOAc (3×). The combined organic extracts were dried over Na$_2$SO$_4$, filtered, and concentrated under reduced pressure. The resultant residue was purified by flash column chromatography, eluting with 5% MeOH/CH$_2$Cl$_2$ to give compound 379 (83 mg). $^1$H NMR (CDCl$_3$): δ 7.59-7.64 (d, J=8.8 Hz, 2H), 7.53 (d, J=2.0 Hz, 1H), 7.455 (d, J=8.0 Hz, 1H), 7.37-7.44 (m, 5H), 7.23-7.28 (m, 2H), 6.955 (d, J=8.84 Hz, 2H), 5.05 (s, 2H), 4.31 (br. s, 1H), 4.11-4.27 (m, 2H), 4.00-4.10 (m, 1H), 3.91 (br. s, 1H), 3.64-3.82 (m, 1H), 3.48 (br. s, 2H), 3.18-3.27 (m, 1H), 2.42 (br. s, 4H). MS m/z (M+H$^+$) 524.0.

Following the procedure described above for Example 26 and substituting the appropriate reagents, starting materials and purification methods known to those skilled in the art, the following compounds of the present invention were prepared:

| Cpd | Cpd Name and Data |
|---|---|
| 380 | 1-(1-{[4-(Naphthalen-2-ylmethoxy)phenyl]carbonyl}azetidin-3-yl)-4-(phenylcarbonyl)piperazine<br>$^1$H NMR (CDCl$_3$): δ 7.80-7.88 (m, 4H), 7.59-7.64 (m, J = 8.8 Hz, 2H), 7.45-7.53 (m, 3H), 7.36-7.43 (m, 5H), 7.00 (d, J = 8.8 Hz, 2H), 5.22 (s, 2H), 4.24-4.32 (m, 1H), 4.08-4.24 (m, 2H), 4.03 (br. s., 1H), 3.60-3.79 (m, 1H), 3.31-3.52 (m, 2H), 3.10-3.22 (m, 1H), 2.38 (br. s., 4H).<br>MS m/z (M + H$^+$) 506.2 |
| 381 | 1-[1-({4-[(2,3-Dichlorobenzyl)oxy]phenyl}carbonyl)azetidin-3-yl]-4-(phenylcarbonyl)piperazine<br>$^1$H NMR (CDCl$_3$): δ 7.625 (d, J = 8.4 Hz, 2H), 7.44 (dd, J = 8.0, 2.1 Hz, 2H), 7.37-7.41 (m, 5H), 7.23 (t, J = 8.1, 1H), 6.97 (d, J = 8.8 Hz, 2H), 5.18 (s, 2H), 4.26-4.36 (m, 1H), 4.12-4.26 (m, 2H), 4.07 (br. s, 1H), 3.88 (br. s., 1H), 3.74 (br. s., 1H), 3.47 (br. s., 2H), 3.14-3.27 (m, 1H), 2.41 (br. s., 3H), 2.22 (s, 1H).<br>MS m/z (M + H$^+$) 524.0 |
| 382 | 1-[1-({4-[(4-Fluorobenzyl)oxy]phenyl}carbonyl)azetidin-3-yl]-4-(phenylcarbonyl)piperazine<br>MS m/z (M + H$^+$) 474.2 |
| 383 | 1-(Phenylcarbonyl)-4-{1-[(4-{[4-(trifluoromethyl)benzyl]oxy}phenyl)carbonyl]azetidin-3-yl}piperazine<br>MS m/z (M + H$^+$) 524.2 |
| 384 | 1-[1-({4-[(4-Chlorobenzyl)oxy]phenyl}carbonyl)azetidin-3-yl]-4-(phenylcarbonyl)piperazine<br>MS m/z (M + H$^+$) 490.2 |
| 385 | 1-[1-({4-[(2,4-Dichlorobenzyl)oxy]phenyl}carbonyl)azetidin-3-yl]-4-(phenylcarbonyl)piperazine<br>MS m/z (M + H$^+$) 524.1 |
| 386 | 4-{[4-({3-[4-(Phenylcarbonyl)piperazin-1-yl]azetidin-1-yl}carbonyl)phenoxy]methyl}benzonitrile<br>MS m/z (M + H$^+$) 481.2 |

-continued

| Cpd | Cpd Name and Data |
|---|---|
| 387 | 1-[1-({4-[2-(4-Chlorophenyl)ethoxy]phenyl}carbonyl)azetidin-3-yl]-4-(phenylcarbonyl)piperazine<br>MS m/z (M + H$^+$) 504.2 |
| 388 | 1-[1-({4-[2-(4-Fluorophenyl)ethoxy]phenyl}carbonyl)azetidin-3-yl]-4-(phenylcarbonyl)piperazine<br>MS m/z (M + H$^+$) 488.2 |
| 389 | 1-(Phenylcarbonyl)-4-(1-{[4-({4-[(trifluoromethyl)sulfanyl]benzyl}oxy)phenyl]carbonyl}azetidin-3-yl)piperazine<br>MS m/z (M + H$^+$) 556.2 |
| 390 | 1-(Phenylcarbonyl)-4-{1-[(4-{[4-(trifluoromethoxy)benzyl]oxy}phenyl)carbonyl]azetidin-3-yl}piperazine<br>MS m/z (M + H$^+$) 540.2 |
| 391 | 1-[1-({4-[(3-Chlorobenzyl)oxy]phenyl}carbonyl)azetidin-3-yl]-4-(phenylcarbonyl)piperazine<br>MS m/z (M + H$^+$) 490.2 |
| 392 | 1-[1-({4-[(3-Chloro-4-fluorobenzyl)oxy]phenyl}carbonyl)azetidin-3-yl]-4-(phenylcarbonyl)piperazine<br>MS m/z (M + H$^+$) 508.2 |
| 393 | 1-(Phenylcarbonyl)-4-{1-[(4-{[3-(trifluoromethoxy)benzyl]oxy}phenyl)carbonyl]azetidin-3-yl}piperazine<br>MS m/z (M + H$^+$) 540.2 |
| 394 | 4-[(4-{[4-({3-[4-(Phenylcarbonyl)piperazin-1-yl]azetidin-1-yl}carbonyl)phenoxy]methyl}phenyl)sulfonyl]morpholine<br>MS m/z (M + H$^+$) 605.2 |
| 395 | 1-{1-[(4-{[3-Fluoro-4-(trifluoromethyl)benzyl]oxy}phenyl)carbonyl]azetidin-3-yl}-4-(phenylcarbonyl)piperazine<br>MS m/z (M + H$^+$) 542.2 |
| 396 | 1-(Phenylcarbonyl)-4-(1-{[4-(pyridin-4-ylmethoxy)phenyl]carbonyl}azetidin-3-yl)piperazine<br>MS m/z (M + H$^+$) 457.2 |

Example 27

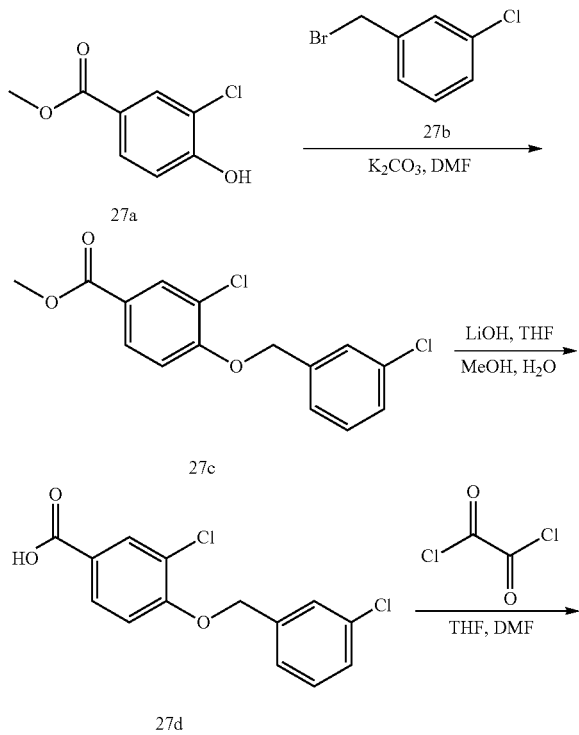

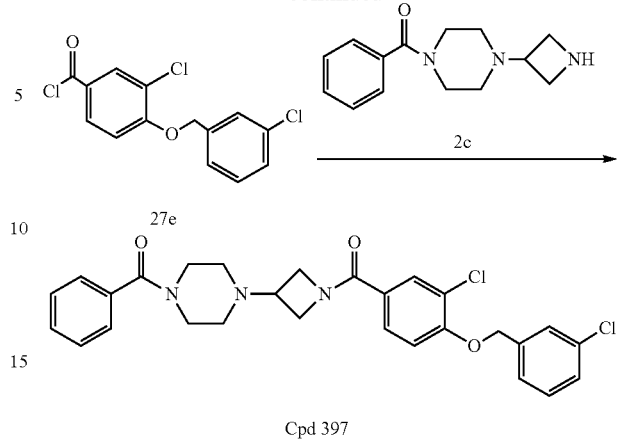

Cpd 397

A. Methyl 4-(3-chlorobenzyloxy)-3-chlorobenzoate, 27c. A mixture of compound 27a (500 mg, 2.7 mmol), compound 27b (0.53 mL, 4.03 mmol), and K$_2$CO$_3$ (745 mg, 5.4 mmol) in DMF was stirred at room temperature for 18 h. Water was added to the reaction mixture and the mixture was extracted with EtOAc (3×). The combined organic extracts were dried over Na$_2$SO$_4$, filtered, and concentrated under reduced pressure. The resultant residue was purified by silica gel flash column chromatography, eluting with 30% EtOAc/hexanes to give compound 27c (662 mg).

B. 4-(3-Chlorobenzyloxy)-3-chlorobenzoic acid, 27d. A mixture of compound 27c (662 mg, 2.0 mmol) and LiOH (192 mg, 8 mmol) in a solvent mixture of THF/MeOH/H$_2$O (3/3/3 mL) was stirred at room temperature for 4 h, then acidified with 15% citric acid in H$_2$O. The mixture was extracted with EtOAc (3×), and the combined extracts washed sequentially with water and brine. The extracts were dried over Na$_2$SO$_4$, filtered, and concentrated under reduced pressure. The resultant crude compound 3b was dried under reduced pressure for 18 h and used in the following reaction without further purification.

C. 4-(3-Chlorobenzyloxy)-3-chlorobenzoyl chloride, 27e. To a solution of compound 27d (67 mg, 0.33 mmol) in THF (2 mL) was added oxalyl dichloride (43 µL, 0.50 mmol) dropwise at 0° C., followed by the addition of 2 drops of DMF. The resultant mixture was stirred at 0° C. for 3 h, and then was warmed up to room temperature over 18 h. The solvents were removed under reduced pressure. The resultant residue, crude compound 27e, was dried under reduced pressure for 2 h and used in the following step without further purification.

D. 1-[1-({3-Chloro-4-[(3-chlorobenzyl)oxy]phenyl}carbonyl)azetidin-3-yl]-4-(phenylcarbonyl)piperazine, Cpd 397. To a mixture of compound 2c (84 mg, 0.30 mmol), Et$_3$N (0.5 mL), and CH$_2$Cl$_2$ (2.5 mL) was added a solution of compound 27e in CH$_2$Cl$_2$ (1 mL). The resultant mixture was stirred at room temperature for 4 h. The solvent was removed under reduced pressure. The resultant residue was dissolved in CH$_2$Cl$_2$ (1 mL), loaded on a silica gel column, and purified by flash column chromatography, eluting with 5% MeOH/CH$_2$Cl$_2$ to give compound 397 (32 mg). $^1$H NMR (CDCl$_3$): δ 7.695 (d, 1H, J=2.0 Hz), 7.515 (dd, 1H, J1=2.0 Hz, J2=8.6 Hz), 7.44 (s, 1H), 7.38-7.43 (m, 5H), 7.30-7.35 (m, 3H), 6.91-6.97 (d, 1H, J=8.6 Hz), 5.15 (s, 2H), 4.26-4.37 (m, 1H), 4.15-4.26 (m, 2H), 3.84-3.98 (m, 1H), 3.68-3.82 (m, 1H), 3.48 (br. s, 2H), 3.18-3.29 (m, 1H), 2.56-2.16 (m, 4H). MS m/z (M+H$^+$) 524.0.

Following the procedure described above for Example 27 and substituting the appropriate reagents, starting materials and purification methods known to those skilled in the art, the following compounds of the present invention were prepared:

| Cpd | Cpd Name and Data |
|---|---|
| 398 | 1-(1-{[3-Chloro-4-(pyridin-4-ylmethoxy)phenyl]carbonyl}azetidin-3-yl)-4-(1,3-thiazol-2-ylcarbonyl)piperazine<br>$^1$H NMR (CDCl$_3$): δ 8.64 (d, J = 5.8 Hz, 2H), 7.2 (d, J = 2.0 Hz, 1H), 7.53 (dd, J1 = 2.1, 8.4 Hz, 1H), 7.36-7.45 (m, 7H), 6.88-6.95 (d, J = 8.6 Hz, 1H), 5.19 (s, 2H), 4.27-4.37 (m, 1H), 4.11-4.27 (m, 2H), 3.99-4.08 (m, 1H), 3.81-3.96 (m, 1H), 3.73 (br. s, 1H), 3.48 (br. s., 2H), 3.17-3.30 (m, 1H), 2.41 (br. s., 4H). MS m/z (M + H$^+$) 498.0 |
| 399 | 1-[1-({3-Chloro-4-[(3,4-dichlorobenzyl)oxy]phenyl}carbonyl)azetidin-3-yl]-4-(phenylcarbonyl)piperazine<br>$^1$H NMR (CDCl$_3$): δ 7.70 (d, J = 2.0 Hz, 1H), 7.56 (s, 1H), 7.53 (dd, J = 8.6, 2.0 Hz, 1H), 7.48 (d, J = 8.2 Hz, 1H), 7.37-7.44 (m, 5H), 7.28-7.32 (m, 1H), 6.93 (d, J = 8.2 Hz, 1H), 5.14 (s, 2H), 4.28-4.37 (m, 1H), 4.12-4.27 (m, 2H), 4.05 (br. s., 1H), 3.91 (br. s., 1H), 3.74 (br. s., 1H), 3.49 (br. s., 2H), 3.16-3.27 (m, 1H), 2.42 (br. s., 4H).<br>MS m/z (M + H$^+$) 558.0 |
| 400 | 1-[1-({4-[(3,4-Dichlorobenzyl)oxy]-3 fluorophenyl}carbonyl)azetidin-3-yl]-4-(1,3-thiazol-2-ylcarbonyl)piperazine<br>$^1$H NMR (CDCl$_3$): δ 7.88 (d, J = 3.3 Hz, 1H), 7.53-7.57 (m, 2H), 7.41-7.48 (m, 2H), 7.39 (dd, J = 8.5, 1.1 Hz, 1H), 7.25-7.30 (m, 1H), 6.97 (t, J = 8.3 Hz, 1H), 5.12 (s, 2H), 4.52 (br. d., J = 33.8 Hz, 1H), 4.37-4.47 (m, 1H), 4.32 (d, J = 6.8 Hz, 1H), 4.15-4.28 (m, 2H), 4.07 (d, J = 8.3 Hz, 1H), 3.85 (d, J = 17.4 Hz, 2H), 3.20-3.28 (m, 1H), 2.48 (t, J = 4.8 Hz, 4H).<br>MS m/z (M + H$^+$) 549.0. |
| 401 | 1-[1-({3-Chloro-4-[(3-chlorobenzyl)oxy]phenyl}carbonyl)azetidin-3-yl]-4-(1,3-thiazol-2-ylcarbonyl)piperazine<br>$^1$H NMR (CDCl$_3$): δ 7.88 (d, J = 3.3 Hz, 1H), 7.71 (d, J = 2.0 Hz, 1H), 7.50-7.57 (m, 2H), 7.45 (s, 1H), 7.30-7.35 (m, 3H), 6.95 (d, J = 8.6 Hz, 1H), 5.17 (s, 2H), 4.43 (br. s., 1H), 4.28-4.38 (m, 1H), 4.17-4.28 (m, 1H), 4.03-4.15 (m, 2H), 3.85 (d, J = 19.5 Hz, 2H), 3.19-3.29 (m, 1H), 2.48 (m, 4H).<br>MS m/z (M + H$^+$) 531.0 |
| 402 | 1-(1-{[3-Chloro-4-(pyridin-3-ylmethoxy)phenyl]carbonyl}azetidin-3-yl)-4-(1,3-thiazol-2-ylcarbonyl)piperazine<br>$^1$H NMR (CDCl$_3$): δ 8.71 (s, 1H), 8.61 (d, J = 3.5 Hz, 1H), 7.88 (d, J = 3.0 Hz), 1H), 7.84 (d, J = 7.8 Hz, 1H), 7.72 (d, J = 2.3 Hz, 1H), 7.56 (d, J = 2.0 Hz, 1H), 7.55 (d, J = 3.6 Hz, 1H), 7.36 (dd, J = 7.8, 4.8 Hz, 1H), 7.00 (d, J = 8.6 Hz, 1H), 5.21 (s, 2H), 4.52 (br. S, 1H), 4.43 (br. S, 1H), 4.32 (m, 1H), 4.16-4.29 (m, 2H), 4.03-4.16 (m, 1H), 3.76-3.95 (m, 2H), 3.20-3.30 (m, 1H), 2.57-2.36 (m, 4H).<br>MS m/z (M + H$^+$) 498.0. |
| 403 | 1-(1-{[4-(Pyridin-4-ylmethoxy)phenyl]carbonyl}azetidin-3-yl)-4-(1,3-thiazol-2-ylcarbonyl)piperazine<br>$^1$H NMR (CDCl$_3$): δ 8.63 (d, J = 5.8 Hz, 2H), 7.88 (d, J = 3.0 Hz, 1H), 7.63 (d, J = 8.8 Hz, 2H), 7.55 (d, J = 3.3 Hz, 1H), 7.36 (d, J = 6.1 Hz, 2H), 6.96 (d, J = 8.84 Hz, 2H), 5.14 (s, 2H), 4.52 (br. s, 1H), 4.43 (br. s, 1H), 4.36-4.29 (m, 1H), 4.16-4.29 (m, 2H), 4.04-4.16 (m, 1H), 3.75-3.93 (m, 2H), 3.18-3.28 (m, 1H), 2.37-2.58 (m, 4H).<br>MS m/z (M + H$^+$) 464.0 |
| 404 | 1-[1-({3-Chloro-4-[(3,4-dichlorobenzyl)oxy]phenyl}carbonyl)azetidin-3-yl]-4-(1,3-thiazol-2-ylcarbonyl)piperazine<br>$^1$H NMR (CDCl$_3$): δ 7.88 (d, J = 3.0 Hz, 1H), 7.71 (d, J = 2.0 Hz, 1H), 7.51-7.58 (m, 3H), 7.47 (dd, J = 8.3, 4.0 Hz, 1H), 7.30 (dd, J = 8.1, 2.0 Hz, 1H), 6.94 (d, J = 8.6 Hz, 1H), 5.14 (s, 2H), 4.52 (br. s., 1H), 4.37 (br. s., 1H), 4.29-4.37 (m, 1H), 4.22 (br. s., 2H), 4.01-4.14 (m, 1H), 3.88 (br. s., 2H), 3.19-3.32 (m, 1H), 2.40-2.55 (m, 4H)<br>MS m/z (M + H$^+$) 564.6, 566.8 |
| 405 | 1-[1-({4-[(2,3-Dichlorobenzyl)oxy]-3-fluorophenyl}carbonyl)azetidin-3-yl]-4-(1,3-thiazol-2-ylcarbonyl)piperazine<br>$^1$H NMR (CDCl$_3$): δ 7.88 (d, J = 3.3 Hz, 1H), 7.55 (d, J = 3.3 Hz, 1H), 7.50 (d, J = 7.8 Hz, 1H), 7.47 (s, 1H), 7.43-7.46 (m, 1H), 7.40 (dd, J = 8.6, 1.3 Hz, 1H), 7.28 (d, J = 2.3 Hz, 1H), 7.25 (d, J = 7.8 Hz, 1H), 7.00 (t, J = 8.3 Hz, 1H), 5.28 (s, 2H), |

-continued

| Cpd | Cpd Name and Data |
|---|---|
| | 4.49 (d, J = 33.2 Hz, 2H), 4.31-4.39 (m, 1H), 4.22 (br. s., 2H), 4.03-4.16 (m, 1H), 3.88 (br. s., 2H), 3.19-3.31 (m, 1H), 2.40-2.58 (m, 4H).<br>MS m/z (M + H$^+$) 549.0 |
| 406 | 1-(1-{[3-Chloro-4-(pyridin-2-ylmethoxy)phenyl]carbonyl}azetidin-3-yl)-4-(phenylcarbonyl)piperazine<br>$^1$H NMR (CDCl$_3$): δ 8.59 (d, J = 4.5 Hz, 1H), 7.76 (dd, J = 1.5, 7.6 Hz, 1H), 7.73 (d, J = 2.0 Hz, 1H), 7.61 (d, J = 7.8 Hz, 1H), 7.50 (dd, J = 8.6, 2.0 Hz, 1H), 7.37-7.44 (m, 5H), 7.25 (dd, J = 6.9, 5.2 Hz, 1H), 7.00 (d, J = 8.6 Hz, 1H), 5.28-5.35 (m, 2H), 4.27-4.37 (m, 1H), 4.12-4.27 (m, 2H), 3.99-4.12 (m, 1H), 3.89 (br. s., 1H), 3.74 (br. s., 1H), 3.47 (br. s., 2H), 3.17-3.27 (m, 1H), 2.42 (br. s., 3H), 2.27 (br. s., 1H). |
| 407 | 1-(1-{[3-Chloro-4-(pyridine-2-ylmethoxy)phenyl]carbonyl}azetidin-3-yl)-4-(1,3-thiazol-2-ylcarbonyl)piperazine<br>$^1$H NMR (CDCl$_3$): δ 8.54 (br. s, 1H), 8.49 (br. s, 1H), 7.62-7.68 (m, 1H), 7.53 (d, J = 8.6 Hz, 2H), 7.37-7.44 (m, 5H), 7.29 (d, J = 9.1 Hz, 2H), 7.23 (dd, J = 7.8, 4.8 Hz, 1H), 4.17-4.32 (m, 2H), 4.09-4.17 (m, 3H), 4.00-4.08 (m, 1H), 3.89 (br. s., 1H), 3.74 (br. s, 1H), 3.47 (br. s, 2H), 3.15-3.28 (m, 1H), 2.41 (br. s., 3H), 2.17 (br. s, 1H)<br>MS m/z (M + H$^+$) 498.0 |
| 408 | 1-(1-{[3-Chloro-4-(pyridin-4-ylmethoxy)phenyl]carbonyl}azetidin-3-yl)-4-(phenylcarbonyl)piperazine<br>MS m/z (M + H$^+$) 491.2 |
| 409 | 1-(1-{[3-Chloro-4-(pyridin-3-ylmethoxy)phenyl]carbonyl}azetidin-3-yl)-4-(phenylcarbonyl)piperazine<br>MS m/z (M + H$^+$) 491.2 |
| 481 | 1-[1-({4-[(4-Chlorobenzyl)oxy]-3-fluorophenyl}carbonyl)azetidin-3-yl]-4-(phenylcarbonyl)piperazine<br>MS m/z (M + H$^+$) 508.2 |
| 482 | 1-[1-({4-[(3,4-Dichlorobenzyl)oxy]-3-fluorophenyl}carbonyl)azetidin-3-yl]-4-(phenylcarbonyl)piperazine<br>MS m/z (M + H$^+$) 542.1 |
| 483 | 1-[1-({4-[(2,3-Dichlorobenzyl)oxy]-3-fluorophenyl}carbonyl)azetidin-3-yl]-4-(phenylcarbonyl)piperazine<br>MS m/z (M + H$^+$) 542.1 |
| 484 | 1-[1-({4-[(4-Chlorobenzyl)oxy]-3-iodophenyl}carbonyl)azetidin-3-yl]-4-(phenylcarbonyl)piperazine<br>MS m/z (M + H$^+$) 616.1 |
| 972 | 1-[1-({4-[(5-Chlorothiophen-2-yl)methoxy]phenyl}carbonyl)azetidin-3-yl]-4-(phenylcarbonyl)piperazine<br>MS m/z (M + H$^+$) 496.0 |
| 560 | 2-{[4-({3-[4-(Phenylcarbonyl)piperazin-1-yl]azetidin-1-yl}carbonyl)phenoxy]methyl}quinoline<br>MS m/z (M + H$^+$) 507.0 |
| 552 | 1-[1-({4-[(6-Bromopyridin-2-yl)methoxy]phenyl}carbonyl)azetidin-3-yl]-4-(phenylcarbonyl)piperazine<br>MS m/z (M + H$^+$) 535.0 |
| 957 | 1-[1-({4-[(3-Chlorobenzyl)oxy]phenyl}carbonyl)azetidin-3-yl]-4-(1,3-thiazol-2-ylcarbonyl)piperazine<br>MS m/z (M + H$^+$) 497.0 |
| 962 | 1-[1-({4-[(5-Chlorothiophen-2-yl)methoxy]phenyl}carbonyl)azetidin-3-yl]-4-(1,3-thiazol-2-ylcarbonyl)piperazine<br>MS m/z (M + H$^+$) 503.0 |
| 967 | 2-{[4-({3-[4-(1,3-Thiazol-2-ylcarbonyl)piperazin-1-yl]azetidin-1-yl}carbonyl)phenoxy]methyl}quinoline<br>MS m/z (M + H$^+$) 514.0 |
| 983 | 1-[1-({4-[(6-Bromopyridin-2-yl)methoxy]phenyl}carbonyl)azetidin-3-yl]-4-(1,3-thiazol-2-ylcarbonyl)piperazine<br>MS m/z (M + H$^+$) 543.8 |
| 960 | 1-[1-({4-[(3-Chlorobenzyl)oxy]phenyl}carbonyl)azetidin-3-yl]-4-(1,3-thiazol-4-ylcarbonyl)piperazine<br>MS m/z (M + H$^+$) 497.0 |

-continued

| Cpd | Cpd Name and Data |
|---|---|
| 963 | 1-[1-({4-[(5-Chlorothiophen-2-yl)methoxy]phenyl}carbonyl)azetidin-3-yl]-4-(1,3-thiazol-4-ylcarbonyl)piperazine<br>MS m/z (M + H$^+$) 503.0 |
| 970 | 2-{[4-({3-[4-(1,3-Thiazol-4-ylcarbonyl)piperazin-1-yl]azetidin-1-yl}carbonyl)phenoxy]methyl}quinoline<br>MS m/z (M + H$^+$) 514.0 |
| 987 | 1-[1-({4-[(6-Bromopyridin-2-yl)methoxy]phenyl}carbonyl)azetidin-3-yl]-4-(1,3-thiazol-4-ylcarbonyl)piperazine<br>MS m/z (M + H$^+$) 542.0 |

Example 27a

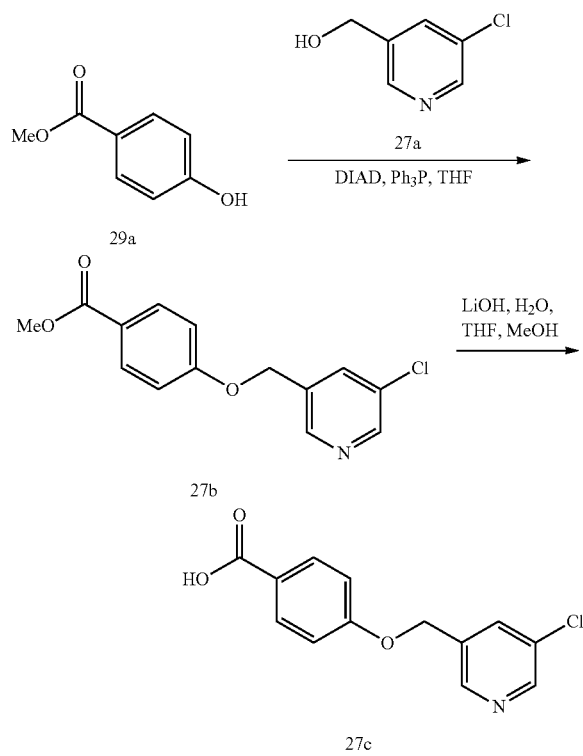

E. Methyl 4-((5-chloropyridin-3-yl)methoxy)benzoate, 27b. DIAD (2.35 mmol, 0.45 mL) was added to an ice-cold solution of methyl 4-hydroxybenzoate 29a (2.35 mmol, 358 mg), (5-chloropyridin-3-yl)methanol 27a (1.57 mmol, 225 mg), and Ph$_3$P (2.35 mmol, 616 mg) in 8 mL of THF. The mixture was stirred at 0° C. for 1 h at room temperature overnight. Water was added and the crude product was purified by flash column chromatography (silica gel, 20% EtOAc/hexanes) to afford 300 mg (68%) of 27b.

F. 4-((5-Chloropyridin-3-yl)methoxy)benzoic acid, 27c. Compound 27b (1.22 mmol, 340 mg) was combined with LiOH (4.9 mmol, 118 mg) in 3 mL of THF, 3 mL of MeOH, and 3 mL of water. The mixture was stirred at room temperature for 4 h and was then combined with 15% aqueous citric acid and extracted with EtOAc. The extracts were washed with water and brine, dried over Na$_2$SO$_4$, and concentrated under vacuum to give 288 mg of 27c.

Following the procedure described above for Example 1 or Example 27, and substituting the appropriate reagents, starting materials and purification methods known to those skilled in the art, the following compounds of the present invention were prepared:

| Cpd | Cpd Name and Data |
|---|---|
| 554 | 1-[1-({4-[(5-Chloropyridin-3-yl)methoxy]phenyl}carbonyl)azetidin-3-yl]-4-(phenylcarbonyl)piperazine<br>MS m/z (M + H$^+$) 491.0 |
| 978 | 1-[1-({4-[(5-Chloropyridin-3-yl)methoxy]phenyl}carbonyl)azetidin-3-yl]-4-(1,3-thiazol-2-ylcarbonyl)piperazine<br>MS m/z (M + H$^+$) 498.0 |
| 981 | 1-[1-({4-[(5-Chloropyridin-3-yl)methoxy]phenyl}carbonyl)azetidin-3-yl]-4-(1,3-thiazol-4-ylcarbonyl)piperazine<br>MS m/z (M + H$^+$) 498.0 |

Example 27b

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 958 | 1-[1-({4-[(3-Chlorobenzyl)oxy]phenyl}carbonyl)azetidin-3-yl]-4-(trifluoroacetyl)piperazine<br>MS m/z (M + H$^+$) 482.0 | N-TFA |
| 961 | 1-[1-({4-[(5-Chlorothiophen-2-yl)methoxy]phenyl}carbonyl)azetidin-3-yl]-4-(trifluoroacetyl)piperazine<br>MS m/z (M + H$^+$) 488.0 | N-TFA |
| 968 | 2-{[4-({3-[4-(Trifluoroacetyl)piperazin-1-yl]azetidin-1-yl}carbonyl)phenoxy]methyl}quinoline<br>MS m/z (M + H$^+$) 499.0 | N-TFA |
| 979 | 1-[1-({4-[(5-Chloropyridin-3-yl)methoxy]phenyl}carbonyl)azetidin-3-yl]-4-(trifluoroacetyl)piperazine | N-TFA |
| 984 | 1-[1-({4-[(6-Bromopyridin-2-yl)methoxy]phenyl}carbonyl)azetidin-3-yl]-4-(trifluoroacetyl)piperazine<br>MS m/z (M + H$^+$) 535.0 | N-TFA |

Example 28

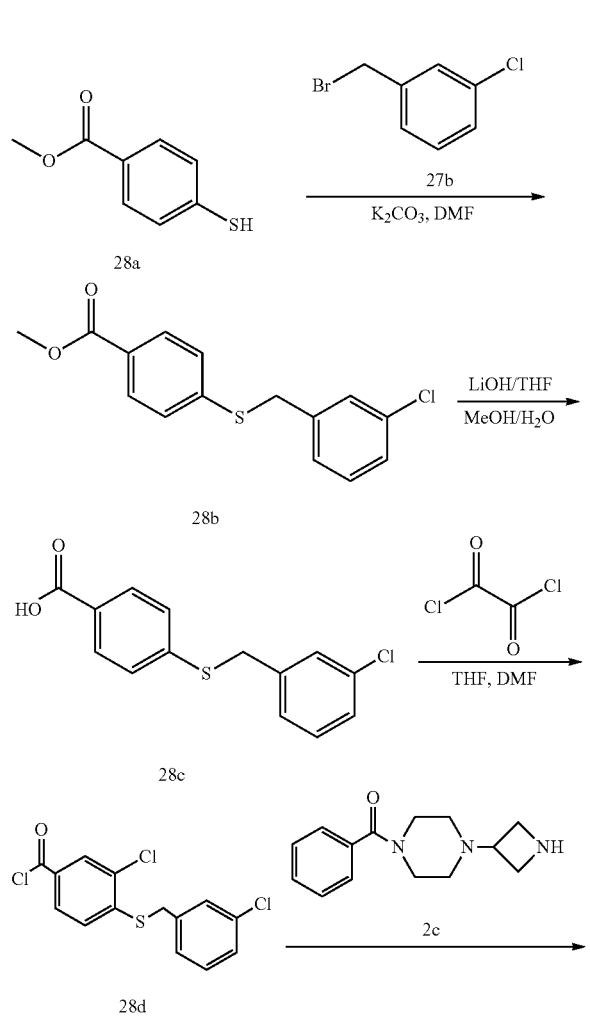

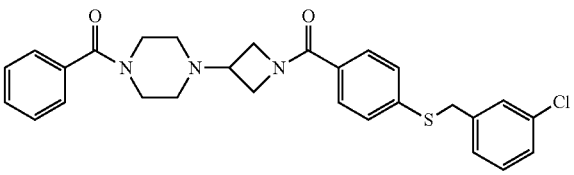

Cpd 410

A. Methyl 4-(3-chlorobenzylsulfanyl)benzoate, 28b. The title compound 28c was prepared using the method described in Example 27, substituting compound 28a for compound 27a in Procedure A.

B. 4-(3-Chlorobenzylsulfanyl)benzoic acid, 28c. The title compound 28c was prepared using the method described in Example 27, substituting compound 28b for compound 27c in Procedure B.

C. 4-(3-Chlorobenzylsulfanyl)benzoyl chloride, 28d. The title compound 28d was prepared using the method described in Example 27, substituting compound 28c for compound 27d in Procedure C.

D. 1-[1-({4-[(3-Chlorobenzyl)sulfanyl]phenyl}carbonyl)azetidi-3-yl]-4-(phenylcarbonyl)piperazine, Cpd 410. The title compound 410 was prepared using the method described in Example 27, substituting compound 28d for compound 27e in Procedure D. $^1$H NMR (CDCl$_3$): δ 7.52 (d, J=8.6 Hz, 2H), 7.37-7.44 (m, 5H), 7.24-7.29 (m, 3H), 7.18-7.24 (m, 3H), 4.18-4.33 (m, 2H), 4.09-4.17 (m, 3H), 4.01-4.08 (m, 1H), 3.92 (br. S, 1H), 3.74 (br. s, 1H), 3.35-3.63 (m, 2H), 3.17-3.29 (m, 1H), 2.20-2.50 (m, 4H); MS m/z (M+H$^+$) 506.0.

Following the procedure described above for Example 28 and substituting the appropriate reagents, starting materials and purification methods known to those skilled in the art, the following compounds of the present invention were prepared:

| Cpd | Cpd Name and Data |
|---|---|
| 411 | 1-[1-({4-[(2,3-Dichlorobenzyl)sulfanyl]phenyl}carbonyl)azetidin-3-yl]-4-(phenylcarbonyl)piperazine<br>$^1$H NMR (CDCl$_3$): δ 7.52 (d, J = 8.3 Hz, 2H), 7.38-7.43 (m, 5H), 7.29 (d, J = 8.6 Hz, 2H), 7.27 (d, J = 7.1 Hz, 1H), 7.2 (d, J = 7.4 Hz, 1H), 7.11 (q, J = 7.8 Hz, 1H), 4.24-4.38 (m, 4H), 4.22 (br. s., 1H), 4.12-4.21 (m, 1H), 4.02-4.12 (m, 1H), 3.91 (br. s., 1H), 3.77 (br. s., 1H), 3.47 (s, 2H), 3.15-3.29 (m, 1H), 2.44 (br. s., 4H).<br>MS m/z (M + H$^+$) 540.0 |
| 412 | 1-[1-({4-[(3-Chlorobenzyl)sulfanyl]phenyl}carbonyl)azetidin-3-yl]-4-(1,3-thiazol-2-ylcarbonyl)piperazine<br>$^1$H NMR (CDCl$_3$): δ 7.88 (d, J = 3.3 Hz, 1H), 7.49-7.57 (m, 3H), 7.25-7.30 (m, 3H), 7.18-7.25 (m, 3H), 4.51 (br. s., 2H), 4.21-4.34 (m, 2H), 4.03-4.21 (m, 4H), 3.72-3.94 (m, 2H), 3.18-3.29 (m, 1H), 2.35-2.59 (m, 4H).<br>MS m/z (M + H$^+$) 513.0 |
| 413 | 1-[1-({4-[(2,3-Dichlorobenzyl)sulfanyl]phenyl}carbonyl)azetidin-3-yl]-4-(1,3-thiazol-2-ylcarbonyl)piperazine<br>$^1$H NMR (CDCl$_3$): δ 7.88 (d, J = 3.0 Hz, 1H), 7.50-7.57 (m, 3H), 7.38 (dd, J = 7.8, 1.5 Hz, 1H), 7.26-7.33 (m, 3H), 7.22 (dd, J = 7.7, 1.4 Hz, 1H), 7.11 (t, J = 7.8 Hz, 1H), 4.44 (br. d., J = 32.6 Hz, 2H), 4.22-4.35 (m, 4H), 4.15-4.22 (m, 1H), 4.04-4.15 (m, 1H), 3.85 (d, J = 17.4 Hz, 2H), 3.19-3.29 (m, 1H), |

| Cpd | Cpd Name and Data |
|---|---|
| | 2.37-2.56 (m, 4H).<br>MS m/z (M + H⁺) 547.0. |
| 414 | 1-[1-({4-[(3,4-Dichlorobenzyl)sulfanyl]phenyl}carbonyl)azetidin-3-yl]-4-(1,3-thiazol-2-ylcarbonyl)piperazine<br>$^1$H NMR (CDCl$_3$): δ 7.88 (d, J = 3.3 Hz, 1H), 7.54 (d, J = 3.3 Hz, 2H), 7.51-7.53 (m, 1H), 7.40 (d, J = 2.0 Hz, 1H), 7.36 (d, J = 8.3 Hz, 1H), 7.24-7.29 (m, 3H), 7.13-7.17 (m, 1H), 4.48-4.59 (m, 1H), 4.35-4.48 (m, 1H), 4.20-4.34 (m, 2H), 4.13-4.20 (m, 1H), 4.01-4.13 (m, 4H), 3.79-3.94 (m, 2H), 3.19-3.29 (m, 1H), 2.37-2.57 (m, 4H).<br>MS m/z (M + H⁺) 547.0. |
| 415 | 1-[1-({4-[(4-Chlorobenzyl)sulfanyl]phenyl}carbonyl)azetidin-3-yl]-4-(1,3-thiazol-2-ylcarboyl)piperazine<br>$^1$H NMR (CDCl$_3$): δ 7.87 (d, J = 3.3 Hz, 1H), 7.55 (d, J = 3.3 Hz, 1H), 7.53 (d, J = 8.6 Hz, 2H), 7.27-7.29 (m, 2H), 7.24-7.27 (m, 4H), 4.51 (br. s., 1H), 4.35-4.47 (m, 1H), 4.20-4.33 (m, 2H), 4.02-4.20 (m, 4H), 3.76-3.93 (m, 2H), 3.18-3.28 (m, 1H), 2.38-2.54 (m, 4H).<br>MS m/z (M + H⁺) 513.0 |
| 416 | 1-[1-({4-[(Pyridin-3-ylmethyl)sulfanyl]phenyl}carbonyl)azetidin-3-yl]-4-(1,3-thiazol-2-ylcarbonyl)piperazine<br>$^1$H NMR (CDCl$_3$): δ 8.55 (s, 1H), 8.48 (s, 1H), 7.82-7.93 (m, 1H), 7.65 (br. s., 1H), 7.47-7.60 (m, 3H), 7.18-7.36 (m, 3H), 4.44 (d, J = 33.9 Hz, 2H), 4.03-4.32 (m, 5H), 3.86 (br. s., 2H), 3.23 (br. s., 1H), 2.47 (br. s., 4H) |
| 417 | 1-[1-({4-[(3,4-Dichlorobenzyl)sulfanyl]phenyl}carbonyl)azetidin-3-yl]-4-(phenylcarbonyl)piperazine<br>MS m/z (M + H⁺) 540.1 |
| 418 | 1-[1-({4-[(4-Chlorobenzyl)sulfanyl]phenyl}carbonyl)azetidin-3-yl]-4-(phenylcarbonyl)piperazine<br>MS m/z (M + H⁺) 506.2 |
| 555 | 1-(Phenylcarbonyl)-4-[1-({4-[(pyridin-3-ylmethyl)sulfanyl]phenyl}carbonyl)azetidin-3-yl]piperazine<br>MS m/z (M + H⁺) 473.0 |
| 550 | 1-(Phenylcarbonyl)-4-{1-[(4-{[3-(trifluoromethyl)benzyl]sulfanyl}phenyl)carbonyl]azetidin-3-yl}piperazine<br>MS m/z (M + H⁺) 540.0 |
| 973 | 1-(1,3-Thiazol-2-ylcarbonyl)-4-{1-[(4-{[3-(trifluoromethyl)benzyl]sulfanyl}phenyl)carbonyl]azetidin-3-yl}piperazine<br>MS m/z (M + H⁺) 547.0 |
| 975 | 1-(1,3-Thiazol-4-ylcarbonyl)-4-{1-[(4-{[3-(trifluoromethyl)benzyl]sulfanyl}phenyl)carbonyl]azetidin-3-yl}piperazine<br>MS m/z (M + H⁺) 531.8 |

Example 28a

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 974 | 1-(Trifluoroacetyl)-4-{1-[(4-{[3-(trifluoromethyl)benzyl]sulfanyl}phenyl)carbonyl]-azetidin-3-yl}piperazine<br>MS m/z (M + H⁺) 532.0 | N-TFA |

Example 29

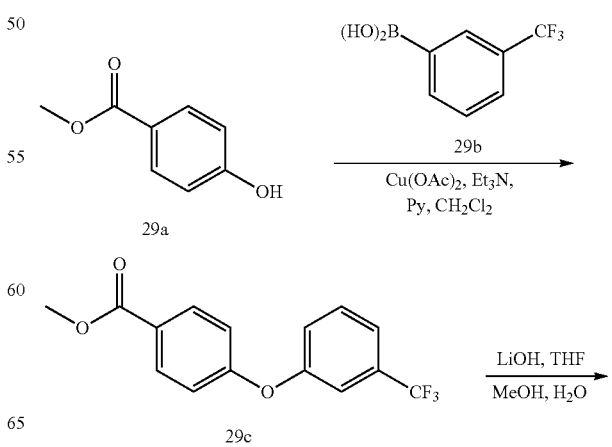

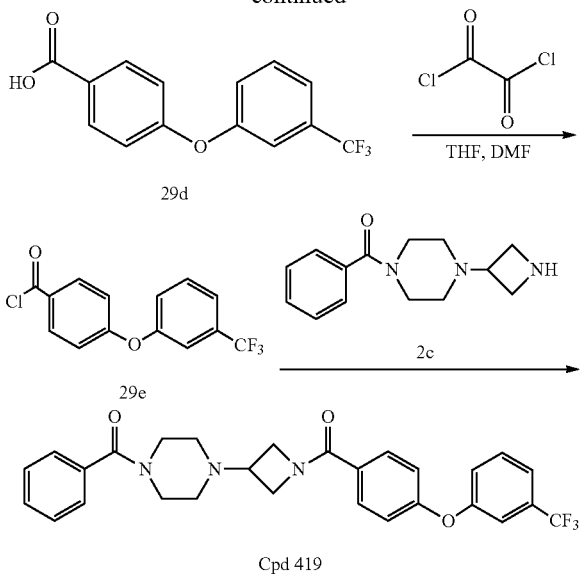

Cpd 419

A. Methyl 4-(3-trifluoromethyl-phenoxy)-benzoate, 29c. To a solution of compound 29a (400 mg, 2.63 mmol) and compound 29b (1.0 g, 5.26 mmol) in CH$_2$Cl$_2$ (24 mL) was added Cu(OAc)$_2$ (714 mg, 3.94 mmol), 4A sieves (400 mg, powder, activated), pyridine (2 mL), and Et$_3$N (2 mL). The resultant reaction mixture was stirred at room temperature for 2 days. Water was added to the mixture, and the mixture was filtered. The filtrate was extracted with EtOAc (3×), the combined organic extracts dried over Na$_2$SO$_4$, filtered, and concentrated under reduced pressure. The residue was purified by silica gel flash column chromatography, eluting with 20% EtOAc/hexanes to give compound 29c (470 mg).

B. 4-(3-Trifluoromethyl-phenoxy)-benzoic acid (29d). A mixture of compound 29c (577 mg, 1.95 mmol) and LiOH (187 mg, 7.80 mmol) in THF/MeOH/H$_2$O (4/4/4 mL) was stirred for 4 h. A 15% citric acid solution (20 mL) was added, and the mixture was then extracted with EtOAc (3×). The combined extracts were washed with brine, dried over Na$_2$SO$_4$, filtered, and concentrated under reduced pressure. The residue, compound 29d, was dried under reduced pressure for 18 h and was used without purification.

C. 4-(3-Trifluoromethyl-phenoxy)-benzoyl chloride, 29e. To a solution of compound 29d (100 mg, 0.35 mmol) in THF (2 mL) was added oxalyl dichloride (46 µL, 0.53 mmol) dropwise at 0° C., followed by addition of 2 drops of DMF. The resulting mixture was stirred at 0° C. for 3 h, and was then warmed up to room temperature overnight. The solvents were removed under reduced pressure, and the residue, compound 29e, was dried under reduced pressure for 2 h and then used in the next step without further purification.

D. 1-(Phenylcarbonyl)-4-[1-({4-[3-(trifluoromethyl)phenoxy]phenyl}carbonyl)azetidin-3-yl]piperazine, Cpd 419. To a mixture of compound 2c (80 mg, 0.32 mmol), Et$_3$N (0.5 mL), and CH$_2$Cl$_2$ (2.5 mL) was added a solution of compound 29e in CH$_2$Cl$_2$ (1 mL). The resultant mixture was stirred at room temperature for 4 h. The solvent was removed under reduced pressure, and the resultant residue was dissolved in CH$_2$Cl$_2$ (1 mL), directly loaded onto a silica gel column, and purified by silica gel flash column chromatography with 5% MeOH/CH$_2$Cl$_2$ to give compound 419 (53 mg). $^1$H NMR (CDCl$_3$): δ 7.65 (d, J=8.6 Hz, 2H), 7.45-7.53 (m, 1H), 7.41 (br. s, 6H), 7.25-7.34 (m, 1H), 7.17-7.25 (m, 1H), 7.01 (d, J=7.3 Hz, 2H), 4.17-4.38 (m, 3H), 4.11 (br. s, 1H), 3.92 (br. s, 1H), 3.78 (br. s, 1H), 3.49 (br. s, 2H), 3.19-3.32 (m, 1H), 2.45 (br. s, 4H). MS m/z (M+H$^+$) 510.0.

Following the procedure described above for Example 29 and substituting the appropriate reagents, starting materials and purification methods known to those skilled in the art, the following compounds of the present invention were prepared:

| Cpd | Cpd Name and Data |
|---|---|
| 420 | 1-(1-{[4-(4-Chlorophenoxy)phenyl]carbonyl}azetidin-3-yl)-4-(1,3-thiazol-2-ylcarbonyl)piperazine<br>$^1$H NMR (CDCl$_3$): δ 7.88 (d, J = 3.0 Hz, 1H), 7.64 (d, J = 8.6 Hz, 2H), 7.55 (d, J = 3.0 Hz, 1H), 7.33 (d, J = 8.8 Hz, 2H), 6.98 (d, J = 8.8 Hz, 4H), 4.52 (br. s., 1H), 4.38-4.48 (br. S, 1H), 4.15-4.37 (m, 3H), 4.10 (br. s., 1H), 3.88 (br. s., 1H), 3.82 (br. s., 1H), 3.19-3.31 (m, 1H), 2.35-2.60 (m, 4H).<br>MS m/z (M + H$^+$) 483.1 |
| 421 | 1-(1-{[4-(3-Chlorophenoxy)phenyl]carbonyl}azetidin-3-yl)-4-(1,3-thiazol-2-ylcarbonyl)piperazine<br>$^1$H NMR (CDCl$_3$): δ 7.88 (d, J = 3.3 Hz, 1H), 7.65 (tt, J1 = 2 Hz, J2 = 8.8 Hz, 2H), 7.545 (d, J = 3.3 Hz, 1H), 7.26-7.30 (m, 1H), 7.14 (dt, J = 8.1, 1.0 Hz, 1H), 6.98-7.06 (m, 3H), 6.93-6.95 (m, 1H), 6.91-6.95 (m, 1H), 4.56 (br.s, 1H), 4.43 (br. s., 1H), 4.17-4.38 (m, 3H), 4.04-4.16 (m, 1H), 3.75-3.96 (m, 2H), 3.20-3.31 (m, 1H), 2.39-2.60 (m, 4H).<br>MS m/z (M + H$^+$) 483.0 |
| 422 | 1-(1-{[4-(3,4-Dichlorophenoxy)phenyl]carbonyl}azetidin-3-yl)-4-(phenylcarbonyl)piperazine.<br>$^1$H NMR (CDCl$_3$): δ 7.65 (d, J = 8.6 Hz, 2H), 7.37-7.46 (m, 6H), 7.12 (d, J = 2.8 Hz, 1H), 7.00 (d, J = 8.8 Hz, 2H), 6.89 (dd, J = 8.8, 2.8 Hz, 1H), 4.16-4.37 (m, 3H), 4.10 (br. s., 1H), 3.92 (br. s., 1H), 3.68-3.84 (m, 1H), 3.46 (s, 2H), 3.19-3.30 (m, 1H), 2.44 (br. s., 4H).<br>MS m/z (M + H$^+$) 510.0 |
| 423 | 1-(1-{[4-(3,4-Dichlorophenoxy)phenyl]carbonyl}azetidin-3-yl)-4-(1,3-thiazol-2-ylcarbonyl)piperazine<br>$^1$H NMR (CDCl$_3$): δ 7.88 (d, J = 3.3 Hz, 1H), 7.66 (d, J = 8.8 Hz, 2H), 7.55 (d, J = 3.3 Hz, 1H), 7.42 (d J = 8.8 Hz, 1H), 7.13 (d, J = 2.8 Hz, 1H), 7.0 (d, J = 8.6 Hz, 2H), 6.90 (dd, J = 8.8, 2.8 Hz, 1H), 4.53 (br. s., 1H), 4.44 (br. S, 1H), 4.17-4.38 (m, 3H), 4.11 (dd, J = 9.0, 4.7 Hz, 1H), 3.88 (br. s., 1H), 3.83 (br. s., 1H), 3.20-3.32 (m, 1H), 2.50 (t, J = 4.7 Hz, 4H).<br>MS m/z (M + H$^+$) 517.0 |
| 424 | 1-(1,3-Thiazol-2-ylcarbonyl)-4-[1-({4-[3-(trifluoromethyl)phenoxy]phenyl}carbonyl)azetidin-3-yl]piperazine<br>$^1$H NMR (CDCl$_3$): δ 7.88 (d, J = 3.3 Hz, 1H), 7.67 (d, J = 8.6 Hz, 2H), 7.55 (d, J = 3.0 Hz, 1H), 7.49 (t, J = 8.0 Hz, 1H), 7.41 (d, J = 7.8 Hz, 1H), 7.21 (d, J = 8.1 Hz, 1H), 7.03 (d, J = 8.6 Hz, 2H), 4.53 (br. s., 1H), 4.44 (br. s, 1H), 4.17-4.38 (m, 3H), 4.16-4.05 (m, 1H), 3.86 (d, J = 19.2 Hz, 2H), 3.20-3.33 (m, 1H), 2.37-2.60 (m, 4H).<br>MS m/z (M + H$^+$) 517.0 |
| 425 | 1-(1-{[4-(4-Chlorophenoxy)phenyl]carbonyl}azetidin-3-yl)-4-(phenylcarbonyl)piperazine<br>MS m/z (M + H$^+$) 476.2 |
| 426 | 1-(1-{[4-(3-Chlorophenoxy)phenyl]carbonyl}azetidin-3-yl)-4-(phenylcarbonyl)piperazine<br>MS m/z (M + H$^+$) 476.2 |
| 662 | 1-(1-{[4-(3-Chlorophenoxy)-3-fluorophenyl]carbonyl}azetidin-3-yl)-4-(1,3-thiazol-4-ylcarbonyl)piperazine<br>MS m/z (M + H$^+$) 500.8 |

Example 29a

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 931 | 1-(1-{[4-(3-Chlorophenoxy)-3-fluorophenyl]carbonyl}azetidin-3-yl)-4-(trifluoroacetyl)piperazine<br>MS m/z (M + H$^+$) 485.8 | N-TFA |

Example 30

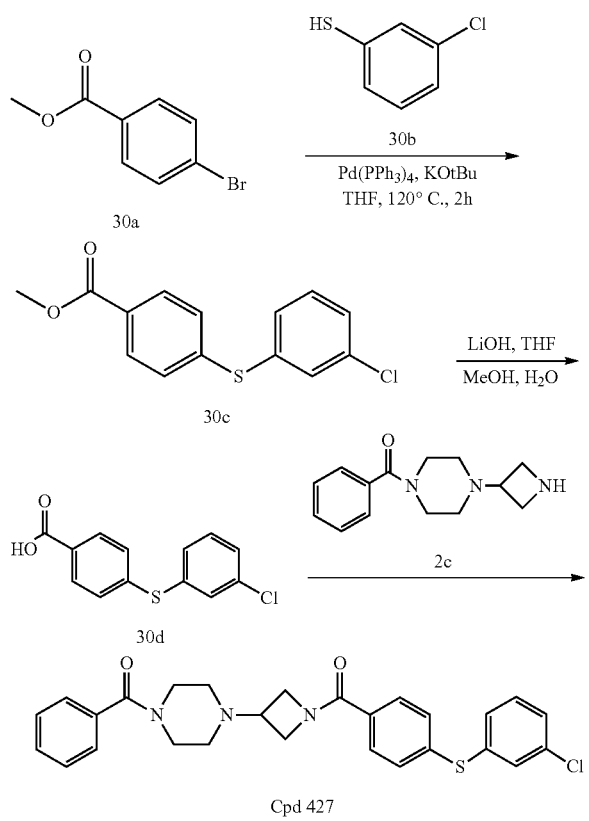

Cpd 427

A. Methyl 4-(3-chloro-phenylsulfanyl)-benzoate (30c). A mixture of compound 30a (400 mg, 1.86 mmol), compound 30b (321 mg, 2.23 mmol), Pd(PPh$_3$)$_4$ (215 mg, 0.186 mmol), KOtBu (2.23 mL, 2.23 mmol, 1M solution in THF), and THF (3.5 mL) were heated in a microwave reactor at 130° C. for 2 h, then poured into water (50 mL). The mixture was extracted with EtOAc (3×). The combined organic extracts were dried over Na$_2$SO$_4$, filtered, and concentrated under reduced pressure. The residue was purified by silica gel flash column chromatography, eluting with 5% EtOAc/hexanes to give compound 30c (220 mg).

B. 4-(3-Chloro-phenylsulfanyl)benzoic acid (30d). A mixture of compound 30c (320 mg, 1.15 mmol), LiOH (110 mg, 4.59 mmol) in THF/MeOH/H$_2$O (3/3/3 mL) was stirred for 4 h. A 15% aqueous citric acid solution (10 mL) was added. The mixture was then extracted with EtOAc (3×). The combined organic extracts were washed with brine, filtered, dried over Na$_2$SO$_4$, and concentrated under reduced pressure. The resultant residue (compound 30d, 290 mg) was dried under reduced pressure for 18 h and was used without further purification.

C. 4-(1-{[4-(3-Chloro-phenylsulfanyl)phenyl]carbonyl}azetidin-3-yl)-1-(phenylcarbonyl)-piperazine, Cpd 427. A mixture of compound 30d (60 mg, 0.23 mmol), compound 2c (83 mg, 0.29 mmol), and HATU (129 mg, 0.34 mmol) in Et$_3$N and DMF (1 mL/3 mL) was stirred for 18 h, and then poured into water (10 mL). The mixture was then extracted with EtOAc (3×). The combined organic extracts were washed with brine (2×), dried over Na$_2$SO$_4$, filtered, and concentrated under reduced pressure. The resultant residue was purified on silica gel, eluting with 5% MeOH/CH$_2$Cl$_2$ to give compound 427 (33 mg). MS m/z (M+H$^+$) 492.1.

Following the procedure described above for Example 30 and substituting the appropriate reagents, starting materials and purification methods known to those skilled in the art, the following compounds of the present invention were prepared:

| Cpd | Cpd Name and Data |
|---|---|
| 428 | 1-[1-({4-[(3-Chlorophenyl)sulfanyl]phenyl}carbonyl)azetidin-3-yl]-4-(1,3-thiazol-2-ylcarbonyl)piperazine<br>MS m/z (M + H$^+$) 499.1 |
| 429 | 1-[1-({4-[(3-Chlorophenyl)sulfanyl]phenyl}carbonyl)azetidin-3-yl]-4-(1,3-thiazol-4-ylcarbonyl)piperazine<br>MS m/z (M + H$^+$) 499.1 |
| 430 | 1-(Phenylcarbonyl)-4-{1-[(4-{[3-(trifluoromethyl)phenyl]sulfanyl}phenyl)carbonyl]azetidin-3-yl}piperazine<br>MS m/z (M + H$^+$) 526.2 |
| 431 | 1-(1,3-Thiazol-2-ylcarbonyl)-4-{1-[(4-{[3-(trifluoromethyl)phenyl]sulfanyl}phenyl)carbonyl]azetidin-3-yl}piperazine<br>MS m/z (M + H$^+$) 533.1 |
| 432 | 1-(1,3-Thiazol-4-ylcarbonyl)-4-{1-[(4-{[3-(trifluoromethyl)phenyl]sulfanyl}phenyl)carbonyl]azetidin-3-yl}piperazine<br>MS m/z (M + H$^+$) 533.1 |

Example 30a

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 677 | 1-[1-({4-[(3-Chlorophenyl)sulfanyl]phenyl}carbonyl)azetidin-3-yl]-4-(trifluoroacetyl)piperazine<br>MS m/z (M + H$^+$) 483.8 | N-TFA |
| 790 | 1-(Trifluoroacetyl)-4-{1-[(4-{[3-(trifluoromethyl)phenyl]sulfanyl}phenyl)carbonyl]-azetidin-3-yl}piperazine<br>MS m/z (M + H$^+$) 517.9 | N-TFA |

Example 31

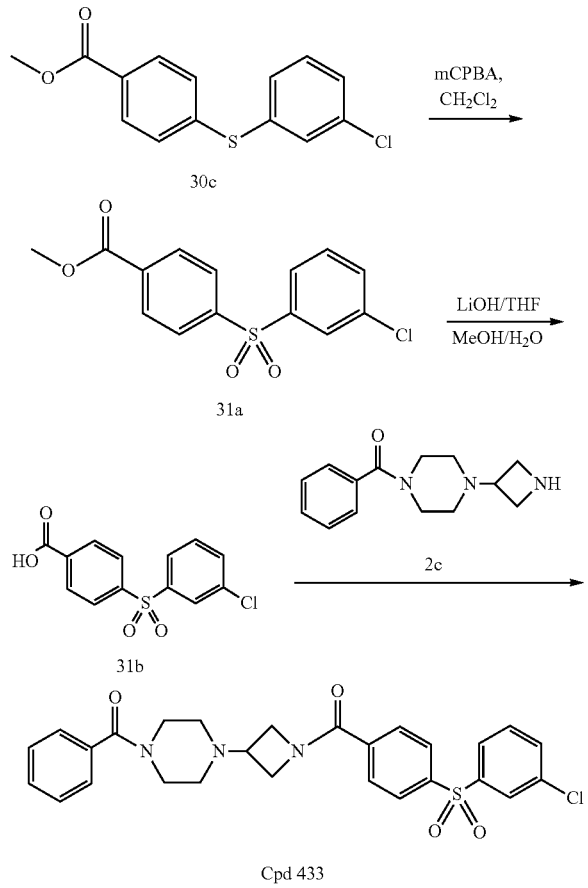

Cpd 433

A. 4-(3-Chloro-benzensulfonyl)-benzoic acid methyl ester (31a).
To a solution of compound 30c (200 mg, 0.72 mmol) in $CH_2Cl_2$ (5 mL) was added mCPBA (320 mg, 1.43 mmol) at 0° C. After 2 h, the mixture was poured into 2N KOH solution (20 mL) and extracted with EtOAc (3×). The combined organic extracts were dried over $Na_2SO_4$, filtered, and concentrated under reduced pressure. The residue was purified by flash column chromatography on silica gel, eluting with 5% EtOAc/hexanes to give compound 31a (138 mg).

B. 4-(3-Chloro-benzensulfonyl)-benzoic acid (31b). A mixture of compound 31a (138 mg, 0.44 mmol) and LiOH (42 mg, 1.77 mmol) in THF/MeOH/$H_2O$ (2/2/2 mL) was stirred for 4 h. A 15% citric acid solution (10 mL) was added. The mixture was then extracted with EtOAc (3×). The combined organic extracts were washed with brine, dried over $Na_2SO_4$, filtered, and concentrated under reduced pressure. The resultant residue, compound 31b (130 mg) was dried under reduced pressure for 18 h and used without further purification.

C. 1-[1-({4-[(3-Chlorophenyl)sulfonyl]phenyl}carbonyl)azetidin-3-yl]-4-(phenylcarbonyl)piperazine, Cpd 433. A mixture of compound 31b (40 mg, 0.14 mmol), compound 2c (49 mg, 0.18 mmol), and HATU (80 mg, 0.20 mmol) in $Et_3N$ (1 mL) and DMF (2 mL) was stirred for 18 h, and was then poured into water (10 mL). The mixture was then extracted with EtOAc (3×). The combined organic extracts were washed with brine (2×), dried over $Na_2SO_4$, filtered, and concentrated under reduced pressure. The residue was purified by flash column chromatography on silica gel, eluting with 5% MeOH/$CH_2Cl_2$ to give compound 428 (29 mg). MS m/z (M+H$^+$) 524.1.

Following the procedure described above for Example 31, and substituting the appropriate reagents, starting materials and purification methods known to those skilled in the art, the following compounds of the present invention were prepared:

| Cpd | Cpd Name and Data |
|---|---|
| 508 | 1-(Phenylcarbonyl)-4-{1-[(4-{[3-(trifluoromethyl)phenyl]sulfonyl}phenyl)carbonyl]azetidin-3-yl}piperazine<br>MS m/z (M + H$^+$) 558.0 |
| 876 | 1-[1-({4-[(3-Chlorophenyl)sulfonyl]phenyl}carbonyl)azetidin-3-yl]-4-(1,3-thiazol-2-ylcarbonyl)piperazine<br>MS m/z (M + H$^+$) 530.8 |
| 651 | 1-(1,3-Thiazol-2-ylcarbonyl)-4-{1-[(4-{[3-(trifluoromethyl)phenyl]sulfonyl}phenyl)carbonyl]azetidin-3-yl}piperazine<br>MS m/z (M + H$^+$) 564.8 |
| 1507 | 1-(1,3-Thiazol-4-ylcarbonyl)-4-{1-[(4-{[3-(trifluoromethyl)benzyl]sulfonyl}phenyl)carbonyl]azetidin-3-yl}piperazine<br>MS m/z (M + H$^+$) 578.8 |
| 738 | 1-(1,3-Thiazol-4-ylcarbonyl)-4-{1-[(4-{[3-(trifluoromethyl)phenyl]sulfonyl}phenyl)carbonyl]azetidin-3-yl}piperazine<br>MS m/z (M + H$^+$) 564.6 |

Example 31a

Following the procedure described above for Example 31 and substituting the appropriate reagents, starting materials, and purification methods known to those skilled in the art, the following intermediate compounds were prepared:

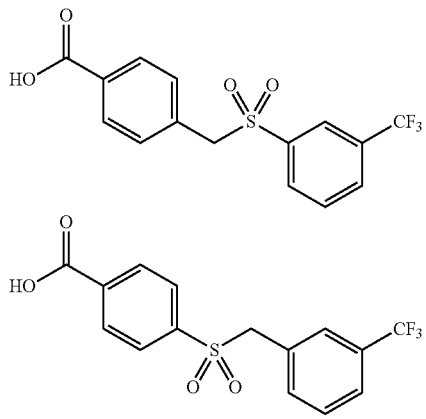

Following the procedure described above for Example 31 and substituting the appropriate reagents, starting materials and purification methods known to those skilled in the art, the following compounds of the present invention were prepared:

| Cpd | Cpd Name and Data |
|---|---|
| 976 | 1-(1,3-Thiazol-2-ylcarbonyl)-4-(1-{[4-({[3-(trifluoromethyl)phenyl]sulfonyl}methyl)phenyl]carbonyl}azetidin-3-yl)piperazine |

| Cpd | Cpd Name and Data |
|---|---|
| | $^1$H NMR (CDCl$_3$): δ 7.80-7.97 (m, 4H), 7.63-7.73 (m, 1H), 7.56 (dd, J = 5.7, 2.4 Hz, 2H), 7.18 (d, J = 8.1 Hz, 2H), 4.34-4.60 (m, 3H), 4.20-4.33 (m, 2H), 4.03-4.20 (m, 2H), 3.86 (br. s., 2H), 3.15-3.32 (m, 1H), 2.37-2.60 (m, 4H), MS m/z (M + H$^+$) 578.8 |
| 564 | 1-(Phenylcarbonyl)-4-(1-{[4-({[3-(trifluoromethyl)phenyl]sulfonyl}methyl)phenyl]carbonyl}azetidin-3-yl)piperazine<br>MS m/z (M + H$^+$) 572.0 |
| 971 | 1-(1,3-Thiazol-2-ylcarbonyl)-4-{1-[(4-{[3-(trifluoromethyl)benzyl]sulfonyl}phenyl)carbonyl]azetidin-3-yl}piperazine<br>$^1$H NMR (CDCl$_3$): δ 7.88 (d, J = 3.3 Hz, 1H), 7.65-7.77 (m, 4H), 7.52-7.65 (m, 2H), 7.35-7.52 (m, 2H), 7.24 (s, 1H), 4.39 (s, 4H), 4.17-4.33 (m, 2H), 4.12 (q, J = 7.1 Hz, 2H), 3.86 (br. s., 2H), 3.19-3.34 (m, 1H), 2.38-2.59 (m, 4H).<br>MS m/z (M + H$^+$) 578.8 |
| 977 | 1-(1,3-Thiazol-4-ylcarbonyl)-4-(1-{[4-({[3-(trifluoromethyl)phenyl]sulfonyl}methyl)phenyl]carbonyl}azetidin-3-yl)piperazine<br>MS m/z (M + H$^+$) 578.6 |

Example 31b

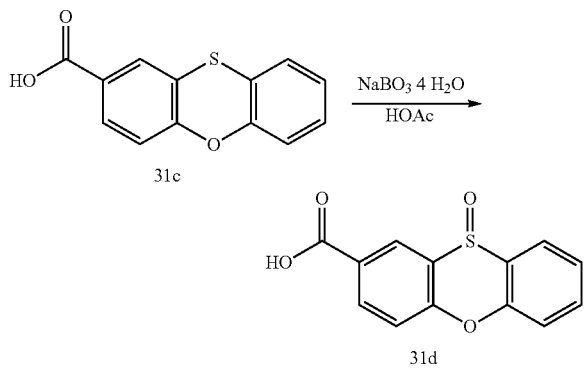

D. 10-Oxidophenoxathiine-2-carboxylic acid, 31d. A mixture of phenoxathiine-2-carboxylic acid 31c (0.41 mmol, 100 mg) and sodium perborate tetrahydrate (0.82 mmol, 126 mg) in 3 mL of HOAc was stirred for 6 days at room temperature. TLC indicated 90% conversion to 31d. Water was added and the resulting precipitate was filtered and dried to give 65 mg of 31d, 90% pure.

Following the procedure described above for Example 9 and substituting the appropriate reagents, starting materials and purification methods known to those skilled in the art, the following compounds of the present invention were prepared:

| Cpd | Cpd Name and Data |
|---|---|
| 807 | 1-{1-[(10-Oxidophenoxathiin-2-yl)carbonyl]azetidin-3-yl}-4-(1,3-thiazol-2-ylcarbonyl)piperazine<br>MS m/z (M + H$^+$) 495.1 |

Example 31c

Following the procedure described above for Example 1c, and substituting the appropriate reagents, starting materials and purification methods known to those skilled in the art, the following compound of the present invention was prepared:

| Cpd | Cpd Name and Data | Salt Form |
|---|---|---|
| 914 | 1-[1-({4-[(3-Chlorophenyl)sulfonyl]phenyl}carbonyl)azetidin-3-yl]-4-(trifluoroacetyl)piperazine<br>MS m/z (M + H$^+$) 516.8 | N-TFA |
| 1493 | 1-(Trifluoroacetyl)-4-{1-[(4-{[3-(trifluoromethyl)phenyl]sulfonyl}phenyl)carbonyl]azetidin-3-yl}piperazine<br>MS m/z (M + H$^+$) 550.5 | N-TFA |
| 1498 | 1-(Trifluoroacetyl)-4-(1-{[4-({[3-(trifluoromethyl)phenyl]sulfonyl}methyl)phenyl]carbonyl}azetidin-3-yl)piperazine<br>MS m/z (M + H$^+$) 563.8 | N-TFA |

Example 32

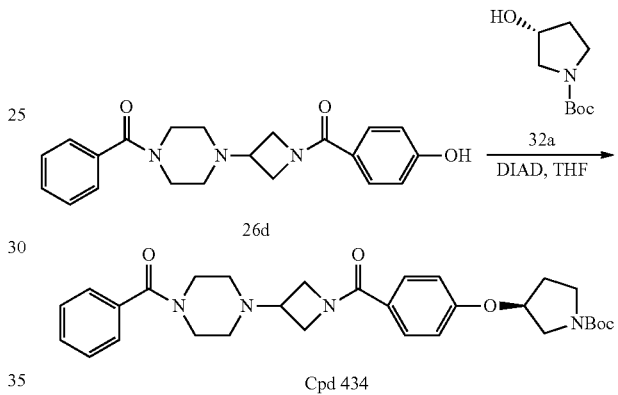

tert-Butyl (3S)-3-[4-({3-[4-(phenylcarbonyl)piperazin-1-yl]azetidin-1-yl}carbonyl)phenoxy]pyrrolidine-1-carboxylate, Cpd 434. To a solution of compound 26d (100 mg, 0.273 mmol) and (R)—N-Boc-3-hydroxyproline in THF was added DIAD at 0° C. The resulting reaction mixture was stirred for 18 h. After dilution with water and extraction with EtOAc (3×), the combined organic extracts were dried over Na$_2$SO$_4$, filtered, and concentrated under reduced pressure. The resultant residue was purified by flash column chromatography on silica gel using 5% MeOH/CH$_2$Cl$_2$ to give compound 434 (95 mg). $^1$H NMR (CDCl$_3$): δ 7.52 (d, J=8.6 Hz, 2H), 7.37-7.44 (m, 5H), 7.24-7.29 (m, 3H), 7.18-7.24 (m, 3H), 4.18-4.33 (m, 2H), 4.09-4.17 (m, 3H), 4.01-4.08 (m, 1H), 3.92 (br. S, 1H), 3.74 (br. s, 1H), 3.35-3.63 (m, 2H), 3.17-3.29 (m, 1H), 2.20-2.50 (m, 4H); MS m/z (M+H$^+$) 506.0.

Following the procedure described above for Example 32 and substituting the appropriate reagents, starting materials and purification methods known to those skilled in the art, the following compounds of the present invention were prepared:

| Cpd | Cpd Name and Data |
|---|---|
| 435 | 1-(1-{[4-(Cyclohexyloxy)phenyl]carbonyl}azetidin-3-yl)-4-(phenylcarbonyl)piperazine<br>$^1$H NMR (CDCl$_3$): δ 7.58 (d, J = 8.8 Hz, 2H), 7.36-7.44 (m, 5H), 6.88 (d, J = 8.8 Hz, 2H), 4.26-4.38 (m, 2H), 4.25-4.12 (m, 2H), 4.07 (br. s, 1H), 3.82-3.99 (m, 1H), 3.48 (br. s., 2H), 3.15-3.26 (m, 1H), 2.17-2.54 (m, 4H), 1.93-2.03 (m, 1H), 1.75-1.89 (m, 2H), 1.46-1.63 (m, 2H), |

-continued

| Cpd | Cpd Name and Data |
|---|---|
| | 1.31-1.46 (m, 3H), 1.21-1.31 (m, 2H).<br>MS m/z (M + H+) 448.0 |
| 436 | 1-(1-{[4-(Cyclopentyloxy)phenyl]carbonyl}azetidin-3-yl)-4-(phenylcarbonyl)piperazine<br>MS m/z (M + H+) 434.2 |
| 437 | tert-Butyl 4-[4-({3-[4-(phenylcarbonyl)piperazin-1-yl]azetidin-1-yl}carbonyl)phenoxy]piperidine-1-carboxylate<br>MS m/z (M + H+) 549.3 |
| 438 | tert-Butyl (3R)-3-[4-({3-[4-(phenylcarbonyl)piperazin-1-yl]azetidin-1-yl}carbonyl)phenoxy]pyrrolidine-1-carboxylate<br>MS m/z (M + H+) 535.3 |

Example 33

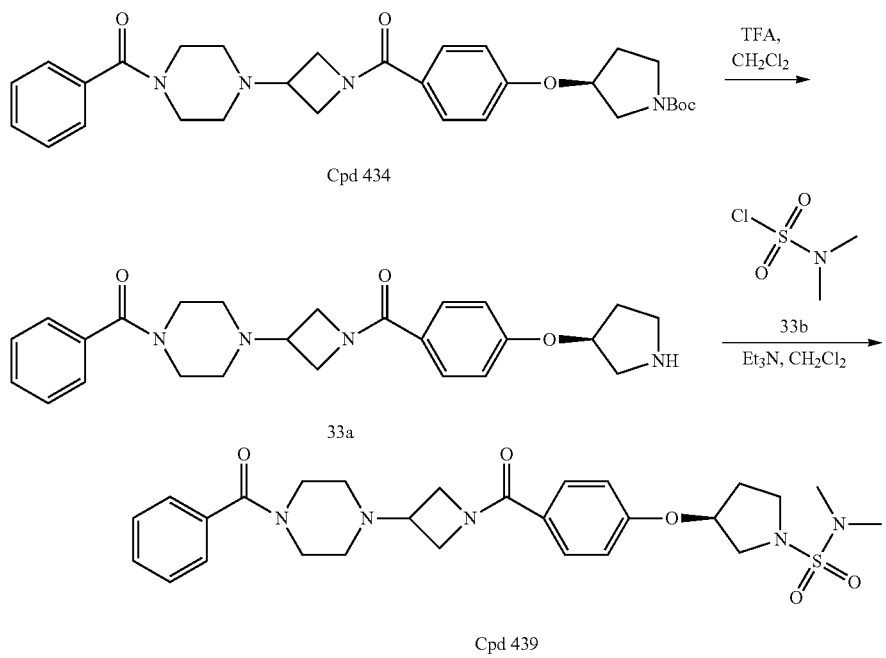

A. (3S)-3-[4-({3-[4-(phenylcarbonyl)piperazin-1-yl]azetidin-1-yl}carbonyl)phenoxy]pyrrolidine, 33a. To a solution of compound 434 (87.7 mg, 0.164 mmol) in CH$_2$Cl$_2$ (1 mL) was added TFA (0.5 mL). The resulting mixture was stirred at room temperature for 4 h. The reaction mixture was concentrated under reduced pressure to give compound 33a, which was used without further purification.

B. (3S)—N,N-Dimethyl-3-[4-({3-[4-(phenylcarbonyl)piperazin-1-yl]azetidin-1-yl}carbonyl)phenoxy]pyrrolidine-1-sulfonamide, Cpd 439. A solution of compound 33a (0.164 mmol) and Et$_3$N (0.5 mL) in CH$_2$Cl$_2$ (2 mL) was treated with N,N-dimethylsulfamoyl chloride (26 uL, 0.246 mmol) at room temperature. The resulting mixture was stirred for 3 h, and the solvent was then removed under reduced pressure. The resultant residue was directly loaded onto a silica gel column and was purified by silica gel flash column chromatography, eluting with 5% MeOH/CH$_2$Cl$_2$ to give compound 439 (51.5 mg). $^1$H NMR (CDCl$_3$): δ 7.61 (d, J=8.21 Hz, 2H), 7.36-7.46 (m, 5H), 6.86 (d, J=8.6 Hz, 2H), 4.98 (m, 1H), 4.31 (br. s, 1H), 4.11-4.26 (m, 2H), 4.05 (br. s, 1H), 3.87-3.96 (m, 1H), 3.84 (m, 1H), 3.70-3.79 (m, 1H), 3.66 (dd, J=11.4, 4.8 Hz, 1H), 3.39-3.58 (m, 4H), 3.21-3.26 (m, 1H), 2.82 (s, 6H), 2.42 (br. s, 4H), 2.19-2.29 (m, 2H); MS m/z (M+H+) 542.0.

Following the procedure described above for Example 33 and substituting the appropriate reagents, starting materials and purification methods known to those skilled in the art, the following compounds of the present invention were prepared:

| Cpd | Cpd Name and Data |
|---|---|
| 440 | 1-(Phenylcarbonyl)-4-{1-[(4-{[1-(phenylcarbonyl)piperidin-4-yl]oxy}phenyl)carbonyl]azetidin-3-yl}piperazine<br>MS m/z (M + H+) 553.3 |
| 441 | 1-[1-({4-[(1-Acetylpiperidin-4-yl)oxy]phenyl}carbonyl)azetidin-3-yl]-4-(phenylcarbonyl)piperazine<br>MS m/z (M + H+) 491.3 |

-continued

| Cpd | Cpd Name and Data |
|---|---|
| 442 | 1-(Phenylcarbonyl)-4-{1-[(4-{[(3S)-1-(phenylcarbonyl)pyrrolidin-3-yl]oxy}phenyl)carbonyl]azetidin-3-yl}piperazine<br>MS m/z (M + H+) 539.3 |
| 443 | 1-{1-[(4-{[(3R)-1-(Cyclohexylcarbonyl)pyrrolidin-3-yl]oxy}phenyl)carbonyl]azetidin-3-yl}-4-(phenylcarbonyl)piperazine<br>MS m/z (M + H+) 545.3 |
| 444 | 1-(Phenylcarbonyl)-4-{1-[(4-{[(3R)-1-(phenylcarbonyl)pyrrolidin-3-yl]oxy}phenyl)carbonyl]azetidin-3-yl}piperazine<br>MS m/z (M + H+) 539.3 |
| 445 | 1-{1-[(4-{[(3R)-1-(2,2-Dimethylpropanoyl)pyrrolidin-3-yl]oxy}phenyl)carbonyl]azetidin-3-yl}-4-(phenylcarbonyl)piperazine<br>MS m/z (M + H+) 519.3 |
| 446 | (3S)—N,N-Dimethyl-3-[4-({3-[4-(phenylcarbonyl)piperazin-1-yl]azetidin-1-yl}carbonyl)phenoxy]pyrrolidine-1-carboxamide<br>MS m/z (M + H+) 506.3 |

-continued

| Cpd | Cpd Name and Data |
|---|---|
| 447 | 1-(Phenylcarbonyl)-4-{1-[(4-{[(3S)-1-(pyrrolidin-1-ylsulfonyl)pyrrolidin-3-yl]oxy}phenyl)carbonyl]azetidin-3-yl}piperazine<br>MS m/z (M + H$^+$) 568.3 |
| 448 | 1-(Phenylcarbonyl)-4-{1-[(4-{[(3S)-1-(pyrrolidin-1-ylcarbonyl)pyrrolidin-3-yl]oxy}phenyl)carbonyl]azetidin-3-yl}piperazine<br>MS m/z (M + H$^+$) 532.3 |
| 449 | 4-({(3S)-3-[4-({3-[4-(Phenylcarbonyl)piperazin-1-yl]azetidin-1-yl}carbonyl)phenoxy]pyrrolidin-1-yl}carbonyl)morpholine<br>MS m/z (M + H$^+$) 548.3 |

Example 34

A. tert-Butyl 3-(2-iodo-4-methoxycarbonyl-phenoxy)-pyrrolidine-1-carboxylate, 34b. To a solution of compound 34a (500 mg, 1.8 mmol), compound 32a (504 mg, 2.7 mmol) and PPh$_3$ (707 mg, 2.7 mmol) in THF (10 mL) was added DIAD (0.52 mL, 2.7 mmol) at 0° C. The resulting mixture was stirred at 0° C. for 1 h, then warmed up to room temperature and stirred for 18 h. The mixture was poured into water and extracted with EtOAc (3×). The combined organic extracts were dried over Na$_2$SO$_4$, filtered, and concentrated under reduced pressure. The residue was purified by flash column chromatography eluting with 50% EtOAc/hexanes to give compound 34b (704 mg).

B. Methyl 3-iodo-4-[1-(pyrrolidine-1-carbonyl)-pyrrolidin-3-yloxy]-benzoate, 34d. To a solution of compound 34b (210 mg, 0.47 mmol) in CH$_2$Cl$_2$ (3 mL) was added TFA (1.5 mL) at room temperature. The resulting mixture was stirred at

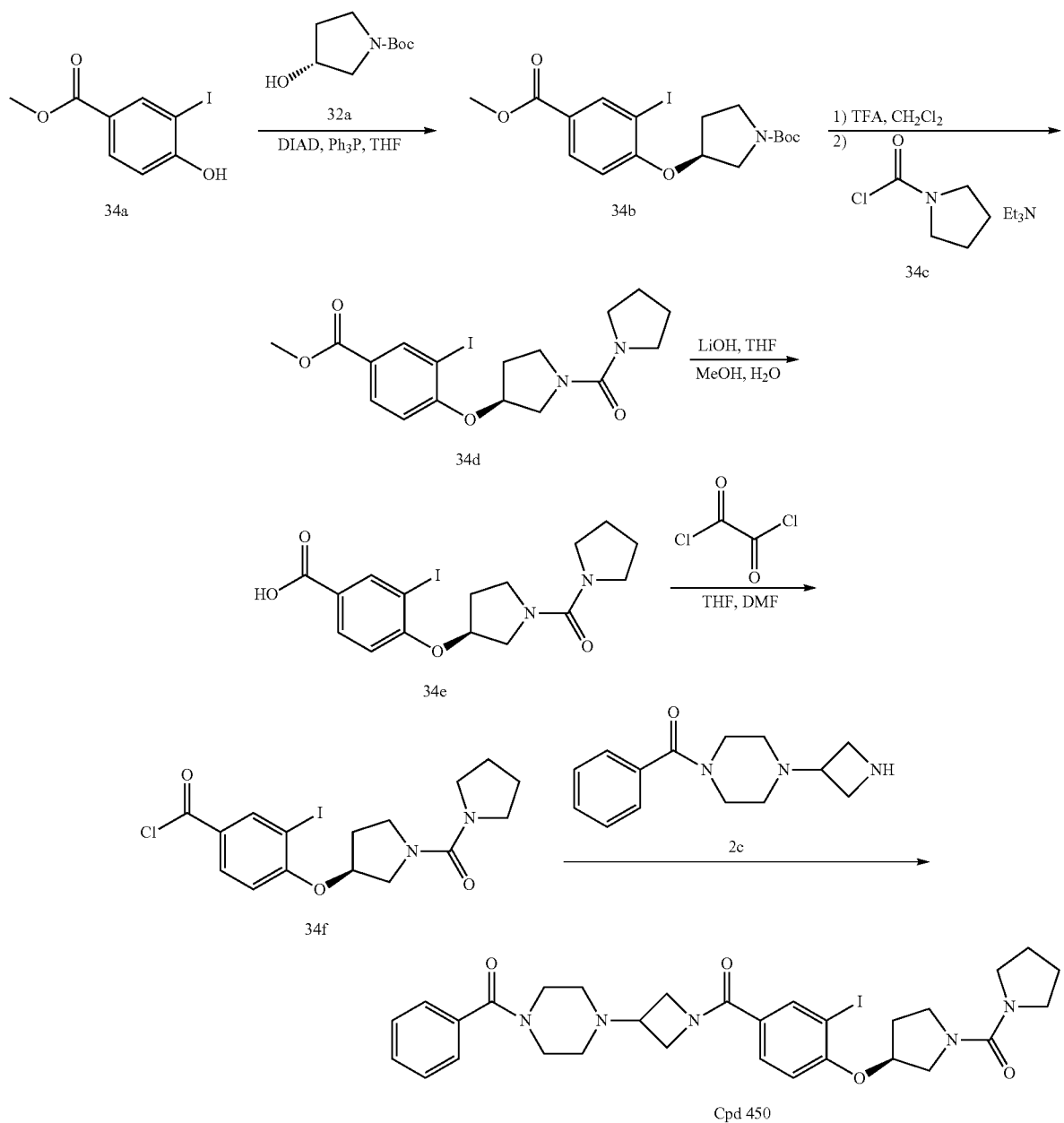

room temperature for 4 h. The solvent was removed under reduced pressure. The resultant residue was dried under reduced pressure for 2 h. To the residue was added CH$_2$Cl$_2$ (3 mL) and Et$_3$N (1 mL), followed by the addition of compound 34c (77 μL, 0.7 mmol). The resulting mixture was stirred for 2 h, then poured into water (50 mL) and extracted with EtOAc (3×). The combined organic extracts were dried over Na$_2$SO$_4$, filtered, and concentrated under reduced pressure. The residue was purified by flash column chromatography, eluting with 80% EtOAc/hexanes to give compound 34d (180 mg).

C. 3-Iodo-4-[1-(pyrrolidine-1-carbonyl)-pyrrolidin-3-yloxy]-benzoic acid, 34e. A mixture of compound 34d (180 mg, 0.41 mmol), LiOH (39 mg, 1.62 mmol), THF (3 mL), MeOH (3 mL), and H$_2$O (3 mL) was stirred at room temperature for 4 h. The mixture was acidified with 15% aqueous citric acid and extracted with EtOAc (3×). The combined organic extracts were washed with brine, dried over Na$_2$SO$_4$, filtered, and concentrated under reduced pressure. The resultant residue was dried under reduced pressure for 2 h to give compound 34e (166 mg).

D. 3-Iodo-4-[1-(pyrrolidine-1-carbonyl)-pyrrolidin-3-yloxy]-benzoyl chloride, 34f. To a solution of compound 34e (166 mg, 0.39 mmol) in THF (4 mL) was added oxalyl dichloride (43 μL, 0.50 mmol) dropwise at 0° C., followed by the addition of 2 drops of DMF. The resulting mixture was stirred at 0° C. for 3 h, warmed to room temperature, and stirred for 18 h. The solvents were removed under reduced pressure. The resultant residue, compound 34f, was dried under reduced pressure for 2 h and used in the following step without further purification.

E. 1-{1-[(3-Iodo-4-{[(3S)-1-(pyrrolidin-1-ylcarbonyl)pyrrolidin-3-yl]oxy}phenyl)carbonyl]azetidin-3-yl}-4-(phenylcarbonyl)piperazine, Cpd 450. To a mixture of compound 2c (61 mg, 0.25 mmol), Et$_3$N (0.5 mL), and CH$_2$Cl$_2$ (2.5 mL) was added a solution of compound 34f in CH$_2$Cl$_2$ (1 mL). The resulting mixture was stirred at room temperature for 2 h. The solvent was removed under reduced pressure. The residue was dissolved in CH$_2$Cl$_2$ (1 mL), directly loaded onto a silica gel column, and purified by flash column chromatography, eluting with 5% MeOH/CH$_2$Cl$_2$ to give compound 451 (56 mg). $^1$H NMR (CDCl$_3$): δ 8.06 (d, J=2.3 Hz, 1H), 7.60 (dd, J=8.5, 2.1 Hz, 1H), 7.34-7.48 (m, 5H), 6.80 (d, J=8.6 Hz, 1H), 5.01 (br. s, 1H), 3.66-4.36 (m, 8H), 3.28-3.64 (m, 8H), 3.12-3.27 (m, 1H), 2.05-2.56 (m, 6H), 1.55-1.97 (m, 4H).

Following the procedure described above for Example 34 and substituting the appropriate reagents, starting materials and purification methods known to those skilled in the art, the following compounds of the present invention were prepared:

| Cpd | Cpd Name and Data |
|---|---|
| 451 | (3S)-3-[2-Iodo-4-({3-[4-(phenylcarbonyl)piperazin-1-yl]azetidin-1-yl}carbonyl)phenoxy]-N,N-dimethylpyrrolidine-1-carboxamide<br>MS m/z (M + H$^+$) 632.2 |
| 452 | 1-{1-[(3-Iodo-4-{[(3S)-1-(pyrrolidin-1-ylcarbonyl)pyrrolidin-3-yl]oxy}phenyl)carbonyl]azetidin-3-yl}-4-(1,3-thiazol-2-ylcarbonyl)piperazine<br>MS m/z (M + H$^+$) 665.2 |

Example 35

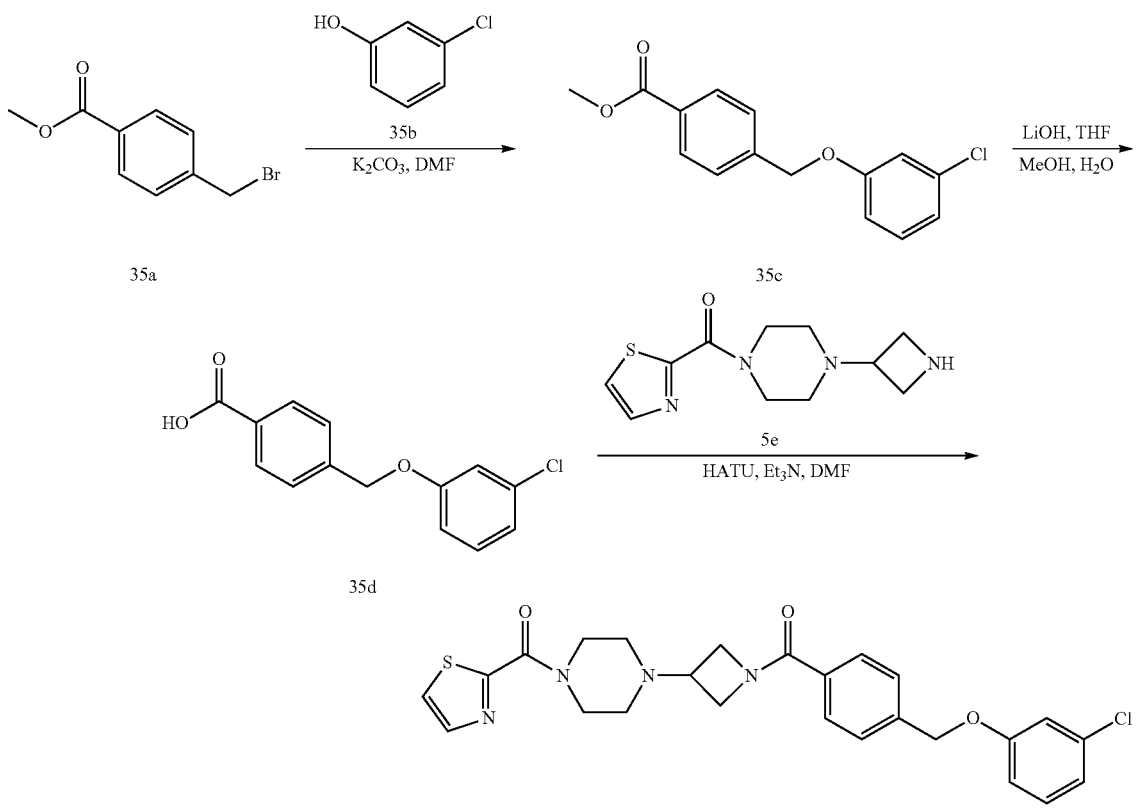

Cpd 453

A. Methyl 4-[(3-Chlorophenoxy)methyl]benzoate, 35c. To a mixture of compound 35a (300 mg, 1.31 mmol) and $K_2CO_3$ (400 mg, 2.88 mmol) in DMF (1 mL) was added compound 35b (251 mg, 2.0 mmol). The resulting mixture was stirred at room temperature for 6 h. The mixture was poured into water (50 mL) and extracted with EtOAc (3×). The combined organic extracts were washed with brine, dried over $NaSO_4$, filtered, and concentrated under reduced pressure. The resultant residue was purified by silica gel flash column chromatography, eluting with 20% EtOAc/hexanes to yield compound 35c (340 mg).

B. 4-[(3-Chlorophenoxy)methyl]benzoic acid, 35d. A mixture of compound 35c (340 mg, 1.18 mmol) and LiOH (114 mg, 4.74 mmol) in $THF/MeOH/H_2O$ (3/3/3 mL) was stirred for 4 h. A 15% citric acid solution (10 mL) was added. The mixture was then extracted with EtOAc (3×). The combined organic extracts were washed with brine, dried over $Na_2SO_4$, and concentrated under reduced pressure. The resultant residue, compound 35d (230 mg) was dried under reduced pressure for 18 h and used without further purification.

C. 1-[1-({4-[(3-Chlorophenoxy)methyl]phenyl}carbonyl)azetidin-3-yl]-4-(1,3-thiazol-2-ylcarbonyl)piperazine, Cpd 453. A mixture of compound 35d (77 mg, 0.29 mmol), compound 5e (108 mg, 0.38 mmol) and HATU (165 mg, 0.44 mmol) in $Et_3N$ (1 mL) and DMF (3 mL) was stirred for 18 h, and then poured into water (10 mL). The mixture was then extracted with EtOAc (3×). The combined organic extracts were washed with brine (2×), dried over $Na_2SO_4$, filtered, and concentrated under reduced pressure. The resultant residue was purified by flash column chromatography, eluting with 5% $MeOH/CH_2Cl_2$, to give compound 453 (67 mg). MS m/z $(M+H^+)$ 497.1. $^1H$ NMR $(CD_3OD)$: δ 7.95 (d, J=2.0 Hz, 1H), 7.8 (d, J=2.0 Hz, 1H), 7.65 (d, J=8.1 Hz, 2H), 7.51 (d, J=8.1 Hz, 2H), 7.25 (t, J=8.0 Hz, 1H), 7.02 (s, 1H), 6.90-6.98 (m, 2H), 5.15 (s, 2H), 4.32-4.45 (m, 2H), 4.15-4.25 (m, 2H), 4.00-4.10 (m, 1H), 3.70-3.82 (br. s, 2H), 2.47 (br. s, 4H).

Following the procedure described above for Example 35 and substituting the appropriate reagents, starting materials and purification methods known to those skilled in the art, the following compounds of the present invention were prepared:

| Cpd | Cpd Name and Data |
|---|---|
| 454 | 1-{1-[(4-{[(3-Chlorophenyl)sulfanyl]methyl}phenyl)carbonyl]azetidin-3-yl}-4-(1,3-thiazol-2-ylcarbonyl)piperazine<br>MS m/z (M + H⁺) 513.1 |
| 455 | 3-Chloro-N-[4-({3-[4-(1,3-thiazol-2-ylcarbonyl)piperazin-1-yl]azetidin-1-yl}carbonyl)benzyl]aniline<br>MS m/z (M + H⁺) 496.1 |
| 548 | 1-[1-({4-[(3-Chlorophenoxy)methyl]phenyl}carbonyl)azetidin-3-yl]-4-(phenylcarbonyl)piperazine<br>MS m/z (M + H⁺) 490.0 |
| 959 | 1-[1-({4-[(3-Chlorophenoxy)methyl]phenyl}carbonyl)azetidin-3-yl]-4-(1,3-thiazol-4-ylcarbonyl)piperazine<br>MS m/z (M + H⁺) 497.0 |

Example 35a

Following the procedure described above for Example 35 and substituting the appropriate reagents, starting materials, and purification methods known to those skilled in the art, the following intermediate compounds were prepared:

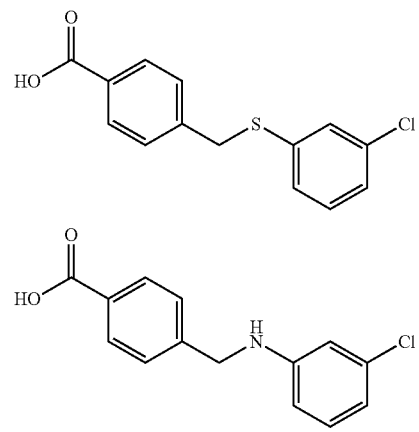

Following the procedure described above for Example 35 or Example 1, and substituting the appropriate reagents, starting materials and purification methods known to those skilled in the art, the following compounds of the present invention were prepared:

| Cpd | Cpd Name and Data |
|---|---|
| 551 | 1-{1-[(4-{[(3-Chlorophenyl)sulfanyl]methyl}phenyl)carbonyl]azetidin-3-yl}-4-(phenylcarbonyl)piperazine<br>MS m/z (M + H⁺) 506.0 |
| 549 | 3-Chloro-N-[4-({3-[4-(phenylcarbonyl)piperazin-1-yl]azetidin-1-yl}carbonyl)benzyl]aniline<br>MS m/z (M + H⁺) 489.0 |
| 956 | 1-{1-[(4-{[(3-Chlorophenyl)sulfanyl]methyl}phenyl)carbonyl]azetidin-3-yl}-4-(1,3-thiazol-4-ylcarbonyl) piperazine<br>MS m/z (M + H⁺) 513.0 |
| 969 | 3-Chloro-N-[4-({3-[4-(1,3-thiazol-4-ylcarbonyl)piperazin-1-yl]azetidin-1-yl}carbonyl)benzyl]aniline<br>MS m/z (M + H⁺) 496.0 |

Example 35b

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 955 | 1-{1-[(4-{[(3-Chlorophenyl)sulfanyl]methyl}phenyl)carbonyl]azetidin-3-yl}-4-(trifluoroacetyl)piperazine<br>MS m/z (M + H⁺) 498.0 | N-TFA |
| 964 | 3-Chloro-N-[4-({3-[4-(trifluoroacetyl)piperazin-1-yl]azetidin-1-yl}carbonyl)benzyl]aniline<br>MS m/z (M + H⁺) 481.0 | N-TFA |

Example 36

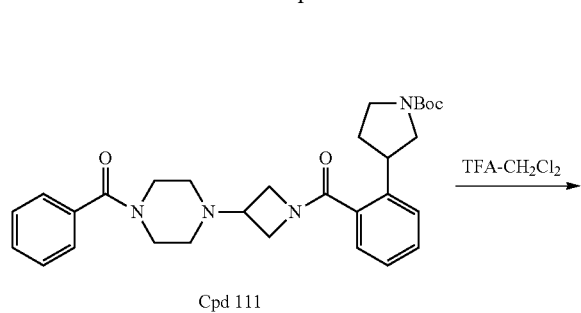

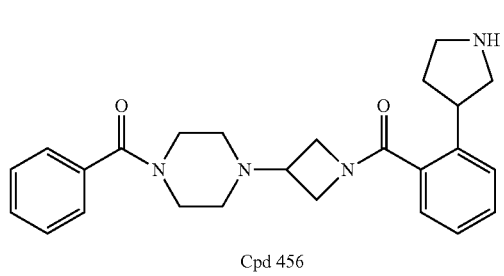

1-(Phenylcarbonyl)-4-{1-[(2-pyrrolidin-3-ylphenyl)carbonyl]azetidin-3-yl}piperazine, Cpd 456. To a solution of compound III (300 mg, 0.58 mmol) in 1,4-dioxane (10 mL) was added 6N HCl (3 mL). After stirring for 4 h, the solvent was evaporated in vacuo. The residue was partitioned between EtOAc and 3N NaOH, and the organic phase was isolated and dried over MgSO$_4$. The mixture was filtered, the filtrate concentrated under reduced pressure, and the residue was purified by reverse phase HPLC to give compound 456 (52.3 mg). LC/MS m/z (M+H$^+$) 419.36 (calculated for C$_{25}$H$_{30}$N$_4$O$_4$, 418.54).

Example 37

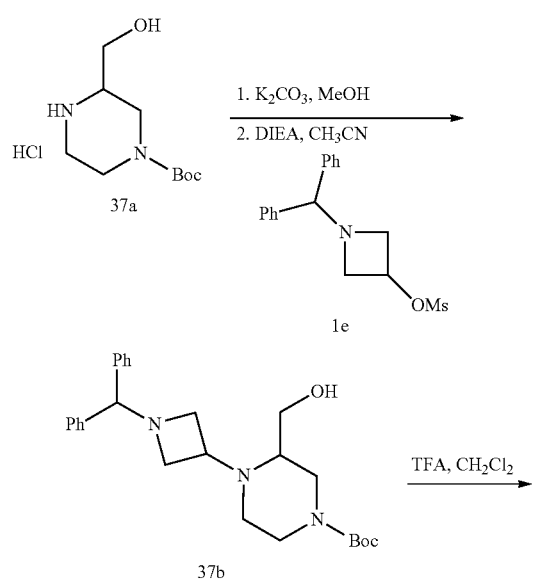

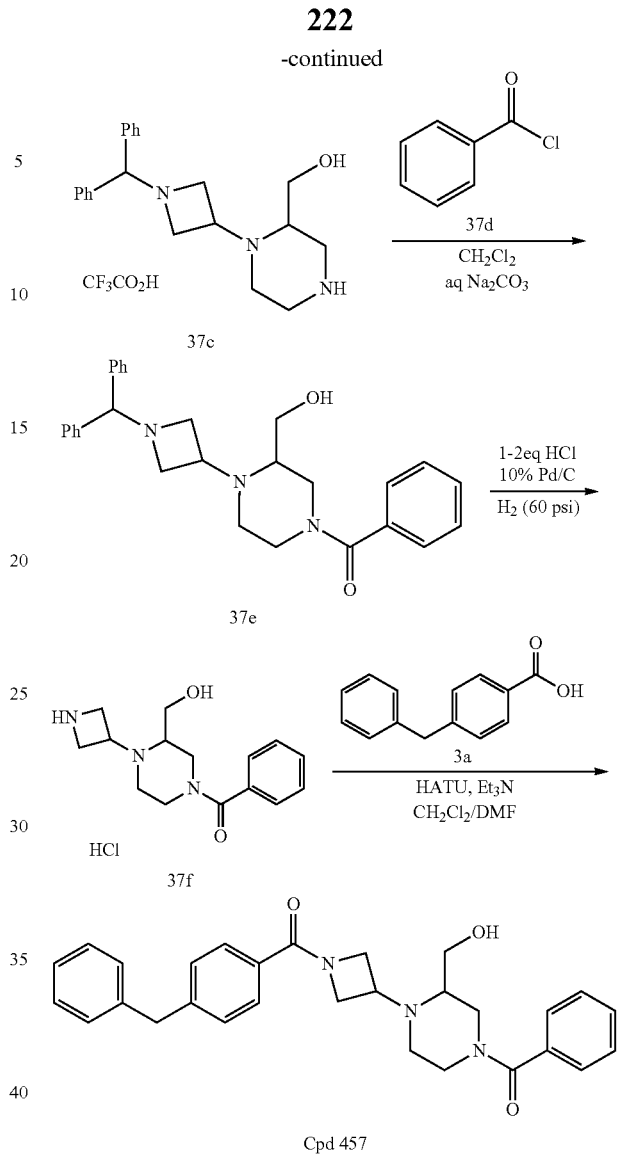

A. tert-Butyl 4-[1-(diphenylmethyl)azetidin-3-yl]-3-(hydroxymethyl)piperazine-1-carboxylate, 37b. Compound 37a (811 mg, 3.21 mmol) was added in one portion to a stirring suspension of anhydrous K$_2$CO$_3$ (1.07 g, 7.9 mmol) in MeOH (4 mL). The mixture was stirred for 1.5 h at room temperature, and the MeOH was then removed under reduced pressure to near-dryness. The resulting white slurry was triturated with CH$_2$Cl$_2$ (40 mL) and filtered through a medium-porosity glass fritted funnel. The solids were washed with additional CH$_2$Cl$_2$ and the combined filtrates were concentrated and dried under reduced pressure to give compound 37a (733 mg) as a white solid, the free base of the HCl salt of 37a.

The material was suspended in CH$_3$CN (8 mL) with compound 1e (1.07 g, 3.37 mmol). Diisopropylethylamine (1.23 mL, 7.06 mmol) was added and the mixture was heated at 60° C. for 14 h. EtOAc (100 mL) was added and the organic phase was washed with water (20 mL) and brine (20 mL), dried over Na$_2$SO$_4$, filtered, and concentrated under reduced pressure to give a crude residue (1.42 g) as a pale orange foam. The material was purified by medium pressure liquid chromatography (MPLC) using an ISCO CombiFlash system (silica gel, 10-50% EtOAc/hexanes) to give compound 37b (979 mg) as a white foam. $^1$H NMR (400 MHz, CDCl$_3$): δ 7.39 (d, J=8.1

Hz, 4H), 7.23-7.33 (m, 4H), 7.14-7.23 (m, 2H), 4.34 (s, 1H), 3.28-3.58 (m, 8H), 2.76-2.95 (m, 2H), 2.26-2.75 (m, 4H), 2.20 (dt, J=12.3, 4.9 Hz, 1H), 1.44 (s, 9H); LCMS m/z (M+H$^+$) 438.5, (M+Na$^+$) 460.5.

B. {1-[1-(Diphenylmethyl)azetidin-3-yl]-piperazin-2-yl}methanol, 37c. Compound 37b (450 mg, 1.03 mmol) was dissolved in CH$_2$Cl$_2$ (6 mL) and TFA (3 mL) and was stirred at 20° C. for 2.5 h. The reaction mixture was concentrated to dryness under reduced pressure to give the TFA salt of compound 37c as an orange foam. Compound 37c was used in the following step without further purification. MS m/z (M+H$^+$) 338.2.

C. {1-[1-(Diphenylmethyl)azetidin-3-yl]-4-(phenylcarbonyl)piperazin-2-yl}methanol, 37e. Compound 37c (1.03 mmol) was dissolved in CH$_2$Cl$_2$ (5 mL) and cooled in an ice water bath to 0° C. A 10% aqueous Na$_2$CO$_3$ solution (5 mL) was added and a solution of compound 37d (143 µL, 1.23 mmol) dissolved in CH$_2$Cl$_2$ (1 mL) was added dropwise. The resultant mixture was allowed to warm to 20° C. and then stirred rapidly for 62 h. CH$_2$Cl$_2$ (10 mL) was added to the reaction mixture and the aqueous phase was extracted with CH$_2$Cl$_2$ (2×20 mL). The combined organic extracts were washed with brine, dried over Na$_2$SO$_4$, filtered, and concentrated to give compound 37e (465 mg) as an off white foam. Compound 37e was used in the following step without further purification. $^1$H NMR (400 MHz, CDCl$_3$): δ 7.39 (m, 9H), 7.22-7.32 (m, 4H), 7.14-7.23 (m, 2H), 4.35 (s, 1H), 4.07 (br. s, 1H), 3.30-3.71 (complex, 8H), 2.2-3.0 (complex, 6H); LCMS m/z (M+H$^+$) 442.2.

D. [1-Azetidin-3-yl-4-(phenylcarbonyl)piperazin-2-yl]methanol, 37f. Compound 37e (450 mg, 1.02 mmol) was added to a 500 mL-Parr hydrogenation bottle and dissolved in absolute EtOH (6 mL). A 12N conc. HCl solution (95 µL, 1.14 mmol) was added and the bottle was purged with N$_2$. 10% Pd/C (264 mg) was added and the mixture was shaken under 60 psi of H$_2$ for 14 h. An additional amount of 10% Pd/C (430 mg) was added and the mixture was returned to 60 psi of H$_2$ and shaken 5 h more. The mixture was filtered through a pad of diatomaceous earth, and the solids were rinsed thoroughly with MeOH. The fitrate was concentrated to dryness under reduced pressure to afford crude compound 37f as a sticky oil (428 mg) which was used in the following step without further purification. LC/MS m/z (M+H$^+$) 276.3.

E. [1-{1-[(4-Benzylphenyl)carbonyl]azetidin-3-yl}-4-(phenylcarbonyl)piperazin-2-yl]methanol, Cpd 457. Compound 3a (142 mg, 0.67 mmol) and HATU (256 mg, 0.67 mmol) were suspended in CH$_2$Cl$_2$ (1 mL) and DMF (0.2 mL). Et$_3$N (195 µL, 1.4 mmol) was added and the solution was stirred for 15 min at 20° C. Crude compound 37f (214 mg, approximately 0.56 mmol) was dissolved in 1:1 CH$_2$Cl$_2$/DMF (3 mL) and was added in portions to the solution of compound 3a and the mixture was stirred for 64 h. The organic solution was diluted with EtOAc (50 mL), and washed sequentially with water (3×10 mL), and brine (10 mL). The organic phase was dried over Na$_2$SO$_4$, filtered, and the filtrate concentrated under reduced pressure to give a yellow oil (310 mg). The crude oil was purified by MPLC (4 g Silicycle SiO$_2$ cartridge, 15-80% acetone/hexanes) to give compound 457 as a white foam (104 mg). $^1$H NMR (400 MHz, CDCl$_3$) δ: 7.53 (d, J=7.8 Hz, 2H), 7.42 (br. s, 5H), 7.11-7.37 (m, 7H), 4.26 (m, 5H), 4.00 (s, 2H), 3.71-3.89 (m, 1H), 3.54-3.71 (m, 3H), 3.25-3.54 (m, 3H), 2.92 (br. s, 1H), 2.64 (br. s, 1H), 2.41 (br. s, 1H); LCMS m/z (M+H$^+$) 470.5.

Following the procedure described above for Example 37 and substituting the appropriate reagents, starting materials and purification methods known to those skilled in the art, the following compounds of the present invention were prepared:

| Cpd | Cpd Name and Data |
| --- | --- |
| 458 | {1-[1-(Biphenyl-4-ylcarbonyl)azetidin-3-yl]-4-(phenylcarbonyl)piperazin-2-yl}methanol<br>$^1$H NMR (400 MHz, CDCl$_3$): δ 7.65-7.73 (m, 2H), 7.61 (dd, J = 11.6, 8.1 Hz, 4H), 7.33-7.50 (m, 10H), 3.96-4.49 (m, 5H), 3.76-3.91 (m, 1H), 3.63 (m, 3H), 3.32-3.53 (m, 1H), 2.95 (br. s., 1H), 2.64 (br. s., 1H), 2.45 (br. s., 1H)<br>LCMS m/z (M + H$^+$) 456.5 |
| 459 | [4-{1-[(4-Benzylphenyl)carbonyl]azetidin-3-yl}-1-(phenylcarbonyl)piperazin-2-yl]methanol<br>$^1$H NMR (400 MHz, CDCl$_3$): δ 7.55 (d, J = 8.1 Hz, 2H), 7.35-7.46 (m, 5H), 7.10-7.34 (m, 7H), 4.82 (br. s., 1H), 4.01 (s, 2H), 3.72-4.40 (m, 5H), 3.52 (br. s., 1H), 3.16 (br. s., 1H), 2.54-3.04 (m, 2H), 1.93-2.30 (m, 4H)<br>LCMS m/z (M + H$^+$) 470.5 |
| 460 | {4-[1-(Biphenyl-4-ylcarbonyl)azetidin-3-yl]-1-(phenylcarbonyl)piperazin-2-yl}methanol<br>$^1$H NMR (400 MHz, CDCl$_3$): δ 7.67-7.75 (d, J = 8.3 Hz, 2H), 7.55-7.67 (m, 4H), 7.34-7.52 (m, 8H), 3.39-4.96 (m, 9H), 3.20 (quin, 1H), 2.51-3.05 (m, 3H), 2.22 (br. s., 1H), 2.04 (br. s., 1H)<br>LCMS m/z (M + H$^+$) 456.5 |

Example 38

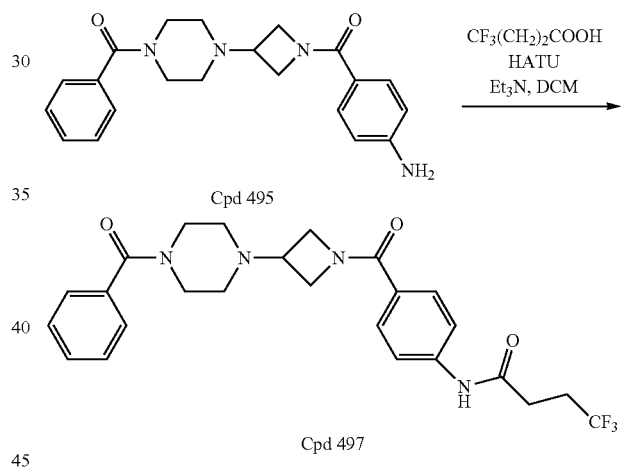

Cpd 495

Cpd 497

4,4,4-Trifluoro-N-[4-({3-[4-(phenylcarbonyl)piperazin-1-yl]azetidin-1-yl}carbonyl)phenyl]butanamide, Cpd 497. A mixture of Cpd 495 (65 mg, prepared according to Example 9), 4,4,4-trifluorobutanoic acid (30 mg), HATU (116 mg), and TEA (0.12 mL) in DCM 1.5 mL) was stirred at room temperature for 5 hr. The reaction mixture was diluted with DCM and water. The normal work-up followed by chromatography gave Cpd 497 (71 mg). MS m/z (M+H$^+$) 489.5.

Following the procedure described above for Example 38 and substituting the appropriate reagents, starting materials and purification methods known to those skilled in the art, the following compounds of the present invention were prepared:

| Cpd | Cpd Name and Data |
| --- | --- |
| 498 | 2-Phenyl-N-[4-({3-[4-(phenylcarbonyl)piperazin-1-yl]azetidin-1-yl}carbonyl)phenyl]acetamide<br>MS m/z (M + H$^+$) 483.6 |

-continued

| Cpd | Cpd Name and Data |
|---|---|
| 499 | N-[4-({3-[4-(Phenylcarbonyl)piperazin-1-yl]azetidin-1-yl}carbonyl)phenyl]cyclohexanecarboxamide<br>MS m/z (M + H$^+$) 475.6 |
| 500 | 2-Ethyl-N-[4-({3-[4-(phenylcarbonyl)piperazin-1-yl]azetidin-1-yl}carbonyl)phenyl]butanamide<br>MS m/z (M + H$^+$) 463.6$^+$ |
| 501 | N-[4-({3-[4-(Phenylcarbonyl)piperazin-1-yl]azetidin-1-yl}carbonyl)phenyl]benzamide<br>MSm/z (M + H$^+$) 469.2 |

Example 39

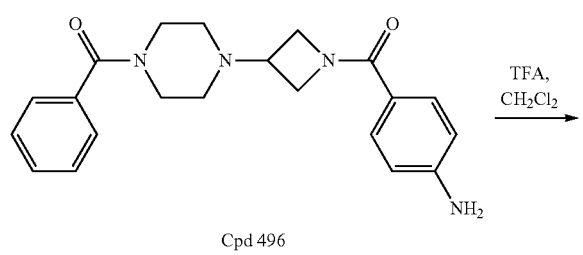

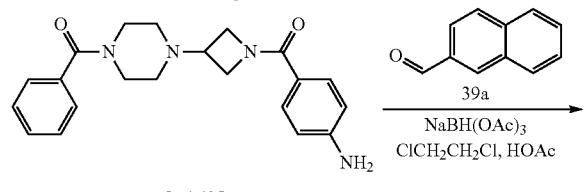

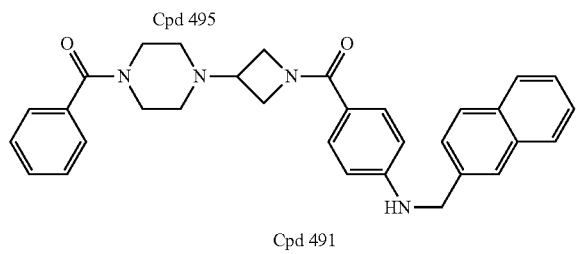

A. N-(Naphthalen-2-ylmethyl)-4-({3-[4-(phenylcarbonyl)piperazin-1-yl]azetidin-1-yl}carbonyl)aniline, Cpd 495. Cpd 496 was dissolved in CH$_2$Cl$_2$ and TFA and was stirred at 20° C. The reaction mixture was concentrated to dryness under reduced pressure to give Cpd 495, which was used in the following step without further purification. MS m/z (M+H$^+$) 365.

B. N-(Naphthalen-2-ylmethyl)-4-({3-[4-(phenylcarbonyl)piperazin-1-yl]azetidin-1-yl}carbonyl)aniline, Cpd 491. A mixture of Cpd 495 (100 mg, 0.27 mmol), compound 39a (75 mg, 0.48 mmol) and AcOH (0.5 mL) in 1,2 dichloroethane (3 mL) was stirred for 1 h, then NaBH(OAc)$_3$ (136 mg, 0.64 mmol) was added. The resulting mixture was stirred overnight, then was poured into 2N aqueous KOH solution (20 mL) and extracted with EtOAc. The combined extracts were dried over Na$_2$SO$_4$ and concentrated under reduced pressure. The residue was purified by flash column chromatography, eluting with 5% MeOH/CH$_2$Cl$_2$ to give 33.2 mg of Cpd 491. $^1$H NMR (400 MHz, CDCl$_3$): δ 7.75-7.85 (m, 4H), 7.43-7.53 (m, 5H), 7.35-7.42 (m, 5H), 6.61 (d, J=8.8 Hz, 2H), 4.64 (br. s, 1H), 4.51 (s, 2H), 4.27 (br. s, 1H), 4.08-4.35 (m, 3H), 4.02 (s, 1H), 3.89 (s, 1H), 3.71 (br. s, 1H), 3.34-3.55 (m, 2H), 3.10-3.22 (m, 1H), 2.13-2.49 (m, 3H); MS m/z (M+H$^+$) 505.3.

Following the procedure described above for Example 39 and substituting the appropriate reagents, starting materials and purification methods known to those skilled in the art, the following compounds of the present invention were prepared:

| Cpd | Cpd Name and Data |
|---|---|
| 492 | N-(2-Chlorobenzyl)-4-({3-[4-(phenylcarbonyl)piperazin-1-yl]azetidin-1-yl}carbonyl)aniline<br>MS (m/z) (M + H$^+$) 489.2 |
| 493 | N-(3,4-Dichlorobenzyl)-4-({3-[4-(phenylcarbonyl)piperazin-1-yl]azetidin-1-yl}carbonyl)aniline<br>MS (m/z) (M + H$^+$) 523.2 |
| 494 | N-[4-Fluoro-3-(trifluoromethyl)benzyl]-4-({3-[4-(phenylcarbonyl)piperazin-1-yl]azetidin-1-yl}carbonyl)aniline<br>MS (m/z) (M + H$^+$) 541.2 |

Example 40

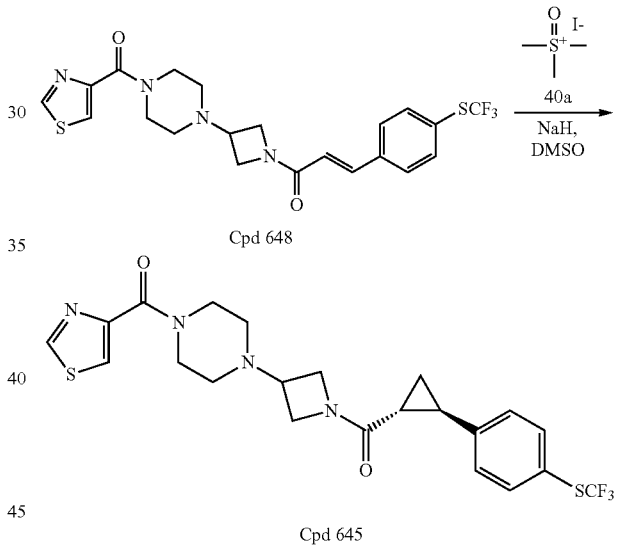

1-(1,3-Thiazol-4-ylcarbonyl)-4-(1-{[(1RS,2RS)-2-{4-[(trifluoromethyl)sulfanyl]phenyl}cyclopropyl]carbonyl}azetidin-3-yl)piperazine, Cpd 645 (racemic, trans). Trimethylsulfoxonium iodide 40a (1.15 mmol, 253 mg) and sodium hydride (60% dispersion in mineral oil, 1.1 mmol, 44 mg) were combined in 3 mL of dry DMSO and stirred 20 min at room temperature. Cpd 648, prepared in Example 5, was added and the mixture was stirred 15 min at room temperature, then heated at 50° C. overnight. After cooling, the mixture was partitioned between EtOAc and water, The organic layer was separated and concentrated to give crude product that was purified by preparative reverse-phase chromatography to afford 9.1 mg (2%) of Cpd 645 as the mono-TFA salt. MS m/z (M+H$^+$) 497.2.

Following the procedure described above for Example 40, and substituting the appropriate reagents, starting materials, and purification methods known to those skilled in the art, the following compound of the present invention was prepared:

| Cpd | Cpd Name and Data |
|---|---|
| 642 | 1-(1-{[(1RS,2RS)-2-(2-Chlorophenyl)cyclopropyl]carbonyl}azetidin-3-yl)-4-(1,3-thiazol-2-ylcarbonyl)piperazine<br>MS m/z (M + H⁺) 431.1 |

Example 41

Intentionally Left Blank

Example 42

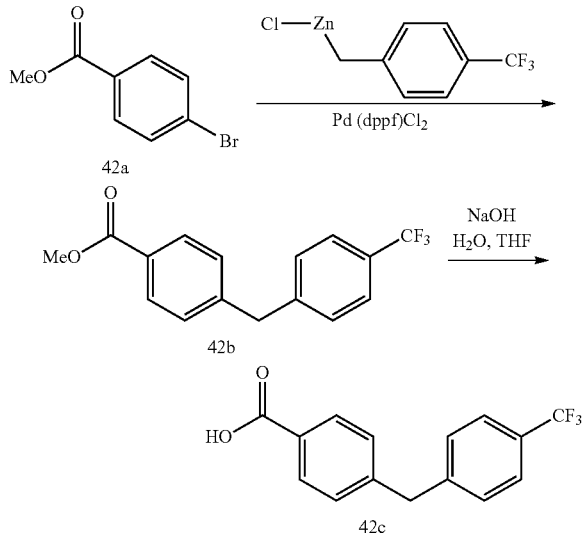

A. Methyl 4-(4-(trifluoromethyl)benzyl)benzoate, 42b. Argon was bubbled through a mixture of methyl 4-bromobenzoate 42a (9.3 mmol, 2.0 g), 2 mL of THF, and 4-trifluoromethylbenzylzinc chloride (0.5 M in THF, 46.5 mmol, 93 mL) for 5 min. Pd(dffp)Cl₂.CH₂Cl₂ (0.5 mol, 409 mg) was added and the reaction tube was capped and heated at 70° C. for 16 h. The mixture was cooled and filtered through Celite. Water was added to the filtrate and the resulting solid was filtered off. The organic solution was dried over MgSO₄ and concentrated. The crude product was purified by flash chromatography (silica gel, 0-10% EtOAc in heptane) to give 1.5 g (55%) of methyl 4-(4-(trifluoromethyl)benzyl)benzoate, 42b.

B. 4-(4-(Trifluoromethyl)benzyl)benzoic acid, 42c. Following the procedure described in Example 91, Step P, methyl 4-(4-(trifluoromethyl)benzyl)benzoate 42b (1.5 g, 5.1 mmol) was converted to methyl 1.31 g (92%) of 4-(4-(trifluoromethyl)benzyl)benzoic acid, 42c. MS m/z (M+H⁺) 279.1.

Following the procedure described above for Example 42 and substituting the appropriate reagents, starting materials, and purification methods known to those skilled in the art, the following intermediate compounds were prepared:

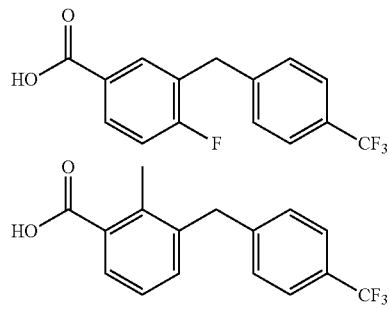

Intermediate compounds were optionally prepared by an alternative procedure:

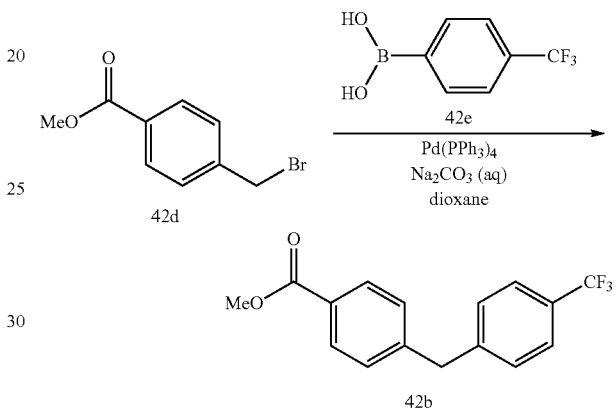

C. Methyl 4-(4-(trifluoromethyl)benzyl)benzoate, 42b. A mixture of 4-bromomethyl-benzoic acid methyl ester 42d (1.0 g, 4.37 mmol), 4-trifluorophenyl boronic acid 42e (0.995 g, 5.24 mmol), and Pd(PPh₃)₄ (50 mg, 0.044 mmol) in dioxane (15 mL) was stirred at room temperature for 1 min. Next, 4 mL of 2 M aqueous Na₂CO₃ solution was added. The resulting solution was heated at 90° C. for 5 h and was then cooled to rt. EtOAc and water were added to the reaction mixture. The organics were concentrated and purified by flash chromatography (silica gel, 5% EtOAc/hexanes) to give methyl 4-(4-(trifluoromethyl)benzyl)benzoate, 42b.

Following the procedure described above for Example 2 and substituting the appropriate reagents, starting materials and purification methods known to those skilled in the art, the following compounds of the present invention were prepared:

| Cpd | Cpd Name and Data |
|---|---|
| 96 | 1-[1-(1,3-Thiazol-4-ylcarbonyl)azetidin-3-yl]-4-({4-[4-(trifluoromethyl)benzyl]phenyl}carbonyl)piperazine<br>¹H NMR (400 MHz, CDCl₃): δ 9.23 (s, 1H); 8.44 (s, 1H); 8.0-7.8 (m, 2H); 7.76-7.63 (m, 2H); 7.5 (d, 1H); 7.44-7.32 (m, 3H); 4.9-4.7 (m, 3H); 4.3-4.2 (m, 2H); 4.19-4.04 (m, 3H)<br>MS m/z (M + H⁺) 515.1 |
| 97 | 1-[1-(1,3-Thiazol-2-ylcarbonyl)azetidin-3-yl]-4-({4-[4-(trifluoromethyl)benzyl]phenyl}carbonyl)piperazine<br>¹H NMR (400 MHz, CDCl₃): δ 8.12 (m, 2H); 7.68 (m, 2H); 7.5 (m, 2H); 7.4 (m, 4H); 4.85 (bs, 2H); 4.47-4.26 (bm, 3H); 3.52 (bs, 4H); 3.02 (bs, 2H).<br>MS m/z (M + H⁺) 495.1 |
| 006 | 1-({4-Fluoro-3-[4-(trifluoromethyl)benzyl]phenyl}carbonyl)-4-[1-(1,3-thiazol- |

-continued

| Cpd | Cpd Name and Data |
|---|---|
|  | 2-ylcarbonyl)azetidin-3-yl]piperazine<br>MS m/z (M + H+) 533.1 |
| 016 | 1-({2-Methyl-3-[4-(trifluoromethyl)benzyl]phenyl}carbonyl)-4-[1-(1,3-thiazol-5-ylcarbonyl)azetidin-3-yl]piperazine<br>MS m/z (M + H+) 529.2 |

Following the procedure described above for Example 9 and substituting the appropriate reagents, starting materials and purification methods known to those skilled in the art, the following compounds of the present invention were prepared:

| Cpd | Cpd Name and Data |
|---|---|
| 563 | 1-[1-({4-Fluoro-3-[4-(trifluoromethyl)benzyl]phenyl}carbonyl)azetidin-3-yl]-4-(phenylcarbonyl)piperazine<br>MS m/z (M + H+) 526.1 |
| 1007 | 1-[1-({4-Fluoro-3-[4-(trifluoromethyl)benzyl]phenyl}carbonyl)azetidin-3-yl]-4-(1,3-thiazol-2-ylcarbonyl)piperazine<br>$^1$H NMR (400 MHz, CDCl$_3$): δ 7.89 (s, 1H); 7.78 (s, 1H); 7.50 (m, 5H); 7.82 (m, 2H); 7.12 (t, 1H); 4.69 (bm, 2H); 4.48 (bm, 2H); 4.32 (bm, 2H); 4.0 (s, bm, 5H); 3.5 (bm, s 2H)<br>MS m/z (M + H+) 533.1 |
| 1008 | 1-[1-({2-Methyl-3-[4-(trifluoromethyl)benzyl]phenyl}carbonyl)azetidin-3-yl]-4-(1,3-thiazol-2-ylcarbonyl)piperazine<br>MS m/z (M + H+) 529.2 |
| 1009 | 1-[1-({2-Methyl-3-[4-(trifluoromethyl)benzyl]phenyl}carbonyl)azetidin-3-yl]-4-(1,3-thiazol-4-ylcarbonyl)piperazine<br>MS m/z (M + H+) 529.2 |
| 1013 | 1-[1-({2-Methyl-3-[4-(trifluoromethyl)benzyl]phenyl}carbonyl)azetidin-3-yl]-4-(1H-pyrrol-2-ylcarbonyl)piperazine<br>MS m/z (M + H+) 511.2 |
| 1014 | 1-(Isothiazol-5-ylcarbonyl)-4-[1-({2-methyl-3-[4-(trifluoromethyl)benzyl]phenyl}carbonyl)azetidin-3-yl]piperazine<br>MS m/z (M + H+) 529.2 |
| 1015 | 1-[1-({2-Methyl-3-[4-(trifluoromethyl)benzyl]phenyl}carbonyl)azetidin-3-yl]-4-(1,3-thiazol-5-ylcarbonyl)piperazine<br>MS m/z (M + H+) 529.2 |
| 995 | 1-(1,3-Thiazol-2-ylcarbonyl)-4-[1-({4-[3-(trifluoromethyl)benzyl]phenyl}carbonyl)azetidin-3-yl]piperazine<br>MS m/z 515 (M + H+) |
| 985 | 1-(1,3-Thiazol-2-ylcarbonyl)-4-[1-({4-[4-(trifluoromethyl)benzyl]phenyl}carbonyl)azetidin-3-yl]piperazine<br>MS m/z (M + H+) 515 |
| 998 | 1-(1,3-Thiazol-4-ylcarbonyl)-4-[1-({4-[3-(trifluoromethyl)benzyl]phenyl}carbonyl)azetidin-3-yl]piperazine<br>MS m/z (M + H+) 515 |
| 999 | 1-(1,3-Thiazol-4-ylcarbonyl)-4-[1-({4-[4-(trifluoromethyl)benzyl]phenyl}carbonyl)azetidin-3-yl]piperazine<br>MS m/z (M + H+) 515 |
| 771 | 1-(Phenylcarbonyl)-4-[1-({4-[4-(trifluoromethyl)benzyl]phenyl}carbonyl)azetidin-3-yl]piperazine<br>MS m/z (M + H+) 508 |
| 547 | 1-(Phenylcarbonyl)-4-[1-({4-[3-(trifluoromethyl)benzyl]phenyl}carbonyl)azetidin-3-yl]piperazine<br>MS m/z (M + H+) 508 |

Exmple 43

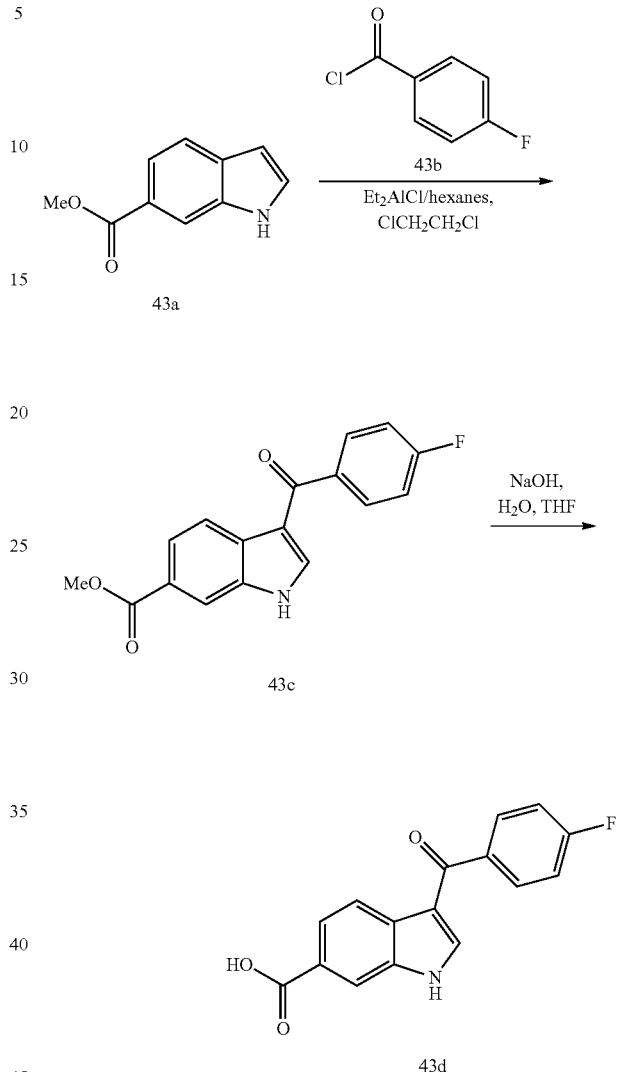

A. Methyl 3-(4-fluorobenzoyl)-1H-indole-6-carboxylate, 43c. A solution of 4-fluorobenzoyl chloride 43b (2 mmol, 0.24 mL) in 8 mL of DCE was added dropwise to an ice-cold solution of methyl 1H-indole-6-carboxylate 43a (1.43 mmol, 250 mg) and diethylaluminum chloride (1 M in hexanes, 1.86 mmol, 1.86 mL) in 8 mL of DCE. After 2 h at 0° C., the mixture was warmed to room temperature and was stirred overnight. To the mixture was added pH 7 buffer; the resulting solid was filtered and washed with CH$_2$Cl$_2$ to give 162 mg (38%) of methyl 3-(4-fluorobenzoyl)-1H-indole-6-carboxylate 43c. MS m/z (M+H+) 298.0.

B. 3-(4-Fluorobenzoyl)-1H-indole-6-carboxylic acid, 43d. Following the procedure described in Example 91, Step P, 110 mg (72%) of 3-(4-fluorobenzoyl)-1H-indole-6-carboxylic acid was obtained.

Following the procedure described above for Example 43 and substituting the appropriate reagents, starting materials, and purification methods known to those skilled in the art, the following intermediate compounds were prepared:

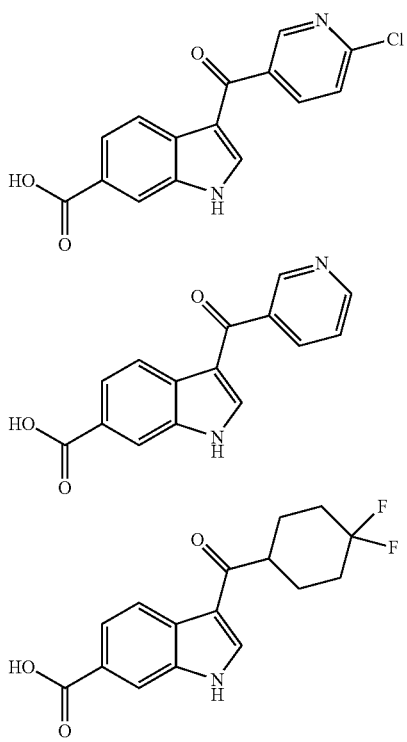

Following the procedure described above for Example 9 and substituting the appropriate reagents, starting materials and purification methods known to those skilled in the art, the following compounds of the present invention were prepared:

| Cpd | Cpd Name and Data |
|---|---|
| 1025 | (4-Fluorophenyl)[6-({3-[4-(1,3-thiazol-2-ylcarbonyl)piperazin-1-yl]azetidin-1-yl}carbonyl)-1H-indol-3-yl]methanone<br>MS m/z (M + H⁺) 518.2 |
| 802 | ((4,4-Difluorocyclohexyl)[6-({3-[4-(1,3-thiazol-2-ylcarbonyl)piperazin-1-yl]azetidin-1-yl}carbonyl)-1H-indol-3-yl]methanone<br>MS m/z (M + H⁺) 542.1 |
| 949 | (6-Chloropyridin-3-yl)[6-({3-[4-(1,3-thiazol-2-ylcarbonyl)piperazin-1-yl]azetidin-1-yl}carbonyl)-1H-indol-3-yl]methanone<br>MS m/z (M + H⁺) 535.0 |
| 950 | Pyridin-3-yl[6-({3-[4-(1,3-thiazol-2-ylcarbonyl)piperazin-1-yl]azetidin-1-yl}carbonyl)-1H-indol-3-yl]methanone<br>MS m/z (M + H⁺) 501.0 |

Example 44

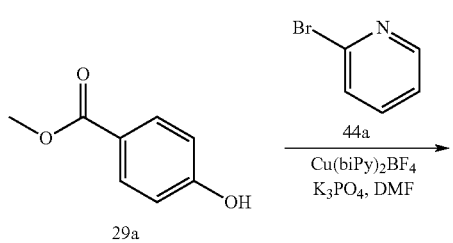

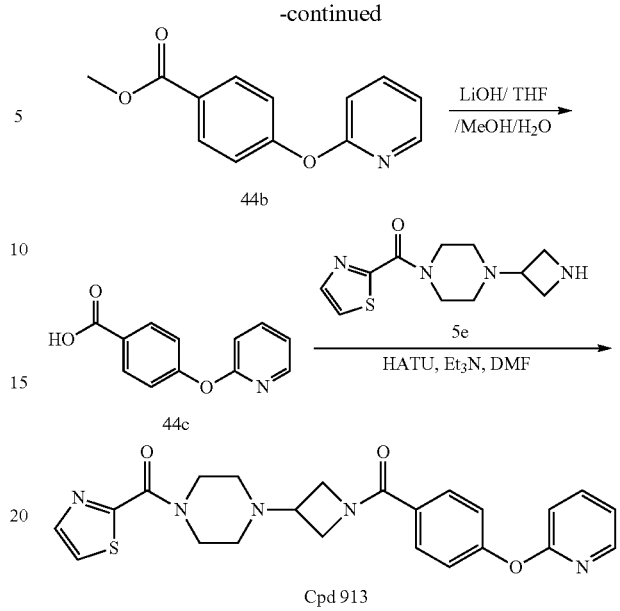

A. Methyl 4-(pyridin-2-yloxy)-benzoate, 44b. A mixture of 29a (433 mg, 2.85 mmol), 44a (300 mg, 1.90 mmol), Cu(biPy)₂BF₄ (88 mg, 0.19 mmol), K₃PO₄ (805 mg, 3.80 mmol), and DMF (1.5 mL) was heated at 140° C. for 1 h. After 0.5 h, the mixture was poured into water (60 mL) and extracted with EtOAc. The combined extracts were washed with brine, dried over Na₂SO₄ and concentrated. The crude product was purified by flash column chromatography (silica gel, 20% EtOAc/hexanes) to give 298 mg of 44b.

B. 4-(Pyridin-2-yloxy)-benzoic acid, 44c. A mixture of 44b (430 mg, 1.87 mmol), LiOH (180 mg, 7.5 mmol), THF (3 mL), MeOH (3 mL), and H₂O (3 mL) was stirred at room temperature for 4 h. Then the reaction mixture was acidified with 15% citric acid (10 mL). The mixture was extracted with EtOAc. The organic layer was washed with brine, dried over Na₂SO₄, and concentrated to give 44c (350 mg).

C. 1-(1-{[4-(Pyridin-2-yloxy)phenyl]carbonyl}azetidin-3-yl)-4-(1,3-thiazol-2-ylcarbonyl)piperazine, Cpd 913. A mixture of 44c (60 mg, 0.28 mmol), 5e (105 mg, 0.36 mmol), HATU (159 mg, 0.42 mmol), Et₃N (1 mL), and DMF (3 mL) was stirred at room temperature overnight, and then poured into water (10 mL). The mixture was extracted with EtOAc. The extracts were washed with brine, dried over Na₂SO₄ and concentrated. The residue was purified by flash column chromatography (silica gel, 7% MeOH/CH₂Cl₂) to give 98 mg of Cpd 913. MS m/z (M+H⁺) 450.0.

Following the procedure described above for Example 44, Steps A and B, and substituting the appropriate reagents, starting materials and purification methods known to those skilled in the art, the following intermediate compounds were prepared.

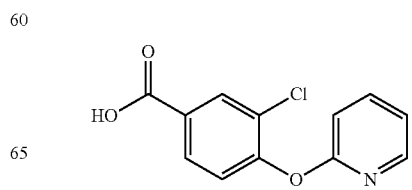

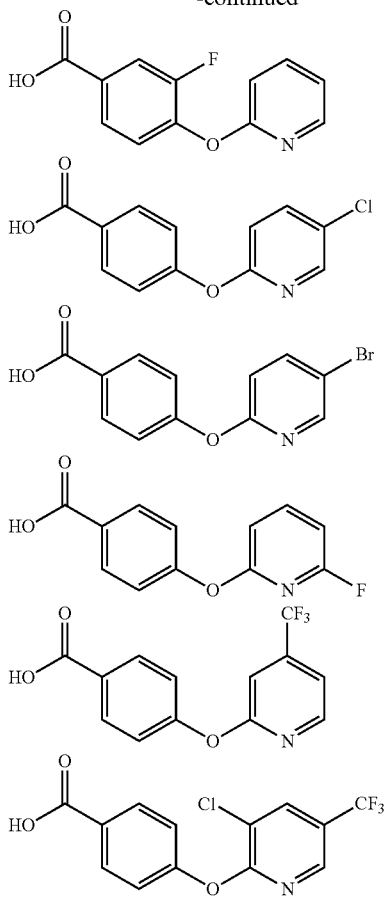

Following the procedure described above for Example 44, Step C, and substituting the appropriate reagents, starting materials and purification methods known to those skilled in the art, the following compounds of the present invention were prepared.

| Cpd | Cpd Name and Data |
|---|---|
| 527 | 1-(Phenylcarbonyl)-4-(1-{[4-(pyridin-3-yloxy)phenyl]carbonyl}azetidin-3-yl)piperazine<br>MS m/z (M + H⁺) 443.0 |
| 507 | 1-{1-[(4-{[3-Chloro-5-(trifluoromethyl)pyridin-2-yl]oxy}phenyl)carbonyl]azetidin-3-yl}-4-(phenylcarbonyl)piperazine<br>MS m/z (M + H⁺) 545.0 |
| 533 | 1-[1-({4-[(5-Methoxypyridin-3-yl)oxy]phenyl}carbonyl)azetidin-3-yl]-4-(phenylcarbonyl)piperazine<br>MS m/z (M + H⁺) 497.0 |
| 1484 | 1-(Phenylcarbonyl)-4-(1-{[4-(pyridin-2-yloxy)phenyl]carbonyl}azetidin-3-yl)piperazine<br>MS m/z (M + H⁺) 443.0 |
| 875 | 1-(1-{[4-(3-Chlorophenoxy)-3-fluorophenyl]carbonyl}azetidin-3-yl)-4-(1,3-thiazol-2-ylcarbonyl)piperazine<br>MS m/z (M + H⁺) 500.8 |
| 663 | 1-{1-[(4-{[3-Chloro-5-(trifluoromethyl)pyridin-2-yl]oxy}phenyl)carbonyl]azetidin-3-yl}-4-(1,3-thiazol-2-ylcarbonyl)piperazine<br>MS m/z (M + H⁺) 551.8 |
| 734 | 1-(1-{[4-(Pyridin-3-yloxy)phenyl]carbonyl}azetidin-3-yl)-4-(1,3-thiazol-2-ylcarbonyl)piperazine<br>MS m/z (M + H⁺) 450.0 |
| 904 | 1-[1-({4-[(5-Methoxypyridin-3-yl)oxy]phenyl}carbonyl)azetidin-3-yl]-4-(1,3-thiazol-2-ylcarbonyl)piperazine<br>MS m/z (M + H⁺) 480.0 |
| 532 | 1-[1-({4-[(5-Bromopyridin-2-yl)oxy]phenyl}carbonyl)azetidin-3-yl]-4-(phenylcarbonyl)piperazine<br>MS m/z (M + H⁺) 522.8 |
| 537 | 1-(1-{[3-Fluoro-4-(pyridin-2-yloxy)phenyl]carbonyl}azetidin-3-yl)-4-(phenylcarbonyl)piperazine<br>MS m/z (M + H⁺) 461.0 |
| 520 | 1-[1-({4-[(5-Chloropyridin-2-yl)oxy]phenyl}carbonyl)azetidin-3-yl]-4-(phenylcarbonyl)piperazine<br>MS m/z (M + H⁺) 477.0 |
| 525 | 1-(1-{[3-Chloro-4-(pyridin-2-yloxy)phenyl]carbonyl}azetidin-3-yl)-4-(phenylcarbonyl)piperazine<br>MS m/z (M + H⁺) 477.0 |
| 522 | 1-[1-({4-[(6-Fluoropyridin-2-yl)oxy]phenyl}carbonyl)azetidin-3-yl]-4-(phenylcarbonyl)piperazine<br>MS m/z (M + H⁺) 504.0 |
| 518 | 1-(Phenylcarbonyl)-4-{1-[(4-{[4-(trifluoromethyl)pyridin-2-yl]oxy}phenyl)carbonyl]azetidin-3-yl}piperazine<br>MS m/z (M + H⁺) 511.0 |
| 877 | 1-[1-({4-[(5-Bromopyridin-2-yl)oxy]phenyl}carbonyl)azetidin-3-yl]-4-(1,3-thiazol-2-ylcarbonyl)piperazine<br>MS m/z (M + H⁺) 529.8 |
| 765 | 1-[1-({4-[(5-Bromopyridin-2-yl)oxy]phenyl}carbonyl)azetidin-3-yl]-4-(1,3-thiazol-4-ylcarbonyl)piperazine<br>MS m/z (M + H⁺) 529.8 |
| 909 | 1-(1-{[3-Fluoro-4-(pyridin-2-yloxy)phenyl]carbonyl}azetidin-3-yl)-4-(1,3-thiazol-2-ylcarbonyl)piperazine<br>MS m/z (M + H⁺) 468.0 |
| 717 | 1-[1-({4-[(5-Chloropyridin-2-yl)oxy]phenyl}carbonyl)azetidin-3-yl]-4-(1,3-thiazol-2-ylcarbonyl)piperazine<br>MS m/z (M + H⁺) 484.0 |
| 752 | 1-(1-{[3-Chloro-4-(pyridin-2-yloxy)phenyl]carbonyl}azetidin-3-yl)-4-(1,3-thiazol-2-ylcarbonyl)piperazine<br>MS m/z (M + H⁺) 484.0 |
| 715 | 1-[1-({4-[(6-Fluoropyridin-2-yl)oxy]phenyl}carbonyl)azetidin-3-yl]-4-(1,3-thiazol-2-ylcarbonyl)piperazine<br>MS m/z (M + H⁺) 468.0 |
| 652 | 1-(1,3-Thiazol-2-ylcarbonyl)-4-{1-[(4-{[4-(trifluoromethyl)pyridin-2-yl]oxy}phenyl)carbonyl]azetidin-3-yl}piperazine<br>MS m/z (M + H⁺) 518.0 |

Example 44a

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 837 | 1-(Trifluoroacetyl)-4-{1-[(4-{[4-(trifluoromethyl)pyridin-2-yl]oxy}phenyl)carbonyl]azetidin-3-yl}piperazine<br>MS m/z (M + H⁺) 503.0 | N-TFA |
| 869 | 1-(1-{[4-(Pyridin-2-yloxy)phenyl]carbonyl}azetidin-3-yl)-4- | N-TFA |

-continued

| Cpd | Cpd Name and Data | Salt Form |
|---|---|---|
|  | (trifluoroacetyl)piperazine<br>MS m/z (M + H+) 435.0 |  |
| 872 | 1-[1-({4-[(5-Bromopyridin-2-yl)oxy]phenyl}carbonyl)azetidin-3-yl]-4-(trifluoroacetyl)piperazine<br>MS m/z (M + H+) 512.8 | N-TFA |
| 802 | 1-{1-[(4-{[3-Chloro-5-(trifluoromethyl)pyridin-2-yl]oxy}phenyl)carbonyl]azetidin-3-yl}-4-(trifluoroacetyl)piperazine<br>MS m/z (M + H+) 536.8 | N-TFA |

-continued

| Cpd | Cpd Name and Data |
|---|---|
| 769 | 1-(1,3-Thiazol-4-ylcarbonyl)-4-{1-[(4-{[4-(trifluoromethyl)pyridin-2-yl]oxy}phenyl)carbonyl]azetidin-3-yl}piperazine<br>MS m/z (M + H+) 518.0 |
| 720 | 1-{1-[(4-{[3-Chloro-5-(trifluoromethyl)pyridin-2-yl]oxy}phenyl)carbonyl]azetidin-3-yl}-4-(1,3-thiazol-4-ylcarbonyl)piperazine<br>MS m/z (M + H+) 551.8 |

Example 45

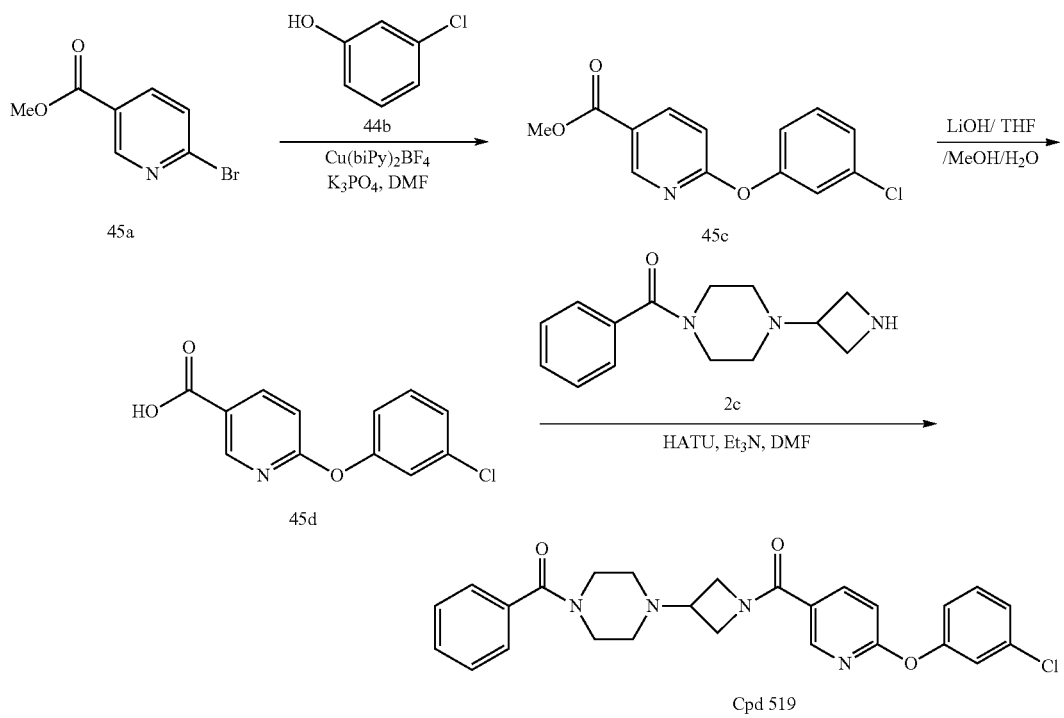

Example 44b

Following the procedure described above for Example 1, and substituting the appropriate reagents, starting materials and purification methods known to those skilled in the art, the following compounds of the present invention were prepared.

| Cpd | Cpd Name and Data |
|---|---|
| 922 | 1-(1-{[4-(Pyridin-2-yloxy)phenyl]carbonyl}azetidin-3-yl)-4-(1,3-thiazol-4-ylcarbonyl)piperazine<br>MS m/z (M + H+) 450.0 |
| 757 | 1-[1-({4-[(5-Chloropyridin-2-yl)oxy]phenyl}carbonyl)azetidin-3-yl]-4-(1,3-thiazol-4-ylcarbonyl)piperazine<br>MS m/z (M + H+) 484.0 |
| 784 | 1-[1-({4-[(6-Fluoropyridin-2-yl)oxy]phenyl}carbonyl)azetidin-3-yl]-4-(1,3-thiazol-4-ylcarbonyl)piperazine<br>MS m/z (M + H+) 468.0 |

A. Methyl 6-(3-chloro-phenoxy)-nicotinate, 5c. A mixture of 45a (200 mg, 0.926 mmol), 45b (178 mg, 1.39 mmol), Cu(biPy)$_2$BF$_4$ (43 mg, 0.09 mmol), K$_3$PO$_4$ (392 mg, 1.85 mmol), and DMF (1.0 mL) was heated at 140° C. for 1 h. The reaction mixture was then poured into water (30 mL) and extracted with EtOAc. The extracts were washed with brine, dried over Na$_2$SO$_4$, and concentrated. The crude product was purified by flash column chromatography (silica gel, 20% EtOAc/hexanes) to give 202 mg of 45c.

B. 6-(3-Chloro-phenoxy)-nicotinic acid, 5d. A mixture of 45c (202 mg, 0.766 mmol), LiOH (74 mg, 3.06 mmol), THF (2 mL), MeOH (2 mL) and H$_2$O (2 mL) was stirred at room temperature for 4 h. The reaction mixture was acidified with 15% citric acid (10 mL) and extracted with EtOAc. The extracts were washed with brine, dried over Na$_2$SO$_4$, and concentrated to give 177 mg of 45d.

C. 1-(1-{[6-(3-Chlorophenoxy)pyridin-3-yl]carbonyl}azetidin-3-yl)-4-(phenylcarbonyl)piperazine, Cpd 519. A mixture of 45d (60 mg, 0.24 mmol), 2c (101 mg, 0.36 mmol), HATU (137 mg, 0.36 mmol), Et$_3$N (0.5 mL), and DMF (3 mL) was stirred at room temperature overnight. The mixture was poured into water (30 mL) and extracted with EtOAc. The extracts were washed with brine, dried over $Na_2SO_4$, and concentrated. The residue was purified by flash column chromatography (silica gel, 5% $MeOH/CH_2Cl_2$) to give 50 mg of Cpd 519. $^1H$ NMR ($CDCl_3$): δ 8.35-8.49 (m, 1H), 8.06 (dd, J=8.5, 2.1 Hz, 1H), 7.32-7.49 (m, 6H), 7.14-7.27 (m, 2H), 6.94-7.11 (m, 2H), 4.24 (br. s, 1H), 4.15 (br. s, 2H), 4.00-4.14 (m, 2H), 3.65-3.94 (m, 2H), 3.37-3.60 (m, 2H), 3.16-3.33 (m, 1H), 2.44 (br. s, 4H). MS m/z (M+H+) 477.0.

Following the procedure described above for Example 45, Steps A and B, and substituting the appropriate reagents, starting materials and purification methods known to those skilled in the art, the following intermediate compounds were prepared.

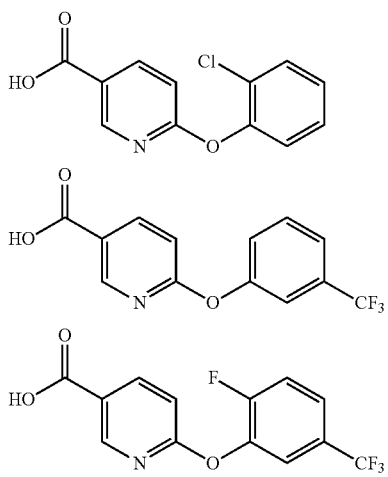

Following the procedure described above for Example 45, Step C, and substituting the appropriate reagents, starting materials and purification methods known to those skilled in the art, the following compounds of the present invention were prepared.

| Cpd | Cpd Name and Data |
|---|---|
| 514 | 1-(Phenylcarbonyl)-4-[1-({6-[3-(trifluoromethyl)phenoxy]pyridin-3-yl}carbonyl)azetidin-3-yl]piperazine<br>MS m/z (M + H+) 511.0 |
| 521 | 1-(1-{[6-(2-Chlorophenoxy)pyridin-3-yl]carbonyl}azetidin-3-yl)-4-(phenylcarbonyl)piperazine<br>MS m/z (M + H+) 477.0 |
| 683 | 1-(1-{[6-(3-Chlorophenoxy)pyridin-3-yl]carbonyl}azetidin-3-yl)-4-(1,3-thiazol-2-ylcarbonyl)piperazine<br>MS m/z (M + H+) 484.0 |
| 660 | 1-(1,3-Thiazol-2-ylcarbonyl)-4-[1-({6-[3-(trifluoromethyl)phenoxy]pyridin-3-yl}carbonyl)azetidin-3-yl]piperazine<br>MS m/z (M + H+) 518.0 |
| 708 | 1-(1-{[6-(2-Chlorophenoxy)pyridin-3-yl]carbonyl}azetidin-3-yl)-4-(1,3-thiazol-2-ylcarbonyl)piperazine<br>MS m/z (M + H+) 484.0 |
| 878 | 1-[1-({6-[2-Fluoro-5-(trifluoromethyl)phenoxy]pyridin-3-yl}carbonyl)azetidin-3-yl]-4-(1,3-thiazol-2-ylcarbonyl)piperazine<br>MS m/z (M + H+) 536.0 |

Example 45a

Following the procedure described above for Example 1, and substituting the appropriate reagents, starting materials and purification methods known to those skilled in the art, the following compounds of the present invention were prepared.

| Cpd | Cpd Name and Data |
|---|---|
| 803 | 1-(1-{[6-(3-Chlorophenoxy)pyridin-3-yl]carbonyl}azetidin-3-yl)-4-(1,3-thiazol-4-ylcarbonyl)piperazine<br>MS m/z (M + H+) 504.0 |
| 689 | 1-(1,3-Thiazol-4-ylcarbonyl)-4-[1-({6-[3-(trifluoromethyl)phenoxy]pyridin-3-yl}carbonyl)azetidin-3-yl]piperazine<br>MS m/z (M + H+) 518.0 |
| 811 | 1-(1-{[6-(2-Chlorophenoxy)pyridin-3-yl]carbonyl}azetidin-3-yl)-4-(1,3-thiazol-4-ylcarbonyl)piperazine<br>MS m/z (M + H+) 484.0 |

Example 46

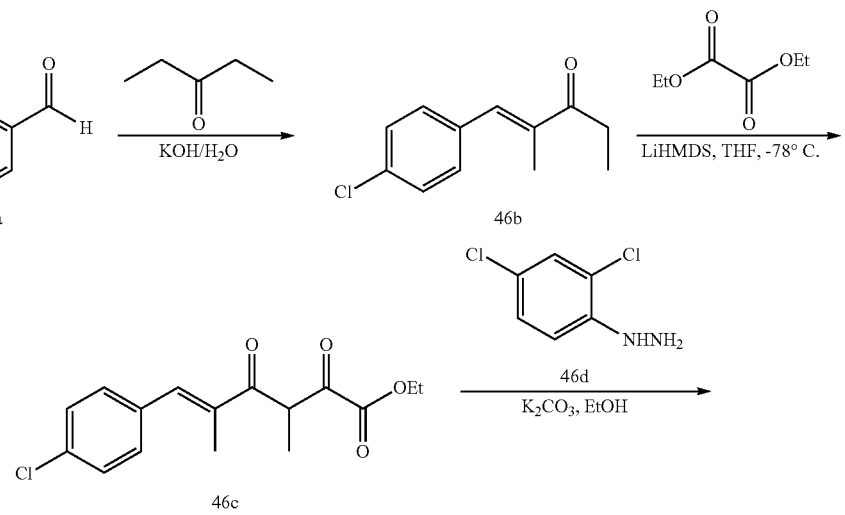

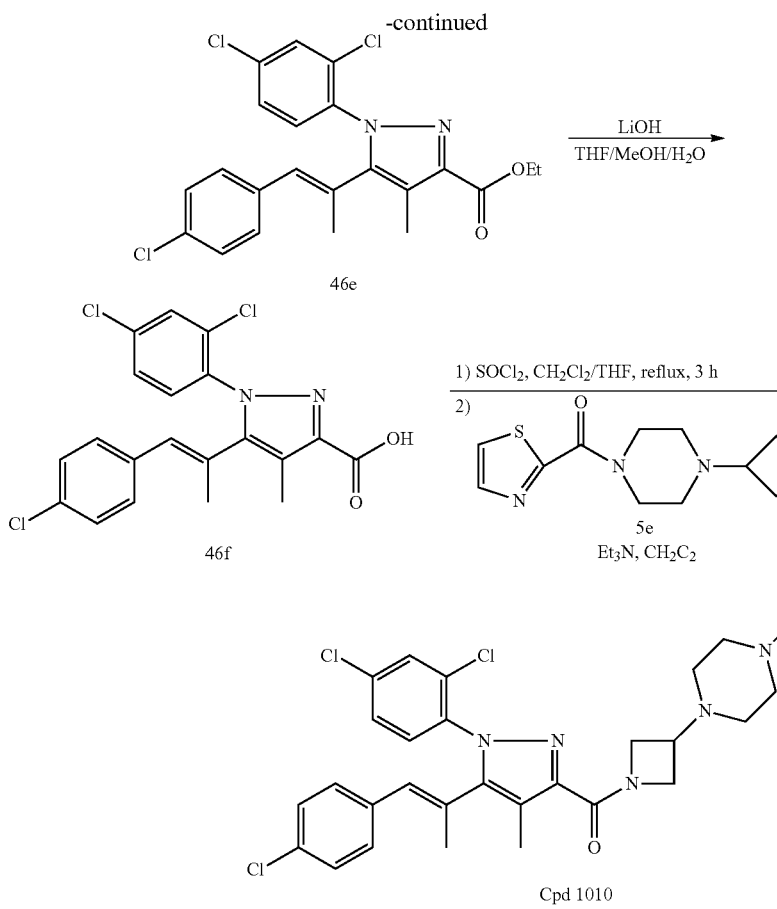

A. 1-(4-Chloro-phenyl)-2-methyl-pent-1-en-3-one, 46b. To 4-chlorobenzaldehyde 46a (99.6 mmol, 14 g) in water (44 mL) was added KOH (44.6 mmol, 2.5 g). The mixture was heated at 65° C. and 3-pentanone (99.6 mmol, 8.58 g) was added dropwise over 10 min. After refluxing for 8 h, the reaction mixture was cooled to room temperature and stirred overnight. Following addition of 260 mL 1N aqueous HCl, the mixture was extracted with EtOAc. The organic layer was dried over $Na_2SO_4$ and concentrated. The crude product was purified by flash column chromatography (silica gel, 5% EtOAc/heptane) to give 8.59 g of 46b.

B. Ethyl 6-(4-chloro-phenyl)-3,5-dimethyl-2,4-dioxo-hex-5-enoate, 46c. To a solution of LiHMDS (1N solution in THF, 5.48 mmol, 5.17 mL) in THF (16 mL) at −78° C. was added a solution of 46b (4.98 mmol, 1.04 g) in THF (2.5 mL) drop wise. After stirring at −78° C. for 1 h, the mixture was treated with a solution of diethyl oxalate (4.98 mmol, 0.73 g) in THF (2.5 mL). After stirring at −78° C. for 1 h, then the mixture was warmed up to room temperature and stirred overnight. The solvent was evaporated and the crude product was taken up in EtOAc, and washed with 1N HCl and brine. The organic layer was dried over $Na_2SO_4$ and concentrated to give 1.5 g of 46c.

C. 5-[2-(4-chloro-phenyl)-1-methyl-vinyl]-1-(2,4-dichloro-phenyl)-4-methyl-1H-pyrazole-3-carboxylate, 46e. A mixture of 46c (15.6 mmol, 4.82 g), 2,4-dichlorophenyl-hydrazine 46d (17.2 mmol, 3.67 g), $K_2CO_3$ (17.2 mmol, 2.37 g) and EtOH (137 mL) was stirred at 70° C. overnight. The solid was filtered off and washed with EtOH. The filtrates were concentrated and purified by flash column chromatography (silica gel, 5% EtOAc/heptane) to give 2.25 g of 46e.

D. 5-[2-(4-Chloro-phenyl)-1-methyl-vinyl]-1-(2,4-dichloro-phenyl)-4-methyl-1H-pyrazole-3-carboxylic acid, 46f. The mixture of 46e (3.34 mmol, 1.5 g), LiOH (13.3 mmol, 319 mg), THF (7 mL), MeOH (7 mL), and $H_2O$ (37 mL) was stirred at room temperature for 4 h. The mixture was acidified with 1N HCl to pH=5 and extracted with EtOAc. The organic layer was dried over $Na_2SO_4$ and concentrated to give 46f (202 mg).

E. 5-[2-(4-Chlorophenyl)-1-methyl-vinyl]-1-(2,4-dichloro-phenyl)-4-methyl-1H-pyrazole-3-carboxylic acid, Cpd 1010. To a solution of 46f (0.138 mmol, 60 mg) in $CH_2Cl_2$ and THF was added $SOCl_2$ (2 N solution in THF, 0.414 mmol, 0.212 mL). After refluxing for 4 h, the mixture was concentrated and dried under vacuum for 1 h. In another flask was added 5e (0.18 mmol, 52 mg), $CH_2Cl_2$ (3 mL), and DIPEA (0.69 mmol, 0.12 mL). To this solution was added the crude product from the $SOCl_2$ reaction dissolved in $CH_2Cl_2$ (1 mL). After stirring at room temperature for 1 h, the mixture was diluted with $CH_2Cl_2$ (15 mL), washed with 3N NaOH aqueous solution (30 mL) and brine (30 mL), dried over $Na_2SO_4$, and concentrated. The crude product was purified by flash column chromatography (silica gel, 4% MeOH/$CH_2Cl_2$) to give 74 mg of Cpd 1010. $^1$H NMR (CDCl$_3$): δ 7.87 (d, J=3.5 Hz, 1H), 7.55 (t, J=2.3 Hz, 2H), 7.33-7.36 (m, 2H), 7.30 (d, J=8.6 Hz, 2H), 7.13 (d, J=8.6 Hz, 2H), 6.41 (s, 1H), 4.49-4.62 (m, 2H), 4.41 (dd, J=10.4, 5.3 Hz, 2H), 4.22 (dd, J=10.0, 7.2 Hz, 1H), 4.04-4.10 (m, 1H), 3.87 (br. s, 1H), 3.82 (br. s, 1H), 3.18-3.26 (m, 1H), 2.41-2.58 (m, 4H), 2.39 (s, 3H), 1.88 (s, 3H). MS m/z (M+H$^+$) 657.0.

Following the procedure described above for Example 46, Steps A-D or B-D, and substituting the appropriate reagents, starting materials and purification methods known to those skilled in the art, the following intermediate compounds were prepared.

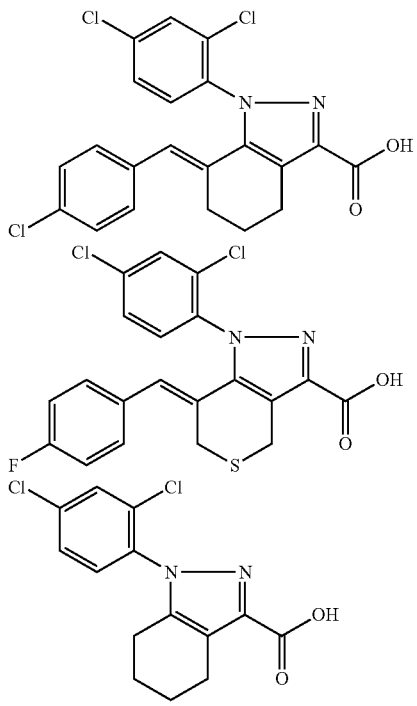

Following the procedure described above for Example 46, Step E, or Example 1, and substituting the appropriate reagents, starting materials and purification methods known to those skilled in the art, the following compounds of the present invention were prepared.

| Cpd | Cpd Name and Data |
|---|---|
| 1011 | 1-[1-({5-[(E)-2-(4-Chlorophenyl)-1-methylethenyl]-1-(2,4-dichlorophenyl)-4-methyl-1H-pyrazol-3-yl}carbonyl)azetidin-3-yl]-4-(1H-pyrrol-2-ylcarbonyl)piperazine<br>MS m/z (M + H$^+$) 639.2 |
| 1018 | (7E)-7-[(4-Chlorophenyl)methylidene]-1-(2,4-dichlorophenyl)-3-({3-[4-(1,3-thiazol-2-ylcarbonyl)piperazin-1-yl]azetidin-1-yl}carbonyl)-4,5,6,7-tetrahydro-1H-indazole<br>MS m/z (M + H$^+$) 669.0 |
| 1019 | (7E)-7-[(4-Chlorophenyl)methylidene]-1-(2,4-dichlorophenyl)-3-({3-[4-(1H-pyrrol-2-ylcarbonyl)piperazin-1-yl]azetidin-1-yl}carbonyl)-4,5,6,7-tetrahydro-1H-indazole<br>MS m/z (M + H$^+$) 651.2 |
| 1021 | (7Z)-1-(2,4-Dichlorophenyl)-7-[(4-fluorophenyl)methylidene]-3-({3-[4-(1,3-thiazol-2-ylcarbonyl)piperazin-1-yl]azetidin-1-yl}carbonyl)-1,4,6,7-tetrahydrothiino[4,3-c]pyrazole<br>MS m/z (M + H$^+$) 671.0 |
| 1024 | (7Z)-1-(2,4-Dichlorophenyl)-7-[(4-fluorophenyl)methylidene]-3-({3-[4-(1H-pyrrol-2-ylcarbonyl)piperazin-1-yl]azetidin-1-yl}carbonyl)-1,4,6,7-tetrahydrothiino[4,3-c]pyrazole<br>MS m/z (M + H$^+$) 651.2 |
| 1267 | 1-(2,4-Dichlorophenyl)-3-({3-[4-(1,3-thiazol-2-ylcarbonyl)piperazin-1-yl]azetidin-1-yl}carbonyl)-4,5,6,7-tetrahydro-1H-indazole<br>MS m/z (M + H$^+$) 645.2 |
| 1309 | 1-(2,4-Dichlorophenyl)-3-({3-[4-(1H-pyrrol-2-ylcarbonyl)piperazin-1-yl]azetidin-1-yl}carbonyl)-4,5,6,7-tetrahydro-1H-indazole<br>MS m/z (M + H$^+$) 627.2 |
| 1023 | (7E)-7-[(4-Chlorophenyl)methylidene]-1-(2,4-dichlorophenyl)-3-({3-[4-(1,3-thiazol-4-ylcarbonyl)piperazin-1-yl]azetidin-1-yl}carbonyl)-4,5,6,7-tetrahydro-1H-indazole<br>MS m/z (M + H$^+$) 669.1 |
| 1304 | 1-(2,4-Dichlorophenyl)-3-({3-[4-(1,3-thiazol-4-ylcarbonyl)piperazin-1-yl]azetidin-1-yl}carbonyl)-4,5,6,7-tetrahydro-1H-indazole<br>MS m/z (M + H$^+$) 545.2 |

Example 46a

Following the procedure described above for Example 1c, and substituting the appropriate reagents, starting materials and purification methods known to those skilled in the art, the following compounds of the present invention were prepared:

| Cpd | Cpd Name and Data | Salt Form |
|---|---|---|
| 1012 | 1-[1-({5-[(E)-2-(4-Chlorophenyl)-1-methylethenyl]-1-(2,4-dichlorophenyl)-4-methyl-1H-pyrazol-3-yl}carbonyl)azetidin-3-yl]-4-(trifluoroacetyl)piperazine<br>MS m/z (M + H$^+$) 642.9 | N-TFA |
| 1020 | (7E)-7-[(4-Chlorophenyl)methylidene]-1-(2,4-dichlorophenyl)-3-({3-[4-(trifluoroacetyl)piperazin-1-yl]azetidin-1-yl}carbonyl)-4,5,6,7-tetrahydro-1H-indazole<br>MS m/z (M + H$^+$) 654.0 | N-TFA |
| 1022 | (7Z)-1-(2,4-Dichlorophenyl)-7-[(4-fluorophenyl)methylidene]-3-({3-[4-(trifluoroacetyl)piperazin-1-yl]azetidin-1-yl}carbonyl)-1,4,6,7-tetrahydrothiino[4,3-c]pyrazole<br>MS m/z (M + H$^+$) 654.1 | N-TFA |
| 1311 | 1-(2,4-Dichlorophenyl)-3-({3-[4-(trifluoroacetyl)piperazin-1-yl]azetidin-1-yl}carbonyl)-4,5,6,7-tetrahydro-1H-indazole<br>MS m/z (M + H$^+$) 530.2 | N-TFA |

Example 47

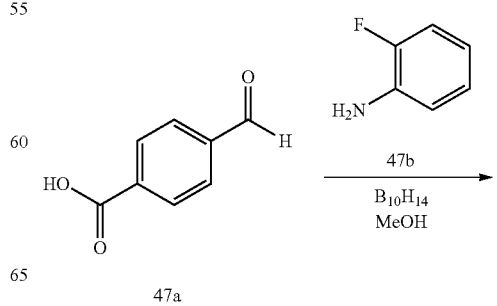

47a

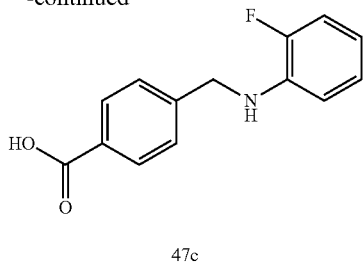

47c 4-(((2-fluorophenyl)amino)methyl)benzoic acid, 47c. A mixture of 4-formylbenzoic acid 47a (3.33 mmol, 500 mg), 2-fluoroaniline 47b (3.33 mmol, 370 mg), and decaborane (1 mmol, 122 mg) in 8 mL of MeOH was stirred at room temperature for 15 min. The mixture was concentrated and purified by preparative reverse-phase chromatography to afford 0.81 g (99%) of 47c.

Following the procedure described above for Example 47, and substituting the appropriate reagents, starting materials and purification methods known to those skilled in the art, the following intermediate compounds were prepared.

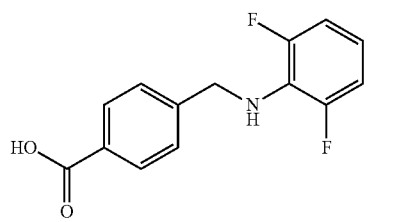

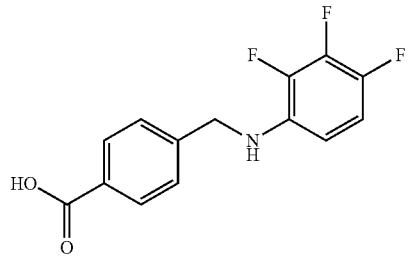

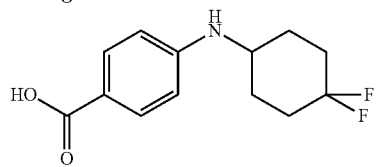

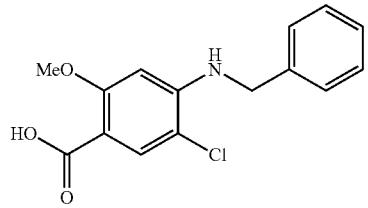

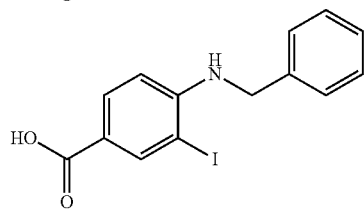

Following the procedure described above for Example 1 or Example 9, and substituting the appropriate reagents, starting materials and purification methods known to those skilled in the art, the following compounds of the present invention were prepared.

| Cpd | Cpd Name and Data |
|---|---|
| 553 | 2-Fluoro-N-[4-({3-[4-(phenylcarbonyl)piperazin-1-yl]azetidin-1-yl}carbonyl)benzyl]aniline<br>MS m/z (M + H⁺) 473.1 |
| 529 | N-Benzyl-2-chloro-5-methoxy-4-({3-[4-(phenylcarbonyl)piperazin-1-yl]azetidin-1-yl}carbonyl)aniline<br>MS m/z (M + H⁺) 520.2 |
| 530 | N-(4,4-Difluorocyclohexyl)-4-({3-[4-(phenylcarbonyl)piperazin-1-yl]azetidin-1-yl}carbonyl)aniline<br>MS m/z (M + H⁺) 483.2 |
| 561 | 2-Fluoro-N-[3-({3-[4-(phenylcarbonyl)piperazin-1-yl]azetidin-1-yl}carbonyl)benzyl]aniline<br>MS m/z (M + H⁺) 473.1 |
| 556 | 2,6-Difluoro-N-[4-({3-[4-(phenylcarbonyl)piperazin-1-yl]azetidin-1-yl}carbonyl)benzyl]aniline<br>MS m/z (M + H⁺) 491.0 |
| 542 | N-Benzyl-2-iodo-4-({3-[4-(phenylcarbonyl)piperazin-1-yl]azetidin-1-yl}carbonyl)aniline<br>MS m/z (M + H⁺) 581.0 |
| 557 | 2,3,4-Trifluoro-N-[4-({3-[4-(phenylcarbonyl)piperazin-1-yl]azetidin-1-yl}carbonyl)benzyl]aniline<br>MS m/z (M + H⁺) 509.2 |
| 1005 | 2-Fluoro-N-[3-({3-[4-(1,3-thiazol-2-ylcarbonyl)piperazin-1-yl]azetidin-1-yl}carbonyl)benzyl]aniline<br>MS m/z (M + H⁺) 480.3 |

Example 48

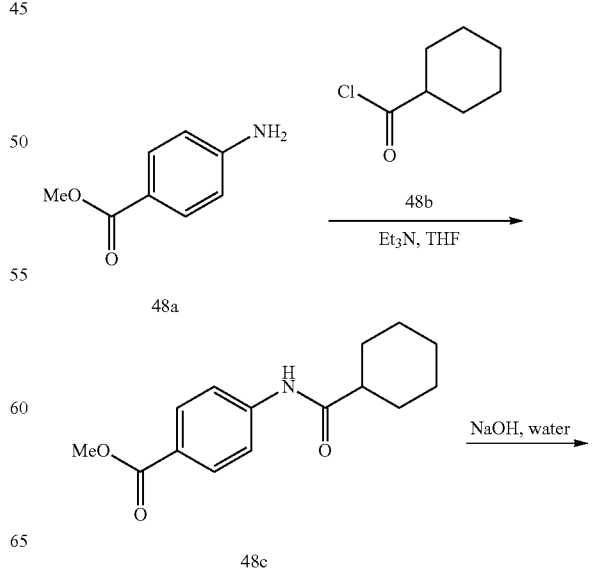

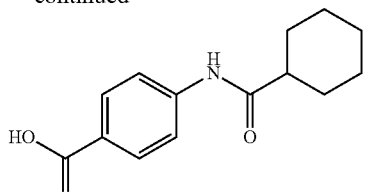

48d 4-(Cyclohexanecarboxamido)benzoic acid, 48d. A mixture of 4-aminobenzoic acid 48a (1.98 mmol, 300 mg), cyclohexanecarbonyl chloride 48b (1.98 mmol, 291 mg), and Et$_3$N (2.52 mmol, 0.43 mL) in 6 mL of THF was stirred at room temperature overnight. 1N aqueous NaOH (7.9 mmol, 7.9 mL) was added to the mixture (containing methyl 4-(cyclohexanecarboxamido)benzoate 48c) and the reaction mixture was stirred for 5 h at room temperature. The THF was removed by rotary evaporation and 1N aqueous HCl was added to precipitate the product, which was filtered to give 480 mg (92%) of 48d.

Following the procedure described above for Example 9, and substituting the appropriate reagents, starting materials and purification methods known to those skilled in the art, the following compound of the present invention was prepared.

| Cpd | Cpd Name and Data |
|---|---|
| 709 | N-[4-({3-[4-(1,3-Thiazol-2-ylcarbonyl)piperazin-1-yl]azetidin-1-yl}carbonyl)phenyl]cyclohexanecarboxamide<br>MS m/z (M + H$^+$) 482.1 |

Example 49

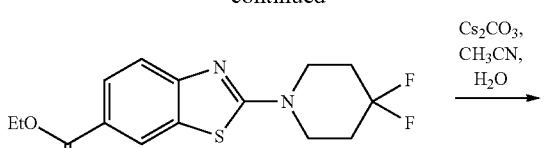

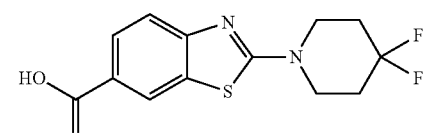

2-(4,4-Difluoropiperidin-1-yl)benzo[d]thiazole-6-carboxylic acid, 49d. A mixture of ethyl 2-bromo-benzo[d]thiazole-6-carboxylate 49a (1.75 mmol, 500 mg), 4,4-difluoropiperidine 49b (1.92 mmol, 303 mg), and Cs$_2$CO$_3$ (5.24 mmol, 1.71 g) in 15 mL of CH$_3$CN was refluxed overnight. The suspension was cooled to room temperature and 15 mL of water was added to the mixture (containing ethyl 2-(4,4-difluoropiperidin-1-yl)benzo[d]thiazole-6-carboxylate 49c). The reaction mixture was heated at 60° C. for 18 h. After cooling, the mixture was acidified using 3N aqueous HCl and the resulting precipitate was filtered to give 575 mg (99%) of 49d. MS m/z (M+H$^+$) 299.1.

Following the procedure described above for Example 9, and substituting the appropriate reagents, starting materials and purification methods known to those skilled in the art, the following compound of the present invention was prepared.

| Cpd | Cpd Name and Data |
|---|---|
| 671 | 2-(4,4-Difluoropiperidin-1-yl)-6-({3-[4-(1,3-thiazol-2-ylcarbonyl)piperazin-1-yl]azetidin-1-yl}carbonyl)-1,3-benzothiazole<br>MS m/z (M + H$^+$) 533.2 |

Example 50

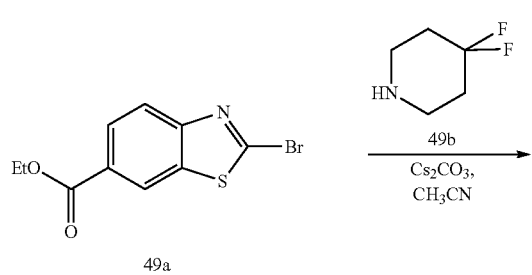

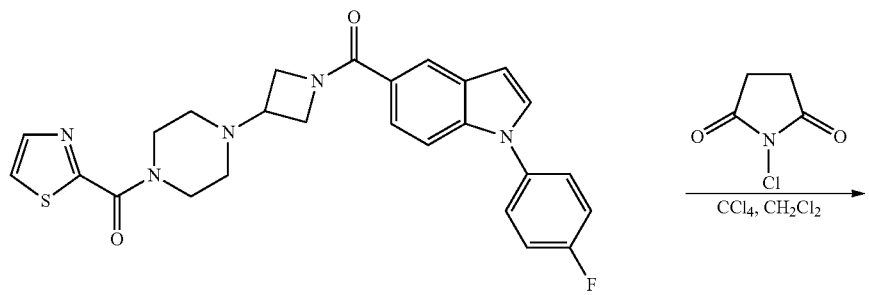

Cpd 487

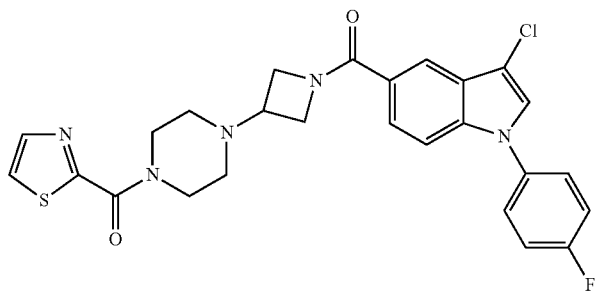

Cpd 1365

3-Chloro-1-(4-fluorophenyl)-5-({3-[4-(1,3-thiazol-2-yl-carbonyl)piperazin-1-yl]azetidin-1-yl}carbonyl)-1H-indole, Cpd 1365. To a solution of Cpd 487 (0.2 mmol, 100 mg) in CCl₄ (4 mL) and CH₂Cl₂ (4 mL) was added NCS (0.25 mmol, 33 mg). The reaction mixture was stirred at room temperature for 4 h. It was then diluted with CH₂Cl₂ and washed with 1N aqueous NaOH and H₂O, dried over Na₂SO₄, and concentrated. Purification by flash column chromatography (silica gel, 3% MeOH/CH₂Cl₂) gave 51 mg of Cpd 1365. MS m/z (M+H⁺) 524.

Example 51

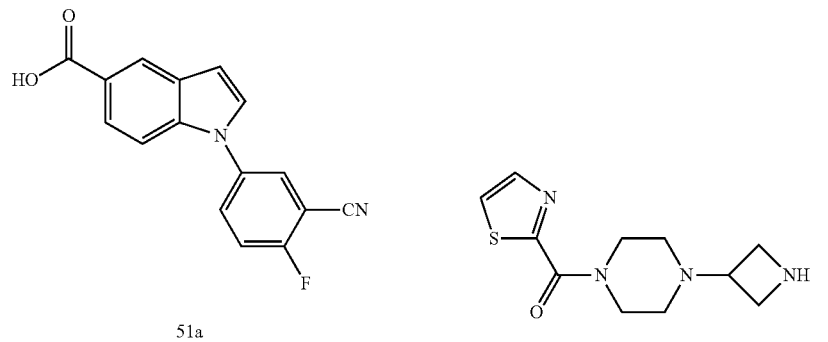

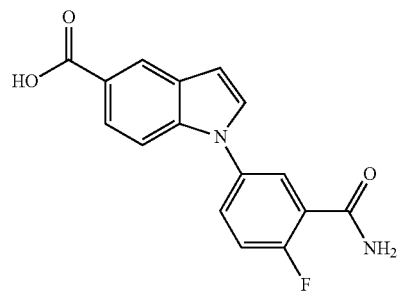

51b

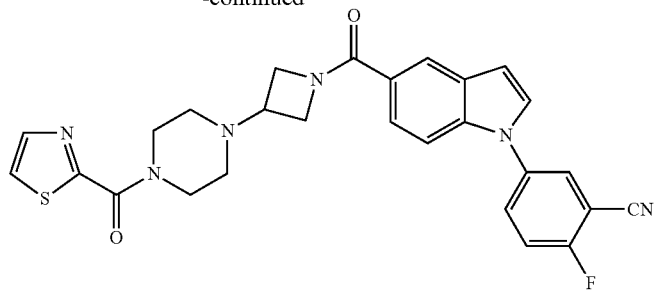

Cpd 1417

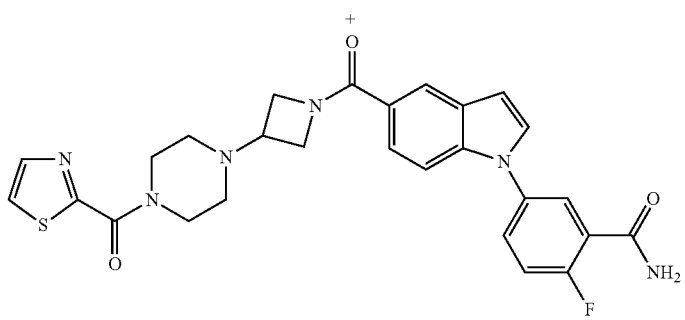

Cpd 1418

A. 1-(3-cyano-4-fluoro-phenyl)-indole-5-carboxylic acid, 51a and 1-(3-carbamoyl-4-fluoro-phenyl)-indole-5-carboxylic acid, 51b. Intermediates 51a and 51b were prepared according to Example 9e, and were obtained as a ~1:1 mixture.

B. 2-Fluoro-5-[5-({3-[4-(1,3-thiazol-2-ylcarbonyl)piperazin-1-yl]azetidin-1-yl}carbonyl)-1H-indol-1-yl]benzonitrile, Cpd 1417 and 2-fluoro-5-[5-({3-[4-(1,3-thiazol-2-ylcarbonyl)piperazin-1-yl]azetidin-1-yl}carbonyl)-1H-indol-1-yl]benzamide, Cpd 1418. Cpd 1417 and Cpd 1418 were prepared according to Example 9 from 5a bis HCl salt (0.22 mmol, 72 mg), the ~1:1 mixture of 51a and 51b (0.19 mmol, 54 mg), HATU (0.22 mmol, 85 mg), and Et$_3$N (1.11 mmol, 0.15 mL) in 4 mL of CH$_2$Cl$_2$. After workup, purification by flash column chromatography (silica gel, 3-4% MeOH/CH$_2$Cl$_2$) gave 28 mg (59%) of Cpd 1417 followed by 15 mg (31%) of Cpd 1418. Cpd 1417: MS m/z (M+H$^+$) 515. Cpd 1418: MS m/z (M+H$^+$) 533.

Example 52

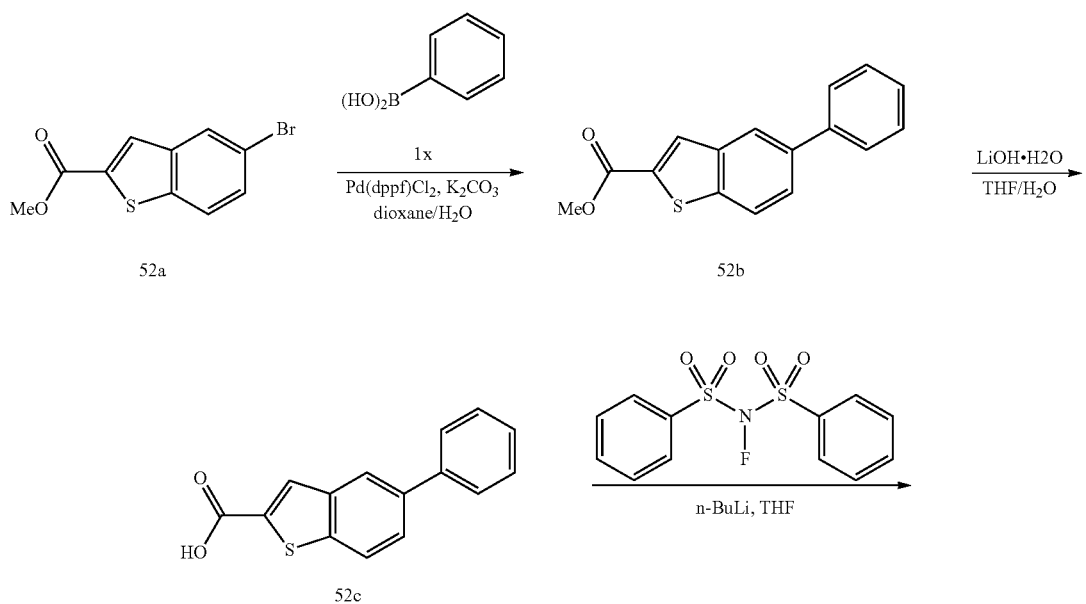

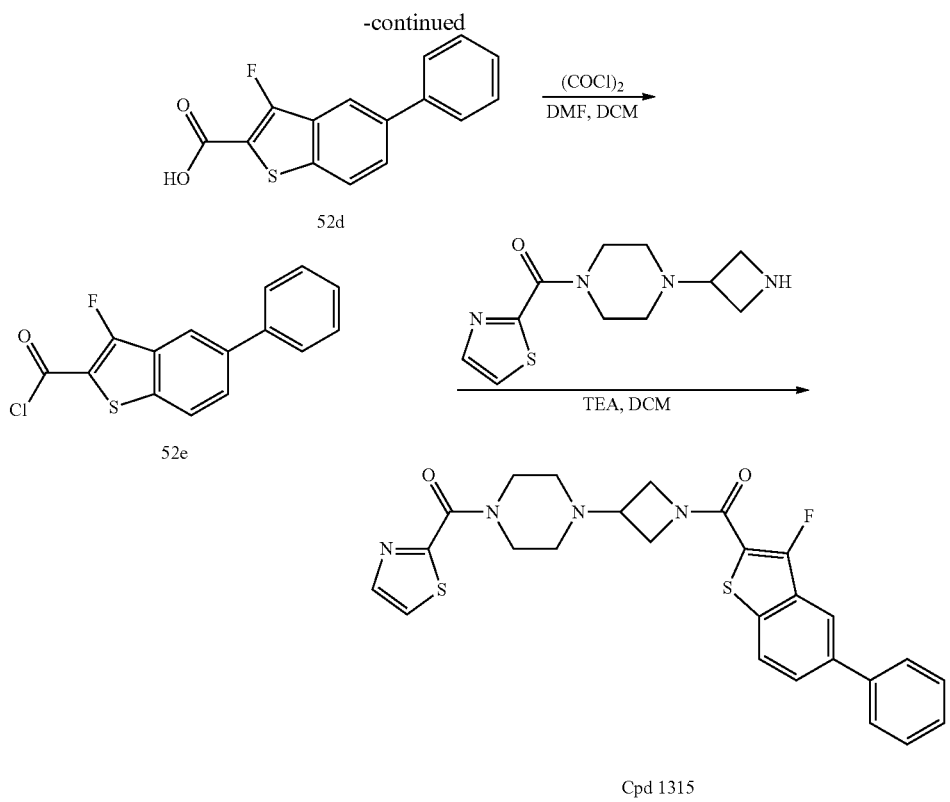

Cpd 1315

A. Methyl 5-Phenyl-benzo[b]thiophene-2-carboxylate, 52b. A mixture of compound 52a (542.3 mg, 2 mmol), phenyl boronic acid 1x (268.2 mg, 2.2 mmol), Pd(dppf)Cl$_2$·CH$_2$Cl$_2$ (98 mg, 0.12 mmol), and K$_2$CO$_3$ (414.6 mg, 3 mmol), in a dioxane (4 mL)/water (1 mL) mixture, was placed in a capped vial and heated at 80° C. overnight. The reaction mixture was then diluted with EtOAc and water. The organic layer was concentrated under reduced pressure and purified by flash column chromatography (silica gel, 2-10% EtOAc/heptane) to give compound 52b (510 mg). MS m/z (M+H$^+$) 269.1.

B. 5-Phenyl-benzo[b]thiophene-2-carboxylic acid, 52c. A solution of compound 52b (510 mg, 1.9 mmol) and LiOH·H$_2$O (319 mg, 7.6 mmol) in THF/H$_2$O (10/10 mL) was stirred at room temperature overnight. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give 52c (479 mg), which was used in the next reaction without further purification. MS m/z (M+H$^+$) 255.0.

C. 3-Fluoro-5-phenyl-benzo[b]thiophene-2-carboxylic acid, 52d. To a solution of compound 52c (507 mg, 1.99 mmol) in THF (8 mL) at −70° C. was added n-BuLi (1.6 M in hexane, 2.62 mL, 4.19 mmol). The mixture was stirred at −70° C. for 1 h; then a solution of N-fluorobenzenesulfonimide (817.3 mg, 2.59 mmol) in THF (2 mL) was slowly added. The reaction mixture was allowed to warm to room temperature and was stirred overnight. The resulting mixture was partitioned between dilute aqueous HCl and EtOAc. The organic solution was washed with water and brine, dried over Na$_2$SO$_4$, and concentrated. The residue was tritrated from CH$_2$Cl$_2$, filtered and dried the solid to give compound 52d (391.9 mg). MS m/z (M+H$^+$) 273.0.

D. 3-Fluoro-5-phenyl-benzo[b]thiophene-2-carbonyl chloride, 52e. To a solution of compound 52d (136.2 mg, 0.5 mmol) in CH$_2$Cl$_2$ (5 mL) at room temperature was added (COCl)$_2$ (0.064 mL, 0.75 mmol), followed by DMF (0.01 mL, 0.125 mmol). The reaction mixture was stirred at room temperature for 18 h. The reaction mixture was then concentrated to give compound 52e (light pink powder), which was used in the next reaction without further purification.

E. 1-{1-[(3-Fluoro-5-phenyl-1-benzothiophen-2-yl)carbonyl]azetidin-3-yl}-4-(1,3-thiazol-2-ylcarbonyl)piperazine, Cpd 1315. To a solution of compound 5e (42.7 mg, 0.131 mmol) and Et$_3$N (0.07 mL, 0.5 mmol) in CH$_2$Cl$_2$ (2 mL) at 0° C. was slowly added a solution of compound 52e (36.3 mg, 0.125 mmol) in CH$_2$Cl$_2$ (1 mL). The reaction was stirred at 0° C. for 2 h, diluted with CH$_2$Cl$_2$, and washed with aqueous NaHCO$_3$. The organic layer was dried over Na$_2$SO$_4$ and concentrated. The residue was purified by flash column chromatography (silica gel, 2% MeOH/EtOAc) to give compound Cpd 1315 (16.7 mg). $^1$H NMR (400 MHz, CDCl$_3$): δ 7.98 (d, J=1.2 Hz, 1H), 7.89 (d, J=3.2 Hz, 1H), 7.80-7.86 (m, 1H), 7.73 (dd, J=8.6, 1.7 Hz, 1H), 7.62-7.68 (m, 2H), 7.55 (d, J=3.2 Hz, 1H), 7.46-7.53 (m, 2H), 7.37-7.44 (m, 1H), 4.22-4.67 (m, 5H), 4.05-4.20 (m, 1H), 3.77-4.01 (m, 2H), 3.25-3.37 (m, 1H), 2.42-2.68 (m, 4H). MS m/z (M+H$^+$) 507.0.

Following the procedure described above for Example 52, and substituting the appropriate reagents, starting materials and purification methods known to those skilled in the art the following compounds of the present invention were prepared:

| Cpd | Cpd Name and Data |
|---|---|
| 1092 | 1-[1-({3-Fluoro-5-[4-(trifluoromethyl)phenyl]-1-benzothiophen-2-yl}carbonyl)azetidin-3-yl]-4-(1,3-thiazol-2-ylcarbonyl)piperazine<br>MS m/z (M + H$^+$) 575.1. |

253
-continued

| Cpd | Cpd Name and Data |
|---|---|
| 1063 | 1-[1-({3-Fluoro-6-[4-(trifluoromethyl)phenyl]-1-benzothiophen-2-yl}carbonyl)azetidin-3-yl]-4-(1,3-thiazol-2-ylcarbonyl)piperazine<br>MS m/z (M + H⁺) 575.1. |

Example 53

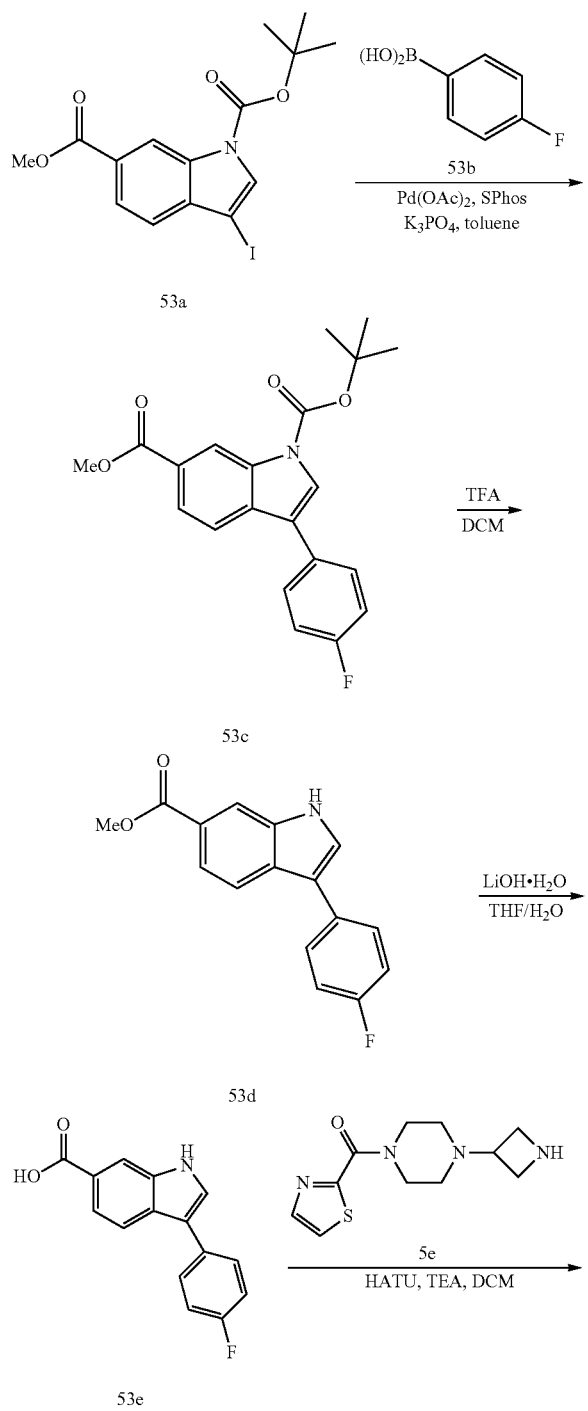

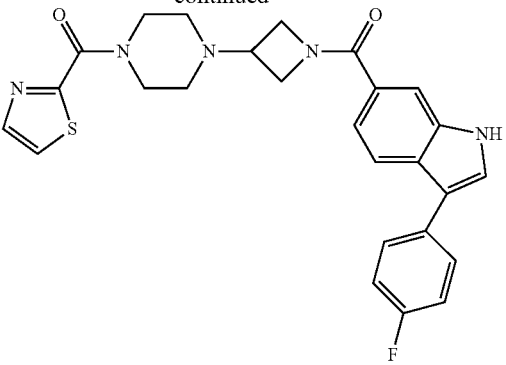

Cpd 1317

A. 1-tert-Butyl 6-methyl 3-(4-fluorophenyl)-1H-indole-1,6-dicarboxylate, 53c. A mixture of compound 53a (1.00 g, 2.49 mmol), 4-fluorophenyl boronic acid 53b (523 mg, 3.74 mmol), Pd(OAc)$_2$ (44.8 mg, 0.2 mmol), 2-dicyclohexylphosphino-2',6'-dimethoxybiphenyl (SPhos, 204.7 mg, 0.5 mmol), and K$_3$PO$_4$ (1.06 g, 4.99 mmol), in toluene (5 mL) was placed in a capped vial and heated at 90° C. under N$_2$ for 3 h. The reaction mixture was then diluted with EtOAc and water. The organic layer was washed with brine, concentrated under reduced pressure, and purified by flash column chromatography (silica gel, 2-10% EtOAc/heptane) to give compound 53c as a light yellow solid, which was further recrystallized from heptane to obtain white solid (707 mg). MS m/z (M+H⁺) 370.2.

B. Methyl 3-(4-fluorophenyl)-1H-indole-6-carboxylate, 53d. To a solution of compound 53c (705 mg, 1.91 mmol) in CH$_2$Cl$_2$ (4 mL) was added trifluoroacetic acid (1.5 mL) at room temperature. The mixture was stirred at room temperature for 2 h. The resulting mixture was concentrated to give compound 53d (603.3 mg) as a white solid. MS m/z (M+H⁺) 270.1.

C. 3-(4-Fluoro-phenyl)-1H-indole-6-carboxylic acid, 53e. A solution of compound 53d (303 mg, 0.79 mmol), and LiOH.H$_2$O (132.7 mg, 3.16 mmol) in THF/H$_2$O (10 mL/10 mL) was stirred at 45° C. for 5 h. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give 53e (249 mg), which was used in the next reaction without further purification. MS m/z (M+H⁺) 256.0.

D. 3-(4-Fluorophenyl)-6-({3-[4-(1,3-thiazol-2-ylcarbonyl)piperazin-1-yl]azetidin-1-yl}carbonyl)-1H-indole, Cpd 1317. To a mixture of compound 5e (42.9 mg, 0.132 mmol), compound 53e (30.6 mg, 0.12 mmol), and Et$_3$N (0.084 mL, 0.6 mmol) in CH$_2$Cl$_2$ (1 mL) at room temperature was added HATU (70 mg, 0.168 mmol). The reaction mixture was stirred at room temperature overnight. The mixture was diluted with CH$_2$Cl$_2$ and H$_2$O, washed with aq. NaHCO$_3$ and brine, dried over Na$_2$SO$_4$, filtered, and concentrated. The residue was purified by flash column chromatography (silica gel, 2-4% MeOH/EtOAc) to give Cpd 1317 (45.4 mg). $^1$H NMR (400 MHz, CDCl$_3$): δ 8.56 (br. s, 1H), 7.83-7.94 (m, 3H), 7.57-7.65 (m, 2H), 7.55 (d, J=3.2 Hz, 1H), 7.46 (d, J=2.4 Hz, 1H), 7.40-7.45 (m, 1H), 7.13-7.20 (m, 2H), 4.07-4.66 (m, 6H), 3.76-4.01 (m, 2H), 3.21-3.36 (m, 1H), 2.38-2.64 (m, 4H). MS m/z (M+H⁺) 490.2.

Following the procedure described above for Example 53, and substituting the appropriate reagents, starting materials and purification methods known to those skilled in the art, the following intermediate compounds were prepared:

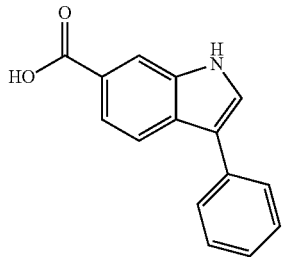

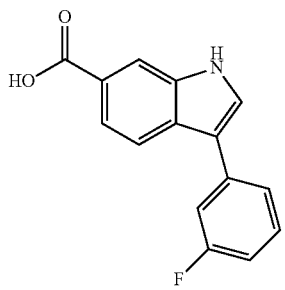 [SMILES: Cn1cc(-c2cccc(F)c2)c2ccc(C(=O)O)cc21]

Following the procedure described above for Example 53, and substituting the appropriate reagents, starting materials and purification methods known to those skilled in the art, the following compounds of the present invention were prepared:

| Cpd | Cpd Name and Data |
|---|---|
| 1316 | 3-Phenyl-6-({3-[4-(1,3-thiazol-2-ylcarbonyl)piperazin-1-yl]azetidin-1-yl}carbonyl)-1H-indole<br>MS m/z (M + H⁺) 472.2. |
| 1319 | 3-(3-Fluorophenyl)-6-({3-[4-(1,3-thiazol-2-ylcarbonyl)piperazin-1-yl]azetidin-1-yl}carbonyl)-1H-indole<br>MS m/z (M + H⁺) 490.2. |

Example 53a

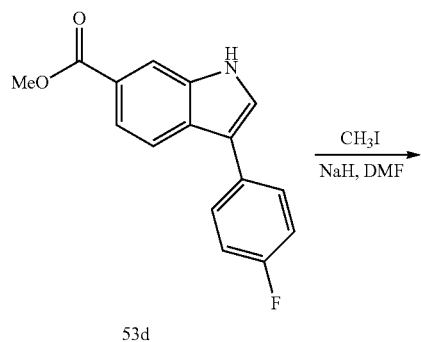

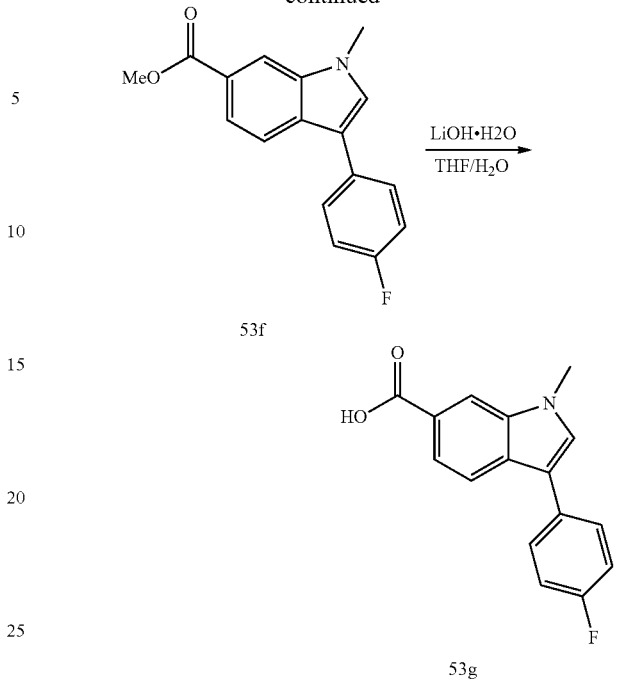

E. Methyl 3-(4-Fluoro-phenyl)-1-methyl-1H-indole-6-carboxylate, 53f. To a solution of compound 53d (300 mg, 0.78 mmol) in DMF (3 mL) was added NaH (60% in mineral oil, 68.9 mg, 1.72 mmol) at 0° C. The mixture was stirred at 0° C. for 30 min, then CH₃I (0.053 mL, 0.86 mmol) was added and stirring continued at 0° C. for another 1 h. The resulting mixture was diluted with EtOAc and water. The organic layer was washed with brine and concentrated. The residue was recrystallized from heptane, filtered and dried the solid to give compound 53f (265 mg) as a light yellow solid. MS m/z (M+H⁺) 284.1.

F. 3-(4-Fluoro-phenyl)-1-methyl-1H-indole-6-carboxylic acid, 53g. To a solution compound 53f (264 mg, 0.93 mmol), and LiOH.H₂O (156.4 mg, 3.73 mmol) in THF/H₂O (10 mL/10 mL) was stirred at 45° C. for 5 h. The resulting mixture was concentrated and diluted with water. The water layer was acidified with 1N aqueous HCl to pH~4 and extracted with CH₂Cl₂. The organic solution was dried over Na₂SO₄ and concentrated to give compound 53g (252 mg), which was used in the next reaction without further purification. MS m/z (M+H⁺) 270.1.

Following the procedure described above for Example 53a and substituting the appropriate reagents, starting materials and purification methods known to those skilled in the art, the following intermediate compound was prepared:

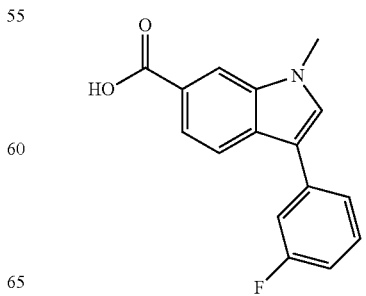

Following the procedure described above for Example 53 and substituting the appropriate reagents, starting materials and purification methods known to those skilled in the art, the following compounds of the present invention were prepared:

| Cpd | Cpd Name and Data |
|---|---|
| 1318 | 3-(4-Fluorophenyl)-1-methyl-6-({3-[4-(1,3-thiazol-2-ylcarbonyl)piperazin-1-yl]azetidin-1-yl}carbonyl)-1H-indole<br>$^1$H NMR (400 MHz, CDCl$_3$): δ 7.89 (d, J = 2.9 Hz, 1H), 7.79-7.87 (m, 2H), 7.51-7.63 (m, 3H), 7.39 (d, J = 8.3 Hz, 1H), 7.31 (s, 1H), 7.15 (t, J = 8.7 Hz, 2H), 4.21-4.67 (m, 5H), 4.08-4.21 (m, 1H), 3.89 (s, 3H), 3.77-3.98 (m, 2H), 3.19-3.35 (m, 1H), 2.36-2.65 (m, 4H)<br>MS m/z (M + H$^+$) 504.1 |
| 1142 | 3-(3-Fluorophenyl)-1-methyl-6-({3-[4-(1,3-thiazol-2-ylcarbonyl)piperazin-1-yl]azetidin-1-yl}carbonyl)-1H-indole<br>MS m/z (M + H$^+$) 504.1 |

Example 54

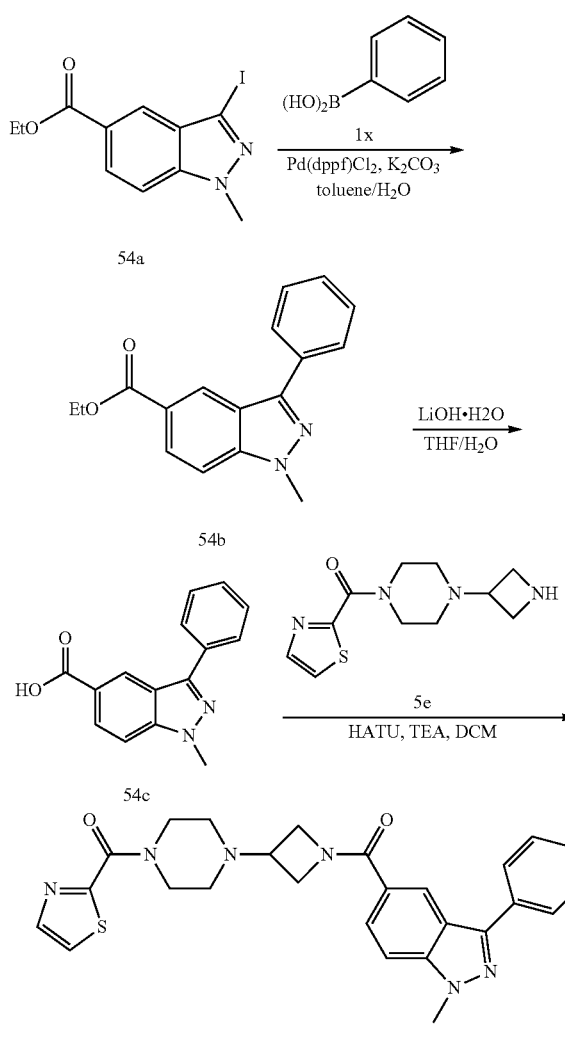

A. Ethyl 1-Methyl-3-phenyl-1H-indazole-5-carboxylate, 54b. A mixture of compound 54a (300 mg, 0.91 mmol), phenyl boronic acid 1x (133 mg, 1.09 mmol), Pd(dppf)Cl$_2$·CH$_2$Cl$_2$ (40 mg, 0.055 mmol), and K$_2$CO$_3$ (251.2 mg, 1.82 mmol), in a toluene (2 mL)/water (0.4 mL) mixture, was placed in a capped vial and heated at 90° C. overnight. The reaction mixture was then diluted with EtOAc and water. The organic layer was concentrated under reduced pressure and purified by flash column chromatography (silica gel, 2-10% EtOAc/Heptanes) to give compound 54b (231 mg). MS m/z (M+H$^+$) 281.1.

B. 1-Methyl-3-phenyl-1H-indazole-5-carboxylic acid, 54c. A solution compound 54b (230 mg, 0.58 mmol), and LiOH·H$_2$O (98 mg, 2.33 mmol) in THF/H$_2$O (10/10 mL) was stirred at 45° C. for 8 h. The resulting mixture was concentrated and diluted with water. The water layer was acidified with 1N aqueous HCl to pH~4 and extracted with CH$_2$Cl$_2$. The organic solution was dried over Na$_2$SO$_4$ and concentrated to give 54c (206 mg), which was used in the next reaction without further purification. MS m/z (M+H$^+$) 253.1.

C. 1-Methyl-3-phenyl-5-({3-[4-(1,3-thiazol-2-ylcarbonyl)piperazin-1-yl]azetidin-1-yl}carbonyl)-1H-indazole, Cpd 1137. To a mixture of compound 5e (42.9 mg, 0.132 mmol), compound 54c (30.3 mg, 0.12 mmol), and Et$_3$N (0.084 mL, 0.6 mmol) in CH$_2$Cl$_2$ (1 mL) at room temperature was added HATU (70 mg, 0.168 mmol). The reaction mixture was stirred at room temperature overnight. The mixture was diluted with CH$_2$Cl$_2$ and H$_2$O, washed with aq. NaHCO$_3$ and brine, dried over Na$_2$SO$_4$, filtered, and concentrated. The residue was purified by flash column chromatography (silica gel, 2-4% MeOH/EtOAc) to give Cpd 1137 (48.1 mg). $^1$H NMR (400 MHz, CDCl$_3$): δ 8.32 (s, 1H), 7.94 (d, J=7.3 Hz, 2H), 7.88 (d, J=3.2 Hz, 1H), 7.74 (d, J=9.5 Hz, 1H), 7.49-7.58 (m, 3H), 7.39-7.48 (m, 2H), 4.16 (s, 3H), 4.09-4.62 (m, 6H), 3.86 (m, 2H), 3.21-3.33 (m, 1H), 2.39-2.63 (m, 4H). MS m/z (M+H$^+$) 487.2.

Following the procedure described above for Example 54 and substituting the appropriate reagents, starting materials and purification methods known to those skilled in the art, the following intermediate compounds were prepared:

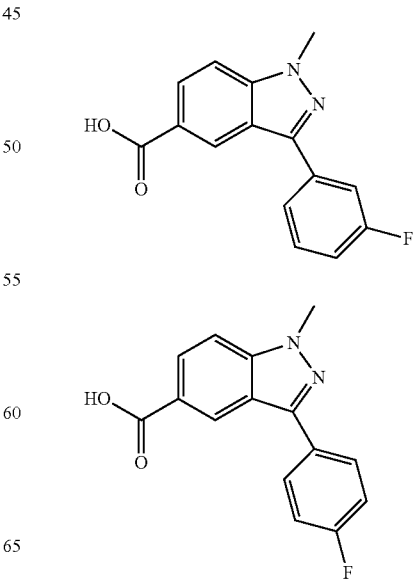

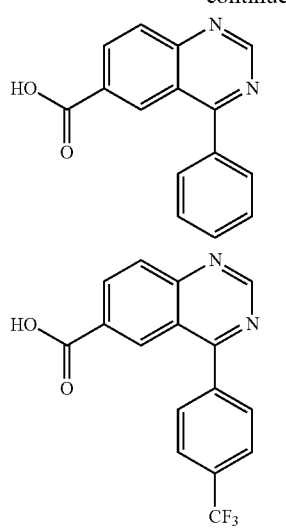

Following the procedure described above for Example 54 and substituting the appropriate reagents, starting materials and purification methods known to those skilled in the art, the following compounds of the present invention were prepared:

| Cpd | Cpd Name and Data |
|---|---|
| 1170 | 3-(3-Fluorophenyl)-1-methyl-5-({3-[4-(1,3-thiazol-2-ylcarbonyl)piperazin-1-yl]azetidin-1-yl}carbonyl)-1H-indazole<br>MS m/z (M + H⁺) 505.2 |
| 1195 | 3-(4-Fluorophenyl)-1-methyl-5-({3-[4-(1,3-thiazol-2-ylcarbonyl)piperazin-1-yl]azetidin-1-yl}carbonyl)-1H-indazole<br>MS m/z (M + H⁺) 505.2 |
| 1130 | 4-Phenyl-7-({3-[4-(1,3-thiazol-2-ylcarbonyl)piperazin-1-yl]azetidin-1-yl}carbonyl)quinazoline<br>MS m/z (M + H⁺) 485 |
| 1086 | 7-({3-[4-(1,3-Thiazol-2-ylcarbonyl)piperazin-1-yl]azetidin-1-yl}carbonyl)-4-[4-(trifluoromethyl)phenyl]quinazoline<br>MS m/z (M + H⁺) 553 |
| 604 | 4-Phenyl-7-({3-[4-(phenylcarbonyl)piperazin-1-yl]azetidin-1-yl}carbonyl)quinazoline<br>MS m/z (M + H⁺) 478 |
| 597 | 7-({3-[4-(Phenylcarbonyl)piperazin-1-yl]azetidin-1-yl}carbonyl)-4-[4-(trifluoromethyl)phenyl]quinazoline<br>MS m/z (M + H⁺) 546 |

Example 55

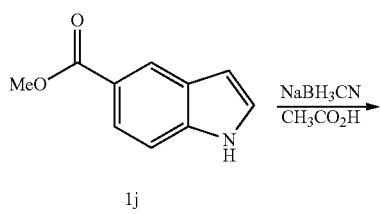

1j

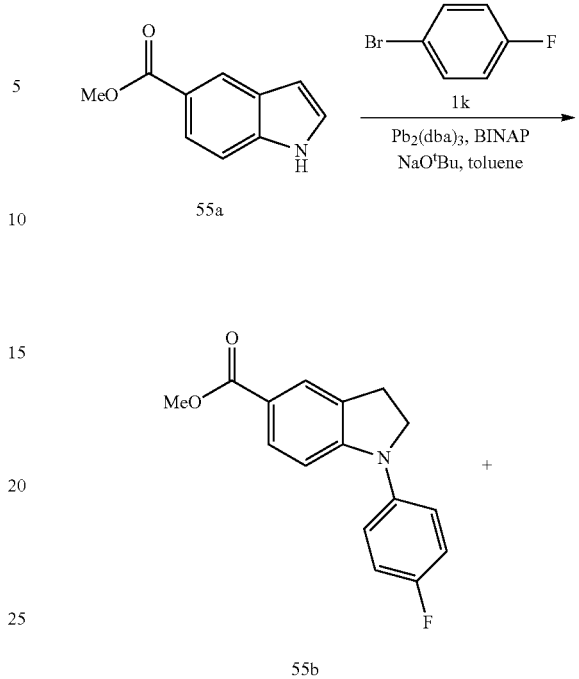

55a

55b

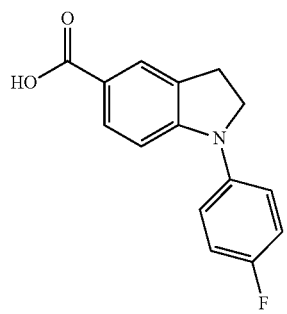

55c

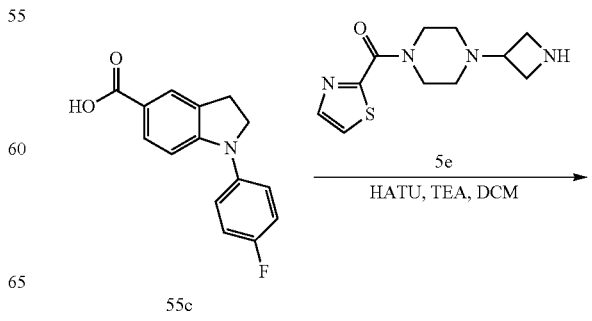

55c

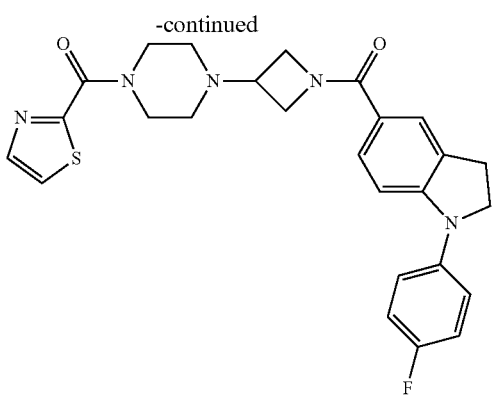

Cpd 885

A. Methyl 2,3-dihydro-1H-indole-5-carboxylate, 55a. To a solution of methyl 1H-indole-5-carboxylate 1j (2 g, 11.4 mmol) in glacial acetic acid (15 mL) at 0° C. was added sodium cyanoborohydride (1.08 g, 17.2 mmol) slowly. The mixture was allowed to warm up and stirred at room temperature for 2 h. Water was added to the resulting mixture at 0° C., and pH of the solution was adjusted to ~12 with 1N aqueous NaOH. The mixture was extracted with $CH_2Cl_2$ and the organic layer was washed with brine and dried over $Na_2SO_4$. The solution was concentrated and purified by flash column chromatography (silica gel, 15% EtOAc/heptane) to give compound 55a (1.79 g). MS m/z (M+H$^+$) 178.1.

B. Methyl 1-(4-fluoro-phenyl)-2,3-dihydro-1H-indole-5-carboxylate, 55b, and 1-(4-fluoro-phenyl)-2,3-dihydro-1H-indole-5-carboxylic acid, 55c. A mixture of compound 55a (500 mg, 2.82 mmol), 1-bromo-4-fluoro-benzene 1k (0.31 mL, 2.82 mmol), $Pd_2(dba)_3$ (129 mg, 0.14 mmol), BINAP (132 mg, 0.21 mmol), and sodium t-butoxide (325 mg, 3.39 mmol) in toluene (25 mL) was placed in a capped vial and heated at 80° C. overnight. The reaction mixture was then diluted with EtOAc and water, and the water layer was basified to pH~8 with 1N aqueous NaOH. The organic layer was concentrated under reduced pressure and purified by flash column chromatography (silica gel, 5-30% EtOAc/heptane) to give compound 55b (145 mg), MS m/z (M+H$^+$) 272.1, and compound 55c (232 mg), MS m/z (M+H$^+$) 258.0.

C. 1-(4-Fluoro-phenyl)-2,3-dihydro-1H-indole-5-carboxylic acid, 55d. A solution of compound 55b (144 mg, 0.53 mmol) and $LiOH \cdot H_2O$ (89.1 mg, 2.12 mmol) in $THF/H_2O$ (5 mL/5 mL) was stirred at 45° C. overnight. The resulting mixture was concentrated and diluted with water. The water layer was acidified with 1N aqueous HCl to pH~4 and extracted with $CH_2Cl_2$. The organic solution was dried over $Na_2SO_4$ and concentrated to give 55d (138 mg), which was used in the next reaction without further purification. MS m/z (M+H$^+$) 258.0.

D. 1-(4-Fluorophenyl)-5-({3-[4-(1,3-thiazol-2-ylcarbonyl)piperazin-1-yl]azetidin-1-yl}carbonyl)-2,3-dihydro-1H-indole, Cpd 885. To a mixture of compound 5e (42.9 mg, 0.132 mmol), compound 55d (30.9 mg, 0.12 mmol), and $Et_3N$ (0.084 mL, 0.6 mmol) in $CH_2Cl_2$ (1 mL) at room temperature was added HATU (70 mg, 0.168 mmol). The reaction mixture was stirred at room temperature overnight. The mixture was diluted with $CH_2Cl_2$ and washed with $H_2O$, aqueous $NaHCO_3$ and brine, and then dried over $Na_2SO_4$, filtered, and concentrated. The residue was purified by flash column chromatography (silica gel, 2-4% MeOH/EtOAc) to give compound Cpd 885 (44.4 mg). $^1$H NMR (400 MHz, CDCl$_3$): δ 7.89 (d, J=3.2 Hz, 1H), 7.55 (d, J=3.2 Hz, 1H), 7.51 (d, J=1.2 Hz, 1H), 7.38 (dd, J=8.3, 1.7 Hz, 1H), 7.16-7.25 (m, 2H), 7.03-7.12 (m, 2H), 6.88 (d, J=8.3 Hz, 1H), 4.05-4.67 (m, 6H), 3.99 (t, J=8.6 Hz, 2H), 3.76-3.94 (m, 2H), 3.20-3.30 (m, 1H), 3.16 (t, J=8.6 Hz, 2H), 2.37-2.64 (m, 4H); MS m/z (M+H$^+$) 492.1.

Following the procedure described above for Example 55 and substituting the appropriate reagents, starting materials and purification methods known to those skilled in the art, the following intermediate compound was prepared:

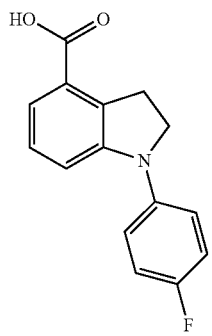 [SMILES: O=C(O)c1cccc2c1CCN2c1ccc(F)cc1]

Following the procedure described above for Example 55 and substituting the appropriate reagents, starting materials and purification methods known to those skilled in the art, the following compounds of the present invention were prepared:

| Cpd | Cpd Name and Data |
| --- | --- |
| 884 | 1-(4-Fluorophenyl)-4-({3-[4-(1,3-thiazol-2-ylcarbonyl)piperazin-1-yl]azetidin-1-yl}carbonyl)-2,3-dihydro-1H-indole<br>MS m/z (M + H$^+$) 492.1 |
| 1081 | 1-(4-Fluorophenyl)-5-({3-[4-(1,3-thiazol-4-ylcarbonyl)piperazin-1-yl]azetidin-1-yl}carbonyl)-2,3-dihydro-1H-indole<br>MS m/z (M + H$^+$) 492.1 |
| 1099 | 1-(4-Fluorophenyl)-5-({3-[4-(1H-pyrrol-2-ylcarbonyl)piperazin-1-yl]azetidin-1-yl}carbonyl)-2,3-dihydro-1H-indole<br>MS m/z (M + H$^+$) 474.1 |

Example 55a

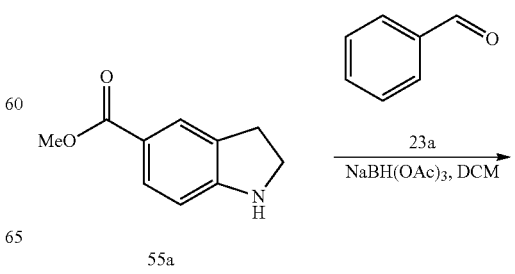

-continued

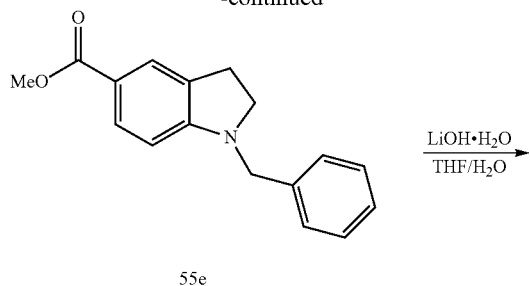

55e

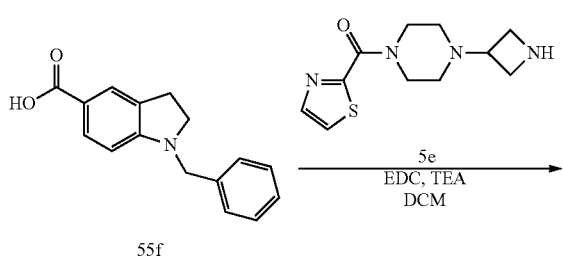

55f

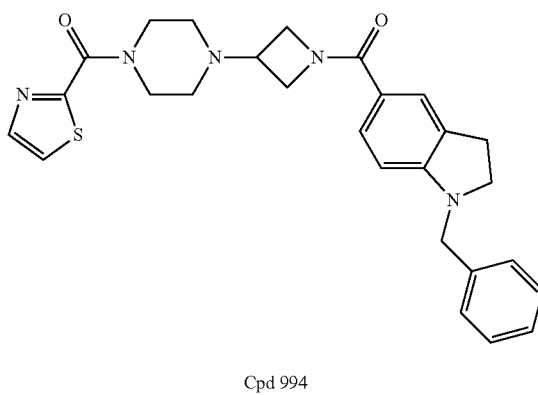

Cpd 994

E. Methyl 1-benzyl-2,3-dihydro-1H-indole-5-carboxylate, 55e. A solution of methyl 2,3-dihydro-1H-indole-5-carboxylate HCl salt 55a (88.6 mg, 0.42 mmol), and benzaldehyde 23a (0.060 mL, 0.55 mmol) in $CH_2Cl_2$ (4 mL) was stirred at room temperature for 30 min. Sodium triacetoxyborohydride (159 mg, 0.75 mmol) was added to the mixture and stirring was continued for 2 h. Water was added to the resulting mixture at 0° C., and pH of the solution was adjusted to ~8 with 1N aqueous NaOH. The mixture was extracted with $CH_2Cl_2$ and the organic layer was washed with brine and dried over $Na_2SO_4$. The solution was concentrated and purified by flash column chromatography (silica gel, 10-25% EtOAc/Heptanes) to give 55e (81.3 mg). MS m/z (M+H$^+$) 268.0.

F. 1-Benzyl-2,3-dihydro-1H-indole-5-carboxylic acid, 55f. A solution of compound 55e (80.2 mg, 0.3 mmol), and LiOH.H$_2$O (50.4 mg, 1.2 mmol) in THF/H$_2$O (1.2/1.2 mL) was stirred at room temperature overnight. The resulting mixture was concentrated and diluted with water. The water layer was acidified with 1N aqueous HCl to pH ~4 and extracted with $CH_2Cl_2$. The organic solution was dried over $Na_2SO_4$ and concentrated to give 55f (60 mg), which was used in the next reaction without further purification. MS m/z (M+H$^+$) 254.1.

G. 1-Benzyl-5-({3-[4-(1,3-thiazol-2-ylcarbonyl)piperazin-1-yl]azetidin-1-yl}carbonyl)-2,3-dihydro-1H-indole, Cpd 994. To a solution of compound 5e (89.5 mg, 0.261 mmol), compound 55f (60 mg, 0.237 mmol), and EDC (68.1 mg, 0.356 mmol) in $CH_2Cl_2$ (5 mL) was added Et$_3$N (0.1 mL, 0.711 mmol). The reaction mixture was stirred at room temperature overnight. The mixture was diluted with $CH_2Cl_2$ and $H_2O$ and the water layer was acidified to pH ~6 with 1 N aqueous HCl. The organic solution was dried over $Na_2SO_4$ and concentrated. The residue was purified by reverse phase chromatography to give Cpd 994 as a TFA salt (40.4 mg). $^1$H NMR (400 MHz, CD$_3$OD): δ 7.98 (d, J=3.2 Hz, 1H), 7.89 (d, J=3.2 Hz, 1H), 7.36-7.44 (m, 2H), 7.29-7.36 (m, 4H), 7.22-7.29 (m, 1H), 6.52 (d, J=8.3 Hz, 1H), 4.39-4.91 (m, 6H), 4.38 (s, 2H), 3.99-4.23 (m, 3H), 3.48 (t, J=8.6 Hz, 2H), 3.42 (br. s, 4H), 3.01 (t, J=8.6 Hz, 2H). MS m/z (M+H$^+$) 488.1.

Following the procedure described above for Example 55a and substituting the appropriate reagents, starting materials and purification methods known to those skilled in the art, the following intermediate compounds were prepared:

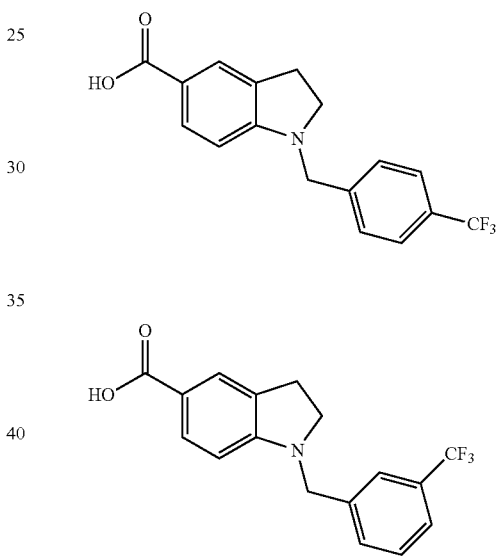

Following the procedure described above for Example 55a and substituting the appropriate reagents, starting materials and purification methods known to those skilled in the art, the following compounds of the present invention were prepared:

| Cpd | Cpd Name and Data |
|---|---|
| 881 | 5-({3-[4-(1,3-Thiazol-2-ylcarbonyl)piperazin-1-yl]azetidin-1-yl}carbonyl)-1-[3-(trifluoromethyl)benzyl]-2,3-dihydro-1H-indole<br>MS m/z (M + H$^+$) 556.0 |
| 882 | 5-({3-[4-(1,3-Thiazol-2-ylcarbonyl)piperazin-1-yl]azetidin-1-yl}carbonyl)-1-[4-(trifluoromethyl)benzyl]-2,3-dihydro-1H-indole<br>MS m/z (M + H$^+$) 556.0 |

Example 55b

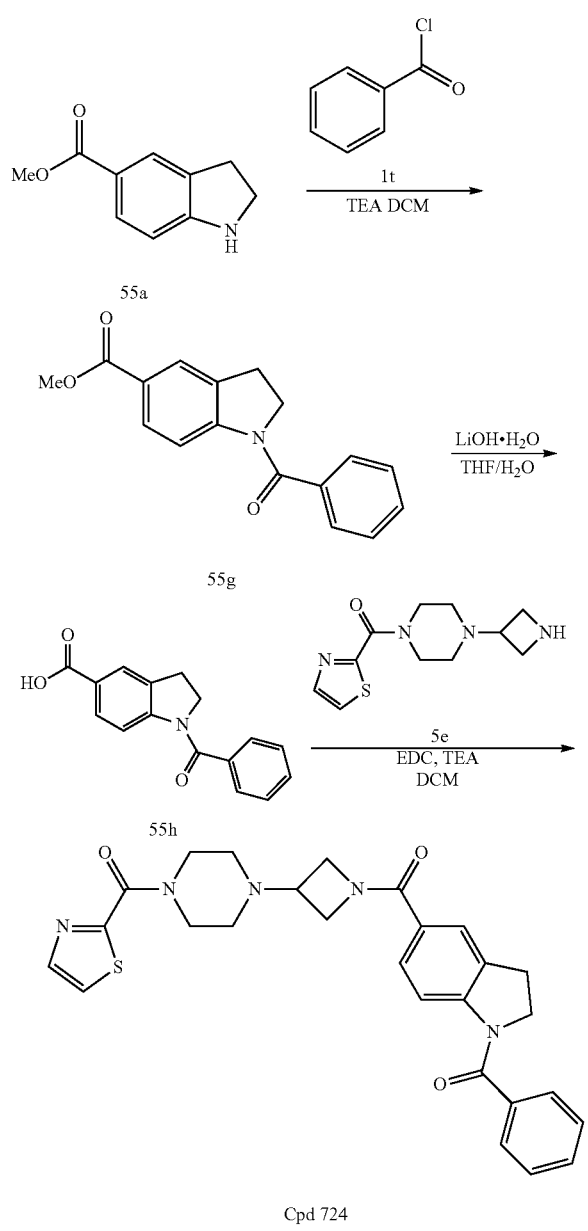

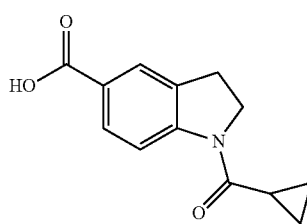

H. 1-Benzoyl-2,3-dihydro-1H-indole-5-carboxylic acid methyl ester, 55g. To a solution of methyl 2,3-dihydro-1H-indole-5-carboxylate HCl salt 55a (64.1 mg, 0.3 mmol), and benzoyl chloride 1t (0.042 mL, 0.36 mmol) in $CH_2Cl_2$ (1 mL) was added $Et_3N$ (0.13 mL, 0.9 mmol) at 0° C. The reaction mixture was stirred at 0° C. for 2 h. The resulting mixture was partitioned between $CH_2Cl_2$ and $H_2O$. The organic solution was dried over $Na_2SO_4$ and concentrated. Purification of the residue by flash column chromatography (silica gel, 10-20% EtOAc/Heptanes) gave 55g (88 mg). MS m/z (M+H$^+$) 282.0.

I. 1-Benzoyl-2,3-dihydro-1H-indole-5-carboxylic acid, 55h. A solution of compound 55g (87 mg, 0.31 mmol), and LiOH·H$_2$O (52 mg, 1.24 mmol) in THF/H$_2$O (2/2 mL) was stirred at room temperature overnight. The resulting mixture was concentrated and diluted with water. The water layer was acidified with 1N aqueous HCl to pH ~6 and extracted with $CH_2Cl_2$. The organic solution was dried over $Na_2SO_4$ and concentrated to give 55h (82 mg), which was used in the next reaction without further purification. MS m/z (M+H$^+$) 268.0.

J. 1-(Phenylcarbonyl)-5-({3-[4-(1,3-thiazol-2-ylcarbonyl)piperazin-1-yl]azetidin-1-yl}carbonyl)-2,3-dihydro-1H-indole, Cpd 724. To a solution of compound 5e (115.9 mg, 0.34 mmol), compound 55h (82 mg, 0.31 mmol) and EDC (87.9 mg, 0.46 mmol) in $CH_2Cl_2$ (5 mL) was added $Et_3N$ (0.13 mL, 0.92 mmol). The reaction mixture was stirred at room temperature overnight. The mixture was diluted with $CH_2Cl_2$ and $H_2O$ and the water layer was acidified to pH ~6 with 1 N aqueous HCl. The organic solution was dried over $Na_2SO_4$ and concentrated. The residue was purified by flash column chromatography (silica gel, 2% MeOH/EtOAc) to give compound Cpd 724 (64.4 mg). $^1$H NMR (400 MHz, CDCl$_3$): δ 7.89 (d, J=3.2 Hz, 1H), 7.31-7.63 (m, 9H), 4.38-4.63 (m, 2H), 4.03-4.37 (m, 6H), 3.74-3.96 (m, 2H), 3.20-3.29 (m, 1H), 3.16 (t, J=8.3 Hz, 2H), 2.38-2.61 (m, 4H). MS m/z (M+H$^+$) 502.0.

Following the procedure described above for Example 55b and substituting the appropriate reagents, starting materials and purification methods known to those skilled in the art, the following intermediate compound was prepared:

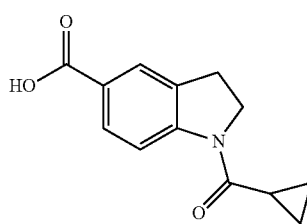

Following the procedure described above for Example 55b and substituting the appropriate reagents, starting materials and purification methods known to those skilled in the art, the following compound of the present invention was prepared:

| Cpd | Cpd Name and Data |
|---|---|
| 773 | 1-(Cyclopropylcarbonyl)-5-({3-[4-(1,3-thiazol-2-ylcarbonyl)piperazin-1-yl]azetidin-1-yl}carbonyl)-2,3-dihydro-1H-indole<br>MS m/z (M + H$^+$) 466.0 |

Example 56

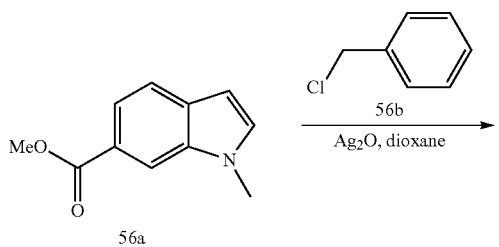

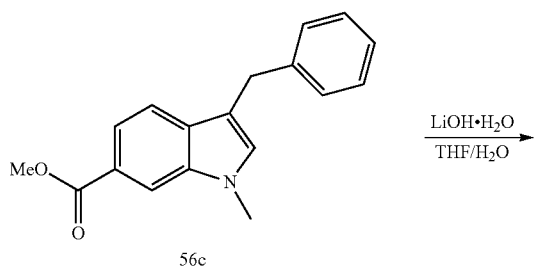

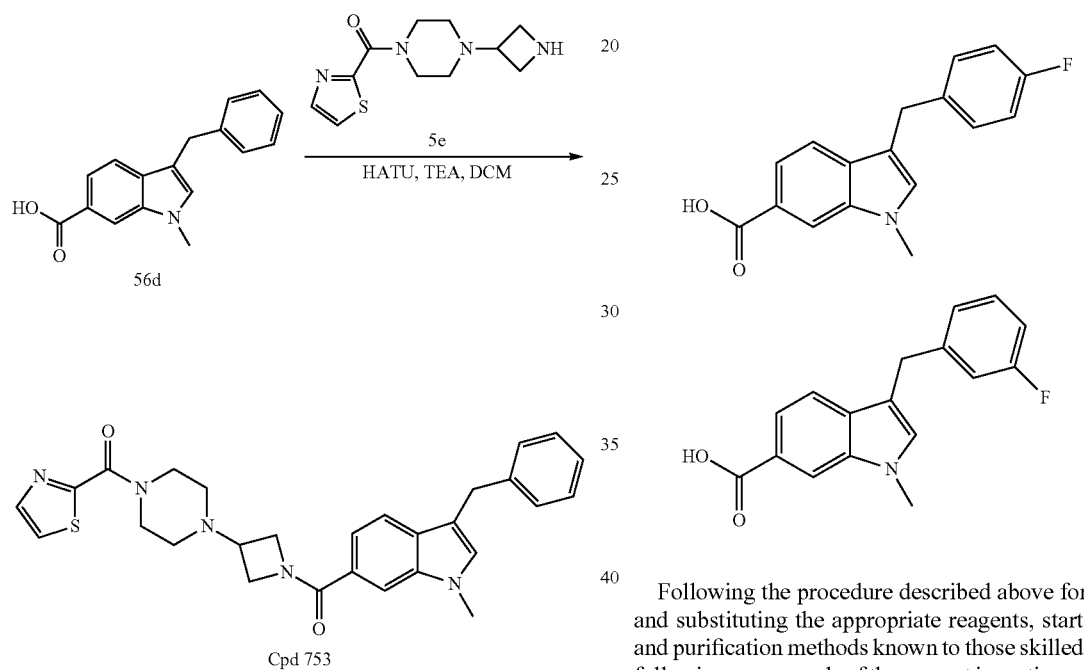

A. Methyl 3-Benzyl-1-methyl-1H-indole-6-carboxylate, 56c. To a solution of compound 56a (500 mg, 2.64 mmol) and benzyl chloride 56b (0.33 mL, 2.91 mmol) in dioxane (5 mL) was added silver oxide (673.6 mg, 2.91 mmol). The mixture was stirred at 80° C. overnight. The resulted mixture was filtered through celite and washed with EtOAc. The filtrate was concentrated and purified by flash column chromatography (silica gel, 20-60% $CH_2Cl_2$/Heptanes) to give compound 56c (168 mg). MS m/z (M+H$^+$) 280.2.

B. 3-Benzyl-1-methyl-1H-indole-6-carboxylic acid, 56d. To a solution compound 56c (168 mg, 0.60 mmol), and $LiOH.H_2O$ (101 mg, 2.41 mmol) in THF/$H_2O$ (3/3 mL) was stirred at room temperature for 6 h. Concentrated the resulted mixture, extracted the residue with $CH_2Cl_2$, $H_2O$, acidified the water layer with 1N HCl(aq) to pH~4. The organic solution was dried over $Na_2SO_4$ and concentrated to give 56d (172.2 mg), which was used in the next reaction without further purification. MS m/z (M+H$^+$) 266.2.

C. 3-Benzyl-1-methyl-6-({3-[4-(1,3-thiazol-2-ylcarbonyl)piperazin-1-yl]azetidin-1-yl}carbonyl)-1H-indole, Cpd 753. To a mixture of compound 5e (71.6 mg, 0.22 mmol), compound 56d (53.1 mg, 0.2 mmol), and $Et_3N$ (0.14 mL, 1.0 mmol) in $CH_2Cl_2$ (1 mL) at room temperature was added HATU (106.5 mg, 0.28 mmol). The reaction mixture was stirred at room temperature overnight. The mixture was diluted with $CH_2Cl_2$ and $H_2O$, washed with aqueous $NaHCO_3$ and brine, dried over $Na_2SO_4$, filtered, and concentrated. Purification of the residue by flash column chromatography (silica gel, 2-4% MeOH/EtOAc) gave compound Cpd 753 (20.8 mg). $^1$H NMR (400 MHz, $CDCl_3$): δ 7.89 (d, J=2.4 Hz, 1H), 7.74 (s, 1H), 7.55 (d, J=2.7 Hz, 1H), 7.49 (d, J=8.3 Hz, 1H), 7.15-7.35 (m, 6H), 6.89 (s, 1H), 4.06-4.60 (m, 8H), 3.79-3.98 (m, 2H), 3.78 (s, 3H), 3.17-3.31 (m, 1H), 2.35-2.64 (m, 4H). MS m/z (M+H$^+$) 500.3.

Following the procedure described above for Example 56 and substituting the appropriate reagents, starting materials and purification methods known to those skilled in the art, the following intermediate compounds were prepared:

Following the procedure described above for Example 56 and substituting the appropriate reagents, starting materials and purification methods known to those skilled in the art, the following compounds of the present invention were prepared:

| Cpd | Cpd Name and Data |
| --- | --- |
| 1026 | 3-(4-Fluorobenzyl)-1-methyl-6-({3-[4-(1,3-thiazol-2-ylcarbonyl)piperazin-1-yl]azetidin-1-yl}carbonyl)-1H-indole MS m/z (M + H$^+$) 518.1 |
| 1027 | 3-(4-Fluorobenzyl)-1-methyl-6-({3-[4-(1,3-thiazol-4-ylcarbonyl)piperazin-1-yl]azetidin-1-yl}carbonyl)-1H-indole MS m/z (M + H$^+$) 518.1 |
| 1028 | 3-(4-Fluorobenzyl)-1-methyl-6-({3-[4-(1H-pyrrol-2-ylcarbonyl)piperazin-1-yl]azetidin-1-yl}carbonyl)-1H-indole MS m/z (M + H$^+$) 500.1 |
| 1033 | 3-(3-Fluorobenzyl)-1-methyl-6-({3-[4-(1,3-thiazol-2-ylcarbonyl)piperazin-1-yl]azetidin-1-yl}carbonyl)-1H-indole m/z (M + H$^+$) 518.2 |

Example 57

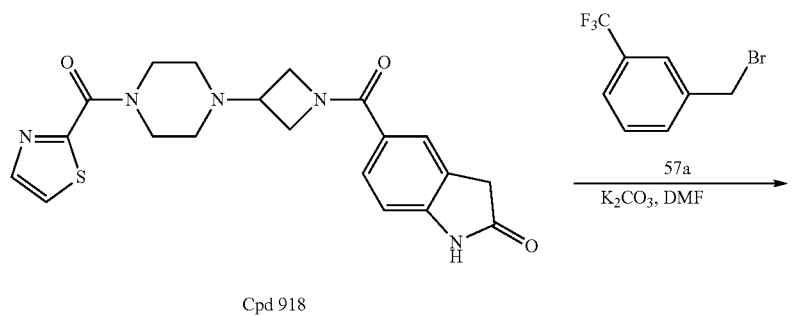

Cpd 918

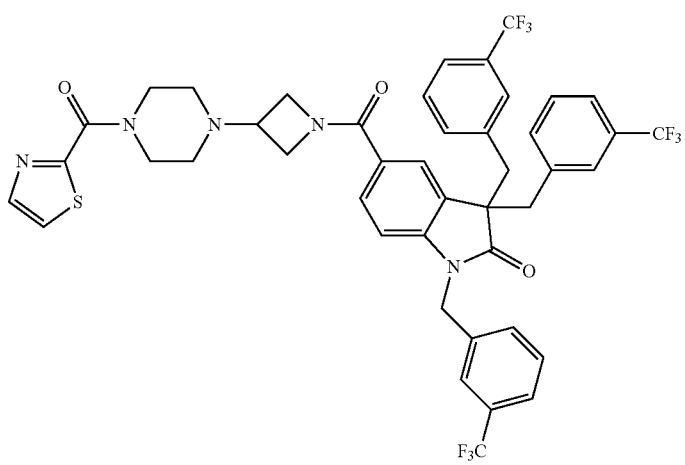

Cpd 1430

5-({3-[4-(1,3-Thiazol-2-ylcarbonyl)piperazin-1-yl]azetidin-1-yl}carbonyl)-1,3,3-tris[3-(trifluoromethyl)benzyl]-1,3-dihydro-2H-indol-2-one, Cpd 1430. To a solution of Cpd 918 from Example 9) (25 mg, 0.061 mmol) and K$_2$CO$_3$ (16.9 mg, 0.122 mmol) in DMF (0.8 mL) was added 3-trifluoromethyl-benzyl bromide (20.4 mg, 0.085 mmol). The mixture was stirred at room temperature overnight. The resulting mixture was extracted with EtOAc and H$_2$O. The organic solution was dried over Na$_2$SO$_4$ and concentrated. The residue was purified by reverse phase chromatography to give Cpd 1430 as a TFA salt (3.6 mg), MS m/z (M+H$^+$) 885.9.

Following the procedure described above for Example 57 and substituting the appropriate reagents, starting materials and purification methods known to those skilled in the art, the following compounds of the present invention were prepared:

| Cpd | Cpd Name and Data |
| --- | --- |
| 1431 | 1,3,3-Tribenzyl-5-({3-[4-(1,3-thiazol-2-ylcarbonyl)piperazin-1-yl]azetidin-1-yl}carbonyl)-1,3-dihydro-2H-indol-2-one<br>MS m/z (M + H$^+$) 682.0 |
| 992 | 5-({3-[4-(1,3-Thiazol-2-ylcarbonyl)piperazin-1-yl]azetidin-1-yl}carbonyl)-3,3-bis[3-(trifluoromethyl)benzyl]-1,3-dihydro-2H-indol-2-one<br>MS m/z (M + H$^+$) 728.0 |

Example 58

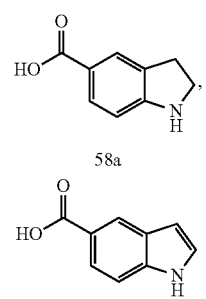

58a

58b

5e

Example 59

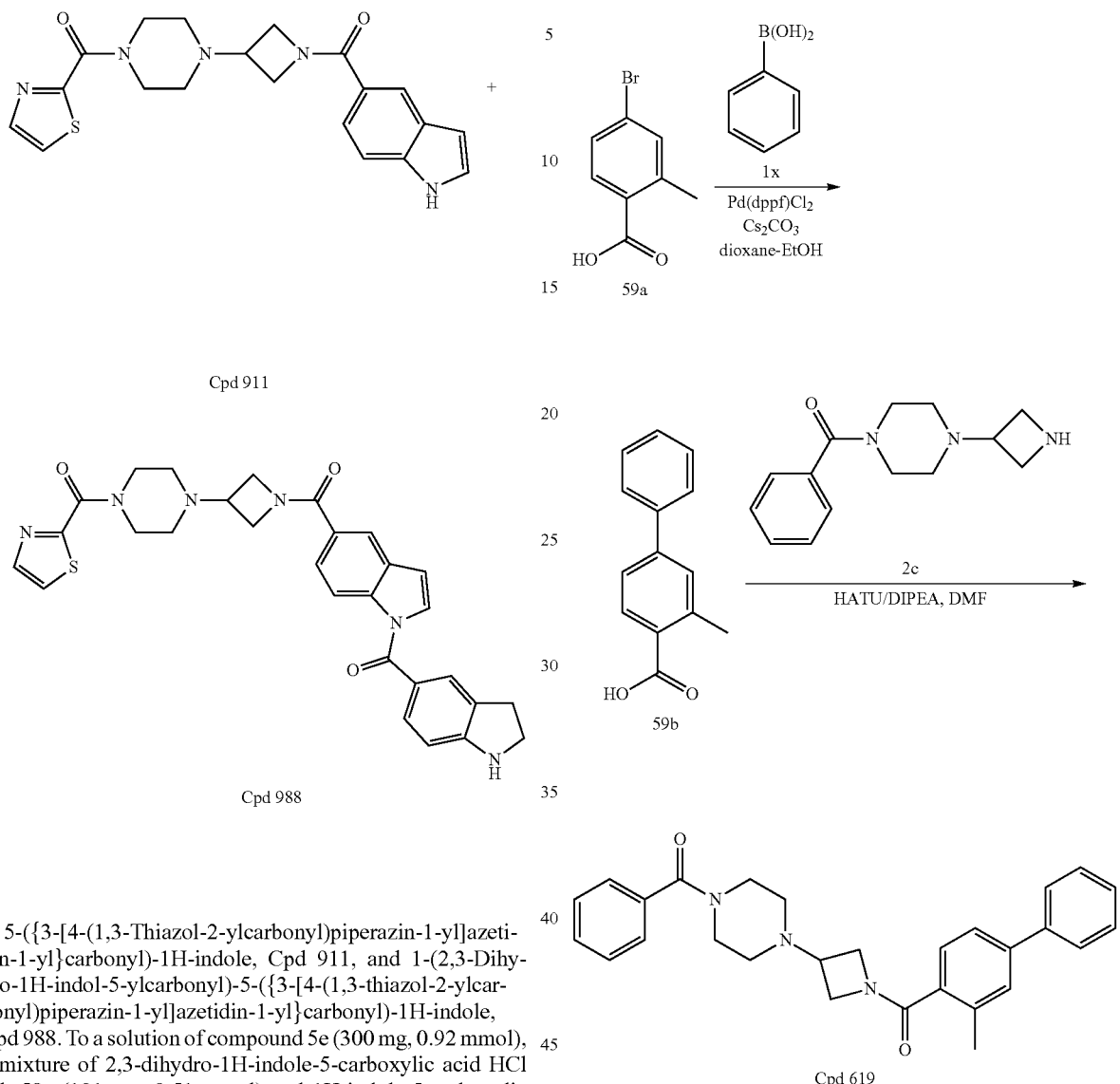

Cpd 911

Cpd 988

5-({3-[4-(1,3-Thiazol-2-ylcarbonyl)piperazin-1-yl]azetidin-1-yl}carbonyl)-1H-indole, Cpd 911, and 1-(2,3-Dihydro-1H-indol-5-ylcarbonyl)-5-({3-[4-(1,3-thiazol-2-ylcarbonyl)piperazin-1-yl]azetidin-1-yl}carbonyl)-1H-indole, Cpd 988. To a solution of compound 5e (300 mg, 0.92 mmol), a mixture of 2,3-dihydro-1H-indole-5-carboxylic acid HCl salt 58a (101 mg, 0.51 mmol) and 1H-indole-5-carboxylic acid HCl salt 58b (100 mg, 0.51 mmol), and EDC (265 mg, 1.38 mmol) in $CH_2Cl_2$ (10 mL) was added $Et_3N$ (0.39 mL, 2.77 mmol). The reaction mixture was stirred at room temperature overnight. The resulting mixture was extracted with $CH_2Cl_2$ and washed with $H_2O$. The organic solution was dried over $Na_2SO_4$ and concentrated. The residue was purified by reverse phase chromatography to give Cpd 911 as a TFA salt (89.4 mg) and Cpd 988 as a TFA salt (13.8 mg).

Cpd 911: $^1$H NMR (400 MHz, $CD_3OD$): δ 10.93 (br. s, 1H), 7.98 (d, J=3.2 Hz, 1H), 7.95 (s, 1H), 7.89 (d, J=3.2 Hz, 1H), 7.47 (s, 2H), 7.36 (d, J=3.2 Hz, 1H), 6.57 (d, J=2.9 Hz, 1H), 4.25-4.84 (m, 6H), 3.91-4.15 (m, 4H), 2.80 (br. s, 4H). MS m/z (M+H$^+$) 396.0. Cpd 988: $^1$H NMR (400 MHz, $CD_3OD$): δ 7.98 (d, J=3.2 Hz, 1H), 7.88 (d, J=3.2 Hz, 1H), 7.85 (d, J=1.0 Hz, 1H), 7.58 (s, 1H), 7.27-7.56 (m, 5H), 6.56 (d, J=3.2 Hz, 1H), 4.29-4.89 (m, 6H), 4.20 (t, J=8.3 Hz, 2H), 3.96-4.15 (m, 3H), 3.32-3.43 (m, 4H), 3.17 (t, J=8.3 Hz, 2H). MS m/z (M+H$^+$) 541.0.

A. 3-Methyl-[1,1'-biphenyl]-4-carboxylic acid, 59b. The title compound 59b was prepared using the method described in Example 6, Step F, substituting 4-bromo-2-methylbenzoic acid 59a for Cpd 173 and substituting phenylboronic acid 1x for compound 6e. The crude product 59b was purified by reverse phase chromatography. MS m/z (M+H$^+$) 213.1.

B. 1-{1-[(3-Methylbiphenyl-4-yl)carbonyl]azetidin-3-yl}-4-(phenylcarbonyl)piperazine, Cpd 619. The title compound Cpd 619 was prepared using the method described in Example 9, substituting compound 59b for compound 9c and substituting compound 2c for compound 5e. The crude compound Cpd 619 was purified by reverse phase chromatography. MS m/z (M+H$^+$) 440.1.

Following the procedure described above for Example 59 and substituting the appropriate reagents, starting materials and purification methods known to those skilled in the art, the following intermediate compounds were prepared:

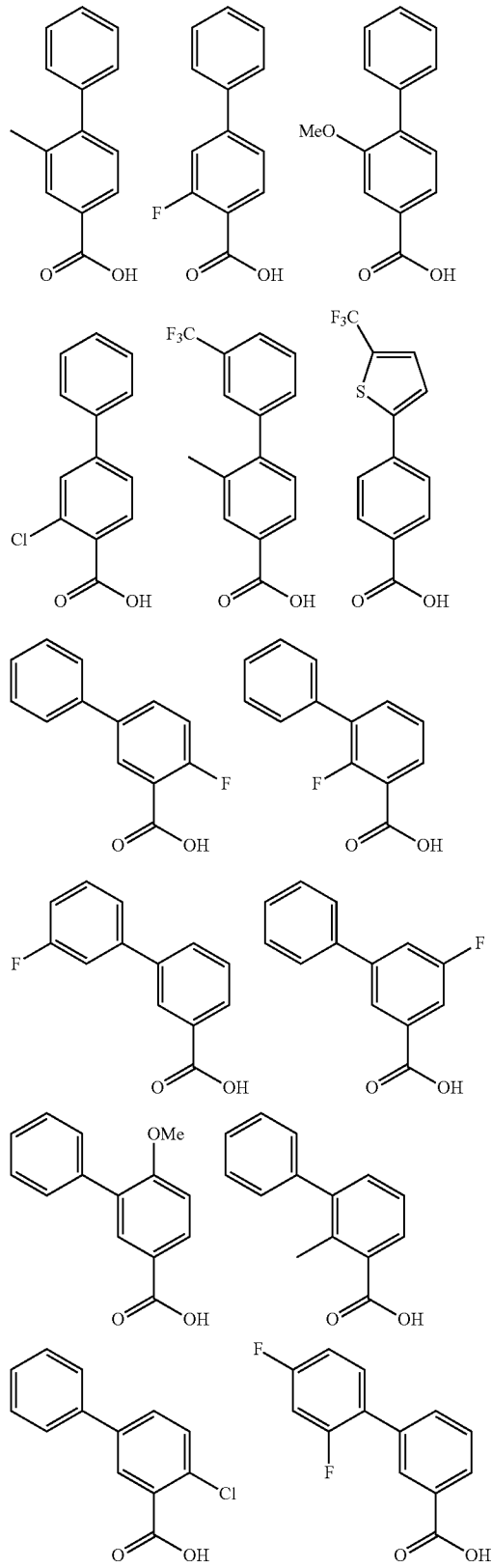

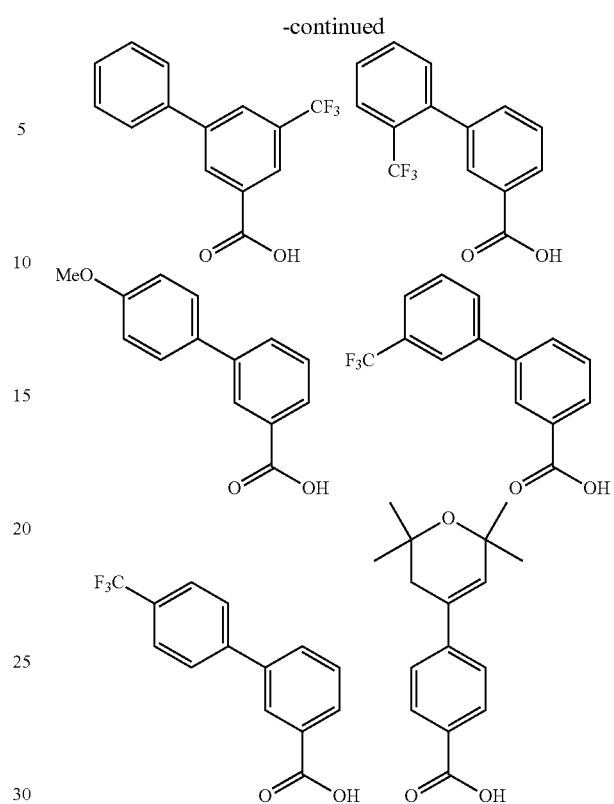

Following the procedure described above for Example 59 and substituting the appropriate reagents, starting materials and purification methods known to those skilled in the art, the following compounds of the present invention were prepared:

| Cpd | Cpd Name and Data |
|---|---|
| 613 | 1-{1-[(2-Methylbiphenyl-4-yl)carbonyl]azetidin-3-yl}-4-(phenylcarbonyl)piperazine<br>MS m/z (M + H⁺) 440.2 |
| 614 | 1-{1-[(3-Fluorobiphenyl-4-yl)carbonyl]azetidin-3-yl}-4-(phenylcarbonyl)piperazine<br>MS m/z (M + H⁺) 444.1 |
| 615 | 1-{1-[(2-Methoxybiphenyl-4-yl)carbonyl]azetidin-3-yl}-4-(phenylcarbonyl)piperazine<br>MS m/z (M + H⁺) 456.1 |
| 612 | 1-{1-[(3-Chlorobiphenyl-4-yl)carbonyl]azetidin-3-yl}-4-(phenylcarbonyl)piperazine<br>MS m/z (M + H⁺) 460.2 |
| 706 | 1-(1-{[4-(2,2,6,6-Tetramethyl-3,6-dihydro-2H-pyran-4-yl)phenyl]carbonyl}azetidin-3-yl)-4-(1,3-thiazol-2-ylcarbonyl)piperazine<br>MS m/z (M + H⁺) 495.3 |
| 1074 | 1-{1-[(3-Methylbiphenyl-4-yl)carbonyl]azetidin-3-yl}-4-(1,3-thiazol-2-ylcarbonyl)piperazine<br>1H NMR (300 MHz, CD₃OD): δ 7.97 (d, 1H), 7.87 (d, 1H), 7.33-7.66 (m, 8H), 4.62-4.76 (m, 2H), 4.38-4.51 (m, 1H), 4.13-4.35 (m, 3H), 3.84-4.07 (m, 3H), 3.02-3.19 (m, 4H), 2.47 (s, 1H)<br>MS m/z (M + H⁺) 447.1 |
| 1322 | 1-{1-[(2-Methylbiphenyl-4-yl)carbonyl]azetidin-3-yl}-4-(1,3-thiazol-2-ylcarbonyl)piperazine<br>1H NMR (300 MHz, CD₃OD): δ 7.98 (d, 1H), 7.88 (d, 1H), 7.59 (s, 1H), 7.54 (dd, 1H), 7.27-7.49 (m, 6H), 4.61-4.78 (m, 3H), 4.39-4.61 (m, 2H), 4.33 (M, 1H), 3.88-4.11 (m, 3H), 3.10-3.26 (m, 4H), 2.30 (s, 3H)<br>MS m/z (M + H⁺) 447.1 |
| 1405 | 1-{1-[(3-Fluorobiphenyl-4-yl)carbonyl]azetidin-3-yl}-4-(1,3-thiazol-2-ylcarbonyl)piperazine |

| Cpd | Cpd Name and Data |
|---|---|
|  | 1H NMR (300 MHz, CD$_3$OD): δ 7.97 (d, 1H), 7.87 (d, 1H), 7.36-7.73 (m, 8H), 4.23-4.76 (m, 6H), 3.85-4.07 (m, 3H), 3.04-3.20 (m, 4H)<br>MS m/z (M + H$^+$) 451.2 |
| 1377 | 1-{1-[(2-Methoxybiphenyl-4-yl)carbonyl]azetidin-3-yl}-4-(1,3-thiazol-2-ylcarbonyl)piperazine<br>MS m/z (M + H$^+$) 463.2 |
| 1323 | 1-{1-[(3-Chlorobiphenyl-4-yl)carbonyl]azetidin-3-yl}-4-(1,3-thiazol-2-ylcarbonyl)piperazine<br>MS m/z (M + H$^+$) 467.1 |
| 1406 | 1-{1-[(2-Methylbiphenyl-4-yl)carbonyl]azetidin-3-yl}-4-(1,3-thiazol-4-ylcarbonyl)piperazine<br>MS m/z (M + H$^+$) 447.1 |
| 1108 | 1-{1-[(3-Fluorobiphenyl-4-yl)carbonyl]azetidin-3-yl}-4-(1,3-thiazol-4-ylcarbonyl)piperazine<br>1H NMR (300 MHz, CD$_3$OD): δ 9.06 (s, 1H), 8.22 (d, 1H), 7.38-7.71 (m, 8H), 4.28-4.53 (m, 4H), 3.94-4.25 (m, 5H), 3.16-3.27 (m, 4H)<br>MS m/z (M + H$^+$) 451.1 |
| 1253 | 1-{1-[(2-Methoxybiphenyl-4-yl)carbonyl]azetidin-3-yl}-4-(1,3-thiazol-4-ylcarbonyl)piperazine<br>MS m/z (M + H$^+$) 463.2 |
| 1221 | 1-{1-[(3-Chlorobiphenyl-4-yl)carbonyl]azetidin-3-yl}-4-(1,3-thiazol-4-ylcarbonyl)piperazine<br>MS m/z (M + H$^+$) 467.1 |
| 1185 | 1-(1,3-Thiazol-4-ylcarbonyl)-4-(1-{[2'-(trifluoromethyl)biphenyl-3-yl]carbonyl}azetidin-3-yl)piperazine<br>MS m/z (M + H$^+$) 501.0 |
| 1278 | 1-(1,3-Thiazol-4-ylcarbonyl)-4-(1-{[4'-(trifluoromethyl)biphenyl-3-yl]carbonyl}azetidin-3-yl)piperazine<br>MS m/z (M + H$^+$) 501.0 |
| 1250 | 1-{1-[(4'-Methoxybiphenyl-3-yl)carbonyl]azetidin-3-yl}-4-(1,3-thiazol-4-ylcarbonyl)piperazine<br>MS m/z (M + H$^+$) 563.0 |
| 1091 | 1-{1-[(4'-Methoxybiphenyl-3-yl)carbonyl]azetidin-3-yl}-4-(1,3-thiazol-2-ylcarbonyl)piperazine<br>MS m/z (M + H$^+$) 463.0 |
| 1093 | 1-(1,3-Thiazol-2-ylcarbonyl)-4-(1-{[3'-(trifluoromethyl)biphenyl-3-yl]carbonyl}azetidin-3-yl)piperazine<br>MS m/z (M + H$^+$) 501.0 |
| 1124 | 1-{1-[(3'-Fluorobiphenyl-3-yl)carbonyl]azetidin-3-yl}-4-(1,3-thiazol-2-ylcarbonyl)piperazine<br>MS m/z (M + H$^+$) 451.0 |
| 1117 | 1-{1-[(2',4'-Difluorobiphenyl-3-yl)carbonyl]azetidin-3-yl}-4-(1,3-thiazol-2-ylcarbonyl)piperazine<br>1H NMR (300 MHz, CD$_3$OD): δ 7.97 (d, 1H), 7.87 (d, 1H), 7.80 (d, 1H), 7.66-7.75 (m, 2H), 7.50-7.64 (m, 2H), 7.05-7.16 (d, 1H), 4.24-4.75 (m, 6H), 3.83-4.06 (m, 3H), 3.02-3.18 (m, 4H)<br>MS m/z (M + H$^+$) 469.0 |
| 1188 | 1-(1,3-Thiazol-4-ylcarbonyl)-4-(1-{[3'-(trifluoromethyl)biphenyl-3-yl]carbonyl}azetidin-3-yl)piperazine<br>MS m/z (M + H$^+$) 501.0 |
| 1228 | 1-{1-[(3'-Fluorobiphenyl-3-yl)carbonyl]azetidin-3-yl}-4-(1,3-thiazol-4-ylcarbonyl)piperazine<br>MS m/z (M + H$^+$) 451.0 |
| 1239 | 1-{1-[(2',4'-Difluorobiphenyl-3-yl)carbonyl]azetidin-3-yl}-4-(1,3-thiazol-4-ylcarbonyl)piperazine<br>MS m/z (M + H$^+$) 469.0 |
| 1172 | 1-{1-[(2-Fluorobiphenyl-3-yl)carbonyl]azetidin-3-yl}-4-(1,3-thiazol-2-ylcarbonyl)piperazine<br>MS m/z (M + H$^+$) 451.0 |
| 1200 | 1-{1-[(4-Chlorobiphenyl-3-yl)carbonyl]azetidin-3-yl}-4-(1,3-thiazol-2-ylcarbonyl)piperazine<br>MS m/z (M + H$^+$) 467.0 |
| 1168 | 1-{1-[(6-Methoxybiphenyl-3-yl)carbonyl]azetidin-3-yl}-4-(1,3-thiazol-2-ylcarbonyl)piperazine<br>MS m/z (M + H$^+$) 463.0 |
| 1234 | 1-{1-[(2-Methylbiphenyl-3-yl)carbonyl]azetidin-3-yl}-4-(1,3-thiazol-2-ylcarbonyl)piperazine<br>MS m/z (M + H$^+$) 447.0 |
| 1240 | 1-{1-[(2-Fluorobiphenyl-3-yl)carbonyl]azetidin-3-yl}-4-(1,3-thiazol-4-ylcarbonyl)piperazine<br>MS m/z (M + H$^+$) 451.0 |
| 1288 | 1-{1-[(4-Chlorobiphenyl-3-yl)carbonyl]azetidin-3-yl}-4-(1,3-thiazol-4-ylcarbonyl)piperazine<br>MS m/z (M + H$^+$) 467.0 |
| 1265 | 1-{1-[(6-Methoxybiphenyl-3-yl)carbonyl]azetidin-3-yl}-4-(1,3-thiazol-4-ylcarbonyl)piperazine<br>MS m/z (M + H$^+$) 463.0 |
| 1285 | 1-{1-[(2-Methylbiphenyl-3-yl)carbonyl]azetidin-3-yl}-4-(1,3-thiazol-4-ylcarbonyl)piperazine<br>MS m/z (M + H$^+$) 447.0 |
| 1208 | 1-{1-[(4-Fluorobiphenyl-3-yl)carbonyl]azetidin-3-yl}-4-(1,3-thiazol-2-ylcarbonyl)piperazine<br>MS m/z (M + H$^+$) 451.0 |
| 1280 | 1-{1-[(4-Fluorobiphenyl-3-yl)carbonyl]azetidin-3-yl}-4-(1,3-thiazol-4-ylcarbonyl)piperazine<br>MS m/z (M + H$^+$) 451.0 |
| 1144 | 1-(1,3-Thiazol-2-ylcarbonyl)-4-(1-{[5-(trifluoromethyl)biphenyl-3-yl]carbonyl}azetidin-3-yl)piperazine<br>1H NMR (300 MHz, CD$_3$OD): δ 8.12 (s, 1H), 8.07 (s, 1H), 7.96 (d, 1H), 7.92 (s, 1H), 7.86 (d, 1H), 7.67-7.74 (m, 2H), 7.42-7.57 (m, 3H), 4.57-4.74 (m, 3H), 4.38-4.55 (m, 2H), 4.33 (m, 1H), 3.91-4.02 (m, 2H), 3.85 (m, 1H), 3.01-3.13 (m, 4H)<br>MS m/z (M + H$^+$) 501.0 |
| 1104 | 1-{1-[(5-Fluorobiphenyl-3-yl)carbonyl]azetidin-3-yl}-4-(1,3-thiazol-2-ylcarbonyl)piperazine<br>$^1$H NMR (300 MHz, CD$_3$OD): δ 7.97 (d, 1H), 7.88 (d, 1H), 7.64-7.74 (m, 3H), 7.56-7.63 (dt, 1H), 7.35-7.53 (m, 4H), 4.31-4.83 (m, 6H), 3.94-4.10 (m, 3H), 3.19-3.27 (m, 4H)<br>MS m/z (M + H$^+$) 451.0 |
| 1259 | 1-(1,3-Thiazol-4-ylcarbonyl)-4-(1-{[5-(trifluoromethyl)biphenyl-3-yl]carbonyl}azetidin-3-yl)piperazine<br>MS m/z (M + H$^+$) 501.0 |
| 1273 | 1-{1-[(5-Fluorobiphenyl-3-yl)carbonyl]azetidin-3-yl}-4-(1,3-thiazol-4-ylcarbonyl)piperazine<br>MS m/z (M + H$^+$) 451.0 |
| 1114 | 1-(Isothiazol-5-ylcarbonyl)-4-(1-{[2-methyl-3'-(trifluoromethyl)biphenyl-4-yl]carbonyl}azetidin-3-yl)piperazine<br>$^1$H NMR (400 MHz, CDCl$_3$): δ 8.56 (d, 1H); 7.92 (d, 1H); 7.78-7.56 (m, 5H); 7.46 (m, 1H); 4.45 (m, 1H); 4.41-4.19 (m, 3H); 3.94 (bs, 5H); 3.12 (bs, 4H); 2.5 (s, 3H)<br>MS m/z (M + H$^+$) 515.2 |
| 1138 | 1-(1H-Pyrrol-2-ylcarbonyl)-4-[1-({4-[5-(trifluoromethyl)thiophen-2-yl]phenyl}carbonyl)azetidin-3-yl]piperazine<br>MS m/z (M + H$^+$) 489 |
| 1268 | 1-(1,3-Thiazol-5-ylcarbonyl)-4-[1-({4-[5-(trifluoromethyl)thiophen-2-yl]phenyl}carbonyl)azetidin-3-yl]piperazine<br>MS m/z (M + H$^+$) 507.1 |

Example 59a

Following the procedure described above for Example 2 and substituting the appropriate reagents, starting materials and purification methods known to those skilled in the art, the following compounds of the present invention were prepared:

| Cpd | Cpd Name and Data |
|---|---|
| 1212 | 1-{[3-Methyl-3'-(trifluoromethyl)biphenyl-4-yl]carbonyl}-4-[1-(1,3-thiazol-4-ylcarbonyl)azetidin-3-yl]piperazine<br>MS m/z (M + H$^+$) 515.12 |
| 1136 | 1-[1-(1,3-Thiazol-4-ylcarbonyl)azetidin-3-yl]-4-({4-[5-(trifluoromethyl)thiophen-2-yl]phenyl}carbonyl)piperazine<br>MS m/z (M + H$^+$) 507.05 |
| 1260 | 1-{[3-Methyl-3'-(trifluoromethyl)biphenyl-4-yl]carbonyl}-4-[1-(1,3-thiazol-2-ylcarbonyl)azetidin-3-yl]piperazine<br>MS m/z (M + H$^+$) 515.2 |

-continued

| Cpd | Cpd Name and Data |
|---|---|
| 1161 | 1-[1-(1,3-Thiazol-2-ylcarbonyl)azetidin-3-yl]-4-({4-[5-(trifluoromethyl)thiophen-2-yl]phenyl}carbonyl)piperazine<br>MS m/z (M + H$^+$) 507.1 |
| 1162 | 1-[1-(1H-Pyrrol-2-ylcarbonyl)azetidin-3-yl]-4-({4-[5-(trifluoromethyl)thiophen-2-yl]phenyl}carbonyl)piperazine<br>MS m/z (M + H$^+$) 489.2 |

Example 60

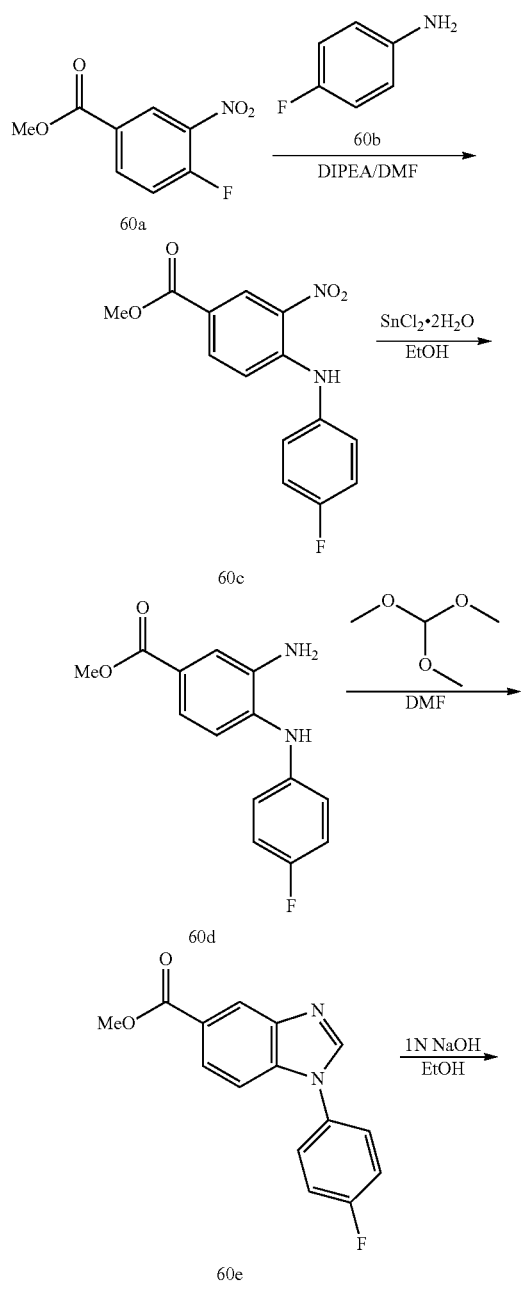

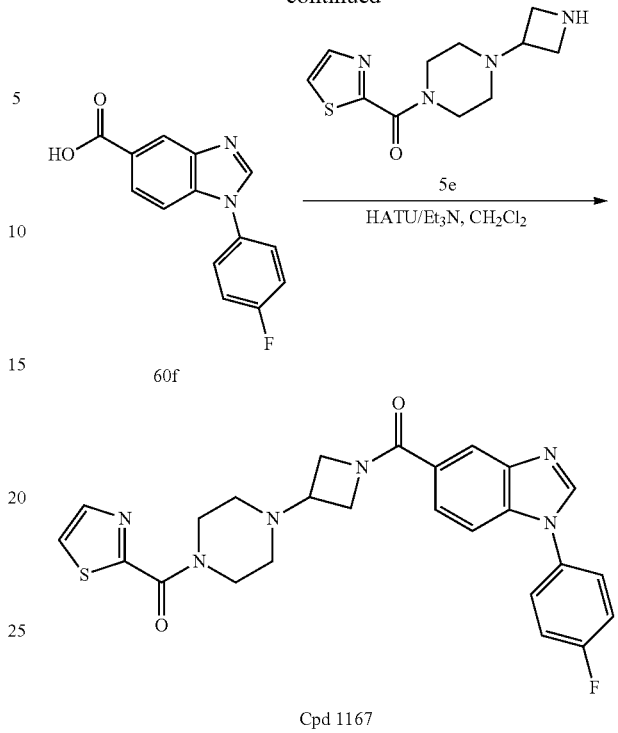

Cpd 1167

A. Methyl 4-((4-fluorophenyl)amino)-3-nitrobenzoate, 60c. A mixture of methyl 4-fluoro-3-nitrobenzoate 60a (1 g, 5.02 mmol), 4-fluoroaniline 60b (4.34 mL, 5.02 mmol), and DIPEA (1.04 mL, 6.03 mmol) in DMF (10 mL) was stirred at room temperature for 2 h. Water was added to the mixture; the resulting solid was filtered, washed with water, and dried. The crude product 60c was used in the next reaction without purification.

B. Methyl 3-amino-4-((4-fluorophenyl)amino)benzoate, 60d. A mixture of 60c (1.4 g, 4.8 mmol) and SnCl$_2$·2H$_2$O (4.9 g, 21.7 mmol) in EtOH (50 mL) was stirred at 80° C. After 4 h, the mixture was cooled to room temperature and was slowly added to saturated aqueous NaHCO$_3$. The solid was filtered and washed with H$_2$O. The solid was triturated with EtOAc and the filtrate was concentrated. The crude product 60d was used in the next reaction without purification. MS m/z (M+H$^+$) 261.1.

C. Methyl 1-(4-fluorophenyl)-1H-benzo[d]imidazole-5-carboxylate, 60e. A mixture of 60d (0.18 g, 0.693 mmol) and trimethyl orthoformate (0.7 mL, 6.39 mmol) in DMF (2 mL) was refluxed for 5 h and then cooled to room temperature. Water was added to the mixture. The resulting solid was filtered, washed, with water, and dried. The crude product 60e was used in the next reaction without purification. MS m/z (M+H$^+$) 271.1.

D. 1-(4-Fluorophenyl)-1H-benzo[d]imidazole-5-carboxylic acid, 60f. To a solution of 60e (0.18 g, 0.666 mmol) in EtOH (10 mL) was added 1N aqueous NaOH (2.5 mL, 2.5 mmol). The mixture was stirred at room temperature for 4 d. The solvent was evaporated and 1N aqueous HCl was added, followed by extraction with EtOAc. The organic layer was dried over MgSO$_4$ and concentrated. The crude product 60f was purified by preparative reverse phase chromatography. MS m/z (M+H$^+$) 257.1.

E. 1-(4-Fluorophenyl)-5-({3-[4-(1,3-thiazol-2-ylcarbonyl)piperazin-1-yl]azetidin-1-yl}carbonyl)-1H-benzimidazole, Cpd 1167. To a solution of 5e (0.058 g, 0.178 mmol) and HATU (0.081 g, 0.214 mmol) in CH$_2$Cl$_2$ (3 mL) was added Et$_3$N (0.099 mL, 0.713 mmol). The mixture was stirred at room temperature for 30 min, and then 60f (0.050 g, 0.196 mmol) was added. The reaction mixture was stirred at room temperature overnight. Water (6 mL) was added and the mixture was extracted with EtOAc. The organic layer was dried over MgSO$_4$ and concentrated. The crude product Cpd 1167 was purified by preparative reverse phase chromatography. MS m/z (M+H$^+$) 491.2.

Following the procedure described above for Example 60 and substituting the appropriate reagents, starting materials and purification methods known to those skilled in the art, the following intermediate compounds were prepared.

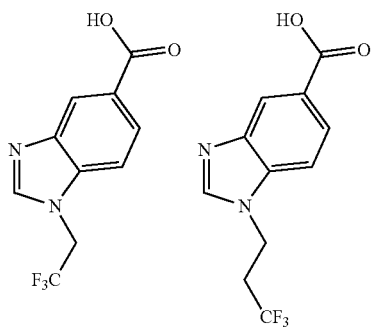

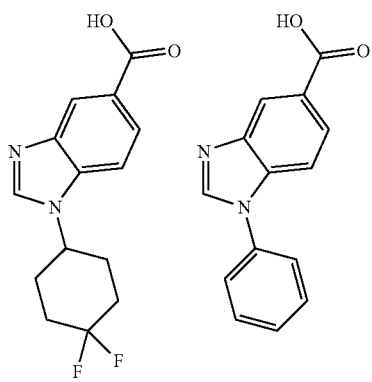

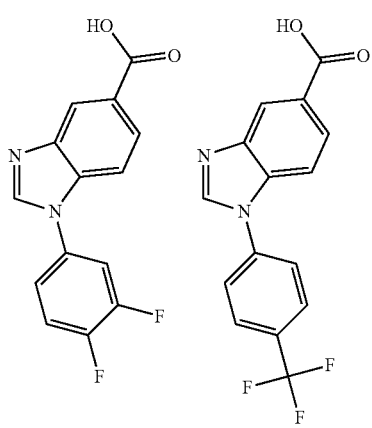

Following the procedure described above for Example 60 and substituting the appropriate reagents, starting materials and purification methods known to those skilled in the art, the following compounds of the present invention were prepared.

| | | |
|---|---|---|
| 1186 | 1-(3,4-Difluorophenyl)-5-({3-[4-(1,3-thiazol-2-ylcarbonyl)piperazin-1-yl]azetidin-1-yl}carbonyl)-1H-benzimidazole | |
| | MS m/z (M + H$^+$) 509.2 | |
| 1064 | 5-({3-[4-(1,3-Thiazol-2-ylcarbonyl)piperazin-1-yl]azetidin-1-yl}carbonyl)-1-[4-(trifluoromethyl)phenyl]-1H-benzimidazole | |
| | 1H NMR (300 MHz, CD$_3$OD): d 8.82 (s, 1H), 8.14 (s, 1H), 7.96-8.03 (m, 3H), 7.86-7.95 (m, 3H), 7.76-7.85 (m, 2H), 7.08 (d, 1H), 4.36-4.86 (m, 6H), 3.97-4.16 (m, 3H), 3.32-3.42 (m, 4H) | |
| | MS m/z (M + H$^+$) 541.2 | |
| 761 | 5-({3-[4-(1,3-Thiazol-2-ylcarbonyl)piperazin-1-yl]azetidin-1-yl}carbonyl)-1-(2,2,2-trifluoroethyl)-1H-benzimidazole | |
| | MS m/z (M + H$^+$) 479.1 | |
| 780 | 5-({3-[4-(1,3-Thiazol-2-ylcarbonyl)piperazin-1-yl]azetidin-1-yl}carbonyl)-1-(3,3,3-trifluoropropyl)-1H-benzimidazole | |
| | MS m/z (M + H$^+$) 493.2 | |
| 759 | 1-(4,4-Difluorocyclohexyl)-5-({3-[4-(1,3-thiazol-2-ylcarbonyl)piperazin-1-yl]azetidin-1-yl}carbonyl)-1H-benzimidazole | |
| | MS m/z (M + H$^+$) 515.2 | |
| 1281 | 1-Phenyl-5-({3-[4-(1,3-thiazol-4-ylcarbonyl)piperazin-1-yl]azetidin-1-yl}carbonyl)-1H-benzimidazole | |
| | MS m/z (M + H$^+$) 473.2 | |
| 1274 | 1-(4-Fluorophenyl)-5-({3-[4-(1,3-thiazol-4-ylcarbonyl)piperazin-1-yl]azetidin-1-yl}carbonyl)-1H-benzimidazole | |
| | MS m/z (M + H$^+$) 491.2 | |
| 1270 | 1-(3,4-Difluorophenyl)-5-({3-[4-(1,3-thiazol-4-ylcarbonyl)piperazin-1-yl]azetidin-1-yl}carbonyl)-1H-benzimidazole | |
| | MS m/z (M + H$^+$) 509.1 | |
| 1231 | 5-({3-[4-(1,3-Thiazol-4-ylcarbonyl)piperazin-1-yl]azetidin-1-yl}carbonyl)-1-[4-(trifluoromethyl)phenyl]-1H-benzimidazole | |
| | MS m/z (M + H$^+$) 541.2 | |
| 841 | 5-({3-[4-(1,3-Thiazol-4-ylcarbonyl)piperazin-1-yl]azetidin-1-yl}carbonyl)-1-(2,2,2-trifluoroethyl)-1H-benzimidazole | |
| | MS m/z (M + H$^+$) 479.1 | |
| 851 | 5-({3-[4-(1,3-Thiazol-4-ylcarbonyl)piperazin-1-yl]azetidin-1-yl}carbonyl)-1-(3,3,3-trifluoropropyl)-1H-benzimidazole | |
| | MS m/z (M + H$^+$) 493.2 | |
| 834 | 1-(4,4-Difluorocyclohexyl)-5-({3-[4-(1,3-thiazol-4-ylcarbonyl)piperazin-1-yl]azetidin-1-yl}carbonyl)-1H-benzimidazole | |
| | MS m/z (M + H$^+$) 515.2 | |
| 1207 | 1-Phenyl-5-({3-[4-(1,3-thiazol-2-ylcarbonyl)piperazin-1-yl]azetidin-1-yl}carbonyl)-1H-benzimidazole | |
| | MS m/z (M + H$^+$) 473 | |

Example 60a

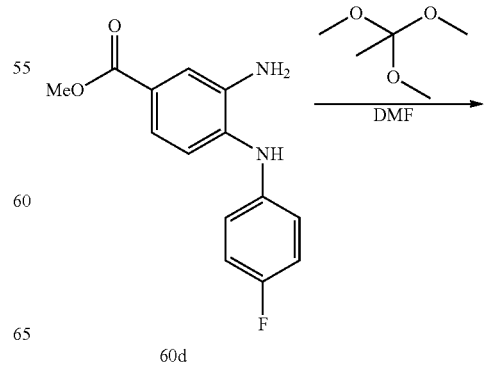

60d

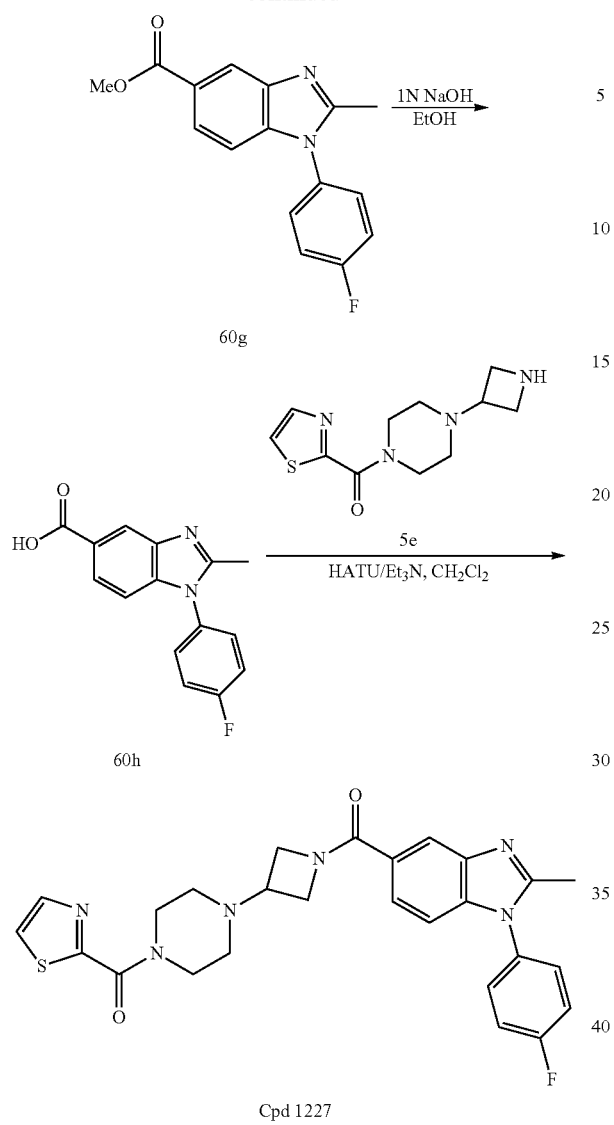

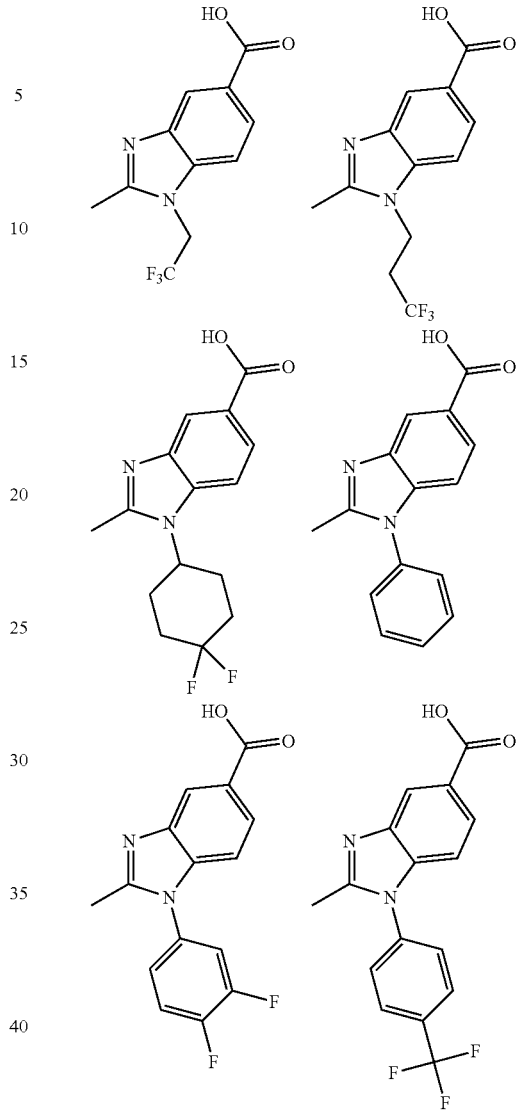

F. Methyl 2-methyl-1-(4-fluorophenyl)-1H-benzo[d]imidazole-5-carboxylate, 60g. The title compound 60g was prepared using the method described in Example 60, substituting trimethyl orthoacetate for trimethyl orthoformate in Step C. The crude product 60g was used in the next reaction without purification. MS m/z (M+H$^+$) 285.1.

G. 2-Methyl-1-(4-fluorophenyl)-1H-benzo[d]imidazole-5-carboxylate, 60h. The title compound 60h was prepared using the method described in Example 60, substituting 60g for 60e in Step D. The crude product 60h was used in the next reaction without purification. MS m/z (M+H$^+$) 271.2.

H. Cpd 1227. The title compound Cpd 1227 was prepared using the method described in Example 60, substituting 60h for 60f in Step E. The crude product Cpd 1227 was purified by preparative reverse phase chromatography. MS m/z (M+H$^+$) 505.2.

Following the procedure described above for Example 60a and substituting the appropriate reagents, starting materials and purification methods known to those skilled in the art, the following intermediate compounds were prepared.

Following the procedure described above for Example 60a and substituting the appropriate reagents, starting materials and purification methods known to those skilled in the art, the following compounds of the present invention were prepared.

| Cpd | Cpd Name and Data |
|---|---|
| 1229 | 2-Methyl-1-phenyl-5-({3-[4-(1,3-thiazol-2-ylcarbonyl)piperazin-1-yl]azetidin-1-yl}carbonyl)-1H-benzimidazole<br>MS m/z (M + H$^+$) 487.2 |
| 1206 | 1-(3,4-Difluorophenyl)-2-methyl-5-({3-[4-(1,3-thiazol-2-ylcarbonyl)piperazin-1-yl]azetidin-1-yl}carbonyl)-1H-benzimidazole<br>MS m/z (M + H$^+$) 523.2 |
| 1215 | 2-Methyl-5-({3-[4-(1,3-thiazol-2-ylcarbonyl)piperazin-1-yl]azetidin-1-yl}carbonyl)-1-[4-(trifluoromethyl)phenyl]-1H-benzimidazole<br>MS m/z (M + H$^+$) 555.2 |
| 789 | 2-Methyl-5-({3-[4-(1,3-thiazol-2-ylcarbonyl)piperazin-1-yl]azetidin-1-yl}carbonyl)-1-(2,2,2-trifluoroethyl)-1H-benzimidazole<br>MS m/z (M + H$^+$) 493.2 |

-continued

| Cpd | Cpd Name and Data |
|---|---|
| 777 | 2-Methyl-5-({3-[4-(1,3-thiazol-2-ylcarbonyl)piperazin-1-yl]azetidin-1-yl}carbonyl)-1-(3,3,3-trifluoropropyl)-1H-benzimidazole<br>MS m/z (M + H$^+$) 507.2 |
| 798 | 1-(4,4-Difluorocyclohexyl)-2-methyl-5-({3-[4-(1,3-thiazol-2-ylcarbonyl)piperazin-1-yl]azetidin-1-yl}carbonyl)-1H-benzimidazole<br>MS m/z (M + H$^+$) 529.2 |
| 1291 | 1-(4-Fluorophenyl)-2-methyl-5-({3-[4-(1,3-thiazol-4-ylcarbonyl)piperazin-1-yl]azetidin-1-yl}carbonyl)-1H-benzimidazole<br>MS m/z (M + H$^+$) 505.2 |
| 1296 | 2-Methyl-1-phenyl-5-({3-[4-(1,3-thiazol-4-ylcarbonyl)piperazin-1-yl]azetidin-1-yl}carbonyl)-1H-benzimidazole<br>MS m/z (M + H$^+$) 487.2 |
| 1264 | 1-(3,4-Difluorophenyl)-2-methyl-5-({3-[4-(1,3-thiazol-4-ylcarbonyl)piperazin-1-yl]azetidin-1-yl}carbonyl)-1H-benzimidazole<br>MS m/z (M + H$^+$) 523.2 |
| 1289 | 2-Methyl-5-({3-[4-(1,3-thiazol-4-ylcarbonyl)piperazin-1-yl]azetidin-1-yl}carbonyl)-1-[4-(trifluoromethyl)phenyl]-1H-benzimidazole<br>MS m/z (M + H$^+$) 555.2 |
| 858 | 2-Methyl-5-({3-[4-(1,3-thiazol-4-ylcarbonyl)piperazin-1-yl]azetidin-1-yl}carbonyl)-1-(2,2,2-trifluoroethyl)-1H-benzimidazole<br>MS m/z (M + H$^+$) 493.2 |
| 866 | 2-Methyl-5-({3-[4-(1,3-thiazol-4-ylcarbonyl)piperazin-1-yl]azetidin-1-yl}carbonyl)-1-(3,3,3-trifluoropropyl)-1H-benzimidazole<br>MS m/z (M + H$^+$) 507.1 |
| 1506 | 1-(4,4-Difluorocyclohexyl)-2-methyl-5-({3-[4-(1,3-thiazol-4-ylcarbonyl)piperazin-1-yl]azetidin-1-yl}carbonyl)-1H-benzimidazole<br>MS m/z (M + H$^+$) 529.2 |
| 635 | 2-Methyl-1-phenyl-5-({3-[4-(phenylcarbonyl)piperazin-1-yl]azetidin-1-yl}carbonyl)-1H-benzimidazole<br>MS m/z (M + H$^+$) 480 |

Example 60b

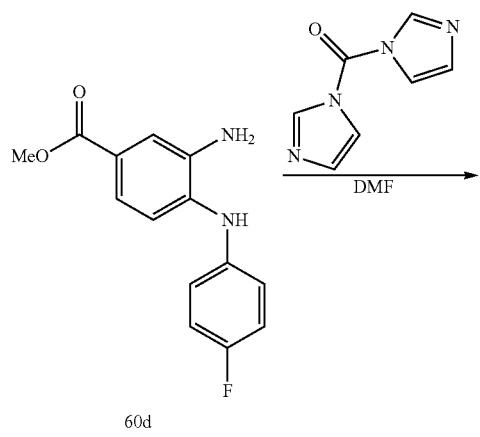

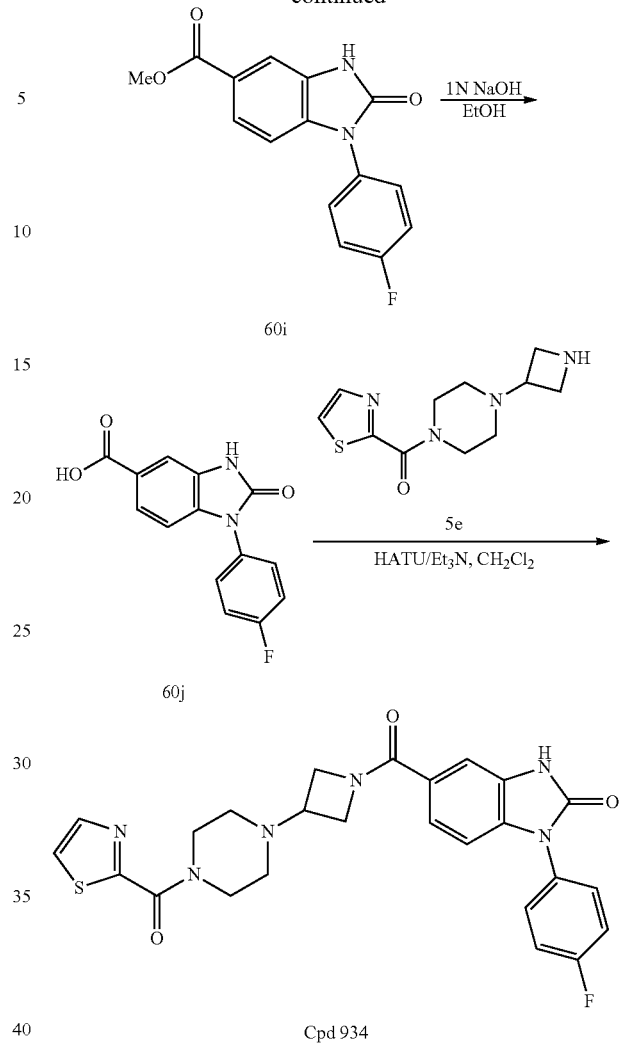

I. Methyl 1-(4-fluorophenyl)-2-oxo-2,3-dihydro-1H-benzo[d]imidazole-5-carboxylate, 60i. A mixture of 60d (0.20 g, 0.826 mmol) and 1,1'-carbonyldiimidazole (0.535 g, 3.3 mmol) in DMF (8 mL) was heated at 90° C. for 2 h. The solvent was removed and the residue was triturated with water (15 mL). The resulting precipitate was collected by filtration and washed several times with water. The crude product 60i was used in the next reaction without further purification. MS m/z (M+H$^+$) 287.1.

J. 1-(4-Fluorophenyl)-2-oxo-2,3-dihydro-1H-benzo[d]imidazole-5-carboxylate, 60j. The title compound 60j was prepared using the method described in Example 60, substituting 60i for 60e in Step D. The crude product 60j was used in the next reaction without purification. MS m/z (M+H$^+$) 273.1.

K. 1-(4-Fluorophenyl)-5-({3-[4-(1,3-thiazol-2-ylcarbonyl)piperazin-1-yl]azetidin-1-yl}carbonyl)-1,3-dihydro-2H-benzimidazol-2-one, Cpd 934. The title compound Cpd 934 was prepared using the method described in Example 60, substituting 60j for 60f in Step E. The crude product Cpd 934 was purified by preparative reverse phase chromatography. MS m/z (M+H$^+$) 507.1.

Following the procedure described above for Example 60b and substituting the appropriate reagents, starting materials and purification methods known to those skilled in the art, the following intermediate compounds were prepared.

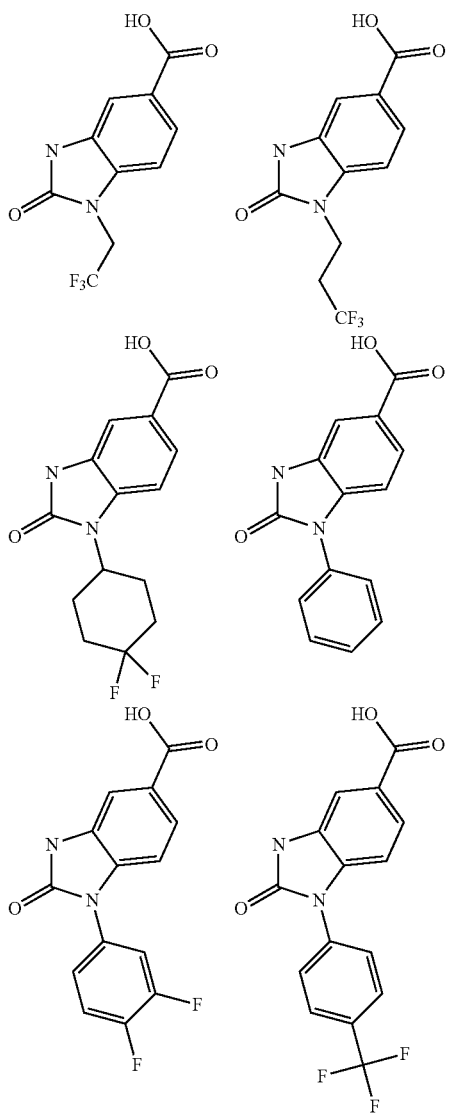

Following the procedure described above for Example 60b and substituting the appropriate reagents, starting materials and purification methods known to those skilled in the art, the following compounds of the present invention were prepared.

| Cpd | Cpd Name and Data |
|---|---|
| 933 | 1-Phenyl-5-({3-[4-(1,3-thiazol-2-ylcarbonyl)piperazin-1-yl]azetidin-1-yl}carbonyl)-1,3-dihydro-2H-benzimidazol-2-one<br>$^1$H NMR (300 MHz, CD$_3$OD): δ 7.97 (d, 1H), 7.88 (d, 1H), 7.56-7.66 (m, 2H), 7.46-7.55 (m, 4H), 7.42 (dd, 1H), 7.08 (d, 1H), 4.26-4.81 (m, 6H), 3.93-4.10 (m, 3H), 3.18-3.27 (m, 4H)<br>MS m/z (M + H$^+$) 489.1 |
| 932 | 1-(4,4-Difluorocyclohexyl)-5-({3-[4-(1,3-thiazol-2-ylcarbonyl)piperazin-1-yl]azetidin-1-yl}carbonyl)-1,3-dihydro-2H-benzimidazol-2-one<br>MS m/z (M + H$^+$) 531.0 |
| 935 | 1-(3,4-Difluorophenyl)-5-({3-[4-(1,3-thiazol-2-ylcarbonyl)piperazin-1-yl]azetidin-1-yl}carbonyl)-1,3-dihydro-2H-benzimidazol-2-one<br>MS m/z (M + H$^+$) 525.1 |
| 936 | 5-({3-[4-(1,3-Thiazol-2-ylcarbonyl)piperazin-1-yl]azetidin-1-yl}carbonyl)-1-[4-(trifluoromethyl)phenyl]-1,3-dihydro-2H-benzimidazol-2-one<br>MS m/z (M + H$^+$) 557.0 |
| 937 | 5-({3-[4-(1,3-Thiazol-2-ylcarbonyl)piperazin-1-yl]azetidin-1-yl}carbonyl)-1-(2,2,2-trifluoroethyl)-1,3-dihydro-2H-benzimidazol-2-one<br>MS m/z (M + H$^+$) 495.1 |
| 938 | 5-({3-[4-(1,3-Thiazol-2-ylcarbonyl)piperazin-1-yl]azetidin-1-yl}carbonyl)-1-(3,3,3-trifluoropropyl)-1,3-dihydro-2H-benzimidazol-2-one<br>MS m/z (M + H$^+$) 509.1 |
| 939 | 1-Phenyl-5-({3-[4-(1,3-thiazol-4-ylcarbonyl)piperazin-1-yl]azetidin-1-yl}carbonyl)-1,3-dihydro-2H-benzimidazol-2-one<br>MS m/z (M + H$^+$) 489.1 |
| 940 | 1-(4-Fluorophenyl)-5-({3-[4-(1,3-thiazol-4-ylcarbonyl)piperazin-1-yl]azetidin-1-yl}carbonyl)-1,3-dihydro-2H-benzimidazol-2-one<br>MS m/z (M + H$^+$) 507.1 |
| 941 | 1-(3,4-Difluorophenyl)-5-({3-[4-(1,3-thiazol-4-ylcarbonyl)piperazin-1-yl]azetidin-1-yl}carbonyl)-1,3-dihydro-2H-benzimidazol-2-one<br>MS m/z (M + H$^+$) 525.2 |
| 942 | 5-({3-[4-(1,3-Thiazol-4-ylcarbonyl)piperazin-1-yl]azetidin-1-yl}carbonyl)-1-[4-(trifluoromethyl)phenyl]-1,3-dihydro-2H-benzimidazol-2-one<br>MS m/z (M + H$^+$) 557.2 |
| 943 | 5-({3-[4-(1,3-Thiazol-4-ylcarbonyl)piperazin-1-yl]azetidin-1-yl}carbonyl)-1-(2,2,2-trifluoroethyl)-1,3-dihydro-2H-benzimidazol-2-one<br>MS m/z (M + H$^+$) 495.2 |
| 944 | 5-({3-[4-(1,3-Thiazol-4-ylcarbonyl)piperazin-1-yl]azetidin-1-yl}carbonyl)-1-(3,3,3-trifluoropropyl)-1,3-dihydro-2H-benzimidazol-2-one<br>MS m/z (M + H$^+$) 509.2 |
| 945 | 1-(4,4-Difluorocyclohexyl)-5-({3-[4-(1,3-thiazol-4-ylcarbonyl)piperazin-1-yl]azetidin-1-yl}carbonyl)-1,3-dihydro-2H-benzimidazol-2-one<br>MS m/z (M + H$^+$) 531.2 |

Example 61

Example 62

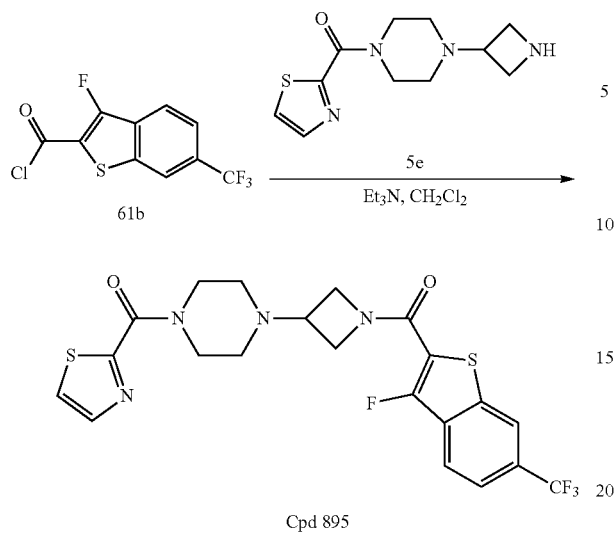

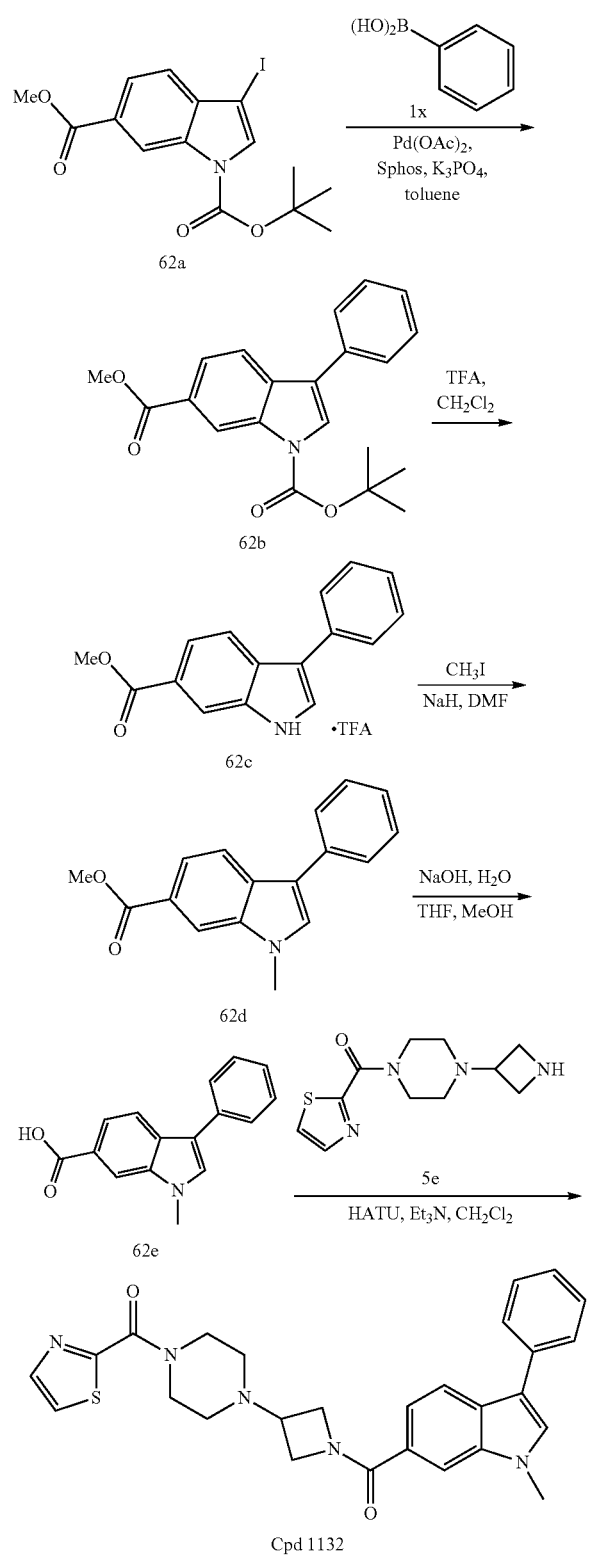

A. 3-Fluoro-6-trifluoromethyl-benzo[b]thiophene-2-carboxylic acid, 61a. A solution of 6-trifluoromethyl-benzo[b]thiophene-2-carboxylic acid 10a (2.031 mmol, 0.50 g) in THF (8 mL) at −70° C. was treated with a 1.6 M solution of n-BuLi in hexanes (4.26 mmol, 2.66 mL). After 1 h at −70° C., N-fluorobenzenesulfonimide (2.64 mmol, 0.833 g) in THF (2 mL) was slowly added and the reaction was warmed to room temperature. After 1 h the mixture was partitioned between dilute aqueous HCl and EtOAc. The organic layer was washed with water and brine, and then concentrated. The residue was triturated with $CH_2Cl_2$. The off-white precipitate was filtered and collected to provide 61a.

B. 3-Fluoro-6-trifluoromethyl-benzo[b]thiophene-2-carbonyl chloride, 61b. The title compound 61b was prepared using the method described in Example 10, substituting 61a for 10a in Step A.

C. 1-(1-{[3-Fluoro-6-(trifluoromethyl)-1-benzothiophen-2-yl]carbonyl}azetidin-3-yl)-4-(1,3-thiazol-2-ylcarbonyl)piperazine, Cpd 895. The title compound Cpd 895 was prepared using the method described in Example 10, substituting 61b for 10b in Step B. MS m/z (M+H$^+$) 499.

Following the procedure described above for Example 61 and substituting the appropriate reagents, starting materials and purification methods known to those skilled in the art, the following compounds of the present invention were prepared:

| Cpd | Cpd Name and Data |
|---|---|
| 653 | 1-(1-{[3-Fluoro-6-(trifluoromethyl)-1-benzothiophen-2-yl]carbonyl}azetidin-3-yl)-4-(1,3-thiazol-4-ylcarbonyl)piperazine<br>MS m/z (M + H$^+$) 499 |
| 509 | 1-(1-{[3-Fluoro-6-(trifluoromethyl)-1-benzothiophen-2-yl]carbonyl}azetidin-3-yl)-4-(phenylcarbonyl)piperazine<br>MS m/z (M + H$^+$) 492 |

A. 1-tert-Butyl 6-methyl 3-phenyl-1H-indole-1,6-dicarboxylate, 62b. A mixture of 1-tert-butyl 6-methyl 3-iodo-1H-indole-1,6-dicarboxylate 62a (5.02 mmol, 2.016 g), phenylboronic acid 1x (7.53 mmol, 0.92 g), Pd(OAc)$_2$ (0.402 mmol, 90 mg), Sphos 0.904 mmol, (0.37 g), and K$_3$PO$_4$ (10.1 mmol, 2.13 g) in toluene (10 mL) in sealed reaction vial was stirred at room temperature for 2 min and then heated at 90° C. under N$_2$ for 4 h. The reaction mixture was quenched with EtOAc and water. The organic layer was concentrated and purified by flash column chromatography (silica gel, 8% EtOAc/hexanes). The desired product was collected as a light yellow solid that was washed with small amount of hexanes to obtain 62b as a white solid.

B. Methyl 3-phenyl-1H-indole-6-carboxylate TFA salt, 62c. To a solution of 1-tert-butyl 6-methyl 3-phenyl-1H-indole-1,6-dicarboxylate 62b (4.04 mmol, 1.42 g) in CH$_2$Cl$_2$ (8 mL) was added 6 mL of TFA. The resulting solution was stirred for 3 h. The mixture was then concentrated and washed with hexanes to afford 62c.

C. Methyl 1-methyl-3-phenyl-1H-indole-6-carboxylate, 62d. NaH (60% dispersion in mineral oil, 4.52 mmol, 186 mg) was added portion-wise to a solution of methyl 3-phenyl-1H-indole-6-carboxylate TFA salt 62c (2.07 mmol, 757 mg) in DMF at 0° C. and the mixture was stirred for 20 min. Methyl iodide (2.28 mmol, 0.14 mL) was added and the reaction mixture was maintained at 0° C. for 1 h. Water was then added and the reaction was extracted with EtOAc. The organics were concentrated and purified by flash column chromatography (silica gel, 15% EtOAc/hexanes) to give 62d.

D. 1-Methyl-3-phenyl-1H-indole-6-carboxylic acid, 62e. The title compound 62e was prepared using the method described in Example 29, substituting 62d for 29c in Step B.

E. 1-Methyl-3-phenyl-6-({3-[4-(1,3-thiazol-2-ylcarbonyl) piperazin-1-yl]azetidin-1-yl}carbonyl)-1H-indole, Cpd 1132. The title compound Cpd 1132 was prepared using the method described in Example 9, substituting 62d for 9c in Step D. MS m/z (M+H$^+$) 486.

Following the procedure described above for Example 62 and substituting the appropriate reagents, starting materials and purification methods known to those skilled in the art, the following intermediate compounds were prepared:

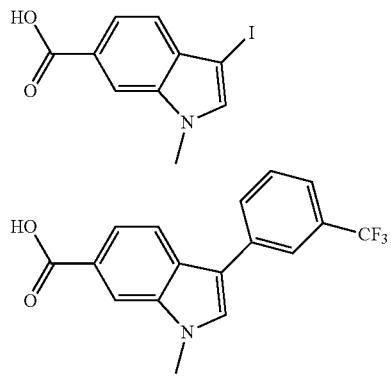

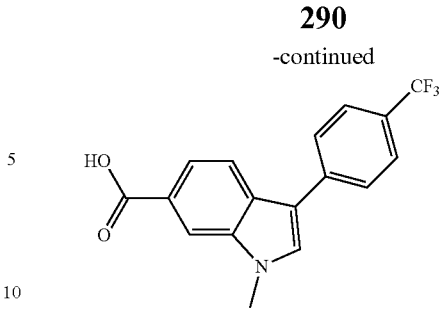

Following the procedure described above for Example 62 and substituting the appropriate reagents, starting materials and purification methods known to those skilled in the art, the following compounds of the present invention were prepared:

| Cpd | Cpd Name and Data |
|---|---|
| 701 | 3-Iodo-1-methyl-6-({3-[4-(1,3-thiazol-2-ylcarbonyl)piperazin-1-yl]azetidin-1-yl}carbonyl)-1H-indole<br>MS m/z (M + H$^+$) 536 |
| 1084 | 1-Methyl-6-({3-[4-(1,3-thiazol-4-ylcarbonyl)piperazin-1-yl]azetidin-1-yl}carbonyl)-3-[3-(trifluoromethyl)phenyl]-1H-indole<br>MS m/z (M + H$^+$) 554 |
| 1148 | 1-Methyl-6-({3-[4-(1,3-thiazol-4-ylcarbonyl)piperazin-1-yl]azetidin-1-yl}carbonyl)-3-[4-(trifluoromethyl)phenyl]-1H-indole<br>MS m/z (M + H$^+$) 554 |
| 1100 | 1-Methyl-6-({3-[4-(1,3-thiazol-2-ylcarbonyl)piperazin-1-yl]azetidin-1-yl}carbonyl)-3-[3-(trifluoromethyl)phenyl]-1H-indole<br>MS m/z (M + H$^+$) 554 |
| 1347 | 1-Methyl-6-({3-[4-(1,3-thiazol-2-ylcarbonyl)piperazin-1-yl]azetidin-1-yl}carbonyl)-3-[4-(trifluoromethyl)phenyl]-1H-indole<br>MS m/z (M + H$^+$) 554 |
| 1155 | 1-Methyl-3-phenyl-6-({3-[4-(1,3-thiazol-4-ylcarbonyl)piperazin-1-yl]azetidin-1-yl}carbonyl)-1H-indole<br>MS m/z (M + H$^+$) 486 |
| 593 | 1-Methyl-6-({3-[4-(phenylcarbonyl)piperazin-1-yl]azetidin-1-yl}carbonyl)-3-[3-(trifluoromethyl)phenyl]-1H-indole<br>MS m/z (M + H$^+$) 547 |
| 585 | 1-Methyl-3-phenyl-6-({3-[4-(phenylcarbonyl)piperazin-1-yl]azetidin-1-yl}carbonyl)-1H-indole<br>MS m/z (M + H$^+$) 479 |

Example 62a

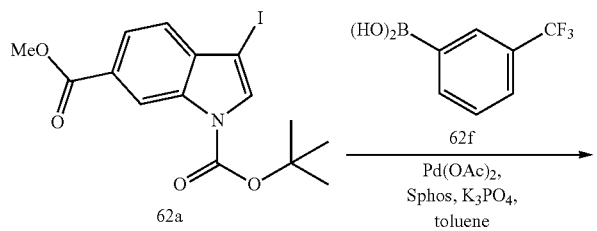

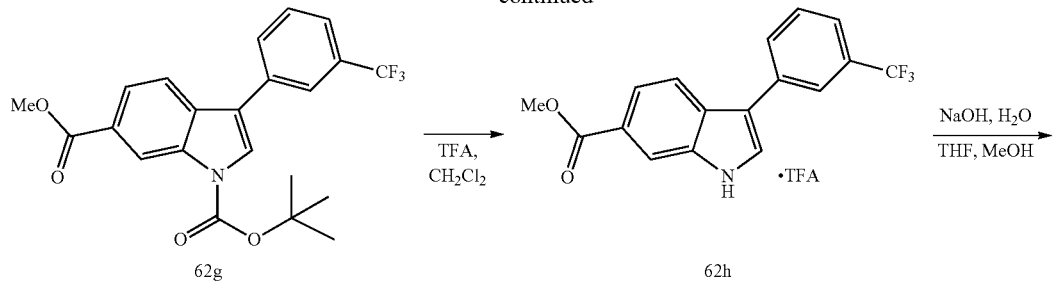

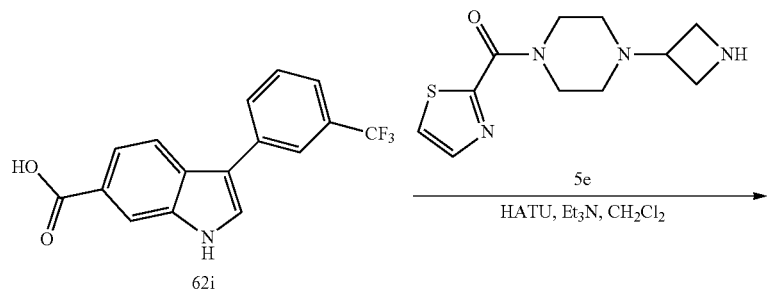

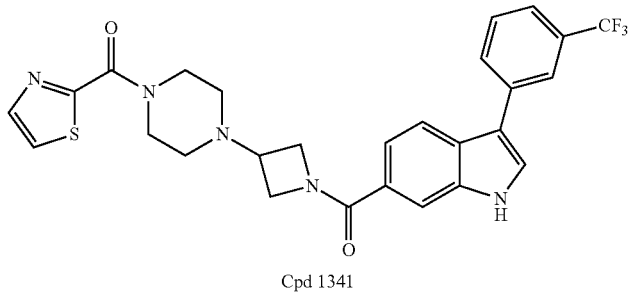

Cpd 1341

F. 1-tert-Butyl 6-methyl 3-(3-(trifluoromethyl)phenyl)-1H-indole-1,6-dicarboxylate, 62g. The title compound 62g was prepared using the method described in Example 62, substituting 62f for 1x in Step A.

G. Methyl 3-(3-(trifluoromethyl)phenyl)-1H-indole-6-carboxylate TFA salt, 62h. The title compound 62h was prepared using the method described in Example 62, substituting 62g for 62b in Step B.

H. 3-(3-(Trifluoromethyl)phenyl)-1H-indole-6-carboxylic acid, 62i. The title compound was prepared using the method described in Example 62, substituting 62h for 62e in Step D.

E. 6-({3-[4-(1,3-Thiazol-2-ylcarbonyl)piperazin-1-yl]azetidin-1-yl}carbonyl)-3-[3-(trifluoromethyl)phenyl]-1H-indole, Cpd 1341. The title compound Cpd 1341 was prepared using the method described in Example 9, substituting 62i for 9c in Step D. MS m/z (M+H$^+$) 540.

Following the procedure described above for Example 62a and substituting the appropriate reagents, starting materials and purification methods known to those skilled in the art, the following intermediate compound was prepared:

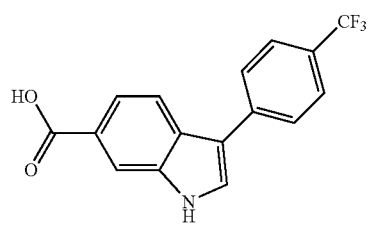 [SMILES: O=C(O)c1ccc2c(-c3ccc(C(F)(F)F)cc3)c[nH]c2c1]

Following the procedure described above for Example 62a and substituting the appropriate reagents, starting materials and purification methods known to those skilled in the art, the following compounds of the present invention were prepared:

| Cpd | Cpd Name and Data |
|---|---|
| 572 | 6-({3-[4-(Phenylcarbonyl)piperazin-1-yl]azetidin-1-yl}carbonyl)-3-[3-(trifluoromethyl)phenyl]-1H-indole MS m/z (M + H$^+$) 533 |

-continued

| Cpd | Cpd Name and Data |
|---|---|
| 634 | 6-({3-[4-(Phenylcarbonyl)piperazin-1-yl]azetidin-1-yl}carbonyl)-3-[4-(trifluoromethyl)phenyl]-1H-indole MS m/z (M + H+) 533 |
| 1340 | 6-({3-[4-(1,3-Thiazol-2-ylcarbonyl)piperazin-1-yl]azetidin-1-yl}carbonyl)-3-[4-(trifluoromethyl)phenyl]-1H-indole MS m/z (M + H+) 540 |

-continued

| Cpd | Cpd Name and Data |
|---|---|
| 1344 | 6-({3-[4-(1,3-Thiazol-4-ylcarbonyl)piperazin-1-yl]azetidin-1-yl}carbonyl)-3-[4-(trifluoromethyl)phenyl]-1H-indole MS m/z (M + H+) 540 |
| 1345 | 6-({3-[4-(1,3-Thiazol-4-ylcarbonyl)piperazin-1-yl]azetidin-1-yl}carbonyl)-3-[3-(trifluoromethyl)phenyl]-1H-indole MS m/z (M + H+) 540 |

Example 63

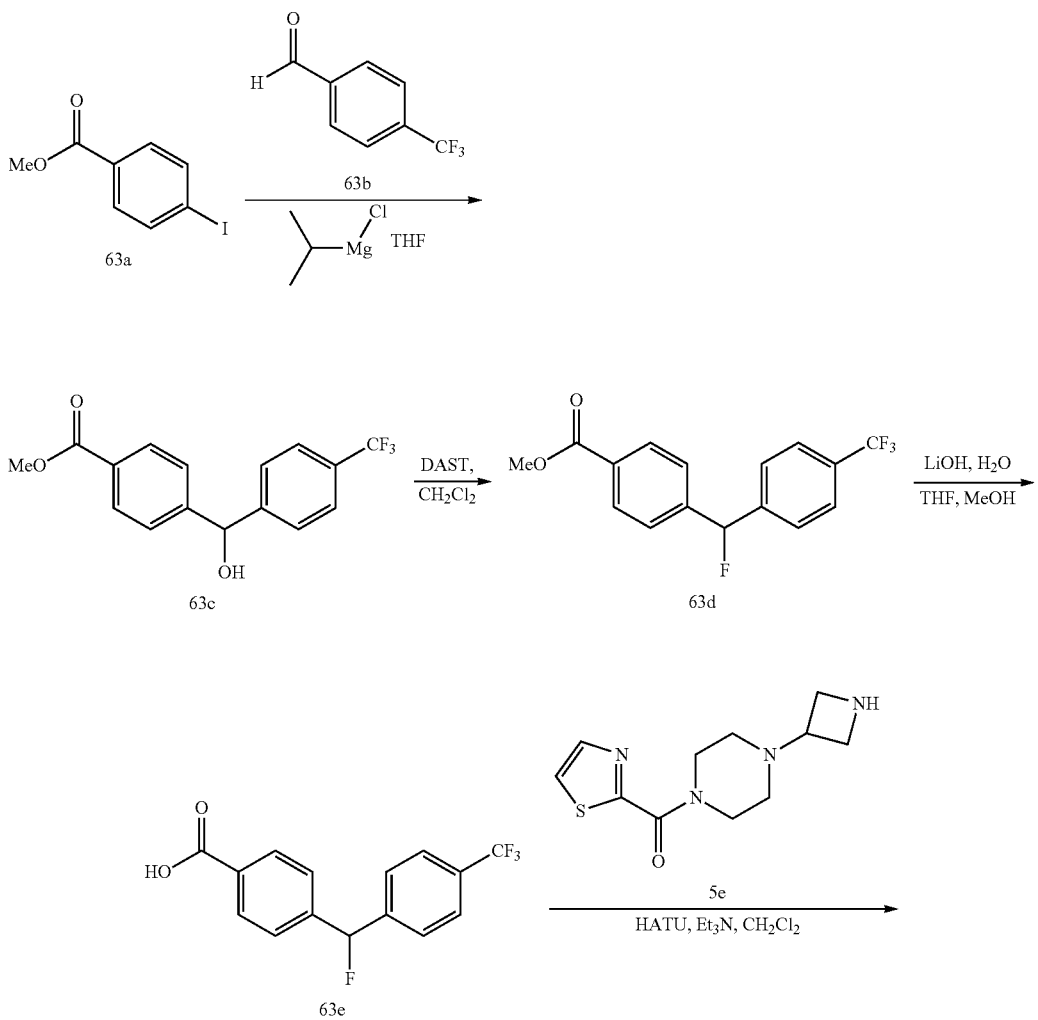

A. Methyl 4-(hydroxy(4-(trifluoromethyl)phenyl)methyl) benzoate, 63c. To a solution of methyl 4-iodobenzoate 63a (8 mmol, 2.1 g) in 10 mL of dry THF was added i-propyl magnesium chloride (2M in THF, 8.4 mmol, 4.2 mL) dropwise under $N_2$ at −20° C. The solution was stirred for 30 min. The formed Grignard reagent in THF was then added slowly to a solution of 4-trifluoromethylbenzaldehyde (8 mmol, 1.1 mL) in THF (20 mL) at −40° C. After 20 min, the reaction mixture was allowed to warm up slowly to room temperature. The reaction was quenched with saturated aqueous $NH_4Cl$ and extracted with EtOAc. The organic layer was concentrated and purified by flash column chromatography (silica gel, 15% EtOAc/hexanes) to give the 63c as white solid.

B. 4 Methyl 4-(fluoro(4-(trifluoromethyl)phenyl)methyl) benzoate, 63d. To a solution of 63c (0.97 mmol, 300 mg) in $CH_2Cl_2$ was added DAST (1.015 mmol, 0.133 mL) dropwise at −78° C. under $N_2$. The reaction was kept at −78° C. for 30 min and then quenched with aqueous $NaHCO_3$ solution at low temperature. Additional $CH_2Cl_2$ was added to the reaction and the organic solution was concentrated. The crude material was purified flash column chromatography (silica gel, 10% EtOAc/hexanes) to give 63d.

C. 4-(Fluoro(4-(trifluoromethyl)phenyl)methyl)benzoic acid, 63e. The title compound was prepared using the method described in Example 29, substituting 63d for 29c in Step B.

D. 1-{1-[(4-{Fluoro[4-(trifluoromethyl)phenyl]methyl} phenyl)carbonyl]azetidin-3-yl}-4-(1,3-thiazol-2-ylcarbonyl)piperazine, Cpd 982. The title compound Cpd 982 was prepared using the method described in Example 9, substituting 63e for 9c in Step D. MS m/z (M+H$^+$) 533.

Example 64

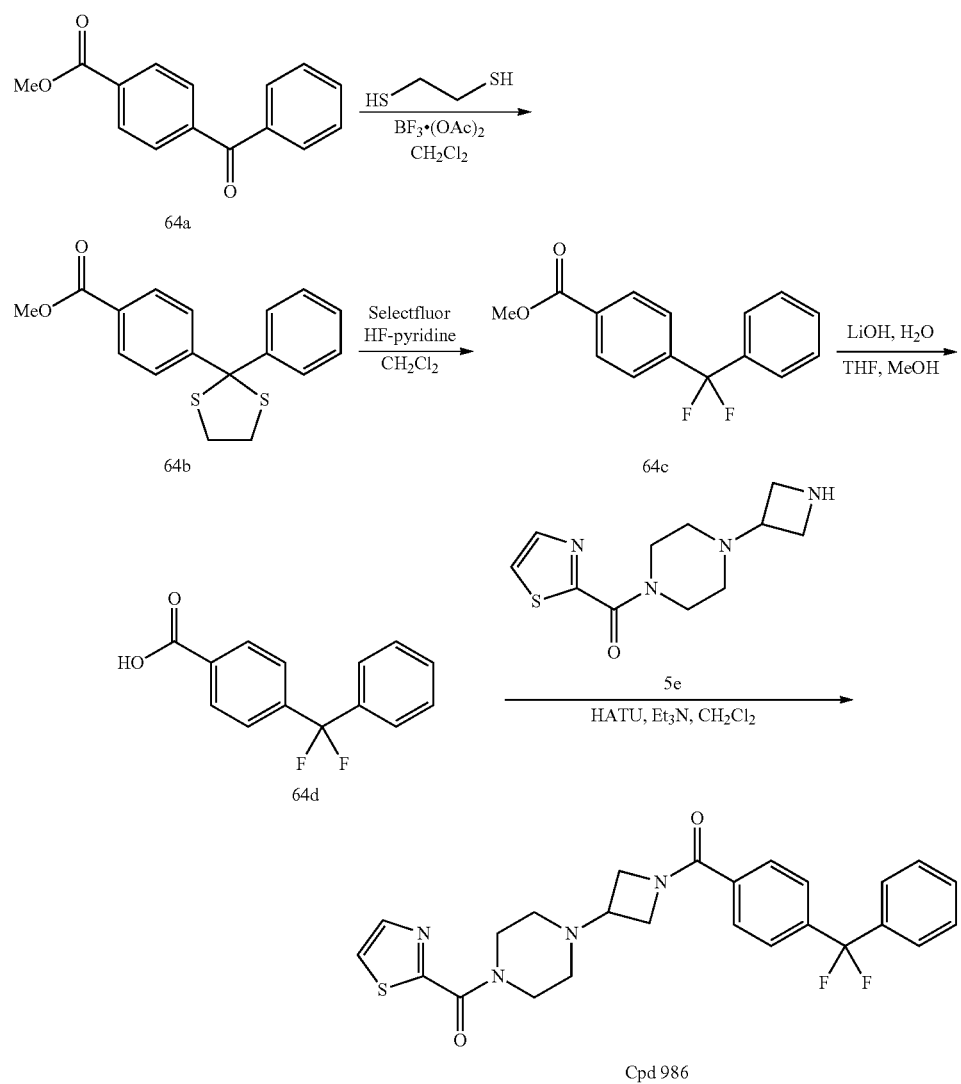

A. Methyl 4-(2-phenyl-1,3-dithiolan-2-yl)benzoate, 64b. Methyl 4-benzoylbenzoate 64a (2.08 mmol, 0.50 g) and $BF_3 \cdot (OAc)_2$ (5.2 mmol, 0.73 mL) were dissolved in dry $CH_2Cl_2$ under $N_2$. Ethane-1,2-dithiol (3.95 mmol, 0.333 mL) was added and the solution was stirred overnight. The reaction mixture was partitioned between $CH_2Cl_2$ and water. The organic layer was concentrated and purified by flash column chromatography (silica gel, 10% EtOAc/hexanes) to afford compound 64b.

B. Methyl 4-(difluoro(phenyl)methyl)benzoate, 64c. Selectfluor (1.07 mmol, 381 mg) and HF-pyridine reagent (1.5 mL, HF: Pyridine=70:30 wt %) were dissolved in CH$_2$Cl$_2$ (4 mL) in a polyethylene bottle and cooled to 0° C. A solution of 64b (0.512 mmol, 162 mg) in CH$_2$Cl$_2$ (2 mL) was slowly added and the mixture was stirred for 45 min at room temperature. When TLC indicated the consumption of all 64b, the reaction was diluted with CH$_2$Cl$_2$. The combined organics were dried over anhydrous Na$_2$SO$_4$ and concentrated. The crude product was purified by flash column chromatography (silica gel, 5% EtOAc/hexanes) to afford compound 64c as a clear oil.

C. 4-(Difluoro(phenyl)methyl)benzoic acid, 64d. The title compound 64d was prepared using the method described in Example 29, substituting 64c for 29c in Step B.

D. 1-[1-({4-[Difluoro(phenyl)methyl]phenyl}carbonyl) azetidin-3-yl]-4-(1,3-thiazol-2-ylcarbonyl)piperazine, Cpd 986. The title compound Cpd 986 was prepared using the method described in Example 9, substituting 64d for 9c in Step D. MS m/z (M+H$^+$) 483.

Example 65

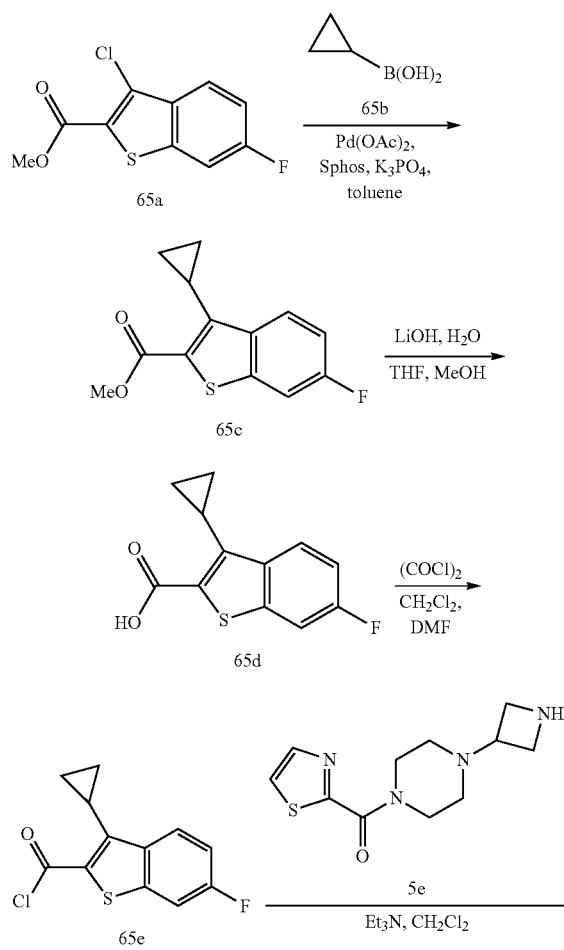

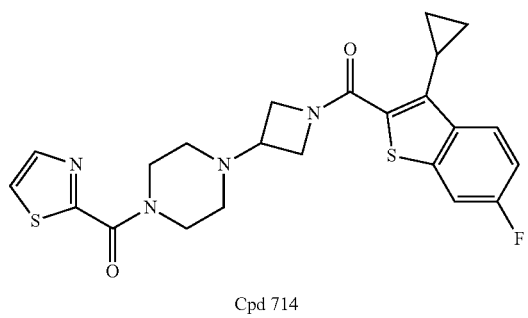

Cpd 714

A. Methyl 3-cyclopropyl-6-fluorobenzo[b]thiophene-2-carboxylate, 65c. A mixture of methyl 3-chloro-6-fluorobenzo[b]thiophene-2-carboxylate 65a (0.613 mmol, 150 mg), cyclopropylboronic acid 65b (0.92 mmol, 79 mg), Pd(OAc)$_2$ (0.09 mmol, 20 mg), SPhos (0.215 mmol, 88 mg), and K$_3$PO$_4$ (1.23 mmol, 0.26 g) in toluene (2 mL) was heated to 100° C. for 3 h in a sealed reaction vessel. The reaction was diluted with EtOAc and water. The organic layer was concentrated and purified by flash column chromatography (silica gel, 10% EtOAc/hexanes) to give compound 65c.

B. 3-Cyclopropyl-6-fluoro-benzo[b]thiophene-2-carboxylic acid, 65d. The title compound 65d was prepared using the method described in Example 29, substituting 65c for 29c in Step B.

C. 3-Cyclopropyl-6-fluoro-benzo[b]thiophene-2-carbonyl chloride, 65e. The title compound 65e was prepared using the method described in Example 10, substituting 65d for 10a in Step A.

D. 1-{1-[(3-Cyclopropyl-6-fluoro-1-benzothiophen-2-yl) carbonyl]azetidin-3-yl}-4-(1,3-thiazol-2-ylcarbonyl)piperazine, Cpd 714. The title compound Cpd 714 was prepared using the method described in Example 10, substituting 65e for 10b in Step B. MS m/z (M+H$^+$) 471.

Following the procedure described above for Example 65 and substituting the appropriate reagents, starting materials and purification methods known to those skilled in the art, the following intermediate compound was prepared:

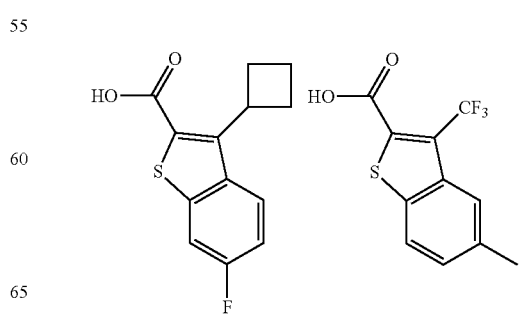

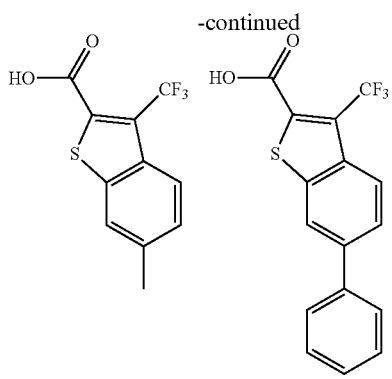

Following the procedure described above for Example 65 and substituting the appropriate reagents, starting materials and purification methods known to those skilled in the art, the following compounds of the present invention were prepared:

| Cpd | Cpd Name and Data |
|---|---|
| 695 | 1-{1-[(3-Cyclobutyl-6-fluoro-1-benzothiophen-2-yl)carbonyl]azetidin-3-yl}-4-(1,3-thiazol-2-ylcarbonyl)piperazine<br>MS m/z (M + H⁺) 485 |
| 528 | 1-{1-[(3-Cyclopropyl-6-fluoro-1-benzothiophen-2-yl)carbonyl]azetidin-3-yl}-4-(phenylcarbonyl)piperazine<br>MS m/z (M + H⁺) 464 |
| 513 | 1-{1-[(3-Cyclobutyl-6-fluoro-1-benzothiophen-2-yl)carbonyl]azetidin-3-yl}-4-(phenylcarbonyl)piperazine<br>MS m/z (M + H⁺) 478 |
| 1346 | 1-{1-[(3-Methyl-5-phenyl-1-benzothiophen-2-yl)carbonyl]azetidin-3-yl}-4-(1,3-thiazol-2-ylcarbonyl)piperazine<br>NMR (CDCl₃) δ: 7.96 (d, J = 1.2 Hz, 1H), 7.84-7.93 (m, 2H), 7.62-7.74 (m, 3H), 7.55 (d, J = 3.2 Hz, 1H), 7.49 (m, 2H), 7.34-7.44 (m, 1H), 4.12-4.47 (m, 6H), 3.87 (m, 2H), 3.19-3.35 (m, 1H), 2.69 (s, 3H), 2.50 (m, 4H)<br>MS m/z (M + H⁺) 503 |
| 1058 | 1-{1-[(3-Methyl-5-phenyl-1-benzothiophen-2-yl)carbonyl]azetidin-3-yl}-4-(1,3-thiazol-4-ylcarbonyl)piperazine; MS m/z (M + H+) 503 |
| 691 | 1-(1-{[5-Methyl-3-(trifluoromethyl)-1-benzothiophen-2-yl]carbonyl}azetidin-3-yl)-4-(1,3-thiazol-2-ylcarbonyl)piperazine; MS m/z (M + H+) 495 |
| 737 | 1-(1-{[5-Methyl-3-(trifluoromethyl)-1-benzothiophen-2-yl]carbonyl}azetidin-3-yl)-4-(1,3-thiazol-4-ylcarbonyl)piperazine; MS m/z (M + H+) 495 |
| 707 | 1-(1-{[6-Methyl-3-(trifluoromethyl)-1-benzothiophen-2-yl]carbonyl}azetidin-3-yl)-4-(1,3-thiazol-2-ylcarbonyl)piperazine; MS m/z (M + H+) 495 |
| 712 | 1-(1-{[6-Methyl-3-(trifluoromethyl)-1-benzothiophen-2-yl]carbonyl}azetidin-3-yl)-4-(1,3-thiazol-4-ylcarbonyl)piperazine; MS m/z (M + H+) 495 |
| 1098 | 1-(1-{[6-Phenyl-3-(trifluoromethyl)-1-benzothiophen-2-yl]carbonyl}azetidin-3-yl)-4-(1,3-thiazol-4-ylcarbonyl)piperazine; MS m/z (M + H+) 557 |
| 1095 | 1-(1-{[6-Phenyl-3-(trifluoromethyl)-1-benzothiophen-2-yl]carbonyl}azetidin-3-yl)-4-(1,3-thiazol-2-ylcarbonyl)piperazine; MS m/z (M + H+) 557 |
| 570 | 1-{1-[(3-Methyl-5-phenyl-1-benzothiophen-2-yl)carbonyl]azetidin-3-yl}-4-(phenylcarbonyl)piperazine; MS m/z (M + H+) 496 |
| 510 | 1-(1-{[6-Methyl-3-(trifluoromethyl)-1-benzothiophen-2-yl]carbonyl}azetidin-3-yl)-4-(phenylcarbonyl)piperazine; MS m/z (M + H+) 488 |

Example 66

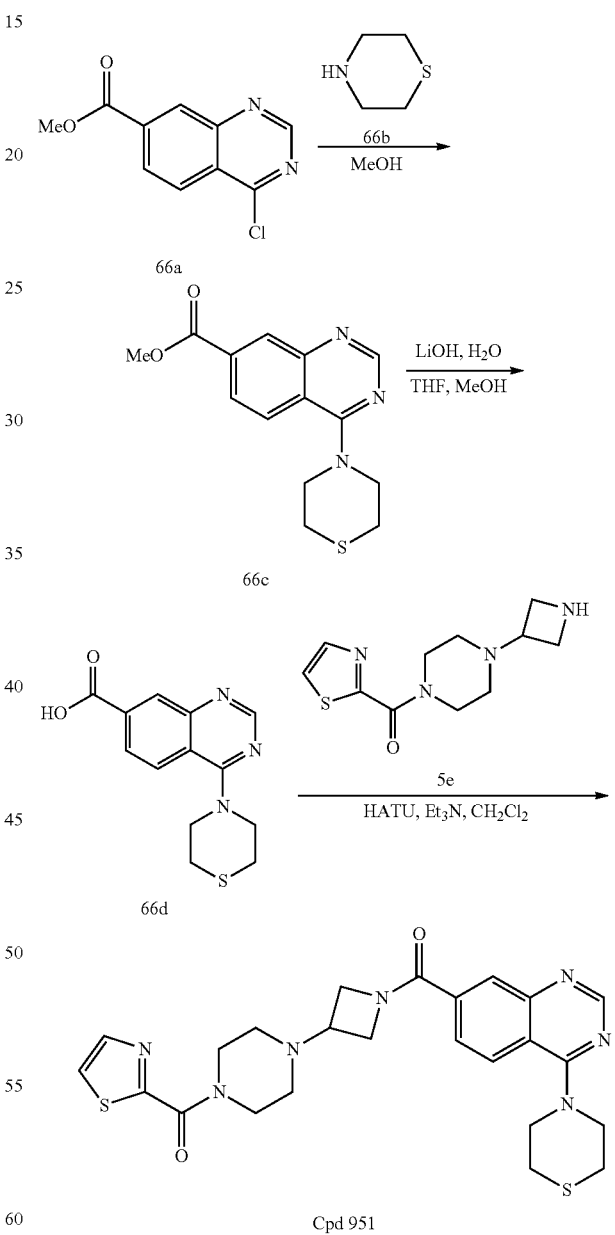

A. Methyl 4-thiomorpholinoquinazoline-7-carboxylate, 66c. A solution of methyl 4-chloroquinazoline-7-carboxylate 66a (1.01 mmol, 225 mg) and thiomorpholine 66b (2.02 mmol, 208 mg) in MeOH (1.6 mL) was refluxed overnight. Compound 66c (30 mg) was isolated after purification.

B. 4-Thiomorpholinoquinazoline-7-carboxylic acid, 66d. The title compound 66d was prepared using the method described in Example 29, substituting 66c for 29c in Step B.

C. 7-({3-[4-(1,3-Thiazol-2-ylcarbonyl)piperazin-1-yl]azetidin-1-yl}carbonyl)-4-thiomorpholin-4-ylquinazoline, Cpd 951. The title compound Cpd 951 was prepared using the method described in Example 9, substituting 66d for 9c in Step D. MS m/z (M+H$^+$) 510.

Example 67

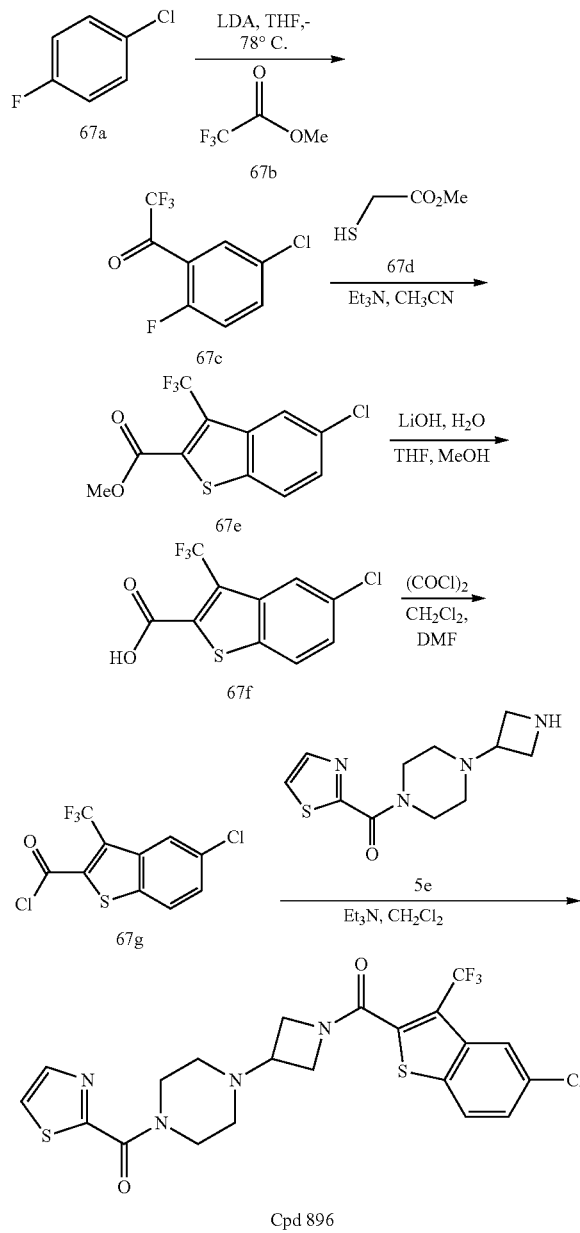

A. 1-(5-Chloro-2-fluoro-phenyl)-2,2,2-trifluoro-ethanone, 67c. To a solution of LDA (2.0 M in THF/heptane/ethylbenzene, 25.3 mmol, 12.6 mL) in dry THF was slowly added 1-fluoro-4-chloro-benzene 67a (23.0 mmol, 2.45 mL) at −78° C. The mixture was stirred for 1 h at −78° C. and ethyl trifluoroacetate 67b (25.3 mmol, 3.02 mL) was added. The reaction mixture was allowed to warm to room temperature overnight and was quenched with saturated aqueous NH$_4$Cl solution. The mixture was extracted with EtOAc. The organic extracts were concentrated and purified by flash column chromatography (silica gel, 15% EtOAc/hexanes) to give a mixture of the compound 67c along with a regio-isomeric by-product, 1-(5-fluoro-2-chloro-phenyl)-2,2,2-trifluoro-ethanone, in a ratio of 5:1 (67c is the major product).

B. Methyl 5-chloro-3-(trifluoromethyl)benzo[b]thiophene-2-carboxylate, 67e. A solution of compound 67c (6.62 mmol, 1.5 g), methyl 2-mercaptoacetate 67d (6.62 mmol, 0.6 mL), and Et$_3$N (8.6 mmol, 1.2 mL) in acetonitrile (12 mL) was heated at 75° C. for 4 h. The reaction was diluted with EtOAc and water. The organic layer was concentrated and purified by flash column chromatography (silica gel, 10% EtOAc/hexanes) to provide the compound 67e.

C. 5-Chloro-3-trifluoromethyl-benzo[b]thiophene-2-carboxylic acid, 67f. The title compound 67f was prepared using the method described in Example 29, substituting 67e for 29c in Step B.

D. 5-Chloro-3-trifluoromethyl-benzo[b]thiophene-2-carbonyl chloride, 67g. The title compound 65e was prepared using the method described in Example 10, substituting 67f for 10a in Step A.

E. 1-(1-{[5-Chloro-3-(trifluoromethyl)-1-benzothiophen-2-yl]carbonyl}azetidin-3-yl)-4-(1,3-thiazol-2-ylcarbonyl)piperazine. The title compound Cpd 896 was prepared using the method described in Example 10, substituting 67g for 10b in Step B. MS m/z (M+H$^+$) 515.

Following the procedure described above for Example 67 and substituting the appropriate reagents, starting materials and purification methods known to those skilled in the art, the following compounds of the present invention were prepared:

| Cpd | Cpd Name and Data |
|-----|-------------------|
| 673 | 1-(1-{[5-Chloro-3-(trifluoromethyl)-1-benzothiophen-2-yl]carbonyl}azetidin-3-yl)-4-(1,3-thiazol-4-ylcarbonyl)piperazine<br>MS m/z (M + H$^+$) 515 |
| 506 | 1-(1-{[5-Chloro-3-(trifluoromethyl)-1-benzothiophen-2-yl]carbonyl}azetidin-3-yl)-4-(phenylcarbonyl)piperazine<br>MS m/z (M + H$^+$) 508 |

Example 67a

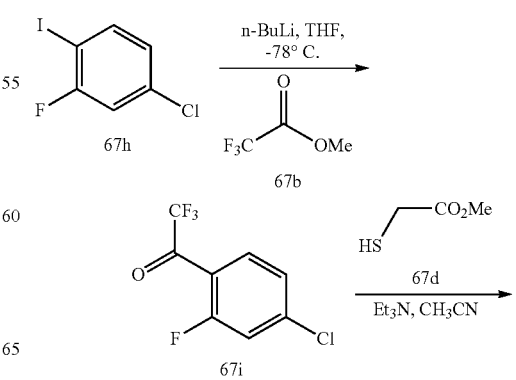

-continued

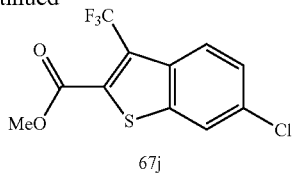

67j

F. 1-(4-Chloro-2-fluoro-phenyl)-2,2,2-trifluoro-ethanone, 67i. To a solution of n-BuLi (1.6 M in hexanes, 4.68 mmol, 2.93 mL) in dry THF was slowly added 4-chloro-2-fluoro-1-iodo-benzene 67h (3.9 mmol, 1.0 g) at −78° C. under $N_2$. The mixture was stirred for 1 h at −78° C. and ethyl trifluoroacetate 67b (0.51 mL, 4.29 mmol) was added. The reaction was allowed to warm to room temperature overnight and was quenched with saturated aqueous $NH_4Cl$ solution. The mixture was extracted with EtOAc. The organic extracts were concentrated and purified by flash column chromatography (silica gel, 15% EtOAc/hexanes) to give compound 67i.

G. Methyl 6-chloro-3-(trifluoromethyl)benzo[b]thiophene-2-carboxylate, 67j. The title compound 67j was prepared using a similar method described in Example 67, substituting 67i for 67c in Step B.

Following the procedure described above for Example 67, Steps C-E, and substituting the appropriate reagents, starting materials and purification methods known to those skilled in the art, the following compounds of the present invention were prepared:

| Cpd | Cpd Name and Data |
|---|---|
| 664 | 1-(1-{[6-Chloro-3-(trifluoromethyl)-1-benzothiophen-2-yl]carbonyl}azetidin-3-yl)-4-(1,3-thiazol-2-ylcarbonyl)piperazine<br>MS m/z (M + H⁺) 515 |
| 699 | 1-(1-{[6-Chloro-3-(trifluoromethyl)-1-benzothiophen-2-yl]carbonyl}azetidin-3-yl)-4-(1,3-thiazol-4-ylcarbonyl)piperazine<br>MS m/z (M + H⁺) 515 |
| 512 | 1-(1-{[6-Chloro-3-(trifluoromethyl)-1-benzothiophen-2-yl]carbonyl}azetidin-3-yl)-4-(phenylcarbonyl)piperazine<br>MS m/z (M + H⁺) 508 |

Example 67b

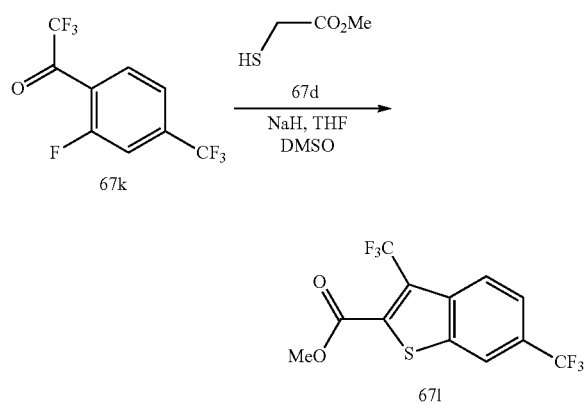 [SMILES: O=C(c1ccc(C(F)(F)F)cc1F)C(F)(F)F ; COC(=O)CS ; COC(=O)c1sc2cc(C(F)(F)F)ccc2c1C(F)(F)F]

H. Methyl 6-chloro-3-(trifluoromethyl)benzo[b]thiophene-2-carboxylate, 67l. The title compound 67l was prepared using a similar method described in Example 67, substituting 67k for 67c, substituting NaH for $Et_3N$, and substituting THF and DMSO for $CH_3CN$ in Step B.

Following the procedure described above for Example 67, Steps C-E, and substituting the appropriate reagents, starting materials and purification methods known to those skilled in the art, the following compounds of the present invention were prepared:

| Cpd | Cpd Name and Data |
|---|---|
| 692 | 1-(Isothiazol-5-ylcarbonyl)-4-(1-{[3-methyl-6-(trifluoromethyl)-1-benzothiophen-2-yl]carbonyl}azetidin-3-yl)piperazine<br>¹H NMR (CDCl₃): δ 8.41 (ar, 1H); 8.22 (ar, 1H); 7.98 (m, 1H); 7.65 (m, 1H); 7.48, (m, 1H); 3.83 (bm, 5H); 3.01 (bm, 4H); 2.5 (s, 3H)<br>MS m/z (M + H⁺) 477.0 |
| 505 | 1-(1-{[3-Methyl-6-(trifluoromethyl)-1-benzothiophen-2-yl]carbonyl}azetidin-3-yl)-4-(phenylcarbonyl)piperazine<br>MS m/z (M + H⁺) 488 |
| 899 | 1-(1-{[3-Methyl-6-(trifluoromethyl)-1-benzothiophen-2-yl]carbonyl}azetidin-3-yl)-4-(1,3-thiazol-2-ylcarbonyl)piperazine<br>¹H NMR (CDCl₃, 400 MHz): δ 8.11 (s, 1 H), 7.83-7.95 (m, 2 H), 7.65 (d, J = 8.6 Hz, 1 H), 7.55 (d, J = 3.1 Hz, 1 H), 3.99-4.67 (m, 6 H), 3.87 (br. s., 2 H), 3.16-3.41 (m, 1 H), 2.66 (s, 3 H), 2.50 (br. s., 4 H).<br>MS m/z (M + H⁺) 495 |
| 674 | 1-(1-{[3-Methyl-6-(trifluoromethyl)-1-benzothiophen-2-yl]carbonyl}azetidin-3-yl)-4-(1,3-thiazol-4-ylcarbonyl)piperazine<br>¹H NMR (CDCl₃, 400 MHz): δ 8.79 (s, 1 H), 8.10 (s, 1 H), 8.03 (s, 1 H), 7.89 (d, J = 8 Hz, 1 H), 7.65 (d, J = 8 Hz, 1 H), 3.80-4.40 (m, 8 H), 3.28 (m, 1 H), 2.66 (s, 3 H), 2.49 (br. s., 4 H).<br>MS m/z (M + H⁺) 495 |
| 657 | 1-(1-{[3-Methyl-6-(trifluoromethyl)-1-benzothiophen-2-yl]carbonyl}azetidin-3-yl)-4-(1H-pyrrol-2-ylcarbonyl)piperazine<br>¹H NMR (400 MHz, CDCl₃): δ 8.33 (d, 1H); 8.09 (d, 1H); 7.72 (d, 1H); 6.95 (s, 1H); 6.67 (s, 1H); 6.23 (dd, 1H); 4.59 (bm, 3H); 4.26 (m, 1H); 3.40 (m, 3H); 2.68 (s, 3H)<br>MS m/z (M + H⁺) 477.1 |

Example 68

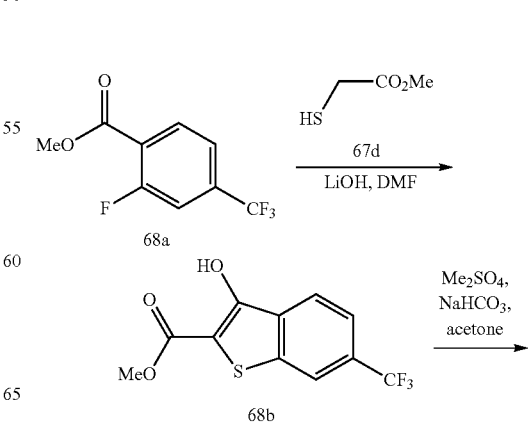

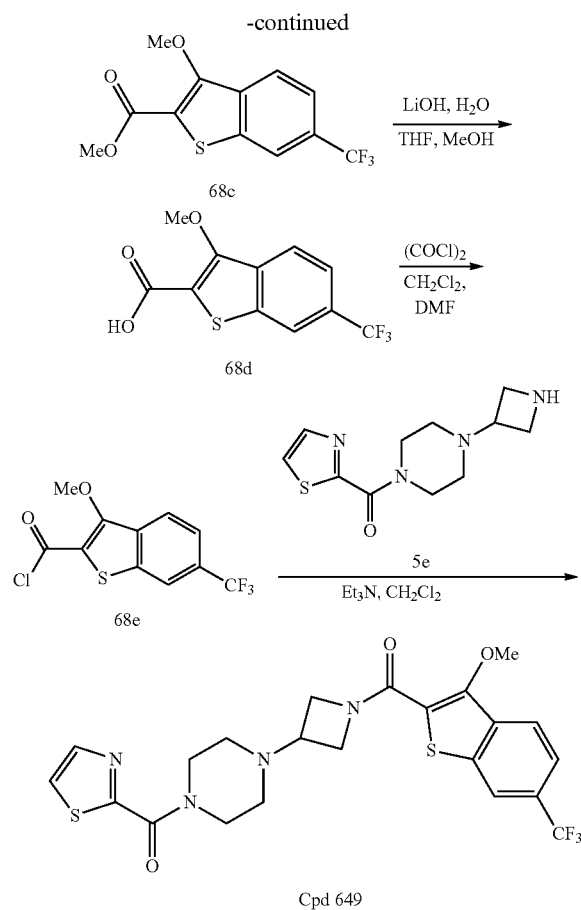

was prepared using the method described in Example 10, substituting 68e for 10b in Step B. $^1$H NMR (CDCl$_3$): δ 8.05 (s, 1H), 7.83-7.96 (m, 2H), 7.62 (dd, J=8.4, 1.1 Hz, 1H), 7.55 (d, J=3.2 Hz, 1H), 4.55-4.45 (m, 2H), 4.24-4.37 (m, 2H), 4.11-4.24 (m, 2H), 4.07 (s, 3H), 3.88 (m, 2H), 3.29 (m, 1H), 2.50 (m, 4H). MS m/z (M+H$^+$) 511.

Following the procedure described above for Example 68 and substituting the appropriate reagents, starting materials and purification methods known to those skilled in the art, the following compounds of the present invention were prepared:

| Cpd | Cpd Name and Data |
|---|---|
| 700 | 1-(1-{[3-Methoxy-6-(trifluoromethyl)-1-benzothiophen-2-yl]carbonyl}azetidin-3-yl)-4-(1,3-thiazol-4-ylcarbonyl)piperazine<br>MS m/z (M + H$^+$) 511 |

Example 68a

Following the procedure described above for Example 2 and substituting the appropriate reagents, starting materials and purification methods known to those skilled in the art, the following compounds of the present invention were prepared:

| Cpd | Cpd Name and Data |
|---|---|
| 705 | 1-{[3-Methyl-6-(trifluoromethyl)-1-benzothiophen-2-yl]carbonyl}-4-[1-(1,3-thiazol-4-ylcarbonyl)azetidin-3-yl]piperazine<br>MS m/z (M + H$^+$) 495.1 |
| 704 | 1-{[3-Methyl-6-(trifluoromethyl)-1-benzothiophen-2-yl]carbonyl}-4-[1-(1,3-thiazol-2-ylcarbonyl)azetidin-3-yl]piperazine<br>MS m/z (M + H$^+$) 495.1 |

A. Methyl 3-Hydroxy-6-trifluoromethylbenzo[b]thiophene-2-carboxylate, 68b. LiOH (4.5 mmol, 0.11 g) was added to a solution of methyl 2-fluoro-4-trifluoromethylbenzoate 68a (2.25 mmol, 0.50 g) and methyl 2-mercaptoacetate 67d (2.25 mmol, 0.21 mL) in DMF (3 mL) at 0° C. The mixture was stirred at 0° C. for 30 min and then warmed to room temperature and stirred for 1 h. Water was added and the resulting solution was acidified with 1N aqueous HCl. The precipitates were filtered, washed with water, and dried to give compound 68b.

B. Methyl 3-methoxy-6-trifluoromethylbenzo[b]thiophene-2-carboxylate, 68c. A mixture of compound 68b (0.543 mmol, 150 mg), dimethyl sulfate (0.608 mmol, 0.058 mL), and sodium bicarbonate (0.57 mmol, 48 mg) in acetone was heated at reflux overnight. The reaction mixture was cooled and filtered. The filtrate was concentrated and the residue was partitioned between EtOAc and water. The organic solution was concentrated and purified by flash column chromatography (silica gel, 10% EtOAc/hexanes) to give compound 68c.

C. 3-Methoxy-6-trifluoromethylbenzo[b]thiophene-2-carboxylic acid, 68d. The title compound 68d was prepared using the method described in Example 29, substituting 68c for 29c in Step B.

D. 3-Methoxy-6-trifluoromethylbenzo[b]thiophene-2-carbonyl chloride, 68e. The title compound 68e was prepared using the method described in Example 10, substituting 68d for 10a in Step A.

E. 1-(1-{[3-Methoxy-6-(trifluoromethyl)-1-benzothiophen-2-yl]carbonyl}azetidin-3-yl)-4-(1,3-thiazol-2-ylcarbonyl)piperazine, Cpd 649. The title compound Cpd 649

Example 69

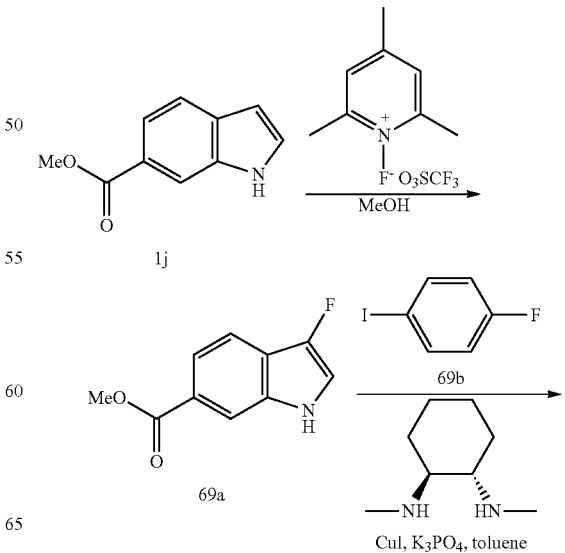

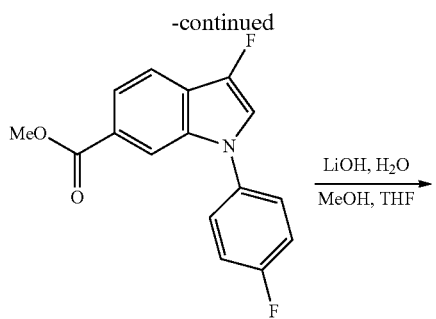

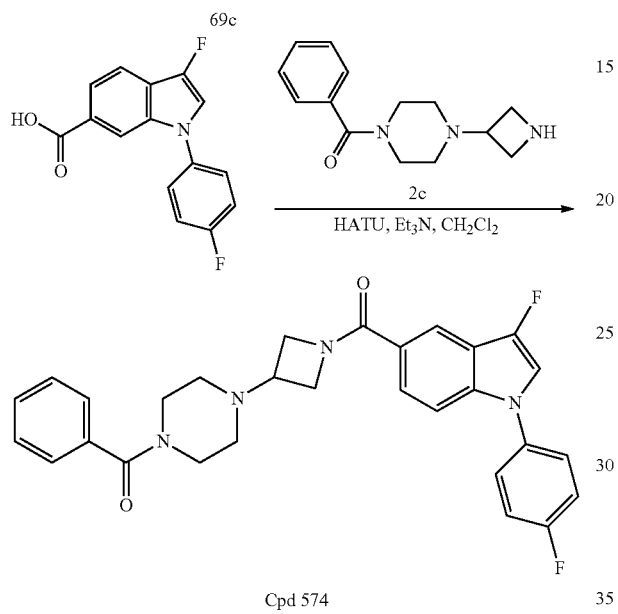

Cpd 574

A. Methyl 3-fluoro-1H-indole-6-carboxylate, 69a. A solution of methyl 1H-indole-6-carboxylate 1j (11.4 mmol, 2.0 g) and N-fluoro-2,4,6-trimethylpyridinium triflate (14.8 mmol, 4.3 g) in MeOH (100 mL) was heated at reflux for 18 h. The reaction mixture was concentrated and purified by flash column chromatography (silica gel, 15-20% EtOAc/hexanes) to give compound 69a as an off-white solid.

B. Methyl 3-fluoro-1-(4-fluorophenyl)-1H-indole-6-carboxylate, 69c. Compound 69a (0.264 mmol, 51 mg), CuI (0.0264 mmol, 5 mg) and $K_3PO_4$ (0.66 mmol, 40 mg) were combined in a sealed reaction tube and the vial was back-flushed with $N_2$. 4-fluoro-iodobenzene 69b (0.264 mmol, 0.0394 mL) and N,N'-dimethylcyclohexane-1,2-diamine (0.0792 mmol, 0.0125 mL) were added via sringe, followed by toluene. The reaction mixture was heated at 95° C. for 6 h. The reaction was diluted with EtOAc and water. The reaction mixture was concentrated and purified by flash column chromatography (silica gel, 20% EtOAc/hexanes) to give compound 69c.

C. 3-Fluoro-1-(4-fluorophenyl)-1H-indole-6-carboxylic acid, 69d. The title compound 69d was prepared using the method described in Example 29, substituting 69c for 29c in Step B.

D. 3-Fluoro-1-(4-fluorophenyl)-5-({3-[4-(phenylcarbonyl)piperazin-1-yl]azetidin-1-yl}carbonyl)-1H-indole, Cpd 574. The title compound Cpd 574 was prepared using the method described in Example 9, substituting 69d for 9c and substituting 2c for 5e in Step D. MS m/z (M+H⁺) 501.

Following the procedure described above for Example 69, and substituting the appropriate reagents, starting materials, and purification methods known to those skilled in the art, the following compounds of the present invention were prepared:

| Cpd | Cpd Name and Data |
|---|---|
| 589 | 3-Fluoro-1-phenyl-5-({3-[4-(phenylcarbonyl)piperazin-1-yl]azetidin-1-yl}carbonyl)-1H-indole<br>MS m/z (M + H⁺) 490 |

Example 70

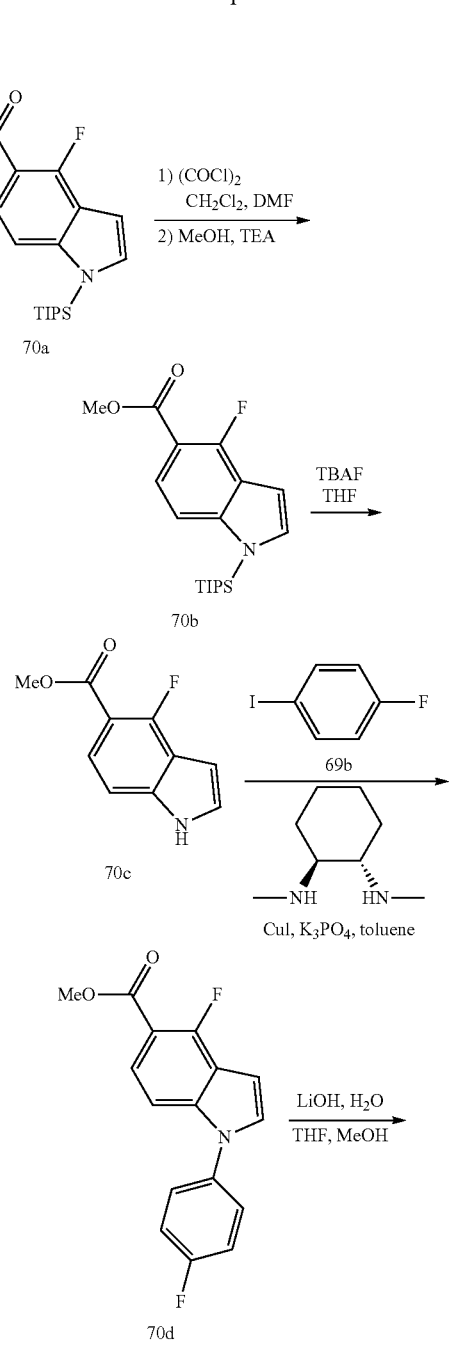

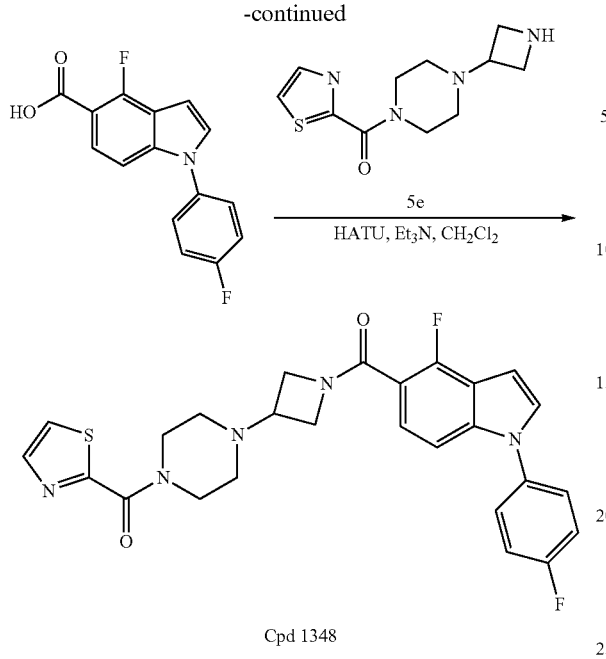
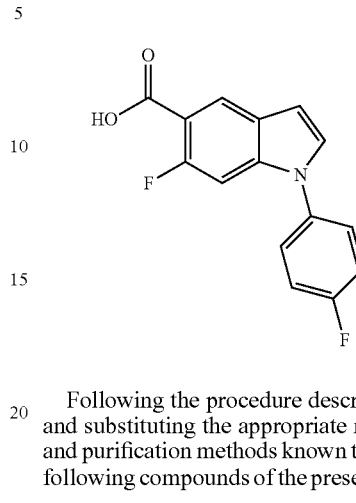

Cpd 1348

A. Methyl 4-fluoro-1-triisopropylsilanyl-1H-indole-5-carboxylate, 70b. To a solution of 4-fluoro-1-triisopropylsilanyl-1H-indole-5-carboxylic acid 70a (prepared using a procedure described in *Eur. J. Org. Chem.* 2006, 2956) (8.08 mmol, 2.71 g) in dry $CH_2Cl_2$ (20 mL) was added oxalyl chloride (9.69 mmol, 0.82 mL) followed by DMF (0.81 mmol, 0.063 mL). The reaction was stirred at rt for 30 min and then concentrated. The residue was dissolved in $CH_2Cl_2$ (20 mL) and cooled to 0° C. $Et_3N$ (40.4 mmol, 5.6 mL) was added, followed by slow addition of MeOH. The reaction mixture was stirred at 0° C. for 30 min and concentrated. The residue was partitioned between EtOAc and water. The organic layer was concentrated and purified by flash column chromatography (silica gel, 5% EtOAc/hexanes) to give compound 70b.

B. Methyl 4-fluoro-1H-indole-5-carboxylate, 70c. TBAF (1M solution in THF, 15.8 mmol, 15.8 mL) was added to a solution of compound 70b (7.9 mmol, 2.76 g) in THF at 0° C. After 10 min at room temperature, the reaction was diluted with EtOAc and washed with brine, saturated $NaHCO_3$, and water. The organic layer was concentrated and purified by flash column chromatography (silica gel, 35% EtOAc/hexanes) to afford compound 70c.

C. Methyl 4-fluoro-1-(4-fluorophenyl)-1H-indole-5-carboxylate, 70d. The title compound 70d was prepared using the method described in Example 69, substituting 70c for 69a in Step B.

D. 4-Fluoro-1-(4-fluoro-phenyl)-1H-indole-5-carboxylic acid, 70e. The title compound 70e was prepared using the method described in Example 29, substituting 70d for 29c in Step B.

E. 4-Fluoro-1-(4-fluorophenyl)-5-({3-[4-(1,3-thiazol-2-ylcarbonyl)piperazin-1-yl]azetidin-1-yl}carbonyl)-1H-indole, Cpd 1348. The title compound Cpd 1348 was prepared using the method described in Example 9, substituting 70e for 9c in Step D. $^1$H NMR ($CDCl_3$): δ 7.87 (d, J=3.2 Hz, 1H), 7.54 (d, J=3.2 Hz, 1H), 7.36-7.47 (m, 3H), 7.30 (d, J=3.2 Hz, 1H), 7.19-7.27 (m, 3H), 6.81 (d, J=3.2 Hz, 1H), 4.52-4.43 (m, 2H), 4.28 (dd, J=9.9, 7.7 Hz, 1H), 4.16-4.24 (m, 1H), 4.05-4.16 (m, 2H), 3.75-3.95 (m, 2H), 3.27 (m, 1H), 2.38-2.58 (m, 4H). MS m/z (M+H$^+$) 508.

Following the procedure described above for Example 70, and substituting the appropriate reagents, starting materials, and purification methods known to those skilled in the art, the following intermediate compound was prepared:

Following the procedure described above for Example 70 and substituting the appropriate reagents, starting materials, and purification methods known to those skilled in the art, the following compounds of the present invention were prepared:

| Cpd | Cpd Name and Data |
|---|---|
| 1069 | 6-Fluoro-1-(4-fluorophenyl)-5-({3-[4-(1,3-thiazol-4-ylcarbonyl)piperazin-1-yl]azetidin-1-yl}carbonyl)-1H-indole<br>MS m/z (M + H$^+$) 508 |
| 1349 | 6-Fluoro-1-(4-fluorophenyl)-5-({3-[4-(1,3-thiazol-2-ylcarbonyl)piperazin-1-yl]azetidin-1-yl}carbonyl)-1H-indole<br>MS m/z (M + H$^+$) 508 |
| 631 | 6-Fluoro-1-(4-fluorophenyl)-5-({3-[4-(phenylcarbonyl)piperazin-1-yl]azetidin-1-yl}carbonyl)-1H-indole<br>MS m/z (M + H$^+$) 501 |
| 632 | 4-Fluoro-1-phenyl-5-({3-[4-(phenylcarbonyl)piperazin-1-yl]azetidin-1-yl}carbonyl)-1H-indole<br>MS m/z (M + H$^+$) 501 |

Example 70a

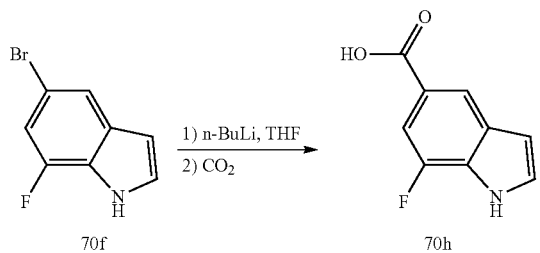 [SMILES: Fc1cc(Br)cc2cc[nH]c12 ; O=C(O)c1cc(F)c2[nH]ccc2c1]

F. 7-Fluoro-1H-indole-5-carboxylic acid, 70h. To a solution of 5-bromo-7-fluoroindole 70f (1.71 mmol, 365 mg) in THF at −60° C. was added n-BuLi (1.6 M solution in hexanes, 5.2 mmol, 3.2 mL). The solution was kept at −60° C. for 4 h and was then poured onto an excess of freshly crushed dry ice. Water was added and the mixture was acidified to pH=4. The organic phase was concentrated and the residue was purified by flash column chromatography (silica gel, 35% EtOAc/hexanes) to give compound 70h.

Following the procedure described above for Example 70 and substituting the appropriate reagents, starting materials, and purification methods known to those skilled in the art, the following intermediate compound was prepared:

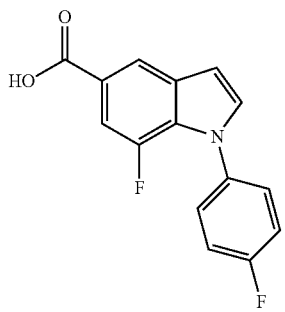 [SMILES: O=C(O)c1cc(F)c2c(ccn2-c2ccc(F)cc2)c1]

Following the procedure described above for Example 70 and substituting the appropriate reagents, starting materials, and purification methods known to those skilled in the art, the following compounds of the present invention were prepared:

| Cpd | Cpd Name and Data |
|---|---|
| 1350 | 7-Fluoro-1-(4-fluorophenyl)-5-({3-[4-(1,3-thiazol-2-ylcarbonyl)piperazin-1-yl]azetidin-1-yl}carbonyl)-1H-indole<br>$^1$H NMR (CDCl$_3$): δ 7.88 (d, J = 3.2 Hz, 1H), 7.76 (d, J = 1.2 Hz, 1H), 7.55 (d, J = 3.2 Hz, 1H), 7.42 (m, 2H), 7.22-7.31 (m, 2H), 7.12-7.22 (m, 2H), 6.69-6.81 (m, 1H), 4.53-4.27 (m, 5H), 4.12 (m, 1H), 3.89-3.83 (m, 2H), 3.26 (m, 1H), 2.50 (m, 4H)<br>MS m/z (M + H$^+$) 508 |
| 1111 | 7-Fluoro-1-(4-fluorophenyl)-5-({3-[4-(1,3-thiazol-4-ylcarbonyl)piperazin-1-yl]azetidin-1-yl}carbonyl)-1H-indole<br>MS m/z (M + H$^+$) 508 |

Example 70b

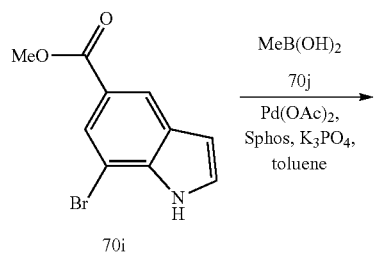

G. Methyl 7-methyl-1H-indole-5-carboxylate, 70k. The titled compound was prepared using the method described in Example 65, substituting 70i for 65a and substituting 70j for 65b in Step A.

Following the procedure described above for Example 70 and substituting the appropriate reagents, starting materials, and purification methods known to those skilled in the art, the following intermediate compound was prepared:

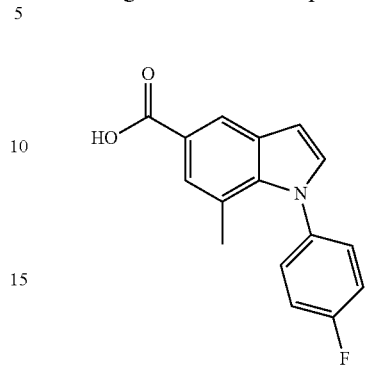

Following the procedure described above for Example 70 and substituting the appropriate reagents, starting materials, and purification methods known to those skilled in the art, the following compounds of the present invention were prepared:

| Cpd | Cpd Name and Data |
|---|---|
| 1355 | 1-(4-Fluorophenyl)-7-methyl-5-({3-[4-(1,3-thiazol-2-ylcarbonyl)piperazin-1-yl]azetidin-1-yl}carbonyl)-1H-indole<br>$^1$H NMR (CDCl$_3$): δ 7.88 (d, J = 2.4 Hz, 1H), 7.81 (s, 1H), 7.54 (d, J = 2.4 Hz, 1H), 7.36 (m, 2H), 7.28 (S, 1H), 7.10-7.21 (m, 3H), 6.67 (d, J = 2.4 Hz, 1H), 4.55-4.26 (m, 5H), 4.12 (m, 1H), 3.89 (m, 2H), 3.25 (m, 1H), 2.50 (m, 4H), 2.02 (s, 3H)<br>MS m/z (M + H$^+$) 504 |
| 1076 | 1-(4-Fluorophenyl)-7-methyl-5-({3-[4-(1,3-thiazol-4-ylcarbonyl)piperazin-1-yl]azetidin-1-yl}carbonyl)-1H-indole<br>MS m/z (M + H$^+$) 504 |

Example 70c

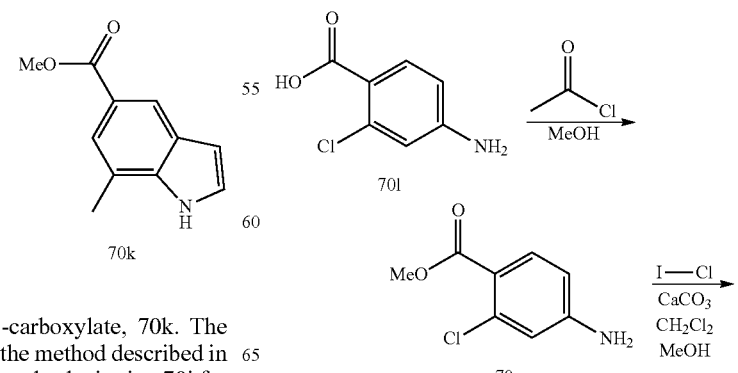

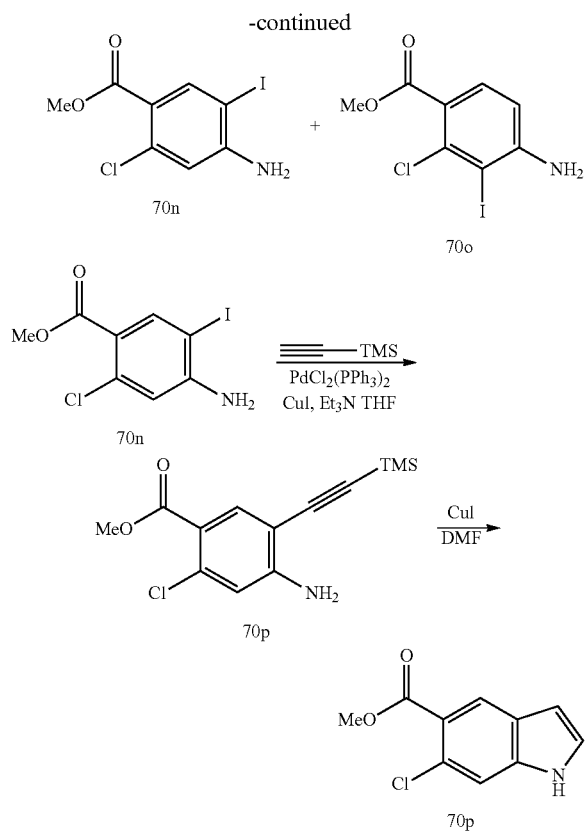

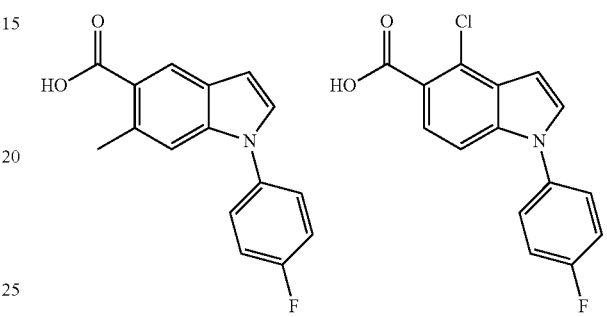

H. Methyl 4-amino-2-chloro-benzoate, 70m. Acetyl chloride (35.2 mmol, 2.5 mL) was added dropwise to a stirring solution of 4-amino-2-chloro-benzoic acid 70l (12.9 mmol, 2.22 g) in methanol (50 mL). The mixture was heated at reflux for 18 h, cooled, and concentrated under vacuum. The residue was taken up in EtOAc, washed with saturated aqueous NaHCO₃ and brine, dried, and concentrated under vacuum. The crude product was purified by flash column chromatography (silica gel, 30% EtOAc/hexanes) to give compound 70m.

I. Methyl 4-amino-2-chloro-5-iodo-benzoate, 70n. To a suspension of compound 70m (1.18 g, 6.38 mmol) and CaCO₃ (12.8 mmol, 1.28 g) in MeOH (13 mL) was added a solution of iodine monochloride (6.70 mmol, 1.09 g) in CH₂Cl₂ (6 mL) dropwise at room temperature. The resulting reaction mixture was stirred at room temperature for 1.5 h. The reaction mixture was concentrated and then partitioned between EtOAc and water. The organic layer was concentrated and purified by flash column chromatography (silica gel, 20-25% EtOAc/hexanes) to provide methyl 4-amino-2-chloro-5-iodo-benzoate 70n as major the product and methyl 4-amino-2-chloro-3-iodo-benzoate 70o as the minor product.

J. Methyl 4-amino-2-chloro-5-((trimethylsilyl)ethynyl)benzoate, 70p. To a mixture of compound 70n (0.642 mmol, 200 mg), CuI (0.064 mmol, 12.2 mg) and Pd(PPh₃)₂Cl₂ (0.064 mmol, 45 mg) in THF (2 mL) was added ethynyltrimethylsilane (0.963 mmol, 95 mg) followed by Et₃N (7.19 mmol, 1 mL) under N₂. The reaction mixture was stirred at room temperature for 1.5 h and then partitioned between EtOAc and water. The organic layer was concentrated and purified by flash column chromatography (silica gel, 15% EtOAc/hexanes) to give compound 70p.

K. Methyl 6-chloro-1H-indole-5-carboxylate, 70q. A mixture of compound 70p (0.532 mmol, 150 mg) and CuI (0.32 mmol, 60 mg) in DMF (1.5 mL) was heated at 110° C. for 5 h and them cooled to room temperature. The reaction was quenched with water and extracted with EtOAc. The organic layer was concentrated and purified by flash column chromatography (silica gel, 15% EtOAc/hexanes) to give compound 70q.

Following the procedure described above for Example 70c and Example 70 and substituting the appropriate reagents, starting materials, and purification methods known to those skilled in the art, the following intermediate compounds were prepared:

Following the procedure described above for Example 70 and substituting the appropriate reagents, starting materials, and purification methods known to those skilled in the art, the following compounds of the present invention were prepared:

| Cpd | Cpd Name and Data |
|---|---|
| 1416 | 6-Chloro-1-(4-fluorophenyl)-5-({3-[4-(1,3-thiazol-2-ylcarbonyl)piperazin-1-yl]azetidin-1-yl}carbonyl)-1H-indole<br>MS m/z (M + H⁺) 525 |
| 1415 | 1-(4-Fluorophenyl)-6-methyl-5-({3-[4-(1,3-thiazol-2-ylcarbonyl)piperazin-1-yl]azetidin-1-yl}carbonyl)-1H-indole<br>MS m/z (M + H⁺) 504 |
| 1414 | 4-Chloro-1-(4-fluorophenyl)-5-({3-[4-(1,3-thiazol-2-ylcarbonyl)piperazin-1-yl]azetidin-1-yl}carbonyl)-1H-indole<br>¹H NMR (CDCl₃): δ 7.87 (d, J = 3.2 Hz, 1H), 7.54 (d, J = 3.2 Hz, 1H), 7.40-7.46 (m, 2H), 7.34-7.39 (m, 2H), 7.19-7.29 (m, 3H), 6.83 (d, J = 3.2 Hz, 1H), 4.52 (m, 1H), 4.35-4.48 (m, 1H), 4.30 (dd, J = 9.9, 7.5 Hz, 1H), 4.08-4.18 (m, 1H), 3.75-4.05 (m, 4H), 3.23-3.33 (m, 1H), 2.37-2.57 (m, 4H)<br>MS m/z (M + H⁺) 525. |

Example 71

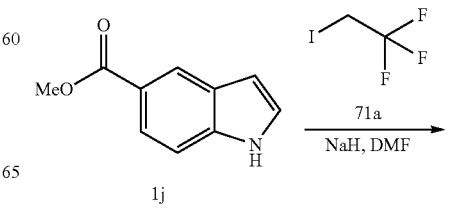

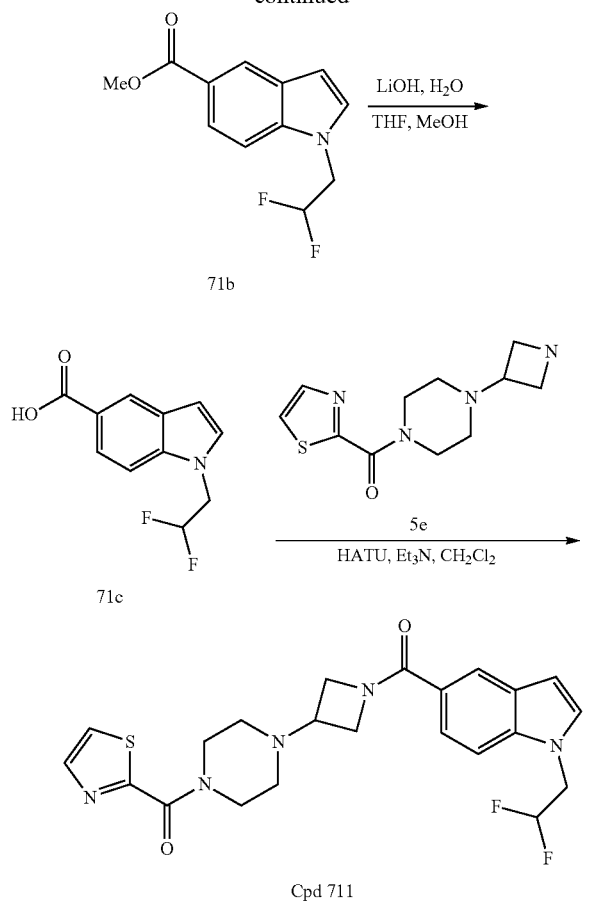

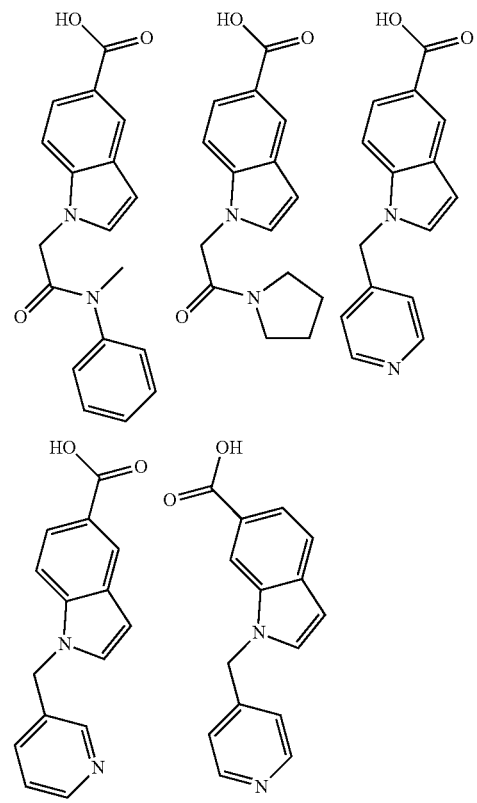

A. Methyl 1-(2,2-difluoroethyl)-1H-indole-5-carboxylate, 71b. To a suspension of NaH (60% dispersion in mineral oil, 1.48 mmol, 59 mg) in DMF (2 mL) was slowly added a solution of 1H-indole-5-carboxylic acid methyl ester 1j (1.14 mmol, 200 mg) in DMF (1 mL) at 0° C. The resulting solution was stirred at 0° C. for 20 min and 1,1-difluoro-2-iodoethane 71a (1.37 mmol, 263 mg) was added. The reaction was warmed to room temperature and stirred for 2 h. The reaction was quenched with water and extracted with EtOAc. The organic layer was concentrated and purified by flash column chromatography (silica gel, 20% EtOAc/hexanes) to afford compound 71b.

B. 1-(2,2-Difluoroethyl)-1H-indole-5-carboxylic acid, 71c. The title compound 71c was prepared using the method described in Example 29, substituting 71b for 29c in Step B.

C. 1-(2,2-Difluoroethyl)-5-({3-[4-(1,3-thiazol-2-ylcarbonyl)piperazin-1-yl]azetidin-1-yl}carbonyl)-1H-indole, Cpd 711. The title compound Cpd 711 was prepared using the method described in Example 9, substituting 71c for 9c in Step D. $^1$H NMR (CDCl$_3$): δ 7.94 (s, 1H), 7.88 (d, J=2.9 Hz, 1H), 7.59 (d, J=8.6 Hz, 1H), 7.54 (d, J=2.9 Hz, 1H), 7.36 (d, J=8.6 Hz, 1H), 7.17 (d, J=2.9 Hz, 1H), 6.63 (d, J=2.9 Hz, 1H), 6.01 (m, 1H), 4.51-4.24 (m, 7H), 4.12 (m, 1H), 3.85 (m, 2H), 3.24 (m, 1H), 2.49 (m, 4H). MS m/z (M+H$^+$) 460.

Following the procedure described above for Example 71, and substituting the appropriate reagents, starting materials, and purification methods known to those skilled in the art, the following intermediate compounds were prepared:

Following the procedure described above for Example 71, and substituting the appropriate reagents, starting materials, and purification methods known to those skilled in the art, the following compounds of the present invention were prepared:

| Cpd | Cpd Name and Data |
|---|---|
| 813 | 1-(2,2-Difluoroethyl)-5-({3-[4-(1,3-thiazol-4-ylcarbonyl)piperazin-1-yl]azetidin-1-yl}carbonyl)-1H-indole<br>MS m/z (M + H$^+$) 460 |
| 1031 | N-Methyl-N-phenyl-2-[5-({3-[4-(1,3-thiazol-2-ylcarbonyl)piperazin-1-yl]azetidin-1-yl}carbonyl)-1H-indol-1-yl]acetamide<br>MS m/z (M + H$^+$) 543 |
| 1032 | N-Methyl-N-phenyl-2-[5-({3-[4-(1,3-thiazol-4-ylcarbonyl)piperazin-1-yl]azetidin-1-yl}carbonyl)-1H-indol-1-yl]acetamide<br>MS m/z (M + H$^+$) 543 |
| 1035 | 1-(2-Oxo-2-pyrrolidin-1-ylethyl)-5-({3-[4-(1,3-thiazol-2-ylcarbonyl)piperazin-1-yl]azetidin-1-yl}carbonyl)-1H-indole<br>MS m/z (M + H$^+$) 507 |
| 1046 | 1-(Pyridin-4-ylmethyl)-5-({3-[4-(1,3-thiazol-2-ylcarbonyl)piperazin-1-yl]azetidin-1-yl}carbonyl)-1H-indole<br>MS m/z (M + H$^+$) 487 |
| 1047 | 1-(Pyridin-4-ylmethyl)-6-({3-[4-(1,3-thiazol-2-ylcarbonyl)piperazin-1-yl]azetidin-1-yl}carbonyl)-1H-indole<br>MS m/z (M + H$^+$) 487 |
| 1048 | 1-(Pyridin-3-ylmethyl)-5-({3-[4-(1,3-thiazol-2-ylcarbonyl)piperazin-1-yl]azetidin-1-yl}carbonyl)-1H-indole<br>MS m/z (M + H$^+$) 487 |

Example 72

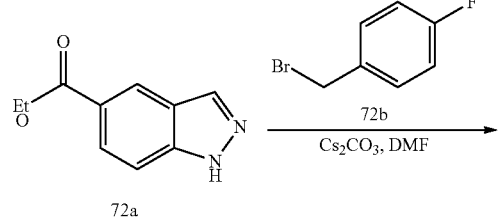

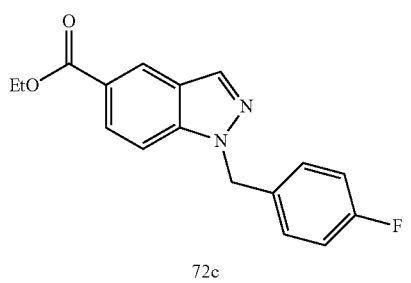

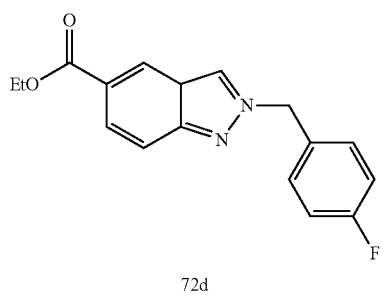

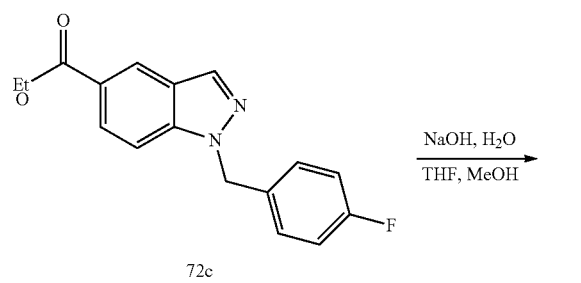

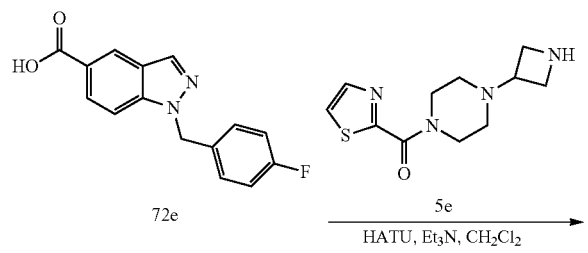

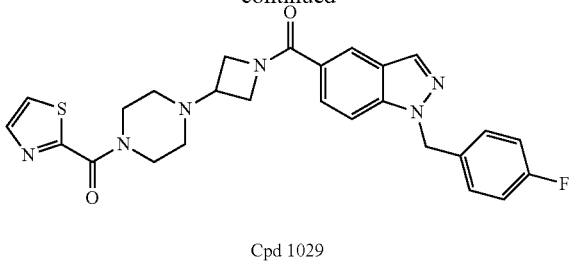

Cpd 1029

A. Ethyl 1-(4-fluorobenzyl)-1H-indazole-5-carboxylate, 72c, and ethyl 2-(4-fluorobenzyl)-2H-indazole-5-carboxylate, 72d. Ethyl 1H-indazole-5-carboxylate 72a (0.79 mmol, 150 mg) and $Cs_2CO_3$ (0.96 mmol, 312 mg) were combined in 2 mL of DMF, producing a clear, red-brown solution. Neat 1-(bromomethyl)-4-fluorobenzene 72b (0.87 mmol, 0.11 mL) was added dropwise and the mixture was stirred at room temperature overnight. EtOAc was added and the organic layer was washed with water and brine. The organic solution was dried over Na2SO4 and concentrated to give 260 mg of orange solid. The crude product was purified by flash column chromatography (silica gel, 15-50% EtOAc/heptanes) to give 133 mg (57%) of compound 72c as an orange solid and 67 mg (28%) of compound 72d as a white solid.

Compound 72c: $^1$H NMR (400 MHz, $CDCl_3$): δ 1.41 (t, J=7.1 Hz, 3H), 4.40 (q, J=7.1 Hz, 2H), 5.58 (s, 2H), 6.99 (t, J=8.7 Hz, 2H), 7.19 (dd, J=8.8, 5.3 Hz, 2H), 7.36 (dt, J=8.9, 0.8 Hz, 1H), 8.04 (dd, J=8.9, 1.5 Hz, 1H), 8.15 (d, J=0.9 Hz, 1H), 8.53 (dd, J=1.5, 0.8 Hz, 1H). MS m/z (M+H$^+$) 299.1.

Compound 72d: $^1$H NMR (400 MHz, $CDCl_3$): δ 1.41 (t, J=7.1 Hz, 3H), 4.39 (q, J=7.1 Hz, 2H), 5.59 (s, 2H), 7.07 (t, J=8.7 Hz, 2H), 7.27-7.34 (m, 2H), 7.72 (dt, J=9.1, 0.9 Hz, 1H), 7.92 (dd, J=9.1, 1.6 Hz, 1H), 8.02-8.06 (m, 1H), 8.48 (dd, J=1.5, 0.9 Hz, 1H). MS m/z (M+H$^+$) 299.1.

B. 1-(4-Fluorobenzyl)-1H-indazole-5-carboxylate, 72e. To a stirring solution of compound 72c (0.43 mmol, 128 mg) in 2.5 mL of THF and 0.5 mL of MeOH was added 3N aqueous NaOH (2.62 mmol, 0.87 mL) and 0.5 mL of water. After stirring at room temperature overnight, the mixture was concentrated under vacuum. The yellow residue was dissolved in 10 mL of water and acidified to pH 2-3 with aqueous HCl. The resulting precipitate was vacuum-filtered through a paper disc and washed with water. The remaining material was pumped at high vacuum to give 108 mg (93%) of compound 72e as a pale yellow solid. $^1$H NMR (400 MHz, $CDCl_3$): δ 1.41 (t, J=7.1 Hz, 3H), 4.39 (q, J=7.1 Hz, 2H), 5.59 (s, 2H), 7.07 (t, J=8.7 Hz, 2H), 7.27-7.34 (m, 2H), 7.72 (dt, J=9.1, 0.9 Hz, 1H), 7.92 (dd, J=9.1, 1.6 Hz, 1H), 8.02-8.06 (m, 1H), 8.48 (dd, J=1.5, 0.9 Hz, 1H). MS m/z (M+H$^+$) 271.2.

C. 1-(4-Fluorobenzyl)-5-({3-[4-(1,3-thiazol-2-ylcarbonyl)piperazin-1-yl]azetidin-1-yl}carbonyl)-1H-indazole, Cpd 1029. The title compound Cpd 1029 was prepared using the method described in Example 9, substituting 72e for 9c and substituting HBTU for HATU in Step D. $^1$H NMR (400 MHz, $CDCl_3$): δ 1.41 (t, J=7.1 Hz, 3H), 4.39 (q, J=7.1 Hz, 2H), 5.59 (s, 2H), 7.07 (t, J=8.7 Hz, 2H), 7.27-7.34 (m, 2H), 7.72 (dt, J=9.1, 0.9 Hz, 1H), 7.92 (dd, J=9.1, 1.6 Hz, 1H), 8.02-8.06 (m, 1H), 8.48 (dd, J=1.5, 0.9 Hz, 1H). MS m/z (M+H$^+$) 505.2.

Following the procedure described above for Example 72, and substituting the appropriate reagents, starting materials, and purification methods known to those skilled in the art, the following intermediate compounds were prepared:

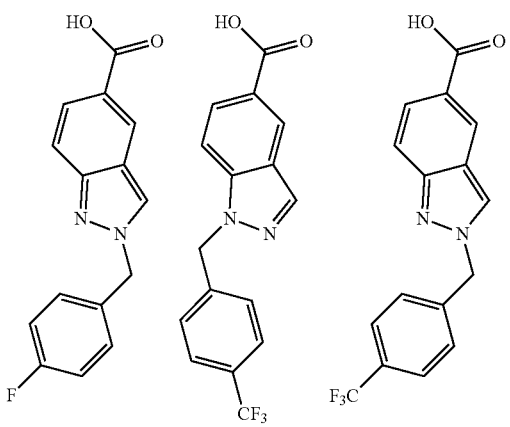
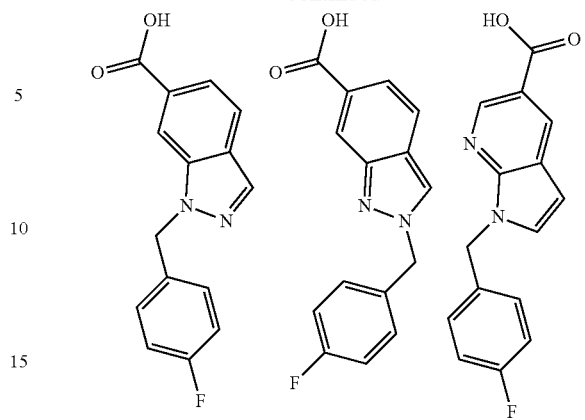
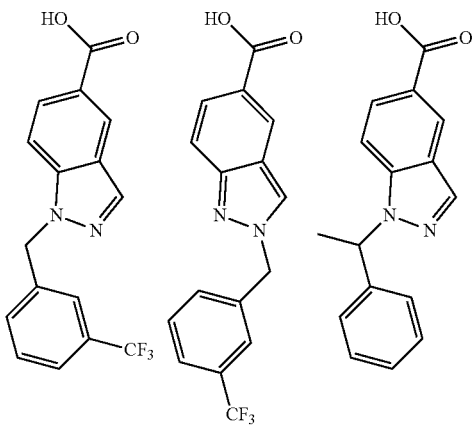

Following the procedure described above for Example 72, and substituting the appropriate reagents, starting materials, and purification methods known to those skilled in the art, the following compounds of the present invention were prepared:

| Cpd | Cpd Name and Data |
|---|---|
| 1030 | 2-(4-Fluorobenzyl)-5-({3-[4-(1,3-thiazol-2-ylcarbonyl)piperazin-1-yl]azetidin-1-yl}carbonyl)-2H-indazole<br>$^1$H NMR (400 MHz, CD$_3$OD): δ 3.19-3.30 (m, 4 H), 4.05 (d, J = 5.6 Hz, 3 H), 4.25-4.88 (m, 6 H), 5.66 (s, 2 H), 7.09 (t, J = 8.4 Hz, 2 H), 7.33-7.43 (m, 2 H), 7.57 (d, J = 9.0 Hz, 1 H), 7.69 (d, J = 9.0 Hz, 1 H), 7.88 (m, J = 2.9 Hz, 1 H), 7.97 (d, J = 2.7 Hz, 1 H), 8.12 (s, 1 H), 8.49 (s, 1 H)<br>MS m/z (M + H$^+$) 505.2 |
| 1036 | 5-({3-[4-(1,3-Thiazol-2-ylcarbonyl)piperazin-1-yl]azetidin-1-yl}carbonyl)-1-[4-(trifluoromethyl)benzyl]-1H-indazole<br>$^1$H NMR (400 MHz, CD$_3$OD): δ 3.24 (br. s., 4 H), 3.89-4.12 (m, 3 H), 4.25-4.85 (m, 6 H), 5.78 (s, 2 H), 7.37 (m, J = 8.1 Hz, 2 H), 7.60 (m, J = 8.1 Hz, 2 H), 7.66 (d, J = 8.8 Hz, 1 H), 7.72 (dd, J = 8.8, 1.5 Hz, 1 H), 7.88 (d, J = 3.0 Hz, 1 H), 7.97 (d, J = 3.3 Hz, 1 H), 8.18 (s, 1 H), 8.23 (s, 1 H)<br>MS m/z (M + H$^+$) 555.2 |
| 1037 | 5-({3-[4-(1,3-Thiazol-2-ylcarbonyl)piperazin-1-yl]azetidin-1-yl}carbonyl)-2-[4-(trifluoromethyl)benzyl]-2H-indazole<br>$^1$H NMR (400 MHz, CD$_3$OD): δ 3.18-3.41 (m, 4 H), 3.92-4.18 (m, 3 H), 4.27-4.86 (m, 6 H), 5.79 (s, 2 H), 7.47 (d, J = 8.1 Hz, 2 H), 7.58 (dd, J = 9.1, 1.5 Hz, 1 H), 7.66 (d, J = 8.1 Hz, 2 H), 7.70 (d, J = 1 H), 7.88 (d, J = 3.0 Hz, 1 H), 7.97 (d, J = 3.0 Hz, 1 H), 8.14 (s, 1 H), 8.56 (s, 1 H)<br>MS m/z (M + H$^+$) 555.2 |
| 1038 | 5-({3-[4-(1,3-Thiazol-2-ylcarbonyl)piperazin-1-yl]azetidin-1-yl}carbonyl)-1-[3-(trifluoromethyl)benzyl]-1H-indazole<br>$^1$H NMR (400 MHz, CD$_3$OD): δ 3.25 (br. s., 4 H), 3.89-4.13 (m, 3 H), 4.22-4.82 (m, 6 H), 5.78 (s, 2 H), 7.40-7.54 (m, 3 H), 7.58 (m, J = 7.3 Hz, 1 H), 7.69 (m, J = 8.6 Hz, 1 H), 7.73 (d, J = 8.8 Hz, 1 H), 7.88 (d, J = 3.3 Hz, 1 H), 7.97 (d, J = 3.3 Hz, 1 H), 8.18 (s, 1 H), 8.24 (s, 1 H)<br>MS m/z (M + H$^+$) 555.2 |
| 1039 | 5-({3-[4-(1,3-Thiazol-2-ylcarbonyl)piperazin-1-yl]azetidin-1-yl}carbonyl)-2-[3-(trifluoromethyl)benzyl]-2H-indazole<br>$^1$H NMR (400 MHz, CD$_3$OD): δ 3.30 (br. s., 4 H), 4.04 (d, J = 6.8 Hz, 3 H), 4.29-4.84 (m, 6 H), 5.78 (s, 2 H), 7.58 (t, J = 7.1 Hz, 3 H), 7.64 (br. s., 2 H), 7.70 (d, J = 9.1 Hz, 1 H), 7.88 (d, J = 3.0 Hz, 1 H), 7.97 (d, J = 3.0 Hz, 1 H), 8.14 (s, 1 H), 8.56 (s, 1 H)<br>MS m/z (M + H$^+$) 555.2 |

| Cpd | Cpd Name and Data |
|---|---|
| 1411 | 1-(1-Phenylethyl)-5-({3-[4-(1,3-thiazol-2-ylcarbonyl)piperazin-1-yl]azetidin-1-yl}carbonyl)-1H-indazole
$^1$H NMR (400 MHz, acetone-$d_6$): δ 2.01 (d, J = 7.1 Hz, 3 H), 3.35 (br. s., 4 H), 4.07 (br. s., 2 H), 4.11-4.19 (m, 1 H), 4.25-4.53 (m, 2 H), 6 4.60 (br. s., 1 H), 4.68-4.96 (m, 3 H), 6.07 (q, J = 7.1 Hz, 1 H), 7.24 (d, J = 7.1 Hz, 1 H), 7.30 (t, J = 7.3 Hz, 2 H), 7.33-7.39 (m, 2 H), 7.58-7.68 (m, 2 H), 7.92 (d, J = 3.3 Hz, 1 H), 7.98 (d, J = 3.0 Hz, 1 H), 8.12 (s, 1 H), 8.18 (s, 1 H)
MS m/z (M + H$^+$) 501.1 |
| 1040 | 2-(1-Phenylethyl)-5-({3-[4-(1,3-thiazol-2-ylcarbonyl)piperazin-1-yl]azetidin-1-yl}carbonyl)-2H-indazole
$^1$H NMR (400 MHz, CD$_3$OD): δ 2.04 (d, J = 7.1 Hz, 3 H), 3.20 (br. s., 4 H), 3.91-4.05 (m, 3 H), 4.25-4.63 (m, 4 H), 4.72 (br. s., 2 4 H), 5.94 (q, J = 6.9 Hz, 1 H), 7.25-7.39 (m, 5 H), 7.57 (dd, J = 9.0, 1.4 Hz, 1 H), 7.69 (d, J = 9.1 Hz, 1 H), 7.88 (d, J = 3.0 Hz, 1 H), 7.97 (d, J = 3.3 Hz, 1 H), 8.12 (s, 1 H), 8.51 (s, 1 H)
MS m/z (M + H$^+$) 501.3 |
| 1043 | 1-(4-Fluorobenzyl)-5-({3-[4-(1,3-thiazol-2-ylcarbonyl)piperazin-1-yl]azetidin-1-yl}carbonyl)-1H-pyrrolo[2,3-b]pyridine
$^1$H NMR (400 MHz, CDCl$_3$): δ 3.49 (br. s., 4 H), 4.12 (br. s., 2 H), 4.23-4.33 (m, 1 H), 4.34-5.17 (m, 6 H), 5.56 (s, 2 H), 6.61 (d, J = 3.5 Hz, 1 H), 7.08 (t, J = 8.7 Hz, 2 H), 7.38 (dd, J = 8.6, 5.6 Hz, 2 H), 7.63 (d, J = 3.5 Hz, 1 H), 7.93 (d, J = 3.3 Hz, 1 H), 7.99 (d, J = 3.3 Hz, 1 H), 8.27 (d, J = 1.8 Hz, 1 H), 8.61 (d, J = 1.8 Hz, 1 H)
MS m/z (M + H$^+$) 505.2 |
| 1049 | 1-[2-(4-Fluorophenyl)ethyl]-5-({3-[4-(1,3-thiazol-2-ylcarbonyl)piperazin-1-yl]azetidin-1-yl}carbonyl)-1H-indazole
$^1$H NMR (400 MHz, acetone-$d_6$): δ 3.24 (t, J = 7.2 Hz, 2 H), 3.40 (br. s., 4 H), 4.09 (br. s., 2 H), 4.16-4.23 (m, 1 H), 4.31-4.65 (m, 4 H), 6 4.69 (t, J = 7.2 Hz, 2 H), 4.85 (br. s., 2 H), 6.96 (t, J = 8.8 Hz, 2 H), 7.19 (dd, J = 8.3, 5.6 Hz, 2 H), 7.49 (d, J = 8.8 Hz, 1 H), 7.62 (dd, J = 8.8, 1.3 Hz, 1 H), 7.93 (d, J = 3.0 Hz, 1 H), 8.00 (d, J = 3.0 Hz, 1 H), 8.09 (s, 1 H), 8.12 (s, 1 H)
MS m/z (M + H$^+$) 519.2 |
| 1050 | 2-[2-(4-Fluorophenyl)ethyl]-5-({3-[4-(1,3-thiazol-2-ylcarbonyl)piperazin-1-yl]azetidin-1-yl}carbonyl)-2H-indazole
$^1$H NMR (400 MHz, acetone-$d_6$): δ 3.35 (t, J = 7.1 Hz, 2 H), 3.38-3.43 (m, 4 H), 4.09 (br. s., 2 H), 4.12-4.20 (m, 1 H), 4.31-4.69 (m, 4 6 H), 4.74 (t, J = 7 .2 Hz, 2 H), 4.84 (br. s., 2 H), 7.01 (t, J = 8.7 Hz, 2 H), 7.21 (dd, J = 8.3, 5.6 Hz, 2 H), 7.55 (dd, J = 9.1, 1.5 Hz, 1 H), 7.66 (d, J = 9.1 Hz, 1 H), 7.93 (d, J = 3.0 Hz, 1 H), 8.00 (d, J = 3.3 Hz, 1 H), 8.03 (s, 1 H), 8.23 (s, 1 H)
MS m/z (M + H$^+$) 519.2 |
| 1051 | 1-(4-Fluorobenzyl)-6-({3-[4-(1,3-thiazol-2-ylcarbonyl)piperazin-1-yl]azetidin-1-yl}carbony1)-1H-indazole
$^1$H NMR (400 MHz, acetone-$d_6$): δ 3.14-3.23 (m, 4 H), 3.91-4.00 (m, 1 H), 4.01-4.12 (m, 2 H), 4.26-4.56 (m, 3 H), 4.57-4.92 (m, 3 6 H), 5.74 (s, 2 H), 7.09 (t, J = 8.8 Hz, 2 H), 7.37-7.46 (m, 3 H), 7.84 (d, J = 8.3 Hz, 1 H), 7.89-7.95 (m, 2 H), 7.99 (d, J = 3.0 Hz, 1 H), 8.12 (s, 1 H)
MS m/z (M + H$^+$) 505.2 |
| 1052 | 2-(4-Fluorobenzyl)-6-({3-[4-(1,3-thiazol-2-ylcarbonyl)piperazin-1-yl]azetidin-1-yl}carbonyl)-2H-indazole
$^1$H NMR (400 MHz, acetone-$d_6$): δ 3.21-3.30 (m, 4 H), 3.94-4.15 (m, 3 H), 4.28-4.52 (m, 2 H), 4.52-4.68 (m, 1 H), 4.68-4.93 (m, 3 6 H), 5.72 (s, 2 H), 7.15 (t, J = 8.8 Hz, 2 H), 7.34 (dd, J = 8.6, 1.3 Hz, 1 H), 7.45-7.52 (m, 2 H), 7.75 (d, J = 8.6 Hz, 1 H), 7.91 (s, 1 H), 7.92 (d, J = 3.3 Hz, 1 H), 7.99 (d, J = 3.3 Hz, 1 H), 8.42 (s, 1 H)
MS m/z (M + H$^+$) 505.2 |

Example 72a

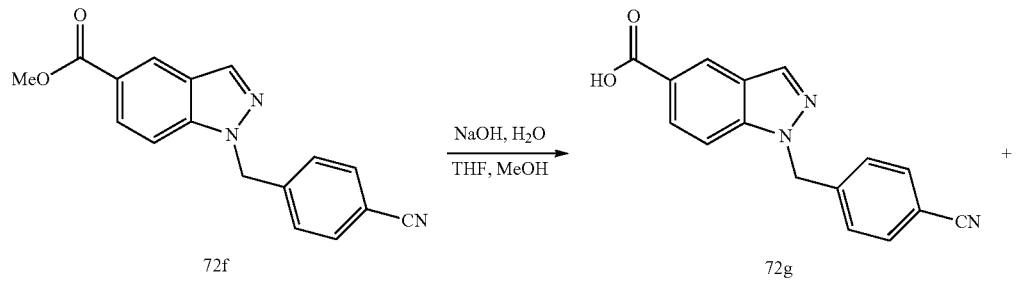

72f → 72g

NaOH, H$_2$O / THF, MeOH

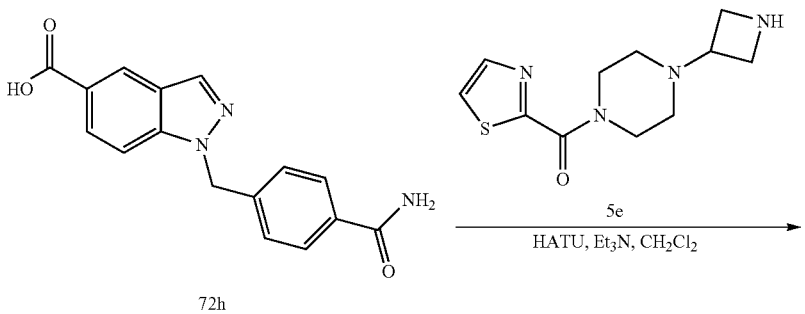

72h

5e / HATU, Et$_3$N, CH$_2$Cl$_2$

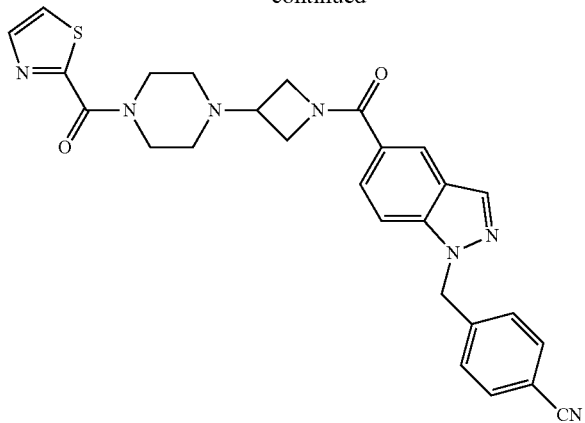

Cpd 1044

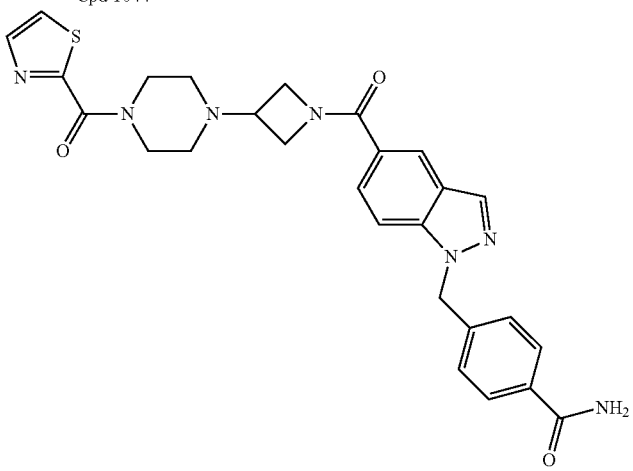

Cpd 1045

D. Methyl 1-(4-cyanobenzyl)-1H-indazole-5-carboxylate, 72f. The title compound 72f was prepared using the procedure described in Example 72, substituting methyl 1H-indazole-5-carboxylate for 72a and substituting 4-(bromomethyl)benzonitrile for 72b. $^1$H NMR (400 MHz, CDCl$_3$): δ 3.95 (s, 3H), 5.67 (s, 2H), 7.26 (d, J=8.2 Hz, 2H), 7.33 (d, J=8.9 Hz, 1H), 7.61 (d, J=8.3 Hz, 2H), 8.06 (dd, J=8.9, 1.4 Hz, 1H), 8.18 (s, 1H), 8.55 (s, 1H). (M+H$^+$) 292.2

E. 1-(4-cyanobenzyl)-1H-indazole-5-carboxylic acid, 72g, and 1-(4-carbamoylbenzyl)-1H-indazole-5-carboxylic acid, 72h. To a stirring solution of compound 72f (0.35 mmol, 102 mg) in 2 mL of THF and 0.5 mL of MeOH was added 3N aqueous NaOH (2.45 mmol, 0.82 mL). After stirring at room temperature overnight, the mixture was concentrated under vacuum. The yellow residue was dissolved in 15 mL of water and acidified to pH 1-2 with aqueous HCl. The resulting precipitate was vacuum-filtered through a paper disc and washed with water. The remaining material was pumped at high vacuum to give 87 mg of a 3:1 mixture (as shown by LC/MS) of compound 72g and compound 72h as an off-white solid. Compound 72g (less polar): MS m/z (M+H$^+$) 278.1. Compound 72h (more polar): MS m/z (M+H$^+$) 296.

F. 4-{[5-({3-[4-(1,3-Thiazol-2-ylcarbonyl)piperazin-1-yl]azetidin-1-yl]carbonyl)-1H-indazol-1-yl}methyl}benzonitrile, Cpd 1045, and 4-{[5-({3-[4-(1,3-Thiazol-2-ylcarbonyl)piperazin-1-yl]azetidin-1-yl]carbonyl)-1H-indazol-1-yl}methyl}benzamide, Cpd 1044.

The title compounds Cpd 1045 and Cpd 1044 were prepared using the method described in Example 9, substituting the mixture of 72g and 72h prepared in Step E above for 9c and substituting HBTU for HATU in Step D. The products were separated by preparative reverse phase chromatography to give 64 mg of Cpd 1045 (less polar) and 6.4 mg of Cpd 1044 (more polar).

Cpd 1045: $^1$H NMR (400 MHz, acetone-d$_6$): δ 3.24-3.49 (m, 4H), 4.00-4.11 (m, 2H), 4.11-4.20 (m, 1H), 4.26-4.96 (m, 6H), 5.85 (s, 2H), 7.45 (d, J=8.3 Hz, 2H), 7.66-7.72 (m, 2H), 7.74 (d, J=8.3 Hz, 2H), 7.92 (d, J=3.3 Hz, 1H), 7.99 (d, J=3.0 Hz, 1H), 8.16 (s, 1H), 8.20 (s, 1H)

Cpd 1044: $^1$H NMR (400 MHz, acetone-d$_6$): δ 3.14 (br. s, 4H), 3.87-3.96 (m, 1H), 3.96-4.08 (m, 2H), 4.35 (br. s, 2H), 4.47-4.85 (m, 4H), 5.78 (s, 2H), 7.35 (d, J=8.3 Hz, 2H), 7.66 (s, J=8.8 Hz, 1H), 7.70 (d, J=8.6, 1.5 Hz, 1H), 7.88 (d, J=8.1 Hz, 2H), 7.91 (d, J=3.3 Hz, 1H), 7.98 (d, J=3.3 Hz, 1H), 8.16 (s, 1H), 8.18 (s, 1H)

Biological Examples

In Vitro Methods

Example 1

MGL Enzyme Activity Assay

All rate-based assays were performed in black 384-well polypropylene polymerase chain reaction ("PCR") microplates (Abgene) in a total volume of 30 μL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM 1,4-piperazinediethanesulfonic acid ("PIPES") buffer (pH=7.0), containing 150 mM NaCl and 0.001% Tween 20. Compounds of Formula (I) were pre-dispensed (50 mL) into the assay plate using a Cartesian Hummingbird prior to adding 4MU-B (25 μL of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The IC$_{50}$ values for compounds of Formula (I) were determined using Excel from a fit of the equation to the concentration-response plot of the fractional activity as a function of inhibitor concentration.

BIOLOGICAL DATA TABLE 1

| Cpd | Chemistry Example | MGL mutant inh IC$_{50}$ (μM) | MGL wild type inh IC$_{50}$ (μM) |
|---|---|---|---|
| 1 | 1 | 0.0283 | |
| 2 | 1 | 0.0081 | |
| 3 | 1 | 5.20 | |
| 4 | 1 | 0.731 | |
| 5 | 1 | 0.0657 | 0.523 |
| 6 | 1 | 0.0080 | |
| 7 | 1 | 0.0346 | 0.131 |
| 8 | 1 | 0.101 | |
| 9 | 1 | 0.0087 | 0.0174 |
| 10 | 1 | 0.329 | |
| 11 | 1 | 2.86 | |
| 12 | 1 | 0.0470 | |
| 13 | 1 | 0.0200 | 0.0192 |
| 14 | 1 | 1.22 | |
| 15 | 1 | 2.18 | |
| 16 | 1 | 0.828 | |
| 17 | 1 | 14.3 | |
| 18 | 1 | 0.124 | |
| 19 | 1 | 0.979 | |
| 20 | 1 | 1.89 | |
| 21 | 1 | 2.35 | |
| 22 | 1 | 4.81 | |
| 23 | 1 | 2.78 | |
| 24 | 1 | 2.45 | |
| 25 | 1 | 2.29 | |
| 26 | 1 | 15.4 | |
| 567 | 1 | 0.018 | 0.015 |
| 579 | 1 | | 0.065 |
| 581 | 1 | | 0.080 |
| 587 | 1 | 0.014 | 0.119 |
| 595 | 1 | 0.098 | 0.500 |
| 598 | 1 | | 0.979 |
| 1061 | 1 | | 0.006 |
| 1071 | 1 | | 0.008 |
| 1139 | 1 | | 0.027 |
| 1147 | 1 | | 0.032 |
| 1163 | 1 | 0.009 | 0.048 |
| 1174 | 1 | <0.005 | 0.066 |
| 1201 | 1 | 0.007 | 0.151 |
| 1248 | 1 | | 0.559 |
| 1356 | 1 | <0.005 | <0.005 |
| 1357 | 1 | <0.005 | <0.005 |
| 1358 | 1 | <0.005 | <0.005 |
| 1359 | 1 | <0.005 | <0.005 |
| 1360 | 1 | <0.005 | |
| 1361 | 1 | | <0.005 |
| 1362 | 1 | | <0.005 |
| 1363 | 1 | | <0.005 |
| 1364 | 1 | | <0.005 |
| 1366 | 1 | | <0.005 |
| 1382 | 1 | 0.069 | |
| 1408 | 1 | <0.005 | |
| 586 | 1b | | 0.112 |
| 596 | 1b | | 0.543 |
| 603 | 1b | | 1.722 |
| 630 | 1b | | 0.714 |
| 1062 | 1b | | 0.007 |
| 1072 | 1b | | 0.008 |
| 1073 | 1b | | 0.034 |
| 1089 | 1b | | 0.010 |
| 1097 | 1b | | 0.012 |
| 1105 | 1b | | 0.013 |
| 1107 | 1b | | 0.014 |
| 1120 | 1b | | 0.018 |
| 1121 | 1b | | 0.018 |
| 1126 | 1b | | 0.019 |
| 1127 | 1b | | 0.020 |
| 1128 | 1b | | 0.021 |
| 1134 | 1b | | 0.025 |
| 1135 | 1b | | 0.025 |
| 1176 | 1b | | 0.070 |
| 1181 | 1b | | 0.077 |
| 1189 | 1b | | 0.097 |
| 1192 | 1b | | 0.109 |
| 1197 | 1b | | 0.133 |
| 1216 | 1b | | 0.216 |
| 1219 | 1b | | 0.235 |
| 1230 | 1b | | 0.307 |
| 1247 | 1b | | 0.539 |
| 1263 | 1b | | 0.968 |
| 1312 | 1b | | <0.00500035 |
| 1314 | 1b | | <0.00500035 |
| 1337 | 1b | | <0.00500035 |
| 1338 | 1b | | <0.00500035 |
| 1339 | 1b | | <0.00500035 |
| 1410 | 1b | | 0.089 |
| 656 | 1c | | 0.008 |
| 1079 | 1c | | 0.009 |
| 1184 | 1c | | 0.086 |
| 1199 | 1c | | 0.146 |
| 1141 | 1d | 0.010 | 0.028 |
| 1151 | 1d | | 0.037 |
| 1158 | 1d | | 0.042 |
| 592 | 1e | 0.078 | 0.253 |
| 1125 | 1e | <0.00500035 | 0.019 |
| 1187 | 1e | <0.00500035 | 0.092 |
| 629 | 1f | | 0.053 |
| 1180 | 1f | | 0.075 |
| 1313 | 1f | | <0.00500035 |
| 1409 | 1g | | |
| 27 | 2 | 14.5 | |
| 487 | 1a | <0.005 | 0.0104 |
| 28 | 2 | 1.63 | |
| 29 | 2 | 0.363 | |
| 30 | 2 | 0.670 | |
| 31 | 2 | 5.07 | |
| 32 | 2 | 0.761 | |
| 33 | 2 | 0.633 | |
| 34 | 2 | 1.38 | |
| 35 | 2 | 0.459 | |
| 36 | 2 | 0.115 | |
| 37 | 2 | 0.117 | 5.99 |
| 38 | 2 | 0.666 | |
| 39 | 2 | 0.0317 | 0.0147 |
| 40 | 2 | 0.0491 | |
| 41 | 2 | 0.0322 | |
| 42 | 2 | 0.354 | |
| 43 | 2 | 0.0310 | 1.26 |
| 44 | 2 | 0.0700 | |
| 45 | 2 | 3.42 | |
| 46 | 2 | 3.43 | |
| 47 | 2 | 0.129 | 0.129 |
| 48 | 2 | 0.551 | |
| 49 | 2 | 5.78 | |
| 50 | 2 | 8.71 | |
| 51 | 2 | 0.227 | |
| 52 | 2 | 1.94 | |
| 53 | 2 | 0.988 | |

BIOLOGICAL DATA TABLE 1-continued

| Cpd | Chemistry Example | MGL mutant inh IC$_{50}$ (µM) | MGL wild type inh IC$_{50}$ (µM) |
|---|---|---|---|
| 54 | 2 | 0.223 | |
| 55 | 2 | 0.307 | |
| 56 | 2 | 13.8 | |
| 57 | 2 | 5.24 | |
| 58 | 2 | 2.63 | |
| 59 | 2 | 3.38 | |
| 60 | 2 | 2.66 | |
| 461 | 2 | 5.28 | |
| 462 | 2 | 5.05 | |
| 463 | 2 | 9.63 | |
| 464 | 2 | 5.82 | |
| 465 | 2 | 8.27 | |
| 466 | 2 | 10.9 | |
| 467 | 2 | 9.82 | |
| 468 | 2 | 2.70 | |
| 469 | 2 | 2.25 | |
| 470 | 2 | 7.06 | |
| 471 | 2 | 3.38 | |
| 472 | 2 | 9.73 | |
| 531 | 2 | 0.766 | |
| 539 | 2 | 11.476 | |
| 541 | 2 | 13.059 | |
| 559 | 2 | 1.287 | |
| 562 | 2 | 13.474 | |
| 565 | 2 | 11.392 | |
| 622 | 2 | 1.360 | |
| 627 | 2 | 13.225 | |
| 628 | 2 | 13.502 | |
| 954 | 2 | | 2.743 |
| 1266 | 2 | | 1.083 |
| 1284 | 2 | | 2.292 |
| 1404 | 2 | 13.286 | |
| 1482 | 2 | >16.9981 | |
| 1483 | 2 | >16.6686 | |
| 1485 | 2 | | >16.6686 |
| 1464 | 2 | >16.6686 | |
| 61 | 3 | 0.0385 | |
| 676 | 3 | <0.005 | 0.021 |
| 703 | 3 | 0.014 | 0.088 |
| 716 | 3 | 0.023 | 0.140 |
| 722 | 3 | 0.051 | 0.180 |
| 741 | 3 | 0.038 | 0.298 |
| 753 | 3 | 0.075 | 0.434 |
| 921 | 3 | 6.331 | |
| 1067 | 3 | <0.005 | 0.007 |
| 1166 | 3 | | 0.052 |
| 1235 | 3 | 0.030 | 0.360 |
| 1236 | 3 | 0.042 | 0.390 |
| 1242 | 3 | 0.146 | 0.461 |
| 1243 | 3 | | 0.463 |
| 1246 | 3 | 0.207 | 0.506 |
| 1276 | 3 | 0.650 | 1.764 |
| 1283 | 3 | 0.063 | 2.171 |
| 1292 | 3 | 0.244 | 3.070 |
| 1383 | 3 | 0.081 | |
| 1400 | 3 | 5.929 | |
| 1401 | 3 | 8.843 | |
| 1402 | 3 | 9.972 | |
| 62 | 4 | 2.95 | |
| 63 | 4 | 4.84 | |
| 64 | 4 | 2.29 | |
| 65 | 4 | 0.893 | |
| 66 | 4 | 1.40 | |
| 67 | 4 | 0.134 | |
| 68 | 4 | 12.7 | |
| 69 | 4 | 4.31 | |
| 70 | 4 | 4.83 | |
| 71 | 4 | 7.58 | |
| 72 | 4 | 0.0270 | 0.326 |
| 73 | 4 | 1.54 | |
| 74 | 4 | 3.34 | |
| 75 | 4 | 0.0939 | |
| 76 | 4 | 2.43 | |
| 77 | 4 | 0.0478 | |
| 78 | 4 | 0.607 | |
| 79 | 4 | 0.125 | |
| 80 | 4 | 4.85 | |
| 81 | 4 | 0.227 | |
| 82 | 4 | 0.466 | |
| 83 | 4 | 0.0989 | |
| 474 | 4 | 4.68 | |
| 473 | 4 | 9.79 | |
| 84 | 4 | 4.67 | |
| 85 | 4 | 4.17 | |
| 86 | 4 | 3.92 | |
| 87 | 4 | 4.81 | |
| 88 | 4 | 1.95 | |
| 89 | 4 | 1.76 | |
| 90 | 4 | 14.7 | |
| 91 | 4 | 1.87 | |
| 92 | 4 | 13.6 | |
| 93 | 4 | 3.93 | |
| 94 | 4 | 1.88 | |
| 95 | 4 | 0.669 | |
| 96 | 4 | 14.0 | |
| 97 | 4 | 0.920 | |
| 98 | 4 | 4.58 | |
| 99 | 4 | 6.36 | |
| 100 | 4 | 3.50 | |
| 101 | 4 | 0.299 | |
| 102 | 4 | 3.04 | |
| 103 | 4 | 8.93 | |
| 104 | 4 | 3.90 | |
| 105 | 4 | 2.97 | |
| 106 | 4 | 0.539 | |
| 107 | 4 | 1.12 | |
| 108 | 4 | 8.63 | |
| 109 | 4 | 0.0385 | |
| 110 | 4 | 1.22 | |
| 111 | 4 | 14.0 | |
| 496 | 4 | 1.30 | |
| 558 | 4 | 0.410 | |
| 618 | 4 | 0.140 | |
| 619 | 4 | 0.142 | |
| 620 | 4 | 0.153 | |
| 621 | 4 | 0.271 | |
| 623 | 4 | 2.423 | |
| 624 | 4 | 4.687 | |
| 625 | 4 | 9.761 | |
| 626 | 4 | 12.74 | |
| 133 | 5 | <0.005 | 0.0673 |
| 134 | 5 | 0.0114 | |
| 135 | 5 | <0.005 | |
| 136 | 5 | <0.005 | |
| 137 | 5 | 0.0073 | |
| 138 | 5 | <0.005 | |
| 139 | 5 | 0.968 | |
| 140 | 5 | 0.653 | |
| 141 | 5 | 0.412 | |
| 142 | 5 | 1.55 | |
| 143 | 5 | 7.14 | |
| 144 | 5 | 4.68 | |
| 145 | 5 | 2.69 | |
| 146 | 5 | 0.518 | |
| 147 | 5 | <0.005 | |
| 148 | 5 | <0.005 | <0.005 |
| 149 | 5 | 0.249 | 0.0769 |
| 150 | 5 | 0.0058 | <0.005 |
| 151 | 5 | 0.114 | |
| 152 | 5 | 3.51 | |
| 153 | 5 | 0.355 | |
| 154 | 5 | 0.127 | |
| 155 | 5 | 3.75 | |
| 156 | 5 | 1.54 | |
| 157 | 5 | 0.853 | |
| 158 | 5 | 0.0339 | 0.657 |
| 159 | 5 | 0.682 | |
| 160 | 5 | 2.54 | |
| 161 | 5 | 0.0050 | 0.0117 |
| 162 | 5 | <0.005 | |
| 163 | 5 | 0.0239 | |
| 164 | 5 | 0.0100 | |
| 165 | 5 | 0.451 | |
| 166 | 5 | <0.005 | <0.005 |

BIOLOGICAL DATA TABLE 1-continued

| Cpd | Chemistry Example | MGL mutant inh IC$_{50}$ (μM) | MGL wild type inh IC$_{50}$ (μM) |
|---|---|---|---|
| 167 | 5 | 0.0500 | 0.0152 |
| 168 | 5 | 0.0059 | <0.005 |
| 169 | 5 | 5.55 | |
| 170 | 5 | 0.0679 | |
| 171 | 5 | 0.380 | |
| 172 | 5 | 0.0088 | 0.0073 |
| 475 | 5 | 0.234 | |
| 476 | 5 | 0.0443 | 0.338 |
| 477 | 5 | 1.38 | |
| 478 | 5 | 3.12 | |
| 479 | 5 | 2.82 | |
| 298 | 5 | 1.16 | |
| 112 | 5 | 1.08 | |
| 113 | 5 | 0.587 | |
| 114 | 5 | 0.840 | |
| 115 | 5 | 0.0180 | 0.0117 |
| 116 | 5 | 1.49 | |
| 117 | 5 | 0.396 | 4.23 |
| 489 | 5 | <0.005 | 0.0090 |
| 490 | 5 | <0.005 | 0.0223 |
| 485 | 5 | <0.005 | 0.102 |
| 502 | 5 | 6.091 | |
| 503 | 5 | 0.152 | |
| 517 | 5 | 0.073 | 1.340 |
| 523 | 5 | | 3.135 |
| 524 | 5 | | 4.368 |
| 526 | 5 | | 8.102 |
| 610 | 5 | | 10.347 |
| 611 | 5 | | 13.253 |
| 636 | 5 | | 0.021 |
| 637 | 5 | | 0.041 |
| 638 | 5 | | 0.189 |
| 639 | 5 | | 0.419 |
| 640 | 5 | | 15.944 |
| 641 | 5 | | <0.005 |
| 643 | 5 | 0.411 | |
| 644 | 5 | 3.086 | |
| 646 | 5 | | 7.158 |
| 648 | 5 | 0.018 | |
| 655 | 5 | | 0.008 |
| 658 | 5 | | 0.009 |
| 667 | 5 | | 0.014 |
| 669 | 5 | | 0.015 |
| 672 | 5 | | 0.017 |
| 675 | 5 | | 0.019 |
| 678 | 5 | | 0.022 |
| 682 | 5 | | 0.030 |
| 687 | 5 | | 0.044 |
| 688 | 5 | | 0.044 |
| 693 | 5 | | 0.047 |
| 694 | 5 | | 0.047 |
| 696 | 5 | | 0.059 |
| 698 | 5 | | 0.065 |
| 702 | 5 | | 0.303 |
| 710 | 5 | | 0.123 |
| 719 | 5 | | 0.154 |
| 721 | 5 | | 0.173 |
| 726 | 5 | | 0.218 |
| 727 | 5 | | 0.219 |
| 728 | 5 | | 0.231 |
| 730 | 5 | | 0.238 |
| 731 | 5 | | 0.238 |
| 732 | 5 | | 0.239 |
| 733 | 5 | | 0.240 |
| 735 | 5 | | 0.268 |
| 739 | 5 | | 0.290 |
| 740 | 5 | | 0.294 |
| 743 | 5 | | 0.324 |
| 744 | 5 | | 0.335 |
| 746 | 5 | | 0.373 |
| 747 | 5 | | 0.377 |
| 748 | 5 | | 0.384 |
| 750 | 5 | | 0.395 |
| 751 | 5 | | 0.402 |
| 754 | 5 | | 0.447 |
| 755 | 5 | | 0.468 |
| 756 | 5 | | 0.519 |
| 758 | 5 | | 0.535 |
| 760 | 5 | | 0.581 |
| 762 | 5 | | 0.632 |
| 763 | 5 | | 0.635 |
| 764 | 5 | | 0.636 |
| 766 | 5 | | 0.680 |
| 768 | 5 | | 0.697 |
| 770 | 5 | | 0.740 |
| 772 | 5 | | 0.799 |
| 774 | 5 | | 0.848 |
| 776 | 5 | | 0.902 |
| 779 | 5 | | 0.944 |
| 781 | 5 | | 1.042 |
| 782 | 5 | | 1.066 |
| 783 | 5 | | 1.086 |
| 785 | 5 | | 1.190 |
| 786 | 5 | | 1.203 |
| 787 | 5 | | 1.209 |
| 788 | 5 | | 1.227 |
| 791 | 5 | | 1.448 |
| 792 | 5 | | 1.458 |
| 793 | 5 | | 1.460 |
| 794 | 5 | | 1.469 |
| 795 | 5 | | 1.502 |
| 796 | 5 | | 1.529 |
| 797 | 5 | | 1.596 |
| 799 | 5 | | 1.667 |
| 800 | 5 | | 1.696 |
| 804 | 5 | 0.058 | 1.993 |
| 808 | 5 | | 2.076 |
| 809 | 5 | | 2.104 |
| 814 | 5 | | 2.434 |
| 815 | 5 | | 2.492 |
| 816 | 5 | | 2.636 |
| 818 | 5 | | 2.702 |
| 821 | 5 | | 2.847 |
| 823 | 5 | | 2.970 |
| 824 | 5 | | 3.120 |
| 825 | 5 | | 3.148 |
| 826 | 5 | | 3.287 |
| 827 | 5 | | 3.308 |
| 828 | 5 | | 3.733 |
| 830 | 5 | | 3.942 |
| 831 | 5 | | 4.097 |
| 835 | 5 | | 4.705 |
| 836 | 5 | | 4.756 |
| 838 | 5 | | 5.113 |
| 839 | 5 | | 5.135 |
| 840 | 5 | | 5.155 |
| 842 | 5 | | 5.526 |
| 843 | 5 | | 5.531 |
| 844 | 5 | | 6.104 |
| 845 | 5 | | 6.421 |
| 846 | 5 | | 6.448 |
| 848 | 5 | | 6.902 |
| 849 | 5 | | 7.011 |
| 850 | 5 | | 7.278 |
| 852 | 5 | | 8.078 |
| 853 | 5 | | 8.344 |
| 854 | 5 | >16.6686 | 8.414 |
| 855 | 5 | | 8.435 |
| 857 | 5 | | 8.724 |
| 859 | 5 | | 8.815 |
| 860 | 5 | | 8.819 |
| 862 | 5 | | 9.510 |
| 863 | 5 | | 10.158 |
| 864 | 5 | | 10.221 |
| 865 | 5 | | 10.287 |
| 868 | 5 | | 12.112 |
| 871 | 5 | | 13.323 |
| 873 | 5 | | 14.703 |
| 874 | 5 | | 15.209 |
| 886 | 5 | | <0.005 |
| 887 | 5 | | <0.005 |
| 888 | 5 | | <0.005 |
| 889 | 5 | | <0.005 |
| 890 | 5 | | <0.005 |

BIOLOGICAL DATA TABLE 1-continued

| Cpd | Chemistry Example | MGL mutant inh IC$_{50}$ (μM) | MGL wild type inh IC$_{50}$ (μM) |
|---|---|---|---|
| 891 | 5 | | <0.005 |
| 892 | 5 | | <0.005 |
| 893 | 5 | | <0.005 |
| 894 | 5 | | <0.005 |
| 905 | 5 | 0.015 | |
| 910 | 5 | 0.194 | |
| 912 | 5 | 0.472 | |
| 915 | 5 | 0.944 | |
| 923 | 5 | 8.756 | |
| 925 | 5 | 9.968 | |
| 926 | 5 | 10.457 | |
| 946 | 5 | | 1.001 |
| 947 | 5 | | 1.065 |
| 952 | 5 | | 0.012 |
| 953 | 5 | | >16.6686 |
| 965 | 5 | 0.037 | |
| 966 | 5 | 0.222 | |
| 993 | 5 | | 1.514 |
| 1000 | 5 | | 0.111 |
| 1001 | 5 | | 1.403 |
| 1002 | 5 | | 5.292 |
| 1003 | 5 | | 1.613 |
| 1004 | 5 | | 0.167 |
| 1017 | 5 | | 0.035 |
| 1041 | 5 | | 0.019 |
| 1042 | 5 | | 5.274 |
| 1053 | 5 | | 0.018 |
| 1082 | 5 | | 0.009 |
| 1083 | 5 | | 0.009 |
| 1103 | 5 | | 0.013 |
| 1119 | 5 | | 0.017 |
| 1122 | 5 | | 0.018 |
| 1123 | 5 | | 0.019 |
| 1146 | 5 | | 0.032 |
| 1150 | 5 | <0.005 | 0.036 |
| 1156 | 5 | | 0.041 |
| 1164 | 5 | | 0.048 |
| 1179 | 5 | | 0.073 |
| 1194 | 5 | | 0.118 |
| 1202 | 5 | | 0.152 |
| 1203 | 5 | | 0.153 |
| 1214 | 5 | | 0.209 |
| 1218 | 5 | | 0.222 |
| 1223 | 5 | | 0.267 |
| 1225 | 5 | | 0.273 |
| 1245 | 5 | | 0.500 |
| 1249 | 5 | | 0.605 |
| 1271 | 5 | | 1.568 |
| 1272 | 5 | | 1.608 |
| 1287 | 5 | | 2.450 |
| 1293 | 5 | | 3.172 |
| 1297 | 5 | | 3.311 |
| 1298 | 5 | | 3.850 |
| 1299 | 5 | | 3.856 |
| 1300 | 5 | | 4.135 |
| 1301 | 5 | | 4.608 |
| 1305 | 5 | | 6.676 |
| 1307 | 5 | | 8.776 |
| 1326 | 5 | | <0.005 |
| 1327 | 5 | | <0.005 |
| 1328 | 5 | | <0.005 |
| 1329 | 5 | | <0.005 |
| 1330 | 5 | | <0.005 |
| 1331 | 5 | | <0.005 |
| 1332 | 5 | | <0.005 |
| 1333 | 5 | | <0.005 |
| 1334 | 5 | | <0.005 |
| 1378 | 5 | 0.009 | |
| 1379 | 5 | 0.022 | |
| 1381 | 5 | 0.065 | |
| 1384 | 5 | 0.092 | |
| 1385 | 5 | 0.152 | |
| 1386 | 5 | 0.180 | |
| 1392 | 5 | 0.693 | |
| 1395 | 5 | 0.866 | |
| 1396 | 5 | 1.159 | |
| 1397 | 5 | 1.165 | |
| 1403 | 5 | 12.331 | |
| 1407 | 5 | <0.005 | |
| 1412 | 5 | | 0.087 |
| 1442 | 5 | | >16.6686 |
| 1444 | 5 | | >16.6686 |
| 1445 | 5 | | >16.6686 |
| 1491 | 5 | | >16.6686 |
| 1460 | 5 | | >16.6686 |
| 1434 | 5 | | >16.6686 |
| 1477 | 5 | >16.6686 | |
| 1432 | 5 | | >16.6686 |
| 1489 | 5 | >16.6686 | >16.6686 |
| 1490 | 5 | | >16.6686 |
| 1481 | 5 | >16.6686 | |
| 1436 | 5 | >16.6686 | >16.6686 |
| 1473 | 5 | | >16.6686 |
| 1475 | 5 | | >16.6686 |
| 1446 | 5 | | >16.6686 |
| 1447 | 5 | | >16.6686 |
| 1448 | 5 | | >16.6686 |
| 1449 | 5 | | >16.6686 |
| 1450 | 5 | | >16.6686 |
| 1451 | 5 | | >16.6686 |
| 1452 | 5 | | >16.6686 |
| 1453 | 5 | | >16.6686 |
| 173 | 6 | 0.532 | |
| 174 | 6 | 0.0062 | |
| 175 | 6 | <0.005 | <0.005 |
| 176 | 6 | <0.005 | |
| 177 | 6 | 0.0088 | |
| 178 | 6 | <0.005 | |
| 179 | 6 | 0.0069 | |
| 180 | 6 | <0.005 | |
| 181 | 6 | <0.005 | |
| 182 | 6 | <0.005 | |
| 183 | 6 | <0.005 | |
| 184 | 6 | 0.0385 | |
| 185 | 6 | 2.63 | |
| 186 | 6 | 0.0068 | 0.0184 |
| 187 | 6 | 0.546 | |
| 188 | 6 | 0.0409 | |
| 189 | 6 | 0.651 | |
| 190 | 6 | 2.51 | |
| 191 | 6 | 1.46 | |
| 192 | 6 | 2.36 | |
| 193 | 6 | 0.460 | |
| 194 | 6 | 0.553 | |
| 195 | 6 | 0.0824 | |
| 196 | 6 | 0.0159 | 0.216 |
| 197 | 6 | 0.931 | |
| 198 | 6 | 0.211 | |
| 199 | 6 | 5.46 | |
| 200 | 6 | 0.168 | |
| 201 | 6 | 1.57 | |
| 202 | 6 | 0.477 | |
| 203 | 6 | 1.05 | |
| 204 | 6 | 0.371 | |
| 205 | 6 | 0.0189 | |
| 206 | 6 | 1.36 | |
| 207 | 6 | 0.0098 | |
| 208 | 6 | 0.0190 | 0.0920 |
| 209 | 6 | 0.0170 | |
| 210 | 6 | 0.0101 | |
| 211 | 6 | 0.0143 | |
| 212 | 6 | <0.005 | <0.005 |
| 213 | 6 | <0.005 | |
| 214 | 6 | <0.005 | |
| 215 | 6 | 0.0540 | |
| 216 | 6 | 0.0113 | |
| 217 | 6 | 0.561 | |
| 218 | 6 | 0.0200 | |
| 219 | 6 | 0.0145 | 0.0320 |
| 220 | 6 | <0.005 | |
| 221 | 6 | <0.005 | |
| 222 | 6 | 0.242 | |
| 223 | 6 | 0.0164 | |
| 224 | 6 | <0.005 | |

BIOLOGICAL DATA TABLE 1-continued

| Cpd | Chemistry Example | MGL mutant inh $IC_{50}$ (μM) | MGL wild type inh $IC_{50}$ (μM) |
|---|---|---|---|
| 225 | 6 | 0.0523 | 0.0547 |
| 226 | 6 | 0.0696 | |
| 227 | 6 | <0.005 | 0.0070 |
| 228 | 6 | 0.0204 | <0.005 |
| 229 | 6 | <0.005 | <0.005 |
| 230 | 6 | 0.0116 | |
| 231 | 6 | 0.516 | |
| 232 | 6 | <0.005 | 0.0829 |
| 233 | 6 | 1.78 | |
| 234 | 6 | 0.157 | |
| 235 | 6 | 1.70 | |
| 236 | 6 | 0.499 | |
| 237 | 6 | <0.005 | <0.005 |
| 238 | 6 | 0.0516 | |
| 239 | 6 | <0.005 | 0.0100 |
| 240 | 6 | <0.005 | 0.0508 |
| 241 | 6 | 0.0070 | |
| 242 | 6 | <0.005 | |
| 243 | 6 | 0.0057 | |
| 244 | 6 | <0.005 | |
| 245 | 6 | <0.005 | 0.0164 |
| 246 | 6 | 0.0200 | |
| 247 | 6 | <0.005 | |
| 248 | 6 | <0.005 | 0.0070 |
| 249 | 6 | 0.0120 | |
| 250 | 6 | <0.005 | <0.005 |
| 251 | 6 | <0.005 | 0.0170 |
| 252 | 6 | 0.0125 | 0.0808 |
| 253 | 6 | <0.005 | 0.0494 |
| 254 | 6 | <0.005 | <0.005 |
| 255 | 6 | 0.0102 | |
| 256 | 6 | 0.0110 | 0.0134 |
| 257 | 6 | <0.005 | <0.005 |
| 258 | 6 | <0.005 | |
| 259 | 6 | 0.0060 | |
| 260 | 6 | 0.0089 | |
| 261 | 6 | <0.005 | 0.0084 |
| 262 | 6 | <0.005 | <0.005 |
| 263 | 6 | <0.005 | 0.0285 |
| 264 | 6 | 0.0050 | |
| 265 | 6 | <0.005 | 0.0190 |
| 266 | 6 | <0.005 | 0.0498 |
| 267 | 6 | <0.005 | |
| 268 | 6 | 0.0544 | |
| 488 | 6 | 0.0173 | 0.382 |
| 1070 | 6 | <0.005 | 0.008 |
| 1102 | 6 | <0.005 | 0.013 |
| 269 | 7 | 0.215 | |
| 270 | 7 | 0.289 | |
| 271 | 7 | 0.210 | |
| 272 | 7 | 2.71 | |
| 273 | 7 | 0.0872 | |
| 274 | 7 | 0.0705 | |
| 275 | 7 | 1.07 | |
| 276 | 7 | 0.341 | |
| 277 | 7 | 4.70 | |
| 278 | 7 | 4.18 | |
| 279 | 7 | 0.640 | |
| 280 | 7 | 0.141 | |
| 281 | 7 | 0.0930 | |
| 282 | 7 | <0.005 | |
| 283 | 7 | 0.0222 | |
| 284 | 7 | 4.88 | |
| 285 | 7 | 13.2 | |
| 286 | 7 | 0.150 | |
| 287 | 7 | 6.81 | |
| 288 | 7 | 3.54 | |
| 289 | 7 | 6.56 | |
| 290 | 7 | 0.0600 | |
| 291 | 7 | 0.0071 | |
| 292 | 7 | 2.59 | |
| 293 | 7 | 0.380 | |
| 294 | 7 | 0.638 | |
| 295 | 7 | 2.13 | |
| 296 | 7 | 1.04 | |
| 297 | 7 | 0.358 | |
| 299 | 8 | 0.683 | |
| 300 | 8 | 6.99 | |
| 301 | 8 | 0.326 | |
| 302 | 8 | 0.143 | |
| 303 | 8 | 0.314 | 0.173 |
| 304 | 8 | 0.358 | |
| 305 | 8 | 0.132 | |
| 306 | 8 | 0.666 | |
| 307 | 8 | 0.408 | |
| 308 | 8 | 6.07 | |
| 309 | 8 | 1.17 | |
| 310 | 8 | 0.0842 | |
| 311 | 8 | 0.0640 | |
| 312 | 8 | 0.0065 | |
| 480 | 8 | 3.38 | |
| 1057 | 8 | | 0.006 |
| 1078 | 8 | | 0.009 |
| 1085 | 8 | | 0.009 |
| 1087 | 8 | | 0.009 |
| 1094 | 8 | | 0.011 |
| 1112 | 8 | | 0.016 |
| 1118 | 8 | | 0.016 |
| 1140 | 8 | | 0.027 |
| 1143 | 8 | | 0.030 |
| 1145 | 8 | | 0.031 |
| 1169 | 8 | | 0.055 |
| 1217 | 8 | | 0.220 |
| 1222 | 8 | | 0.266 |
| 1232 | 8 | | 0.326 |
| 1256 | 8 | | 0.808 |
| 1258 | 8 | | 0.829 |
| 1262 | 8 | | 0.950 |
| 1269 | 8 | | 1.264 |
| 1308 | 8 | | 9.277 |
| 1310 | 8 | | 11.649 |
| 1324 | 8 | | <0.005 |
| 1325 | 8 | | <0.005 |
| 1335 | 8 | | <0.005 |
| 1336 | 8 | | <0.005 |
| 1398 | 8 | 1.222 | |
| 1423 | 8 | | 0.278 |
| 1424 | 8 | | 0.075 |
| 1425 | 8 | | 0.009 |
| 1426 | 8 | | <0.005 |
| 1427 | 8 | | 0.006 |
| 1428 | 8 | | 0.014 |
| 1429 | 8 | | 0.036 |
| 186-A | 8 | | 0.010 |
| 567-A | 8 | | 0.028 |
| 1478 | 8 | >16.6686 | |
| 1465 | 8 | | >16.6686 |
| 313 | 9 | <0.005 | |
| 314 | 9 | 0.0100 | <0.005 |
| 315 | 9 | 5.00 | |
| 316 | 9 | <0.005 | <0.005 |
| 317 | 9 | 0.0050 | <0.005 |
| 318 | 9 | <0.005 | 0.0139 |
| 319 | 9 | 0.0088 | |
| 320 | 9 | 8.53 | |
| 321 | 9 | 0.0378 | |
| 322 | 9 | 13.7 | |
| 606 | 9 | | 2.038 |
| 647 | 9 | | 12.723 |
| 654 | 9 | | 0.007 |
| 681 | 9 | | 0.027 |
| 713 | 9 | | 0.135 |
| 718 | 9 | | 0.148 |
| 723 | 9 | | 0.181 |
| 745 | 9 | | 0.342 |
| 767 | 9 | | 0.691 |
| 775 | 9 | | 0.862 |
| 806 | 9 | | 2.052 |
| 812 | 9 | | 2.192 |
| 817 | 9 | | 2.700 |
| 820 | 9 | | 2.815 |
| 822 | 9 | | 2.856 |
| 829 | 9 | | 3.905 |
| 832 | 9 | | 4.239 |

BIOLOGICAL DATA TABLE 1-continued

| Cpd | Chemistry Example | MGL mutant inh $IC_{50}$ (μM) | MGL wild type inh $IC_{50}$ (μM) |
|---|---|---|---|
| 856 | 9 | | 8.486 |
| 918 | 9 | 2.891 | |
| 1054 | 9 | | 0.005 |
| 1055 | 9 | | 0.005 |
| 1056 | 9 | | 0.006 |
| 1068 | 9 | | 0.007 |
| 1077 | 9 | | 0.008 |
| 1088 | 9 | | 0.010 |
| 1090 | 9 | | 0.010 |
| 1106 | 9 | | 0.014 |
| 1110 | 9 | | 0.015 |
| 1116 | 9 | | 0.016 |
| 1129 | 9 | | 0.021 |
| 1131 | 9 | | 0.022 |
| 1152 | 9 | | 0.038 |
| 1153 | 9 | | 0.039 |
| 1178 | 9 | | 0.071 |
| 1198 | 9 | | 0.143 |
| 1224 | 9 | | 0.270 |
| 1226 | 9 | | 0.282 |
| 1233 | 9 | | 0.343 |
| 1261 | 9 | | 0.932 |
| 1275 | 9 | | 1.722 |
| 1277 | 9 | | 1.834 |
| 1279 | 9 | | 1.902 |
| 1286 | 9 | | 2.417 |
| 1295 | 9 | | 3.278 |
| 1302 | 9 | | 4.948 |
| 1306 | 9 | | 8.151 |
| 1320 | 9 | | <0.005 |
| 1367 | 9 | | <0.005 |
| 1368 | 9 | | <0.005 |
| 1369 | 9 | | <0.005 |
| 1370 | 9 | | <0.005 |
| 1371 | 9 | | <0.005 |
| 1372 | 9 | | <0.005 |
| 1373 | 9 | | <0.005 |
| 1413 | 9 | | 0.015 |
| 1492 | 9 | | >16.6686 |
| 1499 | 9 | | >16.6686 |
| 118 | 9b | 0.664 | |
| 119 | 9b | 3.17 | |
| 120 | 9b | 0.0783 | |
| 121 | 9b | 1.91 | |
| 122 | 9b | 5.97 | |
| 123 | 9b | 0.591 | |
| 124 | 9b | 0.118 | 0.321 |
| 125 | 9b | 0.322 | |
| 126 | 9b | 0.0510 | 0.0200 |
| 127 | 9b | 0.499 | |
| 128 | 9b | 0.0045 | |
| 129 | 9b | 0.281 | |
| 130 | 9b | 0.823 | |
| 131 | 9b | 0.0767 | |
| 132 | 9b | 0.880 | |
| 568 | 9b | | 0.072 |
| 569 | 9b | | 0.021 |
| 571 | 9b | | 0.028 |
| 573 | 9b | | 0.046 |
| 577 | 9b | | 0.052 |
| 578 | 9b | | 0.063 |
| 580 | 9b | | 0.069 |
| 583 | 9b | | 0.104 |
| 584 | 9b | | 0.105 |
| 590 | 9b | | 0.186 |
| 599 | 9b | | 1.031 |
| 617 | 9b | 0.102 | |
| 566 | 9c | | 0.014 |
| 1375 | 9c | | <0.005 |
| 1421 | 9c | | <0.005 |
| 582 | 9d | | 0.097 |
| 588 | 9d | | 0.142 |
| 594 | 9d | | 0.449 |
| 1109 | 9d | | 0.015 |
| 1113 | 9d | | 0.016 |
| 1133 | 9d | | 0.024 |
| 1159 | 9d | | 0.045 |
| 1171 | 9d | | 0.063 |
| 1177 | 9d | | 0.063 |
| 1182 | 9d | | 0.079 |
| 633 | 9e | | 0.062 |
| 1115 | 9e | | 0.016 |
| 575 | 9f | | 0.051 |
| 576 | 9f | | 0.051 |
| 1080 | 9f | | 0.009 |
| 1374 | 9f | | <0.005 |
| 1376 | 9f | | <0.005 |
| 1419 | 9f | | <0.005 |
| 1420 | 9f | | 0.005 |
| 1422 | 9f | | 0.014 |
| 1165 | 9g | | 0.051 |
| 1210 | 9g | | 0.195 |
| 819 | 9h | | 2.790 |
| 601 | 9i | 0.490 | 1.552 |
| 602 | 9i | 0.302 | 1.717 |
| 607 | 9i | 0.894 | 2.905 |
| 608 | 9i | 0.766 | 4.166 |
| 609 | 9i | 0.735 | 4.332 |
| 980 | 9i | 2.442 | 6.792 |
| 989 | 9i | 1.566 | |
| 990 | 9i | 3.870 | |
| 991 | 9i | 0.564 | |
| 1252 | 9i | 0.136 | 0.706 |
| 1255 | 9i | <0.005 | 0.769 |
| 1290 | 9i | 0.187 | 2.700 |
| 1387 | 9i | 0.300 | |
| 1388 | 9i | 0.351 | |
| 1389 | 9i | 0.379 | |
| 1390 | 9i | 0.461 | |
| 1391 | 9i | 0.505 | |
| 1393 | 9i | 0.726 | |
| 1394 | 9i | 0.756 | |
| 1399 | 9i | 2.373 | |
| 1154 | 9j | <0.005 | 0.040 |
| 1173 | 9j | | 0.065 |
| 1190 | 9j | | 0.099 |
| 1191 | 9j | | 0.105 |
| 1193 | 9j | | 0.116 |
| 1220 | 9j | | 0.255 |
| 1237 | 9j | | 0.393 |
| 1238 | 9j | <0.005 | 0.437 |
| 1251 | 9j | | 0.684 |
| 1254 | 9j | 0.023 | 0.765 |
| 1257 | 9j | | 0.827 |
| 1282 | 9j | 0.019 | 2.072 |
| 323 | 10 | 0.0110 | |
| 324 | 10 | <0.005 | <0.005 |
| 325 | 10 | 0.0150 | 0.0695 |
| 686 | 10 | | 0.039 |
| 749 | 10 | | 0.387 |
| 778 | 10 | | 0.933 |
| 801 | 10 | | 1.712 |
| 833 | 10 | | 4.562 |
| 650 | 10a | | 0.006 |
| 666 | 10a | | 0.013 |
| 670 | 10a | | 0.015 |
| 900 | 10a | | <0.005 |
| 659 | 10b | | 0.009 |
| 697 | 10b | | 0.062 |
| 901 | 10b | | <0.005 |
| 902 | 10b | | <0.005 |
| 326 | 11 | <0.005 | <0.005 |
| 327 | 11 | 0.0089 | |
| 328 | 11 | 0.0540 | |
| 329 | 11 | 0.0358 | 1.22 |
| 330 | 11 | 0.0440 | 0.308 |
| 331 | 11 | <0.005 | 0.0457 |
| 332 | 11 | 0.0117 | |
| 333 | 11 | <0.005 | 0.0162 |
| 334 | 11 | 0.0143 | 0.363 |
| 335 | 11 | 0.0060 | 0.0121 |
| 336 | 11 | <0.005 | <0.005 |
| 337 | 11 | <0.005 | 0.0130 |
| 504 | 11 | <0.005 | 0.010 |

BIOLOGICAL DATA TABLE 1-continued

| Cpd | Chemistry Example | MGL mutant inh IC$_{50}$ (μM) | MGL wild type inh IC$_{50}$ (μM) |
|---|---|---|---|
| 516 | 11 | | 0.465 |
| 543 | 11 | <0.005 | |
| 684 | 11 | | 0.031 |
| 742 | 11 | | 0.306 |
| 810 | 11 | | 2.143 |
| 897 | 11 | <0.005 | <0.005 |
| 898 | 11 | <0.005 | <0.005 |
| 908 | 11 | 0.031 | |
| 929 | 11 | <0.005 | |
| 930 | 11 | <0.005 | |
| 338 | 12 | <0.005 | <0.005 |
| 339 | 12 | 0.113 | |
| 340 | 12 | 0.843 | |
| 341 | 12 | 3.63 | |
| 342 | 12 | 0.0440 | |
| 343 | 13 | 0.0059 | |
| 344 | 13 | 0.0270 | |
| 345 | 13 | <0.005 | <0.005 |
| 511 | 13 | | 0.240 |
| 515 | 13 | | 0.455 |
| 591 | 13 | | 0.212 |
| 346 | 14 | 2.83 | |
| 347 | 14 | 0.0877 | |
| 600 | 14 | | 1.154 |
| 605 | 14 | | 1.861 |
| 917 | 14 | 2.107 | |
| 919 | 14 | 4.004 | |
| 920 | 14 | 4.427 | |
| 924 | 14 | 9.685 | |
| 1059 | 14 | | 0.006 |
| 1060 | 14 | | 0.006 |
| 1065 | 14 | | 0.007 |
| 1066 | 14 | | 0.007 |
| 1096 | 14 | | 0.011 |
| 1101 | 14 | | 0.012 |
| 1157 | 14 | | 0.041 |
| 1160 | 14 | | 0.045 |
| 1183 | 14 | | 0.085 |
| 1321 | 14 | | <0.005 |
| 1342 | 14 | | <0.005 |
| 1343 | 14 | | <0.005 |
| 1351 | 14 | | <0.005 |
| 1352 | 14 | | <0.005 |
| 1353 | 14 | | <0.005 |
| 1354 | 14 | | <0.005 |
| 1075 | 14a | | 0.008 |
| 1149 | 14a | | 0.035 |
| 1175 | 14a | | 0.066 |
| 1205 | 14a | | 0.168 |
| 1196 | 14b | | 0.123 |
| 1204 | 14b | | 0.166 |
| 1211 | 14b | | 0.200 |
| 1241 | 14b | | 0.460 |
| 1244 | 14b | | 0.463 |
| 1209 | 14c | | 0.193 |
| 1213 | 14c | | 0.206 |
| 1294 | 14d | | 3.229 |
| 1303 | 14d | | 5.112 |
| 1443 | 14d | | >16.6686 |
| 1476 | 14d | | >16.6686 |
| 348 | 15 | 1.16 | |
| 349 | 16 | 1.03 | |
| 350 | 17 | 0.0991 | |
| 351 | 17 | 1.97 | |
| 352 | 17 | 1.67 | |
| 353 | 17 | 3.97 | |
| 354 | 17 | 1.56 | |
| 546 | 17 | | |
| 1437 | 17 | | >16.6686 |
| 1486 | 17 | >16.6686 | >16.6686 |
| 538 | 17a | 8.813 | |
| 861 | 17a | | 9.221 |
| 903 | 17a | 0.009 | |
| 690 | 17b | | 0.046 |
| 916 | 17b | 1.683 | |
| 355 | 18 | 2.05 | |
| 356 | 19 | 1.62 | |
| 357 | 20 | 0.0385 | 3.75 |
| 358 | 21 | 0.0670 | |
| 359 | 21 | 0.0094 | |
| 360 | 21 | 0.0060 | |
| 361 | 21 | 0.0355 | |
| 362 | 21 | 0.542 | |
| 363 | 21 | 3.12 | |
| 364 | 21 | 0.0085 | 0.210 |
| 365 | 21 | 0.0332 | |
| 665 | 21 | | 0.013 |
| 679 | 21 | 0.010 | 0.024 |
| 685 | 21 | 0.029 | 0.033 |
| 729 | 21 | | 0.236 |
| 736 | 21 | <0.005 | 0.273 |
| 907 | 21 | 0.029 | |
| 366 | 22 | <0.005 | |
| 367 | 22 | 0.0080 | |
| 368 | 22 | 0.0050 | |
| 369 | 22 | 0.165 | |
| 370 | 23 | <0.005 | |
| 371 | 23 | <0.005 | |
| 879 | 23 | 0.006 | <0.005 |
| 880 | 23 | 0.025 | <0.005 |
| 680 | 23a | | 0.025 |
| 1458 | 23a | >16.6686 | |
| 372 | 24 | <0.005 | |
| 373 | 24 | <0.005 | |
| 374 | 24 | <0.005 | |
| 375 | 24 | 0.0414 | |
| 661 | 24 | | 0.010 |
| 668 | 24 | | 0.015 |
| 805 | 24 | | 1.995 |
| 883 | 24 | | <0.005 |
| 376 | 25 | 1.08 | |
| 377 | 25 | 3.35 | |
| 378 | 25 | 5.06 | |
| 379 | 26 | 0.0367 | |
| 380 | 26 | 0.0542 | |
| 381 | 26 | 0.0099 | <0.005 |
| 382 | 26 | 0.913 | |
| 383 | 26 | 0.476 | |
| 384 | 26 | 0.349 | |
| 385 | 26 | 0.110 | |
| 386 | 26 | 1.25 | |
| 387 | 26 | 0.348 | |
| 388 | 26 | 0.429 | |
| 389 | 26 | 9.27 | |
| 390 | 26 | 2.43 | |
| 391 | 26 | 0.227 | |
| 392 | 26 | 0.558 | |
| 393 | 26 | 0.141 | |
| 394 | 26 | 0.434 | |
| 395 | 26 | 0.437 | |
| 396 | 26 | 0.790 | |
| 397 | 27 | 0.0180 | |
| 398 | 27 | 0.0254 | |
| 399 | 27 | 0.0312 | |
| 400 | 27 | <0.005 | |
| 401 | 27 | <0.005 | |
| 402 | 27 | 0.0476 | |
| 403 | 27 | 0.0958 | |
| 404 | 27 | 0.0418 | |
| 405 | 27 | 0.0067 | |
| 406 | 27 | 0.0831 | |
| 407 | 27 | <0.005 | 0.0506 |
| 408 | 27 | 0.239 | |
| 409 | 27 | 1.39 | |
| 481 | 27 | 0.244 | |
| 482 | 27 | 0.236 | |
| 483 | 27 | 0.338 | |
| 484 | 27 | 0.696 | |
| 552 | 27 | 0.147 | |
| 560 | 27 | 1.978 | |
| 957 | 27 | <0.005 | <0.005 |
| 960 | 27 | 0.007 | |
| 962 | 27 | <0.00500035 | |
| 963 | 27 | 0.190 | |

BIOLOGICAL DATA TABLE 1-continued

| Cpd | Chemistry Example | MGL mutant inh $IC_{50}$ (μM) | MGL wild type inh $IC_{50}$ (μM) |
|---|---|---|---|
| 967 | 27 | 0.020 | 0.009 |
| 970 | 27 | 0.805 | |
| 972 | 27 | 0.013 | 0.023 |
| 983 | 27 | 0.006 | |
| 987 | 27 | 0.071 | |
| 554 | 27a | 0.179 | |
| 978 | 27a | <0.00500035 | 0.007 |
| 981 | 27a | 0.186 | |
| 958 | 27b | 0.313 | |
| 961 | 27b | 1.122 | |
| 968 | 27b | | 0.019 |
| 979 | 27b | | 0.648 |
| 984 | 27b | | 2.497 |
| 410 | 28 | 0.0253 | |
| 411 | 28 | 0.0478 | |
| 412 | 28 | 0.0249 | |
| 413 | 28 | 0.0406 | |
| 414 | 28 | 0.0144 | |
| 415 | 28 | 0.0110 | |
| 416 | 28 | 0.0129 | |
| 417 | 28 | 0.197 | |
| 418 | 28 | 0.315 | |
| 550 | 28 | 0.114 | |
| 555 | 28 | 0.196 | |
| 973 | 28 | <0.005 | |
| 975 | 28 | 1.174 | 0.162 |
| 974 | 28a | | 0.177 |
| 419 | 29 | 0.0070 | 0.170 |
| 420 | 29 | 0.0112 | |
| 421 | 29 | 0.0060 | |
| 422 | 29 | 0.0568 | |
| 423 | 29 | 0.0050 | |
| 424 | 29 | <0.005 | <0.005 |
| 425 | 29 | 0.160 | |
| 426 | 29 | 0.278 | |
| 662 | 29 | 0.021 | 0.011 |
| 931 | 29a | | |
| 427 | 30 | 0.0334 | |
| 428 | 30 | <0.005 | |
| 429 | 30 | <0.005 | |
| 430 | 30 | 0.0180 | 0.0236 |
| 431 | 30 | <0.005 | |
| 432 | 30 | <0.005 | <0.005 |
| 677 | 30a | | 0.021 |
| 790 | 30a | | 1.417 |
| 433 | 31 | 0.0249 | |
| 508 | 31 | 0.006 | 0.107 |
| 651 | 31 | <0.005 | 0.007 |
| 738 | 31 | 0.065 | 0.289 |
| 876 | 31 | <0.005 | <0.005 |
| 1507 | 31 | >16.6686 | |
| 564 | 31a | 4.633 | 5.400 |
| 971 | 31a | 1.536 | |
| 976 | 31a | 0.566 | 0.574 |
| 977 | 31a | 5.563 | |
| 807 | 31b | | 2.075 |
| 914 | 31c | 0.760 | |
| 1493 | 31c | | >16.6686 |
| 1498 | 31c | | >16.6686 |
| 434 | 32 | 0.0647 | |
| 435 | 32 | 0.0267 | |
| 436 | 32 | 0.331 | |
| 437 | 32 | 1.52 | |
| 438 | 32 | 0.977 | |
| 439 | 33 | 0.672 | |
| 440 | 33 | 4.07 | |
| 441 | 33 | 10.3 | |
| 442 | 33 | 3.78 | |
| 443 | 33 | 3.35 | |
| 444 | 33 | 3.22 | |
| 445 | 33 | 2.28 | |
| 446 | 33 | 2.36 | |
| 447 | 33 | 0.667 | |
| 448 | 33 | 1.90 | |
| 449 | 33 | 8.12 | |
| 450 | 34 | 0.0088 | |
| 451 | 34 | 0.652 | |
| 452 | 34 | 0.288 | |
| 453 | 35 | <0.005 | |
| 454 | 35 | 0.0060 | |
| 455 | 35 | <0.005 | |
| 548 | 35 | 0.027 | |
| 959 | 35 | 0.005 | <0.005 |
| 549 | 35a | 0.104 | |
| 551 | 35a | 0.125 | |
| 956 | 35a | 0.048 | |
| 969 | 35a | 0.077 | |
| 955 | 35b | 0.713 | |
| 964 | 35b | | 1.701 |
| 456 | 36 | 1.98 | |
| 457 | 37 | 0.876 | |
| 458 | 37 | 3.72 | |
| 459 | 37 | 0.950 | |
| 460 | 37 | 0.548 | |
| 497 | 38 | 2.36 | |
| 498 | 38 | 0.679 | |
| 499 | 38 | 0.418 | |
| 500 | 38 | 1.18 | |
| 501 | 38 | >16.7 | |
| 495 | 39 | >16.7 | |
| 491 | 39 | 0.254 | |
| 492 | 39 | 0.0788 | |
| 493 | 39 | 0.169 | |
| 494 | 39 | 0.0771 | |
| 642 | 40 | 0.069 | |
| 645 | 40 | 5.207 | |
| 1488 | 41 | >16.6686 | |
| 1457 | 41 | >16.6686 | |
| 996 | 42 | | <0.005 |
| 997 | 42 | | <0.005 |
| 1006 | 42 | | 0.374 |
| 1016 | 42 | | 0.085 |
| 547 | 42 | | <0.005 |
| 563 | 42 | | 2.493 |
| 985 | 42 | 0.008 | |
| 995 | 42 | | <0.005 |
| 998 | 42 | | <0.005 |
| 999 | 42 | | 0.008 |
| 1007 | 42 | | 0.027 |
| 1008 | 42 | | <0.005 |
| 1009 | 42 | | 0.065 |
| 1013 | 42 | | 0.161 |
| 1014 | 42 | | 0.257 |
| 1015 | 42 | | 0.777 |
| 771 | 42 | | 0.007 |
| 948 | 43 | | 0.011 |
| 949 | 43 | | 0.163 |
| 950 | 43 | | 1.501 |
| 1025 | 43 | | 0.019 |
| 507 | 44 | 0.013 | 0.052 |
| 518 | 44 | | 1.605 |
| 520 | 44 | | 2.027 |
| 522 | 44 | | 2.680 |
| 525 | 44 | | 6.995 |
| 527 | 44 | 3.512 | 8.566 |
| 532 | 44 | 1.419 | |
| 533 | 44 | 1.804 | |
| 537 | 44 | 7.588 | |
| 652 | 44 | | 0.007 |
| 663 | 44 | <0.005 | 0.011 |
| 715 | 44 | | 0.135 |
| 717 | 44 | | 0.147 |
| 734 | 44 | 0.163 | 0.256 |
| 752 | 44 | | 0.421 |
| 765 | 44 | 0.236 | 0.667 |
| 875 | 44 | <0.005 | <0.005 |
| 877 | 44 | 0.012 | <0.005 |
| 904 | 44 | 0.011 | |
| 909 | 44 | 0.074 | |
| 913 | 44 | 0.516 | |
| 1484 | 44 | >16.6686 | |
| 802 | 44a | | 1.721 |
| 837 | 44a | | 5.036 |
| 869 | 44a | | 12.871 |

BIOLOGICAL DATA TABLE 1-continued

| Cpd | Chemistry Example | MGL mutant inh IC$_{50}$ (μM) | MGL wild type inh IC$_{50}$ (μM) |
|---|---|---|---|
| 872 | 44a | | 13.954 |
| 720 | 44b | | 0.173 |
| 757 | 44b | | 0.530 |
| 769 | 44b | | 0.725 |
| 784 | 44b | | 1.125 |
| 922 | 44b | 6.494 | |
| 514 | 45 | | 0.454 |
| 519 | 45 | | 1.620 |
| 521 | 45 | | 2.190 |
| 660 | 45 | | 0.010 |
| 683 | 45 | | 0.031 |
| 708 | 45 | | 0.106 |
| 878 | 45 | | <0.005 |
| 1494 | 45a | >16.6686 | |
| 689 | 45b | | 0.045 |
| 803 | 45b | | 1.868 |
| 811 | 45b | | 2.151 |
| 1010 | 46 | | <0.005 |
| 1011 | 46 | | <0.005 |
| 1018 | 46 | | 0.101 |
| 1019 | 46 | | 0.006 |
| 1021 | 46 | | 0.015 |
| 1023 | 46 | | 0.041 |
| 1024 | 46 | | 0.069 |
| 1267 | 46 | | 1.125 |
| 1304 | 46 | | 6.035 |
| 1309 | 46 | | 9.363 |
| 1012 | 46a | | 0.013 |
| 1020 | 46a | | 0.063 |
| 1022 | 46a | | 0.067 |
| 1311 | 46a | | 14.615 |
| 529 | 47 | 0.147 | |
| 530 | 47 | 0.165 | |
| 542 | 47 | <0.005 | |
| 553 | 47 | 0.176 | |
| 556 | 47 | 0.293 | |
| 557 | 47 | 0.340 | |
| 561 | 47 | 2.745 | |
| 1005 | 47 | | 0.237 |
| 709 | 48 | | 0.118 |
| 671 | 49 | | 0.016 |
| 1365 | 50 | | <0.005 |
| 1417 | 51 | | <0.005 |
| 1418 | 51 | | 0.016 |
| 1063 | 52 | | 0.007 |
| 1092 | 52 | | 0.011 |
| 1315 | 52 | | <0.005 |
| 1316 | 53 | | <0.005 |
| 1317 | 53 | | <0.005 |
| 1319 | 53 | | <0.005 |
| 1142 | 53a | | 0.029 |
| 1318 | 53a | | <0.005 |
| 597 | 54 | | 0.600 |
| 604 | 54 | | 1.841 |
| 1086 | 54 | | 0.009 |
| 1130 | 54 | | 0.022 |
| 1137 | 54 | | 0.026 |
| 1170 | 54 | | 0.059 |
| 1195 | 54 | | 0.120 |
| 884 | 55 | | <0.005 |
| 885 | 55 | | <0.005 |
| 1081 | 55 | | 0.009 |
| 1099 | 55 | | 0.012 |
| 881 | 55a | | <0.005 |
| 882 | 55a | | <0.005 |
| 994 | 55a | | 0.013 |
| 724 | 55b | | 0.206 |
| 773 | 55b | | 0.845 |
| 1026 | 56 | | 0.016 |
| 1027 | 56 | | 0.014 |
| 1028 | 56 | | 0.016 |
| 1033 | 56 | | <0.005 |
| 1034 | 56 | | <0.005 |
| 992 | 57 | | 7.761 |
| 1430 | 57 | | 9.892 |
| 1431 | 57 | 0.589 | |
| 911 | 58 | 0.272 | |
| 988 | 58 | 0.036 | |
| 612 | 59 | 0.016 | |
| 613 | 59 | 0.019 | |
| 614 | 59 | 0.025 | |
| 615 | 59 | 0.026 | |
| 616 | 59 | 0.076 | |
| 706 | 59 | | 0.103 |
| 1074 | 59 | 0.014 | 0.008 |
| 1091 | 59 | 0.011 | 0.011 |
| 1093 | 59 | <0.005 | 0.011 |
| 1104 | 59 | <0.005 | 0.013 |
| 1108 | 59 | 0.019 | 0.014 |
| 1114 | 59 | | 0.016 |
| 1117 | 59 | <0.005 | 0.016 |
| 1124 | 59 | <0.005 | 0.019 |
| 1138 | 59 | | 0.026 |
| 1144 | 59 | 0.006 | 0.031 |
| 1168 | 59 | <0.005 | 0.053 |
| 1172 | 59 | 0.010 | 0.063 |
| 1185 | 59 | 0.007 | 0.088 |
| 1188 | 59 | 0.027 | 0.094 |
| 1200 | 59 | 0.020 | 0.151 |
| 1208 | 59 | <0.005 | 0.190 |
| 1221 | 59 | 0.008 | 0.258 |
| 1228 | 59 | 0.249 | 0.295 |
| 1234 | 59 | 0.024 | 0.356 |
| 1239 | 59 | 0.338 | 0.449 |
| 1240 | 59 | 0.139 | 0.459 |
| 1250 | 59 | 0.174 | 0.638 |
| 1253 | 59 | 0.031 | 0.725 |
| 1259 | 59 | 0.062 | 0.847 |
| 1265 | 59 | 0.072 | 1.050 |
| 1268 | 59 | | 1.220 |
| 1273 | 59 | 0.234 | 1.609 |
| 1278 | 59 | 1.392 | 1.863 |
| 1280 | 59 | 0.239 | 1.978 |
| 1285 | 59 | 1.041 | 2.317 |
| 1288 | 59 | 1.123 | 2.511 |
| 1322 | 59 | <0.005 | <0.005 |
| 1323 | 59 | 0.012 | <0.005 |
| 1377 | 59 | 0.004 | |
| 1405 | 59 | <0.005 | |
| 1406 | 59 | <0.005 | |
| 1136 | 59a | | 0.025 |
| 1161 | 59a | | 0.046 |
| 1162 | 59a | | 0.047 |
| 1212 | 59a | | 0.204 |
| 1260 | 59a | | 0.862 |
| 759 | 60 | | 0.579 |
| 761 | 60 | | 0.583 |
| 780 | 60 | | 0.978 |
| 834 | 60 | | 4.595 |
| 841 | 60 | | 5.257 |
| 851 | 60 | | 7.870 |
| 1064 | 60 | | 0.007 |
| 1167 | 60 | | 0.053 |
| 1186 | 60 | | 0.088 |
| 1207 | 60 | | 0.179 |
| 1231 | 60 | | 0.316 |
| 1270 | 60 | | 1.429 |
| 1274 | 60 | | 1.660 |
| 1281 | 60 | | 2.023 |
| 635 | 60a | | 0.838 |
| 777 | 60a | | 0.913 |
| 789 | 60a | | 1.366 |
| 798 | 60a | | 1.630 |
| 858 | 60a | | 8.772 |
| 866 | 60a | | 10.325 |
| 1206 | 60a | | 0.171 |
| 1215 | 60a | | 0.216 |
| 1227 | 60a | | 0.287 |
| 1229 | 60a | | 0.306 |
| 1264 | 60a | | 0.986 |
| 1289 | 60a | | 2.603 |
| 1291 | 60a | | 2.785 |
| 1296 | 60a | | 3.299 |
| 1506 | 60a | | >16.6686 |

BIOLOGICAL DATA TABLE 1-continued

| Cpd | Chemistry Example | MGL mutant inh $IC_{50}$ (μM) | MGL wild type inh $IC_{50}$ (μM) |
|---|---|---|---|
| 932 | 60b | | 0.104 |
| 933 | 60b | | 0.191 |
| 934 | 60b | | 0.174 |
| 935 | 60b | | 0.100 |
| 936 | 60b | | 0.013 |
| 937 | 60b | | 0.250 |
| 938 | 60b | | 0.698 |
| 939 | 60b | | 2.357 |
| 940 | 60b | | 2.237 |
| 941 | 60b | | 1.372 |
| 942 | 60b | | 0.216 |
| 943 | 60b | | 10.387 |
| 944 | 60b | | 7.322 |
| 945 | 60b | | 1.476 |
| 509 | 61 | | 0.136 |
| 653 | 61 | | 0.007 |
| 895 | 61 | | <0.005 |
| 585 | 62 | | 0.107 |
| 593 | 62 | | 0.311 |
| 701 | 62 | | 0.077 |
| 1084 | 62 | | 0.009 |
| 1100 | 62 | | 0.012 |
| 1132 | 62 | <0.005 | 0.023 |
| 1148 | 62 | | 0.033 |
| 1155 | 62 | | 0.041 |
| 1347 | 62 | | <0.005 |
| 572 | 62a | | 0.031 |
| 634 | 62a | | 0.057 |
| 1340 | 62a | | <0.005 |
| 1341 | 62a | | <0.005 |
| 1344 | 62a | | <0.005 |
| 1345 | 62a | | <0.005 |
| 982 | 63 | 0.010 | <0.005 |
| 986 | 64 | 0.005 | |
| 510 | 65 | | 0.181 |
| 513 | 65 | | 0.371 |
| 528 | 65 | 0.125 | |
| 570 | 65 | | 0.022 |
| 691 | 65 | | 0.046 |
| 695 | 65 | | 0.057 |
| 707 | 65 | | 0.105 |
| 712 | 65 | | 0.127 |
| 714 | 65 | | 0.135 |
| 737 | 65 | | 0.285 |
| 1058 | 65 | | 0.006 |
| 1095 | 65 | | 0.011 |
| 1098 | 65 | | 0.012 |
| 1346 | 65 | | <0.005 |
| 951 | 66 | | 0.540 |
| 506 | 67 | | 0.048 |
| 673 | 67 | | 0.017 |
| 896 | 67 | | <0.005 |
| 512 | 67a | | 0.260 |
| 664 | 67a | | 0.011 |
| 699 | 67a | | 0.069 |
| 505 | 67b | <0.005 | 0.039 |
| 657 | 67b | | 0.009 |
| 674 | 67b | <0.005 | 0.019 |
| 692 | 67b | | 0.047 |
| 899 | 67b | <0.005 | <0.005 |
| 649 | 68 | | 0.006 |
| 700 | 68 | | 0.072 |
| 704 | 68a | | 0.096 |
| 705 | 68a | | 0.099 |
| 574 | 69 | | 0.049 |
| 589 | 69 | | 0.146 |
| 631 | 70 | | 0.040 |
| 632 | 70 | | 0.281 |
| 1069 | 70 | | 0.007 |
| 1348 | 70 | | <0.005 |
| 1349 | 70 | | <0.005 |
| 1111 | 70a | | 0.016 |
| 1350 | 70a | | <0.005 |
| 1076 | 70b | | 0.008 |
| 1355 | 70b | | <0.005 |
| 1414 | 70c | | 0.011 |
| 1415 | 70c | | 0.115 |
| 1416 | 70c | | 0.039 |
| 711 | 71 | | 0.127 |
| 813 | 71 | | 2.422 |
| 1031 | 71 | | 0.111 |
| 1032 | 71 | | 3.020 |
| 1035 | 71 | | 4.622 |
| 1046 | 71 | | 0.288 |
| 1047 | 71 | | 4.628 |
| 1048 | 71 | | 0.695 |
| 1029 | 72 | | <0.005 |
| 1030 | 72 | | 0.013 |
| 1036 | 72 | | <0.005 |
| 1037 | 72 | | 0.005 |
| 1038 | 72 | | <0.005 |
| 1039 | 72 | | 0.005 |
| 1040 | 72 | | 0.025 |
| 1043 | 72 | | 0.016 |
| 1049 | 72 | | 0.010 |
| 1050 | 72 | | 0.024 |
| 1051 | 72 | | 0.128 |
| 1052 | 72 | | 0.028 |
| 1411 | 72 | | 0.012 |
| 1044 | 72a | | 0.718 |
| 1045 | 72a | | 0.021 |
| 1508 | | 0.046 | |

Example 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of Formula (I) (10 μM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-*AG* accumulation in the presence of compound/2-*AG* accumulation in vehicle)×100.

BIOLOGICAL DATA TABLE 2

| | | Rat Brain 2AG % VehCntrl | | | |
|---|---|---|---|---|---|
| Cpd | Chemistry Example | (%) @0.01 μM | (%) @0.1 μM | (%) @1 μM | (%) @10 μM |
| 2 | 1 | | | | 911 |
| 5 | 1 | 122 | 123 | 156 | 279 |
| 6 | 1 | 75 | 238 | 554 | 623 |
| 7 | 1 | | 216 | 238 | 568 |
| 9 | 1 | 99 | 184 | 529 | 1026 |
| 12 | 1 | | | | 448 |
| 13 | 1 | | | | 730 |
| 567 | 1 | | | 455 | |
| 579 | 1 | | | 265 | |
| 581 | 1 | | | 140 | |
| 587 | 1 | | | 148 | |
| 595 | 1 | | | 128 | |
| 1061 | 1 | | | 618 | |
| 1071 | 1 | | | 552 | |
| 1139 | 1 | | | 654 | |

BIOLOGICAL DATA TABLE 2-continued

Rat Brain 2AG % VehCntrl

| Cpd | Chemistry Example | (%) @0.01 μM | (%) @0.1 μM | (%) @1 μM | (%) @10 μM |
|---|---|---|---|---|---|
| 1147 | 1 | | | 892 | |
| 1163 | 1 | | | 244 | |
| 1174 | 1 | | | 1021 | |
| 1201 | 1 | | | 475 | |
| 1356 | 1 | | | 1420 | |
| 1357 | 1 | | | 2570 | |
| 1358 | 1 | | | 1183 | |
| 1359 | 1 | | | 1016 | |
| 1360 | 1 | | | 576 | |
| 1361 | 1 | | | 994 | |
| 1362 | 1 | | | 635 | |
| 1363 | 1 | | | 628 | |
| 1364 | 1 | | | 944 | |
| 1366 | 1 | | | 586 | |
| 1382 | 1 | | | | 293 |
| 1408 | 1 | | | 1475 | |
| 487 | 1a | | 463 | 2081 | 2182 |
| 1062 | 1b | | | 451 | |
| 1072 | 1b | | | 839 | |
| 1073 | 1b | | | 749 | |
| 1089 | 1b | | | 545 | |
| 1097 | 1b | | | 422 | |
| 1105 | 1b | | | 734 | |
| 1107 | 1b | | | 838 | |
| 1120 | 1b | | | 867 | |
| 1126 | 1b | | | 850 | |
| 1134 | 1b | | | 774 | |
| 1135 | 1b | | | 884 | |
| 1176 | 1b | | | 378 | |
| 1181 | 1b | | | 288 | |
| 1312 | 1b | | | 963 | |
| 1337 | 1b | | | 979 | |
| 1338 | 1b | | | 877 | |
| 1339 | 1b | | | 574 | |
| 1184 | 1c | | | 401 | |
| 1141 | 1d | | 148 | 442 | 996 |
| 1151 | 1d | | | 482 | |
| 1158 | 1d | | | 1623 | |
| 1125 | 1e | | | 1228 | |
| 1187 | 1e | | | 319 | |
| 1313 | 1f | | | 851 | |
| 39 | 2 | | 173 | 168 | 277 |
| 40 | 2 | | | | 490 |
| 41 | 2 | | | | 544 |
| 43 | 2 | | | | 215 |
| 44 | 2 | | | | 238 |
| 61 | 3 | | | | 604 |
| 676 | 3 | | | 437 | |
| 703 | 3 | | | 346 | |
| 716 | 3 | | | 326 | |
| 722 | 3 | | | 240 | |
| 741 | 3 | | | 182 | |
| 753 | 3 | | | 173 | |
| 1067 | 3 | | | 408 | |
| 1166 | 3 | | | 176 | |
| 1235 | 3 | | | 100 | |
| 1236 | 3 | | | 167 | |
| 1283 | 3 | | | 62 | |
| 72 | 4 | | | | 334 |
| 75 | 4 | | | | 193 |
| 77 | 4 | | | | 231 |
| 83 | 4 | | | 105 | |
| 133 | 5 | | | | 623 |
| 134 | 5 | | | | 582 |
| 135 | 5 | | | | 592 |
| 136 | 5 | | | | 612 |
| 137 | 5 | | | | 441 |
| 138 | 5 | | | | 661 |
| 147 | 5 | | | | 676 |
| 148 | 5 | | | | 744 |
| 150 | 5 | | | | 1104 |
| 158 | 5 | | | 126 | 213 |
| 161 | 5 | | | 335 | 1280 |
| 162 | 5 | | | | 1099 |
| 163 | 5 | | | | 923 |
| 164 | 5 | | | | 969 |
| 166 | 5 | | | | 509 |
| 167 | 5 | | | | 481 |
| 168 | 5 | | | | 813 |
| 170 | 5 | | | | 205 |
| 172 | 5 | | | | 217 |
| 476 | 5 | | | | 272 |
| 115 | 5 | | | | 579 |
| 485 | 5 | | 208 | 396 | 818 |
| 489 | 5 | 119 | 235 | 790 | 950 |
| 490 | 5 | 208 | 343 | 756 | 886 |
| 636 | 5 | | | | 296 |
| 637 | 5 | | | | 272 |
| 641 | 5 | | | | 397 |
| 648 | 5 | | | | 126 |
| 655 | 5 | | | | 359 |
| 658 | 5 | | | | 351 |
| 667 | 5 | | | | 856 |
| 669 | 5 | | | | 583 |
| 672 | 5 | | | | 268 |
| 675 | 5 | | | | 330 |
| 678 | 5 | | | | 234 |
| 682 | 5 | | | | 390 |
| 687 | 5 | | | | 698 |
| 688 | 5 | | | | 373 |
| 693 | 5 | | | | 299 |
| 696 | 5 | | | | 444 |
| 702 | 5 | | | | 848 |
| 886 | 5 | | | | 823 |
| 887 | 5 | | | | 270 |
| 888 | 5 | | | | 940 |
| 889 | 5 | | | | 683 |
| 890 | 5 | | | | 823 |
| 891 | 5 | | | | 422 |
| 892 | 5 | | | | 948 |
| 893 | 5 | | | | 626 |
| 894 | 5 | | | | 534 |
| 905 | 5 | | | | 119 |
| 965 | 5 | | | | 591 |
| 1017 | 5 | | | | 307 |
| 1082 | 5 | | | | 742 |
| 1083 | 5 | | | | 299 |
| 1103 | 5 | | | | 698 |
| 1122 | 5 | | | | 143 |
| 1150 | 5 | | 139 | 459 | 715 |
| 1156 | 5 | | | | 681 |
| 1164 | 5 | | | | 250 |
| 1179 | 5 | | | | 996 |
| 1326 | 5 | | | | 944 |
| 1327 | 5 | | | | 966 |
| 1328 | 5 | | | | 1086 |
| 1329 | 5 | | | | 834 |
| 1330 | 5 | | | | 589 |
| 1331 | 5 | | | | 803 |
| 1332 | 5 | | | | 1168 |
| 1333 | 5 | | | | 824 |
| 1378 | 5 | | | | 493 |
| 1379 | 5 | | | | 282 |
| 1381 | 5 | | | | 604 |
| 1384 | 5 | | | | 313 |
| 1407 | 5 | | | | 1287 |
| 174 | 6 | | | | 1258 |
| 175 | 6 | | | 330 | 706 | 1180 |
| 176 | 6 | | | | 1124 |
| 177 | 6 | | | | 768 |
| 178 | 6 | | | | 1192 |
| 179 | 6 | | | | 910 |
| 180 | 6 | | | | 703 |
| 181 | 6 | | | | 1236 |
| 182 | 6 | | | | 1500 |
| 183 | 6 | | | | 1090 |
| 184 | 6 | | | | 956 |
| 186 | 6 | 123 | 199 | 260 | 521 |
| 188 | 6 | | | | 506 |
| 195 | 6 | | | | 365 |

BIOLOGICAL DATA TABLE 2-continued

| Cpd | Chemistry Example | Rat Brain 2AG % VehCntrl | | | |
|---|---|---|---|---|---|
| | | (%) @0.01 μM | (%) @0.1 μM | (%) @1 μM | (%) @10 μM |
| 196 | 6 | | | | 516 |
| 205 | 6 | | | | 1172 |
| 207 | 6 | | | | 402 |
| 208 | 6 | | | 480 | 324 |
| 209 | 6 | | | | 1681 |
| 210 | 6 | | | | 122 |
| 211 | 6 | | | | 725 |
| 212 | 6 | | | | 831 |
| 213 | 6 | | | | 104 |
| 214 | 6 | | | | 769 |
| 215 | 6 | | | | 1091 |
| 216 | 6 | | | | 625 |
| 218 | 6 | | | | 764 |
| 219 | 6 | | | | 851 |
| 220 | 6 | | | | 993 |
| 221 | 6 | | | | 945 |
| 223 | 6 | | | | 1261 |
| 224 | 6 | | | | 906 |
| 225 | 6 | | | | 656 |
| 226 | 6 | | | | 652 |
| 227 | 6 | | | | 938 |
| 228 | 6 | | | | 710 |
| 229 | 6 | | 276 | 552 | 1304 |
| 230 | 6 | | | | 567 |
| 232 | 6 | | | 152 | 427 |
| 237 | 6 | | | 1044 | 1182 |
| 239 | 6 | 153 | 290 | 1097 | 1353 |
| 240 | 6 | | 184 | 538 | 639 |
| 243 | 6 | | | 120 | |
| 245 | 6 | | 224 | 518 | 829 |
| 248 | 6 | | | 312 | |
| 250 | 6 | 180 | 472 | 1011 | 1327 |
| 251 | 6 | | 144 | 586 | 791 |
| 253 | 6 | | 107 | 319 | 624 |
| 254 | 6 | | | 544 | |
| 255 | 6 | | | 115 | |
| 256 | 6 | | | 157 | |
| 257 | 6 | | | 285 | |
| 259 | 6 | | | 156 | |
| 260 | 6 | | | 140 | |
| 261 | 6 | | 148 | 525 | 856 |
| 262 | 6 | | | 386 | |
| 263 | 6 | | | 199 | |
| 264 | 6 | | | 172 | |
| 265 | 6 | | 126 | 162 | 643 |
| 266 | 6 | | | 395 | |
| 267 | 6 | | | 130 | |
| 268 | 6 | | | 110 | |
| 488 | 6 | | 219 | 247.5 | 681 |
| 1070 | 6 | | | 551 | |
| 1102 | 6 | | | 878 | |
| 273 | 7 | | | | 623 |
| 274 | 7 | | | | 876 |
| 281 | 7 | | | | 201 |
| 282 | 7 | | | | 1775 |
| 283 | 7 | | | | 605 |
| 291 | 7 | | | | 1019 |
| 310 | 8 | | | 141 | |
| 311 | 8 | | | 125 | |
| 312 | 8 | | | 198 | |
| 1140 | 8 | | | 200 | |
| 1325 | 8 | | | 575 | |
| 186-A | 8 | | | 149 | |
| 1465 | 8 | | | 110 | |
| 313 | 9 | | | | 814 |
| 314 | 9 | 175 | 237 | 512 | 553 |
| 316 | 9 | 243 | 265 | 760 | 694 |
| 317 | 9 | | | 417 | |
| 318 | 9 | | | 537 | |
| 319 | 9 | | | 396 | |
| 321 | 9 | | | 230 | |
| 654 | 9 | | | 389 | |
| 681 | 9 | | | 406 | |
| 713 | 9 | | | | |
| 718 | 9 | | | | |
| 723 | 9 | | | | |
| 745 | 9 | | | | |
| 767 | 9 | | | | |
| 775 | 9 | | | | |
| 806 | 9 | | | | |
| 812 | 9 | | | | |
| 817 | 9 | | | | |
| 820 | 9 | | | | |
| 822 | 9 | | | | |
| 829 | 9 | | | | |
| 832 | 9 | | | | |
| 856 | 9 | | | | |
| 918 | 9 | | | | |
| 1054 | 9 | | | | 1008 |
| 1055 | 9 | | | | 701 |
| 1056 | 9 | | | | 498 |
| 1068 | 9 | | | | 849 |
| 1077 | 9 | | | | 667 |
| 1088 | 9 | | | | 760 |
| 1090 | 9 | | | | |
| 1106 | 9 | | | | 784 |
| 1110 | 9 | | | | 807 |
| 1116 | 9 | | | | 828 |
| 1129 | 9 | | | | 437 |
| 1131 | 9 | | | | 563 |
| 1152 | 9 | | | | 394 |
| 1153 | 9 | | | | 404 |
| 1178 | 9 | | | | 292 |
| 1198 | 9 | | | | |
| 1224 | 9 | | | | |
| 1226 | 9 | | | | |
| 1233 | 9 | | | | |
| 1261 | 9 | | | | |
| 1275 | 9 | | | | |
| 1277 | 9 | | | | |
| 1279 | 9 | | | | |
| 1286 | 9 | | | | |
| 1295 | 9 | | | | |
| 1302 | 9 | | | | |
| 1306 | 9 | | | | |
| 1320 | 9 | | | | 823 |
| 1367 | 9 | | | | 798 |
| 1368 | 9 | | | | 859 |
| 1369 | 9 | | | | 874 |
| 1370 | 9 | | | | 773 |
| 1371 | 9 | | | | 827 |
| 120 | 9b | | | | 483 |
| 126 | 9b | 128 | 138 | 328 | 715 |
| 128 | 9b | | | | 688 |
| 129 | 9b | | | 499 | |
| 131 | 9b | | | | 1406 |
| 569 | 9b | | | | 198 |
| 571 | 9b | | | | 307 |
| 573 | 9b | | | | 277 |
| 577 | 9b | | | | 207 |
| 580 | 9b | | | | 179 |
| 582 | 9d | | | | 169 |
| 1109 | 9d | | | | 680 |
| 1113 | 9d | | | | 819 |
| 1133 | 9d | | | | 296 |
| 1159 | 9d | | | | 654 |
| 1171 | 9d | | | | 839 |
| 1177 | 9d | | | | 895 |
| 1182 | 9d | | | | 547 |
| 1255 | 9i | | | | 147 |
| 1154 | 9j | | | | 558 |
| 1173 | 9j | | | | 133 |
| 1190 | 9j | | | | 126 |
| 1254 | 9j | | | | 187 |
| 1282 | 9j | | | | 128 |
| 323 | 10 | | | | 494 |
| 324 | 10 | | 941 | 1215 | 1265 |
| 325 | 10 | | | | 478 |
| 686 | 10 | | | | 552 |
| 650 | 10a | | | | 960 |

BIOLOGICAL DATA TABLE 2-continued

Rat Brain 2AG % VehCntrl

| Cpd | Chemistry Example | (%) @0.01 μM | (%) @0.1 μM | (%) @1 μM | (%) @10 μM |
|---|---|---|---|---|---|
| 666 | 10a | | | 359 | |
| 670 | 10a | | | 650 | |
| 900 | 10a | | | 543 | |
| 659 | 10b | | | 576 | |
| 697 | 10b | | | 431 | |
| 901 | 10b | | | 816 | |
| 902 | 10b | | | 585 | |
| 326 | 11 | | | 1336 | |
| 327 | 11 | | | 904 | 2005 |
| 328 | 11 | | | 378 | |
| 329 | 11 | | | | 520 |
| 330 | 11 | | | 197 | |
| 331 | 11 | | | 310 | |
| 332 | 11 | | | 182 | |
| 333 | 11 | | | 291 | |
| 334 | 11 | | | 259 | |
| 335 | 11 | 170 | 438 | 839 | 1059 |
| 336 | 11 | | | 223 | |
| 337 | 11 | 103 | 166 | 272 | 671 |
| 504 | 11 | | | 178.5 | |
| 543 | 11 | | | 158 | |
| 684 | 11 | | | 645 | |
| 897 | 11 | | | 1234 | |
| 898 | 11 | | | 520 | |
| 908 | 11 | | | 217 | |
| 929 | 11 | | | 301 | |
| 930 | 11 | | | 807 | |
| 338 | 12 | | | 2111 | 791 |
| 342 | 12 | | | | 288 |
| 343 | 13 | | | 1371 | |
| 344 | 13 | | | 238 | |
| 345 | 13 | | | 744 | |
| 347 | 14 | | | 125 | |
| 1059 | 14 | | | 507 | |
| 1060 | 14 | | | 671 | |
| 1065 | 14 | | | 531 | |
| 1066 | 14 | | | 609 | |
| 1096 | 14 | | | 449 | |
| 1101 | 14 | | | 501 | |
| 1157 | 14 | | | 252 | |
| 1160 | 14 | | | 260 | |
| 1183 | 14 | | | 549 | |
| 1342 | 14 | | | 346 | |
| 1343 | 14 | | | 838 | |
| 1351 | 14 | | | 718 | |
| 1352 | 14 | | | 548 | |
| 1353 | 14 | | | 545 | |
| 1354 | 14 | | | 750 | |
| 1075 | 14a | | | 833 | |
| 350 | 17 | | | | 498 |
| 903 | 17a | | | 908 | |
| 690 | 17b | | | 367 | |
| 357 | 20 | | | 152 | |
| 358 | 21 | | | 556 | |
| 359 | 21 | | | 176 | |
| 360 | 21 | | | 819 | |
| 361 | 21 | | | 186 | |
| 364 | 21 | | | 581 | |
| 365 | 21 | | | 971 | |
| 665 | 21 | | | 507 | |
| 679 | 21 | | | 751 | |
| 685 | 21 | | | 756 | |
| 736 | 21 | | | 499 | |
| 907 | 21 | | | 867 | |
| 366 | 22 | | | 432 | |
| 367 | 22 | | | 701 | |
| 368 | 22 | | | 434 | |
| 906 | 22 | | | 896 | |
| 927 | 22 | | | 850 | |
| 928 | 22 | | | 1207 | |
| 370 | 23 | | | 888 | |
| 371 | 23 | | | 1138 | |
| 879 | 23 | | | 1027 | |
| 880 | 23 | | | 945 | |
| 680 | 23a | | | 356 | |
| 661 | 24 | | | 764 | |
| 668 | 24 | | | 679 | |
| 883 | 24 | | | 767 | |
| 379 | 26 | | | | 760 |
| 380 | 26 | | | | 773 |
| 381 | 26 | | | | 520 |
| 397 | 27 | | | | 243 |
| 398 | 27 | | | 392 | |
| 400 | 27 | | | | 1076 |
| 401 | 27 | | | | 762 |
| 402 | 27 | | | 97 | |
| 403 | 27 | | | 188 | |
| 405 | 27 | | | | 1591 |
| 406 | 27 | | | 99 | |
| 407 | 27 | | 127 | 441 | 743 |
| 957 | 27 | | | 1442 | |
| 960 | 27 | | | 896 | |
| 962 | 27 | | | 1213 | |
| 967 | 27 | | | 1373 | |
| 972 | 27 | | | 683 | |
| 983 | 27 | | | 194 | |
| 987 | 27 | | | 320 | |
| 978 | 27a | | | 570 | |
| 968 | 27b | | | 360 | |
| 410 | 28 | | | | 720 |
| 411 | 28 | | | | 741 |
| 412 | 28 | | | | 1271 |
| 413 | 28 | | | | 1693 |
| 414 | 28 | | | | 1608 |
| 415 | 28 | | | | 1629 |
| 416 | 28 | | | 228 | |
| 973 | 28 | | | 806 | |
| 419 | 29 | | | 109 | |
| 422 | 29 | | | 120 | |
| 423 | 29 | | | 529 | |
| 424 | 29 | | | 436 | |
| 662 | 29 | | | 274.5 | |
| 427 | 30 | | | 163 | |
| 428 | 30 | | | 734 | |
| 429 | 30 | | | 318 | |
| 430 | 30 | | | 114 | |
| 431 | 30 | | | 703 | |
| 432 | 30 | | | 321 | |
| 677 | 30a | | | 141 | |
| 433 | 31 | | | 159 | |
| 508 | 31 | | | 119 | |
| 651 | 31 | | | 258 | |
| 876 | 31 | | | 363 | |
| 434 | 32 | | | | 737 |
| 435 | 32 | | | | 198 |
| 453 | 35 | | | 917 | |
| 454 | 35 | | | 1066 | |
| 455 | 35 | | | 1013 | |
| 548 | 35 | | | 280 | |
| 959 | 35 | | | 861 | |
| 956 | 35a | | | 514 | |
| 969 | 35a | | | 515 | |
| 494 | 39 | | | | 1121 |
| 642 | 40 | | | 170 | |
| 996 | 42 | | | 458 | |
| 997 | 42 | | | 761 | |
| 1016 | 42 | | | 536 | |
| 547 | 42 | | | 652 | |
| 985 | 42 | | | 1116 | |
| 995 | 42 | | | 1080 | |
| 998 | 42 | | | 639 | |
| 999 | 42 | | | 458 | |
| 1007 | 42 | | | 180 | |
| 1008 | 42 | | | 1125 | |
| 1009 | 42 | | | 706 | |
| 771 | 42.9 | | | 465 | |
| 1025 | 43 | | | 851 | |
| 507 | 44 | | | 190 | |
| 518 | 44 | | | 86 | |
| 663 | 44 | | | 588 | |

BIOLOGICAL DATA TABLE 2-continued

| Cpd | Chemistry Example | Rat Brain 2AG % VehCntrl (%) @0.01 μM | (%) @0.1 μM | (%) @1 μM | (%) @10 μM |
|---|---|---|---|---|---|
| 875 | 44 | | 232 | 499 | 1285 |
| 877 | 44 | | | 475 | |
| 904 | 44 | | | 392 | |
| 909 | 44 | | | 144 | |
| 660 | 45 | | | 410 | |
| 683 | 45 | | | 335 | |
| 878 | 45 | | | 288 | |
| 689 | 45b | | | 136 | |
| 1010 | 46 | | | 1953 | |
| 1011 | 46 | | | 994 | |
| 1019 | 46 | | | 287 | |
| 1021 | 46 | | | 232 | |
| 1023 | 46 | | | 262 | |
| 1024 | 46 | | | 281 | |
| 1012 | 46a | | | 173 | |
| 1020 | 46a | | | 135 | |
| 1022 | 46a | | | 189 | |
| 542 | 47 | | | 366 | |
| 671 | 49 | | | 1035 | |
| 1365 | 50 | | | 909 | |
| 1063 | 52 | | | 846 | |
| 1092 | 52 | | | 838 | |
| 1315 | 52 | | | 486 | |
| 1316 | 53 | | | 602 | |
| 1317 | 53 | | | 722 | |
| 1319 | 53 | | | 1276 | |
| 1142 | 53a | | | 1314 | |
| 1318 | 53a | | | 1282 | |
| 1086 | 54 | | | 488 | |
| 1130 | 54 | | | 553 | |
| 1137 | 54 | | | 582 | |
| 1170 | 54 | | | 258 | |
| 884 | 55 | | | 425 | |
| 885 | 55 | | | 722 | |
| 1081 | 55 | | | 622 | |
| 1099 | 55 | | | 508 | |
| 881 | 55a | | | 847 | |
| 882 | 55a | | | 697 | |
| 994 | 55a | | | 1014 | |
| 1026 | 56 | | | 1014 | |
| 1027 | 56 | | | 785 | |
| 1028 | 56 | | | 647 | |
| 612 | 59 | | | 106 | |
| 613 | 59 | | | 165 | |
| 614 | 59 | | | 87 | |
| 615 | 59 | | | 123 | |
| 616 | 59 | | | 92 | |
| 1074 | 59 | | | 303 | |
| 1091 | 59 | | | 450 | |
| 1093 | 59 | | | 472 | |
| 1104 | 59 | | | 334 | |
| 1108 | 59 | | 117 | 204 | 456 |
| 1114 | 59 | | | 293 | |
| 1117 | 59 | | | 437 | |
| 1124 | 59 | | | 506 | |
| 1138 | 59 | | | 271 | |
| 1144 | 59 | | | 212 | |
| 1168 | 59 | | | 780 | |
| 1172 | 59 | | | 931 | |
| 1185 | 59 | | | 241 | |
| 1188 | 59 | | | 187 | |
| 1200 | 59 | | | 231 | |
| 1208 | 59 | | | 212 | |
| 1221 | 59 | | 198 | 197.5 | 522 |
| 1234 | 59 | | | 226 | |
| 1253 | 59 | | 110 | 190 | 407 |
| 1259 | 59 | | | 159 | |
| 1265 | 59 | | | 192 | |
| 1322 | 59 | | | 457 | |
| 1323 | 59 | | | 297 | |
| 1405 | 59 | | | 197 | |
| 1406 | 59 | | | 169 | |
| 1136 | 59a | | | 325 | |
| 1161 | 59a | | | 459 | |
| 1162 | 59a | | | 237 | |
| 1064 | 60 | | | 570 | |
| 1167 | 60 | | | 345 | |
| 1186 | 60 | | | 393 | |
| 509 | 61 | | | 242 | |
| 653 | 61 | | | 861 | |
| 895 | 61 | | | 1207 | |
| 701 | 62 | | | 475 | |
| 1084 | 62 | | | 1165 | |
| 1100 | 62 | | | 1133 | |
| 1132 | 62 | | | 1259 | |
| 1148 | 62 | | | 344 | |
| 1155 | 62 | | | 617 | |
| 1347 | 62 | | | 741 | |
| 572 | 62a | | | 397 | |
| 634 | 62a | | | 301 | |
| 1340 | 62a | | | 761 | |
| 1341 | 62a | | | 1149 | |
| 1344 | 62a | | | 543 | |
| 1345 | 62a | | | 459 | |
| 982 | 63 | | | 762 | |
| 986 | 64 | | | 626 | |
| 570 | 65 | | | 210 | |
| 691 | 65 | | | 840 | |
| 695 | 65 | | | 497 | |
| 1058 | 65 | | | 590 | |
| 1095 | 65 | | | 484 | |
| 1098 | 65 | | | 296 | |
| 1346 | 65 | | | 406 | |
| 506 | 67 | | | 132 | |
| 673 | 67 | | | 280 | |
| 896 | 67 | | | 648 | |
| 664 | 67a | | | 498 | |
| 699 | 67a | | | 253 | |
| 505 | 67b | | | 236.5 | |
| 657 | 67b | | | 581 | |
| 674 | 67b | | | 891 | |
| 692 | 67b | | | 284 | |
| 899 | 67b | | | 1092 | |
| 649 | 68 | | | 1017 | |
| 700 | 68 | | | 547 | |
| 705 | 68a | | | 487 | |
| 574 | 69 | | | 207 | |
| 1069 | 70 | | | 696 | |
| 1348 | 70 | | | 1428 | |
| 1349 | 70 | | | 846 | |
| 1111 | 70a | | | 508 | |
| 1350 | 70a | | | 873 | |

Example 3

MGL ThermoFluor® Assay—Mutant

The ThermoFluor (TF) assay is a 384-well plate-based binding assay that measures thermal stability of proteins[1,2]. The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-response experiments, the compound aliquots (46 nL) were robotically predisposed directly into 384-well black assay plates (Abgene: TF-0384/k) using the Hummingbird liquid handler. Following compound dispension, protein and dye solutions were added to achieve the final assay volume of 3 µL. The assay solutions were overlayed with 1 µL of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >60D cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

The $K_d$ values for compounds of Formula (I) were determined from a fit of the equation to the concentration-response plot of the fractional activity as a function of $T_m$. For some experiments, quantitative NMR spectroscopy (qNMR) was used to measure concentration of the initial 100% DMSO compound solutions and, using the same fitting method, $qK_d$ values were determined

BIOLOGICAL DATA TABLE 3

| Cpd | Example | MGL mutant ThermoFluor Kd (µM) | MGL mutant ThermoFluor qKd (µM) (using qNMR conc.) |
| --- | --- | --- | --- |
| 1 | 1 | 0.00590 | |
| 2 | 1 | 0.00049 | |
| 3 | 1 | 2.50 | |
| 4 | 1 | 0.143 | |
| 5 | 1 | 0.0548 | |
| 6 | 1 | 0.00360 | |
| 7 | 1 | 0.0466 | |
| 8 | 1 | 0.111 | |
| 9 | 1 | 0.00248 | |
| 10 | 1 | 0.556 | |
| 11 | 1 | 0.454 | |
| 12 | 1 | 0.0143 | |
| 13 | 1 | 0.00300 | |
| 14 | 1 | 0.250 | |
| 15 | 1 | 0.286 | |
| 22 | 1 | >76.7 | |
| 23 | 1 | 5.00 | |
| 24 | 1 | 5.00 | |
| 25 | 1 | 10.0 | |
| 26 | 1 | 3.33 | |
| 567 | 1 | 0.051 | |
| 579 | 1 | 0.067 | |
| 581 | 1 | 0.100 | |
| 587 | 1 | 0.473 | |
| 595 | 1 | 0.404 | |
| 598 | 1 | 0.249 | |
| 1071 | 1 | 0.025 | |
| 1139 | 1 | 0.017 | |
| 1147 | 1 | 0.003 | |
| 1163 | 1 | 0.073 | |
| 1174 | 1 | 0.015 | |
| 1201 | 1 | 0.179 | |
| 1248 | 1 | 0.043 | |
| 1356 | 1 | 0.002 | |
| 1357 | 1 | 0.002 | |
| 1358 | 1 | 0.007 | |
| 1359 | 1 | 0.008 | |
| 1360 | 1 | 0.008 | |
| 1361 | 1 | 0.003 | |
| 1362 | 1 | 0.001 | |
| 1363 | 1 | 0.014 | |
| 1364 | 1 | 0.001 | |
| 1366 | 1 | 0.012 | |
| 1382 | 1 | 0.197 | |
| 1408 | 1 | 0.012 | |
| 487 | 1a | 0.00240 | |
| 586 | 1b | | 0.086 |
| 596 | 1b | | 0.628 |
| 603 | 1b | | 0.448 |
| 630 | 1b | | 0.195 |
| 1062 | 1b | | 0.100 |
| 1072 | 1b | | 0.007 |
| 1073 | 1b | | 0.087 |
| 1089 | 1b | 0.009 | 0.006 |
| 1097 | 1b | 0.032 | |
| 1105 | 1b | | 0.023 |
| 1107 | 1b | | 0.003 |
| 1120 | 1b | | 0.020 |
| 1121 | 1b | | 0.042 |
| 1126 | 1b | | 0.008 |
| 1127 | 1b | | 0.098 |
| 1128 | 1b | | 0.018 |
| 1134 | 1b | | 0.009 |
| 1135 | 1b | | 0.015 |
| 1176 | 1b | | 0.161 |
| 1181 | 1b | | 0.278 |
| 1189 | 1b | | 0.153 |
| 1192 | 1b | | 0.035 |
| 1197 | 1b | | 0.065 |
| 1216 | 1b | | 0.022 |
| 1219 | 1b | | 0.025 |
| 1230 | 1b | 0.009 | |
| 1247 | 1b | | 0.650 |
| 1263 | 1b | | 0.215 |
| 1312 | 1b | | 0.008 |
| 1314 | 1b | | 0.001 |
| 1337 | 1b | 0.040 | |
| 1338 | 1b | 0.015 | |
| 1339 | 1b | 0.013 | |
| 1410 | 1b | | 0.014 |
| 656 | 1c | | 0.101 |
| 1079 | 1c | | 0.272 |
| 1184 | 1c | | 0.244 |
| 1199 | 1c | | 0.264 |
| 1141 | 1d | 0.088 | |
| 1151 | 1d | 0.048 | |
| 1158 | 1d | 0.008 | |
| 592 | 1e | 0.500 | |
| 1125 | 1e | 0.037 | |
| 1187 | 1e | 0.197 | |
| 629 | 1f | 0.145 | |
| 1180 | 1f | | 0.019 |
| 1313 | 1f | 0.003 | 0.001 |
| 1409 | 1g | | |
| 27 | 2 | 4.55 | |
| 28 | 2 | 0.370 | |
| 29 | 2 | 0.100 | |
| 30 | 2 | 0.118 | |
| 31 | 2 | 1.43 | |
| 32 | 2 | 0.192 | |
| 33 | 2 | 0.00910 | |
| 34 | 2 | 0.588 | |
| 35 | 2 | 0.0833 | |
| 36 | 2 | 0.0370 | |
| 37 | 2 | 0.100 | |
| 38 | 2 | 0.182 | |
| 39 | 2 | 0.0250 | |
| 40 | 2 | 0.0242 | |

BIOLOGICAL DATA TABLE 3-continued

| Cpd | Example | MGL mutant ThermoFluor Kd (µM) | MGL mutant ThermoFluor qKd (µM) (using qNMR conc.) |
|---|---|---|---|
| 41 | 2 | 0.00400 | |
| 42 | 2 | 0.0833 | |
| 47 | 2 | 0.0909 | |
| 48 | 2 | 1.00 | |
| 49 | 2 | 6.67 | |
| 50 | 2 | 10.0 | |
| 51 | 2 | 0.250 | |
| 52 | 2 | 3.33 | |
| 53 | 2 | 0.100 | |
| 55 | 2 | 25.0 | |
| 470 | 2 | 2.94 | |
| 471 | 2 | 2.50 | |
| 472 | 2 | 6.67 | |
| 531 | 2 | 2.733 | |
| 539 | 2 | >31.2464 | |
| 541 | 2 | 1.662 | |
| 559 | 2 | 100.000 | |
| 562 | 2 | >31.2464 | |
| 565 | 2 | >31.2464 | |
| 622 | 2 | 3.601 | |
| 627 | 2 | 10.000 | |
| 628 | 2 | 100.000 | |
| 954 | 2 | | 3.438 |
| 1266 | 2 | 0.032 | |
| 1284 | 2 | 0.041 | |
| 1404 | 2 | >31.2464 | |
| 1482 | 2 | >31.2464 | |
| 1483 | 2 | >31.2464 | |
| 1485 | 2 | 10.000 | |
| 1464 | 2 | >31.2464 | |
| 61 | 3 | 0.0290 | |
| 676 | 3 | 0.029 | |
| 703 | 3 | 0.050 | |
| 716 | 3 | 0.040 | |
| 722 | 3 | 0.082 | |
| 741 | 3 | 0.200 | |
| 753 | 3 | 0.515 | |
| 921 | 3 | 4.260 | |
| 1067 | 3 | 0.007 | |
| 1166 | 3 | 0.010 | |
| 1235 | 3 | 0.124 | |
| 1236 | 3 | 0.031 | |
| 1242 | 3 | 0.197 | |
| 1243 | 3 | 0.033 | |
| 1246 | 3 | 0.042 | |
| 1276 | 3 | 0.807 | |
| 1283 | 3 | 0.523 | |
| 1292 | 3 | 0.631 | |
| 1383 | 3 | 0.108 | |
| 1400 | 3 | 4.071 | |
| 1401 | 3 | 1.250 | |
| 1402 | 3 | 2.000 | |
| 76 | 4 | 0.333 | |
| 77 | 4 | 0.00909 | |
| 78 | 4 | 0.0800 | |
| 79 | 4 | 0.0266 | |
| 80 | 4 | 49.5 | |
| 81 | 4 | 0.0667 | |
| 82 | 4 | 0.571 | |
| 83 | 4 | 0.111 | |
| 474 | 4 | 5.00 | |
| 103 | 4 | 6.25 | |
| 104 | 4 | 5.00 | |
| 105 | 4 | 5.00 | |
| 106 | 4 | 0.154 | |
| 107 | 4 | 0.556 | |
| 108 | 4 | 1.25 | |
| 109 | 4 | 0.0333 | |
| 110 | 4 | 5.00 | |
| 111 | 4 | 10.0 | |
| 496 | 4 | 0.287 | |
| 558 | 4 | 0.333 | |
| 618 | 4 | 0.080 | |
| 619 | 4 | 0.172 | |
| 620 | 4 | 0.154 | |
| 621 | 4 | 0.263 | |
| 623 | 4 | 1.000 | |
| 624 | 4 | 0.880 | |
| 625 | 4 | >31.2464 | |
| 626 | 4 | 5.018 | |
| 150 | 5 | 0.00330 | |
| 151 | 5 | 0.0250 | |
| 158 | 5 | 0.476 | |
| 161 | 5 | 0.0112 | |
| 162 | 5 | 0.00067 | |
| 163 | 5 | 0.00345 | |
| 164 | 5 | 0.00111 | |
| 166 | 5 | 0.00500 | |
| 167 | 5 | 0.0558 | |
| 168 | 5 | 0.0100 | |
| 169 | 5 | 30.3 | |
| 170 | 5 | 0.0606 | |
| 171 | 5 | 0.708 | |
| 172 | 5 | 0.100 | |
| 475 | 5 | 0.0250 | |
| 476 | 5 | 0.0667 | |
| 477 | 5 | 2.00 | |
| 478 | 5 | 2.00 | |
| 479 | 5 | 6.67 | |
| 298 | 5 | 2.91 | |
| 113 | 5 | 1.11 | |
| 114 | 5 | 0.00333 | |
| 115 | 5 | 0.0370 | |
| 116 | 5 | 2.00 | |
| 489 | 5 | 0.0104 | |
| 490 | 5 | 0.00840 | |
| 485 | 5 | 0.0257 | |
| 502 | 5 | >76.6655 | |
| 503 | 5 | 0.254 | |
| 517 | 5 | 0.050 | |
| 523 | 5 | 0.686 | |
| 524 | 5 | 1.667 | |
| 526 | 5 | 4.984 | |
| 610 | 5 | 1.295 | |
| 611 | 5 | 5.152 | |
| 636 | 5 | 0.119 | |
| 637 | 5 | 0.053 | |
| 638 | 5 | 0.172 | 0.264 |
| 639 | 5 | 0.132 | |
| 640 | 5 | 24.998 | |
| 641 | 5 | 0.118 | 0.136 |
| 643 | 5 | 1.000 | |
| 644 | 5 | >76.6655 | |
| 646 | 5 | 1.608 | |
| 648 | 5 | 0.146 | |
| 655 | 5 | 0.029 | |
| 658 | 5 | | 0.402 |
| 667 | 5 | 0.013 | |
| 669 | 5 | 0.005 | |
| 672 | 5 | 0.016 | |
| 675 | 5 | | 0.025 |
| 678 | 5 | 0.031 | |
| 682 | 5 | | 0.014 |
| 687 | 5 | 0.004 | |
| 688 | 5 | 0.046 | |
| 693 | 5 | 0.060 | |
| 694 | 5 | | 0.048 |
| 696 | 5 | | 0.063 |
| 698 | 5 | | 0.085 |
| 702 | 5 | | 0.207 |
| 710 | 5 | | 0.197 |
| 719 | 5 | | 0.119 |
| 721 | 5 | 1.138 | |
| 726 | 5 | 0.127 | |
| 727 | 5 | | 0.251 |
| 728 | 5 | | |
| 730 | 5 | | 0.146 |
| 731 | 5 | 0.016 | |
| 732 | 5 | 0.002 | |
| 733 | 5 | | 0.453 |
| 735 | 5 | 0.160 | |
| 739 | 5 | | 0.265 |

BIOLOGICAL DATA TABLE 3-continued

| Cpd | Example | MGL mutant ThermoFluor Kd (µM) | MGL mutant ThermoFluor qKd (µM) (using qNMR conc.) |
|---|---|---|---|
| 740 | 5 | 0.035 | |
| 743 | 5 | | 0.133 |
| 744 | 5 | | |
| 746 | 5 | | 0.263 |
| 747 | 5 | 0.111 | |
| 748 | 5 | 0.040 | |
| 750 | 5 | 0.025 | |
| 751 | 5 | 1.320 | |
| 755 | 5 | 0.328 | |
| 756 | 5 | 0.383 | |
| 758 | 5 | | 0.500 |
| 760 | 5 | 0.199 | |
| 762 | 5 | | 1.000 |
| 763 | 5 | 0.083 | |
| 766 | 5 | | 0.378 |
| 770 | 5 | | 1.132 |
| 772 | 5 | 0.185 | |
| 774 | 5 | | 0.254 |
| 776 | 5 | 0.257 | |
| 779 | 5 | 0.100 | |
| 782 | 5 | | 0.463 |
| 783 | 5 | | 0.732 |
| 785 | 5 | 0.500 | |
| 786 | 5 | | 0.665 |
| 787 | 5 | | 0.247 |
| 788 | 5 | | 1.980 |
| 791 | 5 | | 0.402 |
| 792 | 5 | | 0.973 |
| 793 | 5 | 0.198 | |
| 794 | 5 | 2.113 | |
| 795 | 5 | 1.105 | |
| 796 | 5 | 0.099 | |
| 797 | 5 | | 0.489 |
| 799 | 5 | 0.661 | |
| 800 | 5 | 1.100 | |
| 804 | 5 | 0.105 | |
| 808 | 5 | 62.503 | |
| 809 | 5 | 0.769 | |
| 814 | 5 | >31.0027 | |
| 815 | 5 | 0.250 | |
| 816 | 5 | | 2.842 |
| 818 | 5 | 1.000 | |
| 823 | 5 | | 1.251 |
| 824 | 5 | | 0.074 |
| 825 | 5 | | 4.855 |
| 826 | 5 | | 0.663 |
| 827 | 5 | 0.500 | |
| 828 | 5 | 2.633 | |
| 830 | 5 | | 1.963 |
| 831 | 5 | 0.270 | |
| 835 | 5 | | 2.454 |
| 836 | 5 | | 2.252 |
| 838 | 5 | 0.978 | |
| 839 | 5 | | 2.500 |
| 840 | 5 | 2.000 | |
| 842 | 5 | 0.986 | |
| 843 | 5 | 2.134 | |
| 844 | 5 | 62.503 | |
| 845 | 5 | | 1.619 |
| 848 | 5 | 0.833 | |
| 849 | 5 | 2.697 | |
| 850 | 5 | 1.000 | |
| 852 | 5 | | 1.977 |
| 853 | 5 | 1.000 | |
| 854 | 5 | 100.000 | |
| 857 | 5 | 3.334 | |
| 859 | 5 | 1.429 | |
| 860 | 5 | 1.759 | |
| 862 | 5 | >21.8726 | |
| 863 | 5 | | 4.367 |
| 864 | 5 | 2.410 | |
| 865 | 5 | | 2.500 |
| 868 | 5 | | >23.126 |
| 873 | 5 | | 9.198 |
| 874 | 5 | | 8.461 |
| 887 | 5 | 0.009 | |
| 888 | 5 | 0.000 | |
| 889 | 5 | 0.002 | |
| 890 | 5 | 0.001 | |
| 891 | 5 | 0.008 | |
| 892 | 5 | 0.007 | |
| 893 | 5 | 0.005 | |
| 894 | 5 | 0.006 | |
| 905 | 5 | 0.044 | |
| 910 | 5 | 1.331 | |
| 912 | 5 | 1.319 | |
| 915 | 5 | 5.000 | |
| 923 | 5 | 9.931 | |
| 925 | 5 | >62.5029 | |
| 926 | 5 | 9.443 | |
| 946 | 5 | | 1.693 |
| 947 | 5 | | 0.653 |
| 952 | 5 | | 0.019 |
| 953 | 5 | | >26.872 |
| 965 | 5 | 0.035 | |
| 966 | 5 | 0.334 | |
| 993 | 5 | 0.333 | |
| 1017 | 5 | 0.049 | |
| 1041 | 5 | | 0.397 |
| 1042 | 5 | | 5.000 |
| 1053 | 5 | | 0.247 |
| 1082 | 5 | 0.003 | |
| 1083 | 5 | | 0.065 |
| 1119 | 5 | | 0.020 |
| 1122 | 5 | 0.027 | |
| 1123 | 5 | | 1.351 |
| 1146 | 5 | | 0.080 |
| 1150 | 5 | 0.013 | |
| 1156 | 5 | 0.090 | |
| 1179 | 5 | 0.005 | |
| 1194 | 5 | 0.100 | |
| 1202 | 5 | 0.065 | |
| 1203 | 5 | | 0.015 |
| 1223 | 5 | 0.111 | |
| 1225 | 5 | 0.042 | |
| 1245 | 5 | 0.317 | |
| 1249 | 5 | 0.241 | |
| 1271 | 5 | 1.000 | |
| 1272 | 5 | | 0.399 |
| 1287 | 5 | 0.495 | |
| 1293 | 5 | 1.667 | |
| 1298 | 5 | 0.474 | |
| 1299 | 5 | 1.100 | |
| 1300 | 5 | 3.334 | |
| 1305 | 5 | 0.833 | |
| 1307 | 5 | 4.207 | |
| 1326 | 5 | 0.004 | |
| 1327 | 5 | 0.005 | |
| 1328 | 5 | 0.002 | |
| 1329 | 5 | 0.006 | |
| 1330 | 5 | 0.002 | 0.005 |
| 1331 | 5 | | 0.010 |
| 1332 | 5 | | 0.008 |
| 1333 | 5 | | 0.040 |
| 1334 | 5 | | 0.080 |
| 1378 | 5 | 0.025 | |
| 1379 | 5 | 0.042 | |
| 1381 | 5 | 0.083 | |
| 1384 | 5 | 0.061 | |
| 1385 | 5 | 0.206 | |
| 1386 | 5 | 0.133 | |
| 1392 | 5 | 0.659 | |
| 1395 | 5 | 1.805 | |
| 1396 | 5 | 0.317 | |
| 1397 | 5 | 0.500 | |
| 1403 | 5 | 1.688 | |
| 1407 | 5 | 0.005 | |
| 1412 | 5 | 0.241 | |
| 1444 | 5 | >31.0027 | |
| 1445 | 5 | >31.2464 | |
| 1491 | 5 | 12.500 | |
| 1434 | 5 | 53.753 | |

BIOLOGICAL DATA TABLE 3-continued

| Cpd | Example | MGL mutant ThermoFluor Kd (µM) | MGL mutant ThermoFluor qKd (µM) (using qNMR conc.) |
|---|---|---|---|
| 1477 | 5 | >31.2464 | |
| 1432 | 5 | | >28.4381 |
| 1489 | 5 | 100.000 | |
| 1490 | 5 | >31.2464 | |
| 1481 | 5 | >31.2464 | |
| 1436 | 5 | 100.000 | |
| 1473 | 5 | 6.667 | |
| 1475 | 5 | >31.2464 | |
| 1446 | 5 | 62.503 | |
| 1447 | 5 | | 3.334 |
| 1448 | 5 | 7.091 | |
| 1449 | 5 | 3.194 | |
| 1450 | 5 | | 12.639 |
| 1451 | 5 | | >16.248 |
| 1452 | 5 | | 5.424 |
| 1453 | 5 | | 10.000 |
| 223 | 6 | 0.00670 | |
| 225 | 6 | 0.0200 | |
| 226 | 6 | 0.0200 | |
| 229 | 6 | 0.0125 | |
| 231 | 6 | 0.143 | |
| 233 | 6 | 1.32 | |
| 234 | 6 | 0.0476 | |
| 235 | 6 | 0.588 | |
| 236 | 6 | 0.200 | |
| 237 | 6 | 0.00100 | |
| 238 | 6 | 0.0333 | |
| 239 | 6 | 0.00500 | |
| 240 | 6 | 0.0232 | |
| 241 | 6 | 0.00050 | |
| 242 | 6 | 0.00400 | |
| 243 | 6 | 0.0167 | |
| 244 | 6 | 0.00200 | |
| 245 | 6 | 0.00950 | |
| 246 | 6 | 0.0167 | |
| 247 | 6 | 0.00040 | |
| 248 | 6 | 0.00670 | |
| 249 | 6 | 0.0100 | |
| 250 | 6 | 0.00170 | |
| 251 | 6 | 0.0143 | |
| 252 | 6 | 0.0500 | |
| 253 | 6 | 0.0215 | |
| 254 | 6 | 0.00590 | |
| 255 | 6 | 0.0270 | |
| 256 | 6 | 0.0333 | |
| 257 | 6 | 0.00330 | |
| 258 | 6 | 0.00330 | |
| 259 | 6 | 0.00770 | |
| 260 | 6 | 0.0200 | |
| 261 | 6 | 0.00910 | |
| 262 | 6 | 0.00250 | |
| 263 | 6 | 0.00500 | |
| 264 | 6 | 0.0100 | |
| 265 | 6 | 0.0198 | |
| 266 | 6 | 0.0160 | |
| 267 | 6 | 0.0125 | |
| 268 | 6 | 0.0250 | |
| 488 | 6 | 0.321 | |
| 1070 | 6 | 0.006 | |
| 1102 | 6 | 0.006 | |
| 295 | 7 | 0.833 | |
| 296 | 7 | 0.476 | |
| 297 | 7 | 0.333 | |
| 308 | 8 | 10.0 | |
| 309 | 8 | 0.253 | |
| 310 | 8 | 0.250 | |
| 311 | 8 | 0.0800 | |
| 312 | 8 | 0.0250 | |
| 480 | 8 | >76.7 | |
| 1057 | 8 | | 0.016 |
| 1078 | 8 | | 0.005 |
| 1085 | 8 | | 0.008 |
| 1087 | 8 | | 0.023 |
| 1094 | 8 | | 0.012 |
| 1112 | 8 | | 0.046 |
| 1118 | 8 | | 0.053 |
| 1140 | 8 | 0.112 | |
| 1143 | 8 | | 0.070 |
| 1145 | 8 | | 0.061 |
| 1169 | 8 | | 0.053 |
| 1217 | 8 | | 0.104 |
| 1222 | 8 | 0.068 | |
| 1232 | 8 | 0.345 | |
| 1256 | 8 | 0.393 | |
| 1258 | 8 | 0.020 | |
| 1262 | 8 | 0.278 | |
| 1269 | 8 | 1.165 | |
| 1308 | 8 | 2.056 | |
| 1310 | 8 | 8.348 | |
| 1324 | 8 | 0.016 | |
| 1325 | 8 | 0.006 | |
| 1335 | 8 | | 0.011 |
| 1336 | 8 | | 0.002 |
| 1398 | 8 | 0.182 | |
| 1423 | 8 | | 0.176 |
| 1424 | 8 | | 0.124 |
| 1425 | 8 | | 0.019 |
| 1426 | 8 | | 0.029 |
| 1427 | 8 | | 0.010 |
| 1428 | 8 | | 0.018 |
| 1429 | 8 | | 0.097 |
| 186-A | 8 | 0.016 | |
| 567-A | 8 | | 0.124 |
| 1478 | 8 | >31.2464 | |
| 1465 | 8 | >31.2464 | |
| 314 | 9 | 0.0392 | |
| 316 | 9 | 0.0165 | |
| 317 | 9 | 0.0100 | |
| 318 | 9 | 0.0165 | |
| 606 | 9 | 0.067 | |
| 647 | 9 | >31.2464 | |
| 654 | 9 | 0.040 | |
| 681 | 9 | | 0.067 |
| 713 | 9 | 0.100 | |
| 718 | 9 | 0.072 | |
| 723 | 9 | | 0.292 |
| 745 | 9 | | 0.283 |
| 767 | 9 | | |
| 775 | 9 | 0.333 | |
| 806 | 9 | | 0.989 |
| 812 | 9 | 0.644 | |
| 817 | 9 | | |
| 820 | 9 | | 0.996 |
| 822 | 9 | | |
| 829 | 9 | 0.500 | |
| 832 | 9 | 0.059 | |
| 856 | 9 | | 0.855 |
| 918 | 9 | 2.500 | |
| 1054 | 9 | 0.001 | 0.001 |
| 1055 | 9 | | 0.020 |
| 1056 | 9 | | 0.012 |
| 1068 | 9 | | 0.002 |
| 1077 | 9 | | 0.020 |
| 1088 | 9 | 0.001 | |
| 1090 | 9 | | 0.010 |
| 1106 | 9 | 0.006 | 0.005 |
| 1110 | 9 | | 0.010 |
| 1116 | 9 | | 0.001 |
| 1129 | 9 | | 0.074 |
| 1131 | 9 | 0.016 | |
| 1152 | 9 | 0.007 | |
| 1153 | 9 | | 0.004 |
| 1178 | 9 | | 0.238 |
| 1198 | 9 | 0.030 | |
| 1224 | 9 | | 0.189 |
| 1226 | 9 | | 0.193 |
| 1233 | 9 | 0.190 | |
| 1261 | 9 | 0.831 | |
| 1277 | 9 | | 2.722 |
| 1279 | 9 | | 1.864 |
| 1286 | 9 | 0.032 | |
| 1295 | 9 | | 1.509 |

BIOLOGICAL DATA TABLE 3-continued

| Cpd | Example | MGL mutant ThermoFluor Kd (µM) | MGL mutant ThermoFluor qKd (µM) (using qNMR conc.) |
|---|---|---|---|
| 1302 | 9 | 2.500 | |
| 1306 | 9 | | 12.193 |
| 1320 | 9 | | 0.015 |
| 1367 | 9 | 0.002 | |
| 1368 | 9 | | 0.001 |
| 1369 | 9 | | 0.002 |
| 1370 | 9 | | 0.013 |
| 1371 | 9 | | 0.003 |
| 1372 | 9 | | 0.002 |
| 1373 | 9 | | 0.004 |
| 1413 | 9 | | 0.003 |
| 1492 | 9 | 18.763 | |
| 1499 | 9 | 60.618 | |
| 126 | 9b | 0.0921 | |
| 128 | 9b | 0.00400 | |
| 129 | 9b | 0.0100 | |
| 130 | 9b | 0.250 | |
| 131 | 9b | 0.0941 | |
| 132 | 9b | 0.250 | |
| 568 | 9b | | 0.099 |
| 569 | 9b | | 0.059 |
| 571 | 9b | 0.046 | 0.080 |
| 573 | 9b | | 0.100 |
| 577 | 9b | | 0.026 |
| 578 | 9b | | 0.195 |
| 580 | 9b | | 0.118 |
| 583 | 9b | | 0.051 |
| 590 | 9b | | 0.182 |
| 599 | 9b | 0.481 | |
| 566 | 9c | | 0.031 |
| 1375 | 9c | | 0.003 |
| 1421 | 9c | | 0.044 |
| 582 | 9d | 0.119 | |
| 588 | 9d | | 0.512 |
| 594 | 9d | | 0.743 |
| 1109 | 9d | 0.022 | |
| 1113 | 9d | | 0.010 |
| 1133 | 9d | 0.036 | |
| 1159 | 9d | 0.003 | |
| 1171 | 9d | 0.024 | |
| 1177 | 9d | | 0.088 |
| 1182 | 9d | | 0.210 |
| 633 | 9e | 0.157 | |
| 1115 | 9e | | 0.005 |
| 575 | 9f | | 0.083 |
| 576 | 9f | | 0.088 |
| 1080 | 9f | | 0.006 |
| 1374 | 9f | | 0.007 |
| 1376 | 9f | | 0.013 |
| 1419 | 9f | 0.004 | |
| 1420 | 9f | | 0.080 |
| 1422 | 9f | | 0.195 |
| 1165 | 9g | | 0.090 |
| 1210 | 9g | | 0.097 |
| 601 | 9i | 0.527 | |
| 602 | 9i | 0.500 | |
| 607 | 9i | 1.000 | |
| 608 | 9i | 1.674 | |
| 609 | 9i | 1.000 | |
| 980 | 9i | 5.000 | |
| 989 | 9i | 1.250 | |
| 990 | 9i | 1.000 | |
| 991 | 9i | 0.200 | |
| 1252 | 9i | 0.386 | |
| 1255 | 9i | 0.048 | |
| 1290 | 9i | 0.643 | |
| 1389 | 9i | 0.422 | |
| 1154 | 9j | 0.006 | |
| 1173 | 9j | 0.007 | |
| 1190 | 9j | 0.008 | |
| 1191 | 9j | 0.011 | |
| 1193 | 9j | 0.017 | |
| 1220 | 9j | 0.015 | |
| 1237 | 9j | 0.064 | |
| 1238 | 9j | 0.125 | |
| 1251 | 9j | 0.146 | |
| 1254 | 9j | 0.100 | |
| 1257 | 9j | 0.009 | |
| 1282 | 9j | 0.200 | |
| 1380 | 9j | 0.246 | |
| 323 | 10 | 0.00130 | |
| 324 | 10 | 0.00040 | |
| 325 | 10 | 0.0927 | |
| 686 | 10 | | 0.002 |
| 749 | 10 | | 0.036 |
| 778 | 10 | | 1.195 |
| 801 | 10 | 52.505 | |
| 833 | 10 | | 3.334 |
| 666 | 10a | 0.002 | 0.003 |
| 670 | 10a | 0.001 | 0.001 |
| 900 | 10a | 0.001 | 0.001 |
| 659 | 10b | | 0.006 |
| 697 | 10b | | 0.024 |
| 901 | 10b | | 0.001 |
| 902 | 10b | | 0.004 |
| 326 | 11 | 0.00040 | |
| 327 | 11 | 0.0137 | |
| 328 | 11 | 0.0816 | |
| 329 | 11 | 0.0626 | |
| 330 | 11 | 0.438 | |
| 331 | 11 | 0.00690 | |
| 332 | 11 | 0.109 | |
| 333 | 11 | 0.00390 | |
| 334 | 11 | 0.132 | |
| 335 | 11 | 0.00193 | |
| 336 | 11 | 0.00950 | |
| 337 | 11 | 0.0498 | |
| 504 | 11 | 0.024 | |
| 516 | 11 | 0.040 | |
| 543 | 11 | 0.038 | |
| 684 | 11 | 0.004 | |
| 742 | 11 | 0.020 | |
| 810 | 11 | 0.290 | |
| 897 | 11 | 0.002 | |
| 898 | 11 | 0.009 | |
| 908 | 11 | 0.093 | |
| 929 | 11 | 0.020 | |
| 930 | 11 | 0.005 | |
| 338 | 12 | 0.00110 | |
| 343 | 13 | 0.00040 | |
| 344 | 13 | 0.0100 | |
| 345 | 13 | 0.00310 | |
| 511 | 13 | 0.002 | |
| 515 | 13 | 0.011 | |
| 591 | 13 | 0.007 | |
| 347 | 14 | 0.125 | |
| 600 | 14 | | 1.968 |
| 605 | 14 | 1.892 | |
| 917 | 14 | 4.995 | |
| 919 | 14 | 100.000 | |
| 920 | 14 | 100.000 | |
| 924 | 14 | 100.000 | |
| 1059 | 14 | | 0.066 |
| 1060 | 14 | | 0.032 |
| 1065 | 14 | | 0.036 |
| 1066 | 14 | | 0.031 |
| 1096 | 14 | | 0.080 |
| 1101 | 14 | | 0.044 |
| 1157 | 14 | | 0.179 |
| 1160 | 14 | | 0.139 |
| 1183 | 14 | | 0.067 |
| 1321 | 14 | | 0.067 |
| 1342 | 14 | 0.136 | |
| 1343 | 14 | 0.077 | |
| 1351 | 14 | | 0.043 |
| 1352 | 14 | | 0.008 |
| 1353 | 14 | | 0.018 |
| 1354 | 14 | | 0.009 |
| 1075 | 14a | | 0.010 |
| 1149 | 14a | | 0.004 |
| 1175 | 14a | | 0.010 |
| 1205 | 14a | | 0.008 |

BIOLOGICAL DATA TABLE 3-continued

| Cpd | Example | MGL mutant ThermoFluor Kd (μM) | MGL mutant ThermoFluor qKd (μM) (using qNMR conc.) |
|---|---|---|---|
| 1196 | 14b | | 0.370 |
| 1204 | 14b | | 0.249 |
| 1211 | 14b | | 0.106 |
| 1241 | 14b | | 0.638 |
| 1244 | 14b | | 0.589 |
| 1209 | 14c | | 0.942 |
| 1213 | 14c | | 0.765 |
| 1294 | 14d | | 4.412 |
| 1303 | 14d | | 7.115 |
| 1443 | 14d | >31.2464 | |
| 1476 | 14d | | 7.208 |
| 546 | 17 | 12.365 | |
| 1437 | 17 | 33.335 | |
| 1486 | 17 | >31.2464 | |
| 538 | 17a | 2.594 | |
| 861 | 17a | 2.625 | |
| 903 | 17a | 0.078 | |
| 690 | 17b | 0.104 | |
| 357 | 20 | 0.238 | |
| 358 | 21 | 0.0650 | |
| 359 | 21 | 0.0829 | |
| 360 | 21 | 0.0680 | |
| 361 | 21 | 0.144 | |
| 362 | 21 | 2.40 | |
| 363 | 21 | 6.76 | |
| 665 | 21 | 0.058 | |
| 685 | 21 | 0.067 | |
| 729 | 21 | 0.185 | |
| 736 | 21 | 0.067 | |
| 366 | 22 | 0.0353 | |
| 367 | 22 | 0.0853 | |
| 368 | 22 | 0.0551 | |
| 370 | 23 | 0.00100 | |
| 680 | 23a | 0.053 | |
| 1458 | 23a | 100.000 | |
| 372 | 24 | 0.0494 | |
| 373 | 24 | 0.00550 | |
| 374 | 24 | 0.00220 | |
| 375 | 24 | 0.229 | |
| 661 | 24 | 0.047 | |
| 668 | 24 | 0.025 | |
| 805 | 24 | 6.405 | |
| 883 | 24 | 0.059 | |
| 376 | 25 | 7.14 | |
| 377 | 25 | >76.7 | |
| 378 | 25 | >76.7 | |
| 379 | 26 | 0.0400 | |
| 393 | 26 | 0.0909 | |
| 394 | 26 | 0.846 | |
| 395 | 26 | 0.159 | |
| 396 | 26 | 4.27 | |
| 397 | 27 | 0.0333 | |
| 398 | 27 | 0.0869 | |
| 399 | 27 | 0.0408 | |
| 401 | 27 | 0.00167 | |
| 402 | 27 | 0.141 | |
| 403 | 27 | 0.338 | |
| 404 | 27 | 0.00170 | |
| 405 | 27 | 0.00200 | |
| 406 | 27 | 0.932 | |
| 407 | 27 | 0.0988 | |
| 408 | 27 | 1.94 | |
| 409 | 27 | 2.03 | |
| 483 | 27 | 0.0200 | |
| 552 | 27 | 0.400 | |
| 560 | 27 | 0.652 | |
| 957 | 27 | 0.008 | |
| 960 | 27 | 0.036 | |
| 962 | 27 | 0.005 | |
| 963 | 27 | 0.102 | |
| 967 | 27 | 0.044 | |
| 970 | 27 | 0.535 | |
| 972 | 27 | 0.080 | |
| 983 | 27 | 0.019 | |
| 987 | 27 | 0.327 | |
| 554 | 27a | 1.985 | |
| 978 | 27a | 0.066 | |
| 981 | 27a | 0.937 | |
| 958 | 27b | 0.216 | |
| 961 | 27b | 0.576 | |
| 968 | 27b | | 1.462 |
| 979 | 27b | | 1.143 |
| 984 | 27b | | 1.429 |
| 410 | 28 | 0.0333 | |
| 411 | 28 | 0.0333 | |
| 412 | 28 | 0.0100 | |
| 413 | 28 | 0.00200 | |
| 414 | 28 | 0.0250 | |
| 415 | 28 | 0.00800 | |
| 416 | 28 | 0.160 | |
| 417 | 28 | 0.0667 | |
| 418 | 28 | 0.500 | |
| 555 | 28 | 2.000 | |
| 975 | 28 | 2.000 | |
| 974 | 28a | | 1.776 |
| 419 | 29 | 0.123 | |
| 420 | 29 | 0.00500 | |
| 421 | 29 | 0.00400 | |
| 422 | 29 | 0.0532 | |
| 423 | 29 | 0.00690 | |
| 424 | 29 | 0.00941 | |
| 425 | 29 | 0.200 | |
| 426 | 29 | 0.250 | |
| 662 | 29 | 0.100 | |
| 427 | 30 | 0.0335 | |
| 428 | 30 | 0.00330 | |
| 429 | 30 | 0.0331 | |
| 430 | 30 | 0.0667 | |
| 432 | 30 | 0.0250 | |
| 677 | 30a | | 0.432 |
| 790 | 30a | | 2.494 |
| 508 | 31 | 0.162 | |
| 651 | 31 | 0.025 | |
| 738 | 31 | 0.291 | |
| 564 | 31a | 10.000 | |
| 976 | 31a | 1.837 | |
| 977 | 31a | 19.999 | |
| 807 | 31b | | 3.652 |
| 450 | 34 | 0.0500 | |
| 452 | 34 | 0.200 | |
| 453 | 35 | 0.0120 | |
| 454 | 35 | 0.0147 | |
| 455 | 35 | 0.00850 | |
| 548 | 35 | 0.062 | |
| 959 | 35 | 0.044 | |
| 549 | 35a | 0.060 | |
| 551 | 35a | 0.180 | |
| 956 | 35a | 0.081 | |
| 969 | 35a | 0.069 | |
| 955 | 35b | 1.111 | |
| 964 | 35b | | 3.198 |
| 456 | 36 | >76.7 | |
| 457 | 37 | 4.82 | |
| 458 | 37 | 6.67 | |
| 459 | 37 | 3.33 | |
| 460 | 37 | 9.10 | |
| 491 | 39 | 0.100 | |
| 492 | 39 | 0.167 | |
| 493 | 39 | 0.0250 | |
| 494 | 39 | 0.100 | |
| 642 | 40 | 0.499 | |
| 645 | 40 | 5.443 | |
| 1488 | 41 | >31.2464 | |
| 1457 | 41 | >31.2464 | |
| 997 | 42 | 0.041 | |
| 1006 | 42 | 0.667 | |
| 1016 | 42 | 0.460 | |
| 547 | 42 | 0.072 | |
| 563 | 42 | 2.106 | |
| 985 | 42 | 0.005 | |
| 995 | 42 | 0.002 | |
| 1007 | 42 | 0.259 | |

BIOLOGICAL DATA TABLE 3-continued

| Cpd | Example | MGL mutant ThermoFluor Kd (μM) | MGL mutant ThermoFluor qKd (μM) (using qNMR conc.) |
|---|---|---|---|
| 1008 | 42 | 0.089 | |
| 1009 | 42 | 0.589 | |
| 1013 | 42 | 0.760 | |
| 1014 | 42 | 0.903 | |
| 1015 | 42 | 1.183 | |
| 771 | 42 | 0.050 | |
| 948 | 43 | 0.030 | |
| 949 | 43 | 0.178 | |
| 950 | 43 | | 0.883 |
| 1025 | 43 | | 0.066 |
| 507 | 44 | 0.317 | |
| 520 | 44 | 2.000 | |
| 522 | 44 | 4.708 | |
| 525 | 44 | 2.500 | |
| 527 | 44 | 10.000 | |
| 532 | 44 | 2.331 | |
| 533 | 44 | 10.000 | |
| 537 | 44 | 3.334 | |
| 663 | 44 | 0.020 | |
| 715 | 44 | 0.167 | |
| 717 | 44 | 0.067 | |
| 734 | 44 | 1.255 | |
| 752 | 44 | 0.095 | |
| 765 | 44 | 3.094 | |
| 875 | 44 | 0.010 | |
| 877 | 44 | 0.100 | |
| 904 | 44 | 0.633 | |
| 909 | 44 | 0.325 | |
| 913 | 44 | 1.000 | |
| 1484 | 44 | 19.999 | |
| 802 | 44a | | 1.667 |
| 837 | 44a | | 19.999 |
| 869 | 44a | | 6.202 |
| 872 | 44a | | 10.000 |
| 720 | 44b | 0.347 | |
| 757 | 44b | 0.781 | |
| 769 | 44b | 2.000 | |
| 784 | 44b | 2.149 | |
| 922 | 44b | 3.890 | |
| 514 | 45 | 0.727 | |
| 519 | 45 | 0.962 | |
| 660 | 45 | 0.065 | |
| 683 | 45 | 0.039 | |
| 878 | 45 | 0.088 | |
| 1494 | 45a | | 7.377 |
| 803 | 45b | 2.126 | |
| 811 | 45b | 3.334 | |
| 1010 | 46 | 0.017 | 0.040 |
| 1011 | 46 | 0.124 | |
| 1018 | 46 | 0.207 | |
| 1019 | 46 | 0.166 | 0.132 |
| 1021 | 46 | 0.239 | |
| 1023 | 46 | 0.143 | |
| 1024 | 46 | | 0.135 |
| 1267 | 46 | | 0.741 |
| 1304 | 46 | | 7.903 |
| 1309 | 46 | | 6.540 |
| 1012 | 46a | | 3.337 |
| 1020 | 46a | 3.004 | |
| 1022 | 46a | 0.228 | 1.061 |
| 1311 | 46a | | 67.499 |
| 529 | 47 | 0.317 | |
| 530 | 47 | 0.089 | |
| 542 | 47 | 0.014 | |
| 553 | 47 | 0.372 | |
| 556 | 47 | 0.097 | |
| 557 | 47 | 0.114 | |
| 561 | 47 | 0.542 | |
| 1005 | 47 | 0.083 | |
| 709 | 48 | 0.015 | |
| 671 | 49 | | 0.018 |
| 1365 | 50 | 0.002 | |
| 1417 | 51 | 0.025 | |
| 1418 | 51 | 0.054 | |
| 1063 | 52 | 0.003 | |
| 1092 | 52 | 0.005 | |
| 1315 | 52 | 0.002 | |
| 1316 | 53 | 0.002 | |
| 1317 | 53 | 0.002 | |
| 1319 | 53 | | 0.001 |
| 1142 | 53a | | 0.001 |
| 1318 | 53a | 0.000 | |
| 597 | 54 | 0.153 | |
| 1137 | 54 | 0.010 | |
| 1170 | 54 | 0.014 | |
| 1195 | 54 | 0.023 | |
| 884 | 55 | | 0.017 |
| 885 | 55 | | 0.001 |
| 1081 | 55 | | 0.019 |
| 1099 | 55 | | 0.020 |
| 881 | 55a | 0.006 | |
| 882 | 55a | 0.012 | |
| 994 | 55a | 0.002 | |
| 724 | 55b | 0.050 | |
| 773 | 55b | 0.040 | |
| 1026 | 56 | | 0.001 |
| 1027 | 56 | | 0.012 |
| 1028 | 56 | | 0.011 |
| 1033 | 56 | | 0.000 |
| 1034 | 56 | | 0.000 |
| 992 | 57 | 0.561 | |
| 1430 | 57 | 50.003 | |
| 1431 | 57 | 0.035 | |
| 911 | 58 | 0.333 | |
| 988 | 58 | 0.040 | |
| 612 | 59 | 0.078 | |
| 613 | 59 | 0.051 | |
| 614 | 59 | 0.066 | |
| 615 | 59 | 0.097 | |
| 616 | 59 | >76.6655 | |
| 706 | 59 | 0.001 | |
| 1074 | 59 | 0.011 | |
| 1091 | 59 | 1.644 | |
| 1093 | 59 | 0.240 | |
| 1104 | 59 | 0.199 | |
| 1108 | 59 | 0.063 | |
| 1114 | 59 | 0.049 | |
| 1117 | 59 | 0.214 | |
| 1124 | 59 | 0.250 | |
| 1138 | 59 | 0.018 | |
| 1144 | 59 | 0.181 | |
| 1168 | 59 | 0.067 | |
| 1172 | 59 | 0.178 | |
| 1185 | 59 | 1.318 | |
| 1188 | 59 | 0.855 | |
| 1200 | 59 | 0.500 | |
| 1208 | 59 | 1.000 | |
| 1221 | 59 | 0.081 | |
| 1228 | 59 | 1.422 | |
| 1234 | 59 | 0.394 | |
| 1239 | 59 | 3.040 | |
| 1240 | 59 | 2.488 | |
| 1250 | 59 | 2.000 | |
| 1253 | 59 | 0.088 | |
| 1259 | 59 | 0.667 | |
| 1265 | 59 | 0.660 | |
| 1268 | 59 | | 0.039 |
| 1273 | 59 | 1.827 | |
| 1278 | 59 | 5.192 | |
| 1280 | 59 | 6.422 | |
| 1285 | 59 | 2.450 | |
| 1288 | 59 | 2.159 | |
| 1322 | 59 | 0.002 | |
| 1323 | 59 | 0.004 | |
| 1377 | 59 | 0.006 | |
| 1405 | 59 | 0.002 | |
| 1406 | 59 | 0.029 | |
| 1161 | 59a | 0.025 | |
| 1162 | 59a | | 0.014 |
| 1260 | 59a | 0.221 | |
| 759 | 60 | | 0.037 |
| 761 | 60 | | 0.092 |

BIOLOGICAL DATA TABLE 3-continued

| Cpd | Example | MGL mutant ThermoFluor Kd (µM) | MGL mutant ThermoFluor qKd (µM) (using qNMR conc.) |
|---|---|---|---|
| 780 | 60 | | 0.128 |
| 834 | 60 | | 0.234 |
| 841 | 60 | | 0.917 |
| 851 | 60 | | 0.883 |
| 1064 | 60 | | 0.018 |
| 1167 | 60 | | 0.025 |
| 1186 | 60 | | 0.035 |
| 1207 | 60 | 0.014 | |
| 1231 | 60 | | 0.131 |
| 1270 | 60 | | 0.265 |
| 1274 | 60 | | 0.248 |
| 1281 | 60 | | 0.194 |
| 777 | 60a | | 0.048 |
| 789 | 60a | | 0.043 |
| 798 | 60a | | 0.004 |
| 858 | 60a | | 0.561 |
| 866 | 60a | | 0.824 |
| 1206 | 60a | | 0.018 |
| 1215 | 60a | | 0.006 |
| 1227 | 60a | | 0.011 |
| 1229 | 60a | | 0.011 |
| 1264 | 60a | | 0.251 |
| 1289 | 60a | | 0.130 |
| 1291 | 60a | | 0.179 |
| 1296 | 60a | | 0.197 |
| 932 | 60b | 0.008 | |
| 933 | 60b | 0.034 | |
| 934 | 60b | 0.025 | |
| 935 | 60b | 0.034 | |
| 936 | 60b | 0.012 | |
| 937 | 60b | 0.096 | |
| 938 | 60b | 0.091 | |
| 939 | 60b | 0.302 | |
| 940 | 60b | 0.259 | |
| 941 | 60b | 0.389 | |
| 942 | 60b | 0.135 | |
| 943 | 60b | 1.045 | |
| 944 | 60b | 0.802 | |
| 945 | 60b | 0.083 | |
| 509 | 61 | 0.033 | |
| 653 | 61 | 0.011 | |
| 895 | 61 | 0.000 | |
| 593 | 62 | 0.010 | |
| 701 | 62 | 0.008 | |
| 1132 | 62 | 0.002 | |
| 572 | 62a | 0.030 | |
| 634 | 62a | 0.054 | |
| 1340 | 62a | 0.001 | |
| 1341 | 62a | 0.001 | |
| 1344 | 62a | 0.010 | |
| 1345 | 62a | 0.006 | |
| 982 | 63 | 0.010 | |
| 986 | 64 | 0.005 | |
| 510 | 65 | 0.068 | |
| 513 | 65 | 0.009 | |
| 528 | 65 | 0.049 | |
| 570 | 65 | 0.030 | |
| 691 | 65 | 0.004 | |
| 695 | 65 | 0.001 | |
| 707 | 65 | 0.002 | |
| 712 | 65 | 0.028 | |
| 714 | 65 | 0.005 | |
| 737 | 65 | 0.031 | |
| 1058 | 65 | 0.007 | |
| 1095 | 65 | 0.011 | |
| 1098 | 65 | 0.031 | |
| 1346 | 65 | 0.002 | |
| 951 | 66 | | 0.117 |
| 506 | 67 | 0.059 | |
| 673 | 67 | 0.050 | |
| 896 | 67 | 0.008 | |
| 512 | 67a | 0.050 | |
| 664 | 67a | 0.006 | |
| 699 | 67a | 0.041 | |
| 505 | 67b | 0.010 | |
| 657 | 67b | 0.002 | 0.002 |
| 674 | 67b | 0.003 | |
| 692 | 67b | 0.005 | |
| 899 | 67b | 0.000 | |
| 649 | 68 | | 0.001 |
| 700 | 68 | | 0.006 |
| 704 | 68a | 0.017 | |
| 705 | 68a | 0.012 | |
| 574 | 69 | 0.048 | |
| 631 | 70 | | 0.052 |
| 632 | 70 | | 0.037 |
| 1069 | 70 | 0.028 | |
| 1348 | 70 | 0.000 | 0.002 |
| 1349 | 70 | 0.005 | 0.006 |
| 1111 | 70a | | 0.009 |
| 1350 | 70a | | 0.001 |
| 1076 | 70b | | 0.020 |
| 1355 | 70b | | 0.002 |
| 1414 | 70c | | 0.003 |
| 1415 | 70c | | 0.011 |
| 1416 | 70c | | 0.015 |
| 711 | 71 | | 0.050 |
| 813 | 71 | | 0.499 |
| 1031 | 71 | | 0.134 |
| 1032 | 71 | | 1.100 |
| 1035 | 71 | | 1.008 |
| 1046 | 71 | | 0.064 |
| 1047 | 71 | | 0.471 |
| 1048 | 71 | | 0.146 |
| 1029 | 72 | | 0.006 |
| 1030 | 72 | | 0.033 |
| 1036 | 72 | | 0.005 |
| 1037 | 72 | | 0.022 |
| 1038 | 72 | | 0.002 |
| 1039 | 72 | | 0.007 |
| 1040 | 72 | | 0.014 |
| 1043 | 72 | | 0.055 |
| 1049 | 72 | | 0.050 |
| 1050 | 72 | | 0.085 |
| 1051 | 72 | | 0.175 |
| 1052 | 72 | | 0.065 |
| 1411 | 72 | | 0.001 |
| 1044 | 72a | | 0.945 |
| 1045 | 72a | | 0.190 |
| 534 | | >76.6655 | |
| 535 | | 10.000 | |
| 536 | | 10.000 | |
| 540 | | >31.2464 | |
| 725 | | | 0.293 |
| 847 | | 5.000 | |
| 867 | | >31.2464 | |
| 870 | | 100.000 | |
| 1487 | | >31.2464 | |
| 1454 | | >31.2464 | |
| 1505 | | >31.2464 | |
| 1455 | | >31.2464 | |
| 1456 | | >31.2464 | |
| 1435 | | | 20.012 |
| 1504 | | | |
| 1503 | | >31.2464 | |
| 1502 | | >31.2464 | |
| 1461 | 9i | 100.000 | |

In Vivo Methods

Example 4

CFA-Induced Paw Radiant Heat Hypersensitivity

Each rat was placed in a test chamber on a warm glass surface and allowed to acclimate for approximately 10 min. A radiant thermal stimulus (beam of light) was then focused through the glass onto the plantar surface of each hind paw in turn. The thermal stimulus was automatically shut off by a photoelectric relay when the paw was moved or when the cut-off time was reached (20 sec for radiant heat at ~5 amps). An initial (baseline) response latency to the thermal stimulus was recorded for each animal prior to the injection of complete Freund's adjuvant (CFA). 24 h following intraplantar CFA injection, the response latency of the animal to the thermal stimulus was then re-evaluated and compared to the animal's baseline response time. Only rats that exhibited at least a 25% reduction in response latency (i.e., were hyperalgesic) were included in further analysis. Immediately following the post-CFA latency assessment, the indicated test compound or vehicle was administered orally. Post-compound treatment withdrawal latencies were assessed at fixed time intervals, typically 30, 60, 120, 180, and 300 min.

The percent reversal (% R) of hypersensitivity was calculated in one of two different ways: 1) using group mean values or 2) using individual animal values. More specifically:

Method 1. For all compounds, the % R of hypersensitivity was calculated using the mean value for groups of animals at each time point according to the following formula:

% reversal=[(group treatment response—group CFA response)/(group baseline response—group CFA response)]×100

Results are given for the maximum % reversal observed for each compound at any time point tested.

Method 2. For some compounds, the % R of hypersensitivity was calculated separately for each animal according to the following formula:

% reversal=[(individual treatment response–individual CFA response)/(individual baseline response–individual CFA response)]×100.

Results are given as a mean of the maximum % reversal values calculated for each individual animal.

BIOLOGICAL TABLE 4

CFA thermal hypersensitivity

| cmpd | dose (mg/kg, p.o.) | vehicle | no. of animals | last time point (min) | Method 1: peak % reversal | Method 2: peak % reversal |
|---|---|---|---|---|---|---|
| 5 | 30 | HPβCD | 9 | 180 | 96.6 | 100.5 |
| 7 | 30 | HPβCD | 8 | 180 | 77.8 | 76.2 |
| 9 | 30 | HPβCD | 8 | 180 | 75.4 | 77.4 |
| 39 | 30 | HPβCD | 8 | 180 | 39.1 | 39.7 |
| 126 | 10 | HPβCD | 8 | 300 | 40.8 | 40.4 |
| 126 | 30 | HPβCD | 8 | 300 | 51 | 79.5 |
| 229 | 30 | HPβCD | 8 | 300 | 55.8 | 56.6 |
| 232 | 30 | HPβCD | 8 | 180 | 9.6 | 8 |
| 239 | 30 | HPβCD | 8 | 300 | 81.8 | 87.5 |
| 240 | 30 | HPβCD | 8 | 300 | 43 | 44.4 |
| 250 | 30 | HPβCD | 8 | 300 | 41.7 | 41.9 |
| 251 | 30 | HPβCD | 8 | 300 | 35.1 | 38.5 |
| 253 | 30 | HPβCD | 8 | 300 | 64.3 | 87.2 |
| 261 | 30 | HPβCD | 8 | 300 | 26.4 | 27.5 |
| 266 | 30 | HPβCD | 8 | 300 | 50.5 | 56.1 |
| 314 | 30 | HPβCD | 8 | 180 | 41 | 41.2 |
| 316 | 30 | HPβCD | 8 | 180 | 69.3 | 70.8 |
| 317 | 30 | HPβCD | 8 | 300 | 43 | |
| 318 | 30 | HPβCD | 8 | 300 | 44.7 | |
| 324 | 30 | HPβCD | 8 | 300 | 48.7 | 55.8 |
| 325 | 30 | HPβCD | 9 | 300 | 62.1 | 63.1 |
| 326 | 30 | HPβCD | 8 | 300 | 17.3 | 17.5 |
| 331 | 30 | HPβCD | 8 | 300 | 14.3 | |
| 333 | 30 | HPβCD | 8 | 300 | 27.7 | |
| 335 | 30 | HPβCD | 8 | 300 | 108.2 | 135.2 |
| 337 | 30 | HPβCD | 9 | 300 | 14.3 | 17.6 |
| 345 | 30 | HPβCD | 8 | 300 | 25 | 26.3 |
| 407 | 30 | HPβCD | 8 | 300 | 1.6 | 1.4 |
| 485 | 30 | HPβCD | 8 | 300 | 34.4 | 32.3 |
| 487 | 30 | HPβCD | 8 | 300 | 109.2 | 166.5 |
| 488 | 30 | HPβCD | 8 | 300 | 78 | 85.5 |
| 489 | 30 | HPβCD | 8 | 180 | 27.1 | 43.5 |
| 490 | 30 | HPβCD | 8 | 300 | 18.4 | 19.7 |
| 509 | 30 | HPβCD | 8 | 300 | 17.8 | |
| 567 | 30 | HPβCD | 8 | 300 | 63.1 | |
| 571 | 30 | HPβCD | 8 | 300 | 133.2 | |
| 572 | 30 | HPβCD | 8 | 300 | −5.1 | |
| 650 | 30 | HPβCD | 8 | 300 | 29.9 | |
| 653 | 30 | HPβCD | 8 | 300 | −10.7 | |
| 657 | 30 | HPβCD | 8 | 300 | 66 | |
| 662 | 30 | HPβCD | 8 | 300 | 21 | 24 |
| 663 | 30 | HPβCD | 8 | 300 | 33.9 | |
| 666 | 30 | HPβCD | 8 | 300 | −3.1 | |
| 670 | 30 | HPβCD | 8 | 300 | 20.9 | |
| 674 | 30 | HPβCD | 8 | 300 | 57.7 | |
| 895 | 30 | HPβCD | 8 | 300 | 23.4 | |
| 899 | 30 | HPβCD | 8 | 300 | 80.1 | |
| 900 | 30 | HPβCD | 8 | 300 | 8.5 | |
| 1010 | 30 | HPβCD | 8 | 300 | 23.4 | |
| 1054 | 30 | HPβCD | 8 | 300 | 27.6 | |
| 1070 | 30 | HPβCD | 8 | 300 | 25.7 | 23.1 |
| 1088 | 30 | HPβCD | 8 | 300 | 35.3 | |
| 1102 | 30 | HPβCD | 8 | 300 | 38 | 45.3 |
| 1106 | 30 | HPβCD | 8 | 300 | 45 | |
| 1108 | 30 | HPβCD | 8 | 300 | 84.9 | 99.2 |
| 1117 | 30 | HPβCD | 8 | 300 | 23.2 | |
| 1124 | 30 | HPβCD | 8 | 300 | 88.1 | |
| 1125 | 30 | HPβCD | 8 | 300 | 64.5 | 90.3 |
| 1132 | 30 | HPβCD | 8 | 300 | 0 | |
| 1139 | 30 | HPβCD | 8 | 300 | 43.8 | |
| 1141 | 30 | HPβCD | 8 | 300 | 5.7 | |
| 1174 | 30 | HPβCD | 8 | 300 | 13.6 | |
| 1187 | 30 | HPβCD | 8 | 300 | 16.3 | |
| 1221 | 30 | HPβCD | 8 | 300 | 44.7 | 46.7 |
| 1337 | 30 | HPβCD | 8 | 300 | 6.7 | |
| 1338 | 30 | HPβCD | 8 | 300 | 86.3 | |
| 1340 | 30 | HPβCD | 8 | 300 | 13.1 | |
| 1341 | 30 | HPβCD | 8 | 300 | 7.5 | |
| 1357 | 30 | HPβCD | 8 | 300 | 51 | 46.1 |
| 1358 | 30 | HPβCD | 8 | 300 | 25.4 | |
| 1359 | 30 | HPβCD | 8 | 300 | 5.1 | 12.7 |
| 1360 | 30 | HPβCD | 8 | 300 | 40.5 | 40.5 |
| 1362 | 30 | HPβCD | 8 | 300 | 185.9 | |
| 1363 | 30 | HPβCD | 8 | 300 | 69.7 | |
| 1364 | 30 | HPβCD | 8 | 300 | 17 | |
| 1366 | 30 | HPβCD | 8 | 300 | 47.1 | |

Example 5

CFA-Induced Paw Pressure Hypersensitivity

Prior to testing, rats were acclimated to the handling procedure twice a day for a period of two days. The test consisted of placing the left hindpaw on a Teflon® (polytetrafluoroethylene) coated platform and applying a linearly increasing mechanical force (constant rate of 12.5 mmHg/s) in between the third and fourth metatarsal of the dorsum of the rat's hindpaw, with a dome-tipped plinth (0.7 mm in radius), using an analgesy-meter (Stoelting, Chicago, Ill.), also known as a Randall-Selitto apparatus. The endpoint was automatically reached upon hindpaw withdrawal, and the terminal force was noted (in grams). An initial (baseline) response threshold to the mechanical stimulus was recorded for each animal prior to the injection of complete Freund's adjuvant (CFA). Forty hr following intraplantar CFA injection, the response threshold of the animal to the mechanical stimulus was re-evaluated and compared to the animal's baseline response threshold. A response was defined as a withdrawal of the hindpaw, a struggling to remove the hindpaw or vocalization. Only rats that exhibited at least a 25% reduction in response threshold (i.e., hyperalgesia) were included in further analysis. Immediately following the post-CFA threshold assessment, rats were administered the indicated test compound or vehicle. Post-treatment withdrawal thresholds were assessed at 1 h. Paw withdrawal thresholds were converted to percent reversal of hypersensitivity according to the following formula:

% reversal=[(post treatment response−predose response)/(baseline response−predose response)]×100.

BIOLOGICAL TABLE 5

CFA induced paw pressure hypersensitivity

| cmpd | N | dose | route of administration | vehicle | time (h) | percent reversal |
|---|---|---|---|---|---|---|
| 487 | 8 | 30 | s.c. | HPβCD | 1 | 61.8 |
| 1362 | 10 | 30 | s.c. | HPβCD | 1 | 56.7 |

Example 6

Chronic Constriction Injury (CCI)-Induced Model of Neuropathic Pain—Cold Acetone-Hypersensitivity Test Male Sprague-Dawley rats (225-450 g) were used to evaluate the ability of selected compounds to reverse CCI-induced cold hypersensitivity. Four loose ligatures of 4-0 chromic gut were surgically placed around the left sciatic nerve under inhalation anesthesia as described by Bennett et al. (Bennett G J, Xie Y K. *Pain* 1988, 33(1): 87-107). Fourteen to 35 days following CCI surgery, subjects were placed in elevated observation chambers containing wire mesh floors, and five applications of acetone (0.05 mL/application separated by about 5 min) were spritzed onto the plantar surface of the paw using a multidose syringe. An abrupt withdrawal or lifting of the paw was considered a positive response. The number of positive responses was recorded for each rat over the five trials. Following baseline withdrawal determinations, compounds were administered in the indicated vehicle, by the indicated route (see Table 6). The number of withdrawals was re-determined 1 to 4 h after compound administration. Results are presented as a percent inhibition of shakes, which was calculated for each subject as [1−(test compound withdrawals/pre-test withdrawals)]×100 and then averaged by treatment.

BIOLOGICAL TABLE 6

CCI induced cold sensitivity

| cpd | N | dose (mg/kg) | route of administration | vehicle | last time point (h) | peak percent inhibition |
|---|---|---|---|---|---|---|
| 5 | 9 | 30 | p.o. | HPβCD | 4 | 26.7 |
| 335 | 9 | 30 | p.o. | HPβCD | 4 | 100 |
| 487 | 9 | 30 | p.o. | HPβCD | 4 | 100 |
| 1362 | 6 | 3 | p.o. | HPβCD | 4 | 70.0 |

Example 7

Spinal Nerve Ligation (SNL) Model of Neuropathic Pain—Tactile Allodynia Test

For lumbar 5 ($L_5$) spinal nerve ligation (SNL) studies, anesthesia was induced and maintained on isoflurane inhalation. Fur was clipped over the dorsal pelvic area, and a 2-cm skin incision was made just left of midline over the dorsal aspect of the $L_4$-$S_2$ spinal segments, followed by separation of the paraspinal muscles from spinous processes. The transverse process of $L_6$ was then carefully removed, and the $L_5$ spinal nerve was identified. The left $L_5$ spinal nerve was then ligated tightly with 6-0 silk thread, the muscle was sutured with 4-0 vicryl, and the skin was closed with wound clips. Following surgery, s.c. saline (5 mL) was administered.

Behavioral testing was performed four weeks post-ligation. Following baseline von Frey determinations to verify the presence of mechanical allodynia, $L_5$ SNL rats were orally administered the indicated vehicle or drug. Tactile allodynia was quantified at 30, 60, 100, 180 and 300 min post-dosing by recording the force at which the paw ipsilateral to the nerve ligation was withdrawn from the application of a series of calibrated von Frey filaments (0.4, 0.6, 1.0, 2.0, 4, 6, 8 and 15 g; Stoelting; Wood Dale, Ill.). Beginning at an intermediate stiffness (2.0 g), filaments were applied to the mid-plantar hind paw for approximately 5 seconds. to determine the response threshold, a brisk paw withdrawal led to the presentation of the next lighter stimulus, whereas a lack of a withdrawal response led to the presentation of the next stronger stimulus. A total of four responses after the first threshold detection were collected. The 50% withdrawal thresholds were interpolated by the method of Dixon, Efficient analysis of experimental observations. *Annu. Rev. Pharmacol. Toxicol.* 20:441-462 (1980) as modified by Chaplan et. al., Quantitative assessment of tactile allodynia in the rat paw, *J. Neurosci. Methods.* 53(1):55-63 (1994) and when response thresholds fell above or below the range of detection, respective values of 15.0 or 0.25 g were assigned. Threshold data from von Frey filament testing were reported as withdrawal threshold in grams. Data were normalized and results are presented as % MPE (maximum possible effect) of the drug calculated according to the following formula:

$$\% \ MPE = \frac{x \ \text{g/force} - \text{baseline g/force}}{15 \ \text{g/force} - \text{baseline g/force}} \times 100$$

BIOLOGICAL TABLE 7

Spinal nerve ligation - tactile allodynia

| cmpd | N | dose (mg/kg) | route of administration | vehicle | last time point (h) | peak % MPE |
|---|---|---|---|---|---|---|
| 335 | 6 | 30 | p.o. | HPβCD | 4 | 50.1 |
| 487 | 6 | 30 | p.o. | HPβCD | 4 | 61.2 |
| 1362 | 6 | 30 | p.o. | HPβCD | 4 | 84.3 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

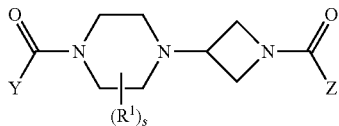

Formula (I)

wherein
Y and Z are independently selected from a) or b) such that one of Y and Z is selected from group a) and the other is selected from group b);
Group a) is
i) substituted $C_{6-10}$ aryl,
ii) $C_{3-8}$ cycloalkyl,
iii) trifluoromethyl; or
iv) heteroaryl selected from the group consisting of thienyl, furanyl, thiazolyl, isothiazolyl, oxazolyl, pyrrolyl, pyridinyl, isoxazolyl, imidazolyl, furazan-3-yl, benzothienyl, thieno[3,2-b]thiophen-2-yl, pyrazolyl, triazolyl, tetrazolyl, and [1,2,3]thiadiazolyl;
wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
Group b) is
i) $C_{6-10}$aryl;
ii) heteroaryl selected from the group consisting of thiazolyl, pyridinyl, indolyl, indazolyl, pyrrolyl, benzoxazolyl, benzothiazolyl, benzothienyl, imidazo[1,2-a]pyridin-2-yl, quinolinyl, thienyl, 1H-pyrrolo[2,3-b]pyridin-5-yl, 1H-thieno[2,3-c]pyrazol-5-yl, and benzimidazolyl;
iii) 7-(4-chloro-benzylidene)-1-(2,4-dichloro-phenyl)-4,5,6,7-tetrahydro-1H-indazol-3-yl;
iv) 2-oxo-3,3-bis-(3-trifluoromethylphenylmethyl)-2,3-dihydro-1H-indol-5-yl;
v) 5-[2-(4-chloro-phenyl)-1-methyl-vinyl]-1-(2,4-dichloro-phenyl)-4-methyl-1H-pyrazol-3-yl;
vi) 1-(2,4-dichloro-phenyl)-7-(4-fluoro-benzylidene)-1,4,6,7-tetrahydro-thiopyrano[4,3-c]pyrazol-3-yl;
vii) 2,3-dihydro-1H-indolyl;
viii) 7-(4-chloro-benzylidene)-1-(2,4-dichloro-phenyl)-4,5,6,7-tetrahydro-1H-indazol-3-yl;
ix) 4-{1-[1-(2,4-dichloro-phenyl)-7-(4-fluoro-benzylidene)-1,4,6,7-tetrahydro-thiopyrano[4,3-c]pyrazol-3-yl;
x) 1,1,3-tris-(3-trifluoromethylphenylmethyl)indan-2-on-6-yl; or
xi) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) 3-trifluoromethyl-phenylaminocarbonylmethoxy;
iv) $C_{6-10}$aryl($C_{1-4}$)alkylthio;
v) phenyl($C_{1-4}$)alkylsulfonyl;
vi) phenylcarbonyl optionally substituted with chloro or fluoro;
vii) 2,3-dihydro-1H-indol-5-ylcarbonyl;
viii) N-methyl-N-phenyl-aminocarbonyl-methyl;
ix) pyrrolidin-1-ylcarbonylmethyl;
x) phenyl($C_{2-6}$)alkynyl;
xi) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
xii) heteroaryl($C_{1-6}$)alkoxy wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
xiii) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent;
xiv) heteroaryl-(Q)-$C_{1-6}$alkyl wherein Q is O or S; wherein heteroaryl is selected from the group consisting of pyridinyl, pyrimidinyl, thiazolyl, benzothienyl, and thienyl, wherein said heteroaryl is optionally substituted with a $C_{1-4}$-alkyl, trifluoromethyl, or chloro substituent; and
xv) phenyl-(Q)-$C_{1-6}$alkyl wherein Q is O, S, $SO_2$, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxy; aminosulfonyl; di($C_{1-4}$alkyl)aminosulfonyl; $C_{1-4}$alkylsulfonyl; di($C_{1-4}$alkyl)aminosulfonyl; and $NR^cR^d$; wherein $R^c$ is hydrogen or $C_{1-6}$alkyl and wherein $R^d$ is hydrogen, $C_{1-6}$alkyl, cyano($C_{1-4}$alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$alkyl)aminocarbonyl, $C_{6-10}$arylcarbonyl; di($C_{1-4}$alkyl)aminosulfonyl, and $C_{1-4}$alkylsulfonyl;
s is 0, 1 or 2; provided that when s is 2, $R^1$ is independently selected from the group consisting of phenyl, $C_{1-3}$alkyl, and $C_{6-10}$aryl($C_{1-3}$)alkyl;
when s is 1, $R^1$ is $C_{6-10}$aryl, $C_{1-3}$alkyl, benzyloxymethyl, hydroxy($C_{1-3}$)alkyl, aminocarbonyl, carboxy, trifluoromethyl, spiro[used cyclopropyl, 3-oxo, or aryl ($C_{1-3}$)alkyl;
or, when s is 2 and $R^1$ is $C_{1-3}$alkyl, the $C_{1-3}$alkyl substituents are taken with the piperizinyl ring to form a 3,8-diaza-bicyclo[3.2.1]octanyl or 2,5-diaza-bicyclo[2.2.2]octanyl ring system;
provided that a compound of formula (I) is other than a compound wherein Y is thiazol-4-yl, Z is 4-(3-trifluoromethylphenylmethylsulfonyl)phenyl, and s is 0;
or a compound wherein Y is thiazol-2-yl, Z is 4-(phenylmethyl)phenyl, s is 1, and $R^1$ is 3-phenyl;

a compound wherein Y is thiazol-2-yl, Z is 2-(pyridin-4-ylmethyl)-3H-benzimidazol-4-yl, and s is 0;

and enantiomers, diastereomers, and pharmaceutically acceptable salts thereof.

2. The compound of claim 1 wherein
Group a) is
i) substituted $C_{6-10}$ aryl,
ii) trifluoromethyl; or
iii) heteroaryl selected from the group consisting of thiazolyl, isothiazolyl, pyrrolyl, and pyridinyl;
   wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl.

3. The compound of claim 2 wherein
Group a) is
i) substituted $C_{6-10}$ aryl,
ii) trifluoromethyl; or
iii) heteroaryl selected from the group consisting of thiazolyl, pyrrolyl, and pyridinyl;
   wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl.

4. The compound of claim 3 wherein
Group a) is
i) substituted phenyl,
ii) trifluoromethyl; or
iii) heteroaryl selected from the group consisting of thiazolyl, pyrrolyl, and pyridinyl;
   wherein phenyl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl.

5. The compound of claim 1 wherein
Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
   wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenyl($C_{1-4}$)alkylsulfonyl;
v) phenylcarbonyl optionally substituted with chloro or fluoro;
vi) 2,3-dihydro-1H-indol-5-ylcarbonyl;
vii) N-methyl-N-phenyl-aminocarbonyl-methyl;
viii) phenyl($C_{2-6}$)alkynyl;
ix) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
x) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
xi) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
xii) phenyl-(Q)-$C_{1-6}$alkyl wherein Q is O, S, $SO_2$, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxyl; di($C_{1-4}$alkyl)aminosulfonyl; and $NR^cR^d$; wherein $R^c$ is hydrogen or $C_{1-6}$alkyl and wherein $R^d$ is hydrogen, $C_{1-6}$alkyl, cyano($C_{1-4}$) alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$alkyl)aminocarbonyl, $C_{6-10}$arylcarbonyl; di($C_{1-4}$alkyl)aminosulfonyl, and $C_{1-4}$alkylsulfonyl.

6. The compound of claim 5 wherein
Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
   wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;

vi) N-methyl-N-phenyl-aminocarbonyl-methyl;
vii) phenyl($C_{2-6}$)alkynyl;
viii) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
ix) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
x) phenyl-(Q)-$C_{1-6}$alkyl wherein Q is O, S, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio.

7. The compound of claim 6 wherein
Group b) is
i) $C_{6-10}$ aryl;
ii) heteroaryl selected from the group consisting of pyridinyl, indolyl, and indazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl;
wherein $C_{6-10}$ aryl, 2,3-dihydro-1H-indolyl, and heteroaryl of Group b) are optionally independently substituted with one to two substituents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$alkylthio;
iv) phenylcarbonyl optionally substituted with chloro or fluoro;
v) 2,3-dihydro-1H-indol-5-ylcarbonyl;
vi) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
vii) heteroaryl($C_{1-2}$)alkylthio, wherein heteroaryl is pyridinyl; wherein said pyridinyl is optionally substituted with a $C_{1-4}$alkyl, trifluoromethyl, or chloro substituent; and
viii) phenyl-(Q)-$C_{1-6}$alkyl wherein Q is O, S, or NH; and phenyl is optionally independently substituted with one to three substituents selected from the group consisting of bromo, chloro, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio.

8. The compound of claim 1 wherein s is 0 or 1.
9. The compound of claim 1 wherein $R^1$ is phenyl or $C_{1-3}$alkyl.
10. The compound of claim 9 wherein $R^1$ is methyl.
11. A compound of Formula (I)

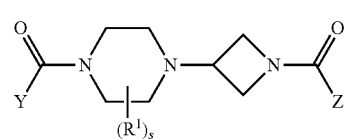

Formula (I)

wherein
Y and Z are independently selected from a) or b) such that one of Y and Z is selected from group a) and the other is selected from group b);
Group a) is
i) substituted $C_{6-10}$ aryl,
ii) trifluoromethyl; or
iii) heteroaryl selected from the group consisting of thiazolyl, isothiazolyl, pyrrolyl, and pyridinyl;
wherein $C_{6-10}$ aryl is substituted with; and the heteroaryl is optionally substituted with; one substituent selected from the group consisting of fluoro, chloro, bromo, $C_{1-4}$-alkyl, cyano, $C_{1-4}$alkylcarbonylamino, and trifluoromethyl;
Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl;
vii) 4-{1-[1-(2,4-dichloro-phenyl)-7-(4-fluoro-benzylidene)-1,4,6,7-tetrahydro-thiopyrano[4,3-c]pyrazol-3-yl;
viii) 1,1,3-tris-(3-trifluoromethylphenylmethyl)indan-2-on-6-yl; or
ix) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$alkylthio;
iv) phenyl($C_{1-4}$)alkylsulfonyl;
v) phenylcarbonyl optionally substituted with chloro or fluoro;
vi) 2,3-dihydro-1H-indol-5-ylcarbonyl;
vii) N-methyl-N-phenyl-aminocarbonyl-methyl;

viii) phenyl($C_{2-6}$)alkynyl;
ix) heteroaryl($C_{1-6}$)alkyl wherein heteroaryl is selected from the group consisting of pyridinyl, quinolinyl, pyrimidinyl, thiazolyl, benzothienyl, and thienyl, wherein said heteroaryl is optionally substituted with a $C_{1-4}$alkyl, trifluoromethyl, bromo, or chloro substituent;
x) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
xi) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
xii) phenyl-(Q)-$C_{1-6}$alkyl wherein Q is O, S, $SO_2$, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkoxycarbonylamino; $C_{1-4}$alkyl; cyanomethyl; $C_{1-4}$alkoxy; one to three fluoro or chloro substituents; trifluoromethyl; trifluoromethoxy; trifluoromethylthio; $C_{1-4}$alkylcarbonyl; $C_{1-4}$alkoxycarbonyl; cyano; carboxy; aminocarbonyl; $C_{1-4}$alkylaminocarbonyl; di($C_{1-4}$alkyl)aminocarbonyl; formyl; nitro; bromo; hydroxyl; di($C_{1-4}$alkyl)aminosulfonyl; and $NR^cR^d$; wherein $R^c$ is hydrogen or $C_{1-6}$alkyl and wherein $R^d$ is hydrogen, $C_{1-6}$alkyl, cyano($C_{1-4}$)alkyl, $C_{3-8}$cycloalkyl, $C_{1-6}$alkylcarbonyl, $C_{3-8}$cycloalkylcarbonyl, $C_{3-8}$cycloalkyl($C_{1-4}$)alkyl, aminocarbonyl, di($C_{1-4}$ alkyl)aminocarbonyl, $C_{6-10}$arylcarbonyl; di($C_{1-4}$ alkyl)aminosulfonyl, and $C_{1-4}$alkylsulfonyl;
s is 0 or 1;
$R^1$ is phenyl or $C_{1-3}$alkyl;
provided that a compound of formula (I) is other than
a compound wherein Y is thiazol-4-yl, Z is 4-(3-trifluoromethylphenylmethylsulfonyl)phenyl, and s is 0; or
a compound wherein Y is thiazol-2-yl, Z is 4-(phenylmethyl)phenyl, s is 1, and $R^1$ is 3-phenyl;
and enantiomers, diastereomers, and pharmaceutically acceptable salts thereof.

12. A compound of Formula (I)

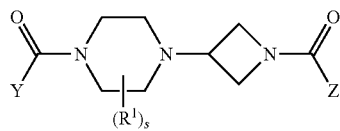

Formula (I)

wherein
Y and Z are independently selected from a) or b) such that one of Y and Z is selected from group a) and the other is selected from group b);
Group a) is
i) substituted $C_{6-10}$ aryl,
ii) trifluoromethyl; or
iii) heteroaryl selected from the group consisting of thiazolyl, pyrrolyl, and pyridinyl;

wherein $C_{6-10}$ aryl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
Group b) is
i) $C_{6-10}$ aryl;
ii) heteroaryl selected from the group consisting of pyridinyl, indolyl, indazolyl, and benzimidazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl;
vii) 4-{1-[1-(2,4-dichloro-phenyl)-7-(4-fluoro-benzylidene)-1,4,6,7-tetrahydro-thiopyrano[4,3-c]pyrazol-3-yl; or
viii) 1,1,3-tris-(phenylmethyl)indan-2-on-6-yl, and s is 0;
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;
vi) N-methyl-N-phenyl-aminocarbonyl-methyl;
vii) phenyl($C_{2-6}$)alkynyl;
viii) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
ix) heteroaryl($C_{1-2}$)alkylthio, wherein heteroaryl is selected from the group consisting of pyridinyl, thiazolyl, benzothienyl, and thienyl; wherein said heteroaryl is optionally substituted with a $C_{1-4}$alkyl, trifluoromethyl, or chloro substituent; and
x) phenyl-(Q)-$C_{1-6}$alkyl wherein Q is O, S, or NH; and phenyl is optionally independently substituted with one to three substitutents selected from the group consisting of bromo, chloro, fluoro, iodo, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio;
s is 0 or 1;
$R^1$ is phenyl or methyl;
provided that a compound of Formula (I) is other than
a compound wherein Y is thiazol-2-yl, Z is 4-(phenylmethyl)phenyl, s is 1, and $R^1$ is 3-phenyl;
and enantiomers, diastereomers, and pharmaceutically acceptable salts thereof.

13. A compound of Formula (I)

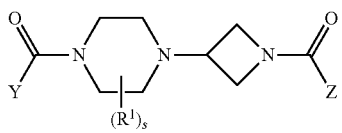

Formula (I)

wherein
Y and Z are independently selected from a) or b) such that one of Y and Z is selected from group a) and the other is selected from group b);
Group a) is
i) substituted phenyl,
ii) trifluoromethyl; or
iii) heteroaryl selected from the group consisting of thiazolyl, pyrrolyl, and pyridinyl;
wherein phenyl is substituted with; and the heteroaryl is optionally substituted with; one substituent selected from the group consisting of fluoro, chloro, bromo, $C_{1-4}$alkyl, cyano, $C_{1-4}$alkylcarbonylamino, and trifluoromethyl;
Group b) is
i) $C_{6-10}$ aryl;
ii) heteroaryl selected from the group consisting of pyridinyl, indolyl, and indazolyl;
iii) 5-[2-(4-chloro-phenyl)-1-methyl-vinyl]-1-(2,4-dichloro-phenyl)-4-methyl-1H-pyrazol-3-yl;
iv) 1-(2,4-dichloro-phenyl)-7-(4-fluoro-benzylidene)-1,4,6,7-tetrahydro-thiopyrano[4,3-c]pyrazol-3-yl;
v) 2,3-dihydro-1H-indolyl;
vi) 7-(4-chloro-benzylidene)-1-(2,4-dichloro-phenyl)-4,5,6,7-tetrahydro-1H-indazol-3-yl; or
vii) 4-{1-[1-(2,4-dichloro-phenyl)-7-(4-fluoro-benzylidene)-1,4,6,7-tetrahydro-thiopyrano[4,3-c]pyrazol-3-yl};
wherein $C_{6-10}$ aryl, 2,3-dihydro-1H-indolyl, and heteroaryl of Group b) are optionally independently substituted with one to two substitutents selected from the group consisting of bromo, chloro, fluoro, iodo, $C_{1-4}$alkyl, $C_{1-4}$alkoxy, and trifluoromethyl; and are substituted with one additional substituent selected from the group consisting of
i) $C_{6-10}$ aryl($C_{1-4}$)alkyl; wherein $C_{1-4}$alkyl is optionally substituted with one to two fluoro substituents;
ii) $C_{6-10}$aryl($C_{1-4}$)alkoxy;
iii) $C_{6-10}$aryl($C_{1-4}$)alkylthio;
iv) phenylcarbonyl optionally substituted with chloro or fluoro;
v) 2,3-dihydro-1H-indol-5-ylcarbonyl;
vi) heteroaryl($C_{1-6}$)alkoxy wherein heteroaryl is selected from the group consisting of pyridinyl and quinolinyl, wherein said heteroaryl is optionally substituted with a $C_{1-4}$alkyl, trifluoromethyl or bromo substituent;
vii) heteroaryl($C_{1-2}$)alkylthio, wherein heteroaryl is pyridinyl; wherein said pyridinyl is optionally substituted with a $C_{1-4}$alkyl, trifluoromethyl, or chloro substituent; and
viii) phenyl-(Q)-$C_{1-6}$alkyl wherein Q is O, S, or NH; and phenyl is optionally independently substituted with one to three substitutents selected from the group consisting of bromo, chloro, $C_{1-4}$alkyl, $C_{1-4}$alkoxy, and trifluoromethyl;
wherein phenyl of the $C_{6-10}$ aryl($C_{1-4}$)alkyl, $C_{6-10}$aryl($C_{1-4}$)alkylthio, phenyl($C_{1-4}$)alkylsulfonyl, and $C_{6-10}$aryl($C_{1-4}$)alkoxy substituents is optionally independently substituted with one to two substituents selected from the group consisting of $C_{1-4}$alkyl; $C_{1-4}$alkoxy; one to three fluoro or chloro substituents; trifluoromethyl; trifluoromethoxy; and trifluoromethylthio;
s is 0 or 1;
$R^1$ is methyl;
and enantiomers, diastereomers, and pharmaceutically acceptable salts thereof.

14. A compound of Formula (I)

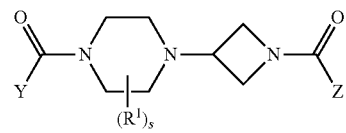

Formula (I)

selected from the group consisting of:
a compound wherein Y is thiazol-2-yl, Z is 4-phenylmethyl-phenyl, s is 1, and $R^1$ is 2-methyl;
a compound wherein Y is thiazol-2-yl, Z is 4-phenylmethyl-phenyl, s is 1, and $R^1$ is 3-methyl;
a compound wherein Y is thiazol-2-yl, Z is 3-chloro-4-(pyridin-4-ylmethoxy)phenyl, and s is 0;
a compound wherein Y is thiazol-2-yl, Z is 3-fluoro-4-(3,4-dichlorophenylmethoxy)phenyl, and s is 0;
a compound wherein Y is thiazol-2-yl, Z is 3-chloro-4-(3-chlorophenylmethoxy)phenyl, and s is 0;
a compound wherein Y is thiazol-2-yl, Z is 3-chloro-4-(pyridin-3-ylmethoxy)-phenyl, and s is 0;
a compound wherein Y is thiazol-2-yl, Z is 4-pyridin-4-ylmethoxy-phenyl, and s is 0;
a compound wherein Y is thiazol-2-yl, Z is 3-chloro-4-(3,4-dichlorophenylmethoxy)phenyl, and s is 0;
a compound wherein Y is thiazol-2-yl, Z is 3-fluoro-4-(2,3-dichlorophenylmethoxy)phenyl, and s is 0;
a compound wherein Y is thiazol-2-yl, Z is 3-chloro-4-(pyridin-2-ylmethoxy)phenyl, and s is 0;
a compound wherein Y is thiazol-2-yl, Z is 4-(3-chlorophenylmethylthio)phenyl, and s is 0;
a compound wherein Y is thiazol-2-yl, Z is 4-(2,3-dichlorophenylmethylthio)phenyl, and s is 0;
a compound wherein Y is thiazol-2-yl, Z is 4-(3,4-dichlorophenylmethylthio)phenyl, and s is 0;
a compound wherein Y is thiazol-2-yl, Z is 4-(4-chlorophenylmethylthio)phenyl, and s is 0;
a compound wherein Y is thiazol-2-yl, Z is 4-(pyridin-3-ylmethylthio)phenyl, and s is 0;
a compound wherein Y is thiazol-2-yl, Z is 4-(3-chlorophenoxymethyl)-phenyl, and s is 0;
a compound wherein Y is thiazol-2-yl, Z is 4-(3-chlorophenylthiomethyl)-phenyl, and s is 0;
a compound wherein Y is thiazol-2-yl, Z is 4-(3-chlorophenylaminomethyl)-phenyl, and s is 0;
a compound wherein Y is trifluoromethyl, Z is 4-(3-chlorophenylthiomethyl)-phenyl, and s is 0;
a compound wherein Y is thiazol-4-yl, Z is 4-(3-chlorophenylthiomethyl)-phenyl, and s is 0;
a compound wherein Y is thiazol-2-yl, Z is 4-(3-chlorophenylmethoxy)-phenyl, and s is 0;
a compound wherein Y is trifluoromethyl, Z is 4-(3-chlorophenylmethoxy)-phenyl, and s is 0;
a compound wherein Y is thiazol-4-yl, Z is 4-(3-chlorophenoxymethyl)-phenyl, and s is 0;

a compound wherein Y is thiazol-4-yl, Z is 4-(3-chlorophenylmethoxy)-phenyl, and s is 0;
a compound wherein Y is trifluoromethyl, Z is 4-(5-chlorothien-2-ylmethoxy)-phenyl, and s is 0;
a compound wherein Y is thiazol-2-yl, Z is 4-(5-chlorothien-2-ylmethoxy)-phenyl, and s is 0;
a compound wherein Y is thiazol-4-yl, Z is 4-(5-chlorothien-2-ylmethoxy)-phenyl, and s is 0;
a compound wherein Y is trifluoromethyl, Z is 4-(3-chlorophenylaminomethyl)-phenyl, and s is 0;
a compound wherein Y is thiazol-2-yl, Z is 2-(4-chlorophenoxymethyl)-4-methyl-thiazol-5-yl, and s is 0;
a compound wherein Y is thiazol-4-yl, Z is 2-(4-chlorophenoxymethyl)-4-methyl-thiazol-5-yl, and s is 0;
a compound wherein Y is thiazol-2-yl, Z is 4-(quinolin-2-ylmethoxy)-phenyl, and s is 0;
a compound wherein Y is trifluoromethyl, Z is 4-(quinolin-2-ylmethoxy)-phenyl, and s is 0;
a compound wherein Y is thiazol-4-yl, Z is 4-(3-chlorophenylaminomethyl)-phenyl, and s is 0;
a compound wherein Y is thiazol-4-yl, Z is 4-(quinolin-2-ylmethoxy)phenyl, and s is 0;
a compound wherein Y is thiazol-2-yl, Z is 4-(3-trifluoromethylphenylmethylsulfonyl)-phenyl, and s is 0;
a compound wherein Y is thiazol-2-yl, Z is 4-(3-trifluoromethylphenylmethylthio)-phenyl, and s is 0;
a compound wherein Y is trifluoromethyl, Z is 4-(3-trifluoromethylphenylmethylthio)-phenyl, and s is 0;
a compound wherein Y is thiazol-4-yl, Z is 4-(3-trifluoromethylphenylmethylthio)-phenyl, and s is 0;
a compound wherein Y is thiazol-2-yl, Z is 4-(3-trifluoromethylphenylsulfonylmethyl)-phenyl, and s is 0;
a compound wherein Y is thiazol-4-yl, Z is 4-(3-trifluoromethyl-phenylsulfonylmethyl)-phenyl, and s is 0;
a compound wherein Y is thiazol-2-yl, Z is 4-(5-chloro-pyridin-3-ylmethoxy)-phenyl, and s is 0;
a compound wherein Y is trifluoromethyl, Z is 4-(5-chloro-pyridin-3-ylmethoxy)-phenyl, and s is 0;
a compound wherein Y is thiazol-2-yl, Z is 2-(phenylmethyl)-1H-benzimidazol-4-yl, and s is 0;
a compound wherein Y is thiazol-4-yl, Z is 4-(5-chloro-pyridin-3-ylmethoxy)-phenyl, and s is 0;
a compound wherein Y is thiazol-2-yl, Z is 4-(4-trifluoromethyl-phenyl-fluoromethyl)-phenyl, and s is 0;
a compound wherein Y is thiazol-2-yl, Z is 4-(6-bromopyridin-2-ylmethoxy)-phenyl, and s is 0;
a compound wherein Y is trifluoromethyl, Z is 4-(6-bromopyridin-2-ylmethoxy)-phenyl, and s is 0;
a compound wherein Y is thiazol-2-yl, Z is 4-(4-trifluoromethylphenylmethyl)phenyl, and s is 0;
a compound wherein Y is thiazol-2-yl, Z is 4-(phenyldifluoromethyl)-phenyl, and s is 0;
a compound wherein Y is thiazol-4-yl, Z is 4-(6-bromopyridin-2-ylmethoxy)-phenyl, and s is 0;
a compound wherein Y is thiazol-2-yl, Z is 1-(2,3-dihydro-1H-indol-5-ylcarbonyl)-1H-indol-5-yl, and s is 0;
a compound wherein Y is thiazol-2-yl, Z is 2-(2-fluorophenylmethyl)-3H-benzimidazol-4-yl, and s is 0;
a compound wherein Y is thiazol-2-yl, Z is 2-(3-fluorophenylmethyl)-3H-benzimidazol-4-yl, and s is 0;
a compound wherein Y is thiazol-2-yl, Z is 2-(4-chlorophenylmethyl)-3H-benzimidazol-4-yl, and s is 0;
a compound wherein Y is thiazol-2-yl, Z is 2-oxo-3,3-bis-(3-trifluoromethylphenylmethyl)-2,3-dihydro-1H-indol-5-yl, and s is 0;
a compound wherein Y is thiazol-2-yl, Z is 1-(phenylmethyl)-indol-3-yl, and s is 0;
a compound wherein Y is thiazol-2-yl, Z is 1-phenylmethyl-2,3-dihydro-1H-indol-5-yl, and s is 0;
a compound wherein Y is thiazol-2-yl, Z is 4-(3-trifluoromethylphenylmethyl)phenyl, and s is 0;
a compound wherein Y is 4-(4-trifluoromethylphenylmethyl)phenyl, Z is thiazol-4-yl, and s is 0;
a compound wherein Y is 4-(4-trifluoromethylphenylmethyl)phenyl, Z is thiazol-2-yl, and s is 0;
a compound wherein Y is thiazol-4-yl, Z is 4-(3-trifluoromethylphenylmethyl)phenyl, and s is 0;
a compound wherein Y is thiazol-4-yl, Z is 4-(4-trifluoromethyl-phenylmethyl)phenyl, and s is 0;
a compound wherein Y is thiazol-2-yl, Z is 2-(phenylethyl)-1H-benzimidazol-5-yl, and s is 0;
a compound wherein Y is thiazol-2-yl, Z is 2-(phenylmethyl)-3H-benzimidazol-5-yl, and s is 0;
a compound wherein Y is 2-(phenylethyl)-3H-benzimidazol-5-yl, Z is thiazol-4-yl, and s is 0;
a compound wherein Y is thiazol-4-yl, Z is 2-(phenylmethyl)-1H-benzimidazol-5-yl, and s is 0;
a compound wherein Y is thiazol-2-yl, Z is 2-(phenylmethyl)-1H-benzimidazol-5-yl, and s is 0;
a compound wherein Y is thiazol-2-yl, Z is 3-(2-fluorophenylaminomethyl)-phenyl, and s is 0;
a compound wherein Y is thiazol-2-yl, Z is 3-(4-trifluoromethylphenyl-methyl)-4-fluoro-phenyl, and s is 0;
a compound wherein Y is thiazol-2-yl, Z is 3-(4-trifluoromethylphenyl-methyl)-4-fluoro-phenyl, and s is 0;
a compound wherein Y is thiazol-2-yl, Z is 2-methyl-3-(4-trifluoromethylphenyl-methyl)phenyl, and s is 0;
a compound wherein Y is thiazol-4-yl, Z is 2-methyl-3-(4-trifluoromethylphenyl-methyl)phenyl, and s is 0;
a compound wherein Y is thiazol-2-yl, Z is 5-[2-(4-chloro-phenyl)-1-methyl-vinyl]-1-(2,4-dichloro-phenyl)-4-methyl-1H-pyrazol-3-yl, and s is 0;
a compound wherein Y is 1H-pyrrol-2-yl, Z is 5-[2-(4-chloro-phenyl)-1-methyl-vinyl]-1-(2,4-dichloro-phenyl)-4-methyl-1H-pyrazol-3-yl, and s is 0;
a compound wherein Y is trifluoromethyl, Z is 5-[2-(4-chloro-phenyl)-1-methyl-vinyl]-1-(2,4-dichloro-phenyl)-4-methyl-1H-pyrazol-3-yl, and s is 0;
a compound wherein Y is 1H-pyrrol-2-yl, Z is 2-methyl-3-(4-trifluoromethylphenyl-methyl)phenyl, and s is 0;
a compound wherein Y is isothiazol-5-yl, Z is 2-methyl-3-(4-trifluoromethylphenyl-methyl)phenyl, and s is 0;
a compound wherein Y is thiazol-4-yl, Z is 2-methyl-3-(4-trifluoromethylphenyl-methyl)-phenyl, and s is 0;
a compound wherein Y is 2-methyl-3-(4-trifluoromethylphenyl-methyl)phenyl, Z is thiazol-5-yl, and s is 0;
a compound wherein Y is thiazol-2-yl, Z is 4-(phenylcarbonyl)phenyl, and s is 0;
a compound wherein Y is thiazol-2-yl, Z is 7-(4-chlorobenzylidene)-1-(2,4-dichloro-phenyl)-4,5,6,7-tetrahydro-1H-indazol-3-yl, and s is 0;
a compound wherein Y is 1H-pyrrol-2-yl, Z is 7-(4-chlorobenzylidene)-1-(2,4-dichloro-phenyl)-4,5,6,7-tetrahydro-1H-indazol-3-yl, and s is 0;
a compound wherein Y is trifluoromethyl, Z is 7-(4-chlorobenzylidene)-1-(2,4-dichloro-phenyl)-4,5,6,7-tetrahydro-1H-indazol-3-yl, and s is 0;
a compound wherein Y is thiazol-2-yl, Z is 1-(2,4-dichloro-phenyl)-7-(4-fluoro-benzylidene)-1,4,6,7-tetrahydro-thiopyrano[4,3-c]pyrazol-3-yl, and s is 0;
a compound wherein Y is trifluoromethyl, Z is 4-{1-[1-(2,4-dichloro-phenyl)-7-(4-fluoro-benzylidene)-1,4,6,7-tetrahydro-thiopyrano[4,3-c]pyrazol-3-yl, and s is 0;

a compound wherein Y is thiazol-4-yl, Z is 7-(4-chloro-benzylidene)-1-(2,4-dichloro-phenyl)-4,5,6,7-tetrahydro-1H-indazol-3-yl, and s is 0;

a compound wherein Y is 1H-pyrrol-2-yl, Z is 4-{1-[1-(2,4-dichloro-phenyl)-7-(4-fluoro-benzylidene)-1,4,6,7-tetrahydro-thiopyrano[4,3-c]pyrazol-3-yl, and s is 0;

a compound wherein Y is thiazol-2-yl, Z is 3-(4-fluorophenylcarbonyl)-indol-6-yl, and s is 0;

a compound wherein Y is thiazol-2-yl, Z is 1-methyl-3-(4-fluorophenylmethyl)-indol-6-yl, and s is 0;

a compound wherein Y is thiazol-4-yl, Z is 1-methyl-3-(4-fluorophenylmethyl)-indol-6-yl, and s is 0;

a compound wherein Y is 1H-pyrrol-2-yl, Z is 1-methyl-3-(4-fluorophenylmethyl)-indol-6-yl, and s is 0;

a compound wherein Y is thiazol-2-yl, Z is 1-(4-fluoro-phenylmethyl)-1H-indazol-5-yl, and s is 0;

a compound wherein Y is thiazol-2-yl, Z is 2-(4-fluorophenylmethyl)-indazol-5-yl, and s is 0;

a compound wherein Y is thiazol-2-yl, Z is 1-(N-methyl-N-phenyl-aminocarbonyl-methyl)-indol-5-yl, and s is 0;

a compound wherein Y is thiazol-4-yl, Z is 1-(N-methyl-N-phenyl-aminocarbonyl-methyl)-indol-5-yl, and s is 0;

a compound wherein Y is thiazol-2-yl, Z is 1-methyl-3-(3-fluorophenylmethyl)-indol-6-yl, and s is 0;

a compound wherein Y is thiazol-2-yl, Z is 1-methyl-3-(phenylmethyl)-indol-6-yl, and s is 0;

a compound wherein Y is thiazol-2-yl, Z is 1-(pyrrolidin-1-ylcarbonylmethyl)-indol-5-yl, and s is 0;

a compound wherein Y is thiazol-2-yl, Z is 1-(4-trifluoromethyl-phenylmethyl)-1H-indazol-5-yl, and s is 0;

a compound wherein Y is thiazol-2-yl, Z is 2-(4-trifluoromethylphenylmethyl)-indazol-5-yl, and s is 0;

a compound wherein Y is thiazol-2-yl, Z is 1-(3-trifluoromethyl-phenylmethyl)-1H-indazol-5-yl, and s is 0;

a compound wherein Y is thiazol-2-yl, Z is 2-(3-trifluoromethylphenylmethyl)-indazol-5-yl, and s is 0;

a compound wherein Y is thiazol-2-yl, Z is (1-phenyl-ethyl)-2H-indazol-5-yl, and s is 0;

a compound wherein Y is thiazol-2-yl, Z is 4-(3-trifluoromethyl-phenylaminocarbonylmethoxy)-phenyl, and s is 0;

a compound wherein Y is thiazol-2-yl, Z is 1-(4-aminosulfonyl-phenylmethyl)-2,5-dimethyl-pyrrol-3-yl, and s is 0;

a compound wherein Y is thiazol-2-yl, Z is 1-(4-fluoro-phenylmethyl)-1H-pyrrolo[2,3-b]pyridin-5-yl, and s is 0;

a compound wherein Y is thiazol-2-yl, Z is 1-(4-aminocarbonyl-phenylmethyl)-indazol-5-yl, and s is 0;

a compound wherein Y is thiazol-2-yl, Z is 1-(4-cyanophenylmethyl)-indazol-5-yl, and s is 0;

a compound wherein Y is thiazol-2-yl, Z is 1-(pyridin-4-ylmethyl)-indol-5-yl, and s is 0;

a compound wherein Y is thiazol-2-yl, Z is 1-(pyridin-4-ylmethyl)-indol-6-yl, and s is 0;

a compound wherein Y is thiazol-2-yl, Z is 1-(pyridin-3-ylmethyl)-indol-5-yl, and s is 0;

a compound wherein Y is thiazol-2-yl, Z is 1-(4-fluoro-phenylethyl)-indazol-5-yl, and s is 0;

a compound wherein Y is thiazol-2-yl, Z is 2-(4-fluoro-phenylethyl)-indazol-5-yl, and s is 0;

a compound wherein Y is thiazol-2-yl, Z is 1-(4-fluoro-phenylmethyl)-indazol-6-yl, and s is 0;

a compound wherein Y is thiazol-2-yl, Z is 2-(4-fluoro-phenylmethyl)-indazol-6-yl, and s is 0;

a compound wherein Y is thiazol-2-yl, Z is 1-(4-chloro-phenylmethyl)-3-methyl-1H-thieno[2,3-c]pyrazol-5-yl, and s is 0;

a compound wherein Y is thiazol-2-yl, Z is 1,1,3-tris-(3-trifluoromethylphenylmethyl)indan-2-on-6-yl, and s is 0;

a compound wherein Y is thiazol-2-yl, Z is 1,1,3-tris-(phenylmethyl)indan-2-on-6-yl, and s is 0;

or a pharmaceutically acceptable salt form thereof.

15. A pharmaceutical composition comprising a compound of claim 1 or 14 and at least one of a pharmaceutically acceptable carrier, a pharmaceutically acceptable excipient, and a pharmaceutically acceptable diluent.

16. A pharmaceutical composition of claim 15, wherein the composition is a solid oral dosage form.

17. A pharmaceutical composition of claim 15, wherein the composition is a syrup, an elixir, or a suspension.

18. A method for treating inflammatory pain in a subject in need thereof comprising administering to the subject a therapeutically effective amount of a compound of claim 1 or 14.

19. The method of claim 18 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

* * * * *